United States Patent
Granger et al.

(10) Patent No.: US 10,450,301 B2
(45) Date of Patent: Oct. 22, 2019

(54) APOPTOSIS SIGNAL-REGULATING KINASE 1 INHIBITORS AND METHODS OF USE THEREOF

(71) Applicant: ENANTA PHARMACEUTICALS, INC., Watertown, MA (US)

(72) Inventors: Brett Granger, Sudbury, MA (US); Guoqiang Wang, Belmont, MA (US); Ruichao Shen, Belmont, MA (US); Jing He, Somerville, MA (US); Yong He, Lexington, MA (US); Xuechao Xing, Wilmington, MA (US); Jun Ma, Belmont, MA (US); Jiang Long, Wayland, MA (US); Bin Wang, Brighton, MA (US); Yat Sun Or, Watertown, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 15/988,806

(22) Filed: May 24, 2018

(65) Prior Publication Data
US 2018/0362503 A1 Dec. 20, 2018

Related U.S. Application Data

(60) Provisional application No. 62/510,986, filed on May 25, 2017.

(51) Int. Cl.
| | |
|---|---|
| *A61K 31/4375* | (2006.01) |
| *A61K 31/4725* | (2006.01) |
| *C07D 401/14* | (2006.01) |
| *C07D 471/04* | (2006.01) |
| *C07D 471/08* | (2006.01) |
| *C07D 417/14* | (2006.01) |
| *C07D 451/02* | (2006.01) |
| *C07D 451/06* | (2006.01) |

(52) U.S. Cl.
CPC ......... *C07D 401/14* (2013.01); *C07D 417/14* (2013.01); *C07D 451/02* (2013.01); *C07D 451/06* (2013.01); *C07D 471/04* (2013.01); *C07D 471/08* (2013.01)

(58) Field of Classification Search
CPC ............ A61K 31/4375; A61K 31/4725; C07D 401/14; C07D 471/04
USPC ........ 514/300, 307, 338, 340; 546/123, 146, 546/148, 272.4, 268.4, 268.1
See application file for complete search history.

(56) References Cited

U.S. PATENT DOCUMENTS

| | | |
|---|---|---|
| 6,534,651 B2 | 3/2003 | Jagtap et al. |
| 8,378,108 B2 | 2/2013 | Corkey et al. |
| 9,254,284 B2 | 2/2016 | Notte |
| 2009/0318425 A1 | 12/2009 | Chang et al. |
| 2011/0009410 A1 | 1/2011 | Corkey et al. |
| 2012/0004267 A1 | 1/2012 | Corkey et al. |
| 2013/0203731 A1 | 8/2013 | Chang et al. |
| 2013/0210810 A1 | 8/2013 | Singh et al. |
| 2014/0018370 A1 | 1/2014 | Corkey et al. |
| 2014/0249135 A1 | 9/2014 | Burger et al. |

(Continued)

FOREIGN PATENT DOCUMENTS

| | | |
|---|---|---|
| CN | 107793400 A | 3/2018 |
| WO | 2005009470 A1 | 2/2005 |
| WO | 2005103288 A1 | 11/2005 |

(Continued)

OTHER PUBLICATIONS

Gibson, et al., "Structure-based drug design of novel ASK1 inhibitors using an integrated lead optimization strategy," Bioorganic & Medicinal Chemistry Letters, pp. 1-5, 2017.

(Continued)

*Primary Examiner* — Matthew P Coughlin
*Assistant Examiner* — Sagar Patel
(74) *Attorney, Agent, or Firm* — Edgar W. Harlan; Carolyn S. Elmore, Esq.; Elmore Patent Law Group, P.C.

(57) ABSTRACT

The present invention discloses compounds of Formula (I), and pharmaceutically acceptable salts and esters thereof:

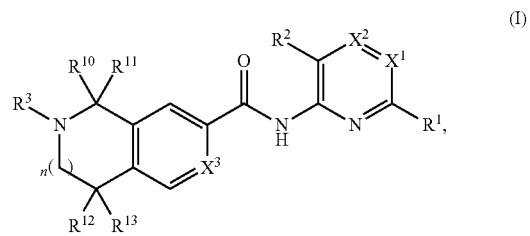

(I)

which inhibit the Apoptosis signal-regulating kinase 1 (ASK-1), which associated with autoimmune disorders, neurodegenerative disorders, inflammatory diseases, chronic kidney disease, cardiovascular disease. The present invention further relates to pharmaceutical compositions comprising the aforementioned compounds for administration to a subject suffering from ASK-1 related disease. The invention also relates to methods of treating an ASK-1 related disease in a subject by administering a pharmaceutical composition comprising the compounds of the present invention. The present invention specifically relates to methods of treating ASK-1 associated with hepatic steatosis, including non-alcoholic fatty liver disease (NAFLD) and non-alcohol steatohepatitis disease (NASH).

20 Claims, No Drawings

(56) References Cited

U.S. PATENT DOCUMENTS

| | | |
|---|---|---|
| 2014/0329850 A1 | 11/2014 | Chang |
| 2015/0005280 A1 | 1/2015 | Sasmal et al. |

FOREIGN PATENT DOCUMENTS

| | | |
|---|---|---|
| WO | 2007000339 A1 | 1/2007 |
| WO | 2008016131 A1 | 2/2008 |
| WO | 2008082579 A1 | 7/2008 |
| WO | 2009027283 A1 | 3/2009 |
| WO | 2009123986 A1 | 10/2009 |
| WO | 2010008843 A1 | 1/2010 |
| WO | 2011008709 A1 | 1/2011 |
| WO | 2011041293 A1 | 4/2011 |
| WO | 2011097079 A1 | 8/2011 |
| WO | 2012003387 A3 | 1/2012 |
| WO | 2012011548 A1 | 1/2012 |
| WO | 2012080735 A1 | 6/2012 |
| WO | 2013112741 A1 | 8/2013 |
| WO | 2014100541 A1 | 6/2014 |
| WO | WO-2014137728 A1 * | 9/2014 ........... C07D 401/14 |
| WO | 2015095059 A1 | 6/2015 |
| WO | 2016049069 A1 | 3/2016 |
| WO | 2016049070 A1 | 3/2016 |
| WO | 2016105453 A1 | 6/2016 |
| WO | 2016106384 A1 | 6/2016 |
| WO | 2018090869 A1 | 5/2018 |
| WO | 2018133856 A1 | 7/2018 |
| WO | 2018133866 A1 | 7/2018 |
| WO | 2018148204 A1 | 8/2018 |
| WO | 2018149284 A1 | 8/2018 |
| WO | 2018151830 A1 | 8/2018 |
| WO | 2018157857 A1 | 9/2018 |

OTHER PUBLICATIONS

Monastyrskyi, et al., "Discovery of 2-arylquinazoline derivatives as a new class of ASK1 inhibitors," Bioorganic & Medicinal Chemistry Letters, 28:400-404, 2018.

Lovering, et al., "Rational approach to highly potent and selective apoptosis signal regulating kinase 1 (ASK1) inhibitors," European Journal of Medicinal Chemistry, 145:606-621, 2018.

Loomba, et al., "The ASK1 Inhibitor Selonsertib in Patients with Nonalcoholic Steatohepatitis: A Randomized, Phase 2 Trial," Hepatology 67(2):549-559, 2018.

Volynets, et al., "Identification of 3H-Naphtho[1,2,3-de]quinoline-2,7-diones as Inhibitors of Apoptosis Signal-Regulating Kinase 1 (ASK1)," Journal of Medicinal Chemistry, 54:2680-2686, 2011.

Volynets, et al., "Rational design of apoptosis signal-regulating kinase 1 inhibitors: Discovering novel structural scaffold," European Journal of Medicinal Chemistry 61:104-115, 2013.

Terao, et al., "Design and biological evaluation of imidazo[1,2-a]pyridines as novel and potent ASK1 inhibitors," Bioorganic & Medicinal Chemistry Letters, 22:7326-7329, 2012.

U.S. Appl. No. 15/979,128, filed May 14, 2018.
U.S. Appl. No. 15/988,763, filed May 24, 2018.
U.S. Appl. No. 15/988,783, filed May 24, 2018.
U.S. Appl. No. 16/113,611, filed Aug. 27, 2018.

Wermuth, C. G., "Molecular Variations Based on Isosteric Replacements", in "The Practice of Medicinal Chemistry", Academic Press Limited, 1996, 203-237.

* cited by examiner

APOPTOSIS SIGNAL-REGULATING KINASE 1 INHIBITORS AND METHODS OF USE THEREOF

RELATED APPLICATIONS

This application claims the benefit of U.S. Provisional Application No. 62/510,986, filed on May 25, 2017. The entire teachings of the above application are incorporated herein by reference.

TECHNICAL FIELD

The present invention relates generally to compounds and pharmaceutical compositions useful as ASK-1 inhibitors. Specifically, the present invention relates to compounds useful as inhibitors of ASK-1 and methods for their preparation and use.

BACKGROUND OF THE INVENTION

Apoptosis signal-regulating kinase 1 (ASK-1) is a member of the mitogen-activated protein kinase kinase kinase (MAPKKK, MAP3K) family, which when activated phosphorylates downstream MAP kinase kinases (MAPKK, MAP2K), which in turn activate MAP kinases (MAPK). MAPKs elicit a response by phosphorylating cellular substrates, thus regulating the activity of transcription factors that ultimately control gene expression. Specifically ASK-1, also known as MAPKKK5, phosphorylates MAPKK4/MAPKK7 or MAPKK3/MAPKK6, which subsequently phosphorylates and activates the c-Jun N-terminal protein kinase (JNK) and p38 MAPKs, respectively (H. Ichijo, et al., *Cell Comm. Signal* 2009, 7, 1-10; K. Takeda, et al., *Annu. Rev. Pharmacol. Toxicol.* 2008, 48, 199-225; H. Nagai, et al., *J. Biochem. Mol. Biol.* 2007, 40, 1-6). Activation of the JNK and p38 pathways triggers a downstream stress response such as apoptosis, inflammation, or differentiation (H. Ichijo, et al., *Science* 1997, 275, 90-94; K. Takeda, et al., *J. Biol. Chem.* 2000, 275, 9805-9813; K. Tobiume, et al., *EMBO Rep.* 2001, 2, 222-228; K. Sayama et al., *J. Biol. Chem.* 2001, 276, 999-1004).

The activity of ASK-1 is regulated by thioredoxin (Trx), which binds to the N-terminal end of ASK-1 (M. Saitoh, et al., *EMBO J.* 1998, 17, 2596-2606). ASK-1 is activated succeeding autophosphorylation at Thr838 in response to environmental stimuli including oxidative stress, lipopolysaccharides (LPS), reactive oxygen species (ROS), endoplasmic reticulum (ER) stress, an increase in cellular calcium ion concentrations, Fas ligand, and various cytokines such as tumor necrosis factor (TNF) (H. Nishitoh, et al., *Genes Dev.* 2002, 16, 1345-1355; K. Takeda, et al., *EMBO Rep.* 2004, 5, 161-166; A. Matsuzawa, et al., *Nat. Immunol.* 2005, 6, 587-592).

ASK-1 has been associated with autoimmune disorders, neurodegenerative disorders, inflammatory diseases, chronic kidney disease, cardiovascular disease, metabolic disorders, and acute and chronic liver diseases (R. Hayakawa, et al., *Proc. Jpn. Acad., Ser. B* 2012, 88, 434-453).

More specifically, ASK-1 has been associated with hepatic steatosis, including non-alcoholic fatty liver disease (NAFLD) and non-alcohol steatohepatitis (NASH). In a mouse model, high fat diets have caused induction of hepatic steatosis, ultimately causing fat accumulation and fatty acid oxidation. This led to the generation of ROS which caused hepatocyte dysfunction and death (S. K. Mantena, et al., *Free Radic. Biol. Med.* 2008, 44, 1259-1272; S. K. Mantena, et al., *Biochem. J.* 2009, 417, 183-193). Moreover, TNF was shown to be critical for apoptosis of hepatocytes through the ASK-1-JNK pathway, and TNF deficient mice showed reduced hepatic steatosis and fibrosis (W. Zhang, et al., *Biochem. Biophys. Res. Commun.* 2010, 391, 1731-1736).

Small molecule compounds which act as ASK-1 inhibitors have been disclosed in the following publications: WO 2008/016131, WO 2009/027283, WO 2009/0318425, WO 2009/123986, US 2009/0318425, WO 2011/041293, WO 2011/097079, US 2011/0009410, G. P. Volynets, et al., *J. Med. Chem.* 2011, 54, 2680-2686, WO 2012/003387, WO 2012/011548, WO 2012/080735, Y. Terao, et al., *Bioorg. Med. Chem. Lett.* 2012, 22, 7326-7329, WO 2013/112741, G. P. Volynets, et al., *Eur. J. Med. Chem.* 2013, 16, 104-115, US 2014/0018370, WO 2014/100541, WO 2015/095059, WO 2016/049069, WO 2016/049070.

There is a need for the development of ASK-1 inhibitors for the treatment and prevention of disease. The present invention has identified compounds which inhibit ASK-1 as well as methods of using these compounds to treat disease.

SUMMARY OF THE INVENTION

In one aspect, the invention provides compounds represented by Formula I, or a pharmaceutically acceptable salt or ester thereof:

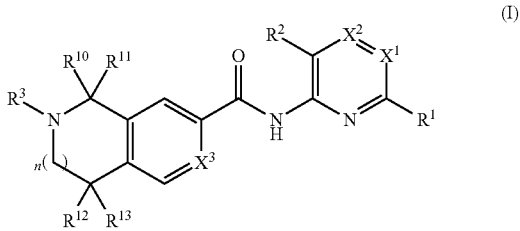

(I)

wherein:
$X^1$ and $X^2$ are each independently $C(R^8)$ or N;
$X^3$ is $C(R^9)$ or N, wherein $R^9$ is selected from the group consisting of hydrogen, optionally substituted —$C_1$-$C_8$ alkyl, optionally substituted —$C_1$-$C_8$ alkoxy and halo;
$R^1$ is selected from

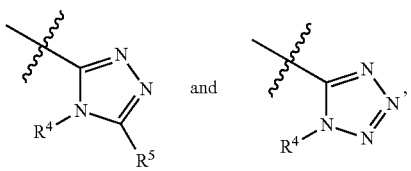

$R^4$ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8-membered heterocycloalkyl;
9) Substituted or unsubstituted heteroaryl; and
10) Substituted or unsubstituted heteroarylalkyl;

$R^2$, $R^5$ and $R^8$ are each independently selected from the group consisting of:
1) Hydrogen;
2) Halogen;
3) —$NO_2$;
4) Cyano;
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;
8) Substituted or unsubstituted —$C_3$-$C_8$ cycloalkyl;
9) Substituted or unsubstituted aryl;
10) Substituted or unsubstituted arylalkyl;
11) Substituted or unsubstituted 3- to 8-membered heterocycloalkyl;
12) Substituted or unsubstituted heteroaryl;
13) Substituted or unsubstituted heteroarylalkyl;
14) —$N(R^6)(R^7)$;
15) —$S(O)_2N(R^6)(R^7)$;
16) —$N(R^6)C(O)R^7$; and
17) —$N(R^6)S(O)_2R^6$;

wherein $R^6$ and $R^7$ are independently hydrogen, —$C_1$-$C_8$ alkyl, —$C_1$-$C_8$ alkenyl, —$C_1$-$C_8$ alkynyl, —$C_3$-$C_5$ cycloalkyl, aryl, arylalkyl, heterocycloalkyl, heteroaryl, and heteroarylalkyl, wherein the —$C_1$-$C_8$ alkyl, —$C_1$-$C_8$ alkenyl, —$C_1$-$C_8$ alkynyl, —$C_3$-$C_8$ cycloalkyl, aryl, arylalkyl, heterocycloalkyl, heteroaryl, and heteroarylalkyl is optionally substituted with 1-3 substituents independently selected from halo, alkyl, —$C_3$-$C_8$ cycloalkyl, alkylamino, dialkylamino, alkyl-C(O)—NH—, aryl-C(O)NH—, heteroaryl-C(O)NH—, —CN, alkoxy, —$CF_3$, aryl, and heteroaryl; or $R^6$ and $R^7$ are taken together with the nitrogen atom to which they are attached to form an optionally substituted heterocycloalkyl;

$R^3$ is selected from the group consisting of:
1) Hydrogen
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8-membered heterocycloalkyl;
9) Substituted or unsubstituted heteroaryl;
10) Substituted or unsubstituted heteroarylalkyl;
11) —$C(O)R^6$
12) —$C(O)OR^6$
13) —$C(O)N(R^6)(R')$; and
14) —$SO_2R^6$;

wherein $R^6$ and $R^7$ are as previously defined;
$R^{10}$ and $R^{11}$ are each independently selected from the group consisting of hydrogen, hydroxyl, and optionally substituted —$C_1$-$C_8$ alkyl; alternatively, $R^{10}$ and $R^{11}$ are taken together with the carbon atom to which they are attached to form C(O), spiro-$C_3$-$C_8$ cycloalkyl, or spiro-3- to 8-membered heterocycloalkyl;

$R^{12}$ and $R^{13}$ are each independently selected from the group consisting of hydrogen, halo, and optionally substituted —$C_1$-$C_8$ alkyl; and
n is 0, 1 or 2; preferably n is 0 or 1.

In another embodiment, the present invention provides a pharmaceutical composition comprising a therapeutically effective amount of a compound or combination of compounds of the present invention, or a pharmaceutically acceptable salt form, stereoisomer, solvate, hydrate or combination thereof, in combination with a pharmaceutically acceptable carrier or excipient.

In another embodiment, the present invention provides a method for the prevention or treatment of an ASK-1 mediated disease or condition. The method comprises administering a therapeutically effective amount of a compound of Formula (I) to a subject in need thereof. The present invention also provides the use of a compound of Formula (I) for the preparation of a medicament for the prevention or treatment of an ASK-1 mediated disease or condition. Such diseases include autoimmune disorders, neurodegenerative disorders, inflammatory diseases, chronic kidney disease, cardiovascular disease, metabolic disorders, and acute and chronic liver diseases.

DETAILED DESCRIPTION OF THE INVENTION

A first embodiment of the invention is a compound represented by Formula I as described above, or a pharmaceutically acceptable salt or esterthereof.

In a certain embodiment, the present invention relates to compounds of Formula I, or a pharmaceutically acceptable salt or ester thereof, wherein $R^4$ is selected from the groups below:

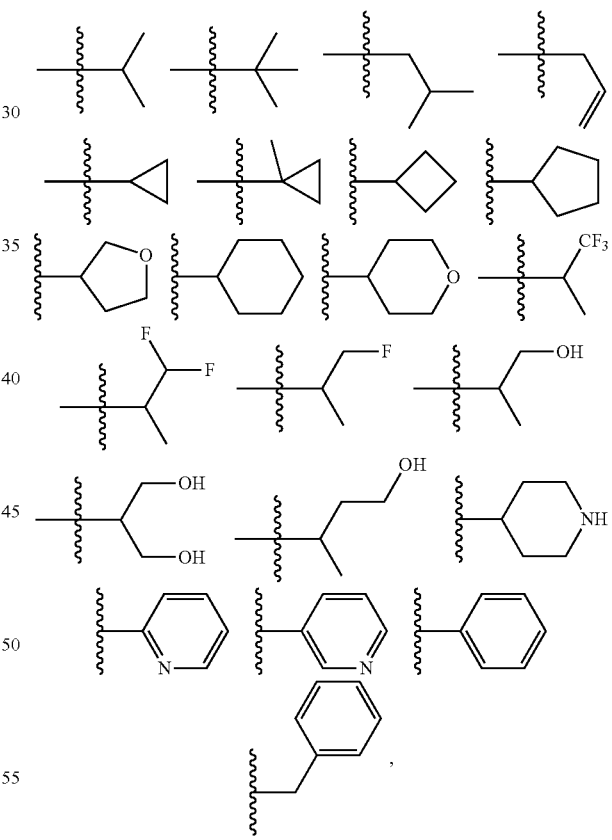

wherein each of the above shown groups is optionally substituted. Preferably, $R^4$ is selected from

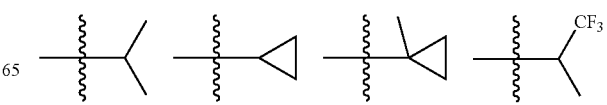

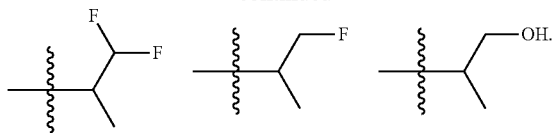

In certain embodiments, the present invention relates to compounds of Formula I, or a pharmaceutically acceptable salt or ester thereof, wherein $R^2$ is hydrogen or halogen.

In certain embodiments, the present invention relates to compounds of Formula I, or a pharmaceutically acceptable salt or ester thereof, wherein $R^5$ is hydrogen.

In certain embodiments, the present invention relates to compounds of Formula I, or a pharmaceutically acceptable salt or ester thereof, wherein $R^2$ is hydrogen, $R^5$ is hydrogen, and n is 0 or 1.

In certain embodiments, the present invention relates to compounds of Formula I, or a pharmaceutically acceptable salt or ester thereof, wherein $R^3$ is

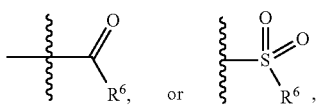

wherein $R^6$ is selected from the groups below:

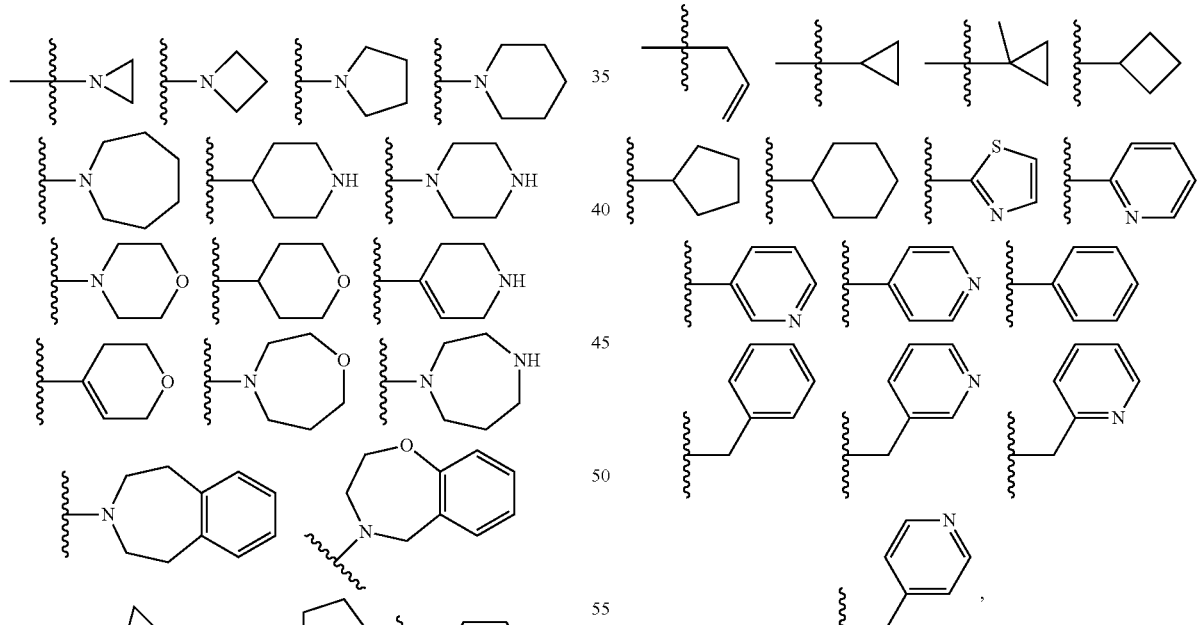

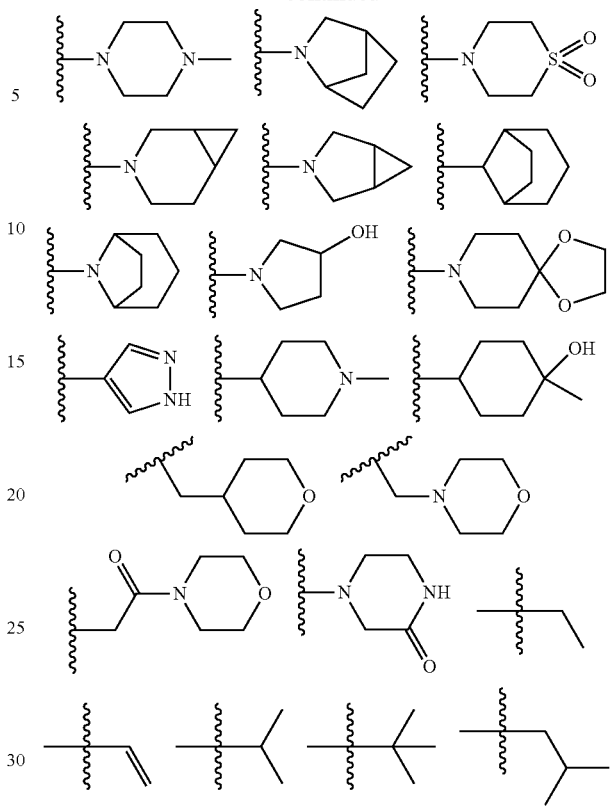

wherein each of the above shown groups is optionally substituted.

In certain embodiments, the present invention relates to compounds of Formula I, or a pharmaceutically acceptable salt or ester thereof, wherein $R^3$ is

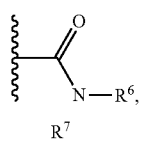

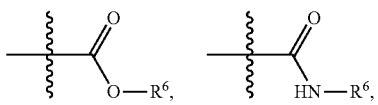

wherein $R^6$ is selected from the groups below:

$R^6$ and $R^7$, together with the nitrogen atom to which they are they attached, form an optionally substituted heterocycloalkyl is selected from the groups below:

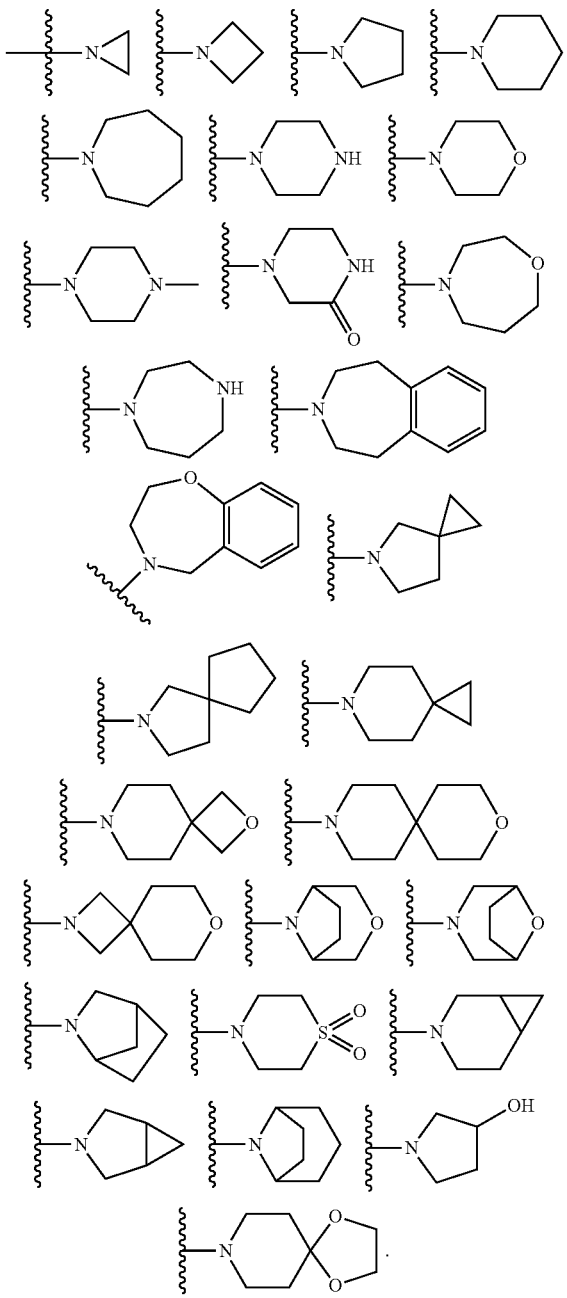

In another embodiment, the present invention relates to compounds of Formula I, or a pharmaceutically acceptable salt or ester thereof, wherein $R^3$ is In certain embodiments, the present invention relates to compounds of Formula I, and pharmaceutically acceptable salts and esters thereof, wherein $R^3$ is selected from the groups below:

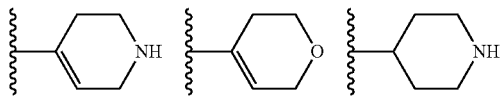

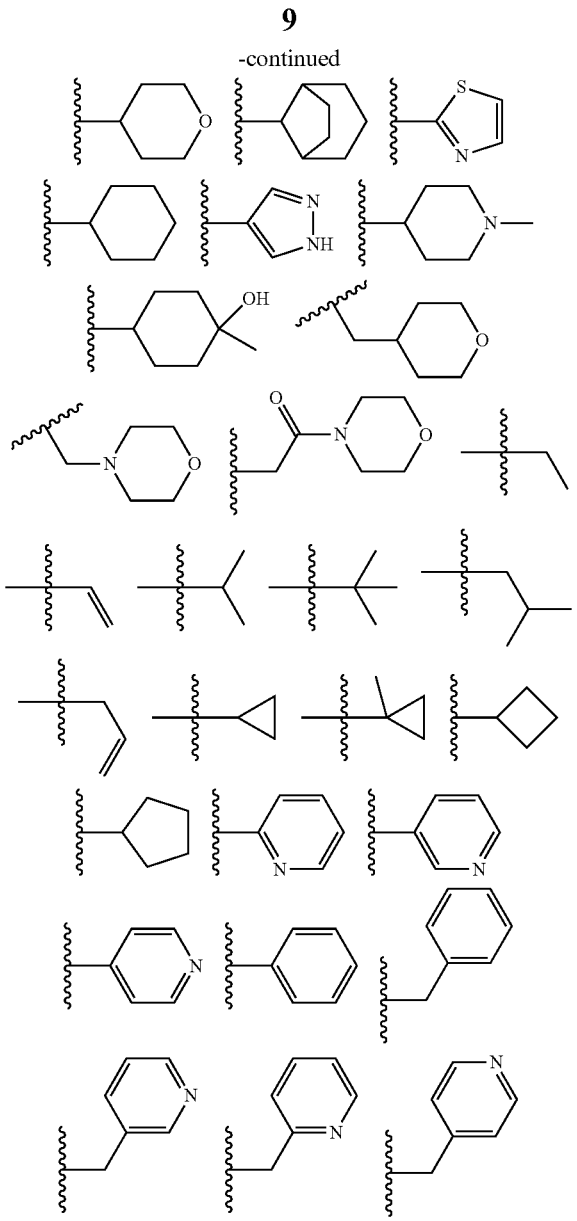

wherein each of these groups is optionally substituted.

In certain embodiments, the present invention relates to compounds of Formula I, or a pharmaceutically acceptable salt or ester thereof, wherein $X^3$ is selected from C—H, C—F, C—OMe, and N.

In certain embodiments, the compound of Formula I is represented by Formula Ia-1, Ia-2, Ib-1, Ib-2, Ic-1, Ic-2, or Ie, or a pharmaceutically acceptable salt or ester thereof:

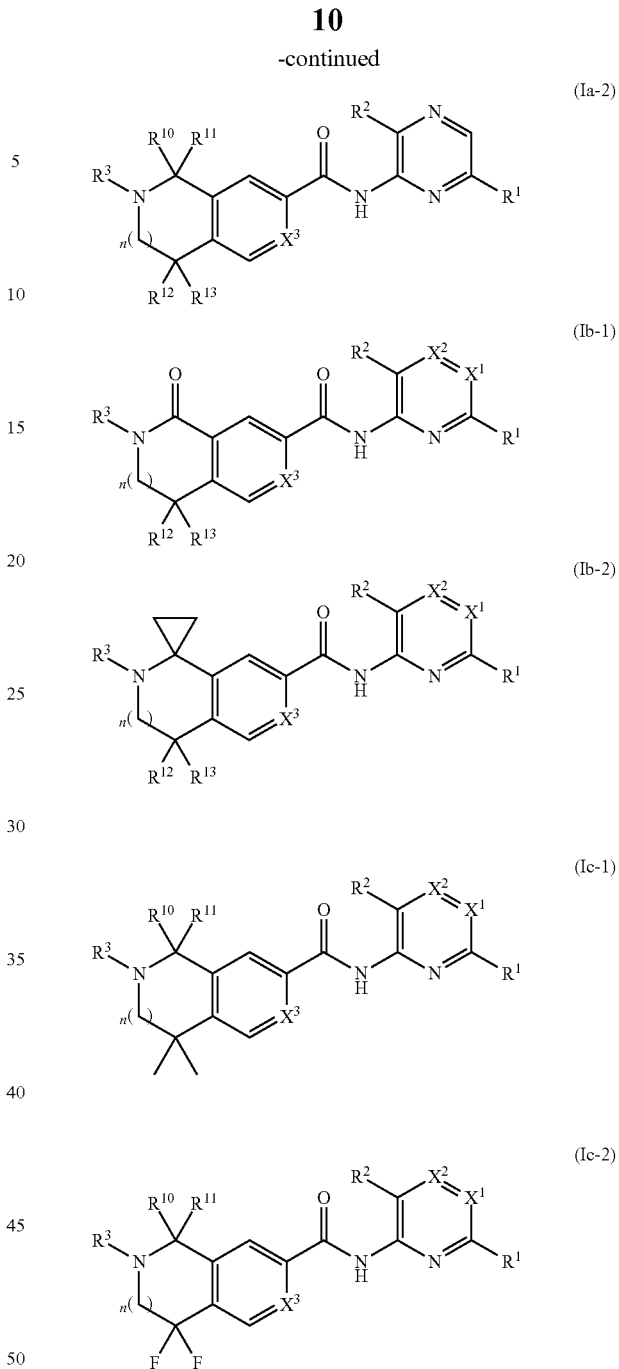

wherein $R^1$, $R^2$, $R^3$, $R^{10}$, $R^{11}$, $R^{12}$, $R^{13}$, $X^1$, $X^2$, $X^3$, and n are as previously defined.

In certain embodiments, the compound of Formula I is represented by Formula II or a pharmaceutically acceptable salt or ester thereof:

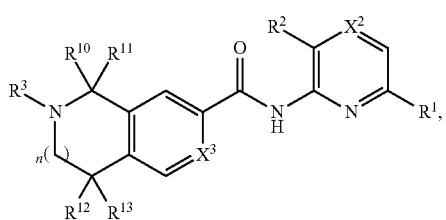
(II)

wherein $R^1$, $R^2$, $R^3$, $R^{10}$, $R^{11}$, $R^{12}$, $R^{13}$, $X^2$, $X^3$ and n are as previously defined.

In certain embodiments, the compound of Formula I is represented by Formula III or a pharmaceutically acceptable salt or ester thereof:

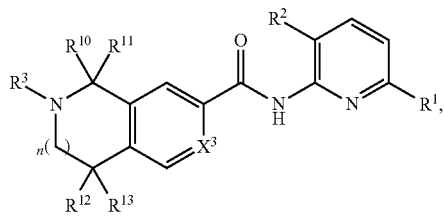
(III)

wherein $R^1$, $R^2$, $R^3$, $R^{10}$, $R^{11}$, $R^{12}$, $R^{13}$, $X^3$ and n are as previously defined.

In certain embodiments, the compound of Formula I is represented by Formula IV or a pharmaceutically acceptable salt or ester thereof:

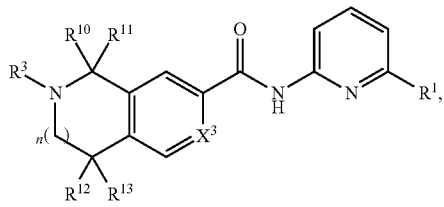
(IV)

wherein $R^1$, $R^3$, $R^{10}$, $R^{11}$, $R^{12}$, $R^{13}$, $X^3$ and n are as previously defined.

In certain embodiments, the compound of Formula I is represented by Formula V or a pharmaceutically acceptable salt or ester thereof:

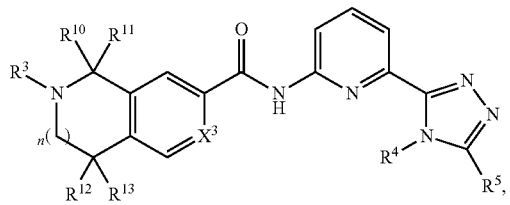
(V)

wherein $R^3$, $R^4$, $R^5$, $R^{10}$, $R^{11}$, $R^{12}$, $R^{13}$, $X^3$ and n are as previously defined.

In certain embodiments, the compound of Formula I is represented by Formula VI or a pharmaceutically acceptable salt or ester:

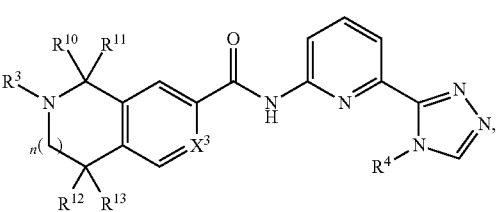
(VI)

wherein $R^3$, $R^4$, $R^{10}$, $R^{11}$, $R^{12}$, $R^{13}$, $X^3$ and n are as previously defined.

In certain embodiments, the compound of Formula I is represented by Formula VII or a pharmaceutically acceptable salt or ester thereof:

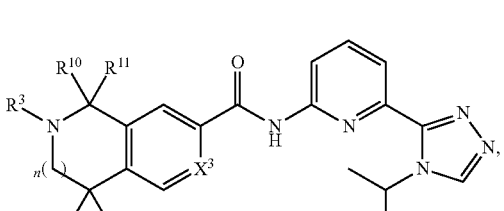
(VII)

wherein $R^3$, $R^{10}$, $R^{11}$, $R^{12}$, $R^{13}$, $X^3$ and n are as previously defined.

In certain embodiments, the compound of Formula I is represented by Formula VIII or a pharmaceutically acceptable salt or ester thereof:

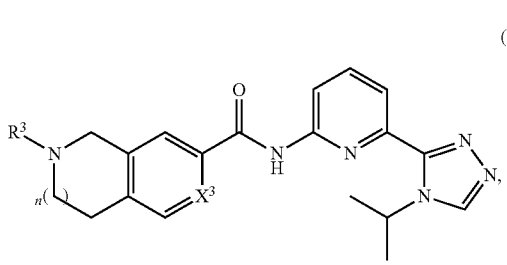
(VIII)

wherein $R^3$, $X^3$, and n are as previously defined.

Representative compounds of the invention include, but are not limited to, the following compounds (compound 1 to compound 300 in Table 1) according to Formula VIII, and pharmaceutically acceptable salts thereof, wherein $R^3$, $X^3$, and n are delineated for each compound in Table 1.

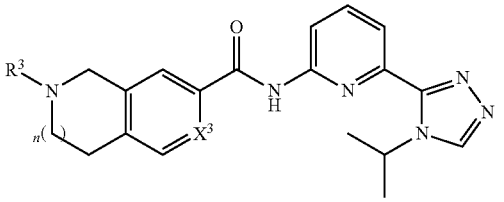
(VIII)

TABLE 1

| compound | R³ | X³ | n |
|---|---|---|---|
| 1 | H | C—H | 0 |
| 2 | Methyl | C—H | 0 |
| 3 | Ethyl | C—H | 0 |
| 4 | Propyl | C—H | 0 |
| 5 | Allyl | C—H | 0 |
| 6 | i-Propyl | C—H | 0 |
| 7 | -(CH₂)₃-OMe | C—H | 0 |
| 8 | i-Butyl | C—H | 0 |
| 9 | t-Butyl | C—H | 0 |
| 10 | cyclopentyl | C—H | 0 |
| 11 | cyclohexyl | C—H | 0 |
| 12 | phenyl | C—H | 0 |
| 13 | 4-t-butylphenyl | C—H | 0 |
| 14 | -C(O)CH₃ | C—H | 0 |
| 15 | -C(O)CH₂CH₃ | C—H | 0 |
| 16 | -C(O)CH₂CH₂OMe | C—H | 0 |
| 17 | -C(O)CH₂CH₂CH₃ | C—H | 0 |
| 18 | -C(O)CH(CH₃)₂ | C—H | 0 |
| 19 | -C(O)C(CH₃)₃ | C—H | 0 |
| 20 | -C(O)phenyl | C—H | 0 |
| 21 | -C(O)(4-t-butylphenyl) | C—H | 0 |
| 22 | -C(O)(thiazol-2-yl) | C—H | 0 |
| 23 | -C(O)OMe | C—H | 0 |
| 24 | -C(O)OEt | C—H | 0 |
| 25 | -C(O)OCH₂CH₂F | C—H | 0 |
| 26 | -C(O)OCH₂CH₂OMe | C—H | 0 |
| 27 | -C(O)O-propyl | C—H | 0 |
| 28 | -C(O)O-allyl | C—H | 0 |
| 29 | -C(O)O-i-propyl | C—H | 0 |
| 30 | -C(O)O-butyl | C—H | 0 |

TABLE 1-continued

| compound | R³ | X³ | n |
|---|---|---|---|
| 31 | butenyl ester (−C(=O)O−CH₂CH₂CH=CH₂) | C—H | 0 |
| 32 | isobutyl ester | C—H | 0 |
| 33 | t-butyl ester | C—H | 0 |
| 34 | cyclopentyl ester | C—H | 0 |
| 35 | cyclohexyl ester | C—H | 0 |
| 36 | benzyl ester | C—H | 0 |
| 37 | N-ethyl amide | C—H | 0 |
| 38 | N-(2-methoxyethyl) amide | C—H | 0 |
| 39 | N-propyl amide | C—H | 0 |
| 40 | N-allyl amide | C—H | 0 |
| 41 | N-butyl amide | C—H | 0 |
| 42 | N-isopropyl amide | C—H | 0 |
| 43 | N-isobutyl amide | C—H | 0 |
| 44 | N-t-butyl amide | C—H | 0 |
| 45 | N-cyclopentyl amide | C—H | 0 |
| 46 | N-benzyl amide | C—H | 0 |
| 47 | N-phenyl amide | C—H | 0 |
| 48 | N,N-dimethyl amide | C—H | 0 |
| 49 | pyrrolidine amide | C—H | 0 |
| 50 | piperidine amide | C—H | 0 |
| 51 | H | C—F | 0 |
| 52 | Methyl | C—F | 0 |
| 53 | Ethyl | C—F | 0 |
| 54 | Propyl | C—F | 0 |
| 55 | Allyl | C—F | 0 |
| 56 | i-Propyl | C—F | 0 |
| 57 | −(CH₂)₃−OMe | C—F | 0 |
| 58 | i-Butyl | C—F | 0 |
| 59 | t-Butyl | C—F | 0 |

TABLE 1-continued
| compound | R³ | X³ | n |
|---|---|---|---|
| 60 | 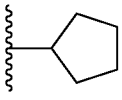 | C—F | 0 |
| 61 | 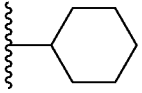 | C—F | 0 |
| 62 | 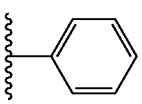 [SMILES: *c1ccccc1] | C—F | 0 |
| 63 | 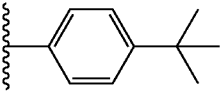 [SMILES: *c1ccc(C(C)(C)C)cc1] | C—F | 0 |
| 64 | 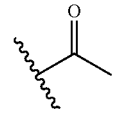 [SMILES: *C(C)=O] | C—F | 0 |
| 65 | 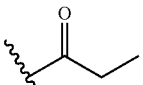 | C—F | 0 |
| 66 | 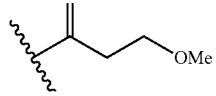 | C—F | 0 |
| 67 | 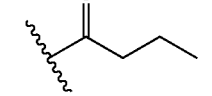 | C—F | 0 |
| 68 | 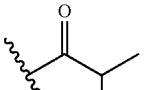 | C—F | 0 |
| 69 | 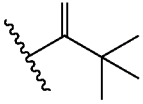 | C—F | 0 |
| 70 | 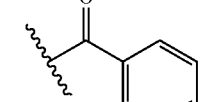 | C—F | 0 |
| 71 | 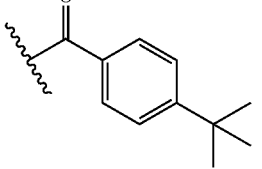 | C—F | 0 |
| 72 | 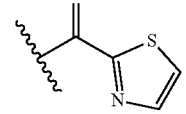 | C—F | 0 |
| 73 | 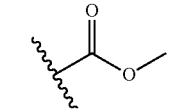 [SMILES: *C(=O)OC] | C—F | 0 |
| 74 | 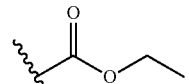 | C—F | 0 |
| 75 | 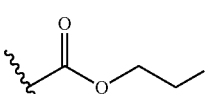 | C—F | 0 |
| 76 | 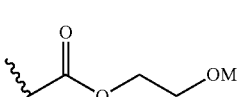 | C—F | 0 |
| 77 | 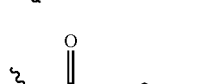 | C—F | 0 |
| 78 | 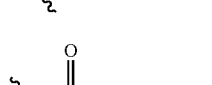 | C—F | 0 |
| 79 | 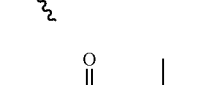 | C—F | 0 |
| 80 | 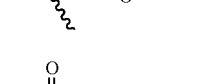 | C—F | 0 |
| 81 | 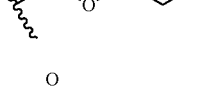 | C—F | 0 |
| 82 | 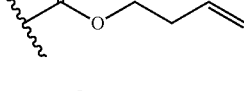 | C—F | 0 |
| 83 | 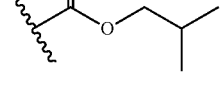 | C—F | 0 |

TABLE 1-continued

| compound | R³ | X³ | n |
|---|---|---|---|
| 84 | cyclopentyl ester (–C(=O)O-cyclopentyl) | C—F | 0 |
| 85 | cyclohexyl ester (–C(=O)O-cyclohexyl) | C—F | 0 |
| 86 | benzyl ester (–C(=O)O-CH₂-Ph) | C—F | 0 |
| 87 | –C(=O)NH-Et | C—F | 0 |
| 88 | –C(=O)NH-CH₂CH₂OMe | C—F | 0 |
| 89 | –C(=O)NH-propyl | C—F | 0 |
| 90 | –C(=O)NH-allyl | C—F | 0 |
| 91 | –C(=O)NH-butyl | C—F | 0 |
| 92 | –C(=O)NH-iPr | C—F | 0 |
| 93 | –C(=O)NH-iBu | C—F | 0 |
| 94 | –C(=O)NH-tBu | C—F | 0 |
| 95 | –C(=O)NH-cyclopentyl | C—F | 0 |
| 96 | –C(=O)NH-CH₂Ph | C—F | 0 |
| 97 | –C(=O)NH-Ph | C—F | 0 |
| 98 | –C(=O)N(Me)₂ | C—F | 0 |
| 99 | –C(=O)-pyrrolidinyl | C—F | 0 |
| 100 | –C(=O)-piperidinyl | C—F | 0 |
| 101 | H | N | 0 |
| 102 | Methyl | N | 0 |
| 103 | Ethyl | N | 0 |
| 104 | Propyl | N | 0 |
| 105 | Allyl | N | 0 |
| 106 | i-Propyl | N | 0 |
| 107 | –(CH₂)₃OMe | N | 0 |
| 108 | i-Butyl | N | 0 |
| 109 | t-Butyl | N | 0 |
| 110 | cyclopentyl | N | 0 |
| 111 | cyclohexyl | N | 0 |
| 112 | phenyl | N | 0 |

TABLE 1-continued

| compound | R³ | X³ | n |
|---|---|---|---|
| 113 | 4-tert-butylphenyl | N | 0 |
| 114 | C(O)CH₃ | N | 0 |
| 115 | C(O)CH₂CH₃ | N | 0 |
| 116 | C(O)CH₂CH₂OMe | N | 0 |
| 117 | C(O)CH₂CH₂CH₃ | N | 0 |
| 118 | C(O)CH(CH₃)₂ | N | 0 |
| 119 | C(O)C(CH₃)₃ | N | 0 |
| 120 | C(O)Ph | N | 0 |
| 121 | C(O)-(4-tert-butylphenyl) | N | 0 |
| 122 | C(O)-(thiazol-2-yl) | N | 0 |
| 123 | C(O)OMe | N | 0 |
| 124 | C(O)OEt | N | 0 |
| 125 | C(O)OCH₂CH₂F | N | 0 |
| 126 | C(O)OCH₂CH₂OMe | N | 0 |
| 127 | C(O)O-n-propyl | N | 0 |
| 128 | C(O)O-allyl | N | 0 |
| 129 | C(O)O-iPr | N | 0 |
| 130 | C(O)O-n-butyl | N | 0 |
| 131 | C(O)OCH₂CH₂CH=CH₂ | N | 0 |
| 132 | C(O)O-iBu | N | 0 |
| 133 | C(O)O-tBu | N | 0 |
| 134 | C(O)O-cyclopentyl | N | 0 |
| 135 | C(O)O-cyclohexyl | N | 0 |

TABLE 1-continued

| compound | R³ | X³ | n |
|---|---|---|---|
| 136 | benzyl ester (-C(O)O-CH₂-C₆H₅) | N | 0 |
| 137 | -C(O)NH-Et | N | 0 |
| 138 | -C(O)NH-CH₂CH₂-OMe | N | 0 |
| 139 | -C(O)NH-propyl | N | 0 |
| 140 | -C(O)NH-allyl | N | 0 |
| 141 | -C(O)NH-butyl | N | 0 |
| 142 | -C(O)NH-iPr | N | 0 |
| 143 | -C(O)NH-iBu | N | 0 |
| 144 | -C(O)NH-tBu | N | 0 |
| 145 | -C(O)NH-cyclopentyl | N | 0 |
| 146 | -C(O)NH-CH₂-phenyl | N | 0 |
| 147 | -C(O)NH-phenyl | N | 0 |
| 148 | -C(O)N(Me)₂ | N | 0 |
| 149 | -C(O)-pyrrolidinyl | N | 0 |
| 150 | -C(O)-piperidinyl | N | 0 |
| 151 | H | C—H | 1 |
| 152 | Methyl | C—H | 1 |
| 153 | Ethyl | C—H | 1 |
| 154 | Propyl | C—H | 1 |
| 155 | Allyl | C—H | 1 |
| 156 | i-Propyl | C—H | 1 |
| 157 | -(CH₂)₃-OMe | C—H | 1 |
| 158 | i-Butyl | C—H | 1 |
| 159 | t-Butyl | C—H | 1 |
| 160 | cyclopentyl | C—H | 1 |
| 161 | cyclohexyl | C—H | 1 |
| 162 | phenyl | C—H | 1 |
| 163 | 4-t-butyl-phenyl | C—H | 1 |
| 164 | -C(O)-Me | C—H | 1 |
| 165 | -C(O)-Et | C—H | 1 |

TABLE 1-continued

| compound | R³ | X³ | n |
|---|---|---|---|
| 166 | -C(O)CH₂CH₂OMe | C—H | 1 |
| 167 | -C(O)CH₂CH₂CH₃ | C—H | 1 |
| 168 | -C(O)CH(CH₃)₂ | C—H | 1 |
| 169 | -C(O)C(CH₃)₃ | C—H | 1 |
| 170 | -C(O)Ph | C—H | 1 |
| 171 | -C(O)-C₆H₄-tBu (para) | C—H | 1 |
| 172 | -C(O)-(thiazol-2-yl) | C—H | 1 |
| 173 | -C(O)OMe | C—H | 1 |
| 174 | -C(O)OEt | C—H | 1 |
| 175 | -C(O)OCH₂CH₂F | C—H | 1 |
| 176 | -C(O)OCH₂CH₂OMe | C—H | 1 |

TABLE 1-continued

| compound | R³ | X³ | n |
|---|---|---|---|
| 177 | -C(O)OCH₂CH₂CH₃ | C—H | 1 |
| 178 | -C(O)OCH₂CH=CH₂ | C—H | 1 |
| 179 | -C(O)OCH(CH₃)₂ | C—H | 1 |
| 180 | -C(O)OCH₂CH₂CH₂CH₃ | C—H | 1 |
| 181 | -C(O)OCH₂CH₂CH=CH₂ | C—H | 1 |
| 182 | -C(O)OCH₂CH(CH₃)₂ | C—H | 1 |
| 183 | -C(O)OC(CH₃)₃ | C—H | 1 |
| 184 | -C(O)O-cyclopentyl | C—H | 1 |
| 185 | -C(O)NH-cyclohexyl | C—H | 1 |
| 186 | -C(O)OCH₂Ph | C—H | 1 |
| 187 | -C(O)NHEt | C—H | 1 |

TABLE 1-continued

| compound | R³ | X³ | n |
|---|---|---|---|
| 188 | -C(=O)NH-CH₂CH₂-OMe | C—H | 1 |
| 189 | -C(=O)NH-propyl | C—H | 1 |
| 190 | -C(=O)NH-allyl | C—H | 1 |
| 191 | -C(=O)NH-butyl | C—H | 1 |
| 192 | -C(=O)NH-iPr | C—H | 1 |
| 193 | -C(=O)NH-iBu | C—H | 1 |
| 194 | -C(=O)NH-tBu | C—H | 1 |
| 195 | -C(=O)NH-cyclopentyl | C—H | 1 |
| 196 | -C(=O)NH-CH₂-phenyl | C—H | 1 |
| 197 | -C(=O)NH-phenyl | C—H | 1 |
| 198 | -C(=O)N(Me)₂ | C—H | 1 |
| 199 | -C(=O)-pyrrolidinyl | C—H | 1 |
| 200 | -C(=O)-piperidinyl | C—H | 1 |
| 201 | H | C—F | 1 |
| 202 | Methyl | C—F | 1 |
| 203 | Ethyl | C—F | 1 |
| 204 | Propyl | C—F | 1 |
| 205 | Allyl | C—F | 1 |
| 206 | i-Propyl | C—F | 1 |
| 207 | -(CH₂)₃-OMe | C—F | 1 |
| 208 | i-Butyl | C—F | 1 |
| 209 | t-Butyl | C—F | 1 |
| 210 | cyclopentyl | C—F | 1 |
| 211 | cyclohexyl | C—F | 1 |
| 212 | phenyl | C—F | 1 |
| 213 | 4-t-butylphenyl | C—F | 1 |
| 214 | -C(=O)Me | C—F | 1 |
| 215 | -C(=O)Et | C—F | 1 |
| 216 | -C(=O)CH₂CH₂-OMe | C—F | 1 |
| 217 | -C(=O)-propyl | C—F | 1 |

TABLE 1-continued

| compound | R³ | X³ | n |
|---|---|---|---|
| 218 | isobutyryl (C(O)CH(CH₃)₂) | C—F | 1 |
| 219 | pivaloyl (C(O)C(CH₃)₃) | C—F | 1 |
| 220 | benzoyl | C—F | 1 |
| 221 | 4-tert-butylbenzoyl | C—F | 1 |
| 222 | thiazol-2-yl carbonyl | C—F | 1 |
| 223 | methoxycarbonyl | C—F | 1 |
| 224 | ethoxycarbonyl | C—F | 1 |
| 225 | 2-fluoroethoxycarbonyl | C—F | 1 |
| 226 | 2-methoxyethoxycarbonyl | C—F | 1 |
| 227 | propoxycarbonyl | C—F | 1 |
| 228 | allyloxycarbonyl | C—F | 1 |
| 229 | isopropoxycarbonyl | C—F | 1 |
| 230 | butoxycarbonyl | C—F | 1 |
| 231 | but-3-en-1-yloxycarbonyl | C—F | 1 |
| 232 | isobutoxycarbonyl | C—F | 1 |
| 233 | tert-butoxycarbonyl | C—F | 1 |
| 234 | cyclopentyloxycarbonyl | C—F | 1 |
| 235 | cyclohexyloxycarbonyl | C—F | 1 |
| 236 | benzyloxycarbonyl | C—F | 1 |
| 237 | ethylaminocarbonyl | C—F | 1 |
| 238 | 2-methoxyethylaminocarbonyl | C—F | 1 |
| 239 | propylaminocarbonyl | C—F | 1 |

TABLE 1-continued

| compound | R³ | X³ | n |
|---|---|---|---|
| 240 | ⁓C(=O)NH-allyl | C—F | 1 |
| 241 | ⁓C(=O)NH-butyl | C—F | 1 |
| 242 | ⁓C(=O)NH-iPr | C—F | 1 |
| 243 | ⁓C(=O)NH-iBu | C—F | 1 |
| 244 | ⁓C(=O)NH-tBu | C—F | 1 |
| 245 | ⁓C(=O)NH-cyclopentyl | C—F | 1 |
| 246 | ⁓C(=O)NH-CH₂Ph | C—F | 1 |
| 247 | ⁓C(=O)NH-Ph | C—F | 1 |
| 248 | ⁓C(=O)N(Me)₂ | C—F | 1 |
| 249 | ⁓C(=O)-pyrrolidinyl | C—F | 1 |
| 250 | ⁓C(=O)-piperidinyl | C—F | 1 |
| 251 | H | N | 1 |
| 252 | Methyl | N | 1 |
| 253 | Ethyl | N | 1 |

TABLE 1-continued

| compound | R³ | X³ | n |
|---|---|---|---|
| 254 | Propyl | N | 1 |
| 255 | Allyl | N | 1 |
| 256 | i-Propyl | N | 1 |
| 257 | ⁓CH₂CH₂CH₂OMe | N | 1 |
| 258 | i-Butyl | N | 1 |
| 259 | t-Butyl | N | 1 |
| 260 | ⁓cyclopentyl | N | 1 |
| 261 | ⁓cyclohexyl | N | 1 |
| 262 | ⁓Ph | N | 1 |
| 263 | ⁓C₆H₄-tBu (para) | N | 1 |
| 264 | ⁓C(=O)Me | N | 1 |
| 265 | ⁓C(=O)Et | N | 1 |
| 266 | ⁓C(=O)CH₂OMe | N | 1 |
| 267 | ⁓C(=O)Pr | N | 1 |
| 268 | ⁓C(=O)iPr | N | 1 |
| 269 | ⁓C(=O)tBu | N | 1 |

TABLE 1-continued
| compound | R³ | X³ | n |
|---|---|---|---|
| 270 | 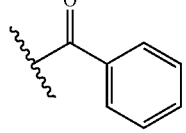 | N | 1 |
| 271 | 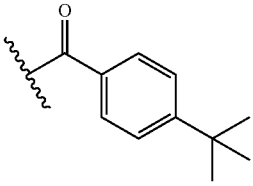 [SMILES: *C(=O)c1ccc(C(C)(C)C)cc1] | N | 1 |
| 272 | 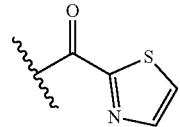 [SMILES: *C(=O)c1nccs1] | N | 1 |
| 273 | 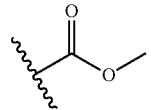 [SMILES: *C(=O)OC] | N | 1 |
| 274 | 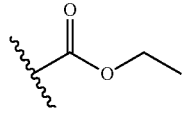 [SMILES: *C(=O)OCC] | N | 1 |
| 275 | 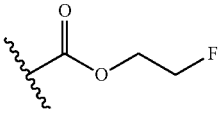 [SMILES: *C(=O)OCCF] | N | 1 |
| 276 | 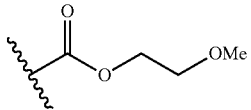 [SMILES: *C(=O)OCCOC] | N | 1 |
| 277 | 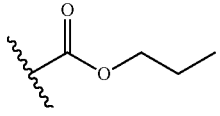 [SMILES: *C(=O)OCCC] | N | 1 |
| 278 | 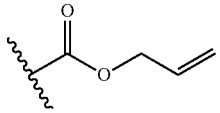 [SMILES: *C(=O)OCC=C] | N | 1 |
| 279 | 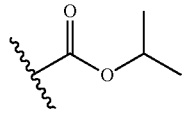 [SMILES: *C(=O)OC(C)C] | N | 1 |
| 280 | 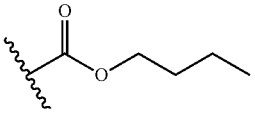 [SMILES: *C(=O)OCCCC] | N | 1 |
| 281 | 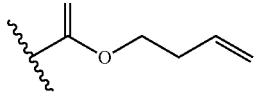 | N | 1 |
| 282 | 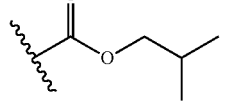 | N | 1 |
| 283 | 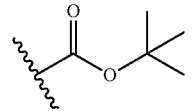 | N | 1 |
| 284 | 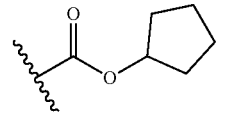 [SMILES: *C(=O)OC1CCCC1] | N | 1 |
| 285 | 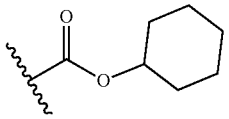 [SMILES: *C(=O)OC1CCCCC1] | N | 1 |
| 286 | 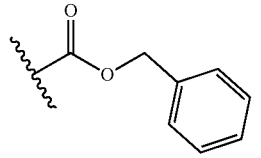 [SMILES: *C(=O)OCc1ccccc1] | N | 1 |
| 287 | 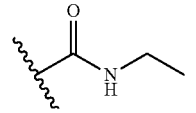 [SMILES: *C(=O)NCC] | N | 1 |
| 288 | 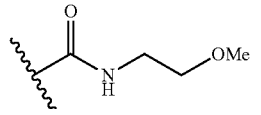 [SMILES: *C(=O)NCCOC] | N | 1 |
| 289 | 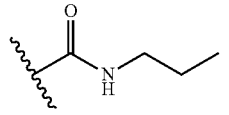 [SMILES: *C(=O)NCCC] | N | 1 |
| 290 | 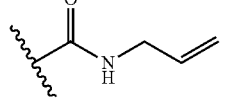 | N | 1 |
| 291 | 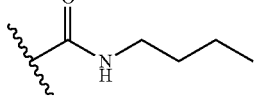 | N | 1 |

TABLE 1-continued

| compound | R³ | X³ | n |
|---|---|---|---|
| 292 | (isopropyl amide) | N | 1 |
| 293 | (isobutyl amide) | N | 1 |
| 294 | (tert-butyl amide) | N | 1 |
| 295 | (cyclopentyl amide) | N | 1 |
| 296 | (benzyl amide) | N | 1 |
| 297 | (phenyl amide) | N | 1 |
| 298 | (N,N-dimethyl amide) | N | 1 |
| 299 | (pyrrolidinyl amide) | N | 1 |
| 300 | (piperidinyl amide) | N | 1 |

In certain embodiments, the compound of Formula I is represented by Formula IX or a pharmaceutically acceptable salt or ester thereof:

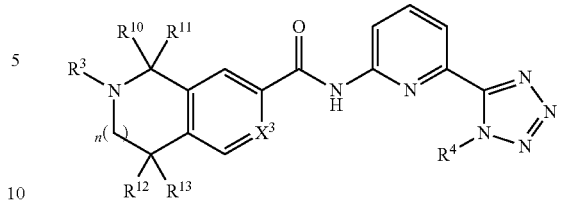

wherein $R^3$, $R^4$, $R^{10}$, $R^{11}$, $R^{12}$, $R^{13}$, $X^3$ and n are as previously defined.

In certain embodiments, the compound of Formula I is represented by Formula X or a pharmaceutically acceptable salt or ester thereof:

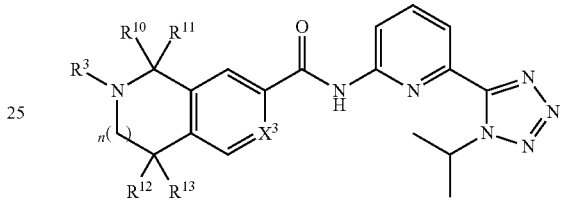

wherein $R^3$, $R^{10}$, $R^{11}$, $R^{12}$, $R^{13}$, $X^3$ and n are as previously defined.

In certain embodiments, the compound of Formula I is represented by Formula XI or a pharmaceutically acceptable salt or ester thereof:

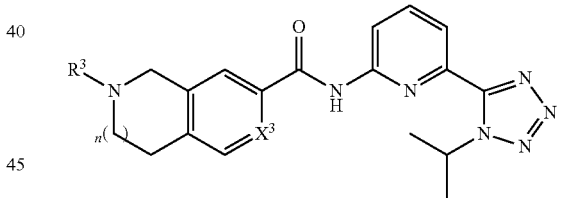

wherein $R^3$, $X^3$, and n are as previously defined.

Representative compounds of the invention include, but are not limited to, the following compounds (compound 301 to compound 600 in Table 2) according to Formula XI, and pharmaceutically acceptable salts thereof, wherein $R^3$, $X^3$, and n are delineated for each compound in Table 2.

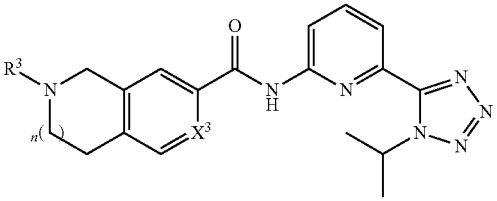

TABLE 2

| compound | R³ | X³ | n |
|---|---|---|---|
| 301 | H | C—H | 0 |
| 302 | Methyl | C—H | 0 |
| 303 | Ethyl | C—H | 0 |
| 304 | Propyl | C—H | 0 |
| 305 | Allyl | C—H | 0 |
| 306 | i-Propyl | C—H | 0 |
| 307 | -(CH₂)₃-OMe | C—H | 0 |
| 308 | i-Butyl | C—H | 0 |
| 309 | t-Butyl | C—H | 0 |
| 310 | cyclopentyl | C—H | 0 |
| 311 | cyclohexyl | C—H | 0 |
| 312 | phenyl | C—H | 0 |
| 313 | 4-t-butylphenyl | C—H | 0 |
| 314 | -C(O)CH₃ | C—H | 0 |
| 315 | -C(O)CH₂CH₃ | C—H | 0 |
| 316 | -C(O)CH₂CH₂OMe | C—H | 0 |
| 317 | -C(O)CH₂CH₂CH₃ | C—H | 0 |
| 318 | -C(O)CH(CH₃)₂ | C—H | 0 |
| 319 | -C(O)C(CH₃)₃ | C—H | 0 |
| 320 | -C(O)-phenyl | C—H | 0 |
| 321 | -C(O)-(4-t-butylphenyl) | C—H | 0 |
| 322 | -C(O)-(thiazol-2-yl) | C—H | 0 |
| 323 | -C(O)OMe | C—H | 0 |
| 324 | -C(O)OEt | C—H | 0 |
| 325 | -C(O)OCH₂CH₂F | C—H | 0 |
| 326 | -C(O)OCH₂CH₂OMe | C—H | 0 |
| 327 | -C(O)O-propyl | C—H | 0 |
| 328 | -C(O)O-allyl | C—H | 0 |
| 329 | -C(O)O-i-propyl | C—H | 0 |
| 330 | -C(O)O-butyl | C—H | 0 |

TABLE 2-continued

| compound | R³ | X³ | n |
|---|---|---|---|
| 331 | butenyl ester (-C(=O)O-CH₂CH₂CH=CH₂) | C—H | 0 |
| 332 | isobutyl ester (-C(=O)O-CH₂CH(CH₃)₂) | C—H | 0 |
| 333 | t-butyl ester (-C(=O)O-C(CH₃)₃) | C—H | 0 |
| 334 | cyclopentyl ester | C—H | 0 |
| 335 | cyclohexyl ester | C—H | 0 |
| 336 | benzyl ester | C—H | 0 |
| 337 | -C(=O)NH-Et | C—H | 0 |
| 338 | -C(=O)NH-CH₂CH₂-OMe | C—H | 0 |
| 339 | -C(=O)NH-propyl | C—H | 0 |
| 340 | -C(=O)NH-allyl | C—H | 0 |
| 341 | -C(=O)NH-butyl | C—H | 0 |
| 342 | -C(=O)NH-iPr | C—H | 0 |
| 343 | -C(=O)NH-iBu | C—H | 0 |
| 344 | -C(=O)NH-tBu | C—H | 0 |
| 345 | -C(=O)NH-cyclopentyl | C—H | 0 |
| 346 | -C(=O)NH-benzyl | C—H | 0 |
| 347 | -C(=O)NH-phenyl | C—H | 0 |
| 348 | -C(=O)N(Me)₂ | C—H | 0 |
| 349 | -C(=O)-pyrrolidinyl | C—H | 0 |
| 350 | -C(=O)-piperidinyl | C—H | 0 |
| 351 | H | C—F | 0 |
| 352 | Methyl | C—F | 0 |
| 353 | Ethyl | C—F | 0 |
| 354 | Propyl | C—F | 0 |
| 355 | Allyl | C—F | 0 |
| 356 | i-Propyl | C—F | 0 |
| 357 | -CH₂CH₂CH₂-OMe | C—F | 0 |
| 358 | i-Butyl | C—F | 0 |
| 359 | t-Butyl | C—F | 0 |

TABLE 2-continued

| compound | R³ | X³ | n |
|---|---|---|---|
| 360 | 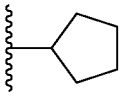 [SMILES: *C1CCCC1] cyclopentyl | C—F | 0 |
| 361 | 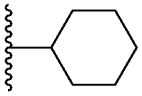 cyclohexyl | C—F | 0 |
| 362 | 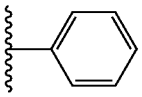 phenyl | C—F | 0 |
| 363 | 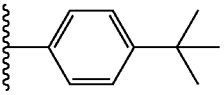 4-tert-butylphenyl | C—F | 0 |
| 364 | 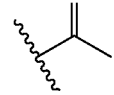 acetyl | C—F | 0 |
| 365 | 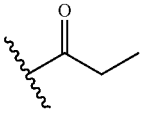 [SMILES: *C(=O)CC] propanoyl | C—F | 0 |
| 366 | 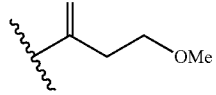 4-methoxy-3-oxobutyl | C—F | 0 |
| 367 | 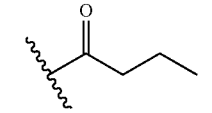 [SMILES: *C(=O)CCC] butanoyl | C—F | 0 |
| 368 | 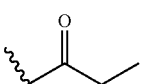 isobutyryl | C—F | 0 |
| 369 | 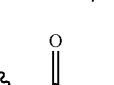 pivaloyl | C—F | 0 |
| 370 | 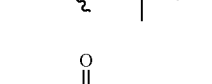 benzoyl | C—F | 0 |
| 371 | 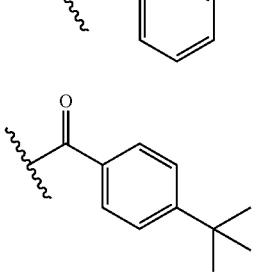 4-tert-butylbenzoyl | C—F | 0 |

TABLE 2-continued

| compound | R³ | X³ | n |
|---|---|---|---|
| 372 | 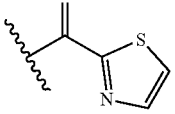 thiazole-2-carbonyl | C—F | 0 |
| 373 | 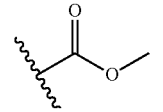 [SMILES: *C(=O)OC] methoxycarbonyl | C—F | 0 |
| 374 | 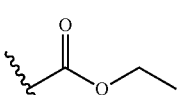 ethoxycarbonyl | C—F | 0 |
| 375 | 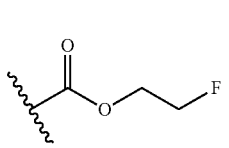 [SMILES: *C(=O)OCCF] 2-fluoroethoxycarbonyl | C—F | 0 |
| 376 | 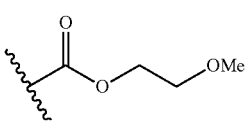 [SMILES: *C(=O)OCCOC] 2-methoxyethoxycarbonyl | C—F | 0 |
| 377 |  propoxycarbonyl | C—F | 0 |
| 378 |  allyloxycarbonyl | C—F | 0 |
| 379 | 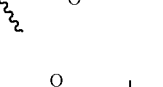 isopropoxycarbonyl | C—F | 0 |
| 380 | 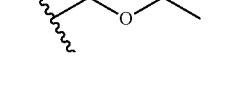 butoxycarbonyl | C—F | 0 |
| 381 | 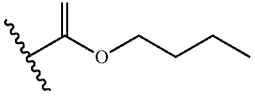 but-3-enyloxycarbonyl | C—F | 0 |
| 382 | 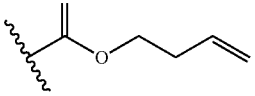 isobutoxycarbonyl | C—F | 0 |

TABLE 2-continued

| compound | R³ | X³ | n |
|---|---|---|---|
| 383 | -C(O)O-tBu | C—F | 0 |
| 384 | -C(O)O-cyclopentyl | C—F | 0 |
| 385 | -C(O)O-cyclohexyl | C—F | 0 |
| 386 | -C(O)O-CH₂-Ph | C—F | 0 |
| 387 | -C(O)NH-Et | C—F | 0 |
| 388 | -C(O)NH-CH₂CH₂-OMe | C—F | 0 |
| 389 | -C(O)NH-Pr | C—F | 0 |
| 390 | -C(O)NH-allyl | C—F | 0 |
| 391 | -C(O)NH-Bu | C—F | 0 |
| 392 | -C(O)NH-iPr | C—F | 0 |
| 393 | -C(O)NH-iBu | C—F | 0 |
| 394 | -C(O)NH-tBu | C—F | 0 |
| 395 | -C(O)NH-cyclopentyl | C—F | 0 |
| 396 | -C(O)NH-CH₂-Ph | C—F | 0 |
| 397 | -C(O)NH-Ph | C—F | 0 |
| 398 | -C(O)N(Me)₂ | C—F | 0 |
| 399 | -C(O)-pyrrolidinyl | C—F | 0 |
| 400 | -C(O)-piperidinyl | C—F | 0 |
| 401 | H | N | 0 |
| 402 | Methyl | N | 0 |
| 403 | Ethyl | N | 0 |
| 404 | Propyl | N | 0 |
| 405 | Allyl | N | 0 |
| 406 | i-Propyl | N | 0 |
| 407 | -CH₂CH₂CH₂-OMe | N | 0 |
| 408 | i-Butyl | N | 0 |
| 409 | t-Butyl | N | 0 |
| 410 | cyclopentyl | N | 0 |
| 411 | cyclohexyl | N | 0 |

TABLE 2-continued

| compound | R³ | X³ | n |
|---|---|---|---|
| 412 | phenyl | N | 0 |
| 413 | 4-tert-butylphenyl | N | 0 |
| 414 | C(O)CH₃ (acetyl) | N | 0 |
| 415 | C(O)CH₂CH₃ | N | 0 |
| 416 | C(O)CH₂CH₂OMe | N | 0 |
| 417 | C(O)CH₂CH₂CH₃ | N | 0 |
| 418 | C(O)CH(CH₃)₂ | N | 0 |
| 419 | C(O)C(CH₃)₃ | N | 0 |
| 420 | C(O)Ph | N | 0 |
| 421 | C(O)-(4-tert-butylphenyl) | N | 0 |
| 422 | C(O)-(thiazol-2-yl) | N | 0 |
| 423 | C(O)OMe | N | 0 |
| 424 | C(O)OEt | N | 0 |
| 425 | C(O)OCH₂CH₂F | N | 0 |
| 426 | C(O)OCH₂CH₂OMe | N | 0 |
| 427 | C(O)OCH₂CH₂CH₃ | N | 0 |
| 428 | C(O)OCH₂CH=CH₂ | N | 0 |
| 429 | C(O)OCH(CH₃)₂ | N | 0 |
| 430 | C(O)OCH₂CH₂CH₂CH₃ | N | 0 |
| 431 | C(O)OCH₂CH₂CH=CH₂ | N | 0 |
| 432 | C(O)OCH₂CH(CH₃)₂ | N | 0 |
| 433 | C(O)OC(CH₃)₃ | N | 0 |
| 434 | C(O)O-cyclopentyl | N | 0 |

TABLE 2-continued

| compound | R³ | X³ | n |
|---|---|---|---|
| 435 | (cyclohexyl ester) | N | 0 |
| 436 | (benzyl ester) | N | 0 |
| 437 | (N-ethyl amide) | N | 0 |
| 438 | (N-(2-methoxyethyl) amide) | N | 0 |
| 439 | (N-propyl amide) | N | 0 |
| 440 | (N-allyl amide) | N | 0 |
| 441 | (N-butyl amide) | N | 0 |
| 442 | (N-isopropyl amide) | N | 0 |
| 443 | (N-isobutyl amide) | N | 0 |
| 444 | (N-tert-butyl amide) | N | 0 |
| 445 | (N-cyclopentyl amide) | N | 0 |
| 446 | (N-benzyl amide) | N | 0 |
| 447 | (N-phenyl amide) | N | 0 |
| 448 | (N,N-dimethyl amide) | N | 0 |
| 449 | (pyrrolidinyl amide) | N | 0 |
| 450 | (piperidinyl amide) | N | 0 |
| 451 | H | C—H | 1 |
| 452 | Methyl | C—H | 1 |
| 453 | Ethyl | C—H | 1 |
| 454 | Propyl | C—H | 1 |
| 455 | Allyl | C—H | 1 |
| 456 | i-Propyl | C—H | 1 |
| 457 | (CH₂CH₂CH₂OMe) | C—H | 1 |
| 458 | i-Butyl | C—H | 1 |
| 459 | t-Butyl | C—H | 1 |
| 460 | cyclopentyl | C—H | 1 |
| 461 | cyclohexyl | C—H | 1 |
| 462 | phenyl | C—H | 1 |
| 463 | 4-tert-butylphenyl | C—H | 1 |

TABLE 2-continued

| compound | R³ | X³ | n |
|---|---|---|---|
| 464 | acetyl (C(=O)CH₃) | C—H | 1 |
| 465 | propanoyl (C(=O)CH₂CH₃) | C—H | 1 |
| 466 | C(=O)CH₂CH₂OMe | C—H | 1 |
| 467 | butanoyl (C(=O)CH₂CH₂CH₃) | C—H | 1 |
| 468 | isobutyryl (C(=O)CH(CH₃)₂) | C—H | 1 |
| 469 | pivaloyl (C(=O)C(CH₃)₃) | C—H | 1 |
| 470 | benzoyl (C(=O)Ph) | C—H | 1 |
| 471 | 4-tert-butylbenzoyl | C—H | 1 |
| 472 | thiazol-2-ylcarbonyl | C—H | 1 |
| 473 | C(=O)OMe | C—H | 1 |
| 474 | C(=O)OEt | C—H | 1 |
| 475 | C(=O)OCH₂CH₂F | C—H | 1 |
| 476 | C(=O)OCH₂CH₂OMe | C—H | 1 |
| 477 | C(=O)OPr | C—H | 1 |
| 478 | C(=O)OCH₂CH=CH₂ | C—H | 1 |
| 479 | C(=O)OiPr | C—H | 1 |
| 480 | C(=O)OBu | C—H | 1 |
| 481 | C(=O)OCH₂CH₂CH=CH₂ | C—H | 1 |
| 482 | C(=O)OiBu | C—H | 1 |
| 483 | C(=O)OtBu | C—H | 1 |
| 484 | C(=O)O-cyclopentyl | C—H | 1 |
| 485 | C(=O)O-cyclohexyl | C—H | 1 |

TABLE 2-continued
| compound | R³ | X³ | n |
|---|---|---|---|
| 486 | 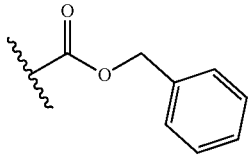 [SMILES: *C(=O)OCc1ccccc1] | C—H | 1 |
| 487 | 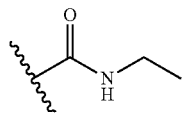 [SMILES: *C(=O)NCC] | C—H | 1 |
| 488 | 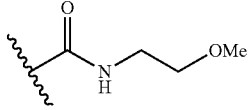 [SMILES: *C(=O)NCCOC] | C—H | 1 |
| 489 | 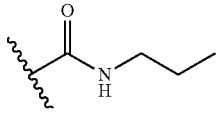 [SMILES: *C(=O)NCCC] | C—H | 1 |
| 490 | 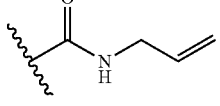 | C—H | 1 |
| 491 | 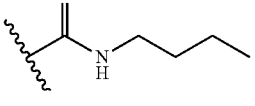 | C—H | 1 |
| 492 | 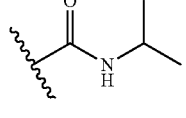 | C—H | 1 |
| 493 | 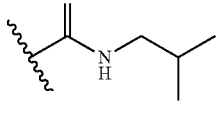 | C—H | 1 |
| 494 | 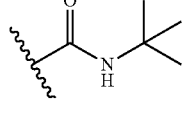 | C—H | 1 |
| 495 | 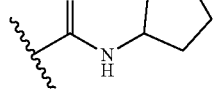 | C—H | 1 |
| 496 | 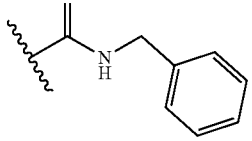 | C—H | 1 |
| 497 | 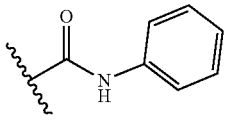 [SMILES: *C(=O)Nc1ccccc1] | C—H | 1 |
| 498 | 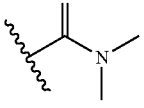 | C—H | 1 |
| 499 | 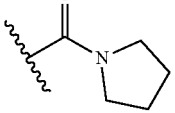 | C—H | 1 |
| 500 | 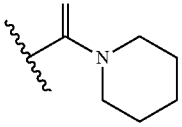 | C—H | 1 |
| 501 | H | C—F | 1 |
| 502 | Methyl | C—F | 1 |
| 503 | Ethyl | C—F | 1 |
| 504 | Propyl | C—F | 1 |
| 505 | Allyl | C—F | 1 |
| 506 | i-Propyl | C—F | 1 |
| 507 | 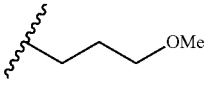 | C—F | 1 |
| 508 | i-Butyl | C—F | 1 |
| 509 | t-Butyl | C—F | 1 |
| 510 | 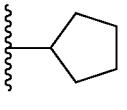 [SMILES: *C1CCCC1] | C—F | 1 |
| 511 | 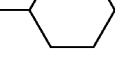 | C—F | 1 |
| 512 | 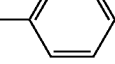 | C—F | 1 |
| 513 | 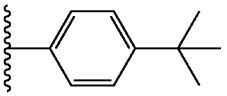 [SMILES: *c1ccc(C(C)(C)C)cc1] | C—F | 1 |
| 514 | 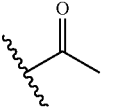 [SMILES: *C(C)=O] | C—F | 1 |
| 515 | 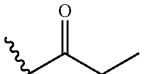 | C—F | 1 |

TABLE 2-continued

| compound | R³ | X³ | n |
|---|---|---|---|
| 516 | -C(O)CH₂CH₂OMe | C—F | 1 |
| 517 | -C(O)CH₂CH₂CH₃ | C—F | 1 |
| 518 | -C(O)CH(CH₃)₂ | C—F | 1 |
| 519 | -C(O)C(CH₃)₃ | C—F | 1 |
| 520 | -C(O)Ph | C—F | 1 |
| 521 | -C(O)-(4-tBu-C₆H₄) | C—F | 1 |
| 522 | -C(O)-(thiazol-2-yl) | C—F | 1 |
| 523 | -C(O)OMe | C—F | 1 |
| 524 | -C(O)OEt | C—F | 1 |
| 525 | -C(O)OCH₂CH₂F | C—F | 1 |
| 526 | -C(O)OCH₂CH₂OMe | C—F | 1 |
| 527 | -C(O)OCH₂CH₂CH₃ | C—F | 1 |
| 528 | -C(O)OCH₂CH=CH₂ | C—F | 1 |
| 529 | -C(O)OCH(CH₃)₂ | C—F | 1 |
| 530 | -C(O)OCH₂CH₂CH₂CH₃ | C—F | 1 |
| 531 | -C(O)OCH₂CH₂CH=CH₂ | C—F | 1 |
| 532 | -C(O)OCH₂CH(CH₃)₂ | C—F | 1 |
| 533 | -C(O)OC(CH₃)₃ | C—F | 1 |
| 534 | -C(O)O-cyclopentyl | C—F | 1 |
| 535 | -C(O)O-cyclohexyl | C—F | 1 |
| 536 | -C(O)OCH₂Ph | C—F | 1 |
| 537 | -C(O)NHEt | C—F | 1 |

TABLE 2-continued

| compound | R³ | X³ | n |
|---|---|---|---|
| 538 | -C(O)NH-CH₂CH₂-OMe | C—F | 1 |
| 539 | -C(O)NH-propyl | C—F | 1 |
| 540 | -C(O)NH-allyl | C—F | 1 |
| 541 | -C(O)NH-butyl | C—F | 1 |
| 542 | -C(O)NH-iPr | C—F | 1 |
| 543 | -C(O)NH-iBu | C—F | 1 |
| 544 | -C(O)NH-tBu | C—F | 1 |
| 545 | -C(O)NH-cyclopentyl | C—F | 1 |
| 546 | -C(O)NH-CH₂Ph | C—F | 1 |
| 547 | -C(O)NH-Ph | C—F | 1 |
| 548 | -C(O)N(Me)₂ | C—F | 1 |

TABLE 2-continued

| compound | R³ | X³ | n |
|---|---|---|---|
| 549 | -C(O)-pyrrolidinyl | C—F | 1 |
| 550 | -C(O)-piperidinyl | C—F | 1 |
| 551 | H | N | 1 |
| 552 | Methyl | N | 1 |
| 553 | Ethyl | N | 1 |
| 554 | Propyl | N | 1 |
| 555 | Allyl | N | 1 |
| 556 | i-Propyl | N | 1 |
| 557 | -(CH₂)₃-OMe | N | 1 |
| 558 | i-Butyl | N | 1 |
| 559 | t-Butyl | N | 1 |
| 560 | cyclopentyl | N | 1 |
| 561 | cyclohexyl | N | 1 |
| 562 | phenyl | N | 1 |
| 563 | 4-t-butylphenyl | N | 1 |
| 564 | -C(O)CH₃ | N | 1 |
| 565 | -C(O)CH₂CH₃ | N | 1 |
| 566 | -C(O)CH₂CH₂OMe | N | 1 |
| 567 | -C(O)CH₂CH₂CH₃ | N | 1 |

TABLE 2-continued

| compound | R³ | X³ | n |
|---|---|---|---|
| 568 | isopropyl ketone | N | 1 |
| 569 | tert-butyl ketone | N | 1 |
| 570 | phenyl ketone | N | 1 |
| 571 | 4-tert-butylphenyl ketone | N | 1 |
| 572 | thiazol-2-yl ketone | N | 1 |
| 573 | methyl ester | N | 1 |
| 574 | ethyl ester | N | 1 |
| 575 | 2-fluoroethyl ester | N | 1 |
| 576 | 2-methoxyethyl ester | N | 1 |
| 577 | propyl ester | N | 1 |
| 578 | allyl ester | N | 1 |
| 579 | isopropyl ester | N | 1 |
| 580 | butyl ester | N | 1 |
| 581 | but-3-enyl ester | N | 1 |
| 582 | isobutyl ester | N | 1 |
| 583 | tert-butyl ester | N | 1 |
| 584 | cyclopentyl ester | N | 1 |
| 585 | cyclohexyl ester | N | 1 |
| 586 | benzyl ester | N | 1 |
| 587 | N-ethyl amide | N | 1 |
| 588 | N-(2-methoxyethyl) amide | N | 1 |
| 589 | N-propyl amide | N | 1 |

TABLE 2-continued

| compound | R³ | X³ | n |
|---|---|---|---|
| 590 | -C(O)NH-allyl | N | 1 |
| 591 | -C(O)NH-butyl | N | 1 |
| 592 | -C(O)NH-iPr | N | 1 |
| 593 | -C(O)NH-iBu | N | 1 |
| 594 | -C(O)NH-tBu | N | 1 |
| 595 | -C(O)NH-cyclopentyl | N | 1 |
| 596 | -C(O)NH-benzyl | N | 1 |
| 597 | -C(O)NH-phenyl | N | 1 |
| 598 | -C(O)N(CH₃)₂ | N | 1 |
| 599 | -C(O)-pyrrolidinyl | N | 1 |
| 600 | -C(O)-piperidinyl | N | 1 |

In another embodiment of the invention, the compound of Formula I is represented by Formula XII-a, Formula XII-b, or a pharmaceutically acceptable salt or ester thereof:

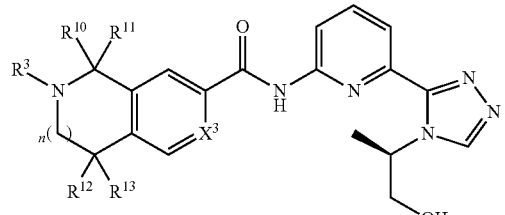

(XII-a)

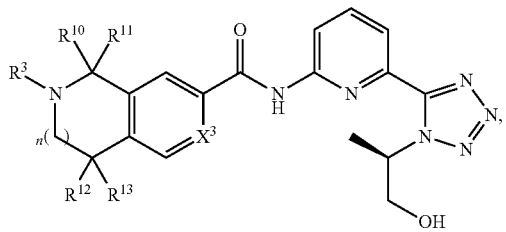

(XII-b)

wherein $R^3$, $R^{10}$, $R^{11}$, $R^{12}$, $R^{13}$, $X^3$ and n are as previously defined.

In another embodiment of the invention, the compound of Formula I is represented by Formula XIII-a, Formula XIII-b, or a pharmaceutically acceptable salt or ester thereof:

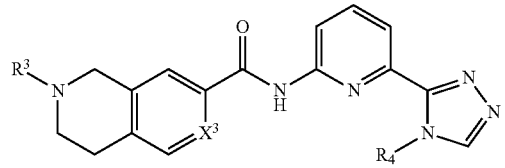

(XIII-a)

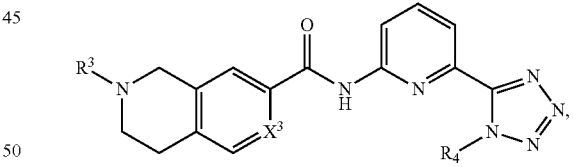

(XIII-b)

wherein $R^3$, $R^4$, and $X^3$ are as previously defined.

In another embodiment of the invention, the compound of Formula I is represented by Formula XIV-a, Formula XIV-b, or a pharmaceutically acceptable salt or ester thereof:

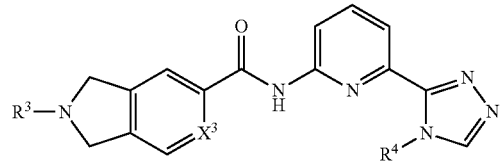

(XIV-a)

-continued (XIV-b)

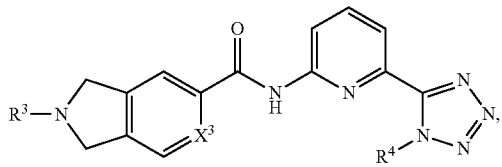

wherein $R^3$, $R^4$, and $X^3$ are as previously defined.

In another embodiment of the invention, the compound of Formula I is represented by Formula XV-a, Formula XV-b, or a pharmaceutically acceptable salt or ester thereof:

(XV-a)

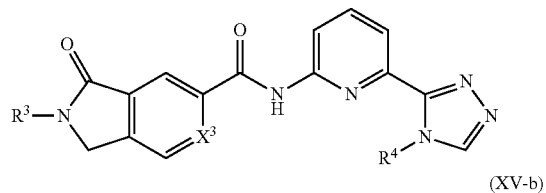

(XV-b)

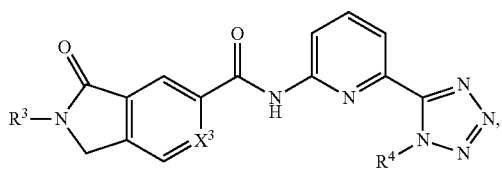

wherein $R^3$, $R^4$, and $X^3$ are as previously defined.

In certain embodiments, the present invention provides a method for the treatment of an ASK-1 mediated disease or condition. The method comprises administering a therapeutically effective amount of a compound of Formula (I). The present invention also provides the use of a compound of Formula (I) for the preparation of a medicament for the treatment of an ASK-1 mediated disease or condition.

In certain embodiments, the ASK-1 mediated disease or condition is an autoimmune disorder, a neurodegenerative disorder, an inflammatory disease, chronic kidney disease, renal disease, cardiovascular disease, a metabolic disease, or an acute or chronic liver disease.

In certain embodiments, the chronic liver disease is primary biliary cirrhosis (PBC), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, or alpha 1-antitrypsin deficiency. In certain embodiments, the gastrointestinal disease is inflammatory bowel disease (IBD) (including Crohn's disease and ulcerative colitis), irritable bowel syndrome (IBS), bacterial overgrowth, malabsorption, post-radiation colitis, or microscopic colitis.

In certain embodiments, the renal disease is diabetic nephropathy, focal segmental glomerulosclerosis (FSGS), hypertensive nephrosclerosis, chronic glomerulonephritis, chronic transplant glomerulopathy, chronic interstitial nephritis, or polycystic kidney disease.

In certain embodiments, the cardiovascular disease is atherosclerosis, arteriosclerosis, reperfusion/ischemia in stroke, cardiac hypertrophy, respiratory diseases, heart attacks, myocardial ischemia.

In certain embodiments, the metabolic disease is insulin resistance, Type I and Type II diabetes, or obesity.

In certain embodiments, the chronic kidney disease is polycystic kidney disease, pyelonephritis, kidney fibrosis and glomerulonephritis.

Yet a further aspect of the present invention is a process of making any of the compounds delineated herein employing any of the synthetic means delineated herein.

Definitions

Listed below are definitions of various terms used to describe this invention. These definitions apply to the terms as they are used throughout this specification and claims, unless otherwise limited in specific instances, either individually or as part of a larger group.

The term "alkyl" as used herein, refers to saturated, straight- or branched-chain hydrocarbon radicals. "$C_1$-$C_3$ alkyl," "$C_1$-$C_6$ alkyl," "$C_1$-$C_{10}$ alkyl" "$C_2$-$C_4$ alkyl," or "$C_3$-$C_6$ alkyl," refer to alkyl groups containing from one to three, one to six, one to ten carbon atoms, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_{10}$ alkenyl," "$C_2$-$C_8$ alkenyl," "$C_2$-$C_4$ alkenyl," or "$C_3$-$C_6$ alkenyl," refer to alkenyl groups containing from two to ten, two to eight, two to four or three to six carbon atoms respectively. Alkenyl groups include, but are not limited to, for example, ethenyl, propenyl, butenyl, 1-methyl-2-buten-1-yl, heptenyl, octenyl, and the like.

The term "alkynyl" as used herein, refers to straight- or branched-chain hydrocarbon radicals having at least one carbon-carbon triple bond by the removal of a single hydrogen atom. "$C_2$-$C_{10}$ alkynyl," "$C_2$-$C_8$ alkynyl," "$C_2$-$C_4$ alkynyl," or "$C_3$-$C_6$ alkynyl," refer to alkynyl groups containing from two to ten, two to eight, two to four or three to six carbon atoms respectively. Representative alkynyl groups include, but are not limited to, for example, ethynyl, 1-propynyl, 1-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic, iminic or oximic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic, iminic or oximic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-1-enyl, bicyclo[4.2.1]non-3-en-9-yl, and the like.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted. The term "bicyclic aryl" or "bicyclic heteroaryl" refers to a ring system consisting of two rings wherein at least one ring is aromatic; and the two rings can be fused or covalently attached.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted.

The term "alkylene" as used herein, refers to a diradical of a branched or unbranched saturated hydrocarbon chain, typically having from 1 to 20 carbon atoms (e.g. 1-10 carbon atoms, or 1, 2, 3, 4, 5, or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like.

The term "substituted" as used herein, refers to independent replacement of one, two, or three or more of the hydrogen atoms thereon with substituents including, but not limited to, deuterium, —F, —Cl, —Br, —I, —OH, protected hydroxy, —$NO_2$, —CN, —$NH_2$, $N_3$, protected amino, alkoxy, thioalkoxy, oxo, $C_1$-$C_{12}$-alkyl, $C_2$-$C_{12}$-alkenyl, $C_2$-$C_{12}$-alkynyl, -halo-$C_1$-$C_{12}$-alkyl, -halo-$C_2$-$C_{12}$-alkenyl, -halo-$C_2$-$C_{12}$-alkynyl, -halo-$C_3$-$C_{12}$-cycloalkyl, —NH—$C_1$-$C_{12}$-alkyl, —NH—$C_2$-$C_{12}$-alkenyl, —NH—$C_2$-$C_{12}$-alkynyl, —NH—$C_3$-$C_{12}$-cycloalkyl, —NH-aryl, —NH-heteroaryl, —NH -heterocycloalkyl, -dialkylamino, -diarylamino, -diheteroarylamino, —O—$C_1$-$C_{12}$-alkyl, —O—$C_2$-$C_{12}$-alkenyl, —O—$C_2$-$C_{12}$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_{12}$-alkenyl, —C(O)—$C_2$-$C_{12}$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_{12}$-alkenyl, —CONH—$C_2$-$C_{12}$-alkynyl, —CONH—$C_3$-$C_{12}$-cycloalkyl, —CONH-aryl, —CONH— heteroaryl, —CONH-heterocycloalkyl, —$OCO_2$—$C_1$-$C_{12}$-alkyl, —$OCO_2$—$C_2$-$C_{12}$-alkenyl, —$OCO_2$—$C_2$-$C_{12}$-alkynyl, —$OCO_2$—$C_3$-$C_{12}$-cycloalkyl, —$OCO_2$-aryl, —$OCO_2$-heteroaryl, —$OCO_2$-heterocycloalkyl, —$OCONH_2$, —OCONH—$C_1$-$C_{12}$-alkyl, —OCONH—$C_2$-$C_{12}$-alkenyl, —OCONH—$C_2$-$C_{12}$-alkynyl, —OCONH—$C_3$-$C_{12}$-cycloalkyl, —OCONH-aryl, —OCONH— heteroaryl, —OCONH— heterocycloalkyl, —NHC(O)—$C_1$-$C_{12}$-alkyl, —NHC(O)—$C_2$-$C_{12}$-alkenyl, —NHC(O)—$C_2$-$C_{12}$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_{12}$-alkenyl, —$NHCO_2$—$C_2$-$C_{12}$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_{12}$-alkenyl, —NHC(O)NH—$C_2$-$C_{12}$-alkynyl, —NHC(O)NH—$C_3$-$C_{12}$-cycloalkyl, —NHC(O) NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_{12}$-alkenyl, —NHC(S)NH—$C_2$-$C_{12}$-alkynyl, —NHC(S)NH—$C_3$-$C_{12}$-cycloalkyl, —NHC(S) NH-aryl, —NHC(S)NH-heteroaryl, —NHC(S)NH-heterocycloalkyl, —NHC(NH)$NH_2$, —NHC(NH)NH—$C_1$-$C_{12}$-alkyl, —NHC(NH)NH—$C_2$-$C_{12}$-alkenyl, —NHC(NH) NH—$C_2$-$C_{12}$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_{12}$-alkenyl, —NHC(NH)—$C_2$-$C_{12}$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_{12}$-alkenyl, —C(NH)NH—$C_2$-$C_{12}$-alkynyl, —C(NH)NH—$C_3$-$C_{12}$-cycloalkyl, —C(NH) NH-aryl, —C(NH)NH-heteroaryl, —C(NH)NH-heterocycloalkyl, —S(O)—$C_1$-$C_{12}$-alkyl, —S(O)—$C_2$-$C_{12}$-alkenyl, —S(O)—$C_2$-$C_{12}$-alkynyl, —S(O)—$C_3$-$C_{12}$-cycloalkyl, —S(O)-aryl, —S(O)-heteroaryl, —S(O)-heterocycloalkyl-$SO_2NH_2$, —$SO_2NH$—$C_1$-$C_{12}$-alkyl, —$SO_2NH$—$C_2$-$C_{12}$-alkenyl, —$SO_2NH$—$C_2$-$C_{12}$-alkynyl, —$SO_2NH$—$C_3$-$C_{12}$-cycloalkyl, —$SO_2NH$-aryl, —$SO_2NH$— heteroaryl, —$SO_2NH$— heterocycloalkyl, —$NHSO_2$—$C_1$-$C_{12}$-alkyl, —$NHSO_2$—$C_2$-$C_{12}$-alkenyl, —$NHSO_2$—$C_2$-$C_{12}$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_3$-$C_{12}$-alkyl, —S—$C_2$-$C_{12}$-alkenyl, —S—$C_2$-$C_{12}$-alkynyl, —S—$C_3$-$C_{12}$-cycloalkyl, —S-aryl, —S-heteroaryl, —S-heterocycloalkyl, methylthiomethyl, or -L'-R', wherein L' is $C_1$-$C_6$alkylene, $C_2$-$C_6$alkenylene or $C_2$-$C_6$alkynylene, and R' is aryl, heteroaryl, heterocyclic, $C_3$-$C_{12}$cycloalkyl or $C_3$-$C_{12}$cycloalkenyl. It is understood that the aryls, heteroaryls, alkyls, and the like can be further substituted. In some cases, each substituent in a substituted moiety is additionally optionally substituted with one or more groups, each group being independently selected from $C_1$-$C_6$-alkyl, —F, —Cl, —Br, —I, —OH, —$NO_2$, —CN, or —$NH_2$.

In accordance with the invention, any of the aryls, substituted aryls, heteroaryls and substituted heteroaryls described herein, can be any aromatic group. Aromatic groups can be substituted or unsubstituted.

It is understood that any alkyl, alkenyl, alkynyl, cycloalkyl and cycloalkenyl moiety described herein can also be an aliphatic group, an alicyclic group or a heterocyclic group. An "aliphatic group" is non-aromatic moiety that may contain any combination of carbon atoms, hydrogen atoms, halogen atoms, oxygen, nitrogen or other atoms, and optionally contain one or more units of unsaturation, e.g., double and/or triple bonds. An aliphatic group may be straight chained, branched or cyclic and preferably contains between about 1 and about 24 carbon atoms, more typically between about 1 and about 12 carbon atoms. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may be used in place of the alkyl, alkenyl, alkynyl, alkylene, alkenylene, and alkynylene groups described herein.

The term "alicyclic" as used herein, denotes a monovalent group derived from a monocyclic or polycyclic saturated carbocyclic ring compound by the removal of a single hydrogen atom. Examples include, but are not limited to, cyclopropyl, cyclobutyl, cyclopentyl, cyclohexyl, bicyclo[2.2.1]heptyl, and bicyclo[2.2.2]octyl. Such alicyclic groups may be further substituted.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 1-propoxy, 2-propoxy (isopropoxy) and the higher homologs and isomers. Preferred alkoxy are ($C_1$-$C_3$) alkoxy.

The term "aryloxy" refers to the group aryl-O— wherein the aryl group is as defined above, and includes optionally substituted aryl groups as also defined above. The term "arylthio" refers to the group R—S—, where R is as defined for aryl.

The terms "heterocyclic" or "heterocycloalkyl" can be used interchangeably and refer to a non-aromatic ring or a bi- or tri-cyclic group fused, bridged or spiro system, where (i) the ring system contains at least one heteroatom independently selected from oxygen, sulfur and nitrogen, (ii) the ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic, iminic or oximic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 1-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, cycloalkyl, heterocyclic and cycloalkenyl moiety described herein can also be an aliphatic group or an alicyclic group.

It will be apparent that in various embodiments of the invention, the substituted or unsubstituted alkyl, alkenyl, alkynyl, cycloalkyl, cycloalkenyl, cycloalkynyl, arylalkyl, heteroarylalkyl, and heterocycloalkyl are intended to be monovalent or divalent. Thus, alkylene, alkenylene, and alkynylene, cycloaklylene, cycloalkenylene, cycloalkynylene, arylalkylene, heteroarylalkylene and heterocycloalkylene groups are to be included in the above definitions, and are applicable to provide the Formulas herein with proper valency.

The terms "halo" and "halogen," as used herein, refer to an atom selected from fluorine, chlorine, bromine and iodine.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

In certain embodiments, the compounds of each formula herein are defined to include isotopically labelled compounds. An "isotopically labelled compound" is a compound in which at least one atomic position is enriched in a specific isotope of the designated element to a level which is significantly greater than the natural abundance of that isotope. For example, one or more hydrogen atom positions in a compound can be enriched with deuterium to a level which is significantly greater than the natural abundance of deuterium, for example, enrichment to a level of at least 1%, preferably at least 20% or at least 50%. Such a deuterated compound may, for example, be metabolized more slowly than its non-deuterated analog, and therefore exhibit a longer half-life when administered to a subject. Such compounds can synthesize using methods known in the art, for example by employing deuterated starting materials. Unless stated to the contrary, isotopically labelled compounds are pharmaceutically acceptable.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)-for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

The term "subject" as used herein refers to a mammal. A subject therefore refers to, for example, dogs, cats, horses, cows, pigs, guinea pigs, and the like. Preferably the subject is a human. When the subject is a human, the subject may be referred to herein as a patient.

As used herein, the term "pharmaceutically acceptable salt" refers to those salts of the compounds formed by the process of the present invention which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art.

Berge, et al. describes pharmaceutically acceptable salts in detail in J. Pharmaceutical Sciences, 66: 1-19 (1977). The salts can be prepared in situ during the final isolation and purification of the compounds of the invention, or separately by reaction of the free base function with a suitable organic acid. Examples of pharmaceutically acceptable salts include, but are not limited to, nontoxic acid addition salts e.g., salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, esters of $C_1$-$C_6$-alkanoic acids, such as acetate, propionate, butyrate and pivalate esters.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, *Prodrugs, Topical and Ocular Drug Delivery,* (Drugs and the Pharmaceutical Sciences; Volume 53), Marcel Dekker, Inc., New York (1992) and in "Prodrugs of Alcohols and Phenols" by S. S. Dhareshwar and V. J. Stella, in *Prodrugs Challenges and Rewards* Part-2, (Biotechnology: Pharmaceutical Aspects), edited by V. J. Stella, et al, Springer and AAPSPress, 2007, pp 31-99.

The term "amino" as used herein, refers to the group —NH$_2$.

The term "substituted amino" as used herein, refers to the group —NRR where each R is independently selected from the group consisting of hydrogen, alkyl, cycloalkyl, aryl, heteroaryl and heterocycloalkyl provided that both R groups are not hydrogen, or a group —Y—Z, in which Y is optionally substituted alkylene and Z is alkenyl, cycloalkenyl, or alkynyl.

The term "amino protecting group" as used herein, refers to a labile chemical moiety which is known in the art to protect an amino group against undesired reactions during synthetic procedures. After said synthetic procedure(s) the amino protecting group as described herein may be selectively removed. Amino protecting groups as known in the are described generally in T. H. Greene and P. G. M. Wuts, *Protective Groups in Organic Synthesis,* 3rd edition, John Wiley & Sons, New York (1999). Examples of amino protecting groups include, but are not limited to, t-butoxycarbonyl, 9-fluorenylmethoxycarbonyl, benzyloxycarbonyl, and the like.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

As used herein, the term "pharmaceutically acceptable ester" refers to esters of the compounds formed by the process of the present invention which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrugs" as used herein refers to those prodrugs of the compounds formed by the process of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention. "Prodrug", as used herein means a compound, which is convertible in vivo by metabolic means (e.g. by hydrolysis) to afford any compound delineated by the Formulae of the instant invention. Various forms of prodrugs are known in the art, for example, as discussed in Bundgaard, (ed.), *Design of Prodrugs*, Elsevier (1985); Widder, et al. (ed.), *Methods in Enzymology*, Vol. 4, Academic Press (1985); Krogsgaard-Larsen, et al., (ed). "Design and Application of Prodrugs, *Textbook of Drug Design and Development*, Chapter 5, 113-191 (1991); Bundgaard, et al., *Journal of Drug Deliver Reviews*, 8:1-38(1992); Bundgaard, *J. of Pharmaceutical Sciences*, 77:285 et seq. (1988); Higuchi and Stella (eds.) Prodrugs as Novel Drug Delivery Systems, *American Chemical Society* (1975); and Bernard Testa & Joachim Mayer, "Hydrolysis In Drug And Prodrug Metabolism: Chemistry, Biochemistry And Enzymology," John Wiley and Sons, Ltd. (2002).

The term "treating", as used herein, means relieving, lessening, reducing, eliminating, modulating, or ameliorating, i.e. causing regression of the disease state or condition. Treating can also include inhibiting, i.e. arresting the development, of an existing disease state or condition, and relieving or ameliorating, i.e. causing regression of an existing disease state or condition, for example when the disease state or condition may already be present.

The term "preventing", as used herein means, to completely or almost completely stop a disease state or condition, from occurring in a patient or subject, especially when the patient or subject is predisposed to such or at risk of contracting a disease state or condition.

Additionally, the compounds of the present invention, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

"Solvates" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

As used herein, the term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar to or comparable in function and appearance to the reference compound.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

The terms "protogenic organic solvent" or "protic solvent" as used herein, refer to a solvent that tends to provide protons, such as an alcohol, for example, methanol, ethanol, propanol, isopropanol, butanol, t-butanol, and the like. Such solvents are well known to those skilled in the art, and individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. Additionally, the various synthetic steps may be performed in an alternate sequence or order to give the desired compounds. In addition, the solvents, temperatures, reaction durations, etc. delineated herein are for purposes of illustration only and variation of the reaction conditions can produce the desired isoxazole products of the present invention. Synthetic chemistry transformations and protecting group methodologies (protection and deprotection) useful in synthesizing the compounds described herein include, for example, those described in R. Larock, *Comprehensive Organic Transformations*, VCH Publishers (1989); T. W. Greene and P. G. M. Wuts, *Protective Groups in Organic Synthesis,* 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending various functionalities via synthetic means delineated herein to enhance selective biological properties. Such modifications include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of the present invention Formulated together with one or more pharmaceutically acceptable carriers. As used herein, the term "pharmaceutically acceptable carrier" means a non-toxic, inert solid, semi-solid or liquid filler, diluent, encapsulating material or Formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the Formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the Formulation may be adjusted with pharmaceutically acceptable acids, bases or buffers to enhance the stability of the Formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1, 3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable Formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable Formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical Formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic Formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Unless otherwise defined, all technical and scientific terms used herein are accorded the meaning commonly known to one with ordinary skill in the art. All publications, patents, published patent applications, and other references mentioned herein are hereby incorporated by reference in their entirety.

Abbreviations

Abbreviations which have been used in the descriptions of the schemes and the examples that follow are:
Alloc for allyloxycarbonyl;
Alloc-Cl for allyl chloroformate;
ASK1 for apoptosis signal-regulating kinase 1;
ATP for adenosine triphosphate;
Boc for tert-butyloxycarbonyl;
BOP—Cl for bis(2-oxo-3-oxazolidinyl)phosphinic chloride;
Cbz for benzyloxycarbonyl;
Cbz-Cl for benzyl chloroformate;
CDI for carbonyldiimidazole;
$(COCl)_2$ for oxalyl chloride;
DBU for 1,8-diazabicycloundec-7-ene;
DCC for N,N-dicyclohexylcarbodiimide;
1,2-DCE for 1,2-dichloroethane;
DCM for dichloromethane;
DIPEA or Hunig's base or i-Pr2NEt for N,N-diisopropylethylamine;
DMAc for N,N-dimethylacetamide;
DMAP for N,N-dimethylaminopyridine;
DMF for N,N-dimethyl formamide;
EDC for 1-(3-diethylaminopropyl)-3-ethylcarbodiimide hydrochloride;
EGTA for ethylene glycol-bis(2-aminoethylether)-N,N,N',N'-tetraacetic acid;
ESI for electrospray ionization;
$Et_3N$ or TEA for triethylamine;
$Et_2O$ for diethylether;
EtOAc for ethyl acetate;
Ghosez's Reagent for 1-chloro-N,N,2-trimethyl-1-propenylamine;
HATU for 1-[bis(dimethylamino)methylene]-1H-1,2,3-triazolo[4,5-b]pyridinium 3-oxid hexafluorophosphate;
HEPES for 4-(2-Hydroxyethyl)piperazine-1-ethanesulfonic acid, N-(2-Hydroxyethyl)piperazine-N'-(2-ethanesulfonic acid);
$IC_{50}$ for half maximal inhibitory concentration;
KOt-Bu for potassium tert-butoxide;
LCMS for liquid chromatography-mass spectrometry;
MeCN for acetonitrile;
MTBE for methyl tert-butyl ether;
m/z for mass-to-charge ratio;
NaOt-Bu for sodium tert-butoxide;
NMP for 1-methyl-2-pyrrolidinone;
NMR for nuclear magnetic resonance spectroscopy;
OMs or mesylate for methanesulfonate;
OTf or triflate for trifluoromethanesulfonate;
OTs or tosylate for para-toluenesulfonate;
$Pd_2(dba)_3$ for tris(dibenzylideneacetone)dipalladium(0);
P(o-tolyl)$_3$ for tri(o-tolyl)phosphine;
PyAOP for 7-azabenzotriazol-1-yloxy)tripyrrolidinophosphonium hexafluorophosphate;
PyBOP for benzotriazol-1-yl-oxytripyrrolidinophosphonium hexafluorophosphate;
STK3 for serine/threonine-protein kinase 3
TEA for triethylamine;
THF for tetrahydrofuran.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

As shown in Scheme 1, compounds of Formula (Ie) are prepared from the compound of Formula (1-1) wherein $X^3$ is as previously defined. Thus, the compound of Formula (1-1) is reacted with Cbz-Cl to afford a compound of Formula (1-2) using a suitable base such as, but not limited to, $Et_3N$, DIPEA, DMAP, or pyridine. The reaction solvent can be, but is not limited to, THF or DCM. The reaction temperature is from −20° C. to 40° C. The compound of Formula (1-2) is hydrolyzed to afford a compound of Formula (1-3) using a suitable hydroxide source such as, but not limited to, NaOH or LiOH. The compound of Formula (1-3) is reacted with a suitable chlorinating reagent such as, but not limited to, oxalyl chloride in combination with a catalytic quantity of DMF, thionyl chloride, or Ghosez's reagent to afford a compound of Formula (1-4). The reaction solvent can be, but is not limited to, THF or DCM. The reaction temperature is from −20° C. to 40° C. For the preparation of compounds of Formula (1-5), see US 2014/0018370. The compound of Formula (1-4) is reacted with a compound of Formula (1-5), wherein $X^1$, $X^2$, $R^1$ and $R^2$ are as previously defined, to afford a compound of Formula (1-6) using a suitable base such as, but not limited to, $Et_3N$, DMAP, pyridine, or DIPEA. The reaction solvent can be, but is not limited to, THF, DCM, pyridine and toluene. The reaction temperature is from −20° C. to 40° C. Alternatively, the compound of Formula (1-3) is reacted with a compound of Formula (1-5) to afford a compound of Formula (1-6) using a suitable coupling reagent such as, but not limited to, BOP—Cl, CDI, DCC, EDC, HATU, PyAOP or PyBOP in the presence of a suitable base such as, but not limited to, $Et_3N$ or DIPEA. The reaction solvent can be, but is not limited to, THF, DCM and DMF. The reaction temperature is from −20° C. to 40° C. The compound of Formula (1-6) is reacted with palladium on carbon in the presence of hydrogen gas to afford a compound of Formula (1-7). The reaction solvent can be, but is not limited to, MeOH, EtOH, EtOAc, and THF. Compounds of Formula (1-7) are reacted with a suitable combination of reagents to afford compounds of Formula (Ie). The reagent combinations may be, but are not limited to:
1) An aldehyde in combination with a suitable reducing agent, such as, but not limited to, $NaBH_4$, $NaBH(OAc)_3$, or $NaBH_3CN$. The reaction solvent can be, but is not limited to, DCM, 1,2-DCE, or THF.
2) A ketone in combination with a suitable reducing agent, such as, but not limited to, $NaBH_4$, $NaBH(OAc)_3$, or $NaBH_3CN$. The reaction solvent can be, but is not limited to, DCM, 1,2-DCE, or THF.
3) An alkyl halide, alkyl mesylate, or alkyl tosylate in combination with a suitable base such as, but not limited to, NaH, NaOt-Bu, KOt-Bu, $Et_3N$, or DIPEA. The reaction solvent can be, but is not limited to, DCM or THF.
4) An aryl-, heteroaryl-, or alkenyl-halide, or an aryl- or heteroaryl-, or alkenyl-triflate in combination with a suitable base, palladium(0) catalyst, ligand, and solvent. The base can be, but is not limited to, NaOt-Bu or KOt-Bu. The palladium(0) catalyst can be, but is not limited to, $Pd(PPh_3)_4$ or $Pd_2(dba)_3$. The ligand can be, but is not limited to, $P(o\text{-tolyl})_3$ or (2-biphenyl)di-tert-butylphosphine. The solvent can be, but is not limited to, toluene or THF.
5) An acyl chloride in the presence of a suitable base such as, but not limited to, $Et_3N$, DIPEA, or DMAP. The reaction solvent can be, but is not limited to, DCM or THF.
6) A chloroformate in the presence of a suitable base such as, but not limited to, $Et_3N$, DIPEA, or DMAP. The reaction solvent can be, but is not limited to, DCM or THF.
7) A sulfonyl chloride in the presence of a suitable base such as, but not limited to, $Et_3N$, DIPEA, or DMAP. The reaction solvent can be, but is not limited to, DCM or THF.
8) An isocyanate in the presence of a suitable base such as, but not limited to, $Et_3N$, DIPEA, or DMAP. The reaction solvent can be, but is not limited to, DCM or THF.
9) A primary or secondary amine in the presence of a suitable activating reagent such as, but not limited to, phosgene, triphosgene, or CDI. The reaction solvent can be, but is not limited to, DCM or THF.

Scheme 1

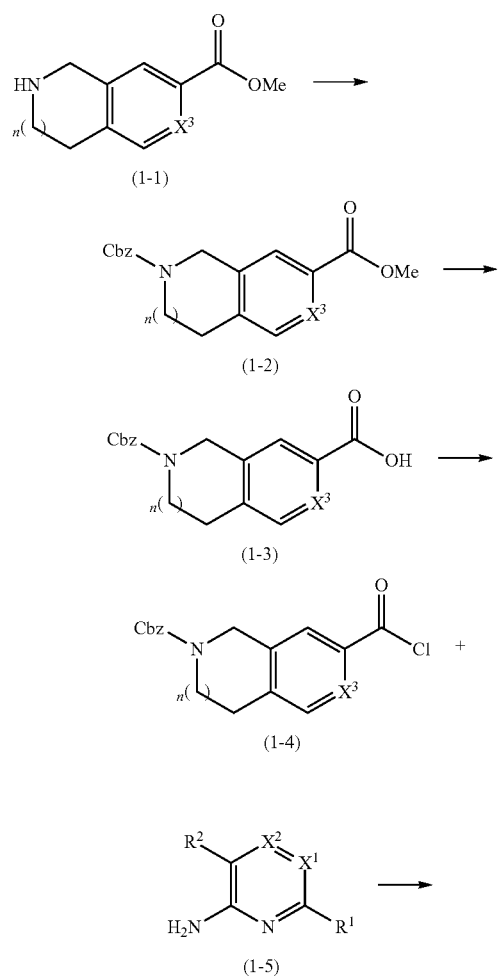

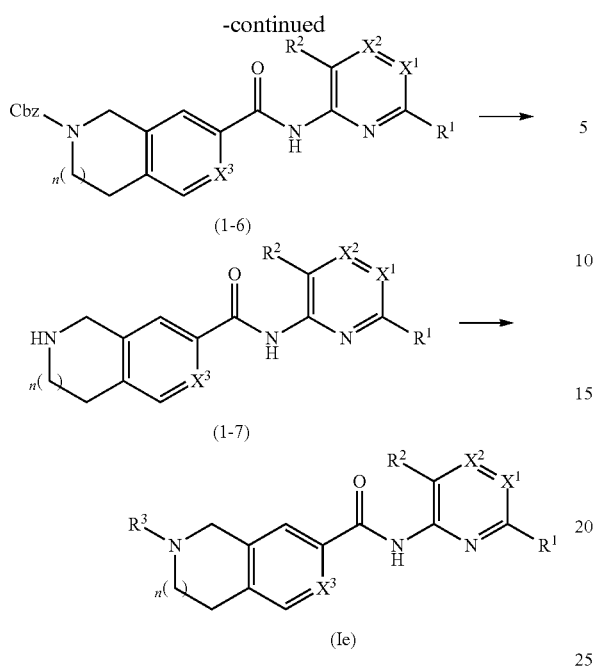

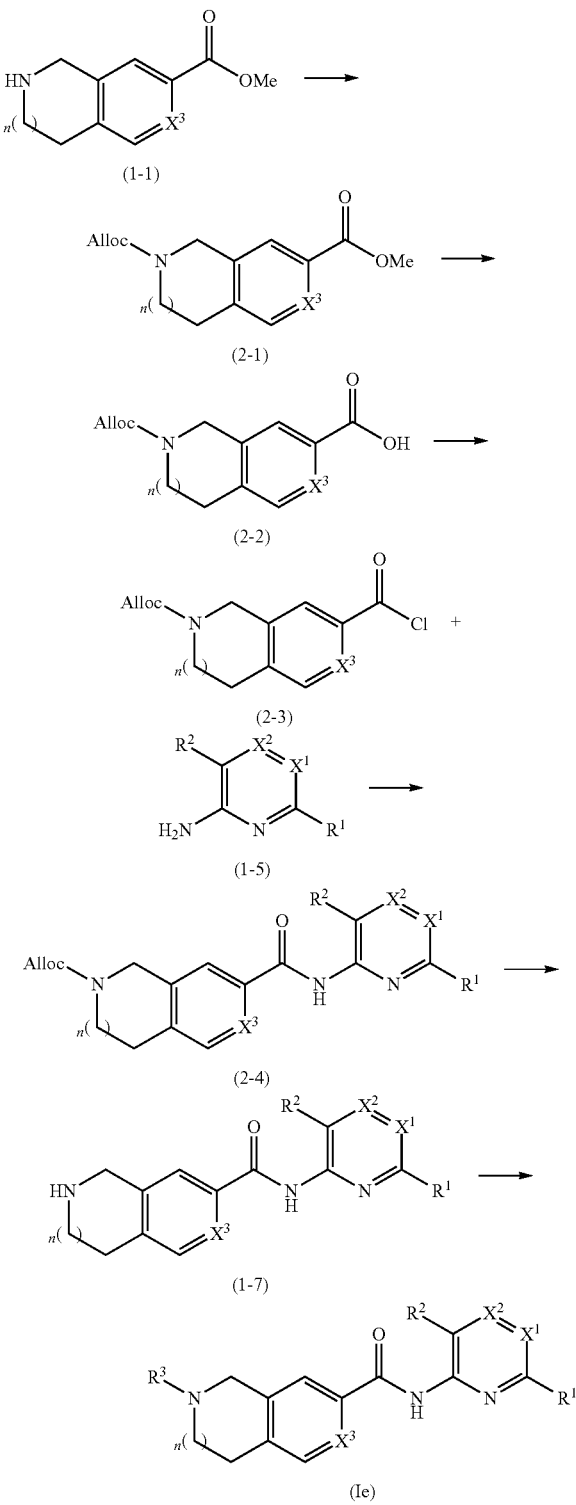

As shown in Scheme 2, novel analogs of the compound of Formula (Ie) are prepared from the compound of Formula (1-1) wherein X³ is as previously defined. Thus, the compound of Formula (1-1) is reacted with Alloc-Cl to afford a compound of Formula (2-1) using a suitable base such as, but not limited to, Et₃N, DIPEA, DMAP, or pyridine. The reaction solvent can be, but is not limited to, THF or DCM. The reaction temperature is from −20° C. to 40° C. The compound of Formula (2-1) is hydrolyzed to afford a compound of Formula (2-2) using a suitable hydroxide source such as, but not limited to, NaOH or LiOH. The compound of Formula (2-2) is reacted with a suitable chlorinating reagent such as, but not limited to, oxalyl chloride in combination with a catalytic quantity of DMF, thionyl chloride, or Ghosez's reagent to afford a compound of Formula (2-3). The reaction solvent can be, but is not limited to, THF or DCM. The reaction temperature is from −20° C. to 40° C. For the preparation of compounds of Formula (1-5), see US 2014/0018370. The compound of Formula (2-3) is reacted with a compound of Formula (1-5), wherein X¹, X², R¹ and R² are as previously defined, to afford a compound of Formula (2-4) using a suitable base such as, but not limited to, Et₃N, DMAP, pyridine, or DIPEA. The reaction solvent can be, but is not limited to, THF, DCM, pyridine and toluene. The reaction temperature is from −20° C. to 40° C. Alternatively, the compound of Formula (2-2) is reacted with a compound of Formula (1-5) to afford a compound of Formula (2-4) using a suitable coupling reagent such as, but not limited to, BOP—Cl, CDI, DCC, EDC, HATU, PyAOP or PyBOP in the presence of a suitable base such as, but not limited to, Et₃N or DIPEA. The reaction solvent can be, but is not limited to, THF, DCM and DMF. The reaction temperature is from −20° C. to 40° C. The compound of Formula (2-4) is reacted with a suitable palladium(0) catalyst in the presence of a suitable nucleophile to afford a compound of Formula (1-7). The palladium (0) catalyst can be, but is not limited to, Pd(PPh₃)₄ or Pd₂(dba)₃ in combination with a catalytic quantity of 1,4-bis(diphenylphosphino)butane. The nucleophile can be, but is not limited to, Et₃SiH or 1,3-dimethylbarbituric acid. The solvent can be, but is not limited to, DCM or THF. Compounds of Formula (1-7) are reacted with a suitable combination of reagents to afford compounds of Formula (Ie), as described previously in Scheme 1.

As shown in Scheme 3, novel analogs of the compound of Formula (3-1) are prepared from the compound of Formula (2-4) wherein $X^1$, $X^2$, $X^3$, $R^1$, $R^2$, and n are as previously defined. Thus, the compound of Formula (2-4) is reacted with a suitable palladium(0) catalyst such as, but not limited to, Pd(PPh$_3$)$_4$ or Pd$_2$(dba)$_3$ in combination with a catalytic quantity of 1,4-bis(diphenylphosphino)butane to afford a compound of Formula (3-1). The solvent can be, but is not limited to, THF or DCM.

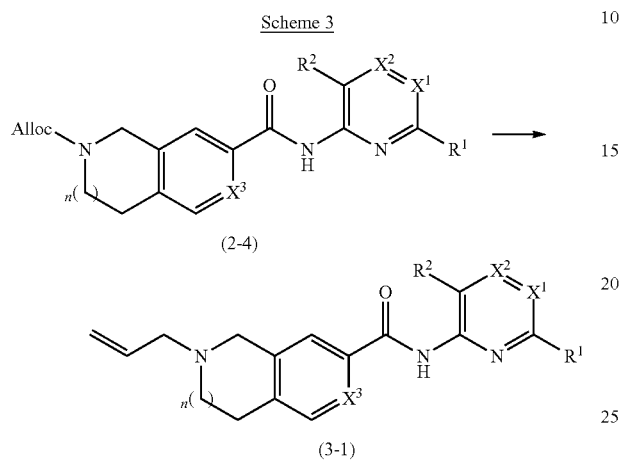

As shown in Scheme 4, novel analogs of the compound of Formula (Ie) are prepared from the compound of Formula (4-1) wherein $X^3$ is as previously defined. Thus, the compound of Formula (4-1) is hydrolyzed to afford a compound of Formula (4-2) using a suitable hydroxide source such as, but not limited to, NaOH or LiOH. The compound of Formula (4-2) is reacted with a suitable chlorinating reagent such as, but not limited to, oxalyl chloride in combination with a catalytic quantity of DMF, thionyl chloride, or Ghosez's reagent to afford a compound of Formula (4-3). The reaction solvent can be, but is not limited to, THF or DCM. The reaction temperature is from −20° C. to 40° C. For the preparation of compounds of Formula (1-5), see US 2014/0018370. The compound of Formula (4-3) is reacted with a compound of Formula (1-5), wherein $X^1$, $X^2$, $R^1$ and $R^2$ are as previously defined, to afford a compound of Formula (4-4) using a suitable base such as, but not limited to, Et$_3$N, DMAP, pyridine, or DIPEA. The reaction solvent can be, but is not limited to, THF, DCM, pyridine and toluene. The reaction temperature is from −20° C. to 40° C. Alternatively, the compound of Formula (4-2) is reacted with a compound of Formula (1-5) to afford a compound of Formula (4-4) using a suitable coupling reagent such as, but not limited to, BOP—Cl, CDI, DCC, EDC, HATU, PyAOP or PyBOP in the presence of a suitable base such as, but not limited to, Et$_3$N or DIPEA. The reaction solvent can be, but is not limited to, THF, DCM and DMF. The reaction temperature is from −20° C. to 40° C. The compound of Formula (4-4) is reacted with a suitable acid to afford a compound of Formula (1-7). The acid can be, but is not limited to HCl or TFA. The solvent can be, but is not limited to, DCM or MeOH. Compounds of Formula (1-7) are reacted with a suitable combination of reagents to afford compounds of Formula (Ie), as described previously in Scheme 1.

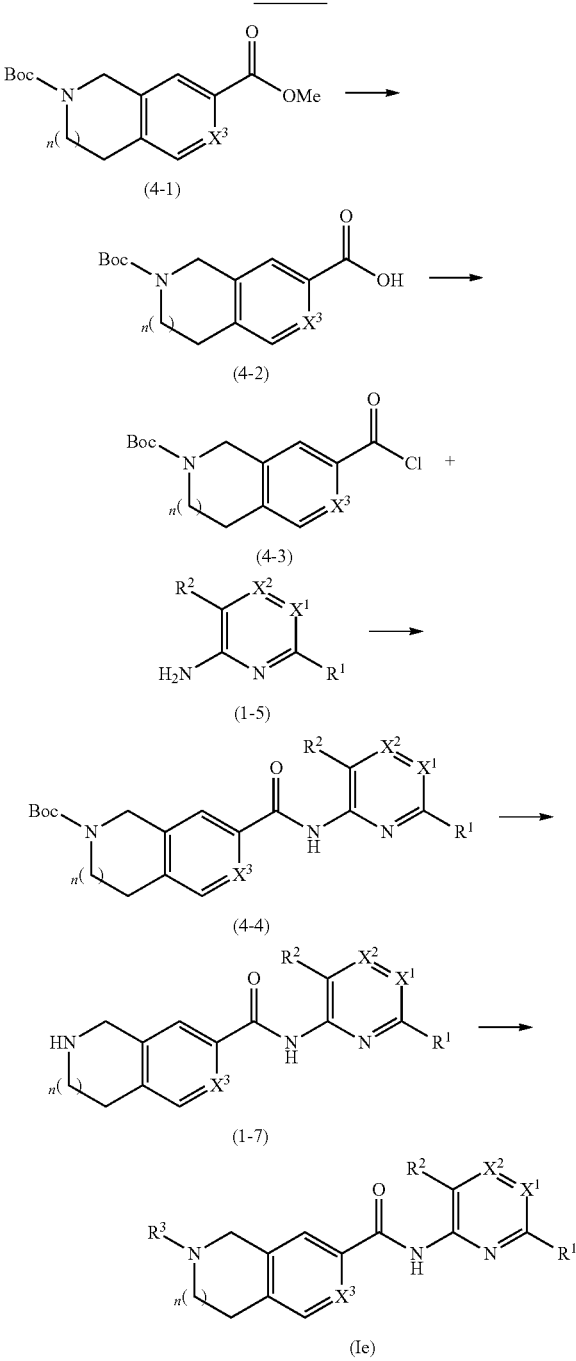

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, Formulations and/or

Example 183a

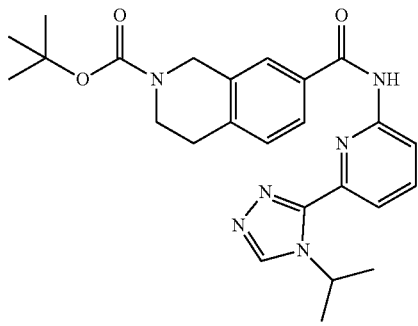 [SMILES: CC(C)n1cnnc1-c1cccc(NC(=O)c2ccc3c(c2)CN(C(=O)OC(C)(C)C)CC3)n1]

Step 4-1:

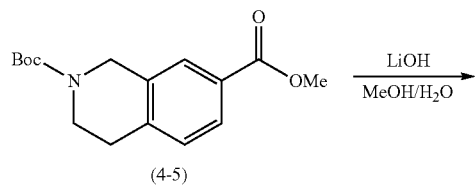

A solution of LiOH (0.22 g, 6.4 mmol, 5.0 eq) in H₂O (2.7 mL) was added to a solution of compound (4-5) (300 mg, 1.0 mmol, 1.0 eq) in MeOH (4.0 mL) and the reaction was stirred for 2 hrs. The reaction was partitioned between Et₂O and H₂O. The layers were separated and the aqueous layer was adjusted to an acidic pH (~5) with 0.1M aqueous HCl. The resulting mixture was extracted with EtOAc (2×). The combined organic layers were dried (MgSO₄), filtered, and concentrated under reduced pressure to afford pure compound (4-6) (286 mg, 1.0 mmol, 100%) as a colorless gum.

Step 4-2:

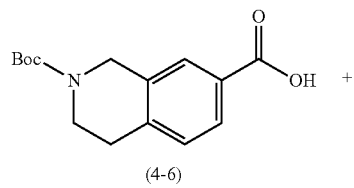

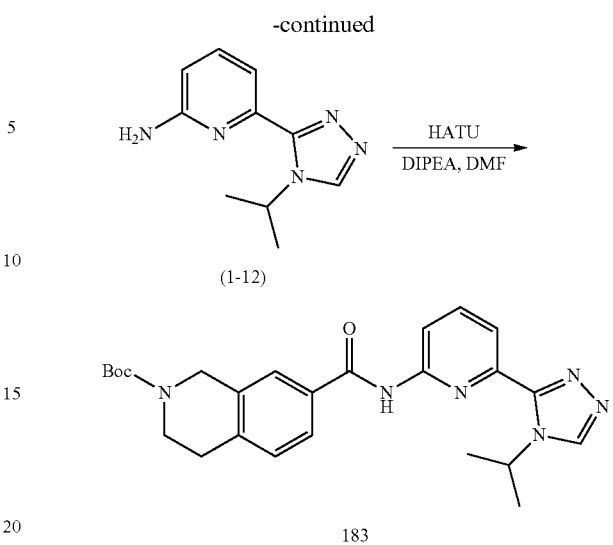

HATU (471 mg, 1.2 mmol, 1.2 eq) was added to a suspension of crude compound (4-6) (286 mg, 1.0 mmol, 1.0 eq) in DMF (2.7 mL). Compound (1-12) (210 mg, 1.0 mmol, 1.0 eq), prepared according to US 2014/0018370 and Hunig's base (0.45 mL, 2.6 mmol, 2.5 eq) were added and the reaction was stirred overnight. The reaction was diluted with EtOAc and the organic layer was washed with 10% citric acid (2×), H₂O (1×), sat. NaHCO₃ (2×), and brine (1×). The organic layer was dried (MgSO₄), filtered, and concentrated under reduced pressure. The resultant yellow gum was purified by column chromatography eluting with hexanes/EtOAc (0% EtOAc→50% EtOAc) to afford pure compound 183a (275 mg, 0.60 mmol, 58%) as a colorless amorphous solid.

Example 1: Synthesis of 6-(1-isopropyl-1H-tetrazol-5-yl)pyridin-2-amine

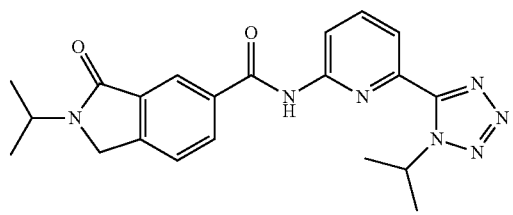 [SMILES: CC(C)N1Cc2ccc(C(=O)Nc3cccc(-c4nnnn4C(C)C)n3)cc2C1=O]

Step 1. Synthesis of N-isopropyl-6-nitropicolinamide

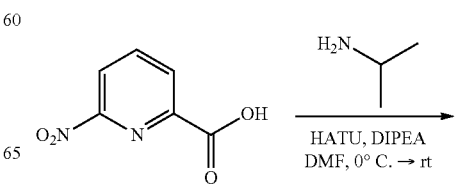

83

-continued

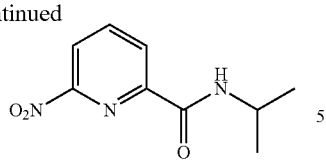

To a solution of 6-nitropicolinic acid (10 g, 59.5 mmol) and Hunig's base (31.1 mL, 178 mmol, 3 eq) in dry DMF (200 mL) at 0° C. was added isopropylamine (6.64 mL, 77 mmol, 1.3 eq) followed by HATU (29.4 g, 77 mmol, 1.3 eq). The resulting mixture was allowed to warm to rt and stirred until the starting material was consumed. The reaction was quenched by the addition of water (500 mL). The mixture was extracted with EtOAc (3×200 mL) and the combined organic layers were washed with $H_2O$ (2×200 mL), brine (200 mL), dried ($Na_2SO_4$) and concentrated under reduced pressure. The resultant residue was purified by $SiO_2$ column chromatography (100% hexanes to 40% EtOAc/Hexanes) to afford N-isopropyl-6-nitropicolinamide (10.81 g, 87% yield) as a light yellow solid: $^1H$ NMR (400 MHz, Chloroform-d) δ 8.58 (dd, J=7.7, 1.0 Hz, 1H), 8.36 (dd, J=8.0, 1.0 Hz, 1H), 8.21 (t, J=7.8 Hz, 1H), 7.70 (s, 1H), 4.31 (hept, J=6.6 Hz, 1H), 1.32 (d, J=6.6 Hz, 6H).

Step 2. Synthesis of 2-(1-isopropyl-1H-tetrazol-5-yl)-6-nitropyridine

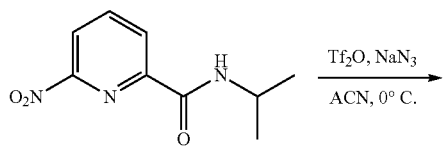

To a mixture of N-isopropyl-6-nitropicolinamide (350 mg, 1.67 mmol) and sodium azide (120 mg, 1.84 mmol) in anhydrous acetonitrile (5.58 mL) under $N_2$ at 0° C. behind a blast shield was added dropwise trifluoromethanesulfonic anhydride (1M solution in DCM, 1.84 mL, 1.84 mmol). The resulting mixture was stirred at 0° C. for 1 h and then rt for 2 hrs. The reaction was then cooled to 0° C. and quenched with sat. $NaHCO_3$ (50 mL). The mixture was extracted with EtOAc (2×). The combined organic layers were washed with sat. $NaHCO_3$ and brine, and concentrated under reduced pressure. The resultant dark red solid was purified by $SiO_2$ chromatography (100% hexanes to 35% EtOAc/Hexanes) to give 2-(1-isopropyl-1H-tetrazol-5-yl)-6-nitropyridine (170 mg, 43% yield) as a colorless solid: $^1H$ NMR (400 MHz, Chloroform-d) δ 8.74 (dd, J=7.7, 0.9 Hz, 1H), 8.41 (dd, J=8.1, 0.9 Hz, 1H), 8.32 (t, J=7.9 Hz, 1H), 5.95 (hept, J=6.7 Hz, 1H), 1.72 (d, J=6.7 Hz, 6H).

84

Step 3. Synthesis of 6-(1-isopropyl-1H-tetrazol-5-yl)pyridin-2-amine

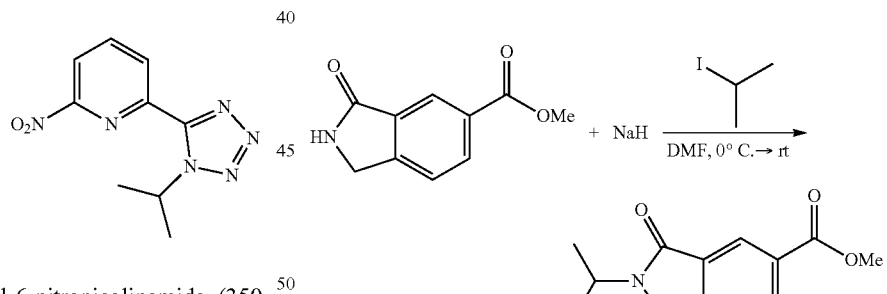

A mixture of 2-(1-isopropyl-1H-tetrazol-5-yl)-6-nitropyridine (100 mg, 0.427 mmol) and Pd/C (10% Pd on dry base, contained 50% water, 23 mg, 0.025 eq) in MeOH (1 mL)/EtOAc (1 mL) was stirred at rt under $H_2$ balloon of $H_2$ overnight. The reaction was filtered and the filtrate was concentrated under reduced pressure to provide 6-(1-isopropyl-1H-tetrazol-5-yl)pyridin-2-amine (85 mg, 97% yield), which was used without further purification. LC-MS, ES$^+$: m/z 163.05 [M+H]$^+$, $^1H$ NMR (400 MHz, Chloroform-d) δ 7.72-7.54 (m, 2H), 6.63 (dd, J=7.4, 1.7 Hz, 1H), 5.85 (hept, J=6.7 Hz, 1H), 4.57 (s, 2H), 1.65 (d, J=6.7 Hz, 6H).

Step 4. Synthesis of methyl 2-isopropyl-3-oxoisoindoline-5-carboxylate

Methyl 3-oxoisoindoline-5-carboxylate (0.5 g, 2.62 mmol) was suspended in dry DMF (13 mL) at 0° C. Sodium hydride, 60% oil dispersion (0.126 g, 3.14 mmol) was added. After stirring at 0° C. for 30 min, 2-iodopropane (0.392 mL, 3.92 mmol) was added and the mixture was allowed to warm to rt and stirred overnight. The reaction mixture was then cooled to 0° C., and quenched with water. The aqueous layer was extracted with EtOAc (2×). The combined EtOAc layers were washed with brine (3×), dried and concentrated. The residue was purified by column chromatography (100% hexanes to 40% EtOAc/hexanes) to provide the desired methyl 2-isopropyl-3-oxoisoindoline-5-carboxylate (80 mg, 13% yield): LC-MS, ES$^+$: m/z 234.08 [M+H]$^+$; $^1H$ NMR (400 MHz, Chloroform-d) δ 8.51 (s, 1H), 8.24 (dd, J=7.9, 1.6 Hz, 1H), 7.54 (d, J=7.9 Hz, 1H), 4.71 (hept, J=6.8 Hz, 1H), 4.41 (s, 2H), 3.96 (s, 3H), 1.32 (d, J=6.8 Hz, 6H).

Step 5. Synthesis of 2-isopropyl-3-oxoisoindoline-5-carboxylic acid

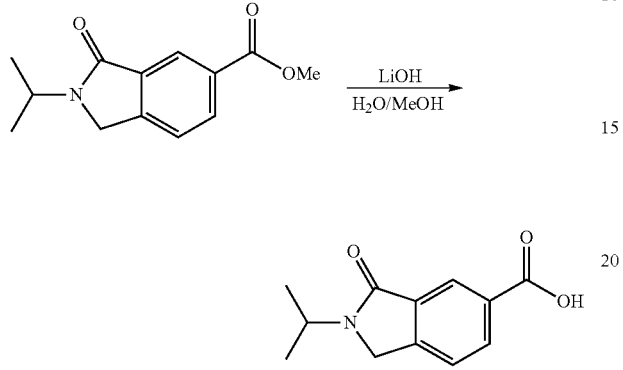

To a solution of methyl 2-isopropyl-3-oxoisoindoline-5-carboxylate (80 mg, 0.343 mmol) in MeOH (0.86 mL) was added lithium hydroxide, 1 M solution (0.86 mL, 0.857 mmol). After stirring at rt for several hours, the reaction mixture was concentrated to remove most of the MeOH, acidified with 1N HCl, and extracted with EtOAc (3×). The combined organic layers were dried over $Na_2SO_4$ and concentrated to afford the desired 2-isopropyl-3-oxoisoindoline-5-carboxylic acid (70 mg, 93% yield), which was directly used in the next step without further purification.

Step 6. Synthesis of 2-isopropyl-3-oxoisoindoline-5-carbonyl chloride

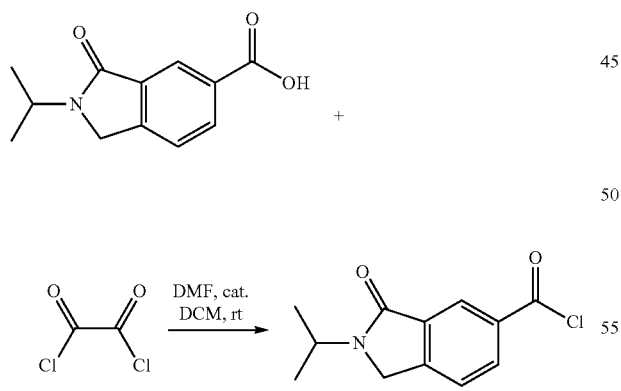

To a solution of 2-isopropyl-3-oxoisoindoline-5-carboxylic acid (70 mg, 0.319 mmol) in dry DCM (1.5 mL) at rt was added one drop of DMF and oxalyl chloride (0.117 mL, 0.234 mmol, 2 M in DCM). The suspension was stirred at rt for 45 min and turned into a clear solution. The mixture was then concentrated under reduced pressure to provide the crude 2-isopropyl-3-oxoisoindoline-5-carbonyl chloride, which was directly used in the next step.

Step 7. Synthesis of 2-isopropyl-N-(6-(1-isopropyl-1H-tetrazol-5-yl)pyridin-2-yl)-3-oxoisoindoline-5-carboxamide

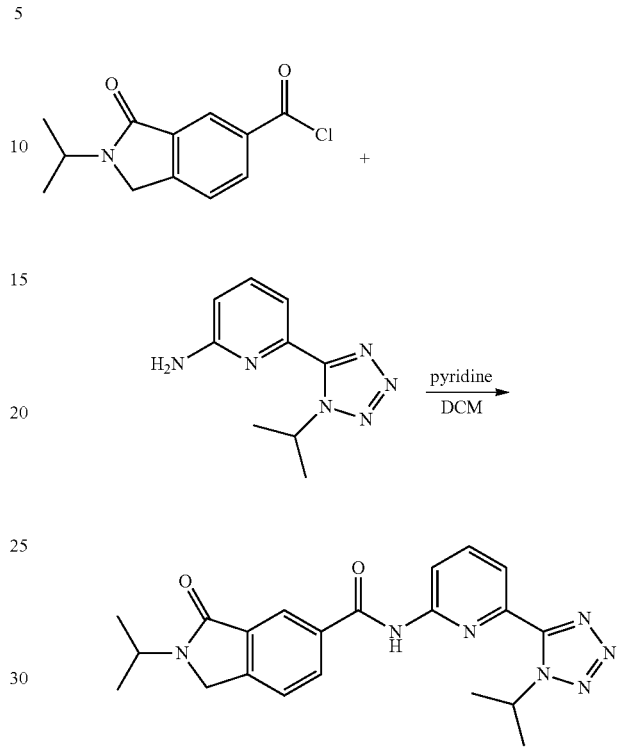

To a solution of 2-isopropyl-3-oxoisoindoline-5-carbonyl chloride (73.2 mg, 0.308 mmol) from the previous step in dry DCM (2 mL) at 0° C. was added 6-(1-isopropyl-1H-tetrazol-5-yl)pyridin-2-amine (0.061 g, 0.30 mmol), followed by the addition of pyridine (0.24 ml, 3.00 mmol). The reaction mixture was allowed to warm to rt and stirred overnight. The reaction mixture was concentrated under reduced pressure, and then partitioned between EtOAc/$H_2O$. The organic layer was separated, washed with water, brine, dried ($Na_2SO_4$) and concentrated under reduced pressure. The residue was purified by $SiO_2$ column chromatography (100% hexanes to 70% EtOAc/hexanes) to provide the desired 2-isopropyl-N-(6-(1-isopropyl-1H-tetrazol-5-yl)pyridin-2-yl)-3-oxoisoindoline-5-carboxamide (82 mg, 72% yield).

Example 3: Synthesis of benzyl 5-((6-(4-isopropyl-4H-1,2,4-triazol-3-yl)pyridin-2-yl)carbamoyl)isoindoline-2-carboxylate

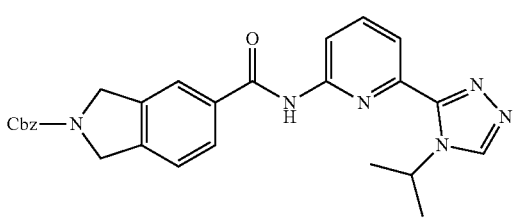 [SMILES: CC(C)n1cnnc1-c1cccc(NC(=O)c2ccc3c(c2)CN(C(=O)OCc2ccccc2)C3)n1]

Step 1. Synthesis of 2-benzyl 5-methyl isoindoline-2,5-dicarboxylate

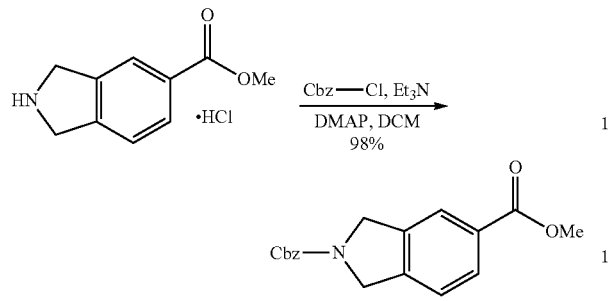

Benzyl chloroformate (1.0 mL, 7.0 mmol) was added dropwise to a solution of methyl isoindoline-5-carboxylate, hydrochloride (1.0 g, 4.7 mmol), Et₃N (1.4 mL, 10.3 mmol), and DMAP (52 mg, 0.43 mmol) in DCM (9.4 mL) at 0° C. The cold bath was removed, and the reaction was stirred for 16 h at rt. The reaction was quenched with sat. NaHCO₃ and diluted with CH₂Cl₂. The layers were separated and the aqueous layer was extracted with CH₂Cl₂ (2×). The combined organic layers were washed with brine, dried (MgSO₄), filtered, and concentrated under reduced pressure. The resultant orange gum was purified by column chromatography eluting with hexanes/EtOAc (0% EtOAc→35% EtOAc) to give 2-benzyl 5-methyl isoindoline-2,5-dicarboxylate (1.4 g, 4.6 mmol, 98% yield) as a pale yellow solid: $^1$H NMR (400 MHz, DMSO-d₆) δ 7.94 (d, J=11.9 Hz, 1H), 7.90 (dd, J=8.1, 1.3 Hz, 1H), 7.48 (dd, J=10.8, 8.0 Hz, 1H), 7.45-7.29 (comp, 5H), 5.16 (d, J=1.3 Hz, 2H), 4.76 (d, J=6.0 Hz, 2H), 4.71 (t, J=2.9 Hz, 2H), 3.85 (d, J=1.4 Hz, 3H).

Step 2. Synthesis of 2-((benzyloxy)carbonyl)isoindoline-5-carboxylic acid

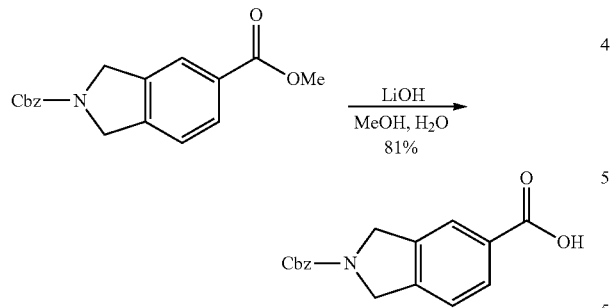

A solution of LiOH (0.96 g, 23.0 mmol) in H₂O (12.3 mL) was added to a suspension of 2-benzyl 5-methyl isoindoline-2,5-dicarboxylate (1.4 g, 4.6 mmol) in MeOH (18.4 mL) and the reaction was stirred for 24 h. The reaction was concentrated under reduced pressure and the resultant residue was partitioned between MTBE and H₂O. The layers were separated and the aqueous layer was acidified with 2 M aqueous HCl. The aqueous layer was extracted with EtOAc (2×). The combined organic layers were dried (MgSO₄), filtered, and concentrated under reduced pressure to give 2-((benzyloxy)carbonyl)isoindoline-5-carboxylic acid (1.1 g, 3.7 mmol, 81% yield) as a white powder: $^1$H NMR (500 MHz, DMSO-d₆) δ 12.96 (br s, 1H), 7.91 (d, J=13.8 Hz, 1H), 7.88 (d, J=8.2 Hz, 1H), 7.42 (ddt, J=20.9, 14.8, 7.7 Hz, 5H), 7.36-7.31 (m, 1H), 5.16 (s, 2H), 4.76 (d, J=6.3 Hz, 2H), 4.70 (s, 2H).

Step 3. Synthesis of benzyl 5-(chlorocarbonyl)isoindoline-2-carboxylate

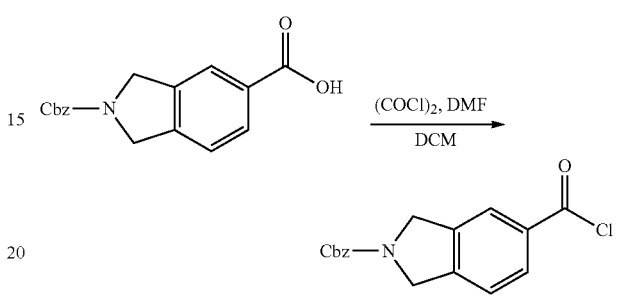

Representative Procedure for Acid Chloride Formation with Oxalyl Chloride

To a mixture of 2-((benzyloxy)carbonyl)isoindoline-5-carboxylic acid (0.75 g, 2.5 mmol) in DCM (7.2 ml) and DMF (0.02 ml, 0.25 mmol) was charged oxalyl chloride (0.38 mL, 4.3 mmol). The mixture was stirred for 3 h. The reaction was concentrated under reduced pressure and the resultant orange oil was used without purification.

Step 4. Synthesis of benzyl 5-((6-(4-isopropyl-4H-1,2,4-triazol-3-yl)pyridin-2-yl)carbamoyl)isoindoline-2-carboxylate

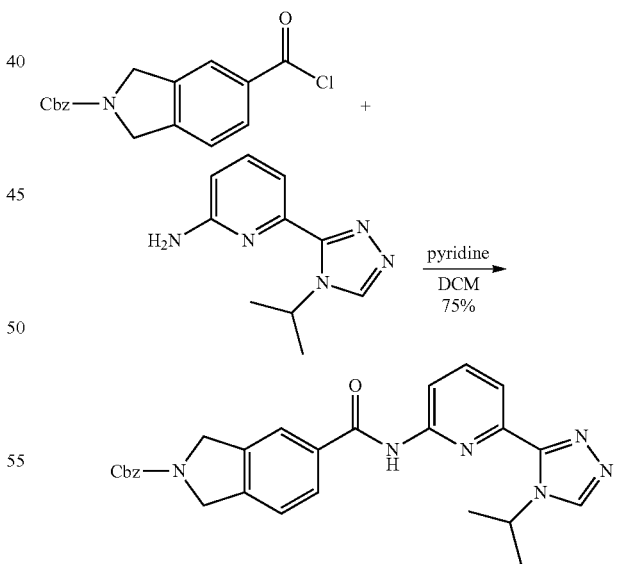

6-(4-isopropyl-4H-1,2,4-triazol-3-yl)pyridin-2-amine was prepared according to the method disclosed in WO 2016106384, the entire contents of which are incorporated herein by reference.

Representative Procedure 1 for Amide Formation

A solution of crude benzyl 5-(chlorocarbonyl)isoindoline-2-carboxylate (398 mg, 1.26 mmol) in DCM (1.8 mL) was added to a suspension of 6-(4-isopropyl-4H-1,2,4-triazol-3-yl)pyridin-2-amine (256 mg, 1.26 mmol) in pyridine (1.8 mL) and the reaction was stirred overnight. The reaction was concentrated under reduced pressure. The resultant brown residue was purified by column chromatography eluting with CH$_2$Cl$_2$/MeOH (0% MeOH→4% MeOH) to give benzyl 5-((6-(4-isopropyl-4H-1,2,4-triazol-3-yl)pyridin-2-yl)carbamoyl)isoindoline-2-carboxylate (454 mg, 0.941 mmol, 75% yield) as a pale yellow amorphous solid.

Example 2 was prepared according to the procedure for the synthesis of Example 3, utilizing 6-(1-isopropyl-1H-tetrazol-5-yl)pyridin-2-amine in Step 4 as the amine coupling partner.

Example 9: Synthesis of N-(6-(4-isopropyl-4H-1,2,4-triazol-3-yl)pyridin-2-yl)isoindoline-5-carboxamide

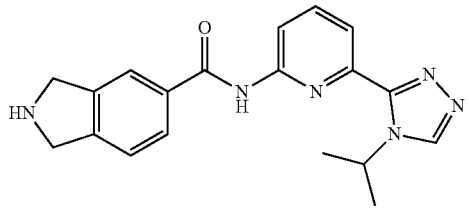 [SMILES: CC(C)n1cnnc1-c1cccc(NC(=O)c2ccc3c(c2)CNC3)n1]

Representative Procedure for Hydrogenolysis

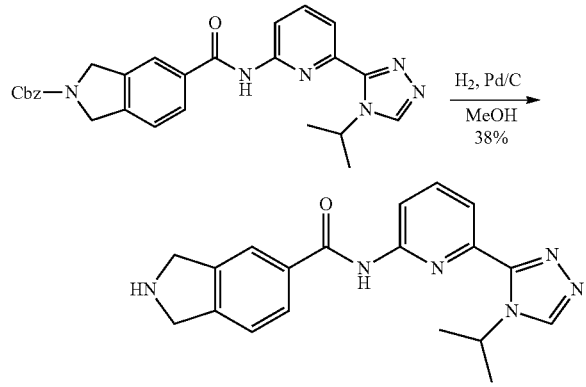

Pd—C (90 mg, 10% loading) was added to a solution of 5-((6-(4-isopropyl-4H-1,2,4-triazol-3-yl)pyridin-2-yl)carbamoyl)isoindoline-2-carboxylate (450 mg, 0.933 mmol) in MeOH (18.7 mL). The reaction was evacuated and backfilled with H$_2$ (3×) and the reaction was stirred overnight under a balloon of H$_2$. The reaction was filtered through Celite, rinsing with MeOH, EtOAc, and DCM and concentrated under reduced pressure. The resultant clear residue was dissolved in DCM/EtOAc and filtered through Celite, rinsing with DCM and EtOAc. The filtrate was concentrated under reduced pressure to give N-(6-(4-isopropyl-4H-1,2,4-triazol-3-yl)pyridin-2-yl)isoindoline-5-carboxamide (123 mg, 0.35 mmol, 38% yield) as a colorless amorphous solid.

Example 8 was prepared according to the representative procedure for hydrogenolysis.

Example 4: Synthesis of N-(6-(4-isopropyl-4H-1,2,4-triazol-3-yl)pyridin-2-yl)-2-((3,3,3-trifluoropropyl)sulfonyl)isoindoline-5-carboxamide

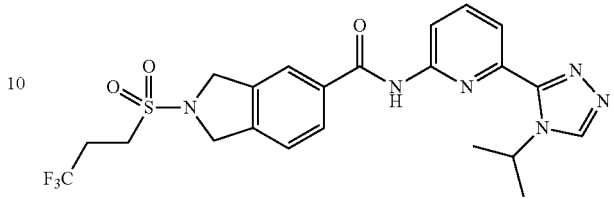

Representative Procedure for Sulfonamide Formation

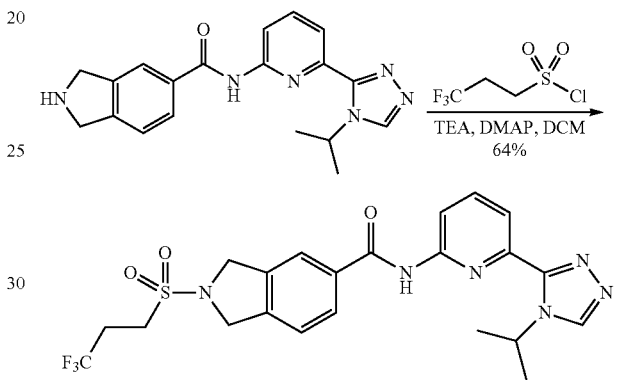

3,3,3-Trifluoropropane-1-sulfonyl chloride (12.2 μL, 0.096 mmol) was added to a solution of N-(6-(4-isopropyl-4H-1,2,4-triazol-3-yl)pyridin-2-yl)isoindoline-5-carboxamide (22.4 mg, 0.064 mmol), DMAP (0.80 mg, 6.4 μmol), and Et$_3$N (21 μL, 0.15 mmol) in DCM (0.61 mL) and the reaction was stirred overnight. The reaction was purified by column chromatography eluting with CH$_2$Cl$_2$/MeOH (0% MeOH→5% MeOH) to give N-(6-(4-isopropyl-4H-1,2,4-triazol-3-yl)pyridin-2-yl)-2-((3,3,3-trifluoropropyl)sulfonyl)isoindoline-5-carboxamide (21 mg, 0.041 mmol, 64% yield) as an orange amorphous solid.

Examples 6, 14, and 15 were prepared according to the representative procedure for sulfonamide formation.

Example 5: Synthesis of N2-ethyl-N5-(6-(4-isopropyl-4H-1,2,4-triazol-3-yl)pyridin-2-yl)-N2-methyl-isoindoline-2,5-dicarboxamide

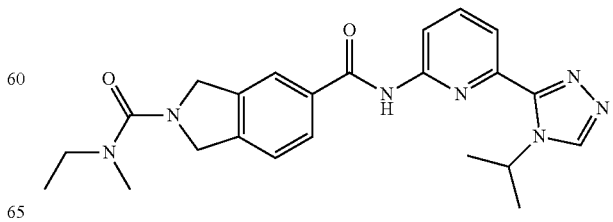

Representative Procedure for Secondary Urea Formation

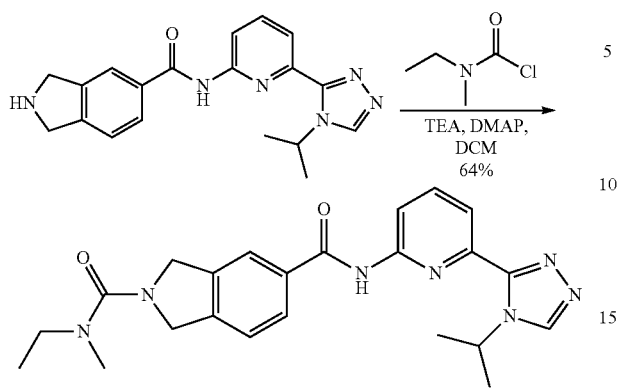

Ethyl(methyl)carbamic chloride (11.7 µL, 0.096 mmol) was added to a solution of N-(6-(4-isopropyl-4H-1,2,4-triazol-3-yl)pyridin-2-yl)isoindoline-5-carboxamide (22.4 mg, 0.064 mmol), DMAP (0.8 mg, 6.4 µmol), and Et$_3$N (21 µL, 0.150 mmol) in DCM (0.611 mL) and the reaction was stirred overnight. The reaction was purified by column chromatography eluting with CH$_2$Cl$_2$/MeOH (0% MeOH→5% MeOH) to give N2-ethyl-N5-(6-(4-isopropyl-4H-1,2,4-triazol-3-yl)pyridin-2-yl)-N2-methylisoindoline-2,5-dicarboxamide (18.0 mg, 0.041 mmol, 64% yield) as a colorless amorphous solid.

Examples 11, 12, 13, and 17 were prepared according to the representative procedure for secondary urea formation.

Example 7: Synthesis of ethyl 5-((6-(4-isopropyl-4H-1,2,4-triazol-3-yl)pyridin-2-yl)carbamoyl)isoindoline-2-carboxylate

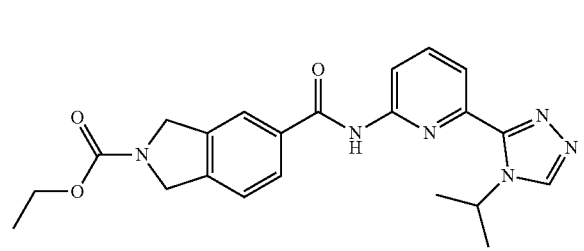 [SMILES: CCOC(=O)N1Cc2ccc(C(=O)Nc3cccc(-c4nncn4C(C)C)n3)cc2C1]

Representative Procedure for Carbamate Formation

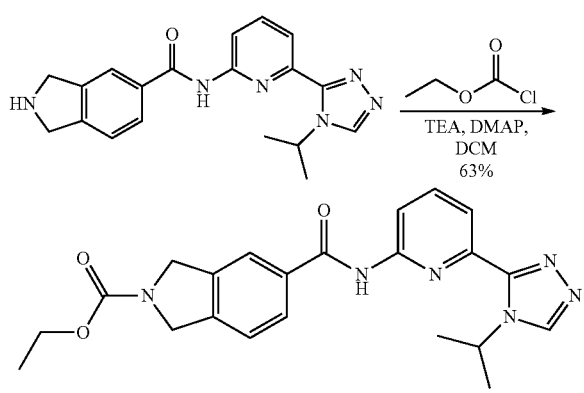

Ethyl chloroformate (9.3 µL, 0.096 mmol) was added to a solution of N-(6-(4-isopropyl-4H-1,2,4-triazol-3-yl)pyridin-2-yl)isoindoline-5-carboxamide (22.4 mg, 0.064 mmol), DMAP (0.8 mg, 6.4 µmol), and Et$_3$N (21 µL, 0.15 mmol) in DCM (0.61 mL) and the reaction was stirred overnight. The reaction was purified by column chromatography eluting with CH$_2$Cl$_2$/MeOH (0% MeOH 5% MeOH) to give ethyl 5-((6-(4-isopropyl-4H-1,2,4-triazol-3-yl)pyridin-2-yl)carbamoyl)isoindoline-2-carboxylate (16.9 mg, 0.04 mmol, 63% yield) as a colorless amorphous solid.

Example 16 was prepared according to the representative procedure for carbamate formation.

Example 10: Synthesis of 2-(N,N-dimethylsulfamoyl)-N-(6-(4-isopropyl-4H-1,2,4-triazol-3-yl)pyridin-2-yl)isoindoline-5-carboxamide

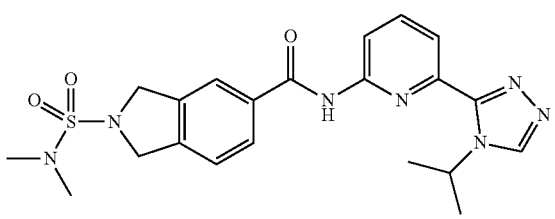 [SMILES: CC(C)n1cnnc1-c1cccc(NC(=O)c2ccc3c(c2)CN(S(=O)(=O)N(C)C)C3)n1]

Representative Procedure for Secondary Sulfonyl Urea Formation

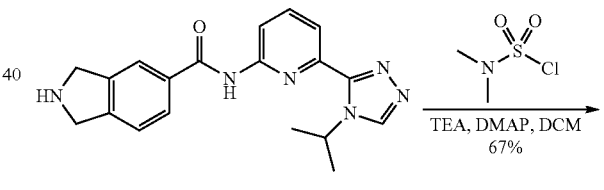

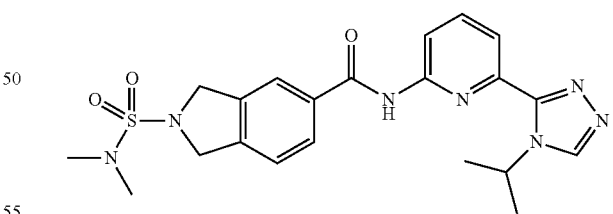

Dimethylsulfamoyl chloride (11.2 µL, 0.104 mmol) was added to a solution of N-(6-(4-isopropyl-4H-1,2,4-triazol-3-yl)pyridin-2-yl)isoindoline-5-carboxamide (24.3 mg, 0.07 mmol), DMAP (0.9 mg, 7.0 µmol), and Et$_3$N (21 µL, 0.15 mmol) in DCM (0.66 mL) and the reaction stirred overnight. The reaction was purified by column chromatography eluting with CH$_2$Cl$_2$/MeOH (0% MeOH→5% MeOH) to give 2-(N,N-dimethylsulfamoyl)-N-(6-(4-isopropyl-4H-1,2,4-triazol-3-yl)pyridin-2-yl)isoindoline-5-carboxamide (21.3 mg, 0.047 mmol, 67.1% yield) as a tan solid.

Example 19: Synthesis of 2-isopropyl-N-(6-(4-iso-propyl-4H-1,2,4-triazol-3-yl)pyridin-2-yl)-1-oxo-2,3-dihydro-1H-pyrrolo[3,4-c]pyridine-6-carboxamide

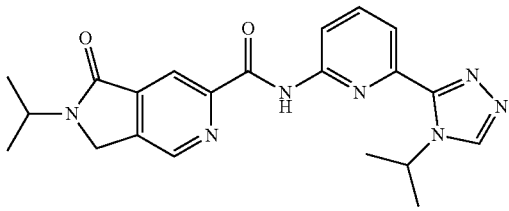 [SMILES: CC(C)N1Cc2cnc(C(=O)Nc3cccc(-c4nncn4C(C)C)n3)cc2C1=O]

Step 1. Synthesis of methyl 2-chloro-5-methylisonicotinate

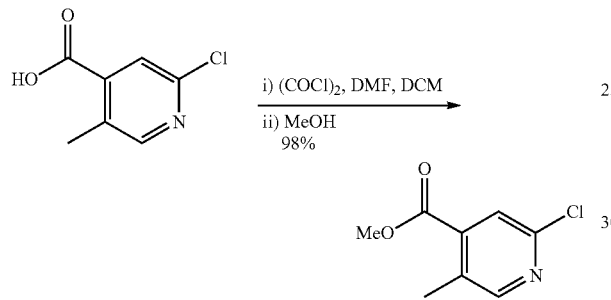

Oxalyl chloride (5.10 mL, 58.3 mmol) was added to a solution of chloro-5-methylisonicotinic acid (5.0 g, 29.1 mmol) in DCM (486 ml). DMF (0.226 ml, 2.91 mmol) was added and the reaction was stirred overnight. MeOH (5.89 ml, 146 mmol) was added and the reaction was stirred for 1 h. The reaction was quenched with sat. NaHCO$_3$ and stirred for 40 min. The layers were separated and the organic layer was washed with brine, dried (MgSO$_4$), filtered, and concentrated to give methyl 2-chloro-5-methylisonicotinate (5.3 g, 28.6 mmol, 98% yield) as a yellow oil: LC-MS, ES$^+$: m/z 186.06 [M+H]$^+$; $^1$H NMR (400 MHz, Chloroform-d) δ 8.33 (t, J=0.8 Hz, 1H), 7.74 (s, 1H), 3.94 (s, 3H), 2.53 (s, 3H).

Step 2. Synthesis of methyl 5-(bromomethyl)-2-chloroisonicotinate

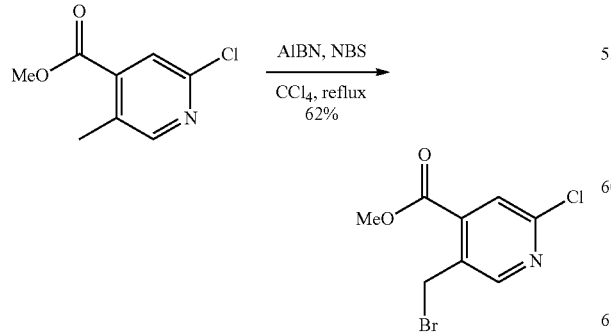

A mixture of methyl 2-chloro-5-methylisonicotinate (5.3 g, 28.6 mmol), AIBN (0.469 g, 2.86 mmol), and NBS (6.10 g, 34.3 mmol) were stirred at reflux overnight. The reaction was cooled to rt and filtered to remove solids, rinsing with DCM. The filtrate was washed with water, and the aqueous phase was extracted with DCM (2×). The combined organic were layers dried (MgSO$_4$), filtered, and concentrated under reduced pressure. The resultant pale yellow oil was purified by column chromatography eluting with hexanes/EtOAc (0% EtOAc→15% EtOAc) to give methyl 5-(bromomethyl)-2-chloroisonicotinate (4.7 g, 28.6 mmol, 62% yield) as a clear oil: LC-MS, ES$^+$: m/z 263.97 [M+H]$^+$; $^1$H NMR (500 MHz, Chloroform-d) δ 8.51 (s, 1H), 7.81 (s, 1H), 4.86 (s, 2H), 4.00 (s, 3H).

Step 3. Synthesis of 6-chlorofuro[3,4-c]pyridin-1(3H)-one

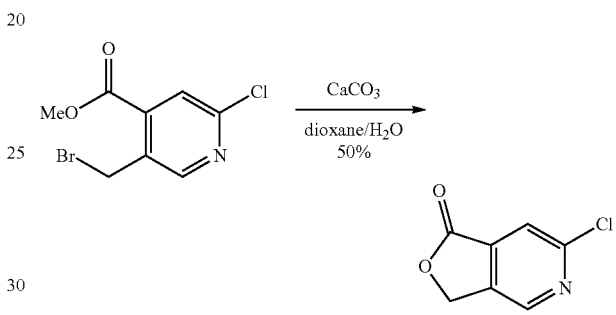

A mixture of methyl 5-(bromomethyl)-2-chloroisonicotinate (4.7 g, 17.8 mmol) and calcium carbonate (10.7 g, 107 mmol) in Dioxane (178 ml)/H$_2$O (178 ml) was heated at reflux for 3.5 hr. The reaction was cooled to rt and filtered to remove solids, rinsing with dioxane. The filtrate was concentrated under reduced pressure, then extracted with DCM (4×). The combined organic layers were dried (MgSO$_4$), filtered, and concentrated to give 6-chlorofuro[3,4-c]pyridin-1(3H)-one (1.5 g, 8.9 mmol, 50% yield) as a pale yellow solid: $^1$H NMR (500 MHz, Chloroform-d) δ 8.73-8.69 (m, 1H), 7.83 (s, 1H), 5.43 (s, 2H).

Step 3. Synthesis of 2-chloro-5-(hydroxymethyl)-N-isopropylisonicotinamide

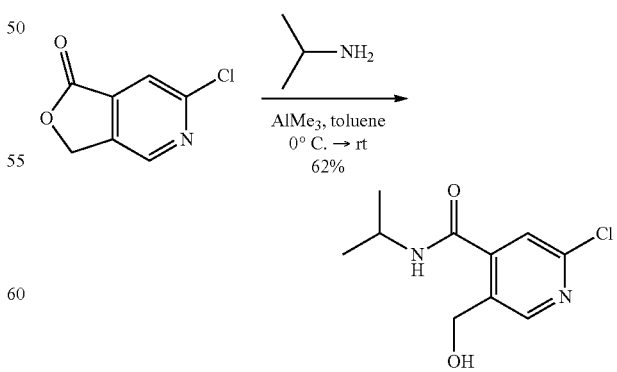

Trimethylaluminum (1.6 mL, 3.26 mmol of a 2.0 M solution in toluene) was added dropwise to a solution of propan-2-amine (0.31 mL, 3.55 mmol) in toluene (9.8 mL)

at 0° C. The reaction was stirred for 5 min at 0° C. whereupon 6-chlorofuro[3,4-c]pyridin-1(3H)-one (502 mg, 2.96 mmol) was added. The cold bath was removed and the reaction was stirred at rt overnight. The reaction was quenched carefully with 1M NaOH (10 mL) and diluted with EtOAc. The organic layer was washed with water and brine. The organic layer was dried (MgSO$_4$), filtered, and concentrated to give 2-chloro-5-(hydroxymethyl)-N-isopropylisonicotinamide (418 mg, 1.83 mmol, 62% yield) as a pink solid: LC-MS, ES$^+$: m/z 229.10 [M+H]$^+$; $^1$H NMR (400 MHz, Chloroform-d) δ 8.33 (s, 1H), 7.39 (s, 1H), 6.55 (s, 1H), 4.57 (d, J=6.5 Hz, 2H), 4.19 (dp, J=7.7, 6.5 Hz, 1H), 3.78 (t, J=6.6 Hz, 1H), 1.22 (d, J=6.6 Hz, 6H).

Step 4. Synthesis of 6-chloro-2-isopropyl-2,3-dihydro-1H-pyrrolo[3,4-c]pyridin-1-one

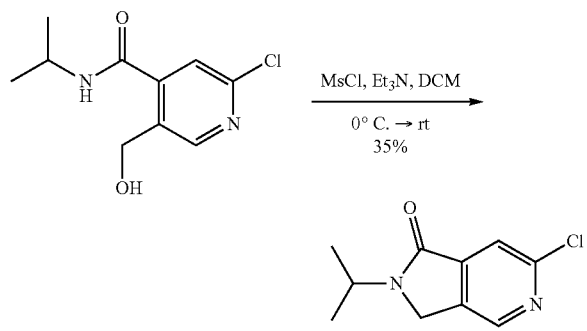

Ms-Cl (0.214 mL, 2.74 mmol) was added to a solution of 2-chloro-5-(hydroxymethyl)-N-isopropylisonicotinamide (418 mg, 1.83 mmol) and Et$_3$N (0.764 mL, 5.48 mmol) in DCM (14.1 mL) at 0° C. The reaction was stirred, slowly warming to rt over 2.5 hr. The reaction was quenched with sat. NaHCO$_3$ and diluted with CH$_2$Cl$_2$. The layers were separated and the aqueous was layer extracted with CH$_2$Cl$_2$ (2×). The combined organic layers were dried (MgSO$_4$), filtered, and concentrated under reduced pressure. The resultant orange solid was purified by column chromatography eluting with hexanes/acetone (0% acetone→15% acetone) to give 6-chloro-2-isopropyl-2,3-dihydro-1H-pyrrolo[3,4-c]pyridin-1-one (136 mg, 0.65 mmol, 35% yield) as a pale yellow gum that solidified upon standing: LC-MS, ES$^+$: m/z 211.18 [M+H]$^+$; $^1$H NMR (400 MHz, Chloroform-d) δ 8.49 (s, 1H), 7.77 (s, 1H), 5.37 (s, 2H), 4.10 (hept, J=6.4 Hz, 1H), 1.21 (d, J=6.4 Hz, 6H).

Representative Procedure for Palladium Catalyzed Carbonylation

Step 5. Synthesis of ethyl 2-isopropyl-1-oxo-2,3-dihydro-1H-pyrrolo[3,4-c]pyridine-6-carboxylate

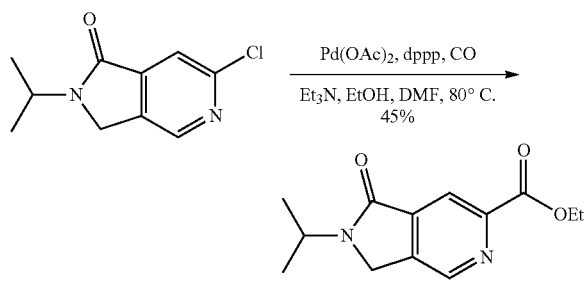

A mixture of 6-chloro-2-isopropyl-2,3-dihydro-1H-pyrrolo[3,4-c]pyridin-1-one (132 mg, 0.63 mmol), Pd(OAc)$_2$ (14.1 mg, 0.063 mmol), 1,3-bis(diphenylphosphino)propane (51.7 mg, 0.125 mmol), and Et$_3$N (0.262 mL, 1.88 mmol) in DMF (1.67 mL)/EtOH (0.84 mL) were stirred under a balloon of CO at 80° C. overnight. The reaction was quenched with H$_2$O/brine and diluted with EtOAc. The layers were separated and the organic layer was washed with water/brine (2×). The organic layer was dried (MgSO$_4$), filtered, and concentrated under reduced pressure. The resultant orange residue was purified by column chromatography eluting with hexanes/acetone (0% acetone→25% acetone) to give ethyl 2-isopropyl-1-oxo-2,3-dihydro-1H-pyrrolo[3,4-c]pyridine-6-carboxylate (69.6 mg, 0.28 mmol, 45% yield) as a tan oil: $^1$H NMR (400 MHz, Chloroform-d) δ 8.87 (d, J=1.0 Hz, 1H), 8.54 (d, J=1.2 Hz, 1H), 5.46 (s, 2H), 4.49 (q, J=7.1 Hz, 2H), 4.14 (hept, J=6.4 Hz, 1H), 1.45 (t, J=7.1 Hz, 3H), 1.24 (d, J=6.4 Hz, 6H).

Step 6. Synthesis of 2-isopropyl-N-(6-(4-isopropyl-4H-1,2,4-triazol-3-yl)pyridin-2-yl)-1-oxo-2,3-dihydro-1H-pyrrolo[3,4-c]pyridine-6-carboxamide Representative Procedure for Amide Formation with Trimethylaluminum

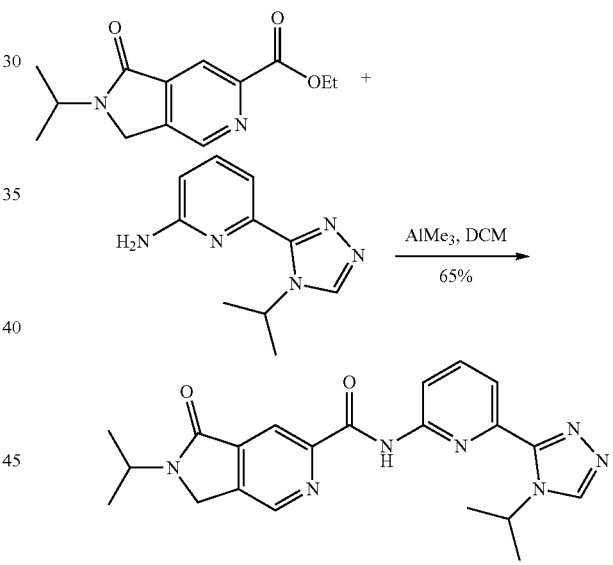

Trimethylaluminum (0.15 mL, 0.29 mmol of a 2.0M solution in toluene) was added dropwise to DCM (0.46 mL) at 0° C. A solution of 6-(4-isopropyl-4H-1,2,4-triazol-3-yl)pyridin-2-amine (30.0 mg, 0.15 mmol) in DCM (0.46 mL) was added at 0° C., and the mixture was stirred for 20 min at 0° C. then for 1 h at rt. A solution of ethyl 2-isopropyl-1-oxo-2,3-dihydro-1H-pyrrolo[3,4-c]pyridine-6-carboxylate (36.5 mg, 0.15 mmol) in DCM (0.37 mL) was added and the reaction was heated at 35° C. overnight. The reaction was quenched with sat. potassium sodium tartrate and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant yellow gum was purified by column chromatography eluting with CH$_2$Cl$_2$/MeOH (0% MeOH→8% MeOH) to give 2-isopropyl-N-(6-(4-isopropyl-4H-1,2,4-triazol-3-yl)pyridin-2-yl)-1-oxo-2,3-dihydro-1H-pyrrolo[3,4-c]pyridine-6-carboxamide (38.6 mg, 0.095 mmol, 65% yield) as a tan solid.

Example 18: Synthesis of (R)—N-(6-(1-(1-hydroxypropan-2-yl)-1H-tetrazol-5-yl)pyridin-2-yl)-2-isopropyl-1-oxo-2,3-dihydro-1H-pyrrolo[3,4-c]pyridine-6-carboxamide

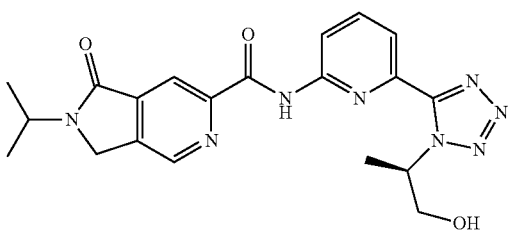 [SMILES: CC(C)N1Cc2cnc(C(=O)Nc3cccc(-c4nnnn4[C@H](C)CO)n3)cc2C1=O]

Step 1. Synthesis of (R)-1-acetoxypropan-2-ammonium 2,2,2-trifluoroacetate

TFA (3.2 mL) was added to a solution of (R)-2-((tert-butoxycarbonyl)amino)propyl acetate (992 mg, 4.57 mmol) in DCM (6.5 mL) and the reaction was stirred for 3.5 hrs. The reaction was concentrated under reduced pressure at 45° C. until TFA was removed. Dried oil under vacuum 40° C. give crude (R)-1-acetoxypropan-2-ammonium 2,2,2-trifluoroacetate as a clear oil that was used without purification: $^1$H NMR (400 MHz, DMSO-$d_6$) δ 4.12 (dd, J=11.8, 4.1 Hz, 1H), 4.02 (dd, J=11.8, 7.1 Hz, 1H), 3.55-3.41 (m, 1H), 2.06 (s, 3H), 1.18 (d, J=6.7 Hz, 3H).

Step 2. Synthesis of (R)-2-(6-nitropicolinamido)propyl acetate

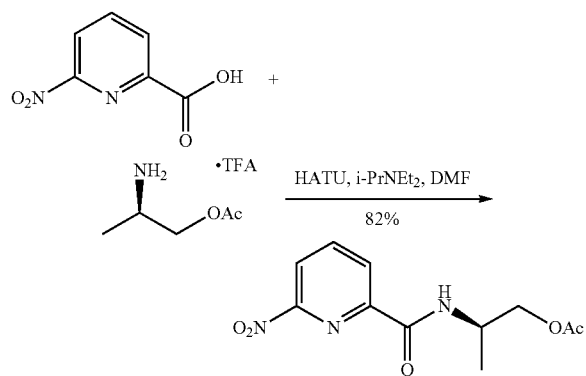

Hunig's base (3.1 mL, 17.6 mmol), a solution of (R)-1-acetoxypropan-2-ammonium 2,2,2-trifluoroacetate (1.1 g, 4.57 mmol) in DMF (5 mL), and HATU (2.0 g, 5.28 mmol) was added to a solution of 6-nitropicolinic acid (592 mg, 3.52 mmol) in DMF (6.73 mL) and the reaction was stirred overnight. The reaction was quenched with H$_2$O and diluted with EtOAc. The layers were separated and the aqueous layer was extracted with EtOAc (2×). The combined organic layers were washed with water (1×), brine (2×), dried (MgSO$_4$), filtered, and concentrated under reduced pressure. The resultant yellow gum was purified by column chromatography eluting with hexanes/EtOAc (0% EtOAc→40% EtOAc) to give (R)-2-(6-nitropicolinamido)propyl acetate (770 mg, 2.88 mmol, 82% yield) as a yellow gum: $^1$H NMR (400 MHz, Chloroform-d) δ 8.57 (dd, J=7.7, 1.0 Hz, 1H), 8.39 (dd, J=8.1, 1.0 Hz, 1H), 8.23 (t, J=7.9 Hz, 1H), 7.92 (d, J=8.6 Hz, 1H), 4.58-4.43 (m, 1H), 4.24 (dd, J=11.3, 4.4 Hz, 1H), 4.18 (dd, J=11.3, 5.5 Hz, 1H), 2.11 (s, 3H), 1.36 (d, J=6.8 Hz, 3H).

Step 3. Synthesis of (R)-2-(5-(6-nitropyridin-2-yl)-1H-tetrazol-1-yl)propyl acetate

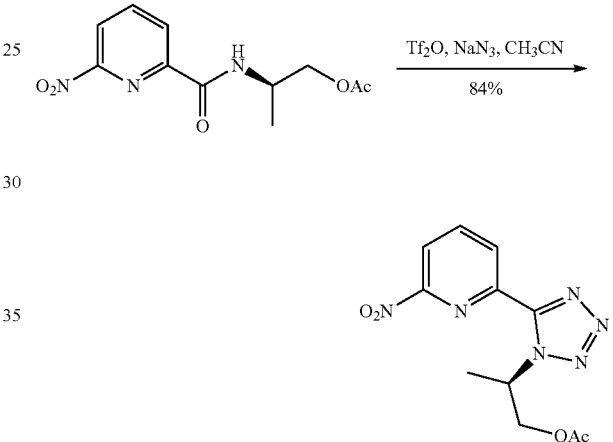

To a mixture of (R)-2-(6-nitropicolinamido)propyl acetate (765 mg, 2.86 mmol) and sodium azide (298 mg, 4.58 mmol) in acetonitrile (19.1 mL) behind a blast shield at 0° C. was added Tf$_2$O (4.29 mL, 4.29 mmol, 1.0M solution in DCM) dropwise, and the resulting mixture was stirred for 30 min at 0° C. The cold bath was removed, and the mixture was stirred at rt for 1 h. The reaction was quenched with sat. NaHCO$_3$ and diluted with EtOAc. The organic layer was separated and washed with brine, dried, filtered and concentrated under reduced pressure. The resultant residue was purified by column chromatography eluting with hexanes/EtOAc (0% EtOAc→60% EtOAc) to give (R)-2-(5-(6-nitropyridin-2-yl)-1H-tetrazol-1-yl)propyl acetate (699 mg, 2.392 mmol, 84% yield) as a pale yellow solid: $^1$H NMR (500 MHz, Chloroform-d) δ 8.79 (dd, J=7.8, 0.9 Hz, 1H), 8.43 (dd, J=8.1, 1.0 Hz, 1H), 8.32 (dd, J=8.4, 7.4 Hz, 1H), 6.17 (pd, J=7.0, 4.5 Hz, 1H), 4.64 (dd, J=11.8, 4.6 Hz, 1H), 4.59 (dd, J=11.7, 7.5 Hz, 1H), 1.88 (d, J=1.0 Hz, 3H), 1.82 (dd, J=6.9, 1.1 Hz, 3H).

Step 4. Synthesis of (R)-2-(5-(6-aminopyridin-2-yl)-1H-tetrazol-1-yl)propyl acetate

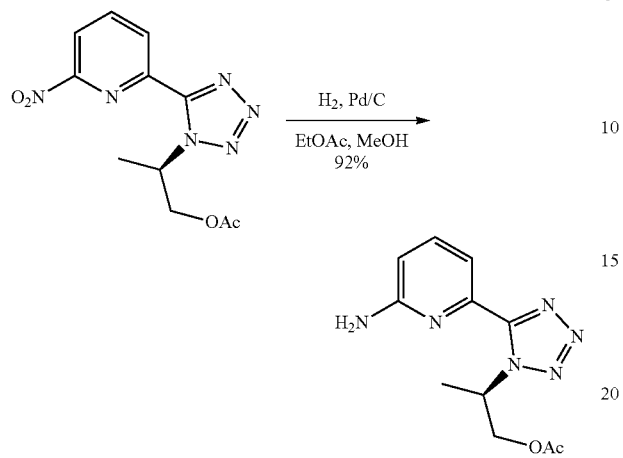

Pd—C (140 mg, 10% loading) was added to a solution of (R)-2-(5-(6-nitropyridin-2-yl)-1H-tetrazol-1-yl)propyl acetate (699 mg, 2.392 mmol) in MeOH (18.4 mL) and EtOAc (18.4 mL). The reaction was evacuated and backfilled with $H_2$ (3×) and the reaction was stirred under a balloon of $H_2$ overnight. The reaction was filtered through Celite, rinsing with DCM. The filtrate was concentrated under reduced pressure, dissolved in DCM, and filtered through Celite, rinsing with DCM. The filtrate was concentrated under reduced pressure to give (R)-2-(5-(6-aminopyridin-2-yl)-1H-tetrazol-1-yl)propyl acetate (575 mg, 2.192 mmol, 92% yield) as a colorless gum that solidified upon standing: $^1$H NMR (500 MHz, Chloroform-d) δ 7.67-7.60 (comp, 2H), 6.66 (d, J=7.0 Hz, 1H), 6.21 (d, J=10.4 Hz, 1H), 4.67 (dd, J=11.4, 4.3 Hz, 1H), 4.30 (dd, J=11.4, 9.4 Hz, 1H), 1.84 (s, 3H), 1.70 (d, J=6.8 Hz, 3H).

Step 5. Synthesis of (R)-2-(5-(6-aminopyridin-2-yl)-1H-tetrazol-1-yl)propan-1-ol

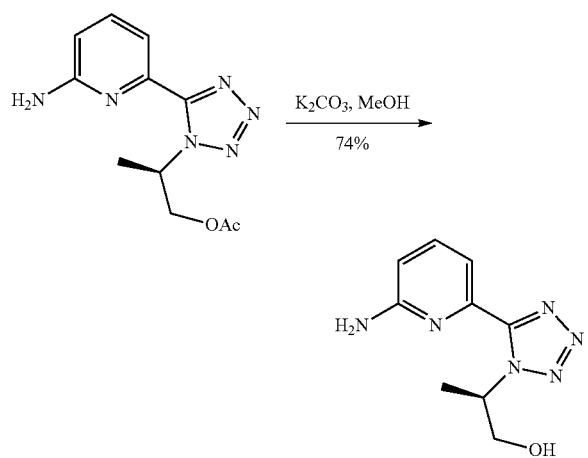

$K_2CO_3$ (1.1 g, 8.20 mmol) was added to a solution of (R)-2-(5-(6-aminopyridin-2-yl)-1H-tetrazol-1-yl)propyl acetate (430 mg, 1.64 mmol) in MeOH (6.6 mL) and the reaction was stirred for 30 min. The reaction was concentrated to remove MeOH and the residue was partitioned between DCM and $H_2O$. The layers were separated and the aqueous layer was extracted with DCM (3×). The combined organic layers were washed with brine, dried ($MgSO_4$), filtered, and concentrated under reduced pressure to give (R)-2-(5-(6-aminopyridin-2-yl)-1H-tetrazol-1-yl)propan-1-ol (327 mg, 1.485 mmol, 91% yield) as a yellow gum: $^1$H NMR (400 MHz, DMSO-$d_6$) δ 7.59 (dd, J=8.4, 7.3 Hz, 1H), 7.27 (dd, J=7.3, 0.8 Hz, 1H), 6.62 (dd, J=8.4, 0.8 Hz, 1H), 6.36 (s, 2H), 5.83-5.76 (m, 1H), 4.96 (t, J=5.6 Hz, 1H), 3.80 (ddd, J=11.2, 8.1, 5.9 Hz, 1H), 3.71 (dt, J=11.0, 5.3 Hz, 1H), 1.52 (d, J=6.8 Hz, 3H).

Step 6. Synthesis of (R)—N-(6-(1-(1-hydroxypropan-2-yl)-1H-tetrazol-5-yl)pyridin-2-yl)-2-isopropyl-1-oxo-2,3-dihydro-1H-pyrrolo[3,4-c]pyridine-6-carboxamide

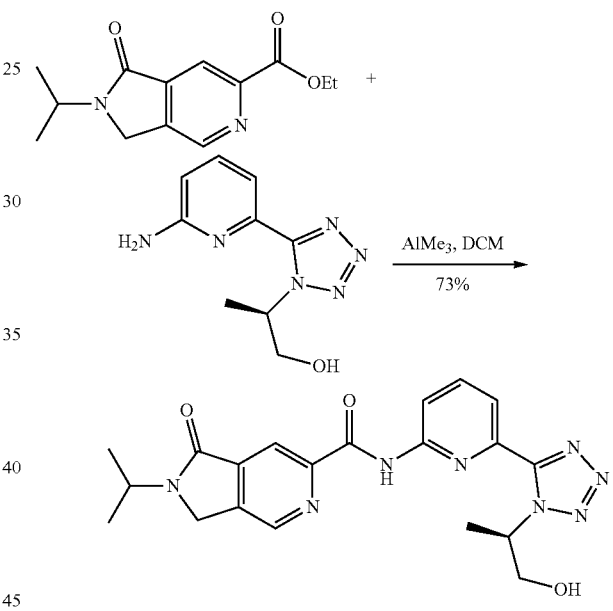

Trimethylaluminum (0.221 mL, 0.441 mmol of a 2.0M solution in toluene) was added dropwise to DCM (0.457 mL) at 0° C. A solution of (R)-2-(5-(6-aminopyridin-2-yl)-1H-tetrazol-1-yl)propan-1-ol (32.4 mg, 0.147 mmol) in DCM (0.457 mL) was added at 0° C., and the mixture was stirred for 20 mins at 0° C. then for 1 h at rt. A solution of ethyl 2-isopropyl-1-oxo-2,3-dihydro-1H-pyrrolo[3,4-c]pyridine-6-carboxylate (36.5 mg, 0.147 mmol) in DCM (0.365 mL) was added and the reaction was heated at 35° C. overnight. The reaction was quenched with sat. potassium sodium tartrate and diluted with $CH_2Cl_2$. The layers were separated and the aqueous layer was extracted with $CH_2Cl$ (2×). The combined organic layers were washed with brine, dried ($MgSO_4$), filtered, and concentrated under reduced pressure. The resultant yellow gum was purified by column chromatography eluting with $CH_2Cl_2$/MeOH (0% MeOH→5% MeOH) to give (R)—N-(6-(1-(1-hydroxypropan-2-yl)-1H-tetrazol-5-yl)pyridin-2-yl)-2-isopropyl-1-oxo-2,3-dihydro-1H-pyrrolo[3,4-c]pyridine-6-carboxamide (45.6 mg, 0.108 mmol, 73% yield) as a tan solid.

Example 53: Synthesis of benzyl 6-fluoro-7-((6-(4-isopropyl-4H-1,2,4-triazol-3-yl)pyridin-2-yl)carbamoyl)-3,4-dihydroisoquinoline-2(1H)-carboxylate

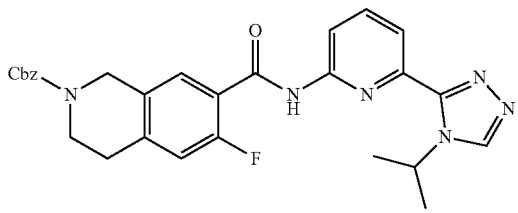 [SMILES: CC(C)n1cnnc1-c1cccc(NC(=O)c2cc3c(cc2F)CCN(C(=O)OCc2ccccc2)C3)n1]

Step 1. Synthesis of 7-bromo-6-fluoro-1,2,3,4-tetrahydroisoquinoline

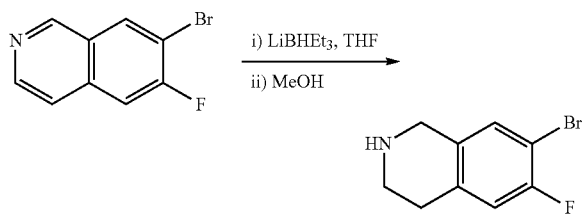

Lithium triethylborohydride (9.73 ml, 9.73 mmol of a 1.0M solution in THF) was added dropwise to a solution of 7-bromo-6-fluoroisoquinoline (1.0 g, 4.42 mmol) in THF (27.6 ml) and the reaction was stirred for 5 hr. The reaction was quenched with MeOH until gas evolution ceased. The reaction was diluted with 1 M HCl and MTBE, and the layers were separated. The aqueous layer was extracted with MTBE (2×). The aqueous layer was made basic (pH 14) with 1 M NaOH, then extracted with DCM (5×). The combined organic layers were dried (MgSO$_4$), filtered, and concentrated under reduced pressure to give 823 mg of crude 7-bromo-6-fluoro-1,2,3,4-tetrahydroisoquinoline as a yellow oil that was used without further purification: $^1$H NMR (400 MHz, Chloroform-d) δ 7.18 (d, J=6.9 Hz, 1H), 6.85 (d, J=9.2 Hz, 1H), 3.95 (s, 2H), 3.10 (t, J=6.0 Hz, 2H), 2.73 (t, J=6.0 Hz, 2H).

Step 2. Synthesis of benzyl 7-bromo-6-fluoro-3,4-dihydroisoqunine-2(1H)-carboxylate

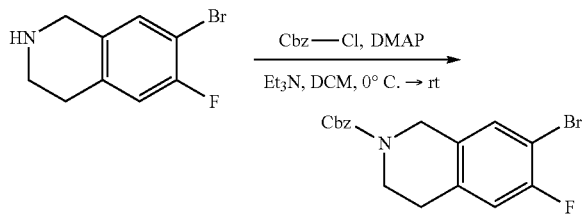

Cbz-Cl (0.77 mL, 5.4 mmol) was added dropwise to a solution of crude 7-bromo-6-fluoro-1,2,3,4-tetrahydroisoquinoline (823 mg, 3.6 mmol), Et$_3$N (1.1 mL, 7.9 mmol), and DMAP (43.7 mg, 0.36 mmol) in DCM (7.2 mL) at 0° C. The reaction was stirred overnight, warming slowly to rt. The reaction was quenched with sat. NaHCO$_3$ and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant yellow oil was purified by column chromatography eluting with hexanes/EtOAc (0% EtOAc→20% EtOAc) to give benzyl 7-bromo-6-fluoro-3,4-dihydroisoquinoline-2(1H)-carboxylate (704 mg, 1.93 mmol, 54% yield over two steps) as a pale yellow oil: $^1$H NMR (400 MHz, Chloroform-d) δ 7.43-7.27 (comp, 6H), 6.91 (d, J=9.0 Hz, 1H), 5.18 (s, 2H), 4.59 (s, 2H), 3.70 (t, J=5.9 Hz, 2H), 2.80 (br s, 2H).

Step 3. Synthesis of 2-((benzyloxy)carbonyl)-6-fluoro-1,2,3,4-tetrahydroisoquinoline-7-carboxylic acid

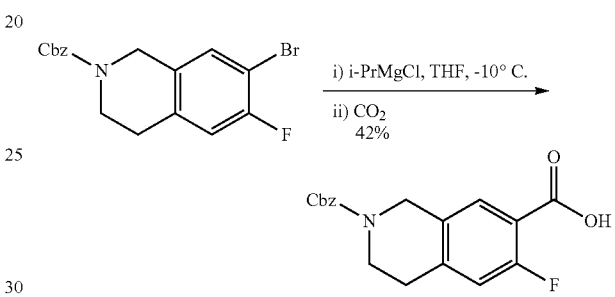

Isopropylmagnesium chloride (1.4 mL, 2.7 mmol of a 2.0M solution in THF) was added dropwise (maintaining internal temperature below 5° C.) to a solution of 7-bromo-6-fluoro-3,4-dihydroisoquinoline-2(1H)-carboxylate (704 mg, 1.9 mmol) in THF (8.4 mL) at −10° C. The reaction was stirred for 1 h at −10° C. CO$_2$ was passed through a tube containing drierite and bubbled slowly through the reaction mixture (exothermic) for 15 min. The cold bath was removed and the reaction was stirred for 1 h at rt. The reaction was quenched with sat. NH$_4$Cl and diluted with EtOAc. The layers were separated and the aqueous layer was extracted with EtOAc (2×). The combined organic layers were dried (MgSO$_4$), filtered, and concentrated under reduced pressure. The resultant pale yellow oil was purified by column chromatography eluting with CH$_2$C$_1$/MeOH (0% MeOH→10% MeOH) to give 2-((benzyloxy)carbonyl)-6-fluoro-1,2,3,4-tetrahydroisoquinoline-7-carboxylic acid (265 mg, 0.805 mmol, 42% yield) as a pale yellow amorphous solid: $^1$H NMR (500 MHz, Chloroform-d) δ 7.77 (br s, 1H), 7.43-7.29 (comp, 6H), 6.96 (d, J=11.0 Hz, 1H), 5.19 (s, 2H), 4.66 (s, 2H), 3.74 (br s, 2H), 2.90 (br s, 2H).

The synthesis of example 53 was completed using the representative procedure for acid chloride formation with oxalyl chloride, followed by the representative procedure 1 for amide formation.

Example 31 was prepared according to the procedure for the synthesis of example 53, utilizing 6-(1-isopropyl-1H-tetrazol-5-yl)pyridin-2-amine as the amine coupling partner during the representative procedure 1 for amide formation.

Example 109 was prepared according to the procedure for the synthesis of example 53, utilizing (R)-2-(5-(6-aminopyridin-2-yl)-1H-tetrazol-1-yl)propyl acetate as the amine coupling partner during the representative procedure 1 for amide formation.

Example 83: Synthesis of benzyl 6-fluoro-7-((6-(5-isopropyl-1H-tetrazol-1-yl)pyridin-2-yl)carbamoyl)-3,4-dihydroisoquinoline-2(1H)-carboxylate

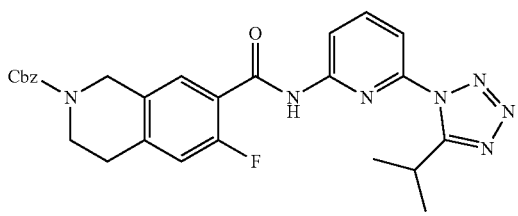 [SMILES: CC(C)c1nnnn1-c1cccc(NC(=O)c2cc3c(cc2F)CCN(C(=O)OCc2ccccc2)C3)n1]

Step 1. Synthesis of N-(6-chloropyridin-2-yl)isobutyramide

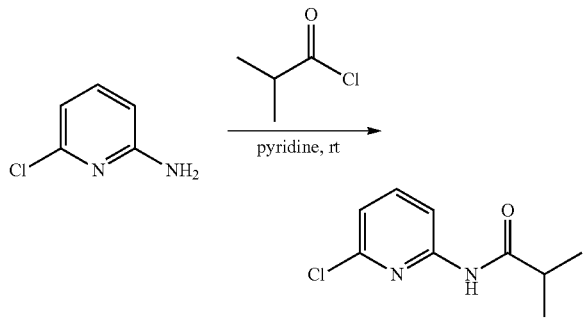

To a solution of 6-chloropyridin-2-amine (1.04 g, 8.09 mmol) in pyridine/DCM (16.4 mL, 1/4) was added isobutyryl chloride (0.91 mL, 8.49 mmol) dropwise at 0° C. The reaction was stirred at 0° C. for 30 min and then at rt for 1 h. The reaction was diluted with DCM and washed with aq. NH$_4$Cl and brine. The organic layer was dried (Na$_2$SO$_4$), filtered, and concentrated under reduced pressure. The crude residue was purified by chromatography on silica gel (0% acetone→20% acetone in hexanes) to provide N-(6-chloro-pyridin-2-yl)isobutyramide as white solid (1.5 g, 95%): $^1$H NMR (500 MHz, Chloroform-d) δ 8.19 (d, J=8.2 Hz, 1H), 7.85 (s, br, 1H), 7.68 (t, J=8.0 Hz, 1H), 7.08 (d, J=7.8 Hz, 1H), 2.62-2.48 (m, 1H), 1.29 (d, J=6.9 Hz, 6H).

Step 2. Synthesis of (Z)—N-(6-chloropyridin-2-yl)isobutyrimidoyl chloride

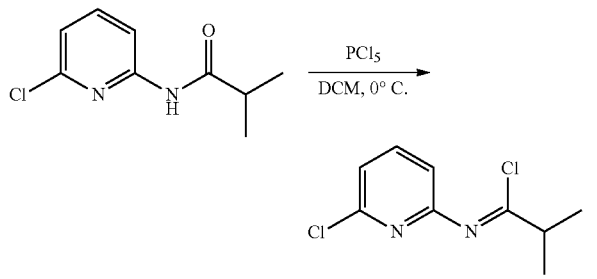

To a solution of N-(6-chloropyridin-2-yl)isobutyramide (1.5 g, 7.67 mmol) in DCM (38 mL) was added PCl$_5$ (1.76 g, 8.05 mmol). The resulting clear solution was stirred at rt for 1 hr. The reaction was concentrated under reduced pressure and directly used in the next step without any purification.

Step 3. Synthesis of 2-chloro-6-(5-isopropyl-1H-tetrazol-1-yl)pyridine

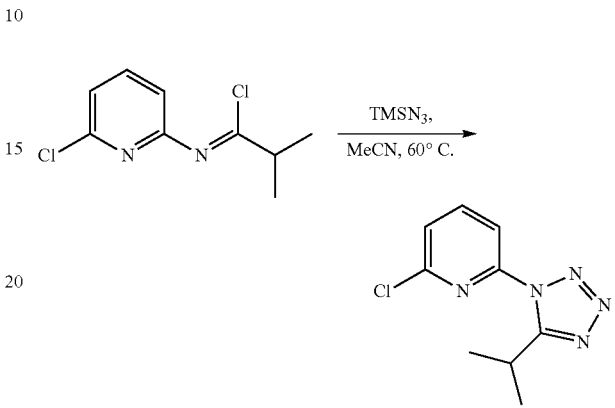

To a solution of (Z)—N-(6-chloropyridin-2-yl)isobutyrimidoyl chloride (0.89 g, 4.09 mmol) in MeCN (10.2 mL) was added TMSN$_3$ (1.09 mL, 8.17 mmol). The reaction was stirred at 60° C. for 2 days. The reaction was cooled to rt and quenched carefully with aq. NaHCO$_3$ and extracted with EtOAc (3×). The combined organic layers were washed with brine, dried (Na$_2$SO$_4$), filtered and concentrated under reduced pressure. The crude residue was purified by chromatography on silica gel (0% EtOAc→30% EtOAc in hexanes) to afford 2-chloro-6-(5-isopropyl-1H-tetrazol-1-yl)pyridine as white solid (396 mg, 43% yield): $^1$H NMR (400 MHz, Chloroform-d) δ 8.00-7.93 (m, 2H), 7.56-7.43 (m, 1H), 4.06-3.94 (m, 1H), 1.51 (d, J=6.9 Hz, 6H).

Step 4. Synthesis of N-(6-(5-isopropyl-1H-tetrazol-1-yl)pyridin-2-yl)-1,1-diphenylmethanimine

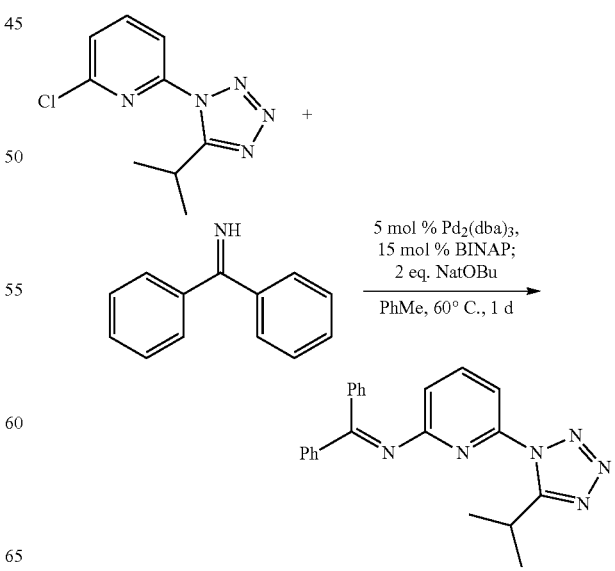

To a solution of 2-chloro-6-(5-isopropyl-1H-tetrazol-1-yl)pyridine (102 mg, 0.456 mmol) in toluene (2.3 mL) was added diphenylmethanimine (0.115 mL, 0.685 mmol), tris(dibenzylideneacetone)dipalladium(0) (20.9 mg, 0.023 mmol), (±)-BINAP (28.4 mg, 0.046 mmol) and sodium tert-butoxide (65.8 mg, 0.685 mmol). The reaction was stirred at 60° C. overnight. The reaction was quenched with aq. NaHCO$_3$, and extracted with EtOAc (3×). The combined organic layers were washed with brine, dried (Na$_2$SO$_4$), filtered, and concentrated under reduced pressure. The crude residue was purified by chromatography on silica gel (0% EtOAc→20% EtOAc in hexanes) to afford N-(6-(5-isopropyl-1H-tetrazol-1-yl)pyridin-2-yl)-1,1-diphenylmethanimine as an off white solid (112.4 mg, 67% yield): LC-MS, ES$^+$: m/z 369.16 [M+H]$^+$.

Step 5. Synthesis of 6-(5-isopropyl-1H-tetrazol-1-yl)pyridin-2-amine

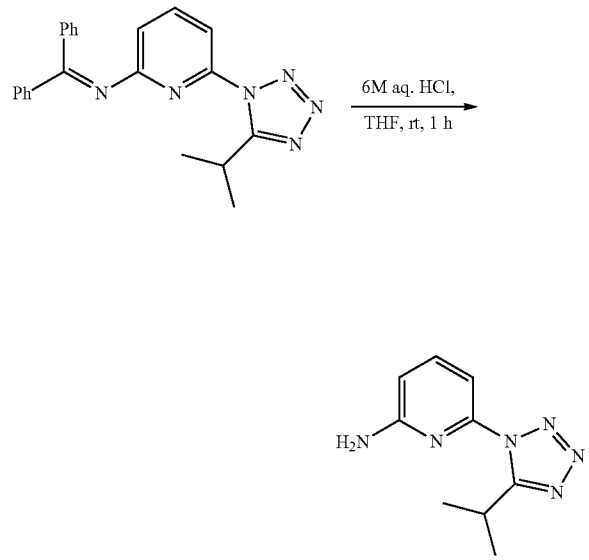

To a solution of N-(6-(5-isopropyl-1H-tetrazol-1-yl)pyridin-2-yl)-1,1-diphenylmethanimine (112.4 mg, 0.305 mmol) in THF (1.5 mL) was added aq. HCl solution (6N, 0.763 mL) and the reaction was stirred at rt for 1 hr. The reaction was quenched with aq. NaHCO$_3$, and extracted with EtOAc (3×). The combined organic layers were washed with brine, dried (Na$_2$SO$_4$), filtered, and concentrated under reduced pressure. The crude residue was purified by chromatography on silica gel (0% EtOAc→60% EtOAc in hexanes) to afford 6-(5-isopropyl-1H-tetrazol-1-yl)pyridin-2-amine as white solid (47 mg, 75% yield): LC-MS, ES$^+$: m/z 205.10 [M+H]$^+$; $^1$H NMR (400 MHz, Chloroform-d) δ 7.71-7.61 (m, 1H), 7.18 (dd, J=7.7, 0.7 Hz, 1H), 6.59 (dd, J=8.2, 0.7 Hz, 1H), 4.62 (s, 2H), 3.89 (p, J=6.9 Hz, 1H), 1.44 (d, J=7.0 Hz, 6H).

Example 83 was prepared according to the procedure for the synthesis of example 53, utilizing 6-(5-isopropyl-1H-tetrazol-1-yl)pyridin-2-amine as the amine coupling partner during the representative procedure 1 for amide formation.

Examples 27, 58, 71, and 81 were prepared according to the representative procedure for hydrogenolysis.

Example 20: Synthesis of 2-(N-cyclopropylsulfamoyl)-6-fluoro-N-(6-(4-isopropyl-4H-1,2,4-triazol-3-yl)pyridin-2-yl)-1,2,3,4-tetrahydroisoquinoline-7-carboxamide

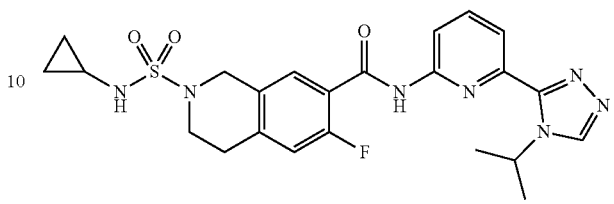

Representative Procedure for Primary Sulfonyl Urea Formation

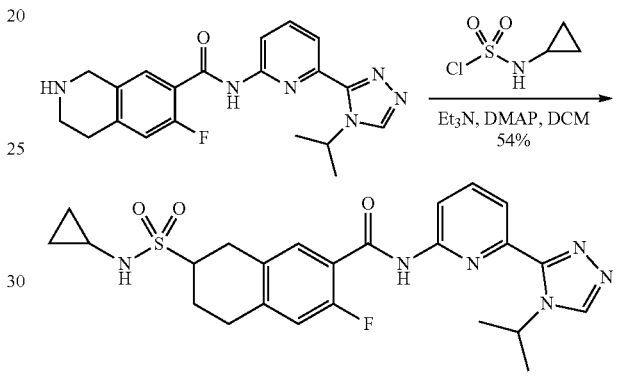

Cyclopropylsulfamoyl chloride (12 μL, 0.075 mmol) was added dropwise to a solution of 6-fluoro-N-(6-(4-isopropyl-4H-1,2,4-triazol-3-yl)pyridin-2-yl)-1,2,3,4-tetrahydroisoquinoline-7-carboxamide (19 mg, 0.050 mmol), DMAP (0.61 mg, 5.0 μmol), and Et$_3$N (15 μL, 0.110 mmol) in DCM (0.50 mL) and the reaction was stirred overnight. The reaction was purified by column chromatography eluting with CH$_2$Cl$_2$/MeOH (0% MeOH→8% MeOH) to give 2-(N-cyclopropyl sulfamoyl)-6-fluoro-N-(6-(4-isopropyl-4H-1,2,4-triazol-3-yl)pyridin-2-yl)-1,2,3,4-tetrahydroisoquinoline-7-carboxamide (13.5 mg, 0.027 mmol, 54% yield) as a colorless amorphous solid.

Example 22 was prepared according to the representative procedure for primary sulfonyl urea formation.

Examples 21, 23, 40, 42, 43, 46, 47, 55, 84, 85, 86, 87, 88, 100, 102, and 103 were prepared according to the representative procedure for sulfonamide formation.

Example 24: Synthesis of 6-fluoro-N-(6-(4-isopropyl-4H-1,2,4-triazol-3-yl)pyridin-2-yl)-2-(3-methoxypropanoyl)-1,2,3,4-tetrahydroisoquinoline-7-carboxamide

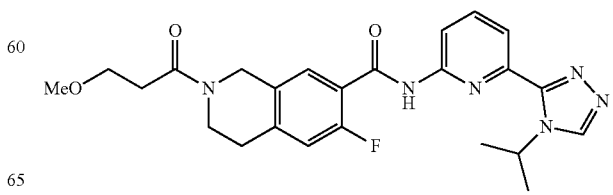

Representative Procedure 2 for Amide Formation

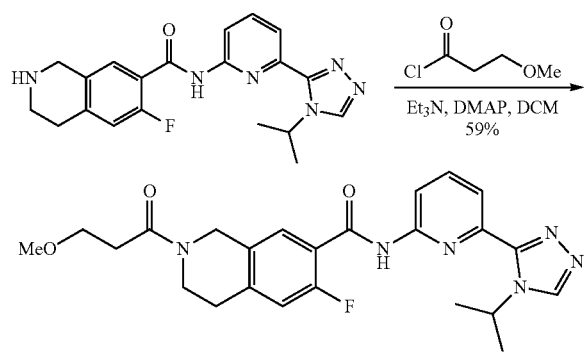

3-Methoxypropanoyl chloride (10.6 µl, 0.087 mmol) was added dropwise to a solution of 6-fluoro-N-(6-(4-isopropyl-4H-1,2,4-triazol-3-yl)pyridin-2-yl)-1,2,3,4-tetrahydroisoquinoline-7-carboxamide (22 mg, 0.058 mmol), DMAP (0.7 mg, 5.7 µmol), and Et₃N (18.0 µL, 0.127 mmol) in DCM (0.58 mL) and the reaction was stirred 3 h. The reaction was purified by column chromatography eluting with CH₂Cl₂/MeOH (0% MeOH→8% MeOH) to give 6-fluoro-N-(6-(4-isopropyl-4H-1,2,4-triazol-3-yl)pyridin-2-yl)-2-(3-methoxypropanoyl)-1,2,3,4-tetrahydroisoquinoline-7-carboxamide (16 mg, 0.034 mmol, 59% yield) as a pale yellow amorphous solid.

Examples 24, 28, 50, 90, 91, 92, 97, 104, 105, and 106 were prepared according to the representative procedure 2 for amide formation.

Examples 25, 26, 30, and 57 were prepared according to the representative procedure for carbamate formation.

Example 29: Synthesis of N2-ethyl-6-fluoro-N7-(6-(1-isopropyl-1H-tetrazol-5-yl)pyridin-2-yl)-3,4-dihydroisoquinoline-2,7(1H)-dicarboxamide

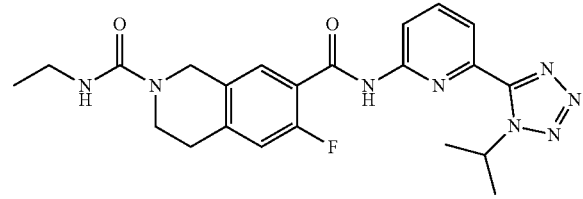 [SMILES: CCNC(=O)N1CCc2cc(F)c(C(=O)Nc3cccc(-c4nnnn4C(C)C)n3)cc2C1]

Representative Procedure for Primary Urea Formation

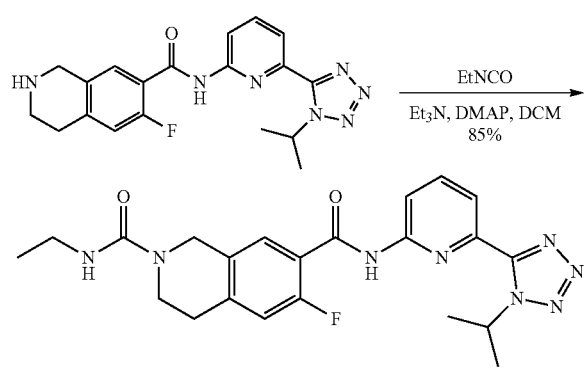

Ethyl isocyanate (7.4 µl, 0.094 mmol) was added dropwise to a solution of 6-fluoro-N-(6-(1-isopropyl-1H-tetrazol-5-yl)pyridin-2-yl)-1,2,3,4-tetrahydroisoquinoline-7-carboxamide (24 mg, 0.063 mmol), DMAP (0.77 mg, 6.3 µmol), and Et₃N (19.0 µL, 0.138 mmol) in DCM (0.63 mL) and the reaction was stirred overnight. The reaction was purified by column chromatography eluting with CH₂Cl₂/MeOH (0% MeOH→8% MeOH) to give N2-ethyl-6-fluoro-N7-(6-(1-isopropyl-1H-tetrazol-5-yl)pyridin-2-yl)-3,4-dihydroisoquinoline-2,7(1H)-dicarboxamide (24.2 mg, 0.053 mmol, 85% yield) as a white amorphous solid.

Examples 51, 52, and 56 were prepared according to the representative procedure for primary urea formation.

Examples 41, 44, 45, 48, 72, 73, 77, 78, 79, 80, 93, 94, 95, 96, 99, 101, and 107 were prepared according to the representative procedure for secondary urea formation.

Examples 49 and 89 were prepared according to the representative procedure for secondary sulfonyl urea formation.

Example 54: Synthesis of 6-fluoro-N-(6-(1-isopropyl-1H-tetrazol-5-yl)pyridin-2-yl)-2-phenyl-1,2,3,4-tetrahydroisoquinoline-7-carboxamide

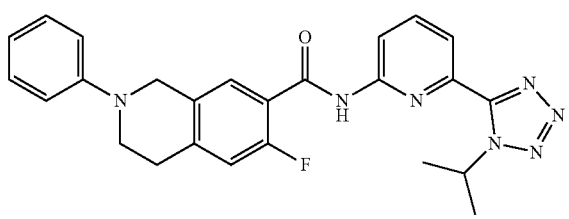 [SMILES: CC(C)n1nnnc1-c1cccc(NC(=O)c2cc3c(cc2F)CCN(c2ccccc2)C3)n1]

Representative Procedure for C—N Coupling

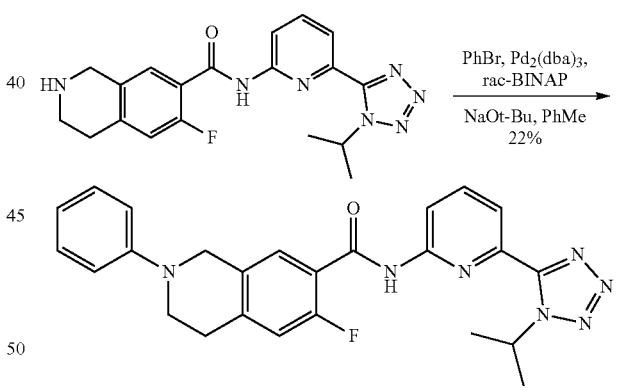

A solution of Pd₂(dba)₃ (2.9 mg, 3.15 µmol) and (±)-BINAP (3.9 mg, 6.29 µmol) in toluene (0.25 mL) was sparged with N₂ for 10 min. The mixture was heated at 110° C. for 10 min. The reaction was cooled to rt whereupon sodium tert-butoxide (13.3 mg, 0.138 mmol), bromobenzene (13.0 µL, 0.126 mmol), and 6-fluoro-N-(6-(1-isopropyl-1H-tetrazol-5-yl)pyridin-2-yl)-1,2,3,4-tetrahydroisoquinoline-7-carboxamide (24 mg, 0.063 mmol) were added and the reaction was heated at 110° C. overnight. The reaction was filtered through Celite, rinsing with EtOAc. The filtrate was concentrated under reduced pressure and purified by column chromatography eluting with hexanes/EtOAc (0% EtOAc→50% EtOAc) to give 6-fluoro-N-(6-(1-isopropyl-1H-tetrazol-5-yl)pyridin-2-yl)-2-phenyl-1,2,3,4-tetrahydroisoquinoline-7-carboxamide (6.3 mg, 0.014 mmol, 22% yield) as a pale yellow solid.

Example 75: Synthesis of (R)-6-fluoro-N7-(6-(1-(1-hydroxypropan-2-yl)-1H-tetrazol-5-yl)pyridin-2-yl)-N2-methyl-N2-(2,2,2-trifluoroethyl)-3,4-dihydroisoquinoline-2,7(1H)-dicarboxamide

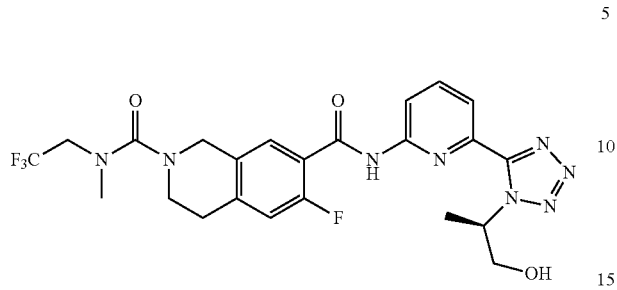

Representative Procedure for Acetate Deprotection

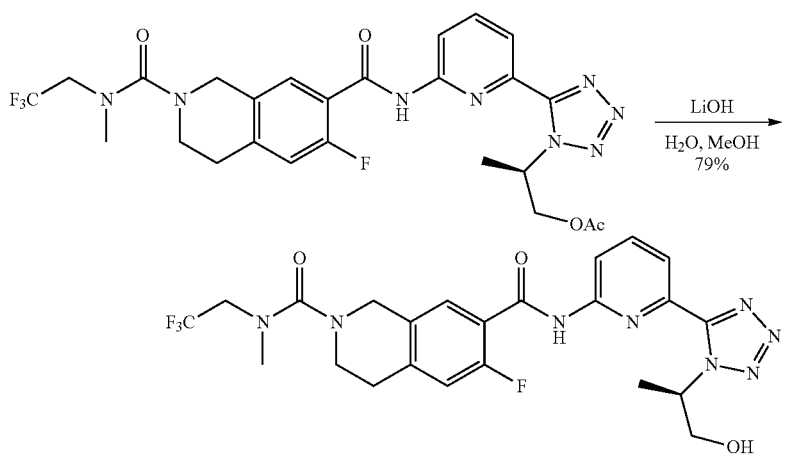

Lithium hydroxide (0.056 mL, 0.056 mmol of a 1.0M solution in H₂O) was added to a solution of (R)-2-(5-(6-(6-fluoro-2-(methyl(2,2,2-trifluoroethyl)carbamoyl)-1,2,3,4-tetrahydroisoquinoline-7-carboxamido)pyridin-2-yl)-1H-tetrazol-1-yl)propyl acetate (27 mg, 0.047 mmol) in MeOH (0.78 mL) and the reaction was stirred for 1 h. The reaction was concentrated under reduced pressure and the residue was diluted with DCM/EtOAc. The mixture was dried (MgSO₄), filtered, and concentrated under reduced pressure. The resultant colorless residue was purified by column chromatography eluting with CH₂Cl₂/MeOH (0% MeOH→6% MeOH) to give (R)-6-fluoro-N7-(6-(1-(1-hydroxypropan-2-yl)-1H-tetrazol-5-yl)pyridin-2-yl)-N₂-methyl-N2-(2,2,2-trifluoroethyl)-3,4-dihydroisoquinoline-2,7(1H)-dicarboxamide (19.7 mg, 0.037 mmol, 79% yield) as a colorless amorphous solid.

Examples 76 and 82 were prepared according to the representative procedure for acetate deprotection.

Example 67: Synthesis of benzyl 7-((6-(4-isopropyl-4H-1,2,4-triazol-3-yl)pyridin-2-yl)carbamoyl)-3,4-dihydroisoquinoline-2(1H)-carboxylate

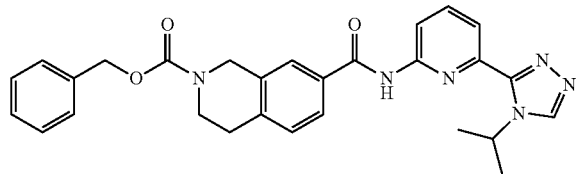 [SMILES: CC(C)n1cnnc1-c1cccc(NC(=O)c2ccc3c(c2)CN(C(=O)OCc2ccccc2)CC3)n1]

Step 1. Synthesis of 2-benzyl 7-methyl 3,4-dihydroisoquinoline-2,7(1H)-dicarboxylate

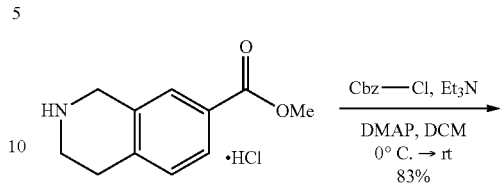

-continued

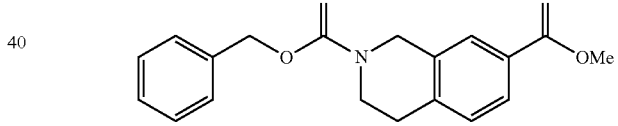

Benzyl chloroformate (0.94 mL, 6.6 mmol, 1.5 eq) was added dropwise to a solution of methyl 1,2,3,4-tetrahydroisoquinoline-7-carboxylate hydrochloride (1.0 g, 4.4 mmol, 1.0 eq), Et₃N (1.35 mL, 9.7 mmol, 2.2 mmol), and DMAP (52 mg, 0.43 mmol, 0.1 eq) in DCM (4.4 mL) at 0° C. The reaction was stirred overnight, warming to room temperature. The reaction was quenched with sat. NaHCO₃ and diluted with DCM. The layers were separated and the aqueous layer was extracted with DCM (2×). The combined organic layers were dried (MgSO₄), filtered, and concentrated under reduced pressure. The resultant orange gum was purified by column chromatography eluting with hexanes/EtOAc (0% EtOAc→30% EtOAc) to afford 2-benzyl 7-methyl 3,4-dihydroisoquinoline-2,7(1H)-dicarboxylate (1.2 g, 3.7 mmol, 83%) as a clear, colorless oil: ¹H NMR (400 MHz, DMSO-d₆) δ 7.81 (d, J=1.7 Hz, 1H), 7.76 (dd, J=7.9, 1.8 Hz, 1H), 7.42-7.29 (comp, 6H), 5.13 (s, 2H), 4.65 (d, J=18.9 Hz, 2H), 3.83 (s, 3H), 3.65 (s, 2H), 2.88 (t, J=5.9 Hz, 2H).

Step 2. Synthesis of 2-((benzyloxy)carbonyl)-1,2,3,4-tetrahydroisoquinoline-7-carboxylic acid

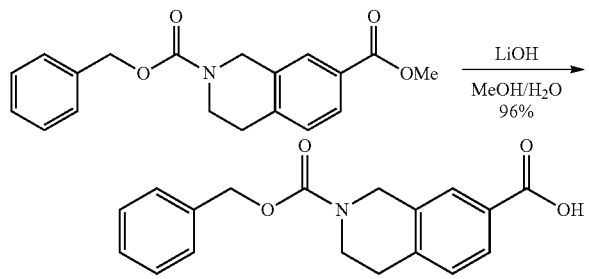

A solution of LiOH (0.77 g, 18.3 mmol, 5.0 eq) in H₂O (9.8 mL) was added to a solution of 2-benzyl 7-methyl 3,4-dihydroisoquinoline-2,7(1H)-dicarboxylate (1.2 g, 3.7 mmol, 1.0 eq) in MeOH (14.6 mL) and the reaction was stirred for 2 hrs. The reaction was partitioned between MTBE and H₂O. The layers were separated and the aqueous layer was adjusted to an acidic pH (~5) with 0.1M aqueous HCl. The resulting mixture was extracted with EtOAc (2×). The combined organic layers were dried (MgSO₄), filtered, and concentrated under reduced pressure to afford 2-((benzyloxy)carbonyl)-1,2,3,4-tetrahydroisoquinoline-7-carboxylic acid (1.1 g, 3.5 mmol, 96%) as a pale yellow solid: $^1$H NMR (400 MHz, DMSO-d₆) δ 7.77 (d, J=1.7 Hz, 1H), 7.73 (dd, J=7.9, 1.7 Hz, 1H), 7.42-7.30 (comp, 4H), 7.29 (d, J=8.0 Hz, 1H), 5.13 (s, 2H), 4.64 (d, J=20.0 Hz, 2H), 3.65 (d, J=6.7 Hz, 2H), 2.87 (t, J=5.9 Hz, 2H).

Example 37 was prepared according to the representative procedure for hydrogenolysis.

Examples 32 and 60 were prepared according to the representative procedure 2 for amide formation.

Examples 33, 61, 62, and 63 were prepared according to the representative procedure for primary urea formation.

Examples 34, 35, 36, 64, 65, and 66 were prepared according to the representative procedure for carbamate formation.

Example 38: Synthesis of N-(6-(4-isopropyl-4H-1,2,4-triazol-3-yl)pyridin-2-yl)-2-(3-methoxypropyl)-1,2,3,4-tetrahydroisoquinoline-7-carboxamide

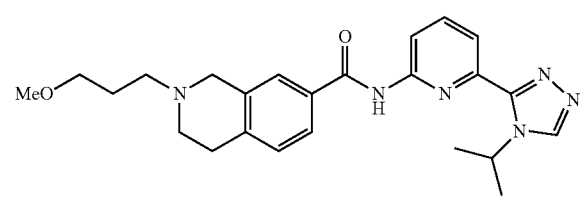 [SMILES: COCCCN1CCc2ccc(C(=O)Nc3cccc(-c4nncn4C(C)C)n3)cc2C1]

Representative Procedure for Reductive Alkylation

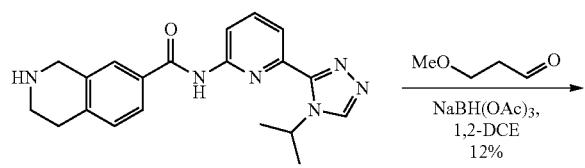

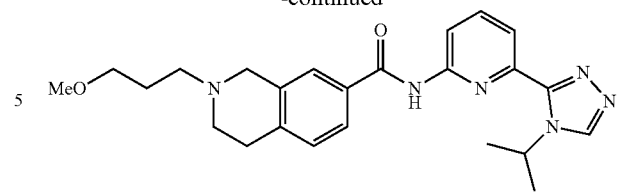

Sodium triacetoxyborohydride (85 mg, 0.40 mmol, 5.0 eq) was added to a solution of N-(6-(4-isopropyl-4H-1,2,4-triazol-3-yl)pyridin-2-yl)-1,2,3,4-tetrahydroisoquinoline-7-carboxamide (29 mg, 0.08 mmol, 1.0 eq) and 3-methoxypropanal (35 μL, 0.40 mmol, 5.0 eq) in 1,2-DCE (1 mL) and the reaction was stirred overnight. The reaction was quenched with sat. NaHCO₃ and diluted with DCM. The layers were separated and the aqueous layer was extracted with DCM (2×). The combined organic layers were dried (MgSO₄), filtered, and concentrated under reduced pressure. The resultant yellow residue was purified by column chromatography eluting with DCM/MeOH (0% MeOH→20% MeOH) to afford N-(6-(4-isopropyl-4H-1,2,4-triazol-3-yl)pyridin-2-yl)-2-(3-methoxypropyl)-1,2,3,4-tetrahydroisoquinoline-7-carboxamide (4.1 mg, 9.4 μmol, 12%) as a yellow gum.

Example 59: Synthesis of allyl 7-((6-(4-isopropyl-4H-1,2,4-triazol-3-yl)pyridin-2-yl)carbamoyl)-3,4-dihydroisoquinoline-2(1H)-carboxylate

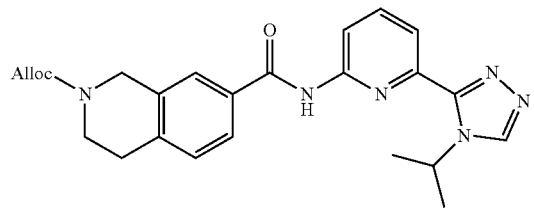

Step 1. Synthesis of 2-allyl 7-methyl 3,4-dihydroisoquinoline-2,7(1H)-dicarboxylate

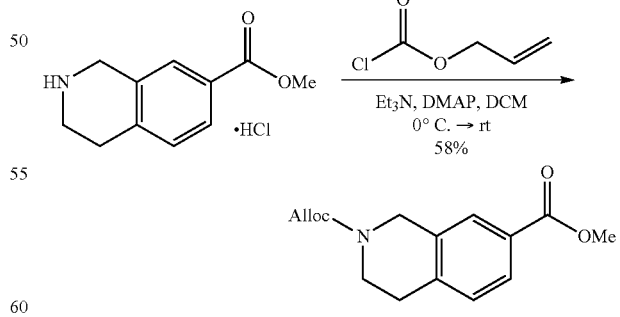

Allyl chloroformate (0.70 mL, 6.6 mmol, 1.5 eq) was added dropwise to a solution of methyl 1,2,3,4-tetrahydroisoquinoline-7-carboxylate hydrochloride (1.0 g, 4.4 mmol, 1.0 eq), Et₃N (1.35 mL, 9.7 mmol, 2.2 mmol), and DMAP (52 mg, 0.43 mmol, 0.1 eq) in DCM (4.4 mL) at 0° C. The reaction was stirred overnight, warming to room temperature. The reaction was quenched with sat. NaHCO₃ and diluted with DCM. The layers were separated and the aqueous layer was extracted with DCM (2×). The combined organic layers were dried (MgSO₄), filtered, and concentrated under reduced pressure. The resultant orange gum was purified by column chromatography eluting with hexanes/EtOAc (0% EtOAc→30% EtOAc) to afford 2-allyl 7-methyl 3,4-dihydroisoquinoline-2,7(1H)-dicarboxylate (0.7 g, 2.5 mmol, 58%) as a clear, colorless oil: LC-MS, ES⁺: m/z 276.10 [M+H]⁺; ¹H NMR (400 MHz, DMSO-d₆) δ 7.81 (d, J=1.7 Hz, 1H), 7.76 (dd, J=8.0, 1.8 Hz, 1H), 7.32 (d, J=8.0 Hz, 1H), 5.95 (ddt, J=17.3, 10.5, 5.2 Hz, 1H), 5.31 (dq, J=17.3, 1.7 Hz, 1H), 5.20 (dq, J=10.5, 1.5 Hz, 1H), 4.63 (d, J=15.3 Hz, 2H), 4.58 (dt, J=5.3, 1.6 Hz, 2H), 3.84 (s, 3H), 3.64 (d, J=7.0 Hz, 2H), 2.88 (t, J=6.0 Hz, 2H).

Step 2. Synthesis of 2-((allyloxy)carbonyl)-1,2,3,4-tetrahydroisoquinoline-7-carboxylic acid

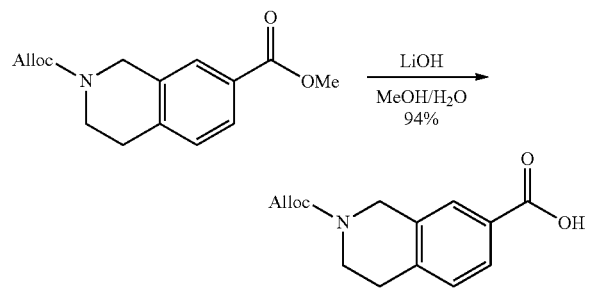

A solution of LiOH (0.25 g, 6.0 mmol, 5.0 eq) in H₂O (3.2 mL) was added to a solution of 2-allyl 7-methyl 3,4-dihydroisoquinoline-2,7(1H)-dicarboxylate (328 mg, 1.2 mmol, 1.0 eq) in MeOH (4.8 mL) and the reaction was stirred for 2 hrs. The reaction was partitioned between MTBE and H₂O. The layers were separated and the aqueous layer was adjusted to an acidic pH (~5) with 0.1M aqueous HCl. The resulting mixture was extracted with EtOAc (2×). The combined organic layers were dried (MgSO₄), filtered, and concentrated under reduced pressure to afford 2-((allyloxy)carbonyl)-1,2,3,4-tetrahydroisoquinoline-7-carboxylic acid (292 mg, 1.2 mmol, 94%) as a colorless gum: ¹H NMR (500 MHz, DMSO-d₆) δ 12.87 (br s, 1H), 7.77 (d, J=1.7 Hz, 1H), 7.74 (dd, J=7.9, 1.7 Hz, 1H), 7.29 (d, J=7.9 Hz, 1H), 5.95 (ddt, J=17.3, 10.5, 5.2 Hz, 1H), 5.31 (dq, J=17.3, 1.7 Hz, 1H), 5.20 (dq, J=10.5, 1.5 Hz, 1H), 4.65-4.57 (comp, 4H), 3.71-3.57 (m, 2H), 2.87 (t, J=6.0 Hz, 2H).

Step 3. Synthesis of allyl 7-(chlorocarbonyl)-3,4-dihydroisoquinoline-2(1H)-carboxylate

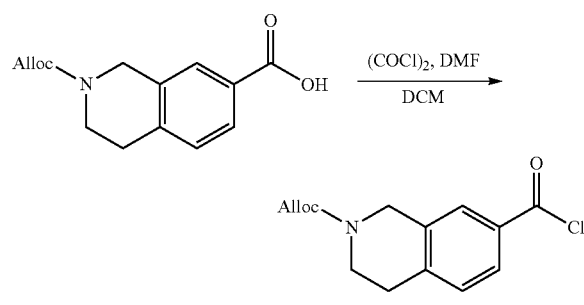

Oxalyl chloride (0.17 mL, 1.9 mmol, 1.7 eq) was added dropwise to a mixture of 2-((allyloxy)carbonyl)-1,2,3,4-tetrahydroisoquinoline-7-carboxylic acid (291 mg, 1.1 mmol, 1.0 eq) and DMF (8.6 μL, 0.11 mmol, 0.1 eq) in DCM (3.1 mL). The mixture was stirred for 1 hr. The reaction was concentrated under reduced pressure to afford crude allyl 7-(chlorocarbonyl)-3,4-dihydroisoquinoline-2(1H)-carboxylate which was used without purification.

Step 4. Synthesis of allyl 7-((6-(4-isopropyl-4H-1,2,4-triazol-3-yl)pyridin-2-yl)carbamoyl)-3,4-dihydroisoquinoline-2(1H)-carboxylate

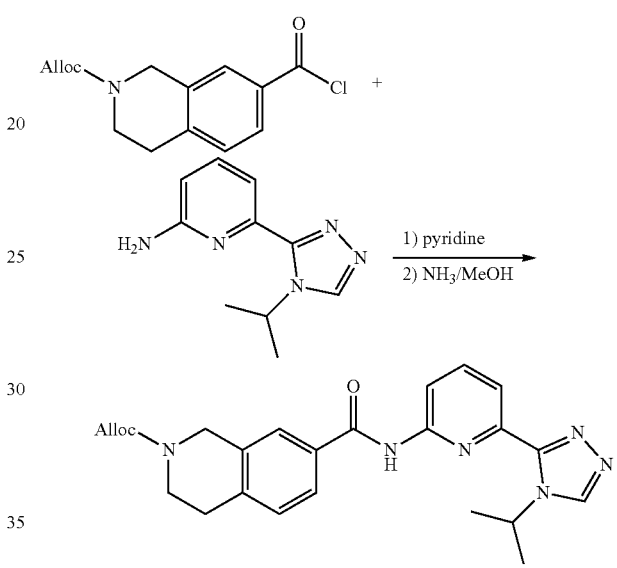

A solution of 6-(4-isopropyl-4H-1,2,4-triazol-3-yl)pyridin-2-amine (205 mg, 1.0 mmol, 1.0 eq), prepared according to US 2014/0018370, in pyridine (2.7 mL) was added to crude allyl 7-(chlorocarbonyl)-3,4-dihydroisoquinoline-2(1H)-carboxylate (312 mg, 1.1 mmol, 1.1 eq) and the reaction was stirred overnight. The reaction was concentrated under reduced pressure. The residue was dissolved in 7N NH₃ in MeOH (7.9 mL) and stirred for 1 hr. The reaction was concentrated under reduced pressure. The resultant brown residue was purified by column chromatography eluting with DCM/MeOH (0% MeOH→6% MeOH) to afford allyl 7-((6-(4-isopropyl-4H-1,2,4-triazol-3-yl)pyridin-2-yl)carbamoyl)-3,4-dihydroisoquinoline-2(1H)-carboxylate (183 mg, 1.0 mmol, 41%) as a tan amorphous solid.

Example 39: Synthesis of 2-allyl-N-(6-(4-isopropyl-4H-1,2,4-triazol-3-yl)pyridin-2-yl)-1,2,3,4-tetrahydroisoquinoline-7-carboxamide

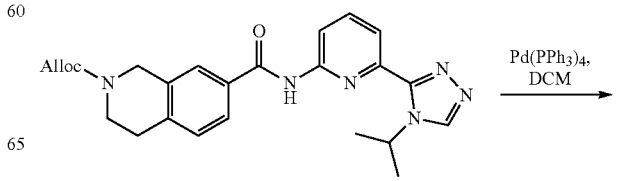

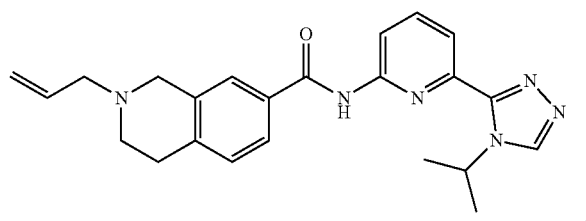

A solution of Pd(PPh₃)₄ (2.7 mg, 2.4 μmol, 0.05 eq) in DCM (0.12 mL) was added to a solution of allyl 7-((6-(4-isopropyl-4H-1,2,4-triazol-3-yl)pyridin-2-yl)carbamoyl)-3,4-dihydroisoquinoline-2(1H)-carboxylate (21 mg, 0.05 mmol, 1.0 eq) in DCM (0.45 mL) and the reaction was stirred for 5 hrs. The reaction was loaded directly onto a column and purified by column chromatography eluting with DCM/MeOH (0% MeOH→15% MeOH) to afford 2-allyl-N-(6-(4-isopropyl-4H-1,2,4-triazol-3-yl)pyridin-2-yl)-1,2,3,4-tetrahydroisoquinoline-7-carboxamide (12 mg, 0.03 mmol, 63%) as a colorless amorphous solid.

Example 74: Synthesis of benzyl 6-fluoro-7-((6-(1-isopropyl-1H-tetrazol-5-yl)pyridin-2-yl)carbamoyl)-1-methyl-3,4-dihydroisoquinoline-2(1H)-carboxylate

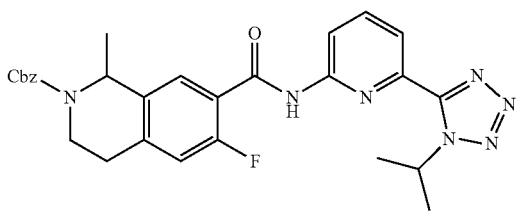 [SMILES: CC1c2cc(C(=O)Nc3cccc(-c4nnnn4C(C)C)n3)c(F)cc2CCN1C(=O)OCc1ccccc1]

Step 1. Synthesis of 7-bromo-6-fluoro-1,2,3,4-tetrahydroisoquinoline

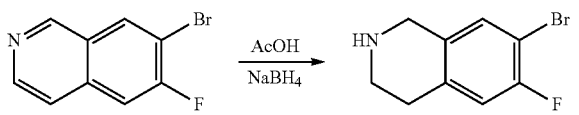 [SMILES: "AcOH" ; Fc1cc2ccncc2cc1Br ; "NaBH4" ; Fc1cc2c(cc1Br)CNCC2]

Sodium borohydride (1.5 g, 38.7 mmol) was added portion wise to a solution of 7-bromo-6-fluoroisoquinoline (2.5 g, 11.1 mmol) in AcOH (55.3 ml) and the reaction was stirred for 2 hr. The reaction was quenched carefully with sat. NaHCO₃ (dropwise, 850 mL) until the mixture was pH ~8, then diluted with CH₂Cl₂ (200 mL). The layers were separated and the aqueous layer was extracted with CH₂Cl₂ (2×150 mL). The combined organic layers were washed with brine, dried (MgSO₄), filtered, and concentrated under reduced pressure to give 2.29 g of crude 7-bromo-6-fluoro-1,2,3,4-tetrahydroisoquinoline as a yellow solid that was used without purification: ¹H NMR (400 MHz, Chloroform-d) δ 7.19 (d, J=7.0 Hz, 1H), 6.85 (dd, J=9.2, 2.5 Hz, 1H), 3.95 (s, 2H), 3.11 (t, J=6.0 Hz, 2H), 2.74 (t, J=6.0 Hz, 2H).

Step 2. Synthesis of 7-bromo-6-fluoro-3,4-dihydroisoquinoline

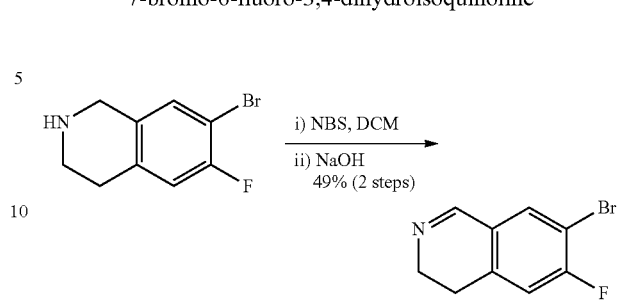

N-Bromosuccinimide (2.2 g, 12.1 mmol) was added portion wise over 20 minutes to a solution of 7-bromo-6-fluoro-1,2,3,4-tetrahydroisoquinoline (2.5 g, 11.0 mmol) in DCM (58.3 mL) and the reaction was stirred for 2 hr. 30% NaOH (15.3 ml) was added and the reaction was stirred for 2.5 hr. The layers were separated and the aqueous layer was extracted with DCM (2×). The organic layer was washed with H₂O. The organic layer was extracted with 10% HCl (3×). The combined acidic extracts were washed with DCM, then made basic with concentrated ammonium hydroxide. This mixture was extracted with DCM (3×). The combined organic layers were dried (MgSO₄), filtered, and concentrated under reduced pressure. The resultant clear gum was purified by column chromatography eluting with hexanes/EtOAc (50% EtOAc→100% EtOAc) to give 7-bromo-6-fluoro-3,4-dihydroisoquinoline (1.23 g, 5.4 mmol, 49% yield) over two steps as a yellow solid: ¹H NMR (400 MHz, Chloroform-d) δ 8.29 (t, J=2.3 Hz, 1H), 7.50 (d, J=6.7 Hz, 1H), 6.96 (dt, J=8.5, 0.9 Hz, 1H), 3.82-3.75 (m, 2H), 2.79-2.70 (m, 2H).

Step 3. Synthesis of benzyl 7-bromo-6-fluoro-1-methyl-3,4-dihydroisoquinoline-2(1H)-carboxylate

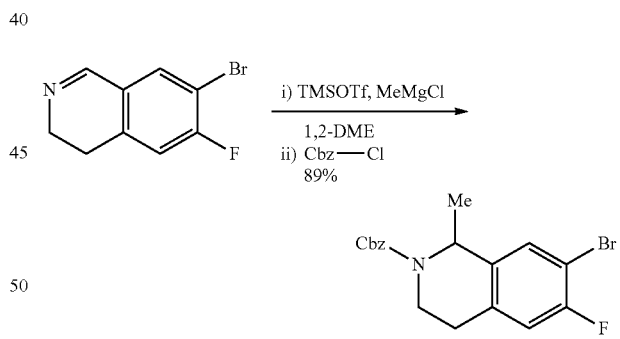

TMSOTf (0.31 mL, 1.71 mmol) was added dropwise to a solution of 7-bromo-6-fluoro-3,4-dihydroisoquinoline (300 mg, 1.315 mmol) in 1,2-dimethoxyethane (1,2-DME) (6.6 mL) at −40° C. The reaction was stirred for 5 min at −40° C., then methylmagnesium chloride (0.88 mL, 2.63 mmol of a 3.0M solution in THF) was added dropwise and the reaction was stirred at −40° C. for 10 min. The cold bath was removed, and the reaction was stirred at rt for 30 min. The reaction was cooled to −40° C., and Cbz-Cl (0.56 mL, 3.95 mmol) was added dropwise. The cold bath was removed and the reaction was stirred for 80 min. The reaction was quenched with sat. NH₄Cl and diluted with H₂O and EtOAc. The layers were separated and the aqueous layer was extracted with EtOAc (2×). The combined organic layers were washed with sat. NaHCO₃, dried (MgSO₄), filtered, and concentrated under reduced pressure. The resultant yellow oil was purified by column chromatography eluting with hexanes/EtOAc (0% EtOAc→20% EtOAc) to give benzyl 7-bromo-6-fluoro-1-methyl-3,4-dihydroisoquinoline-2(1H)-carboxylate (442 mg, 1.17 mmol, 89% yield) as a colorless gum: ¹H NMR (400 MHz, Chloroform-d) δ 7.44-7.27 (comp, 6H), 6.88 (d, J=9.0 Hz, 1H), 5.29-5.13 (comp, 3H), 4.34-4.06 (m, 1H), 3.37-3.10 (m, 1H), 2.93-2.80 (m, 1H), 2.69 (d, J=16.5 Hz, 1H), 1.44 (d, J=6.8 Hz, 3H).

Step 4. Synthesis of 2-((benzyloxy)carbonyl)-6-fluoro-1-methyl-1,2,3,4-tetrahydroisoquinoline-7-carboxylic acid

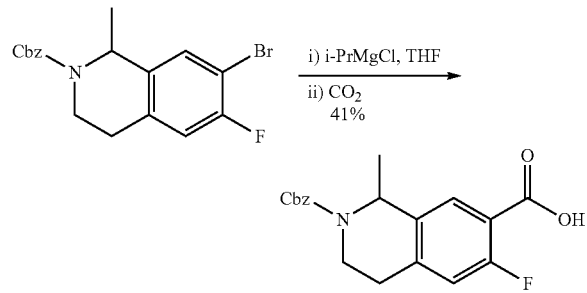

Isopropylmagnesium chloride (0.91 mL, 1.82 mmol) was added dropwise (maintaining internal temperature below 5° C.) to a solution of benzyl 7-bromo-6-fluoro-1-methyl-3,4-dihydroisoquinoline-2(1H)-carboxylate (491 mg, 1.30 mmol) in THF (5.6 mL) at −10° C. The reaction was stirred for 1 h at −10° C. CO₂ was passed through a drying tube containing drierite and was bubbled slowly through the reaction mixture (exothermic) for 15 min. The cold bath was removed and the reaction was stirred for 1 h at rt. The reaction was quenched with sat. NH₄Cl and diluted with EtOAc. The layers were separated and the aqueous layer was extracted with EtOAc (2×). The combined organic layers were dried (MgSO₄), filtered, and concentrated under reduced pressure. The resultant clear gum was purified by column chromatography eluting with CH₂Cl₂/MeOH (0% MeOH→10% MeOH) to give 2-((benzyloxy)carbonyl)-6-fluoro-1-methyl-1,2,3,4-tetrahydroisoquinoline-7-carboxylic acid (181 mg, 0.53 mmol, 41% yield) as a colorless amorphous solid: ¹H NMR (400 MHz, Chloroform-d) δ 7.78 (s, 1H), 7.45-7.29 (comp, 5H), 6.94 (d, J=11.1 Hz, 1H), 5.38-5.17 (comp, 3H), 4.43-4.08 (m, 1H), 3.32-3.24 (m, 1H), 2.96 (br s, 1H), 2.80 (d, J=16.6 Hz, 1H), 1.48 (d, J=6.7 Hz, 3H).

Step 5. Synthesis of benzyl 6-fluoro-7-((6-(1-isopropyl-1H-tetrazol-5-yl)pyridin-2-yl)carbamoyl)-1-methyl-3,4-dihydroisoquinoline-2(1H)-carboxylate

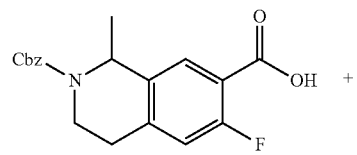

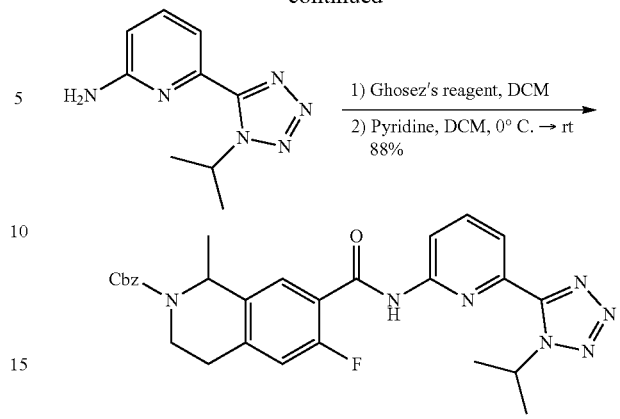

Ghosez's Reagent (0.14 mL, 1.06 mmol) was added dropwise to a solution of 2-((benzyloxy)carbonyl)-6-fluoro-1-methyl-1,2,3,4-tetrahydroisoquinoline-7-carboxylic acid (180 mg, 0.52 mmol) in DCM (1.1 mL) and the reaction was stirred for 3 h. The reaction was concentrated under reduced pressure, chased with DCM, and dried under hi-vac. The resultant residue was dissolved in DCM (1.1 mL) and cooled to 0° C. 6-(1-isopropyl-1H-tetrazol-5-yl)pyridin-2-amine (102 mg, 0.50 mmol) and pyridine (0.16 mL, 2.0 mmol) were added, and the reaction was stirred overnight, slowly warming to rt. The reaction was concentrated under reduced pressure. The resultant yellow gum was purified by column chromatography eluting with hexanes/EtOAc (0% EtOAc→45% EtOAc) to give benzyl 6-fluoro-7-((6-(1-isopropyl-1H-tetrazol-5-yl)pyridin-2-yl)carbamoyl)-1-methyl-3,4-dihydroisoquinoline-2(1H)-carboxylate (233 mg, 0.44 mmol, 88% yield) as a colorless gum.

Example 68 was prepared according to the representative procedure for hydrogenolysis.

Example 69 was prepared according to the representative procedure for secondary urea formation.

Example 70 was prepared according to the representative procedure for sulfonamide formation.

Example 108: Synthesis of 6-fluoro-N-(6-(1-isopropyl-1H-tetrazol-5-yl)pyridin-2-yl)-1-methyl-2-(2-oxo-2-(pyrrolidin-1-yl)ethyl)-1,2,3,4-tetrahydroisoquinoline-7-carboxamide

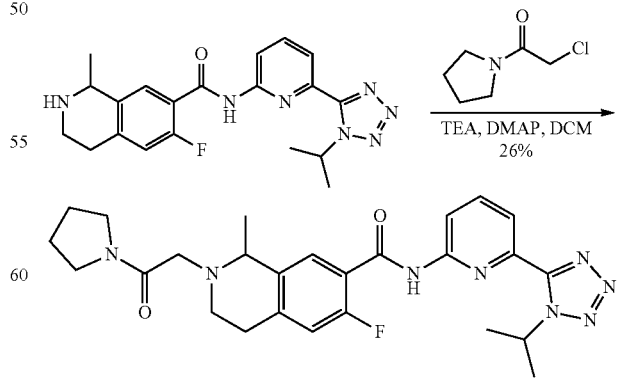

2-Chloro-1-(pyrrolidin-1-yl)ethan-1-one (14.0 mg, 0.095 mmol) was added to a solution of 6-fluoro-N-(6-(1-isopropyl-1H-tetrazol-5-yl)pyridin-2-yl)-1-methyl-1,2,3,4-tetrahydroiso-quinoline-7-carboxamide (25 mg, 0.063 mmol), Et₃N (19.0 μL, 0.139 mmol), and DMAP (0.80 mg, 6.32 μmol) in DCM (0.63 mL) and the reaction was stirred overnight. The reaction was purified by column chromatography eluting with CH₂Cl₂/MeOH (0% MeOH→5% MeOH containing 0.5% Et₃N) to give 6-fluoro-N-(6-(1-isopropyl-1H-tetrazol-5-yl)pyridin-2-yl)-1-methyl-2-(2-oxo-2-(pyrrolidin-1-yl)ethyl)-1,2,3,4-tetrahydroisoquinoline-7-carboxamide (8.4 mg, 0.017 mmol, 26% yield) as a pale yellow solid.

Example 98: Synthesis of 2-ethyl-6-fluoro-N-(6-(1-isopropyl-1H-tetrazol-5-yl)pyridin-2-yl)-1-oxo-1,2,3,4-tetrahydroisoquinoline-7-carboxamide

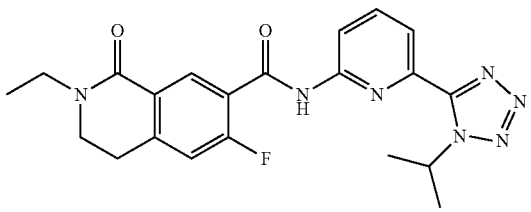 [SMILES: CCN1CCc2cc(F)c(C(=O)Nc3cccc(-c4nnnn4C(C)C)n3)cc2C1=O]

Step 1. Synthesis of 7-bromo-6-fluoro-3,4-dihydroisoquinolin-1(2H)-one

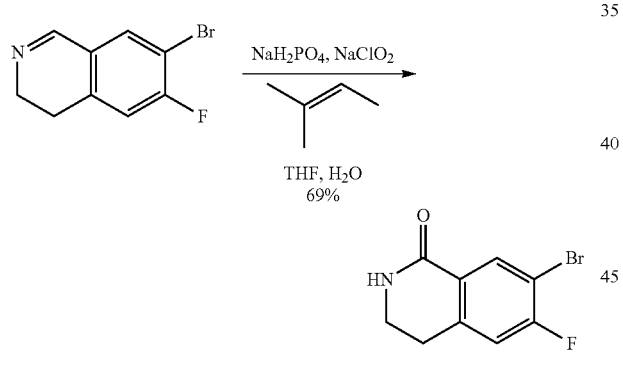

An aqueous solution of sodium dihydrogen phosphate (0.99 mL, 0.99 mmol of a 1.0M solution) was added to a mixture of 2-methylbut-2-ene (2.192 mL, 4.38 mmol of a 2.0M solution in THF) and sodium chlorite (372 mg, 3.29 mmol). A solution of 7-bromo-6-fluoro-3,4-dihydroisoquinoline (150 mg, 0.66 mmol) in THF (1.9 mL) was added over 5 minutes and the reaction was stirred for 1 h. The reaction was diluted with EtOAc and washed with water, 10% Na₂S₂O₃, and brine. The organic layer was dried (MgSO₄), filtered, and concentrated under reduced pressure. The resultant yellow solid was purified by column chromatography eluting with hexanes/EtOAc (0% EtOAc→75% EtOAc) to give 7-bromo-6-fluoro-3,4-dihydroisoquinolin-1(2H)-one (110 mg, 0.45 mmol, 69% yield) as a white solid: ¹H NMR (400 MHz, Chloroform-d) δ 8.29 (d, J=7.1 Hz, 1H), 6.99 (dd, J=8.4, 1.0 Hz, 1H), 6.05 (br s, 1H), 3.58 (td, J=6.6, 2.7 Hz, 2H), 2.97 (t, J=6.6 Hz, 2H).

Step 2. Synthesis of 7-bromo-2-ethyl-6-fluoro-3,4-dihydroisoquinolin-1(2H)-one

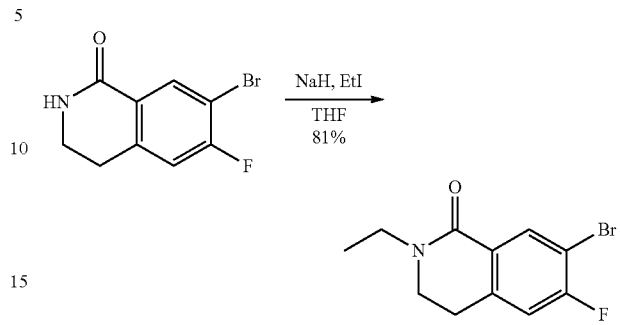

A solution of 7-bromo-6-fluoro-3,4-dihydroisoquinolin-1(2H)-one (107 mg, 0.44 mmol) in THF (2.1 mL) was added dropwise to a suspension of sodium hydride (105 mg, 2.63 mmol) in THF (3.6 mL). Ethyl iodide (0.18 mL, 2.19 mmol) was added dropwise and the reaction was stirred for 24 h. Added more THF (2.1 mL) and ethyl iodide (80 μL, 0.97 mmol) and continued stirring at rt overnight. The reaction was quenched carefully with 1M HCl and diluted with EtOAc. The layers were separated and the aqueous layer was extracted with EtOAc (2×). The combined organic layers were dried (MgSO₄), filtered, and concentrated under reduced pressure. The resultant brown oil was purified by column chromatography eluting with hexanes/EtOAc (0% EtOAc→60% EtOAc) to give 7-bromo-2-ethyl-6-fluoro-3,4-dihydroisoquinolin-1(2H)-one (97 mg, 0.36 mmol, 81% yield) as a colorless gum: ¹H NMR (400 MHz, Chloroform-d) δ 8.29 (d, J=7.1 Hz, 1H), 6.93 (dt, J=8.4, 0.9 Hz, 1H), 3.61 (q, J=7.2 Hz, 2H), 3.60-3.51 (m, 2H), 2.95 (t, J=6.6 Hz, 2H), 1.21 (t, J=7.2 Hz, 3H).

Step 3. Synthesis of 2-isocyanato-6-(1-isopropyl-1H-tetrazol-5-yl)pyridine

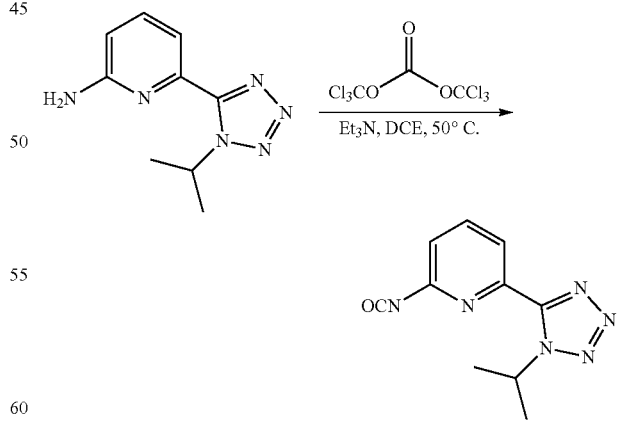

Triphosgene (19 mg, 0.063 mmol) was added portion wise to a solution of 6-(1-isopropyl-1H-tetrazol-5-yl)pyridin-2-amine (36.0 mg, 0.176 mmol) in DCE (0.77 mL). Et₃N (50 μL, 0.352 mmol) was added and the reaction was stirred at 50° C. for 2.5 h. The reaction was concentrated to give a mixture of 2-isocyanato-6-(1-isopropyl-1H-tetrazol-5-yl)pyridine and triethylammonium chloride. This mixture was used without purification.

Step 4. Synthesis of 2-ethyl-6-fluoro-N-(6-(1-isopropyl-1H-tetrazol-5-yl)pyridin-2-yl)-1-oxo-1,2,3,4-tetrahydroisoquinoline-7-carboxamide

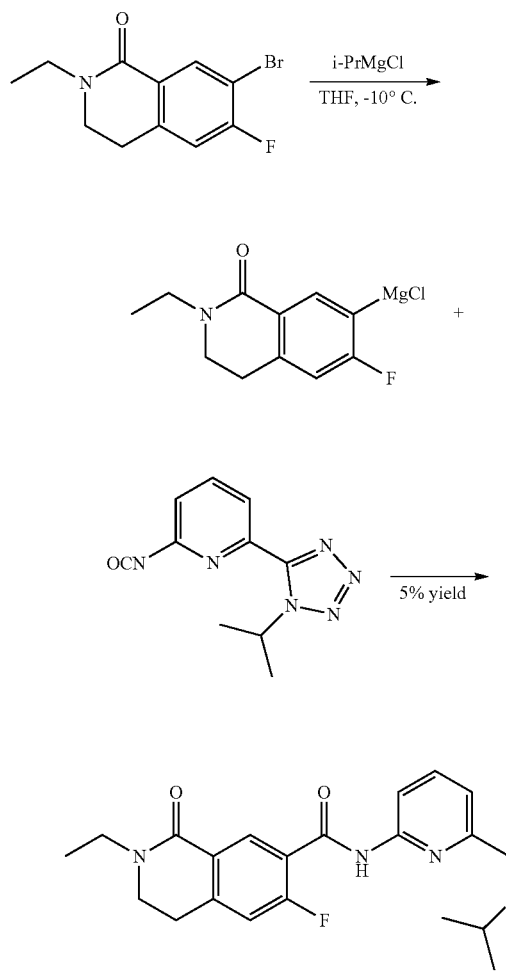

Isopropylmagnesium chloride (81 µL, 0.162 mmol) was added dropwise to a solution of 7-bromo-2-ethyl-6-fluoro-3,4-dihydroisoquinolin-1(2H)-one (40 mg, 0.147 mmol) in THF (0.3 mL) at −10° C. and the reaction was stirred at −10° C. for 1 h. This Grignard solution was added dropwise to a mixture of crude 2-isocyanato-6-(1-isopropyl-1H-tetrazol-5-yl)pyridine (41 mg, 0.176 mmol) in THF (0.7 mL) at 0° C. The cold bath was removed and the reaction was stirred overnight. The reaction was quenched carefully with sat. NH₄Cl and diluted with EtOAc. The layers were separated and the aqueous layer was extracted with EtOAc (2×). The combined organic layers were dried (MgSO₄), filtered, and concentrated under reduced pressure. The resultant yellow gum was purified by column chromatography eluting with hexanes/EtOAc (0% EtOAc→80% EtOAc) to give 2-ethyl-6-fluoro-N-(6-(1-isopropyl-1H-tetrazol-5-yl)pyridin-2-yl)-1-oxo-1,2,3,4-tetrahydroisoquinoline-7-carboxamide (2.9 mg, 6.85 µmol, 5% yield) as an orange residue.

Example 153: Synthesis of tert-butyl 7-((6-(1-isopropyl-1H-tetrazol-5-yl)pyridin-2-yl)carbamoyl)-3,4-dihydro-2,6-naphthyridine-2(1H)-carboxylate

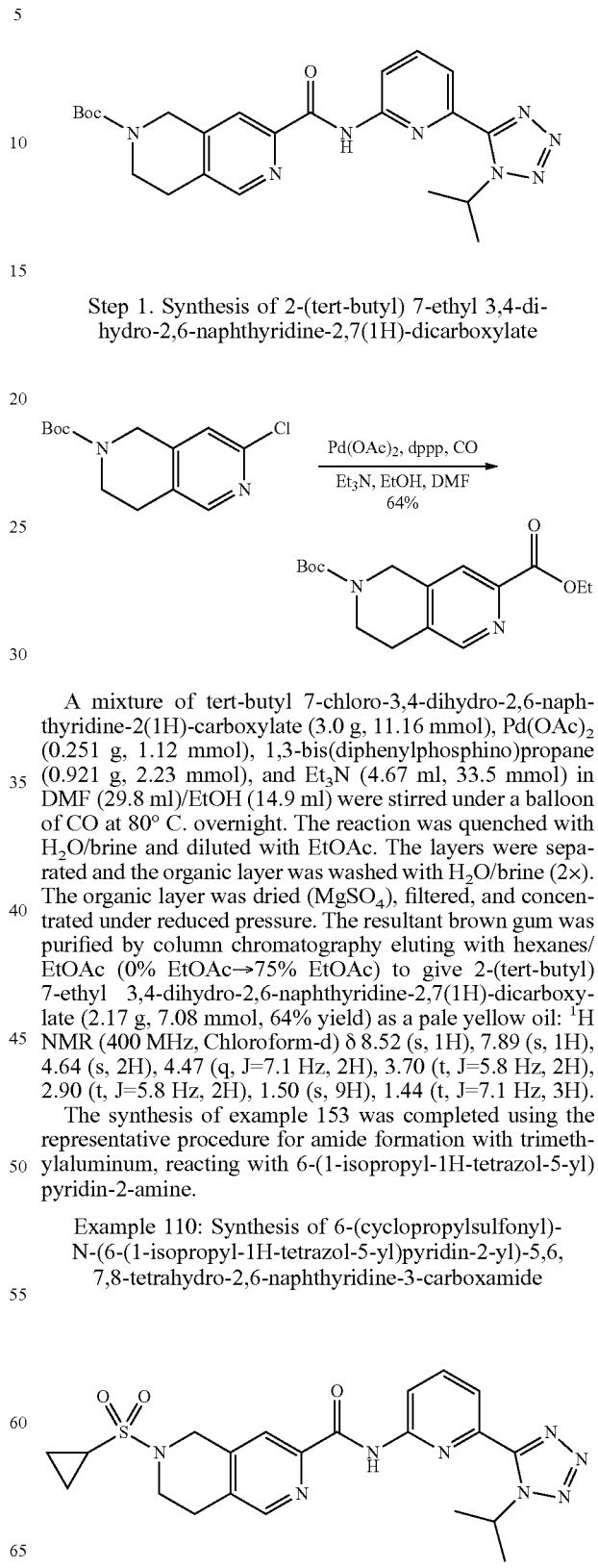

Step 1. Synthesis of 2-(tert-butyl) 7-ethyl 3,4-dihydro-2,6-naphthyridine-2,7(1H)-dicarboxylate A mixture of tert-butyl 7-chloro-3,4-dihydro-2,6-naphthyridine-2(1H)-carboxylate (3.0 g, 11.16 mmol), Pd(OAc)₂ (0.251 g, 1.12 mmol), 1,3-bis(diphenylphosphino)propane (0.921 g, 2.23 mmol), and Et₃N (4.67 ml, 33.5 mmol) in DMF (29.8 ml)/EtOH (14.9 ml) were stirred under a balloon of CO at 80° C. overnight. The reaction was quenched with H₂O/brine and diluted with EtOAc. The layers were separated and the organic layer was washed with H₂O/brine (2×). The organic layer was dried (MgSO₄), filtered, and concentrated under reduced pressure. The resultant brown gum was purified by column chromatography eluting with hexanes/EtOAc (0% EtOAc→75% EtOAc) to give 2-(tert-butyl) 7-ethyl 3,4-dihydro-2,6-naphthyridine-2,7(1H)-dicarboxylate (2.17 g, 7.08 mmol, 64% yield) as a pale yellow oil: ¹H NMR (400 MHz, Chloroform-d) δ 8.52 (s, 1H), 7.89 (s, 1H), 4.64 (s, 2H), 4.47 (q, J=7.1 Hz, 2H), 3.70 (t, J=5.8 Hz, 2H), 2.90 (t, J=5.8 Hz, 2H), 1.50 (s, 9H), 1.44 (t, J=7.1 Hz, 3H).

The synthesis of example 153 was completed using the representative procedure for amide formation with trimethylaluminum, reacting with 6-(1-isopropyl-1H-tetrazol-5-yl)pyridin-2-amine.

Example 110: Synthesis of 6-(cyclopropylsulfonyl)-N-(6-(1-isopropyl-1H-tetrazol-5-yl)pyridin-2-yl)-5,6,7,8-tetrahydro-2,6-naphthyridine-3-carboxamide

123

Step 1. Synthesis of N-(6-(1-isopropyl-1H-tetrazol-5-yl)pyridin-2-yl)-5,6,7,8-tetrahydro-2,6-naphthyridine-3-carboxamide hydrochloride

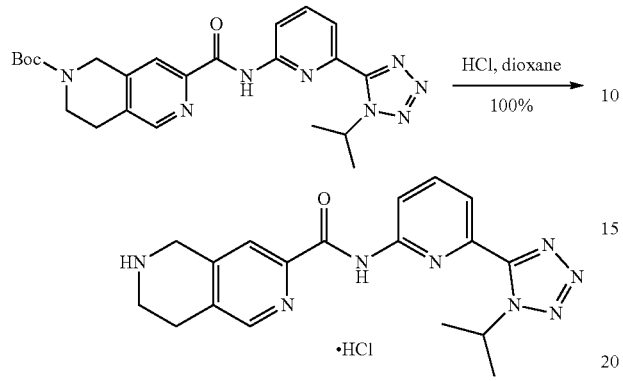

A solution of tert-butyl 7-((6-(1-isopropyl-1H-tetrazol-5-yl)pyridin-2-yl)carbamoyl)-3,4-dihydro-2,6-naphthyridine-2(1H)-carboxylate (500 mg, 1.076 mmol) in MeOH (5.4 mL)/4M HCl in dioxane (5.4 mL) was stirred for 2 h. The reaction was concentrated under reduced pressure to give 431 mg crude N-(6-(1-isopropyl-1H-tetrazol-5-yl)pyridin-2-yl)-5,6,7,8-tetrahydro-2,6-naphthyridine-3-carboxamide hydrochloride as a colorless powder that was used without purification: $^1$H NMR (400 MHz, DMSO-$d_6$) δ 10.80 (s, 1H), 8.67 (s, 1H), 8.44-8.35 (m, 1H), 8.21-8.14 (comp, 2H), 8.00 (d, J=7.5 Hz, 1H), 5.91 (p, J=6.6 Hz, 1H), 4.45 (d, J=5.0 Hz, 2H), 3.47-3.43 (m, 2H), 3.19-3.14 (m, 2H), 1.60 (d, J=6.6 Hz, 6H).

The synthesis of example 110 was completed using the representative procedure for sulfonamide formation, with the following modification: 8 equivalents of Et$_3$N were used.

Examples 138, 139, 140, 141, and 172 were prepared according to the representative procedure for sulfonamide formation, with the following modification: 8 equivalents of Et$_3$N were used.

Example 111 was prepared according to the representative procedure for secondary sulfonyl urea formation, with the following modification: 8 equivalents of Et$_3$N were used.

Examples 112-116, 137, and 173 were prepared according to the representative procedure for secondary urea formation, with the following modification: 8 equivalents of Et$_3$N were used.

Example 117 was prepared according to the representative procedure for primary urea formation, with the following modification: 8 equivalents of Et$_3$N were used.

Example 118 was prepared according to the representative procedure for carbamate, with the following modification: 8 equivalents of Et$_3$N were used.

Example 119 was prepared according to the representative procedure 2 for amide formation, with the following modification: 8 equivalents of Et$_3$N were used.

Example 143 was prepared according to the representative procedure for amide formation with trimethylaluminum, reacting with (R)-2-(5-(6-aminopyridin-2-yl)-1H-tetrazol-1-yl)propan-1-ol, with the following modification: 3 equivalents of trimethylaluminum were used.

124

Example 147: Synthesis of tert-butyl (R)-7-((6-(1-(1-acetoxypropan-2-yl)-1H-tetrazol-5-yl)pyridin-2-yl)carbamoyl)-3,4-dihydro-2,6-naphthyridine-2(1H)-carboxylate

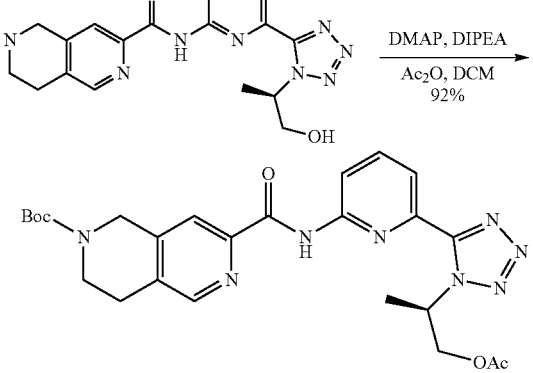

Acetic anhydride (30 µL, 0.31 mmol) was added to a solution of tert-butyl (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate (124 mg, 0.26 mmol), DIPEA (90 µL, 0.52 mmol), and DMAP (3.0 mg, 0.026 mmol) in DCM (2.6 mL) at 0° C. and the reaction was stirred at 0° C. for 30 min. The reaction was concentrated under reduced pressure and purified by column chromatography eluting with hexanes/EtOAc (0% EtOAc→60% EtOAc) to give tert-butyl (R)-7-((6-(1-(1-acetoxypropan-2-yl)-1H-tetrazol-5-yl)pyridin-2-yl)carbamoyl)-3,4-dihydro-2,6-naphthyridine-2(1H)-carboxylate (124 mg, 0.237 mmol, 92% yield) as a colorless amorphous solid.

Example 142: Synthesis of (R)-6-formyl-N-(6-(1-(1-hydroxypropan-2-yl)-1H-tetrazol-5-yl)pyridin-2-yl)-5,6,7,8-tetrahydro-2,6-naphthyridine-3-carboxamide

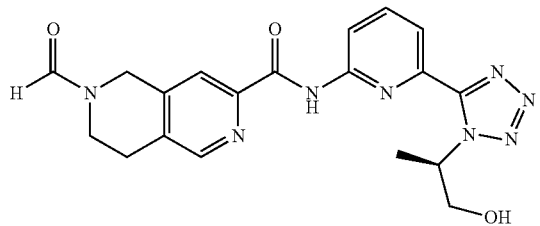 [SMILES: C[C@H](CO)n1nnnc1-c1cccc(NC(=O)c2cc3c(cn2)CCN(C=O)C3)n1]

Step 1. Synthesis of (R)—N-(6-(1-(1-hydroxypropan-2-yl)-1H-tetrazol-5-yl)pyridin-2-yl)-5,6,7,8-tetrahydro-2,6-naphthyridine-3-carboxamide hydrochloride

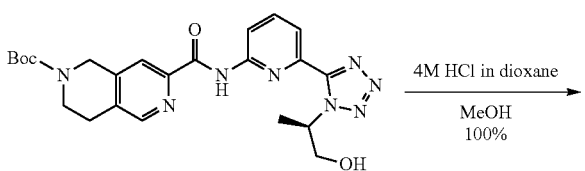

-continued

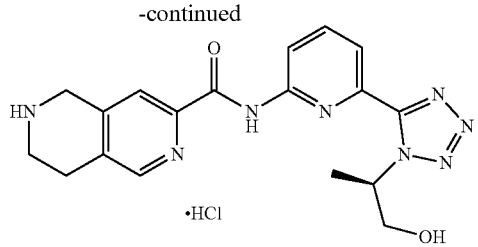

4M HC in 1,4-dioxane (6.9 mL) was added to a solution of tert-butyl (R)-7-(6-(1(1 hydroxypropan-2-yl)-1H-tetrazol-5-yl)pyridin-2-yl)carbamoyl)-3,4-dihydro-2,6-naphthyridine-2(1H)-carboxylate (668 mg, 1.390 mmol) in MeOH (6.9 mL) and the reaction was stirred for 30 min. The reaction was concentrated under reduced pressure to give crude (R)—N-(6-(1-(1-hydroxypropan-2-yl)-1H-tetrazol-5-yl)pyridin-2-yl)-5,6,7,8-tetrahydro-2,6-naphthyridine-3-carboxamide hydrochloride as a tan solid that was used without purification: LC-MS, ES+: m/z 381.18 [M+H]+; 1H NMR (400 MHz, DMSO-$d_6$) δ 10.79 (s, 1H), 8.68 (s, 1H), 8.40 (dd, J=8.4, 0.9 Hz, 1H), 8.21-8.13 (m, 2H), 7.98 (dd, J=7.6, 0.9 Hz, 1H), 5.83 (td, J=7.2, 5.6 Hz, 1H), 4.45 (t, J=4.2 Hz, 2H), 3.78 (d, J=1.0 Hz, 1H), 3.77 (d, J=3.1 Hz, 1H), 3.48-3.40 (m, 2H), 3.19-3.13 (m, 2H), 1.59 (d, J=6.8 Hz, 3H).

Step 2. Synthesis of (R)—N-(6-(1-(1-((tert-butyldimethylsilyl)oxy)propan-2-yl)-1H-tetrazol-5-yl)pyridin-2-yl)-6-formyl-5,6,7,8-tetrahydro-2,6-naphthyridine-3-carboxamide

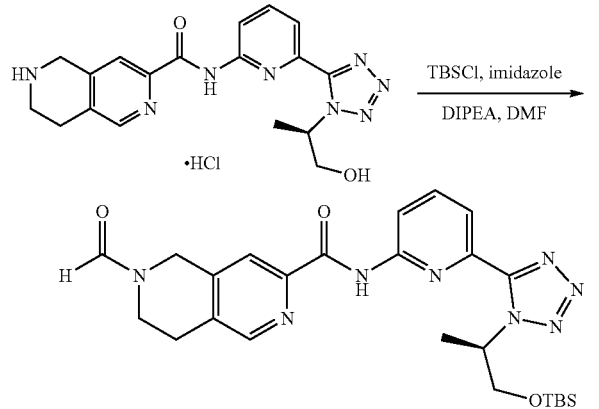

TBS-Cl (1.05 g, 6.95 mmol) was added to a mixture of crude (R)—N-(6-(1-(1-hydroxypropan-2-yl)-1H-tetrazol-5-yl)pyridin-2-yl)-5,6,7,8-tetrahydro-2,6-naphthyridine-3-carboxamide hydrochloride (529 mg, 1.391 mmol), imidazole (473 mg, 6.95 mmol), and DIPEA (1.21 mL, 6.95 mmol) in DMF (13.9 mL) and the reaction was stirred for 48 hrs. The reaction was quenched with sat. NaHCO₃ and diluted with EtOAc. The layers were separated and the organic layer was washed with 10% citric acid, brine, and H₂O. The organic layer was dried (MgSO₄), filtered, and concentrated under reduced pressure to give 727 mg of crude (R)—N-(6-(1-(1-((tert-butyldimethylsilyl)oxy)propan-2-yl)-1H-tetrazol-5-yl)pyridin-2-yl)-6-formyl-5,6,7,8-tetrahydro-2,6-naphthyridine-3-carboxamide as a yellow gum: LC-MS, ES+: m/z 523.26 [M+H]+; 1H NMR (400 MHz, DMSO-$d_6$, as a 2:1 mixture of rotamers) δ 10.73 (s, 0.36H), 10.72 (s, 0.72H), 8.57 (s, 1H), 8.42 (dt, J=8.4, 1.2 Hz, 1H), 8.22 (d, J=9.9 Hz, 1H), 8.16 (t, J=8.0 Hz, 1H), 8.13 (s, 0.72H), 8.07 (s, 0.36H), 7.96 (dt, J=7.6, 1.0 Hz, 1H), 6.06-5.91 (m, 1H), 4.79 (s, 0.67H), 4.74 (s, 1.33H), 3.97 (dd, J=10.6, 4.5 Hz, 1H), 3.89 (dd, J=10.6, 8.8 Hz, 1H), 3.77-3.67 (m, 2H), 2.99 (t, J=5.8 Hz, 1.33H), 2.91 (t, J=6.0 Hz, 0.67H), 1.63 (d, J=6.8 Hz, 3H), 0.85 (s, 3H), 0.84 (s, 6H), 0.01 (s, 2H), −0.04 (s, 4H).

Step 3. Synthesis of (R)-6-formyl-N-(6-(1-(1-hydroxypropan-2-yl)-1H-tetrazol-5-yl)pyridin-2-yl)-5,6,7,8-tetrahydro-2,6-naphthyridine-3-carboxamide

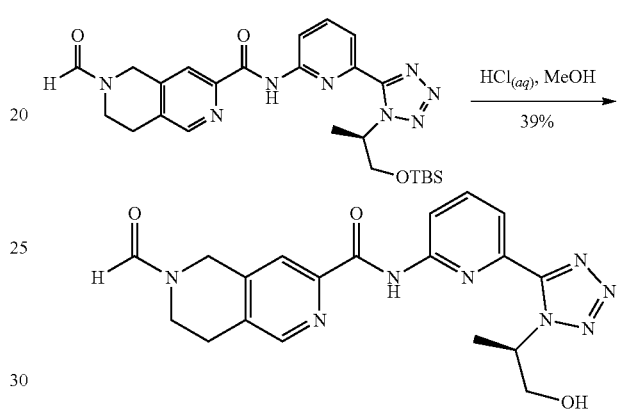

Concentrated HCl (22.00 µl, 0.264 mmol) was added to a solution of (R)—N-(6-(1-(1-((tert-butyldimethylsilyl)oxy)propan-2-yl)-1H-tetrazol-5-yl)pyridin-2-yl)-6-formyl-5,6,7,8-tetrahydro-2,6-naphthyridine-3-carboxamide (23 mg, 0.044 mmol) in MeOH (147 µl) and the reaction was stirred for 1 h. The reaction was quenched carefully with sat. NaHCO₃ and diluted with EtOAc. The layers were separated and the aqueous layer was extracted with EtOAc (2×). The combined organic layers were dried (MgSO₄), filtered, and concentrated under reduced pressure. The resultant white solid was purified by column chromatography eluting with CH₂Cl₂/MeOH (0% MeOH→8% MeOH) to give (R)-6-formyl-N-(6-(1-(1-hydroxypropan-2-yl)-1H-tetrazol-5-yl)pyridin-2-yl)-5,6,7,8-tetrahydro-2,6-naphthyridine-3-carboxamide (7 mg, 0.017 mmol, 39% yield) as a colorless solid.

Example 144: Synthesis of (R)—N-(6-(1-(1-hydroxypropan-2-yl)-1H-tetrazol-5-yl)pyridin-2-yl)-6-(pyrrolidine-1-carbonyl)-5,6,7,8-tetrahydro-2,6-naphthyridine-3-carboxamide

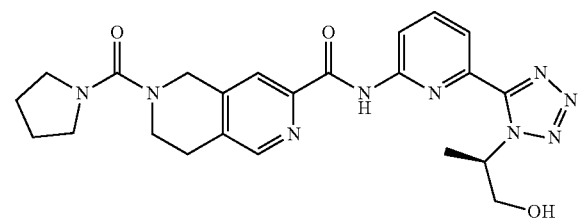 [SMILES: C[C@H](CO)n1nnnc1-c1cccc(NC(=O)c2cc3c(cn2)CCN(C(=O)N2CCCC2)C3)n1]

Step 1. Synthesis of (R)—N-(6-(1-(1-((tert-butyldimethylsilyl)oxy)propan-2-yl)-1H-tetrazol-5-yl)pyridin-2-yl)-5,6,7,8-tetrahydro-2,6-naphthyridine-3-carboxamide

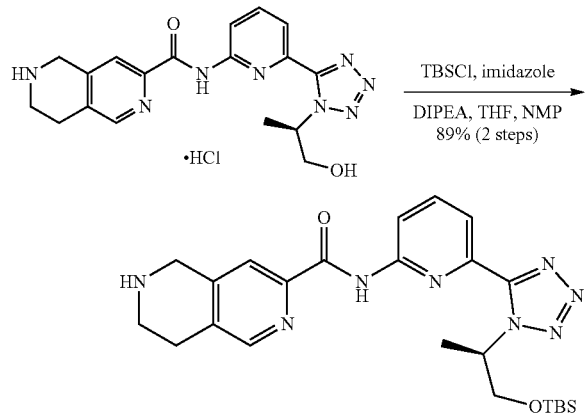

TBS-Cl (1.54 g, 10.2 mmol) was added to a mixture of (R)—N-(6-(1-(1-hydroxypropan-2-yl)-1H-tetrazol-5-yl)pyridin-2-yl)-5,6,7,8-tetrahydro-2,6-naphthyridine-3-carboxamide hydrochloride (0.776 g, 2.04 mmol), imidazole (0.694 g, 10.2 mmol), and DIPEA (1.78 mL, 10.2 mmol) in THF (20 mL)/NMP (10 mL) and the reaction was stirred for 4 hrs. The reaction was quenched with sat. NaHCO$_3$ and diluted with EtOAc. The layers were separated and the organic layer was washed with H$_2$O and brine. The organic layer was dried (MgSO$_4$), filtered, and concentrated under reduced pressure. The resultant yellow gum was purified by column chromatography eluting with CH$_2$Cl$_2$/MeOH (0% MeOH→8% MeOH) to give (R)—N-(6-(1-(1-((tert-butyldimethylsilyl)oxy)propan-2-yl)-1H-tetrazol-5-yl)pyridin-2-yl)-5,6,7,8-tetrahydro-2,6-naphthyridine-3-carboxamide (896 mg, 1.81 mmol, 89% yield over 2 steps) as a colorless amorphous solid: LC-MS, ES$^+$: m/z 495.27 [M+H]$^+$; $^1$H NMR (400 MHz, DMSO-d$_6$) δ 10.70 (s, 1H), 8.46 (s, 1H), 8.42 (dd, J=8.4, 0.9 Hz, 1H), 8.16 (t, J=8.0 Hz, 1H), 7.95 (dd, J=7.6, 0.9 Hz, 1H), 7.93 (s, 1H), 5.98 (ddd, J=8.7, 6.7, 4.5 Hz, 1H), 4.00-3.94 (comp, 3H), 3.89 (dd, J=10.6, 8.8 Hz, 1H), 2.99 (t, J=5.7 Hz, 2H), 2.80 (t, J=5.7 Hz, 2H), 1.63 (d, J=6.8 Hz, 3H), 0.61 (s, 9H), −0.18 (s, 3H), −0.19 (s, 3H).

Step 2. Synthesis of (R)—N-(6-(1-(1-hydroxypropan-2-yl)-1H-tetrazol-5-yl)pyridin-2-yl)-6-(pyrrolidine-1-carbonyl)-5,6,7,8-tetrahydro-2,6-naphthyridine-3-carboxamide

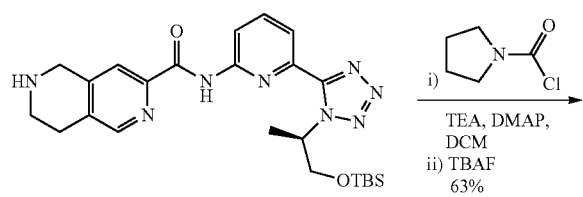

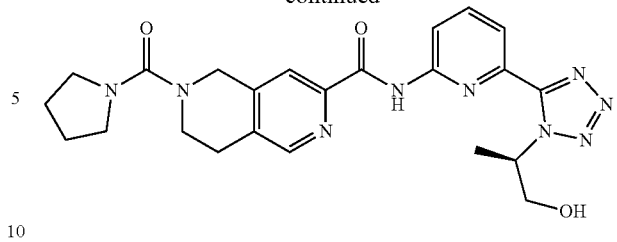

Pyrrolidine-1-carbonyl chloride (5.1 µL, 0.045 mmol) was added dropwise to a solution of (R)—N-(6-(1-(1-((tert-butyldimethylsilyl)oxy)propan-2-yl)-1H-tetrazol-5-yl)pyridin-2-yl)-5,6,7,8-tetrahydro-2,6-naphthyridine-3-carboxamide (15 mg, 0.030 mmol), Et$_3$N (9.3 µL, 0.067 mmol), and DMAP (0.4 mg, 3.03 µmol) in DCM (303 µl) and the reaction was stirred for 1.5 hrs. Another 3 eq (10.2 µL) of pyrrolidine-1-carbonyl chloride and 2.2 eq (9.3 µL) of Et$_3$N were added and the reaction was stirred another 1.5 hrs. TBAF (182 µl, 0.182 mmol of a 1.0M solution in THF) was added and the reaction was stirred overnight. The reaction was quenched with sat. NaHCO$_3$ and diluted with CH$_2$Cl$_2$. The layers were separated and the organic layer was washed with sat. NaHCO$_3$. The organic layer was dried (MgSO$_4$), filtered, and concentrated under reduced pressure. The resultant clear residue was purified by column chromatography eluting with CH$_2$Cl$_2$/MeOH (0% MeOH→5% MeOH, 4 g column) to give (R)—N-(6-(1-(1-hydroxypropan-2-yl)-1H-tetrazol-5-yl)pyridin-2-yl)-6-(pyrrolidine-1-carbonyl)-5,6,7,8-tetrahydro-2,6-naphthyridine-3-carboxamide (9.1 mg, 0.019 mmol, 63% yield) as a clear gum.

Example 146: Synthesis of (R)-6-(cyclopentanecarbonyl)-N-(6-(1-(1-hydroxypropan-2-yl)-1H-tetrazol-5-yl)pyridin-2-yl)-5,6,7,8-tetrahydro-2,6-naphthyridine-3-carboxamide

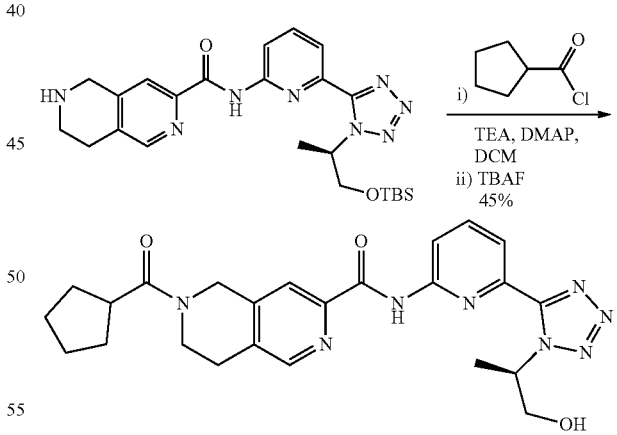

Cyclopentanecarbonyl chloride (5.5 µL, 0.045 mmol) was added dropwise to a solution of (R)—N-(6-(1-(1-((tert-butyldimethylsilyl)oxy)propan-2-yl)-1H-tetrazol-5-yl)pyridin-2-yl)-5,6,7,8-tetrahydro-2,6-naphthyridine-3-carboxamide (15 mg, 0.030 mmol), Et$_3$N (9.3 µL, 0.067 mmol), and DMAP (0.4 mg, 3.03 µmol) in DCM (303 µl) and the reaction was stirred for 1.5 hrs. TBAF (182 µl, 0.182 mmol of a 1.0M solution in THF) was added and the reaction was stirred overnight. The reaction was quenched with sat. NaHCO$_3$ and diluted with CH$_2$Cl$_2$. The layers were separated and the organic layer was washed with sat. NaHCO₃. The organic layer was dried (MgSO₄), filtered, and concentrated under reduced pressure. The resultant clear residue was purified by column chromatography eluting with CH₂Cl₂/MeOH (0% MeOH 5% MeOH) to give (R)-6-(cyclopentanecarbonyl)-N-(6-(1-(1-hydroxypropan-2-yl)-1H-tetrazol-5-yl)pyridin-2-yl)-5,6,7,8-tetrahydro-2,6-naphthyridine-3-carboxamide (6.5 mg, 0.014 mmol, 45% yield) as a colorless solid.

Example 162: Synthesis of isopropyl (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate

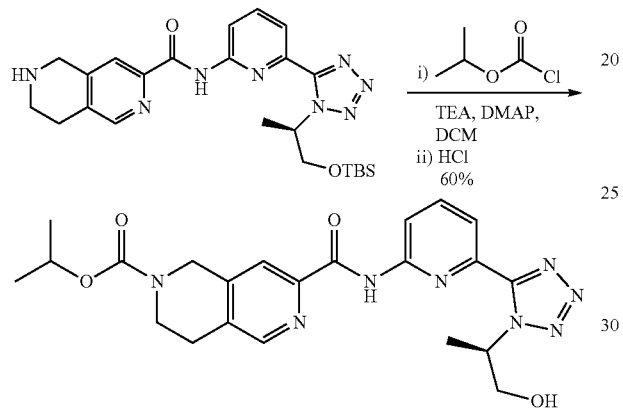

Representative Procedure for N-Functionalization and TBS Deprotection

Isopropyl carbonochloridate (76 µl, 0.076 mmol) was added dropwise to a solution of (R)—N-(6-(1-(1-((tert-butyldimethylsilyl)oxy)propan-2-yl)-1H-tetrazol-5-yl)pyridin-2-yl)-5,6,7,8-tetrahydro-2,6-naphthyridine-3-carboxamide (25 mg, 0.051 mmol), Et₃N (15.5 µl, 0.111 mmol), and DMAP (0.62 mg, 5.05 µmol) in DCM (505 µl) and the reaction was stirred for 3 hrs. Concentrated HCl (25.3 µl1, 0.303 mmol) was added and the reaction was stirred for 3 hrs. The reaction was quenched carefully with sat. NaHCO₃ and diluted with CH₂Cl₂. The layers were separated and the aqueous layer was extracted with CH₂Cl₂ (2×). The combined organic layers were dried (MgSO₄), filtered, and concentrated under reduced pressure. The resultant colorless gum was purified by column chromatography eluting with CH₂Cl₂/MeOH (0% MeOH→5% MeOH) to give (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate (14.1 mg, 0.030 mmol, 60% yield) as a colorless solid.

Examples 126-128, 145, 156-160, and 193-195 were prepared according to the representative procedure for N-functionalization and TB S deprotection, utilizing the corresponding chloroformate reagents.

Examples 120, 148-150, 161, and 200 were prepared according to the representative procedure for N-functionalization and TB S deprotection, utilizing the corresponding sulfonyl chloride reagents.

Examples 121-125, 151, 152, 155, and 191-192 were prepared according to the representative procedure for N-functionalization and TB S deprotection, utilizing the corresponding acid chloride reagents.

Examples 129-132, 169-170, and 196 were prepared according to the representative procedure for N-functionalization and TBS deprotection, utilizing the corresponding isocyanate reagents.

Examples 154, 166, and 199 were prepared according to the representative procedure for N-functionalization and TBS deprotection, utilizing the corresponding sulfamoyl chloride reagents.

Examples 167-168 and 197 were prepared according to the representative procedure for N-functionalization and TBS deprotection, utilizing the corresponding carbamoyl chloride reagents.

Example 163: Synthesis of (R)-6-(cyclopropylmethyl)-N-(6-(1-(1-hydroxypropan-2-yl)-1H-tetrazol-5-yl)pyridin-2-yl)-5,6,7,8-tetrahydro-2,6-naphthyridine-3-carboxamide

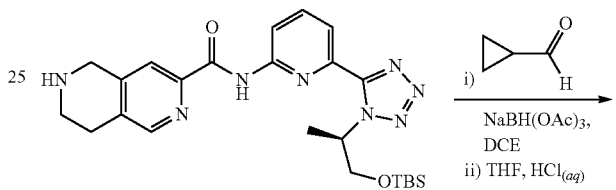

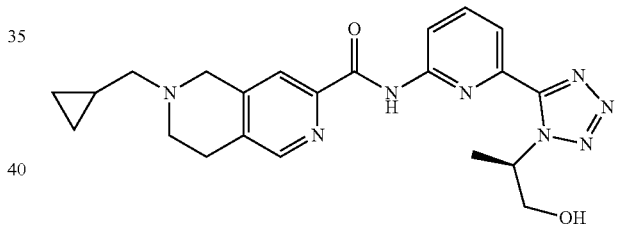

NaBH(OAc)₃ (38.6 mg, 0.8 mmol) was added to a solution of (R)—N-(6-(1-(1-((tert-butyldimethylsilyl)oxy)propan-2-yl)-1H-tetrazol-5-yl)pyridin-2-yl)-5,6,7,8-tetrahydro-2,6-naphthyridine-3-carboxamide (30 mg, 0.06 mmol), and cyclopropanecarbaldehyde (6.4 mg, 0.09 mmol) in DCE (5 mL) and the resulting mixture was stirred for 2 h at rt under a nitrogen atmosphere. The reaction mixture was concentrated under reduced pressure. The residue was diluted with THF (5 mL), then concentrated HCl (0.2 mL) was added and the reaction was stirred for another 1 h. The reaction was neutralized with saturated NaHCO₃ and extracted with EtOAc (2×20 mL). The combined organic layers were dried (Na₂SO₄), filtered, and concentrated under reduced pressure. The crude residue was purified by reverse phase column chromatography eluting with H₂O/MeCN (0% MeCN→55% MeCN) to afford (R)-6-(cyclopropylmethyl)-N-(6-(1-(1-hydroxypropan-2-yl)-1H-tetrazol-5-yl)pyridin-2-yl)-5,6,7,8-tetrahydro-2,6-naphthyridine-3-carboxamide (10.7 mg) as an off-white solid.

Examples 133-136, 164, 165, 171, 181, and 198 were prepared according to the procedure for the synthesis of example 163.

Example 177: Synthesis of 6-fluoro-2-isopropyl-N-(6-(4-isopropyl-4H-1,2,4-triazol-3-yl)pyridin-2-yl)-3-oxoisoindoline-5-carboxamide

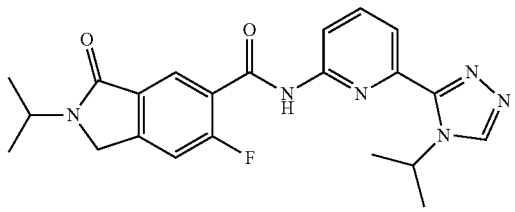 [SMILES: CC(C)N1Cc2cc(F)c(C(=O)Nc3cccc(-c4nncn4C(C)C)n3)cc2C1=O]

Step 1. Synthesis of methyl 5-bromo-4-fluoro-2-methylbenzoate

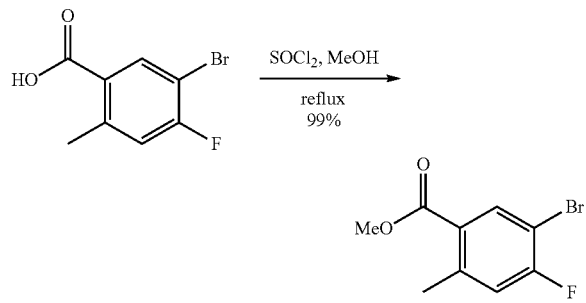

A mixture of 5-bromo-4-fluoro-2-methylbenzoic acid (8.0 g, 34.3 mmol) and SOCl$_2$ (5.0 mL, 68.7 mmol) in MeOH (23 mL) was heated at reflux for 3 hrs. The reaction was concentrated under reduced pressure to give methyl 5-bromo-4-fluoro-2-methylbenzoate (8.4 g, 34.0 mmol, 99% yield) as a tan solid: $^1$H NMR (400 MHz, Chloroform-d) δ 8.16 (d, J=7.3 Hz, 1H), 7.01 (d, J=9.3 Hz, 1H), 3.89 (s, 3H), 2.57 (s, 3H).

Step 2. Synthesis of methyl 5-bromo-2-(bromomethyl)-4-fluorobenzoate

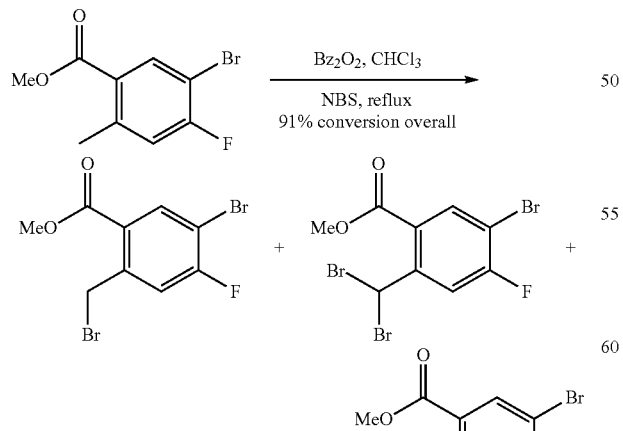

A mixture of 5-bromo-4-fluoro-2-methylbenzoate (4.2 g, 17.0 mmol), benzoyl peroxide (41 mg, 0.17 mmol), and NBS (3.1 g, 17.34 mmol) in CHCl$_3$ (43.6 ml) was heated at reflux overnight. The reaction was quenched with H$_2$O/brine and diluted with CH$_2$Cl$_2$. The layers were separated and the aqueous layer was extracted with CH$_2$Cl$_2$ (2×). The combined organic layers were dried (MgSO$_4$), filtered, and concentrated under reduced pressure to give 5.9 g of a mixture of three compounds with the major component being methyl 5-bromo-2-(bromomethyl)-4-fluorobenzoate (~4.2 g, 76% yield). The mixture was used directly without purification.

Step 3. Synthesis of 6-bromo-5-fluoroisobenzofuran-1 (3H)-one

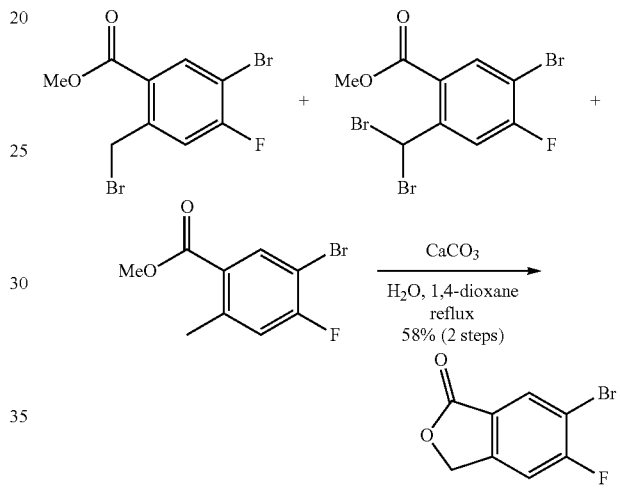

A mixture of crude methyl 5-bromo-2-(bromomethyl)-4-fluorobenzoate (4.2 g, 12.89 mmol) and calcium carbonate (7.74 g, 77 mmol) in H$_2$O (129 ml)/1,4-Dioxane (129 ml) was heated at reflux for 3.5 hrs. The reaction was cooled to rt and filtered to remove solids. The filtrate was concentrated under reduced pressure to remove dioxane. The resultant aqueous mixture was extracted DCM (4×). The combined organic layers were dried (MgSO$_4$), filtered, and concentrated under reduced pressure. The resultant white solid was recrystallized from DCM/hexanes to give 6-bromo-5-fluoroisobenzofuran-1(3H)-one (2.3 g, 9.96 mmol, 58% yield over 2 steps) as a white solid: $^1$H NMR (400 MHz, Chloroform-d) δ 8.16-8.12 (m, 1H), 7.26 (d, J=7.2 Hz, 1H), 5.27 (s, 2H).

Step 4. Synthesis of 5-bromo-4-fluoro-2-(hydroxymethyl)-N-isopropylbenzamide

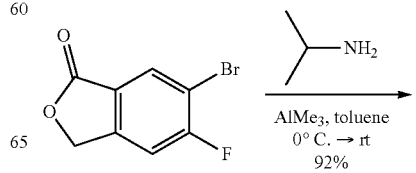

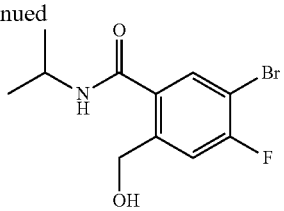

Trimethylaluminum (1.428 mL, 2.86 mmol of a 2.0M solution in toluene) was added dropwise to a solution of propan-2-amine (0.268 mL, 3.12 mmol) in toluene (8.7 mL) at 0° C. The reaction was stirred 5 min at 0° C. 6-bromo-5-fluoroisobenzofuran-1(3H)-one (600 mg, 2.60 mmol) was added, the cold bath was removed, and the reaction was stirred at rt overnight. The reaction was cooled to 0° C., quenched carefully with 1M NaOH (11.3 mL), and diluted with EtOAc. The layers were separated and the organic layer was washed with $H_2O$ and brine, dried ($MgSO_4$), filtered, and concentrated under reduced pressure to give 5-bromo-4-fluoro-2-(hydroxymethyl)-N-isopropylbenzamide (695 mg, 2.40 mmol, 92% yield) as a fluffy white solid: $^1$H NMR (500 MHz, Chloroform-d) δ 7.70 (d, J=6.6 Hz, 1H), 7.18 (d, J=8.7 Hz, 1H), 6.06 (br s, 1H), 4.56 (d, J=6.9 Hz, 2H), 4.25 (dp, J=7.7, 6.5 Hz, 1H), 4.12 (t, J=6.9 Hz, 1H), 1.29 (d, J=6.6 Hz, 6H).

Step 5. Synthesis of 6-bromo-5-fluoro-2-isopropylisoindolin-1-one

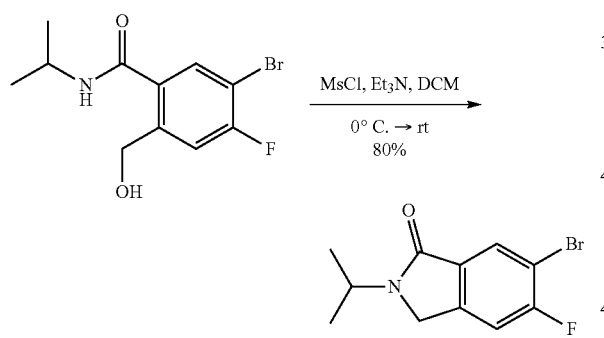

Ms-Cl (0.28 mL, 3.57 mmol) was added to a solution of 5-bromo-4-fluoro-2-(hydroxymethyl)-N-isopropylbenzamide (690 mg, 2.38 mmol) and $Et_3N$ (1.0 mL, 7.13 mmol) in DCM (18.3 mL) at 0° C. The cold bath was removed, and the reaction was stirred at rt for 1.5 hrs. The reaction was quenched with sat. $NaHCO_3$ and diluted with $CH_2Cl_2$. The layers were separated and the aqueous layer was extracted with $CH_2Cl_2$ (2×). The combined organic layers were dried ($MgSO_4$), filtered, and concentrated under reduced pressure. The resultant pale yellow solid was purified by column chromatography eluting with hexanes/EtOAc (0% EtOAc→15% EtOAc) to give 6-bromo-5-fluoro-2-isopropylisoindolin-1-one (519 mg, 1.907 mmol, 80% yield) as a colorless powder: $^1$H NMR (500 MHz, Chloroform-d) δ 8.07 (d, J=6.2 Hz, 1H), 7.10 (d, J=7.4 Hz, 1H), 5.24 (s, 2H), 4.07 (hept, J=6.4 Hz, 1H), 1.20 (d, J=6.4 Hz, 6H).

The synthesis of example 177 was completed according to the representative procedure for palladium catalyzed carbonylation and the representative procedure for amide formation with trimethylaluminum, reacting with 6-(4-isopropyl-4H-1,2,4-triazol-3-yl)pyridin-2-amine.

Example 175: Synthesis of 2-isopropyl-N-(6-(4-isopropyl-4H-1,2,4-triazol-3-yl)pyridin-2-yl)-6-methoxy-3-oxoisoindoline-5-carboxamide

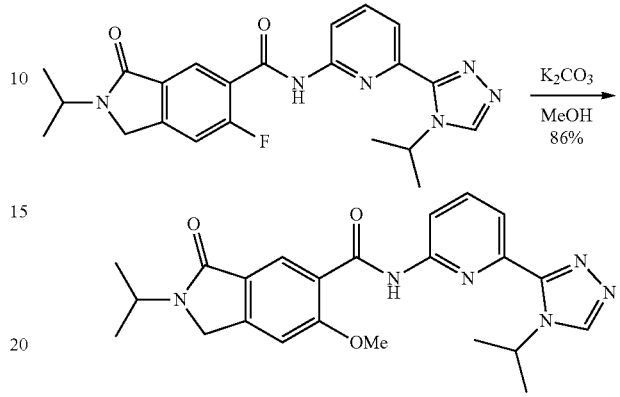

$K_2CO_3$ (25.2 mg, 0.182 mmol) was added to a solution of 6-fluoro-2-isopropyl-N-(6-(4-isopropyl-4H-1,2,4-triazol-3-yl)pyridin-2-yl)-3-oxoisoindoline-5-carboxamide (15.4 mg, 0.036 mmol) in MeOH (0.608 mL) and the reaction was stirred overnight. The reaction was quenched with $H_2O$ and diluted with $CH_2Cl_2$. The layers were separated and the aqueous layer was extracted with $CH_2Cl_2$ (2×). The combined organic layers were dried ($MgSO_4$), filtered, and concentrated under reduced pressure to give 2-isopropyl-N-(6-(4-isopropyl-4H-1,2,4-triazol-3-yl)pyridin-2-yl)-6-methoxy-3-oxoisoindoline-5-carboxamide (13.6 mg, 0.031 mmol, 86% yield) as a colorless solid.

Examples 176 and 174 were prepared in an analogous fashion utilizing the same representative procedures as examples 177 and 175, respectively, and performing the amide formation with 6-(1-isopropyl-1H-tetrazol-5-yl)pyridin-2-amine.

Example 179: Synthesis of benzyl 6-((6-(4-isopropyl-4H-1,2,4-triazol-3-yl)pyridin-2-yl)carbamoyl)-1,3-dihydro-2H-pyrrolo[3,4-c]pyridine-2-carboxylate

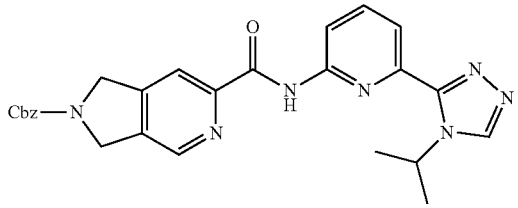 [SMILES: CC(C)n1cnnc1-c1cccc(NC(=O)c2cc3c(cn2)CN(C(=O)OCc2ccccc2)C3)n1]

Step 1. Synthesis of benzyl 6-chloro-1,3-dihydro-2H-pyrrolo[3,4-c]pyridine-2-carboxylate

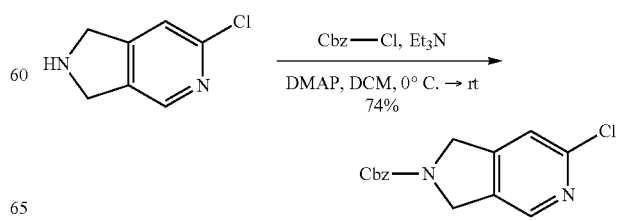

Cbz-Cl (5.6 ml, 39.3 mmol) was added dropwise to a mixture of 6-chloro-2,3-dihydro-1H-pyrrolo[3,4-c]pyridine, Hydrochloride (5.0 g, 26.2 mmol), Et$_3$N (8.0 mL, 57.6 mmol), and DMAP (0.320 g, 2.62 mmol) in DCM (52.3 mL) at 0° C. The reaction was stirred overnight, warming to room temperature. The reaction was quenched with sat. NaHCO$_3$ and diluted with CH$_2$Cl$_2$. The layers were separated and the aqueous layer was extracted with CH$_2$Cl$_2$ (2×). The combined organic layers were washed with brine, dried (MgSO$_4$), filtered, and concentrated under reduced pressure. The resultant brown oil was purified by column chromatography eluting with hexanes/EtOAc (0% EtOAc→25% EtOAc) to give benzyl 6-chloro-1,3-dihydro-2H-pyrrolo[3,4-c]pyridine-2-carboxylate (5.6 g, 19.4 mmol, 74% yield) as a yellow solid: $^1$H NMR (400 MHz, Chloroform-d) δ 8.31 (d, J=22.6 Hz, 1H), 7.44-7.33 (comp, 5H), 7.25 (d, J=27.4 Hz, 1H), 5.22 (s, 2H), 4.81-4.72 (comp, 4H).

The synthesis of example 179 was completed according to the representative procedure for palladium catalyzed carbonylation and the representative procedure for amide formation with trimethylaluminum, reacting with 6-(4-isopropyl-4H-1,2,4-triazol-3-yl)pyridin-2-amine.

Examples 178 and 180 were prepared in an analogous fashion utilizing the same representative procedures as example 179, reacting with the appropriate amine during the amide coupling step.

Example 189: Synthesis of ethyl 6-((6-(4-isopropyl-4H-1,2,4-triazol-3-yl)pyridin-2-yl)carbamoyl)-1,3-dihydro-2H-pyrrolo[3,4-c]pyridine-2-carboxylate

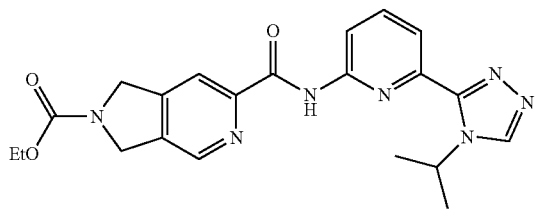 [SMILES: CCOC(=O)N1Cc2cnc(C(=O)Nc3cccc(-c4nncn4C(C)C)n3)cc2C1]

Step 1. Synthesis of N-(6-(4-isopropyl-4H-1,2,4-triazol-3-yl)pyridin-2-yl)-2,3-dihydro-1H-pyrrolo[3,4-c]pyridine-6-carboxamide hydrochloride

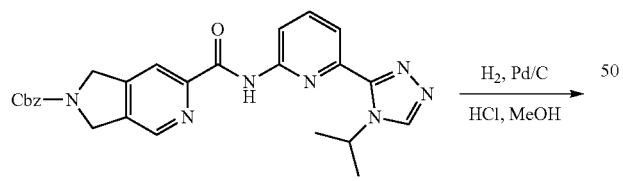

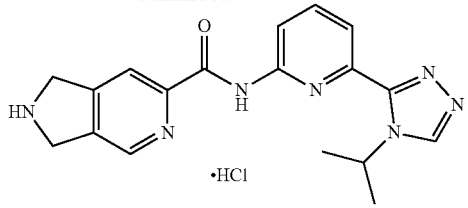

Pd—C (5 mg, 10% loading) was added to a solution of benzyl 6-((6-(4-isopropyl-4H-1,2,4-triazol-3-yl)pyridin-2-yl)carbamoyl)-1,3-dihydro-2H-pyrrolo[3,4-c]pyridine-2-carboxylate (25 mg, 0.052 mmol) and 2 drops of concentrated HCl in MeOH (1.0 mL). The reaction was evacuated and backfilled with H$_2$ (3×) and the reaction was stirred overnight. The reaction was filtered, rinsing with MeOH. The filtrate was concentrated under reduced pressure to give a grey solid. The solid was dissolved in MeOH and filtered through cotton, rinsing with MeOH. The filtrate was concentrated under reduced pressure to give 20.0 mg pale yellow solid that was used without purification: LC-MS, ES$^+$: m/z 350.19 [M+H]$^+$; $^1$H NMR (400 MHz, DMSO-d$_6$) δ 10.68 (s, 1H), 9.09 (s, 1H), 8.81 (s, 1H), 8.37-8.29 (comp, 2H), 8.11 (t, J=8.0 Hz, 1H), 7.91 (d, J=7.6 Hz, 1H), 5.55 (p, J=6.6 Hz, 1H), 4.69 (comp, 4H), 1.51 (d, J=6.7 Hz, 6H).

The synthesis of example 189 was completed according to the representative procedure for carbamate formation, with the following modification: 3.3 equivalents of Et$_3$N were used.

Example 189: Synthesis of 6-((1R,5S)-8-azabicyclo[3.2.1]octane-8-carbonyl)-N-(6-(1-((R)-1-hydroxypropan-2-yl)-1H-tetrazol-5-yl)pyridin-2-yl)-5,6,7,8-tetrahydro-2,6-naphthyridine-3-carboxamide

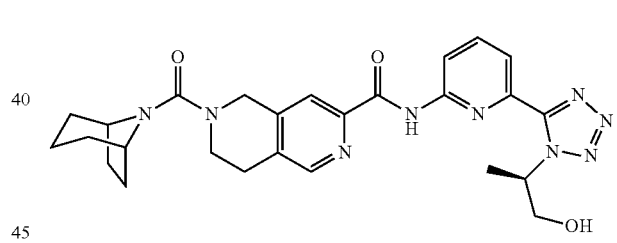

Step 1. Synthesis of 4-nitrophenyl (R)-7-((6-(1-(1-((tert-butyldimethylsilyl)oxy)propan-2-yl)-1H-tetrazol-5-yl)pyridin-2-yl)carbamoyl)-3,4-dihydro-2,6-naphthyridine-2(1H)-carboxylate

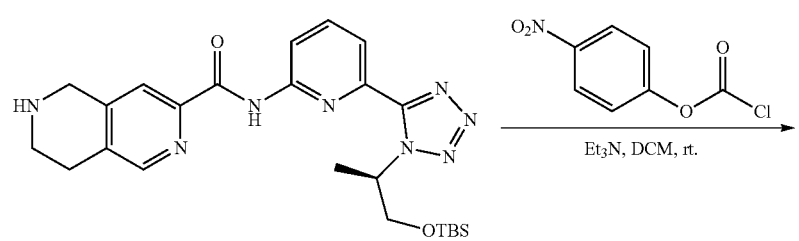

-continued

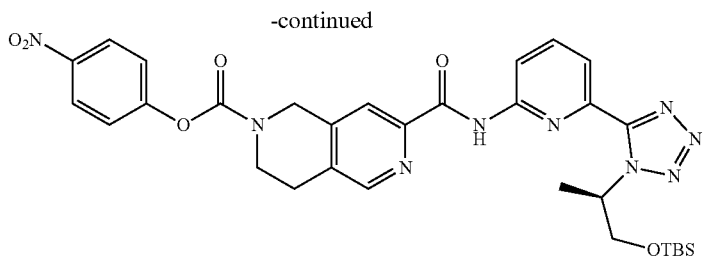

4-Nitrophenyl carbonochloridate (242 mg, 1.2 mmol) was added to (R)—N-(6-(1-(1-(((tert-butyldimethylsilyl)oxy)propan-2-yl)-1H-tetrazol-5-yl)pyridin-2-yl)-5,6,7,8-tetrahydro-2,6-naphthyridine-3-carboxamide (500 mg, 1.0 mmol), and Et$_3$N (303 mg, 3 mmol) in DCM (20 mL) and the mixture was stirred at room temperature overnight. The reaction was diluted with DCM (30 mL) and washed sequentially with H$_2$O (20 mL) and brine (20 mL). The organic phase was dried (Na$_2$SO$_4$), filtered, and concentrated under reduced pressure. The crude residue was purified by column chromatography eluting with DCM/MeOH (50:1) to afford 4-nitrophenyl (R)-7-((6-(1-(1-(((tert-butyldimethylsilyl)oxy)propan-2-yl)-1H-tetrazol-5-yl)pyridin-2-yl)carbamoyl)-3,4-dihydro-2,6-naphthyridine-2(1H)-carboxylate (580 mg, 87%) as an off white solid.

Step 2. Synthesis of 6-((1R,5S)-8-azabicyclo[3.2.1]octane-8-carbonyl)-N-(6-(1-((R)-1-((tert-butyldimethylsilyl)oxy)propan-2-yl)-1H-tetrazol-5-yl)pyridin-2-yl)-5,6,7,8-tetrahydro-2,6-naphthyridine-3-carboxamide

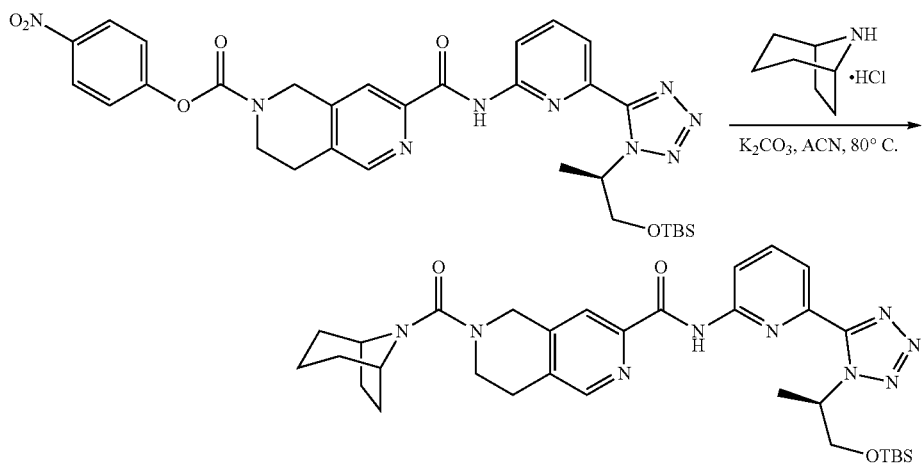

A mixture of 4-nitrophenyl (R)-7-((6-(1-(1-(((tert-butyldimethylsilyl)oxy)propan-2-yl)-1H-tetrazol-5-yl)pyridin-2-yl)carbamoyl)-3,4-dihydro-2,6-naphthyridine-2(1H)-carboxylate (80 mg, 0.12 mmol), K$_2$CO$_3$ (52.79 mg, 0.38 mmol) and 8-aza-bicyclo[3.2.1]octane hydrochloride (89.5 mg, 0.61 mmol) in acetonitrile (5 mL) was stirred for 3 h at 80° C. The reaction was diluted with EtOAc (40 mL) and washed sequentially with H$_2$O (20 mL) and brine (20 mL). The organic layer was dried (Na$_2$SO$_4$), filtered, and concentrated under reduced pressure to give crude 6-((1R,5 S)-8-azabicyclo[3.2.1]octane-8-carbonyl)-N-(6-(1-((R)-1-(((tert-butyldimethylsilyl)oxy)propan-2-yl)-1H-tetrazol-5-yl)pyridin-2-yl)-5,6,7,8-tetrahydro-2,6-naphthyridine-3-carboxamide that was used directly in the next step.

Step 3. Synthesis of 6-((1R,5 S)-8-azabicyclo[3.2.1]octane-8-carbonyl)-N-(6-(1-((R)-1-hydroxypropan-2-yl)-1H-tetrazol-5-yl)pyridin-2-yl)-5,6,7,8-tetrahydro-2,6-naphthyridine-3-carboxamide

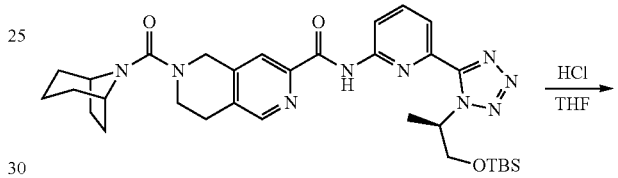

-continued

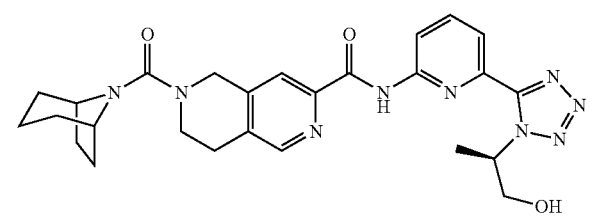 [SMILES: C[C@H](CO)n1nnnc1-c1cccc(NC(=O)c2cc3c(cn2)CCN(C(=O)N2C4CCCC2CC4)C3)n1]

Crude 6-((1R,5S)-8-azabicyclo[3.2.1]octane-8-carbonyl)-N-(6-(1-((R)-1-((tert-butyldimethylsilyl)oxy)propan-2-yl)-1H-tetrazol-5-yl)pyridin-2-yl)-5,6,7,8-tetrahydro-2,6-naphthyridine-3-carboxamide was diluted with THF (3 mL) and concentrated HCl (0.2 mL) was added and the reaction was stirred for 1 h at rt. The reaction was neutralized with saturated NaHCO₃, and extracted with EtOAc (2×20 mL). The combined organic layers were dried (Na₂SO₄), filtered, and concentrated under reduced pressure. The crude residue was purified by reverse phase column chromatography eluting with H₂O/MeCN (0% MeCN→70% MeCN over 15 minutes) to afford 6-((1R,5 S)-8-azabicyclo[3.2.1]octane-8-carbonyl)-N-(6-(1-((R)-1-hydroxypropan-2-yl)-1H-tetrazol-5-yl)pyridin-2-yl)-5,6,7,8-tetrahydro-2,6-naphthyridine-3-carboxamide (13.1 mg) as an off-white solid.

Example 184: Synthesis of (R)—N2-cyclopentyl-N7-(6-(1-(1-hydroxypropan-2-yl)-1H-tetrazol-5-yl)pyridin-2-yl)-N2-methyl-3,4-dihydro-2,6-naphthyridine-2,7(1H)-dicarboxamide

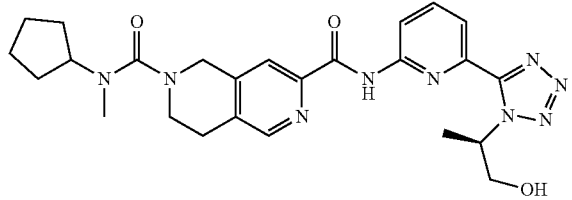 [SMILES: C[C@H](CO)n1nnnc1-c1cccc(NC(=O)c2cc3c(cn2)CCN(C(=O)N(C)C2CCCC2)C3)n1]

Step 1. Synthesis of (R)-7-((6-(1-(1-((tert-butyldimethylsilyl)oxy)propan-2-yl)-1H-tetrazol-5-yl)pyridin-2-yl)carbamoyl)-3,4-dihydro-2,6-naphthyridine-2(1H)-carbonyl chloride

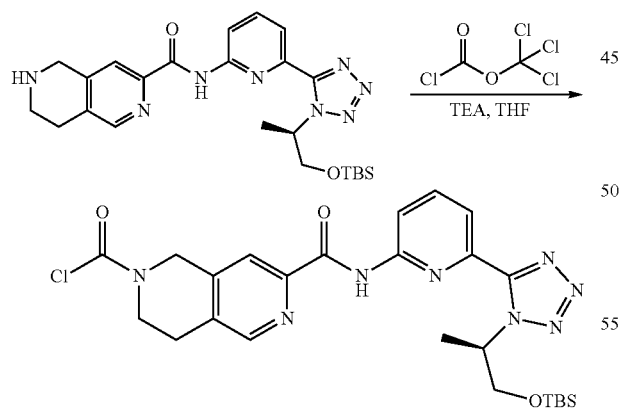

To a solution of (R)—N-(6-(1-(1-((tert-butyldimethylsilyl)oxy)propan-2-yl)-1H-tetrazol-5-yl)pyridin-2-yl)-5,6,7,8-tetrahydro-2,6-naphthyridine-3-carboxamide (50 mg, 0.10 mmol) and TEA (30 mg, 0.30 mmol) in THF was added trichloromethyl carbonochloridate (9 mg, 0.05 mmol) at rt under nitrogen atmosphere. The reaction was stirred for 30 minutes and the solution was used directly in the next step.

Step 2. Synthesis of (R)—N2-cyclopentyl-N7-(6-(1-(1-hydroxypropan-2-yl)-1H-tetrazol-5-yl)pyridin-2-yl)-N2-methyl-3,4-dihydro-2,6-naphthyridine-2,7(1H)-dicarboxamide

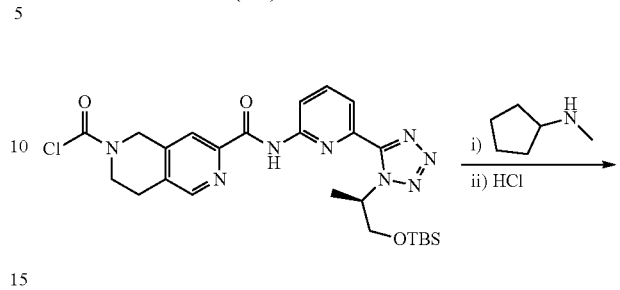

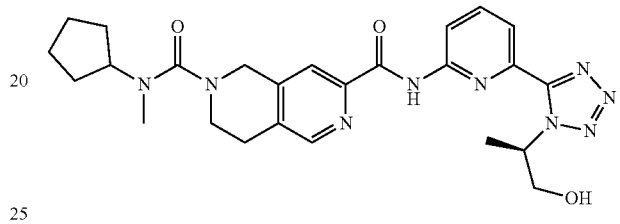

To the above solution was added N-methylcyclopentanamine hydrochloride (21 mg, 0.16 mmol) and the reaction was stirred for 1.5 h at rt under a nitrogen atmosphere. Concentrated HCl (0.2 mL) was added, and the reaction was stirred for 1 h at rt. The reaction was neutralized with saturated NaHCO₃, and extracted with EtOAc (2×20 mL). The organic phase was dried (Na₂SO₄), filtered, and concentrated under reduced pressure. The crude residue was purified by reverse phase column chromatography eluting with H₂O/MeCN (0% MeCN→70% MeCN, 15 minute gradient) to afford (R)—N2-cyclopentyl-N7-(6-(1-(1-hydroxypropan-2-yl)-1H-tetrazol-5-yl)pyridin-2-yl)-N2-methyl-3,4-dihydro-2,6-naphthyridine-2,7(1H)-dicarboxamide (15 mg) as an off-white solid.

Examples 183, 186, and 187 were prepared according to the procedure for the synthesis of example 184.

Example 185: Synthesis of (R)-6-(azetidine-1-carbonyl)-N-(6-(1-(1-hydroxypropan-2-yl)-1H-tetrazol-5-yl)pyridin-2-yl)-5,6,7,8-tetrahydro-2,6-naphthyridine-3-carboxamide

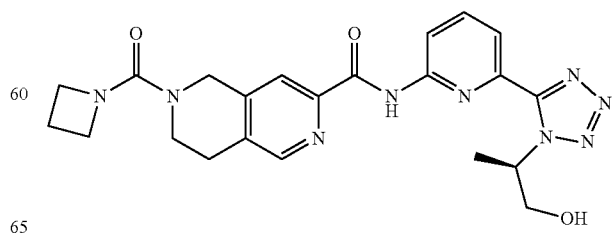

Step 1. Synthesis of 4-nitrophenyl (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate

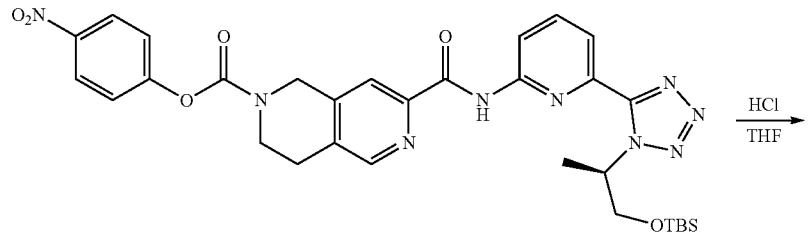

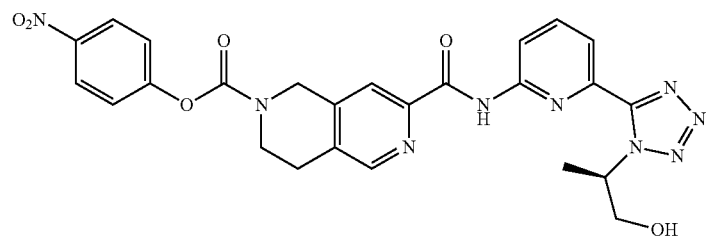

To a solution of 4-nitrophenyl (R)-7-((6-(1-(1-((tert-butyldimethylsilyl)oxy)propan-2-yl)-1H-tetrazol-5-yl)pyridin-2-yl)carbamoyl)-3,4-dihydro-2,6-naphthyridine-2(1H)-carboxylate (50 mg, 0.08 mmol) in THF was added concentrated HCl (0.2 mL) and the reaction was stirred for 1 h at rt. The reaction was neutralized with saturated NaHCO₃, and extracted with EtOAc (2×20 mL). The combined organic layers were dried (Na₂SO₄), filtered, and concentrated under reduced pressure to afford 4-nitrophenyl (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate (37.5 mg, 91%) as an off-white solid.

Step 2. Synthesis of (R)-6-(azetidine-1-carbonyl)-N-(6-(1-(1-hydroxypropan-2-yl)-1H-tetrazol-5-yl)pyridin-2-yl)-5,6,7,8-tetrahydro-2,6-naphthyridine-3-carboxamide

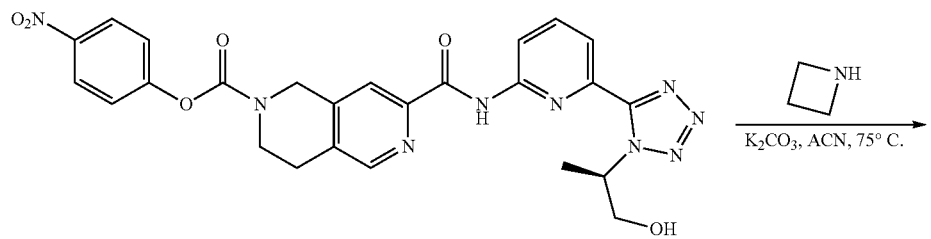

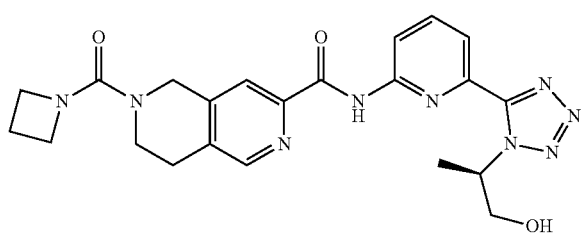 [SMILES: C[C@H](CO)n1nnnc1-c1cccc(NC(=O)c2cc3c(cn2)CCN(C(=O)N2CCC2)C3)n1]

A mixture of 4-nitrophenyl (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate (37.5 mg, 0.07 mmol), azetidine (5.9 mg, 0.10 mmol) and K$_2$CO$_3$ (28.5 mg, 0.21 mmol) in acetonitrile was stirred for 3 h at 75° C. The mixture was filtered and concentrated under reduced pressure. The crude product was purified column chromatography eluting with PE/EtOAc (1:1) to afford (R)-6-(azetidine-1-carbonyl)-N-(6-(1-(1-hydroxypropan-2-yl)-1H-tetrazol-5-yl)pyridin-2-yl)-5,6,7,8-tetrahydro-2,6-naphthyridine-3-carboxamide (10.2 mg) as an off-white solid.

Example 188: Synthesis of (1-ethyl-1H-pyrazol-4-yl)methyl (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate

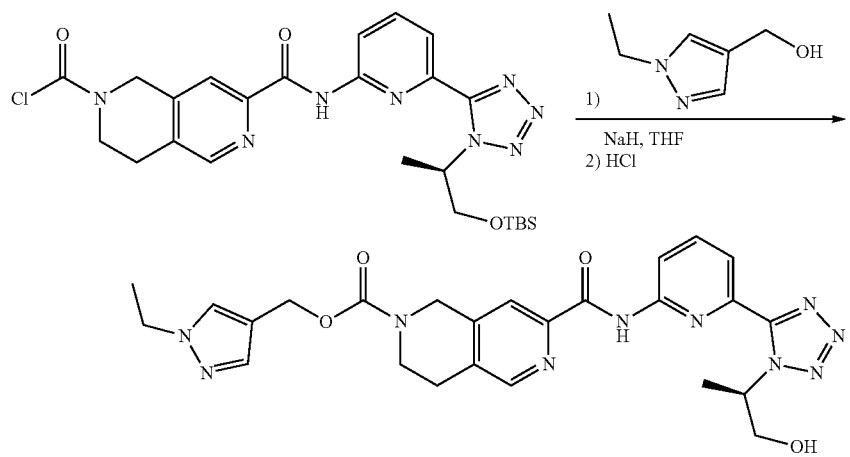

NaH (12.1 mg, 0.51 mmol) was added to a solution of (1-ethyl-1H-pyrazol-4-yl)methanol (25.5 mg, 0.20 mmol) in THF (3 mL) and the reaction was stirred for 30 min at rt. This mixture was added to the crude solution of (R)-7-((6-(1-(1-(((tert-butyldimethylsilyl)oxy)propan-2-yl)-1H-tetrazol-5-yl)pyridin-2-yl)carbamoyl)-3,4-dihydro-2,6-naphthyridine-2(1H)-carbonyl chloride and the reaction was stirred overnight. The reaction was quenched with sat. NH$_4$Cl, and the aqueous layer was extracted with CH$_2$Cl$_2$ (2×50 mL). The combined organic phase was dried (Na$_2$SO$_4$), filtered, and concentrated under reduced pressure. The crude residue was diluted with THF (5 mL) and concentrated HCl (0.2 mL) was added. After stirring for 1 h, the mixture was neutralized with saturated NaHCO$_3$ and extracted with EtOAc (2×20 mL). The combined organic layers were dried (Na$_2$SO$_4$), filtered, and concentrated under reduced pressure. The crude residue was purified by reverse phase column chromatography eluting with H$_2$O/MeCN (0% MeCN→55% MeCN) to afford (1-ethyl-1H-pyrazol-4-yl)methyl (R)-7-((6-(1-(1-hydroxypropan-2-yl)-1H-tetrazol-5-yl)pyridin-2-yl)carbamoyl)-3,4-dihydro-2,6-naphthyridine-2(1H)-carboxylate (26 mg) as an off-white solid.

Example 190: Synthesis of 8-methyl-8-azabicyclo[3.2.1]octan-3-yl 7-((6-(1-((R)-1-hydroxypropan-2-yl)-1H-tetrazol-5-yl)pyridin-2-yl)carbamoyl)-3,4-dihydro-2,6-naphthyridine-2(1H)-carboxylate

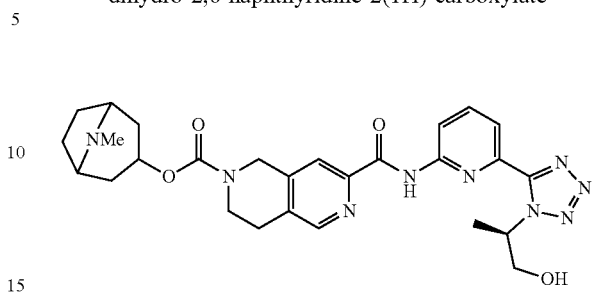

Step 1. Synthesis of 8-methyl-8-azabicyclo[3.2.1]octan-3-yl (4-nitrophenyl) carbonate

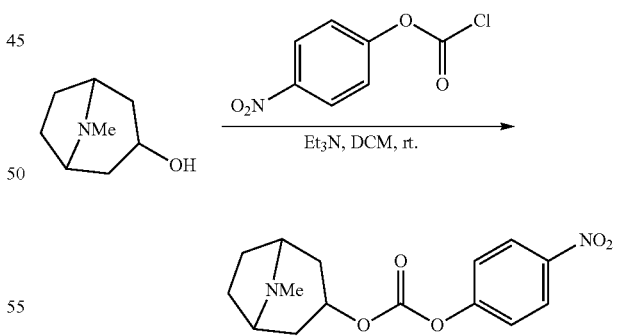

4-Nitrophenyl carbonochloridate (85.6 mg, 0.42 mmol) was added to 8-methyl-8-aza-bicyclo[3.2.1]octan-3-ol (50 mg, 0.35 mmol), and TEA (106 mg, 1.05 mmol) in DCM (5 mL). After stirring overnight at rt, the solution was diluted with EtOAc (20 mL), and washed sequentially with H$_2$O (10 mL) and brine (10 mL). The organic layer was dried (Na$_2$SO$_4$), filtered, and concentrated under reduced pressure to give crude 8-methyl-8-azabicyclo[3.2.1]octan-3-yl (4-nitrophenyl) carbonate that was used without purification.

Step 2. Synthesis of 8-methyl-8-azabicyclo[3.2.1]octan-3-yl 7-((6-(1-((R)-1-hydroxypropan-2-yl)-1H-tetrazol-5-yl)pyridin-2-yl)carbamoyl)-3,4-dihydro-2,6-naphthyridine-2(1H)-carboxylate

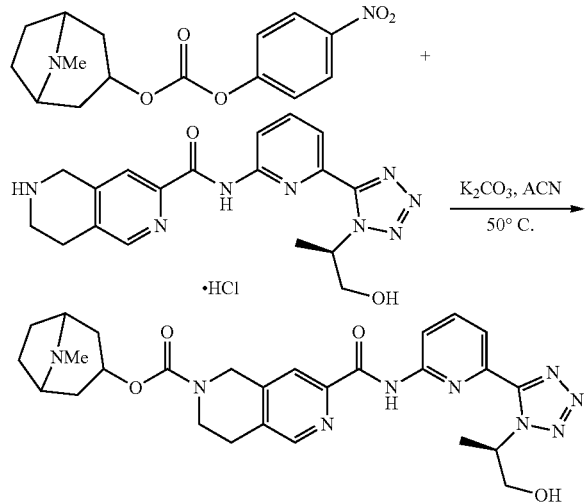

A solution of crude 8-methyl-8-azabicyclo[3.2.1]octan-3-yl (4-nitrophenyl) carbonate was dissolved in acetonitrile (2 mL) was added to a mixture of (R)—N-(6-(1-(1-hydroxypropan-2-yl)-1H-tetrazol-5-yl)pyridin-2-yl)-5,6,7,8-tetrahydro-2,6-naphthyridine-3-carboxamide hydrochloride (20 mg, 0.05 mmol), and K$_2$CO$_3$ (138 mg, 1 mmol) in acetonitrile (2 mL). The mixture was stirred at 50° C. for 2 hours. The reaction was cooled to rt, filtered and concentrated under reduced pressure. The crude residue was purified by reverse phase column chromatography eluting with H$_2$O/MeCN (0% MeCN→80% MeCN) to afford 8-methyl-8-azabicyclo[3.2.1]octan-3-yl 7-((6-(1-((R)-1-hydroxypropan-2-yl)-1H-tetrazol-5-yl)pyridin-2-yl)carbamoyl)-3,4-dihydro-2,6-naphthyridine-2(1H)-carboxylate (8 mg) as an off-white solid.

Example 202: Synthesis of (R)-6-(4-fluorobenzoyl)-N-(6-(4-(1-hydroxypropan-2-yl)-4H-1,2,4-triazol-3-yl)pyridin-2-yl)-5,6,7,8-tetrahydro-2,6-naphthyridine-3-carboxamide

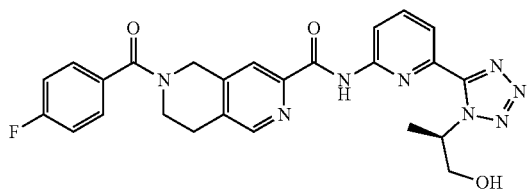 [SMILES: C[C@H](CO)n1nnnc1-c1cccc(NC(=O)c2cc3c(cn2)CCN(C(=O)c2ccc(F)cc2)C3)n1]

Step 1. Synthesis of 6-aminopicolinohydrazide

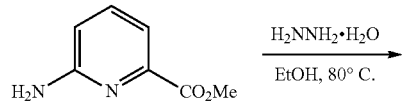

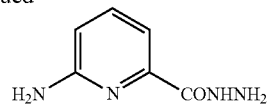

Hydrazine hydrate (32.9 g, 658.00 mmol) was added to a mixture of methyl 6-aminopicolinate (20 g, 131.45 mmol) in EtOH (200 mL), and the resulting solution was stirred for 2 h at 80° C. The reaction was cooled to rt and the solids were collected by filtration and dried in vacuo to give 6-aminopicolinohydrazide (18.2 g, 90.5%) as an off-white solid.

Step 2. Synthesis of (E)-N'-(6-aminopicolinoyl)-N,N-dimethylformohydrazonamide

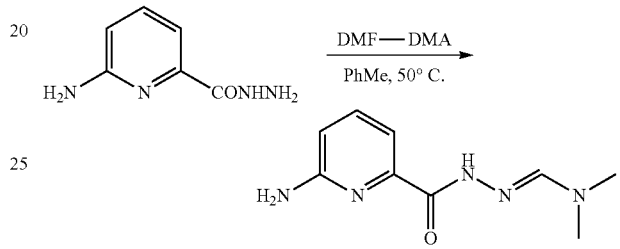

DMF-DMA (21.5 g, 180.4 mmol) was added to a solution of 6-aminopicolinohydrazide (18.3 g, 120.27 mmol) in PhMe (200 mL), and the resulting solution was stirred overnight at 50° C. The reaction was cooled to rt and the solids were collected by filtration and dried in vacuo to give (E)-N'-(6-aminopicolinoyl)-N,N-dimethylformohydrazonamide (23.0 g, 92.3%) as a light yellow solid.

Step 3. Synthesis of (R)-2-(3-(6-aminopyridin-2-yl)-4H-1,2,4-triazol-4-yl)propan-1-ol

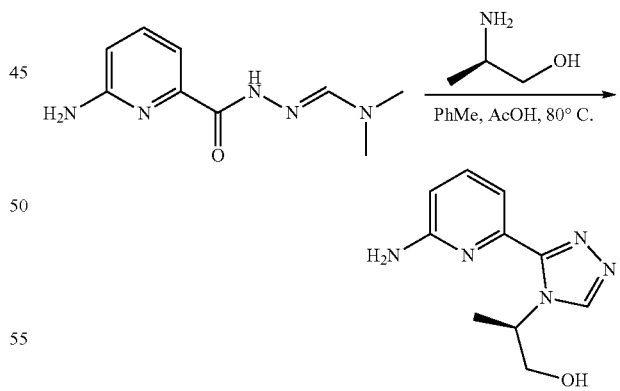

(R)-2-aminopropan-1-ol (25 g, 332.97 mmol) was added to a mixture of ((E)-N'-(6-aminopicolinoyl)-N,N-dimethylformohydrazonamide (23 g, 110.99 mmol) in acetic acid (24 mL) and toluene (120 mL). The resulting solution was stirred overnight at 80° C. The reaction was concentrated under reduced pressure. The crude residue was purified by column chromatography eluting with DCM/MeOH (0% MeOH→10% MeOH), then further purified by reverse phase prep HPLC eluting with H$_2$O/CH$_3$CN (0%

CH₃CN→20% CH₃CN) to give (R)-2-(3-(6-aminopyridin-2-yl)-4H-1,2,4-triazol-4-yl)propan-1-ol (7.8 g, 32%) as an off-white solid.

The synthesis of example 202 was completed from (R)-2-(3-(6-aminopyridin-2-yl)-4H-1,2,4-triazol-4-yl)propan-1-ol and in an analogous fashion to example 162 utilizing the representative procedure for N-functionalization and TB S deprotection and the corresponding acid chloride.

Examples 204 and 205 were prepared according to the representative procedure for N-functionalization and TBS deprotection, utilizing the corresponding chloroformate reagents.

Examples 211 and 212 were prepared according to the representative procedure for N-functionalization and TBS deprotection, utilizing the corresponding sulfonyl chloride reagents.

Example 203 was prepared according to the representative procedure for N-functionalization and TBS deprotection, utilizing the corresponding acid chloride reagents.

Example 206 was prepared according to the representative procedure for N-functionalization and TBS deprotection, utilizing the corresponding isocyanate reagents.

Example 210 was prepared according to the representative procedure for N-functionalization and TBS deprotection, utilizing the corresponding sulfamoyl chloride reagents.

Example 207 was prepared according to the representative procedure for N-functionalization and TBS deprotection, utilizing the corresponding carbamoyl chloride reagents.

Examples 208 and 209 were prepared according to the procedure for the synthesis of example 163.

Example 201 was prepared according to the procedure for the synthesis of example 110, utilizing 6-(4-isopropyl-4H-1,2,4-triazol-3-yl)pyridin-2-amine during the representative procedure for amide formation with trimethylaluminum.

Example 200 was prepared in analogous fashion to the sythesis of example 201.

Examples 191 and 192 were prepared according to the procedure for the synthesis of example 119, utilizing 6-(4-isopropyl-4H-1,2,4-triazol-3-yl)pyridin-2-amine during the representative procedure for amide formation with trimethylaluminum.

Examples 193 and 194 were prepared according to the procedure for the synthesis of example 118, utilizing 6-(4-isopropyl-4H-1,2,4-triazol-3-yl)pyridin-2-amine during the representative procedure for amide formation with trimethylaluminum.

Example 195 was prepared according to the procedure for the synthesis of example 117, utilizing 6-(4-isopropyl-4H-1,2,4-triazol-3-yl)pyridin-2-amine during the representative procedure for amide formation with trimethylaluminum.

Example 196 was prepared according to the procedure for the synthesis of example 116, utilizing 6-(4-isopropyl-4H-1,2,4-triazol-3-yl)pyridin-2-amine during the representative procedure for amide formation with trimethylaluminum.

Example 199 was prepared according to the procedure for the synthesis of example 111, utilizing 6-(4-isopropyl-4H-1,2,4-triazol-3-yl)pyridin-2-amine during the representative procedure for amide formation with trimethylaluminum.

Examples 197 and 198 were prepared according to the procedure for the synthesis of example 163.

Examples 203-205 were prepared according to the representative procedure for N-functionalization and TBS deprotection, utilizing the corresponding chloroformate reagents.

Example 210 was prepared according to the representative procedure for N-functionalization and TBS deprotection, utilizing the corresponding sulfonyl chloride reagents.

Example 202 was prepared according to the representative procedure for N-functionalization and TBS deprotection, utilizing the corresponding acid chloride reagents.

Example 206 was prepared according to the representative procedure for N-functionalization and TBS deprotection, utilizing the corresponding isocyanate reagents.

Example 209 was prepared according to the representative procedure for N-functionalization and TBS deprotection, utilizing the corresponding sulfamoyl chloride reagents.

Example 207 was prepared according to the representative procedure for N-functionalization and TBS deprotection, utilizing the corresponding carbamoyl chloride reagents.

Example 208 was prepared according to the procedure for the synthesis of example 163.

| Example | Structure | LC-MS [M + H]⁺ unless otherwise noted | H-NMR |
|---|---|---|---|
| 1 | 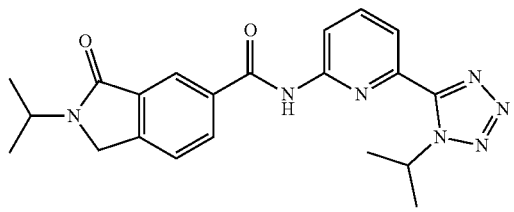 [SMILES: CC(C)N1Cc2ccc(C(=O)Nc3cccc(-c4nnnn4C(C)C)n3)cc2C1=O] | 406.18 | ¹H NMR (400 MHz, Chloroform-d) δ 8.81 (s, 1H), 8.53 (dd, J = 8.4, 0.9 Hz, 1H), 8.33 (d, J = 1.7 Hz, 1H), 8.23 (dd, J = 7.9, 1.7 Hz, 1H), 8.08 (dd, J = 7.7, 1.0 Hz, 1H), 7.98 (t, J = 8.0 Hz, 1H), 7.63 (dd, J = 7.9, 0.8 Hz, 1H), 5.85 (hept, J = 6.7 Hz, 1H), 4.67 (hept, J = 6.8 Hz, 1H), 4.43 (s, 2H), 1.66 (d, J = 6.7 Hz, 6H), 1.30 (d, J = 6.7 Hz, 6H) |

-continued

| Example | Structure | LC-MS [M + H]+ unless otherwise noted | H-NMR |
|---|---|---|---|
| 2 | 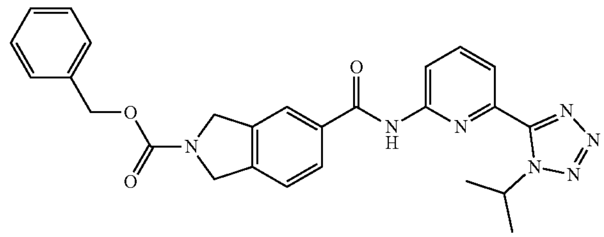 [SMILES: CC(C)n1nnnc1-c1cccc(NC(=O)c2ccc3c(c2)CN(C(=O)OCc2ccccc2)C3)n1] | 484.20 | ¹H NMR (400 MHz, DMSO-d₆) δ 10.93 (s, 1H), 8.60-8.51 (m, 1H), 8.26 (dd, J = 8.2, 1.7 Hz, 1H), 8.11 (t, J = 8.0 Hz, 1H), 7.97 (d, J = 7.5 Hz, 1H), 7.91 (s, 1H), 7.52 (dd, J = 11.2, 8.2 Hz, 1H), 7.45-7.36 (comp, 5H), 6.05 (hept, J = 6.7 Hz, 1H), 5.16 (s, 2H), 4.79 (s, 2H), 4.76-4.72 (m, 2H), 1.54 (dd, J = 6.6, 1.1 Hz, 6H) |
| 3 | 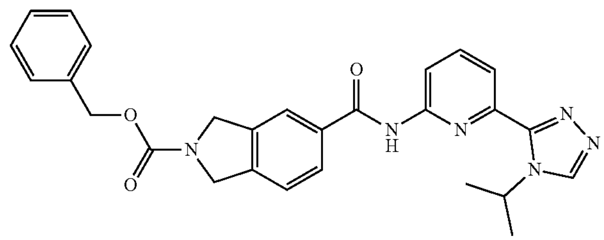 [SMILES: CC(C)n1cnnc1-c1cccc(NC(=O)c2ccc3c(c2)CN(C(=O)OCc2ccccc2)C3)n1] | 483.21 | ¹H NMR (400 MHz, DMSO-d₆) δ 10.77 (s, 1H), 8.84 (s, 1H), 8.19-8.12 (m, 1H), 8.01 (t, J = 8.0 Hz, 1H), 7.96-7.86 (comp, 2H), 7.84 (dd, J = 7.6, 0.9 Hz, 1H), 7.50 (dd, J = 11.0, 8.2 Hz, 1H), 7.45-7.29 (comp, 5H), 5.70-5.59 (m, 1H), 5.15 (s, 2H), 4.78 (s, 2H), 4.73 (s, 2H), 1.42 (d, J = 6.9 Hz, 6H) |
| 4 | 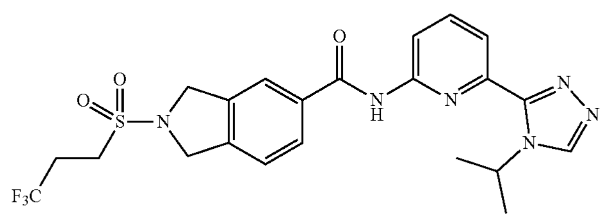 [SMILES: CC(C)n1cnnc1-c1cccc(NC(=O)c2ccc3c(c2)CN(S(=O)(=O)CCC(F)(F)F)C3)n1] | 508.80 | ¹H NMR (400 MHz, DMSO-d₆) δ 10.79 (s, 1H), 8.87 (s, 1H), 8.17 (d, J = 8.4 Hz, 1H), 8.02 (t, J = 8.0 Hz, 1H), 7.98-7.90 (comp, 2H), 7.86 (dd, J = 7.6, 1.0 Hz, 1H), 7.51 (d, J = 8.4 Hz, 1H), 5.69 (hept, J = 6.5 Hz, 1H), 4.81 (s, 4H), 3.56-3.49 (m, 2H), 2.85-2.69 (m, 2H), 1.44 (d, J = 6.7 Hz, 6H) |
| 5 | 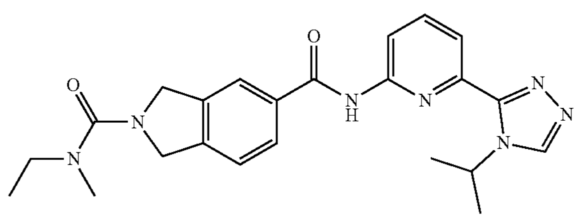 [SMILES: CCN(C)C(=O)N1Cc2ccc(C(=O)Nc3cccc(-c4nncn4C(C)C)n3)cc2C1] | 433.80 | ¹H NMR (400 MHz, DMSO-d₆) δ 10.74 (s, 1H), 8.86 (s, 1H), 8.18 (dd, J = 8.4, 0.9 Hz, 1H), 8.02 (t, J = 8.0 Hz, 1H), 7.92 (d, J = 1.5 Hz, 1H), 7.89 (dd, J = 7.9, 1.7 Hz, 1H), 7.86 (dd, J = 7.6, 0.9 Hz, 1H), 7.49 (d, J = 7.8 Hz, 1H), 5.69 (hept, J = 6.6 Hz, 1H), 4.76 (s, 4H), 3.22 (q, J = 7.1 Hz, 2H), 2.84 (s, 3H), 1.44 (d, J = 6.7 Hz, 6H), 1.13 (t, J = 7.1 Hz, 3H) |
| 6 | 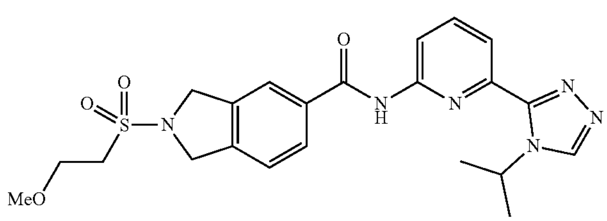 [SMILES: COCCS(=O)(=O)N1Cc2ccc(C(=O)Nc3cccc(-c4nncn4C(C)C)n3)cc2C1] | 472.00 | ¹H NMR (400 MHz, DMSO-d₆) δ 10.78 (s, 1H), 8.87 (s, 1H), 8.17 (dd, J = 8.4, 1.0 Hz, 1H), 8.02 (t, J = 8.0 Hz, 1H), 7.93-7.90 (comp, 3H), 7.86 (dd, J = 7.6, 1.0 Hz, 1H), 7.50 (d, J = 8.3 Hz, 1H), 5.69 (hept, J = 6.9 Hz, 1H), 4.74 (s, 4H), 3.68 (t, J = 5.8 Hz, 2H), 3.51 (t, J = 5.8 Hz, 2H), 1.44 (d, J = 6.6 Hz, 6H) |
| 7 | 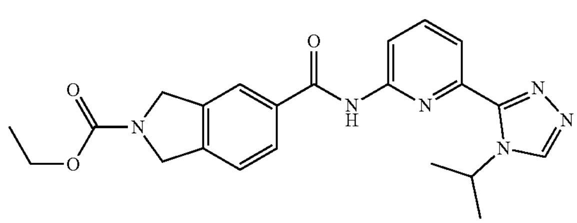 [SMILES: CCOC(=O)N1Cc2ccc(C(=O)Nc3cccc(-c4nncn4C(C)C)n3)cc2C1] | 420.80 | ¹H NMR (400 MHz, DMSO-d₆) δ 10.78 (s, 1H), 8.86 (s, 1H), 8.17 (d, J = 8.7 Hz, 1H), 8.02 (t, J = 8.0 Hz, 1H), 7.97-7.89 (comp, 2H), 7.86 (dd, J = 7.6, 0.9 Hz, 1H), 7.51 (t, J = 8.4 Hz, 1H), 5.69 (hept, J = 6.6 Hz, 1H), 4.72 (d, J = 9.7 Hz, 4H), 4.13 (q, J = 7.1 Hz, 2H), 1.44 (d, J = 6.7 Hz, 6H), 1.25 (t, J = 7.1 Hz, 3H) |

-continued

| Example | Structure | LC-MS [M + H]+ unless otherwise noted | H-NMR |
|---|---|---|---|
| 8 | (isoindoline-5-carboxamide linked to 6-(1-isopropyl-1H-tetrazol-5-yl)pyridin-2-yl) | 349.80 | ¹H NMR (500 MHz, DMSO-d$_6$) δ 10.84 (s, 1H), 8.29 (dd, J = 8.4, 0.9 Hz, 1H), 8.11 (t, J = 8.0 Hz, 1H), 7.97 (dd, J = 7.6, 0.9 Hz, 1H), 7.86 (s, 1H), 7.82 (dd, J = 7.8, 1.6 Hz, 1H), 7.44 (d, J = 7.8 Hz, 1H), 6.14-6.05 (m, 1H), 4.17-4.06 (comp, 4H), 1.56 (d, J = 6.6 Hz, 6H) |
| 9 | (isoindoline-5-carboxamide linked to 6-(4-isopropyl-4H-1,2,4-triazol-3-yl)pyridin-2-yl) | 348.80 | ¹H NMR (500 MHz, DMSO-d$_6$) δ 10.69 (s, 1H), 8.86 (s, 1H), 8.18 (d, J = 8.3 Hz, 1H), 8.01 (t, J = 8.0 Hz, 1H), 7.89-7.79 (comp, 3H), 7.43 (d, J = 7.8 Hz, 1H), 5.74-5.69 (m, 1H), 4.20-4.05 (comp, 4H), 1.44 (d, J = 6.7 Hz, 6H) |
| 10 | (2-(N,N-dimethylsulfamoyl)isoindoline-5-carboxamide derivative) | 456.80 | ¹H NMR (500 MHz, DMSO-d$_6$) δ 10.92 (s, 1H), 8.27 (dd, J = 8.4, 0.9 Hz, 1H), 8.12 (d, J = 8.0 Hz, 1H), 7.98 (dd, J = 7.6, 0.9 Hz, 1H), 7.94-7.91 (comp, 2H), 7.52 (d, J = 8.3 Hz, 1H), 6.07 (hept, J = 6.6 Hz, 1H), 4.69 (s, 4H), 2.82 (s, 6H), 1.56 (d, J = 6.7 Hz, 6H) |
| 11 | (2-(pyrrolidine-1-carbonyl)isoindoline-5-carboxamide derivative) | 447.80 | ¹H NMR (400 MHz, DMSO-d$_6$) δ 10.91 (s, 1H), 8.28 (dt, J = 8.3, 0.7 Hz, 1H), 8.12 (t, J = 8.0 Hz, 1H), 7.98 (dt, J = 7.6, 0.7 Hz, 1H), 7.91-7.89 (comp, 2H), 7.50 (d, J = 7.8 Hz, 1H), 6.08 (hept, J = 6.6 Hz, 1H), 4.79 (s, 4H), 3.44-3.35 (m, 4H), 1.86-1.78 (m, 4H), 1.56 (d, J = 6.6 Hz, 6H) |
| 12 | (2-(N,N-dimethylcarbamoyl)isoindoline-5-carboxamide derivative) | 420.80 | ¹H NMR (500 MHz, DMSO-d$_6$) δ 10.90 (s, 1H), 8.28 (dd, J = 8.4, 0.9 Hz, 1H), 8.12 (t, J = 8.0 Hz, 1H), 7.98 (dd, J = 7.6, 0.9 Hz, 1H), 7.94-7.87 (comp, 2H), 7.50 (d, J = 7.8 Hz, 1H), 6.08 (hept, J = 6.6 Hz, 1H), 4.78 (s, 4H), 2.86 (s, 6H), 1.56 (d, J = 6.6 Hz, 6H) |
| 13 | (2-(N-ethyl-N-methylcarbamoyl)isoindoline-5-carboxamide derivative) | 434.80 | ¹H NMR (400 MHz, DMSO-d$_6$) δ 10.90 (s, 1H), 8.28 (dd, J = 8.4, 0.9 Hz, 1H), 8.12 (t, J = 8.0 Hz, 1H), 7.97 (dd, J = 7.5, 0.8 Hz, 1H), 7.92 (d, J = 1.4 Hz, 1H), 7.90 (dd, J = 7.8, 1.7 Hz, 1H), 7.51 (d, J = 7.9 Hz, 1H), 6.08 (hept, J = 6.7 Hz, 1H), 4.77 (s, 4H), 3.22 (q, J = 7.1 Hz, 2H), 2.84 (s, 3H), 1.56 (d, J = 6.6 Hz, 6H), 1.13 (t, J = 7.0 Hz, 3H) |

-continued

| Example | Structure | LC-MS [M + H]+ unless otherwise noted | H-NMR |
|---|---|---|---|
| 14 | 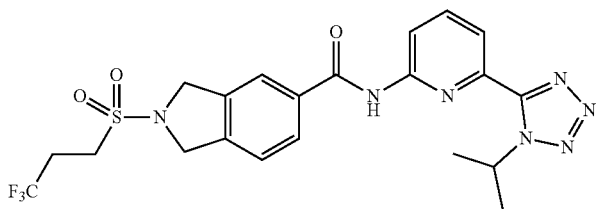 [SMILES: CC(C)n1nnnc1-c1cccc(NC(=O)c2ccc3c(c2)CN(S(=O)(=O)CCC(F)(F)F)C3)n1] | 509.80 | ¹H NMR (500 MHz, DMSO-d₆) δ 10.93 (s, 1H), 8.27 (dd, J = 8.5, 0.9 Hz, 1H), 8.12 (t, J = 8.0 Hz, 1H), 7.98 (dd, J = 7.6, 0.9 Hz, 1H), 7.96-7.93 (comp, 2H), 7.53 (d, J = 8.7 Hz, 1H), 6.06 (hept, J = 7.2, 6.8 Hz, 1H), 4.82 (s, 4H), 3.56-3.49 (m, 2H), 2.82-2.69 (m, 2H), 1.56 (d, J = 6.6 Hz, 6H) |
| 15 | 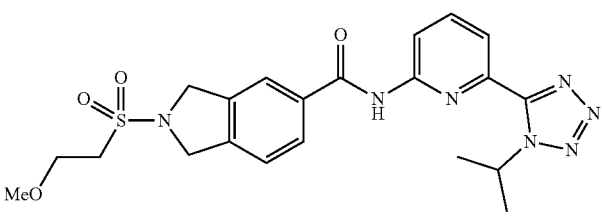 [SMILES: COCCS(=O)(=O)N1Cc2ccc(C(=O)Nc3cccc(-c4nnnn4C(C)C)n3)cc2C1] | 471.80 | ¹H NMR (500 MHz, DMSO-d₆) δ 10.93 (s, 1H), 8.27 (d, J = 8.3 Hz, 1H), 8.12 (t, J = 8.0 Hz, 1H), 7.98 (d, J = 7.6 Hz, 1H), 7.94-7.92 (comp, 2H), 7.52 (d, J = 8.3 Hz, 1H), 6.07 (hept, J = 6.7 Hz, 1H), 4.74 (s, 4H), 3.68 (t, J = 5.8 Hz, 2H), 3.51 (t, J = 5.8 Hz, 2H), 3.16 (s, 3H), 1.56 (d, J = 6.6 Hz, 6H) |
| 16 | 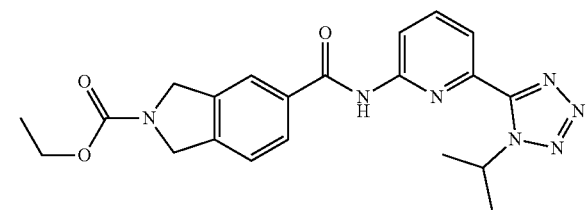 | 421.80 | ¹H NMR (400 MHz, DMSO-d₆) δ 10.93 (s, 1H), 8.28 (dd, J = 8.3, 2.2 Hz, 1H), 8.12 (t, J = 8.0 Hz, 1H), 7.98 (dd, J = 7.6, 0.8 Hz, 1H), 7.96-7.89 (comp, 2H), 7.53 (t, J = 8.5 Hz, 1H), 6.08 (hept, J = 6.6 Hz, 1H), 4.73 (d, J = 9.4 Hz, 4H), 4.13 (q, J = 7.1 Hz, 2H), 1.56 (d, J = 6.6 Hz, 6H), 1.25 (t, J = 7.1 Hz, 3H) |
| 17 | 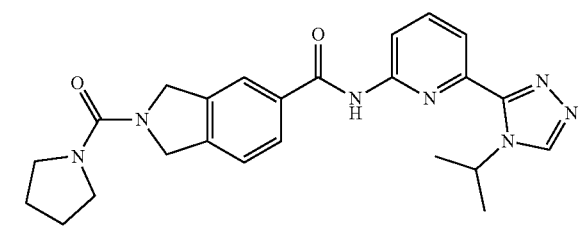 | 445.80 | ¹H NMR (400 MHz, DMSO-d₆) δ 10.75 (s, 1H), 8.86 (s, 1H), 8.18 (d, J = 8.3 Hz, 1H), 8.02 (t, J = 8.0 Hz, 1H), 7.92-7.88 (comp, 2H), 7.86 (d, J = 7.6 Hz, 1H), 7.49 (d, J = 7.8 Hz, 1H), 5.70 (hept, J = 6.7 Hz, 1H), 4.79 (s, 4H), 3.43-3.35 (m, 4H), 1.88-1.79 (m, 4H), 1.44 (d, J = 6.6 Hz, 6H) |
| 18 | 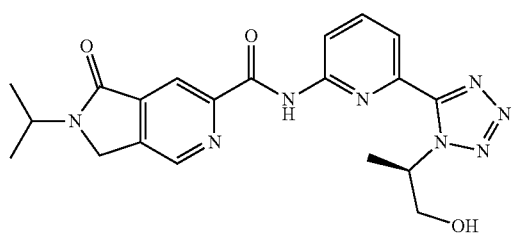 [SMILES: CC(C)N1Cc2cnc(C(=O)Nc3cccc(-c4nnnn4[C@H](C)CO)n3)cc2C1=O] | 423.20 | ¹H NMR (400 MHz, DMSO-d₆) δ 10.88 (s, 1H), 9.05 (d, J = 1.1 Hz, 1H), 8.42 (dd, J = 8.4, 0.9 Hz, 1H), 8.30 (d, J = 1.1 Hz, 1H), 8.17 (t, J = 8.0 Hz, 1H), 7.99 (dd, J = 7.6, 0.9 Hz, 1H), 5.95-5.80 (m, 1H), 5.62 (s, 2H), 4.98 (dd, J = 6.2, 5.3 Hz, 1H), 4.15-3.99 (m, 1H), 3.85-3.72 (m, 2H), 1.59 (d, J = 6.7 Hz, 3H), 1.18 (d, J = 6.4 Hz, 6H) |
| 19 | 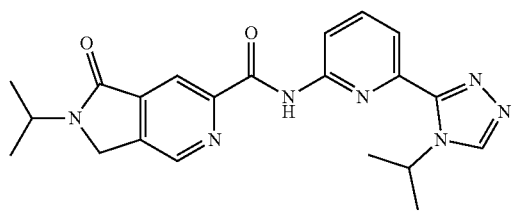 [SMILES: CC(C)N1Cc2cnc(C(=O)Nc3cccc(-c4nncn4C(C)C)n3)cc2C1=O] | 406.21 | ¹H NMR (400 MHz, DMSO-d₆) δ 10.68 (s, 1H), 9.03 (d, J = 1.1 Hz, 1H), 8.90 (s, 1H), 8.33 (dd, J = 8.3, 0.9 Hz, 1H), 8.30 (d, J = 1.1 Hz, 1H), 8.09 (t, J = 8.0 Hz, 1H), 7.91 (dd, J = 7.7, 0.9 Hz, 1H), 5.62 (s, 2H), 5.54 (hept, J = 6.6 Hz, 1H), 4.06 (hept, J = 5.9 Hz, 1H), 1.50 (d, J = 6.7 Hz, 6H), 1.17 (d, J = 6.3 Hz, 6H) |

| Example | Structure | LC-MS [M + H]+ unless otherwise noted | H-NMR |
|---|---|---|---|
| 20 | 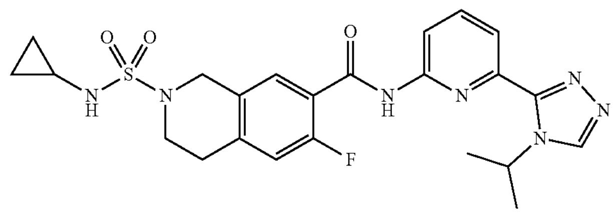 | 500.19 | ¹H NMR (400 MHz, DMSO-d$_6$) δ 10.80 (s, 1H), 8.86 (s, 1H), 8.20 (dd, J = 8.3, 1.0 Hz, 1H), 8.03 (t, J = 8.0 Hz, 1H), 7.89 (dd, J = 7.7, 0.9 Hz, 1H), 7.76 (d, J = 2.3 Hz, 1H), 7.58 (d, J = 7.1 Hz, 1H), 7.22 (d, J = 10.9 Hz, 1H), 5.66 (hept, J = 6.7 Hz, 1H), 4.37 (s, 2H), 3.45 (t, J = 5.9 Hz, 2H), 2.97 (t, J = 6.0 Hz, 2H), 2.41-2.30 (m, 1H), 1.43 (d, J = 6.6 Hz, 6H), 0.60-0.47 (comp, 4H) |
| 21 | 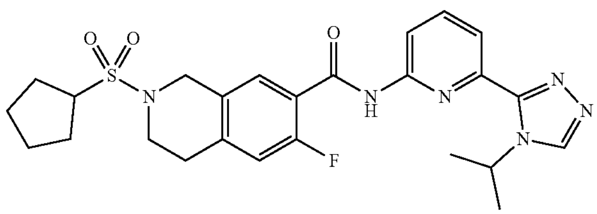 [SMILES: CC(C)n1cnnc1-c1cccc(NC(=O)c2cc3c(cc2F)CCN(S(=O)(=O)C2CCCC2)C3)n1] | 513.20 | ¹H NMR (400 MHz, DMSO-d$_6$) δ 10.80 (s, 1H), 8.86 (s, 1H), 8.20 (dd, J = 8.3, 0.9 Hz, 1H), 8.03 (t, J = 8.0 Hz, 1H), 7.89 (dd, J = 7.7, 0.9 Hz, 1H), 7.57 (d, J = 7.1 Hz, 1H), 7.23 (d, J = 11.0 Hz, 1H), 5.65 (hept, J = 6.9 Hz, 1H), 4.49 (s, 2H), 3.75 (p, J = 8.2 Hz, 1H), 3.55 (t, J = 5.9 Hz, 2H), 2.94 (t, J = 5.9 Hz, 2H), 2.01-1.76 (comp, 4H), 1.74-1.48 (comp, 3H), 1.45-1.40 (comp, 7H) |
| 22 | 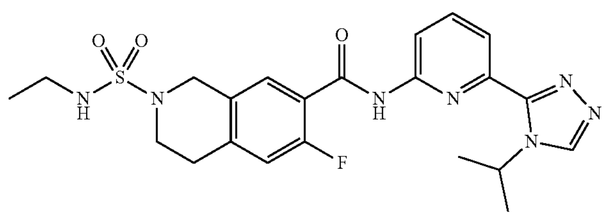 [SMILES: CCNS(=O)(=O)N1CCc2cc(F)c(C(=O)Nc3cccc(-c4nncn4C(C)C)n3)cc2C1] | 488.18 | ¹H NMR (400 MHz, DMSO-d$_6$) δ 10.79 (s, 1H), 8.86 (s, 1H), 8.20 (dd, J = 8.3, 0.9 Hz, 1H), 8.02 (t, J = 8.0 Hz, 1H), 7.89 (dd, J = 7.7, 0.9 Hz, 1H), 7.56 (d, J = 7.1 Hz, 1H), 7.38 (t, J = 5.6 Hz, 1H), 7.21 (d, J = 10.9 Hz, 1H), 5.66 (hept, J = 6.7 Hz, 1H), 4.32 (s, 2H), 3.39 (t, J = 6.0 Hz, 2H), 2.97-2.89 (comp, 4H), 1.43 (d, J = 6.7 Hz, 6H), 1.06 (t, J = 7.2 Hz, 3H) |
| 23 | 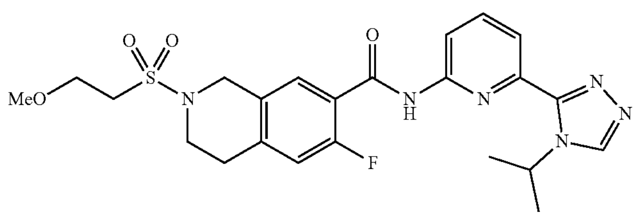 [SMILES: COCCS(=O)(=O)N1CCc2cc(F)c(C(=O)Nc3cccc(-c4nncn4C(C)C)n3)cc2C1] | 503.19 | ¹H NMR (400 MHz, DMSO-d$_6$) δ 10.80 (s, 1H), 8.86 (s, 1H), 8.20 (dd, J = 8.4, 0.9 Hz, 1H), 8.03 (t, J = 8.0 Hz, 1H), 7.89 (dd, J = 7.7, 0.9 Hz, 1H), 7.58 (d, J = 7.0 Hz, 1H), 7.23 (d, J = 10.9 Hz, 1H), 5.65 (hept, J = 6.1 Hz, 1H), 4.44 (s, 2H), 3.68 (t, J = 5.9 Hz, 2H), 3.49 (t, J = 5.9 Hz, 2H), 3.43 (t, J = 5.9 Hz, 2H), 3.25 (s, 3H), 2.96 (t, J = 5.9 Hz, 2H), 1.43 (d, J = 6.1 Hz, 6H) |
| 24 | 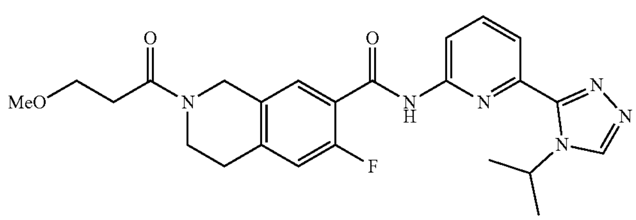 [SMILES: COCCC(=O)N1CCc2cc(F)c(C(=O)Nc3cccc(-c4nncn4C(C)C)n3)cc2C1] | 467.22 | ¹H NMR (400 MHz, DMSO-d$_6$) δ 10.81-10.76 (m, 1H), 8.89-8.85 (m, 1H), 8.20 (d, J = 8.3 Hz, 1H), 8.03 (td, J = 8.0, 1.7 Hz, 1H), 7.89 (dd, J = 7.7, 1.1 Hz, 1H), 7.59 (t, J = 6.4 Hz, 1H), 7.24-7.20 (m, 1H), 5.67 (hept, J = 6.9 Hz, 1H), 4.72 (s, 1H), 4.64 (s, 1H), 3.69 (dt, J = 12.1, 6.0 Hz, 2H), 3.63-3.54 (comp, 2H), 3.25-3.18 (comp, 5H), 2.67 (t, J = 6.5 Hz, 2H), 1.43 (d, J = 6.6 Hz, 6H) |
| 25 | 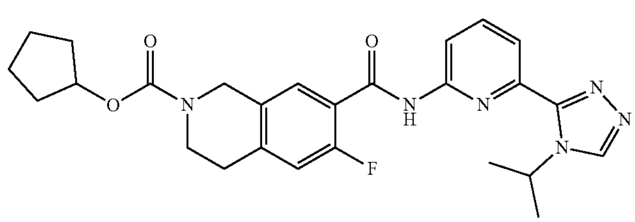 [SMILES: CC(C)n1cnnc1-c1cccc(NC(=O)c2cc3c(cc2F)CCN(C(=O)OC2CCCC2)C3)n1] | 493.23 | ¹H NMR (400 MHz, DMSO-d$_6$) δ 10.79 (s, 1H), 8.86 (s, 1H), 8.20 (dd, J = 8.4, 0.9 Hz, 1H), 8.02 (t, J = 8.0 Hz, 1H), 7.89 (dd, J = 7.7, 0.9 Hz, 1H), 7.59 (d, J = 1.1 Hz, 1H), 7.21 (d, J = 10.9 Hz, 1H), 5.66 (hept, J = 6.1 Hz, 1H), 5.03 (td, J = 5.9, 3.1 Hz, 1H), 4.57 (s, 2H), 3.58 (t, J = 5.9 Hz, 2H), 2.86 (t, J = 6.0 Hz, 2H), 1.89-1.75 (comp, 2H), 1.74-1.51 (comp, 6H), 1.42 (d, J = 6.1 Hz, 6H) |

| Example | Structure | LC-MS [M + H]+ unless otherwise noted | H-NMR |
|---|---|---|---|
| 26 | 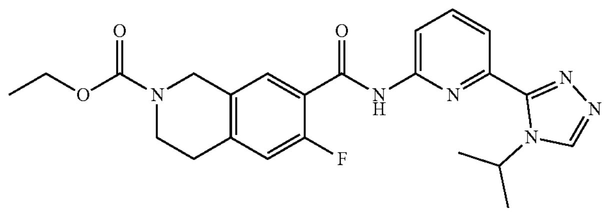 [SMILES: CCOC(=O)N1CCc2cc(F)c(C(=O)Nc3cccc(-c4nncn4C(C)C)n3)cc2C1] | 453.20 | ¹H NMR (400 MHz, DMSO-d$_6$) δ 10.83-10.76 (m, 1H), 8.86 (s, 1H), 8.20 (dd, J = 8.3, 0.9 Hz, 1H), 8.02 (t, J = 8.0 Hz, 1H), 7.89 (dd, J = 7.7, 0.9 Hz, 1H), 7.59 (d, J = 7.1 Hz, 1H), 7.22 (d, J = 10.9 Hz, 1H), 5.66 (hept, J = 7.0 Hz, 1H), 4.59 (s, 2H), 4.09 (q, J = 7.1 Hz, 2H), 3.61 (t, J = 5.9 Hz, 2H), 2.87 (t, J = 5.9 Hz, 2H), 1.42 (d, J = 6.7 Hz, 6H), 1.21 (t, J = 7.1 Hz, 3H) |
| 27 | 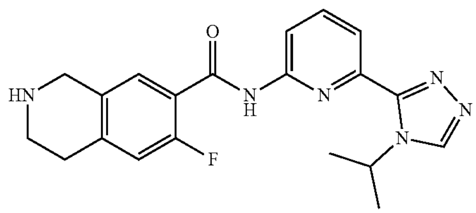 [SMILES: CC(C)n1cnnc1-c1cccc(NC(=O)c2cc3c(cc2F)CCNC3)n1] | 381.17 | ¹H NMR (400 MHz, DMSO-d$_6$) δ 10.69 (s, 1H), 8.86 (s, 1H), 8.19 (dd, J = 8.3, 0.9 Hz, 1H), 8.02 (t, J = 8.0 Hz, 1H), 7.88 (dd, J = 7.6, 0.9 Hz, 1H), 7.40 (d, J = 7.3 Hz, 1H), 7.09 (d, J = 11.3 Hz, 1H), 5.65 (hept, J = 6.6 Hz, 1H), 3.87 (s, 2H), 2.94 (t, J = 5.8 Hz, 2H), 2.75 (t, J = 5.9 Hz, 2H), 1.43 (d, J = 6.7 Hz, 6H) |
| 28 | 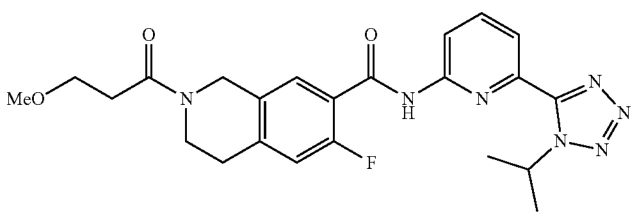 [SMILES: COCCC(=O)N1CCc2cc(F)c(C(=O)Nc3cccc(-c4nnnn4C(C)C)n3)cc2C1] | 468.21 | ¹H NMR (400 MHz, DMSO-d$_6$) δ 10.98 (d, J = 4.7 Hz, 1H), 8.31 (d, J = 8.3 Hz, 1H), 8.13 (td, J = 8.0, 1.5 Hz, 1H), 8.00 (d, J = 7.6 Hz, 1H), 7.60 (dd, J = 7.2, 3.9 Hz, 1H), 7.25 (d, J = 10.8 Hz, 1H), 6.02 (hept, J = 6.1 Hz, 1H), 4.72 (s, 0.8H), 4.65 (s, 1.2H), 3.72-3.67 (m, 2H), 3.58 (t, J = 6.5 Hz, 2H), 3.50 (t, J = 6.3 Hz, 0.4H), 3.24-3.20 (comp, 3.6H), 2.93 (t, J = 6.0 Hz, 1.2H), 2.84 (t, J = 6.1 Hz, 0.8H), 2.67 (t, J = 6.5 Hz, 2H), 1.54 (d, J = 6.6 Hz, 6H) |
| 29 | 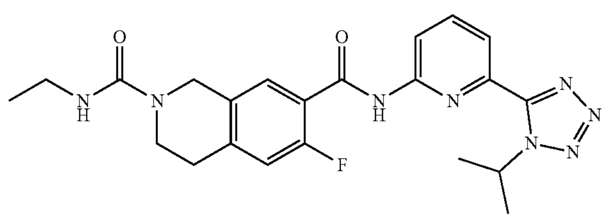 [SMILES: CCNC(=O)N1CCc2cc(F)c(C(=O)Nc3cccc(-c4nnnn4C(C)C)n3)cc2C1] | 453.21 | ¹H NMR (400 MHz, DMSO-d$_6$) δ 10.97 (s, 1H), 8.31 (dd, J = 8.4, 0.9 Hz, 1H), 8.13 (dd, J = 8.4, 7.6 Hz, 1H), 8.00 (dd, J = 7.6, 0.9 Hz, 1H), 7.50 (d, J = 7.0 Hz, 1H), 7.21 (d, J = 10.9 Hz, 1H), 6.59 (t, J = 5.4 Hz, 1H), 6.02 (hept, J = 6.5 Hz, 1H), 4.52 (s, 2H), 3.55 (t, J = 5.9 Hz, 2H), 3.08 (qd, J = 7.1, 5.3 Hz, 2H), 2.84 (t, J = 5.9 Hz, 2H), 1.54 (d, J = 6.6 Hz, 6H), 1.02 (t, J = 7.1 Hz, 3H) |
| 30 | 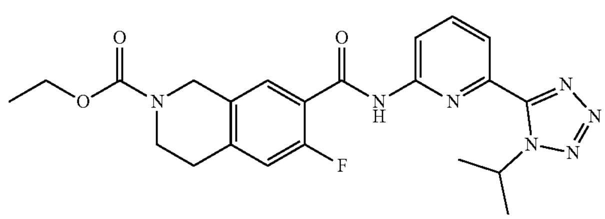 [SMILES: CCOC(=O)N1CCc2cc(F)c(C(=O)Nc3cccc(-c4nnnn4C(C)C)n3)cc2C1] | 454.19 | ¹H NMR (400 MHz, DMSO-d$_6$) δ 10.98 (s, 1H), 8.30 (dd, J = 8.3, 0.9 Hz, 1H), 8.13 (dd, J = 8.4, 7.6 Hz, 1H), 8.00 (dd, J = 7.6, 0.9 Hz, 1H), 7.59 (d, J = 7.1 Hz, 1H), 7.24 (d, J = 10.8 Hz, 1H), 6.01 (hept, J = 6.7 Hz, 1H), 4.59 (s, 2H), 4.09 (q, J = 7.1 Hz, 2H), 3.61 (t, J = 5.9 Hz, 2H), 2.88 (t, J = 6.0 Hz, 2H), 1.54 (d, J = 6.6 Hz, 6H), 1.21 (t, J = 7.1 Hz, 3H) |
| 31 | 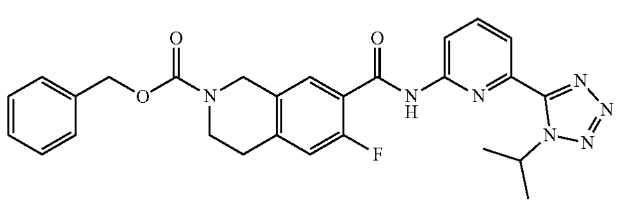 [SMILES: CC(C)n1nnnc1-c1cccc(NC(=O)c2cc3c(cc2F)CCN(C(=O)OCc2ccccc2)C3)n1] | 516.21 | ¹H NMR (400 MHz, DMSO-d$_6$) δ 10.98 (s, 1H), 8.30 (d, J = 8.3 Hz, 1H), 8.12 (t, J = 8.0 Hz, 1H), 8.00 (d, J = 7.7 Hz, 1H), 7.61 (d, J = 7.0 Hz, 1H), 7.46-7.30 (comp, 5H), 7.24 (d, J = 10.7 Hz, 1H), 6.01 (hept, J = 6.6 Hz, 1H), 5.14 (s, 2H), 4.66-4.62 (m, 2H), 3.65 (br s, 2H), 2.89 (t, J = 5.9 Hz, 2H), 1.54 (d, J = 6.6 Hz, 6H) |

-continued

| Example | Structure | LC-MS [M + H]+ unless otherwise noted | H-NMR |
|---|---|---|---|
| 32 | 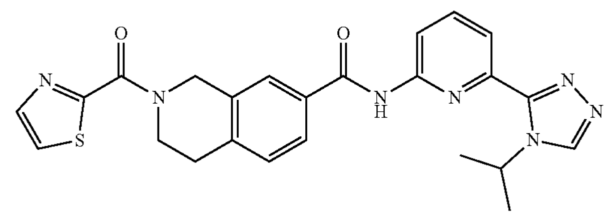 [SMILES: CC(C)n1cnnc1-c1cccc(NC(=O)c2ccc3c(c2)CN(C(=O)c2nccs2)CC3)n1] | 474.16 | ¹H NMR (400 MHz, DMSO-d₆) δ 10.71 (s, 1H), 8.86 (s, 1H), 8.17 (dd, J = 13.2, 8.3 Hz, 1H), 8.07 (s, 2H), 8.02 (t, J = 8.1 Hz, 1H), 7.94-7.77 (comp, 3H), 7.39 (d, J = 8.1 Hz, 1H), 5.68 (dq, J = 12.5, 6.5 Hz, 1H), 5.57 (s, 1H), 4.92 (s, 1H), 4.48 (t, J = 5.8 Hz, 1H), 3.93 (t, J = 6.0 Hz, 1H), 3.12-2.97 (m, 2H), 1.44 (dd, J = 7.7, 4.4 Hz, 6H) |
| 33 | 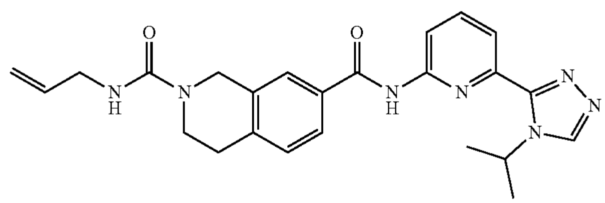 [SMILES: C=CCNC(=O)N1CCc2ccc(C(=O)Nc3cccc(-c4nncn4C(C)C)n3)cc2C1] | 446.22 | ¹H NMR (400 MHz, DMSO-d₆) δ 10.70 (s, 1H), 8.87 (s, 1H), 8.18 (dd, J = 8.4, 0.9 Hz, 1H), 8.02 (t, J = 8.0 Hz, 1H), 7.86 (dd, J = 7.6, 0.9 Hz, 1H), 7.78 (dd, J = 7.9, 1.9 Hz, 1H), 7.75 (d, J = 1.7 Hz, 1H), 7.35 (d, J = 7.9 Hz, 1H), 6.81 (t, J = 5.6 Hz, 1H), 5.84 (ddt, J = 17.2, 10.3, 5.2 Hz, 1H), 5.70 (hept, J = 6.8 Hz, 1H), 5.10 (dq, J = 17.2, 1.8 Hz, 1H), 5.02 (dq, J = 10.3, 1.6 Hz, 1H), 4.61 (s, 2H), 3.71 (tt, J = 5.4, 1.7 Hz, 2H), 3.61 (t, J = 5.9 Hz, 2H), 2.87 (t, J = 5.9 Hz, 2H), 1.44 (d, J = 6.7 Hz, 6H) |
| 34 | 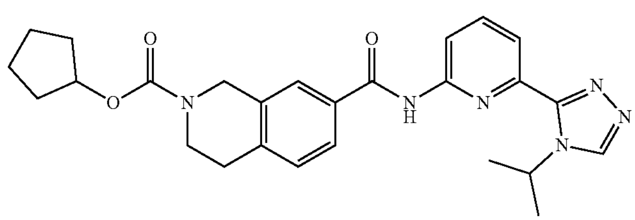 [SMILES: CC(C)n1cnnc1-c1cccc(NC(=O)c2ccc3c(c2)CN(C(=O)OC2CCCC2)CC3)n1] | 475.24 | ¹H NMR (400 MHz, DMSO-d₆) δ 10.68 (s, 1H), 8.86 (s, 1H), 8.17 (d, J = 8.4 Hz, 1H), 8.01 (t, J = 8.0 Hz, 1H), 7.84 (dd, J = 7.6, 0.9 Hz, 1H), 7.81 (d, J = 1.7 Hz, 1H), 7.78 (dd, J = 7.9, 1.8 Hz, 1H), 7.35 (d, J = 8.0 Hz, 1H), 5.68 (hept, J = 6.9 Hz, 1H), 5.04 (tt, J = 5.7, 2.6 Hz, 1H), 4.62 (s, 2H), 3.61 (t, J = 5.9 Hz, 2H), 2.87 (t, J = 5.9 Hz, 2H), 1.87-1.75 (comp, 2H), 1.75-1.51 (comp, 6H), 1.43 (d, J = 6.7 Hz, 6H) |
| 35 | 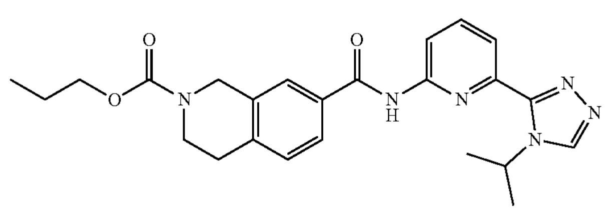 [SMILES: CCCOC(=O)N1CCc2ccc(C(=O)Nc3cccc(-c4nncn4C(C)C)n3)cc2C1] | 449.21 | ¹H NMR (400 MHz, DMSO-d₆) δ 10.68 (s, 1H), 8.86 (s, 1H), 8.17 (dd, J = 8.3, 0.9 Hz, 1H), 8.01 (dd, J = 8.3, 7.6 Hz, 1H), 7.84 (dd, J = 7.7, 0.9 Hz, 1H), 7.82 (d, J = 1.7 Hz, 1H), 7.78 (dd, J = 7.9, 1.9 Hz, 1H), 7.35 (d, J = 7.9 Hz, 1H), 5.68 (hept, J = 6.7 Hz, 1H), 4.65 (br s, 2H), 4.01 (t, J = 6.6 Hz, 2H), 3.64 (br s, 2H), 2.89 (t, J = 5.9 Hz, 2H), 1.61 (h, J = 7.1 Hz, 2H), 1.43 (d, J = 6.7 Hz, 6H), 0.91 (t, J = 7.4 Hz, 3H) |
| 36 | 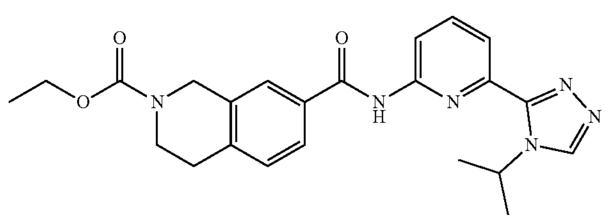 [SMILES: CCOC(=O)N1CCc2ccc(C(=O)Nc3cccc(-c4nncn4C(C)C)n3)cc2C1] | 435.20 | ¹H NMR (400 MHz, DMSO-d₆) δ 10.68 (s, 1H), 8.87 (s, 1H), 8.18 (dd, J = 8.3, 0.9 Hz, 1H), 8.02 (t, J = 8.0 Hz, 1H), 7.85 (dd, J = 7.6, 0.9 Hz, 1H), 7.82 (d, J = 1.8 Hz, 1H), 7.79 (dd, J = 7.9, 1.8 Hz, 1H), 7.36 (d, J = 8.0 Hz, 1H), 5.69 (hept, J = 6.7 Hz, 1H), 4.65 (br s, 2H), 4.11 (q, J = 7.0 Hz, 2H), 3.64 (t, J = 5.9 Hz, 2H), 2.89 (t, J = 5.9 Hz, 2H), 1.44 (d, J = 6.7 Hz, 6H), 1.23 (t, J = 7.1 Hz, 4H) |
| 37 | 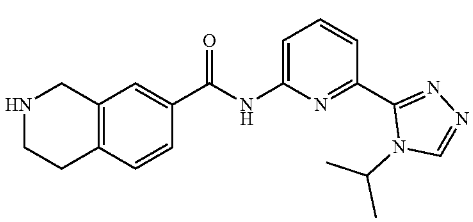 [SMILES: CC(C)n1cnnc1-c1cccc(NC(=O)c2ccc3c(c2)CNCC3)n1] | 363.18 | ¹H NMR (400 MHz, DMSO-d₆) δ 10.62 (s, 1H), 8.86 (s, 1H), 8.16 (dd, J = 8.3, 0.9 Hz, 1H), 8.00 (t, J = 8.0 Hz, 1H), 7.84 (dd, J = 7.7, 0.9 Hz, 1H), 7.71 (dd, J = 7.9, 1.9 Hz, 1H), 7.64 (d, J = 1.8 Hz, 1H), 7.24 (d, J = 8.0 Hz, 1H), 5.68 (hept, J = 6.7 Hz, 1H), 3.92 (br s, 2H), 2.96 (t, J = 5.8 Hz, 2H), 2.76 (t, J = 5.9 Hz, 2H), 1.43 (d, J = 6.6 Hz, 6H) |

-continued

| Example | Structure | LC-MS [M + H]+ unless otherwise noted | H-NMR |
|---|---|---|---|
| 38 | 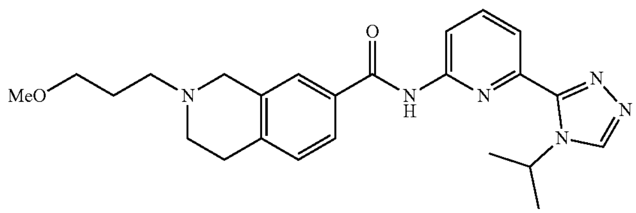 [SMILES: COCCCN1CCc2ccc(C(=O)Nc3cccc(-c4nncn4C(C)C)n3)cc2C1] | 435.25 | ¹H NMR (400 MHz, DMSO-d₆) δ 10.63 (s, 1H), 8.86 (s, 1H), 8.17 (dd, J = 8.3, 0.9 Hz, 1H), 8.01 (t, J = 8.0 Hz, 1H), 7.84 (dd, J = 7.6, 0.9 Hz, 1H), 7.73 (dd, J = 7.9, 1.9 Hz, 1H), 7.68 (d, J = 1.8 Hz, 1H), 7.27 (d, J = 8.0 Hz, 1H), 5.68 (hept, J = 6.7 Hz, 1H), 3.63 (s, 2H), 3.39 (t, J = 6.4 Hz, 2H), 2.88 (t, J = 5.9 Hz, 2H), 2.72-2.65 (m, 2H), 2.54-2.50 (m, 2H), 1.82-1.73 (m, 2H), 1.43 (d, J = 6.7 Hz, 6H) |
| 39 | 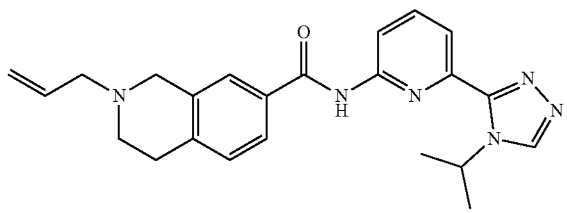 [SMILES: C=CCN1CCc2ccc(C(=O)Nc3cccc(-c4nncn4C(C)C)n3)cc2C1] | 403.21 | ¹H NMR (400 MHz, DMSO-d₆) δ 10.62 (s, 1H), 8.86 (s, 1H), 8.16 (dd, J = 8.3, 0.9 Hz, 1H), 8.00 (t, J = 8.0 Hz, 1H), 7.84 (dd, J = 7.6, 0.9 Hz, 1H), 7.73 (dd, J = 7.9, 1.9 Hz, 1H), 7.68 (d, J = 1.8 Hz, 1H), 7.28 (d, J = 7.9 Hz, 1H), 5.91 (ddt, J = 16.6, 10.2, 6.3 Hz, 1H), 5.68 (hept, J = 6.7 Hz, 1H), 5.27 (dq, J = 17.2, 1.6 Hz, 1H), 5.19 (ddt, J = 10.2, 2.2, 1.1 Hz, 1H), 3.63 (s, 2H), 3.15 (dt, J = 6.4, 1.4 Hz, 2H), 2.89 (t, J = 5.9 Hz, 2H), 2.70 (t, J = 5.9 Hz, 2H), 1.43 (d, J = 6.7 Hz, 6H) |
| 40 | 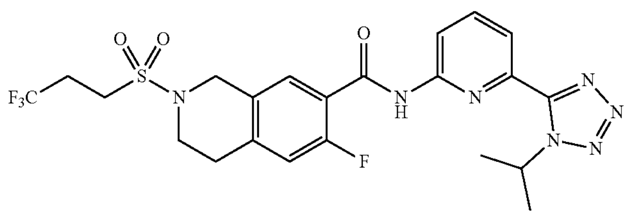 [SMILES: CC(C)n1nnnc1-c1cccc(NC(=O)c2cc3c(cc2F)CCN(S(=O)(=O)CCC(F)(F)F)C3)n1] | 542.16 | ¹H NMR (400 MHz, DMSO-d₆) δ 10.99 (s, 1H), 8.31 (dd, J = 8.4, 2.4 Hz, 1H), 8.13 (td, J = 8.0, 2.4 Hz, 1H), 8.00 (dd, J = 7.7, 2.4 Hz, 1H), 7.58 (dd, J = 6.9, 2.4 Hz, 1H), 7.26 (dd, J = 10.9, 2.4 Hz, 1H), 6.05-5.99 (m, 1H), 4.52 (s, 2H), 3.57 (q, J = 5.2 Hz, 2H), 3.50-3.41 (m, 2H), 2.99-2.96 (m, 2H), 2.84-2.65 (m, 2H), 1.54 (dd, J = 6.6, 2.4 Hz, 6H) |
| 41 | 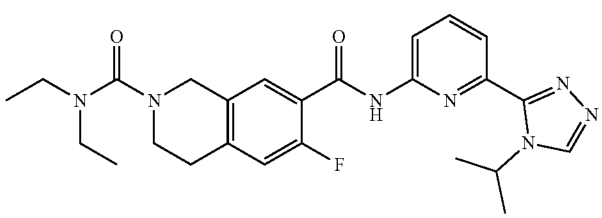 [SMILES: CCN(CC)C(=O)N1CCc2cc(F)c(C(=O)Nc3cccc(-c4nncn4C(C)C)n3)cc2C1] | 480.24 | ¹H NMR (400 MHz, DMSO-d₆) δ 10.77 (s, 1H), 8.86 (s, 1H), 8.20 (dd, J = 8.3, 1.0 Hz, 1H), 8.02 (t, J = 8.0 Hz, 1H), 7.89 (dd, J = 7.7, 0.9 Hz, 1H), 7.55 (d, J = 7.1 Hz, 1H), 7.18 (d, J = 11.0 Hz, 1H), 5.65 (hept, J = 6.9 Hz, 1H), 4.33 (s, 2H), 3.38 (t, J = 5.8 Hz, 2H), 3.16 (q, J = 7.0 Hz, 4H), 2.90 (t, J = 5.8 Hz, 2H), 1.42 (d, J = 6.7 Hz, 6H), 1.07 (t, J = 7.0 Hz, 6H) |
| 42 | 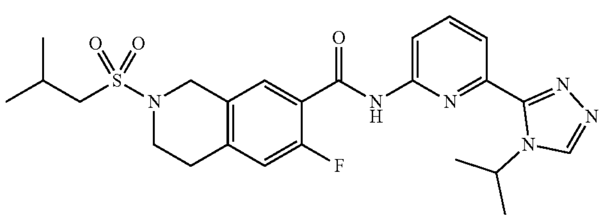 [SMILES: CC(C)CS(=O)(=O)N1CCc2cc(F)c(C(=O)Nc3cccc(-c4nncn4C(C)C)n3)cc2C1] | 501.20 | ¹H NMR (400 MHz, DMSO-d₆) δ 10.80 (s, 1H), 8.86 (s, 1H), 8.20 (d, J = 8.3 Hz, 1H), 8.03 (t, J = 8.0 Hz, 1H), 7.89 (d, J = 8.0 Hz, 1H), 7.58 (d, J = 7.0 Hz, 1H), 7.24 (d, J = 10.9 Hz, 1H), 5.65 (hept, J = 6.6 Hz, 1H), 4.44 (s, 2H), 3.49 (t, J = 5.9 Hz, 2H), 3.01 (d, J = 6.6 Hz, 2H), 2.97 (t, J = 6.0 Hz, 2H), 2.14 (dp, J = 13.4, 6.8 Hz, 1H), 1.43 (d, J = 6.6 Hz, 6H), 1.04 (d, J = 6.7 Hz, 6H) |
| 43 | 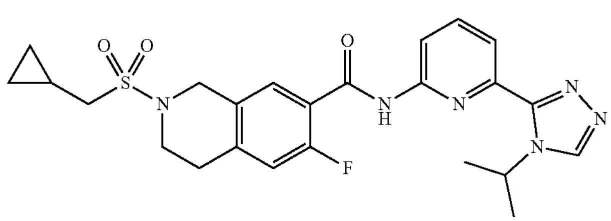 | 499.19 | ¹H NMR (500 MHz, DMSO-d₆) δ 10.80 (s, 1H), 8.86 (s, 1H), 8.20 (dd, J = 8.4, 0.9 Hz, 1H), 8.03 (t, J = 8.0 Hz, 1H), 7.89 (dd, J = 7.7, 0.9 Hz, 1H), 7.57 (d, J = 7.0 Hz, 1H), 7.23 (d, J = 10.9 Hz, 1H), 5.65 (hept, J = 6.9 Hz, 1H), 4.48 (s, 2H), 3.53 (t, J = 6.0 Hz, 2H), 3.12 (d, J = 7.1 Hz, 2H), 2.96 (t, J = 5.9 Hz, 2H), 1.43 (d, J = 6.7 Hz, 6H), 1.08-0.95 (m, 1H), 0.64-0.53 (m, 2H), 0.36-0.33 (m, 2H) |

| Example | Structure | LC-MS [M + H]+ unless otherwise noted | H-NMR |
|---|---|---|---|
| 44 | 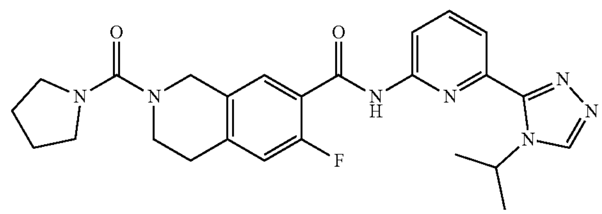 [SMILES: CC(C)n1cnnc1-c1cccc(NC(=O)c2cc3c(cc2F)CCN(C(=O)N2CCCC2)C3)n1] | 478.23 | ¹H NMR (400 MHz, Chloroform-d) δ 9.10 (d, J = 16.6 Hz, 1H), 8.56 (s, 1H), 8.45 (dd, J = 8.3, 0.9 Hz, 1H), 8.08 (dd, J = 7.7, 0.9 Hz, 1H), 8.00-7.88 (comp, 2H), 6.99 (d, J = 12.9 Hz, 1H), 5.55 (hept, J = 6.7 Hz, 1H), 4.50 (s, 2H), 3.56 (t, J = 5.8 Hz, 2H), 3.42 (q, J = 5.3, 3.9 Hz, 4H), 2.97 (t, J = 5.8 Hz, 2H), 1.93-1.81 (m, 4H), 1.62 (d, J = 6.7 Hz, 6H) |
| 45 | 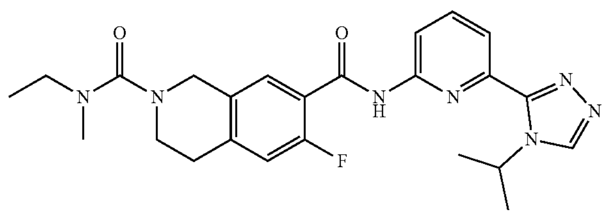 [SMILES: CCN(C)C(=O)N1CCc2cc(F)c(C(=O)Nc3cccc(-c4nncn4C(C)C)n3)cc2C1] | 466.23 | ¹H NMR (500 MHz, DMSO-d₆) δ 10.76 (s, 1H), 8.86 (s, 1H), 8.20 (dd, J = 8.4, 0.9 Hz, 1H), 8.02 (t, J = 8.0 Hz, 1H), 7.88 (dd, J = 7.6, 0.9 Hz, 1H), 7.55 (d, J = 7.1 Hz, 1H), 7.18 (d, J = 10.9 Hz, 1H), 5.65 (hept, J = 6.5 Hz, 1H), 4.34 (s, 2H), 3.38 (t, J = 5.8 Hz, 2H), 3.16 (q, J = 7.1 Hz, 2H), 2.90 (t, J = 5.9 Hz, 2H), 2.78 (s, 3H), 1.42 (d, J = 6.6 Hz, 6H), 1.08 (t, J = 7.0 Hz, 3H) |
| 46 | 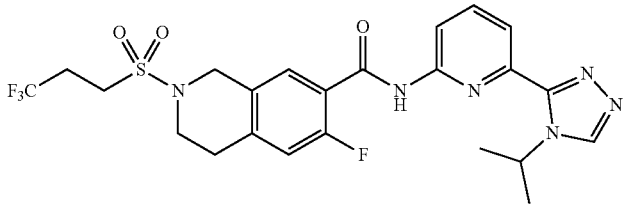 [SMILES: CC(C)n1cnnc1-c1cccc(NC(=O)c2cc3c(cc2F)CCN(S(=O)(=O)CCC(F)(F)F)C3)n1] | 541.16 | ¹H NMR (400 MHz, DMSO-d₆) δ 10.81 (s, 1H), 8.86 (s, 1H), 8.20 (dd, J = 8.3, 0.9 Hz, 1H), 8.03 (t, J = 8.0 Hz, 1H), 7.89 (dd, J = 7.7, 0.9 Hz, 1H), 7.58 (d, J = 7.1 Hz, 1H), 7.25 (d, J = 10.9 Hz, 1H), 5.65 (hept, J = 6.8 Hz, 1H), 4.52 (s, 2H), 3.57 (t, J = 5.9 Hz, 2H), 3.51-3.41 (m, 2H), 2.97 (t, J = 5.9 Hz, 2H), 2.83-2.64 (m, 2H), 1.43 (d, J = 6.7 Hz, 6H) |
| 47 | 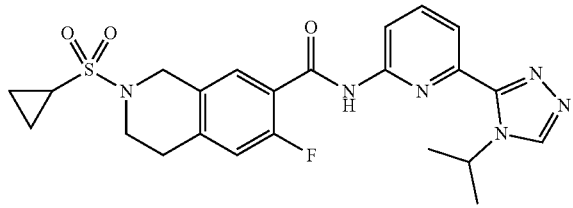 [SMILES: CC(C)n1cnnc1-c1cccc(NC(=O)c2cc3c(cc2F)CCN(S(=O)(=O)C2CC2)C3)n1] | 485.17 | ¹H NMR (400 MHz, DMSO-d₆) δ 10.79 (s, 1H), 8.86 (s, 1H), 8.20 (dd, J = 8.4, 0.9 Hz, 1H), 8.03 (t, J = 8.0 Hz, 1H), 7.89 (dd, J = 7.6, 0.9 Hz, 1H), 7.61 (d, J = 7.1 Hz, 1H), 7.24 (d, J = 10.9 Hz, 1H), 5.65 (hept, J = 6.6 Hz, 1H), 4.48 (s, 2H), 3.53 (t, J = 6.0 Hz, 2H), 2.99 (t, J = 6.1 Hz, 2H), 2.65 (tt, J = 7.6, 5.2 Hz, 1H), 1.43 (d, J = 6.6 Hz, 6H), 1.03-0.94 (comp, 4H) |
| 48 | 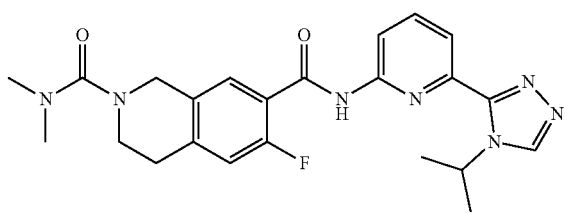 [SMILES: CC(C)n1cnnc1-c1cccc(NC(=O)c2cc3c(cc2F)CCN(C(=O)N(C)C)C3)n1] | 452.21 | ¹H NMR (400 MHz, DMSO-d₆) δ 10.76 (s, 1H), 8.86 (s, 1H), 8.20 (dd, J = 8.4, 0.9 Hz, 1H), 8.02 (t, J = 8.0 Hz, 1H), 7.88 (dd, J = 7.7, 0.9 Hz, 1H), 7.55 (d, J = 7.1 Hz, 1H), 7.18 (d, J = 11.0 Hz, 1H), 5.65 (hept, J = 6.5 Hz, 1H), 4.35 (s, 2H), 3.39 (t, J = 5.8 Hz, 2H), 2.90 (t, J = 5.9 Hz, 2H), 2.79 (s, 6H), 1.42 (d, J = 6.7 Hz, 6H) |
| 49 | 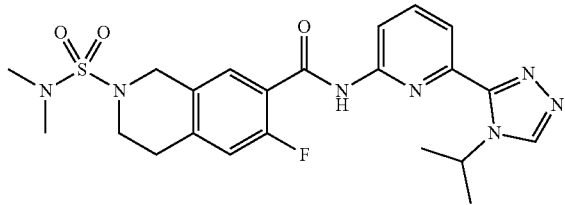 [SMILES: CC(C)n1cnnc1-c1cccc(NC(=O)c2cc3c(cc2F)CCN(S(=O)(=O)N(C)C)C3)n1] | 488.18 | ¹H NMR (400 MHz, DMSO-d₆) δ 10.80 (s, 1H), 8.86 (s, 1H), 8.20 (dd, J = 8.3, 0.9 Hz, 1H), 8.02 (t, J = 8.0 Hz, 1H), 7.89 (dd, J = 7.7, 1.0 Hz, 1H), 7.59 (d, J = 7.1 Hz, 1H), 7.23 (d, J = 10.9 Hz, 1H), 5.66 (hept, J = 6.7 Hz, 1H), 4.42 (s, 2H), 3.50 (t, J = 5.9 Hz, 2H), 2.95 (t, J = 5.9 Hz, 2H), 2.78 (s, 6H), 1.43 (d, J = 6.7 Hz, 6H) |

-continued

| Example | Structure | LC-MS [M + H]+ unless otherwise noted | H-NMR |
|---|---|---|---|
| 50 | 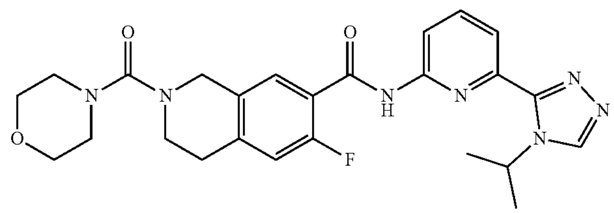 [SMILES: CC(C)n1cnnc1-c1cccc(NC(=O)c2cc3c(cc2F)CCN(C(=O)N2CCOCC2)C3)n1] | 494.23 | ¹H NMR (400 MHz, DMSO-d$_6$) δ 10.76 (d, J = 1.5 Hz, 1H), 8.86 (s, 1H), 8.20 (dd, J = 8.3, 0.9 Hz, 1H), 8.02 (t, J = 8.0 Hz, 1H), 7.89 (dd, J = 7.7, 0.9 Hz, 1H), 7.57 (d, J = 7.1 Hz, 1H), 7.19 (d, J = 10.9 Hz, 1H), 5.68-5.62 (m 1H), 4.42 (s, 2H), 3.60 (t, J = 4.6 Hz, 4H), 3.44 (t, J = 5.8 Hz, 2H), 3.18 (t, J = 4.7 Hz, 5H), 2.90 (t, J = 5.9 Hz, 2H), 1.43 (d, J = 6.7 Hz, 6H) |
| 51 | 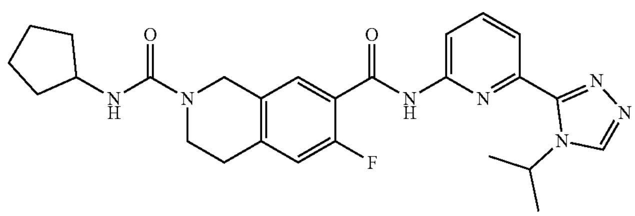 [SMILES: CC(C)n1cnnc1-c1cccc(NC(=O)c2cc3c(cc2F)CCN(C(=O)NC2CCCC2)C3)n1] | 492.25 | ¹H NMR (400 MHz, DMSO-d$_6$) δ 10.77 (s, 1H), 8.86 (s, 1H), 8.20 (d, J = 8.2 Hz, 1H), 8.02 (t, J = 8.0 Hz, 1H), 7.89 (d, J = 7.6 Hz, 1H), 7.49 (d, J = 7.1 Hz, 1H), 7.20 (d, J = 10.9 Hz, 1H), 6.33 (d, J = 6.9 Hz, 1H), 5.66 (hept, J = 6.5 Hz, 1H), 4.52 (s, 2H), 3.92 (p, J = 7.0 Hz, 1H), 3.56 (t, J = 5.9 Hz, 2H), 2.83 (t, J = 5.9 Hz, 2H), 1.85-1.73 (comp, 2H), 1.72-1.56 (comp, 2H), 1.56-1.33 (comp, 10H) |
| 52 | 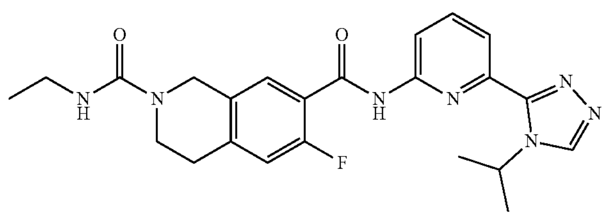 | 452.22 | ¹H NMR (400 MHz, DMSO-d$_6$) δ 10.80 (s, 1H), 8.86 (s, 1H), 8.20 (dd, J = 8.3, 1.0 Hz, 1H), 8.02 (t, J = 8.0 Hz, 1H), 7.89 (dd, J = 7.7, 0.9 Hz, 1H), 7.49 (d, J = 7.1 Hz, 1H), 7.20 (d, J = 10.9 Hz, 1H), 6.58 (t, J = 5.4 Hz, 1H), 5.66 (hept, J = 6.8 Hz, 1H), 4.52 (s, 2H), 3.55 (t, J = 5.9 Hz, 2H), 3.07 (qd, J = 7.1, 5.2 Hz, 2H), 2.83 (t, J = 5.8 Hz, 2H), 1.43 (d, J = 6.6 Hz, 6H), 1.02 (t, J = 7.1 Hz, 3H) |
| 53 | 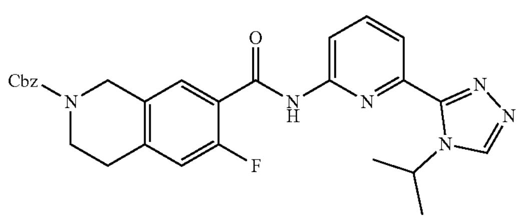 [SMILES: CC(C)n1cnnc1-c1cccc(NC(=O)c2cc3c(cc2F)CCN(C(=O)OCc2ccccc2)C3)n1] | 515.22 | ¹H NMR (400 MHz, DMSO-d$_6$) δ 10.79 (s, 1H), 8.86 (s, 1H), 8.19 (d, J = 8.3 Hz, 1H), 8.02 (t, J = 8.0 Hz, 1H), 7.89 (dd, J = 7.6, 0.9 Hz, 1H), 7.60 (d, J = 7.1 Hz, 1H), 7.44-7.28 (comp, 5H), 7.23 (d, J = 10.8 Hz, 1H), 5.65 (hept, J = 6.6 Hz, 1H), 5.14 (s, 2H), 4.63 (d, J = 17.5 Hz, 2H), 3.65 (s, 2H), 2.89 (t, J = 6.0 Hz, 2H), 1.42 (d, J = 6.6 Hz, 6H) |
| 54 | 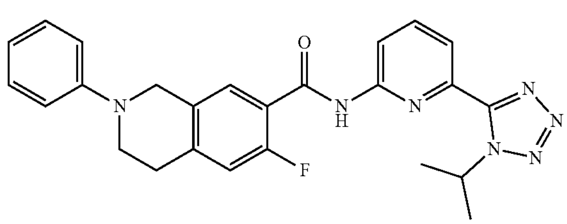 [SMILES: CC(C)n1nnnc1-c1cccc(NC(=O)c2cc3c(cc2F)CCN(c2ccccc2)C3)n1] | 458.20 | ¹H NMR (400 MHz, DMSO-d$_6$) δ 10.96 (s, 1H), 8.32 (dd, J = 8.3, 0.9 Hz, 1H), 8.13 (t, J = 8.0 Hz, 1H), 8.00 (dd, J = 7.7, 0.9 Hz, 1H), 7.63 (d, J = 7.1 Hz, 1H), 7.28-7.20 (comp, 3H), 7.06-7.00 (comp, 2H), 6.76 (tt, J = 7.2, 1.0 Hz, 1H), 6.02 (hept, J = 6.7 Hz, 1H), 4.44 (s, 2H), 3.57 (t, J = 5.9 Hz, 2H), 2.98 (t, J = 5.9 Hz, 2H), 1.54 (d, J = 6.6 Hz, 6H) |
| 55 | 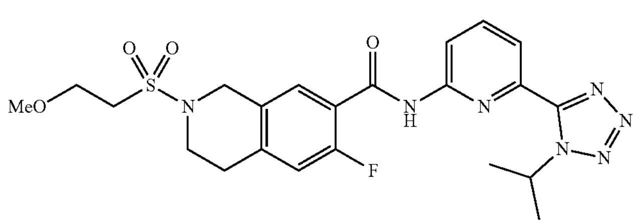 [SMILES: COCCS(=O)(=O)N1CCc2cc(F)c(C(=O)Nc3cccc(-c4nnnn4C(C)C)n3)cc2C1] | 504.18 | ¹H NMR (400 MHz, DMSO-d$_6$) δ 10.99 (s, 1H), 8.31 (dd, J = 8.4, 0.9 Hz, 1H), 8.13 (dd, J = 8.4, 7.6 Hz, 1H), 8.00 (dd, J = 7.6, 0.9 Hz, 1H), 7.58 (d, J = 7.1 Hz, 1H), 7.25 (d, J = 10.9 Hz, 1H), 6.01 (hept, J = 6.5 Hz, 1H), 4.44 (s, 2H), 3.68 (t, J = 5.9 Hz, 2H), 3.49 (t, J = 5.9 Hz, 2H), 3.43 (t, J = 5.9 Hz, 2H), 3.25 (s, 3H), 2.96 (t, J = 6.0 Hz, 2H), 1.54 (d, J = 6.6 Hz, 6H) |

| Example | Structure | LC-MS [M + H]+ unless otherwise noted | H-NMR |
|---|---|---|---|
| 56 | 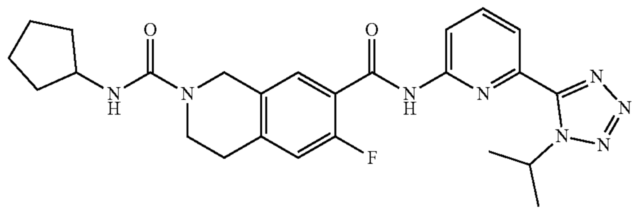 [SMILES: CC(C)n1nnnc1-c1cccc(NC(=O)c2cc3c(cc2F)CCN(C(=O)NC2CCCC2)C3)n1] | 493.24 | ¹H NMR (400 MHz, DMSO-d₆) δ 10.96 (s, 1H), 8.31 (dd, J = 8.4, 0.9 Hz, 1H), 8.13 (dd, J = 8.4, 7.6 Hz, 1H), 8.00 (dd, J = 7.7, 0.9 Hz, 1H), 7.50 (d, J = 7.1 Hz, 1H), 7.21 (d, J = 10.9 Hz, 1H), 6.33 (d, J = 6.9 Hz, 1H), 6.02 (hept, J = 6.6 Hz, 1H), 4.52 (s, 2H), 3.93 (h, J = 7.0 Hz, 1H), 3.56 (t, J = 5.9 Hz, 2H), 2.83 (t, J = 5.8 Hz, 2H), 1.88-1.33 (comp, 13H), 1.31-1.18 (m, 1H) |
| 57 | 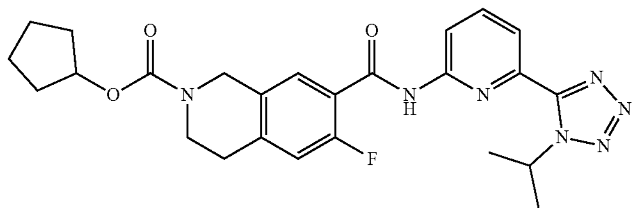 [SMILES: CC(C)n1nnnc1-c1cccc(NC(=O)c2cc3c(cc2F)CCN(C(=O)OC2CCCC2)C3)n1] | 494.23 | ¹H NMR (400 MHz, DMSO-d₆) δ 10.98 (s, 1H), 8.30 (dd, J = 8.4, 0.9 Hz, 1H), 8.13 (t, J = 8.0 Hz, 1H), 8.00 (dd, J = 7.6, 0.9 Hz, 1H), 7.59 (d, J = 7.1 Hz, 1H), 7.23 (d, J = 10.8 Hz, 1H), 6.01 (hept, J = 6.6 Hz, 1H), 5.03 (tt, J = 5.7, 2.6 Hz, 1H), 4.57 (s, 2H), 3.59 (t, J = 6.0 Hz, 2H), 2.86 (t, J = 6.0 Hz, 2H), 1.86-1.74 (comp, 2H), 1.74-1.60 (comp, 3H), 1.60-1.51 (comp, 9H) |
| 58 | 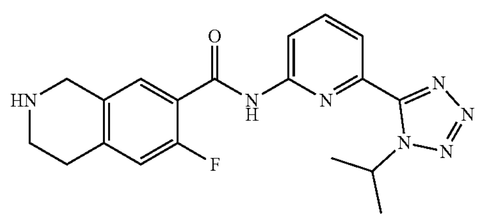 [SMILES: CC(C)n1nnnc1-c1cccc(NC(=O)c2cc3c(cc2F)CCNC3)n1] | 382.16 | ¹H NMR (400 MHz, DMSO-d₆) δ 10.89 (s, 1H), 8.30 (dd, J = 8.4, 0.9 Hz, 1H), 8.12 (dd, J = 8.3, 7.6 Hz, 1H), 7.99 (dd, J = 7.6, 0.9 Hz, 1H), 7.40 (d, J = 7.3 Hz, 1H), 7.10 (d, J = 11.2 Hz, 1H), 6.01 (hept, J = 6.6 Hz, 1H), 3.86 (s, 2H), 2.93 (t, J = 5.8 Hz, 2H), 2.75 (t, J = 5.9 Hz, 2H), 1.54 (d, J = 6.6 Hz, 6H) |
| 59 | 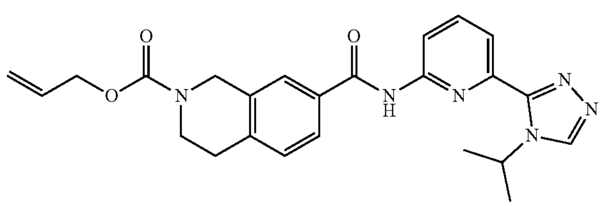 [SMILES: C=CCOC(=O)N1CCc2ccc(C(=O)Nc3cccc(-c4nncn4C(C)C)n3)cc2C1] | 447.20 | ¹H NMR (400 MHz, DMSO-d₆) δ 10.68 (s, 1H), 8.86 (s, 1H), 8.17 (dd, J = 8.3, 0.9 Hz, 1H), 8.06-7.98 (m, 1H), 7.88-7.75 (comp, 3H), 7.36 (d, J = 8.0 Hz, 1H), 5.96 (ddt, J = 17.3, 10.5, 5.2 Hz, 1H), 5.68 (hept, J = 6.5 Hz, 1H), 5.32 (dq, J = 17.2, 1.7 Hz, 1H), 5.21 (dq, J = 10.5, 1.5 Hz, 1H), 4.74-4.62 (m, 2H), 4.59 (dt, J = 5.2, 1.6 Hz, 2H), 3.66 (br s, 2H), 2.90 (t, J = 6.0 Hz, 2H), 1.43 (d, J = 6.7 Hz, 6H) |
| 60 | 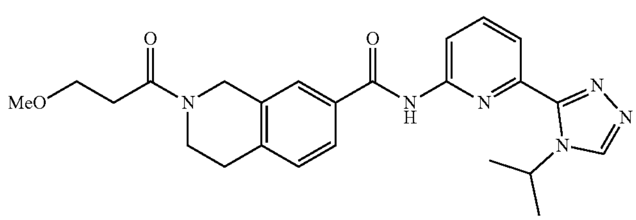 [SMILES: COCCC(=O)N1CCc2ccc(C(=O)Nc3cccc(-c4nncn4C(C)C)n3)cc2C1] | 449.22 | ¹H NMR (400 MHz, DMSO-d₆) δ 10.71 (s, 0.4H), 10.68 (s, 0.6H), 8.87 (s, 1H), 8.18 (dd, J = 8.3, 1.1 Hz, 1H), 8.02 (t, J = 8.0 Hz, 1H), 7.89-7.76 (comp, 3H), 7.37 (d, J = 8.1 Hz, 1H), 5.69 (hept, J = 6.7 Hz, 1H), 4.78 (s, 0.8H), 4.71 (s, 1.2H), 3.72 (dt, J = 10.7, 5.9 Hz, 2H), 3.60 (t, J = 6.5 Hz, 2H), 3.24 (s, 1.8H), 3.23 (s, 1.2H), 2.95 (t, J = 5.9 Hz, 1.2H), 2.86 (t, J = 6.0 Hz, 0.8H), 2.69 (td, J = 6.6, 3.9 Hz, 2H), 1.44 (d, J = 6.7 Hz, 6H) |
| 61 | 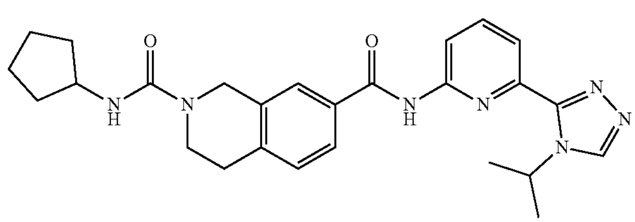 [SMILES: CC(C)n1cnnc1-c1cccc(NC(=O)c2ccc3c(c2)CN(C(=O)NC2CCCC2)CC3)n1] | 474.25 | ¹H NMR (400 MHz, DMSO-d₆) δ 10.69 (s, 1H), 8.86 (s, 1H), 8.18 (dd, J = 8.4, 0.9 Hz, 1H), 8.01 (dd, J = 8.3, 7.6 Hz, 1H), 7.85 (dd, J = 7.6, 0.9 Hz, 1H), 7.77 (dd, J = 7.9, 1.9 Hz, 1H), 7.75 (d, J = 1.7 Hz, 1H), 7.33 (d, J = 7.9 Hz, 1H), 6.33 (d, J = 6.9 Hz, 1H), 5.70 (hept, J = 6.6 Hz, 1H), 4.58 (s, 2H), 3.95 (p, J = 7.1 Hz, 1H), 3.58 (t, J = 5.9 Hz, 2H), 2.84 (t, J = 5.8 Hz, 2H), 1.89-1.72 (m, 2H), 1.70-1.56 (m, 2H), 1.55-1.33 (comp, 10H) |

-continued

| Example | Structure | LC-MS [M + H]+ unless otherwise noted | H-NMR |
|---|---|---|---|
| 62 | 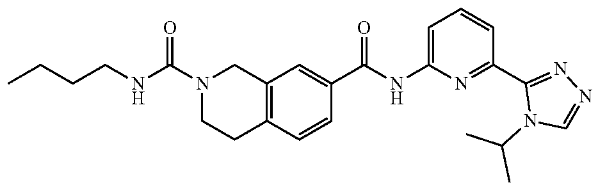 [SMILES: CCCCNC(=O)N1CCc2ccc(C(=O)Nc3cccc(-c4nncn4C(C)C)n3)cc2C1] | 462.25 | ¹H NMR (400 MHz, DMSO-d$_6$) δ 10.69 (s, 1H), 8.86 (s, 1H), 8.18 (dd, J = 8.3, 0.9 Hz, 1H), 8.01 (t, J = 8.0 Hz, 1H), 7.85 (dd, J = 7.6, 0.9 Hz, 1H), 7.77 (dd, J = 7.9, 1.9 Hz, 1H), 7.74 (d, J = 1.7 Hz, 1H), 7.33 (d, J = 8.0 Hz, 1H), 6.56 (t, J = 5.5 Hz, 1H), 5.70 (hept, J = 6.2 Hz, 1H), 4.57 (s, 2H), 3.57 (t, J = 5.9 Hz, 2H), 3.05 (td, J = 7.0, 5.4 Hz, 2H), 2.84 (t, J = 5.9 Hz, 2H), 1.48-1.35 (comp, 8H), 1.34-1.21 (m, 2H), 0.87 (t, J = 7.3 Hz, 3H) |
| 63 | 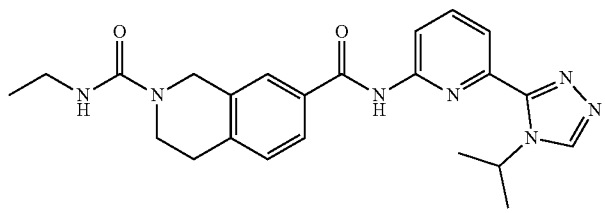 [SMILES: CCNC(=O)N1CCc2ccc(C(=O)Nc3cccc(-c4nncn4C(C)C)n3)cc2C1] | 434.21 | ¹H NMR (400 MHz, DMSO-d$_6$) δ 10.69 (s, 1H), 8.86 (s, 1H), 8.18 (dd, J = 8.3, 0.9 Hz, 1H), 8.01 (t, J = 8.0 Hz, 1H), 7.85 (dd, J = 7.6, 0.9 Hz, 1H), 7.77 (dd, J = 7.9, 1.9 Hz, 1H), 7.74 (d, J = 1.8 Hz, 1H), 7.34 (d, J = 7.9 Hz, 1H), 6.59 (t, J = 5.4 Hz, 1H), 5.70 (hept, J = 6.6 Hz, 1H), 4.57 (s, 2H), 3.57 (t, J = 5.9 Hz, 2H), 3.08 (qd, J = 7.1, 5.3 Hz, 2H), 2.85 (t, J = 5.9 Hz, 2H), 1.44 (d, J = 6.7 Hz, 6H), 1.03 (t, J = 7.1 Hz, 3H) |
| 64 | 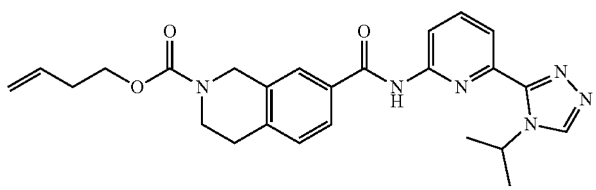 [SMILES: C=CCCOC(=O)N1CCc2ccc(C(=O)Nc3cccc(-c4nncn4C(C)C)n3)cc2C1] | 461.21 | ¹H NMR (400 MHz, DMSO-d$_6$) δ 10.68 (s, 1H), 8.86 (s, 1H), 8.17 (dd, J = 8.3, 0.9 Hz, 1H), 8.01 (t, J = 7.9 Hz, 1H), 7.84 (dd, J = 7.7, 0.9 Hz, 1H), 7.82-7.80 (m, 1H), 7.80-7.76 (m, 1H), 7.35 (d, J = 7.9 Hz, 1H), 5.83 (ddt, J = 17.1, 10.3, 6.7 Hz, 1H), 5.68 (hept, J = 6.7 Hz, 1H), 5.16-5.09 (m, 1H), 5.06 (d, J = 10.1 Hz, 1H), 4.64 (br s, 2H), 4.11 (t, J = 6.5 Hz, 2H), 3.63 (t, J = 5.9 Hz, 2H), 2.88 (t, J = 5.9 Hz, 2H), 2.37 (q, J = 6.6 Hz, 2H), 1.44 (d, J = 6.6 Hz, 6H) |
| 65 | 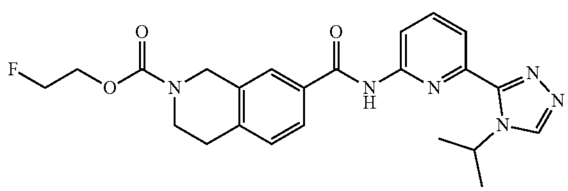 [SMILES: CC(C)n1cnnc1-c1cccc(NC(=O)c2ccc3c(c2)CN(C(=O)OCCF)CC3)n1] | 453.18 | ¹H NMR (400 MHz, DMSO-d$_6$) δ 10.68 (s, 1H), 8.86 (s, 1H), 8.17 (dd, J = 8.3, 0.9 Hz, 1H), 8.02 (t, J = 12.0 Hz, 1H), 7.87-7.82 (comp, 2H), 7.79 (dd, J = 7.9, 1.8 Hz, 1H), 7.36 (d, J = 8.0 Hz, 1H), 5.68 (hept, J = 6.9 Hz, 1H), 4.73-4.63 (comp, 3H), 4.61-4.56 (m, 1H), 4.37-4.34 (m, 1H), 4.30-4.26 (m, 1H), 3.66 (br fs, 2H), 2.90 (t, J = 5.9 Hz, 2H), 1.44 (d, J = 6.7 Hz, 6H) |
| 66 | 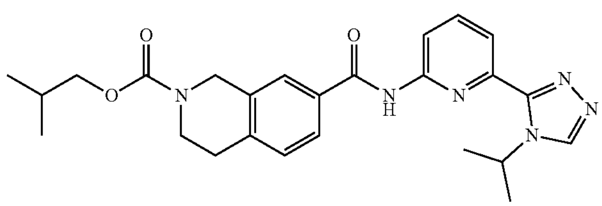 [SMILES: CC(C)COC(=O)N1CCc2ccc(C(=O)Nc3cccc(-c4nncn4C(C)C)n3)cc2C1] | 463.24 | ¹H NMR (400 MHz, DMSO-d$_6$) δ 10.68 (s, 1H), 8.86 (s, 1H), 8.17 (dd, J = 8.3, 1.0 Hz, 1H), 8.01 (dd, J = 8.3, 7.6 Hz, 1H), 7.84 (dd, J = 7.7, 0.9 Hz, 1H), 7.83 (d, J = 1.8 Hz, 1H), 7.78 (dd, J = 7.9, 1.9 Hz, 1H), 5.68 (hept, J = 7.2, 6.8 Hz, 1H), 4.66 (br s, 2H), 3.85 (d, J = 6.6 Hz, 2H), 3.65 (br s, 2H), 2.89 (t, J = 5.9 Hz, 2H), 1.90 (hept, J = 6.1 Hz, 1H), 1.43 (d, J = 6.6 Hz, 6H), 0.92 (d, J = 6.7 Hz, 6H) |
| 67 | 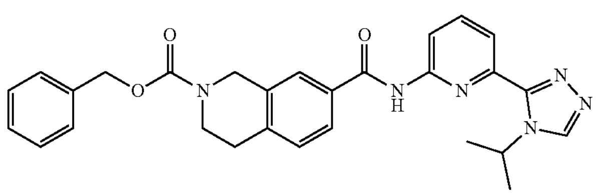 [SMILES: CC(C)n1cnnc1-c1cccc(NC(=O)c2ccc3c(c2)CN(C(=O)OCc2ccccc2)CC3)n1] | 497.23 | ¹H NMR (400 MHz, DMSO-d$_6$) δ 10.67 (s, 1H), 8.86 (s, 1H), 8.17 (d, J = 8.3 Hz, 1H), 8.01 (t, J = 8.0 Hz, 1H), 7.87-7.81 (comp, 2H), 7.78 (dd, J = 7.9, 1.8 Hz, 1H), 7.44-7.28 (comp, 5H), 5.67 (hept, J = 6.6 Hz, 1H), 4.69 (d, J = 17.1 Hz, 2H), 3.68 (br s, 2H), 2.90 (t, J = 5.9 Hz, 2H), 1.43 (d, J = 6.7 Hz, 6H) |
| 68 | 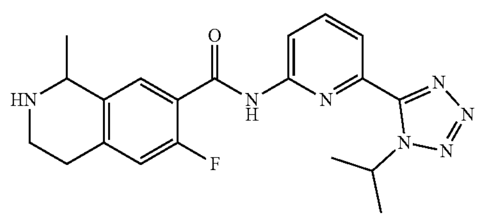 [SMILES: CC1NCCc2cc(F)c(C(=O)Nc3cccc(-c4nnnn4C(C)C)n3)cc21] | 396.18 | ¹H NMR (400 MHz, DMSO-d$_6$) δ 10.89 (s, 1H), 8.31 (dd, J = 8.4, 0.9 Hz, 1H), 8.12 (t, J = 8.0 Hz, 1H), 7.99 (dd, J = 7.6, 0.9 Hz, 1H), 7.49 (d, J = 7.2 Hz, 1H), 7.08 (d, J = 11.1 Hz, 1H), 6.01 (hept, J = 6.7 Hz, 1H), 3.96 (q, J = 6.5 Hz, 1H), 3.15-3.04 (m, 1H), 2.85-2.76 (comp, 2H), 2.75-2.67 (m, 1H), 1.54 (dd, J = 6.6, 4.0 Hz, 6H), 1.36 (d, J = 6.6 Hz, 3H) |

| Example | Structure | LC-MS [M + H]+ unless otherwise noted | H-NMR |
|---|---|---|---|
| 69 | 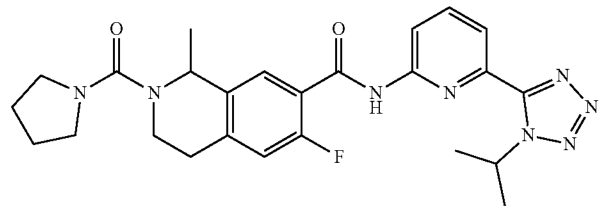 [SMILES: CC1c2cc(C(=O)Nc3cccc(-c4nnnn4C(C)C)n3)c(F)cc2CCN1C(=O)N1CCCC1] | 493.24 | ¹H NMR (400 MHz, DMSO-d$_6$) δ 10.95 (s, 1H), 8.30 (dd, J = 8.4, 0.9 Hz, 1H), 8.13 (dd, J = 8.4, 7.6 Hz, 1H), 7.99 (dd, J = 7.6, 0.9 Hz, 1H), 7.58 (d, J = 7.1 Hz, 1H), 7.15 (d, J = 10.9 Hz, 1H), 6.01 (hept, J = 6.7 Hz, 1H), 4.94 (q, J = 6.6 Hz, 1H), 3.74 (dd, J = 13.7, 5.9 Hz, 1H), 3.42-3.34 (m, 1H), 3.28-3.14 (comp, 4H), 3.01 (ddd, J = 17.7, 12.0, 6.2 Hz, 1H), 2.79-2.70 (m, 1H), 1.86-1.65 (comp, 4H), 1.54 (dd, J = 6.6, 5.4 Hz, 6H), 1.45 (d, J = 6.7 Hz, 3H) |
| 70 | 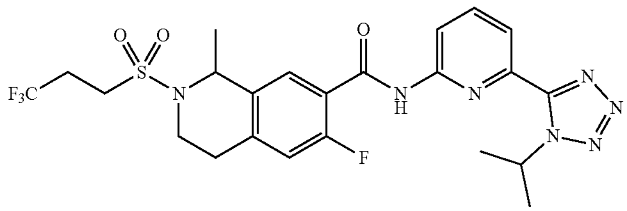 [SMILES: CC1c2cc(C(=O)Nc3cccc(-c4nnnn4C(C)C)n3)c(F)cc2CCN1S(=O)(=O)CCC(F)(F)F] | 556.18 | ¹H NMR (400 MHz, DMSO-d$_6$) δ 11.00 (s, 1H), 8.31 (dd, J = 8.4, 0.9 Hz, 1H), 8.13 (t, J = 8.0 Hz, 1H), 8.00 (dd, J = 7.6, 0.9 Hz, 1H), 7.62 (d, J = 7.1 Hz, 1H), 7.23 (d, J = 10.8 Hz, 1H), 6.01 (hept, J = 6.5 Hz, 1H), 5.11 (q, J = 6.7 Hz, 1H), 3.85 (dd, J = 14.2, 5.9 Hz, 1H), 3.51-3.38 (m, 3H), 3.06-2.93 (m, 1H), 2.91-2.84 (m, 1H) 2.75-2.54 (m, 2H), 1.54 (dd, J = 6.6, 2.5 Hz, 6H), 1.49 (d, J = 6.8 Hz, 3H) |
| 71 | 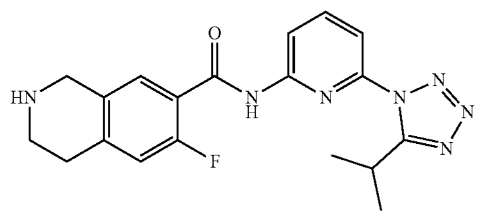 [SMILES: CC(C)c1nnnn1-c1cccc(NC(=O)c2cc3c(cc2F)CCNC3)n1] | 382.17 | ¹H NMR (400 MHz, DMSO-d$_6$) δ 10.97 (s, 1H), 8.32 (d, J = 8.3 Hz, 1H), 8.20 (t, J = 8.1 Hz, 1H), 7.70 (d, J = 7.7 Hz, 1H), 7.39 (d, J = 7.3 Hz, 1H), 7.08 (d, J = 11.2 Hz, 1H), 3.95 (p, J = 7.0 Hz, 1H), 3.85 (s, 2H), 2.93 (t, J = 5.8 Hz, 2H), 2.74 (t, J = 4.8 Hz, 2H), 1.30 (d, J = 6.8 Hz, 6H) |
| 72 | 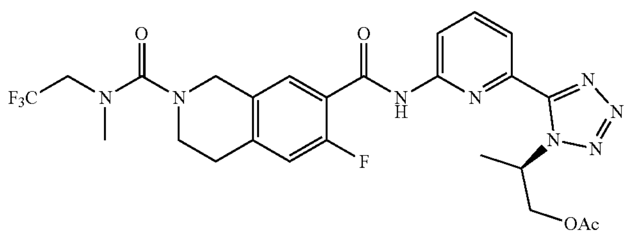 [SMILES: CC(=O)OC[C@@H](C)n1nnnc1-c1cccc(NC(=O)c2cc3c(cc2F)CCN(C(=O)N(C)CC(F)(F)F)C3)n1] | 579.22 | ¹H NMR (400 MHz, DMSO-d$_6$) δ 10.89 (s, 1H), 8.31 (dd, J = 8.4, 0.9 Hz, 1H), 8.14 (t, J = 8.0 Hz, 1H), 8.02 (dd, J = 7.6, 0.9 Hz, 1H), 7.60 (d, J = 7.1 Hz, 1H), 7.23 (d, J = 10.9 Hz, 1H), 6.29-6.23 (m, 1H), 4.49 (dd, J = 11.8, 3.8 Hz, 1H), 4.42 (s, 2H), 4.31 (dd, J = 11.8, 8.0 Hz, 1H), 4.10 (q, J = 9.8 Hz, 2H), 3.46 (t, J = 5.8 Hz, 2H), 3.03 (s, 3H), 2.92 (t, J = 5.9 Hz, 2H), 1.73 (s, 3H), 1.63 (d, J = 6.8 Hz, 3H) |
| 73 | 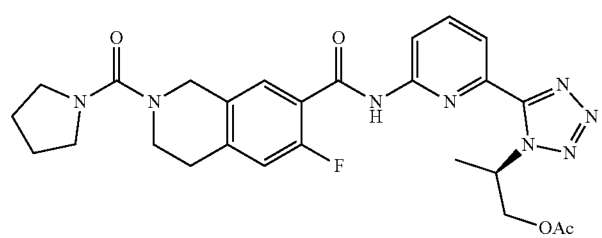 [SMILES: CC(=O)OC[C@@H](C)n1nnnc1-c1cccc(NC(=O)c2cc3c(cc2F)CCN(C(=O)N2CCCC2)C3)n1] | 537.24 | ¹H NMR (400 MHz, DMSO-d$_6$) δ 10.87 (s, 1H), 8.31 (dd, J = 8.4, 0.9 Hz, 1H), 8.14 (t, J = 8.0 Hz, 1H), 8.02 (dd, J = 7.6, 0.9 Hz, 1H), 7.57 (d, J = 7.1 Hz, 1H), 7.21 (d, J = 10.9 Hz, 1H), 6.30-6.22 (m, 1H), 4.50 (dd, J = 11.8, 3.8 Hz, 1H), 4.40 (s, 2H), 4.31 (dd, J = 11.8, 8.0 Hz, 1H), 3.45 (t, J = 5.8 Hz, 2H), 3.34-3.29 (m, 4H), 2.90 (t, J = 5.8 Hz, 2H), 1.80-1.74 (m, 4H), 1.73 (s, 3H), 1.63 (d, J = 6.8 Hz, 3H) |
| 74 | 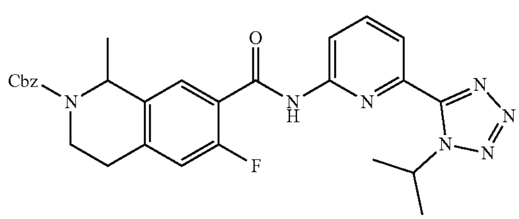 [SMILES: CC1c2cc(C(=O)Nc3cccc(-c4nnnn4C(C)C)n3)c(F)cc2CCN1C(=O)OCc1ccccc1] | 530.23 | ¹H NMR (400 MHz, Chloroform-d) δ 9.07 (d, J = 16.7 Hz, 1H), 8.45 (d, J = 8.3 Hz, 1H), 8.02 (dd, J = 7.7, 0.9 Hz, 1H), 7.92 (dd, J = 9.9, 6.0 Hz, 2H), 7.34-7.23 (comp, 5H), 6.97-6.89 (m, 1H), 5.65 (hept, J = 6.7 Hz, 1H), 5.31 (d, J = 30.6 Hz, 1H), 5.12 (d, J = 6.1 Hz, 2H), 4.19 (d, J = 51.2 Hz, 1H), 3.18 (br s, 1H), 2.92 (br s, 1H), 2.76 (d, J = 16.1 Hz, 1H), 1.64 (dd, J = 6.7, 1.1 Hz, 6H), 1.44 (d, J = 6.8 Hz, 3H) |

-continued

| Example | Structure | LC-MS [M + H]+ unless otherwise noted | H-NMR |
|---|---|---|---|
| 75 | 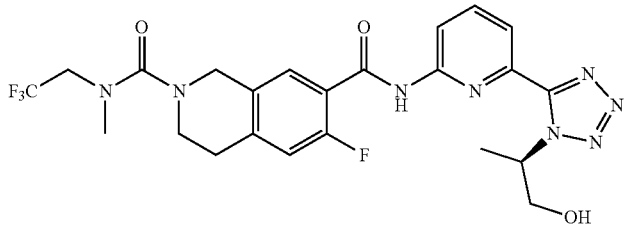 | 537.20 | ¹H NMR (400 MHz, DMSO-d₆) δ 10.97 (s, 1H), 8.30 (dd, J = 8.4, 0.9 Hz, 1H), 8.12 (dd, J = 8.4, 7.6 Hz, 1H), 7.96 (dd, J = 7.6, 0.9 Hz, 1H), 7.59 (d, J = 7.0 Hz, 1H), 7.22 (d, J = 10.9 Hz, 1H), 5.95-5.83 (m, 1H), 4.89 (t, J = 5.5 Hz, 1H), 4.41 (s, 2H), 4.10 (q, J = 9.8 Hz, 2H), 3.79-3.68 (m, 2H), 3.46 (t, J = 5.8 Hz, 2H), 3.03 (s, 3H), 2.92 (t, J = 5.8 Hz, 2H), 1.53 (d, J = 6.8 Hz, 3H) |
| 76 | 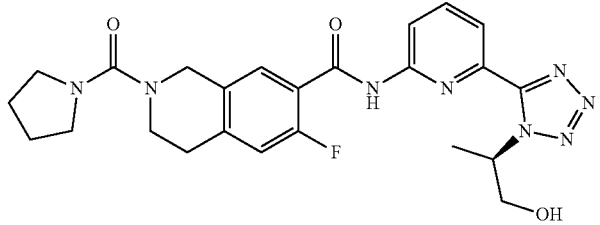 [SMILES: C[C@H](CO)n1nnnc1-c1cccc(NC(=O)c2cc3c(cc2F)CCN(C(=O)N2CCCC2)C3)n1] | 495.22 | ¹H NMR (400 MHz, DMSO-d₆) δ 10.95 (s, 1H), 8.30 (dd, J = 8.4, 0.9 Hz, 1H), 8.12 (dd, J = 8.4, 7.6 Hz, 1H), 7.96 (dd, J = 7.7, 0.9 Hz, 1H), 7.56 (d, J = 7.1 Hz, 1H), 7.20 (d, J = 10.9 Hz, 1H), 5.95-5.84 (m, 1H), 4.89 (t, J = 5.6 Hz, 1H), 4.40 (s, 2H), 3.72 (p, J = 6.6, 6.0 Hz, 2H), 3.44 (t, J = 5.8 Hz, 2H), 3.34-3.27 (m, 4H), 2.90 (t, J = 5.8 Hz, 2H), 1.80-1.73 (m, 4H), 1.53 (d, J = 6.7 Hz, 3H) |
| 77 | 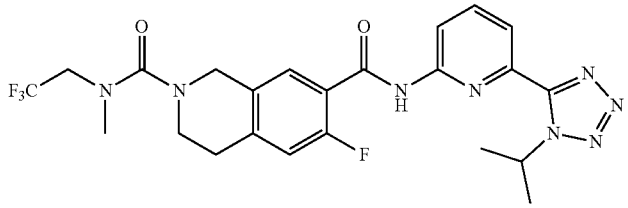 [SMILES: CC(C)n1nnnc1-c1cccc(NC(=O)c2cc3c(cc2F)CCN(C(=O)N(C)CC(F)(F)F)C3)n1] | 521.20 | ¹H NMR (500 MHz, DMSO-d₆) δ 10.97 (s, 1H), 8.30 (dd, H = 8.4, 0.9 Hz, 1H), 8.13 (t, J = 8.0 Hz, 1H), 8.00 (dd, J = 7.6, 0.9 Hz, 1H), 7.59 (d, J = 7.1 Hz, 1H), 7.22 (d, J = 10.8 Hz, 1H), 6.01 (hept, J = 6.6 Hz, 1H), 4.42 (s, 2H), 4.10 (q, J = 9.8 Hz, 2H), 3.46 (t, J = 5.9 Hz, 2H), 2.92 (t, J = 5.9 Hz, 2H), 1.54 (d, J = 6.6 Hz, 6H) |
| 78 | 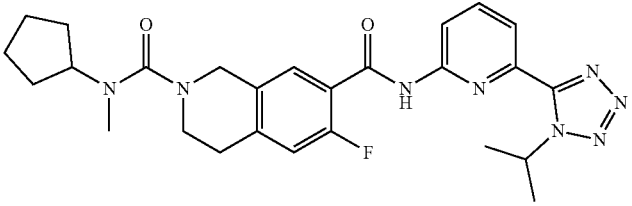 [SMILES: CC(C)n1nnnc1-c1cccc(NC(=O)c2cc3c(cc2F)CCN(C(=O)N(C)C2CCCC2)C3)n1] | 507.26 | ¹H NMR (500 MHz, DMSO-d₆) δ 10.95 (s, 1H), 8.30 (dd, J = 8.4, 0.9 Hz, 1H), 8.13 (t, J = 8.0 Hz, 1H), 7.99 (dd, J = 7.6, 0.9 Hz, 1H), 7.56 (d, J = 7.1 Hz, 1H), 7.20 (d, J = 10.8 Hz, 1H), 6.01 (hept, J = 6.6 Hz, 1H), 4.35 (s, 2H), 4.08 (p, J = 8.2 Hz, 1H), 3.39 (t, J = 5.8 Hz, 2H), 2.91 (t, J = 5.9 Hz, 2H), 2.69 (s, 3H), 1.83-1.71 (m, 2H), 1.70-1.59 (m, 2H), 1.58-1.46 (comp, 10H) |
| 79 | 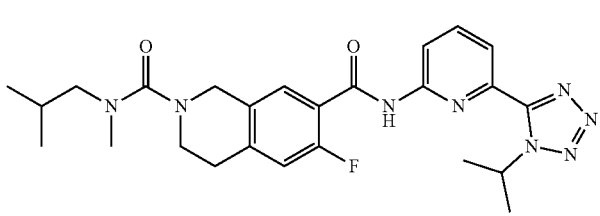 [SMILES: CC(C)CN(C)C(=O)N1CCc2cc(F)c(C(=O)Nc3cccc(-c4nnnn4C(C)C)n3)cc2C1] | 495.26 | ¹H NMR (500 MHz, DMSO-d₆) δ 10.95 (s, 1H), 8.30 (dd, J = 8.4, 0.9 Hz, 1H), 8.13 (t, J = 8.0 Hz, 1H), 7.99 (dd, J = 7.6, 0.9 Hz, 1H), 7.56 (d, J = 7.1 Hz, 1H), 7.20 (d, J = 10.9 Hz, 1H), 6.01 (hept, J = 6.3 Hz, 1H), 4.33 (s, 2H), 3.39 (t, J = 5.8 Hz, 2H), 3.01 (d, J = 7.5 Hz, 2H), 2.91 (t, J = 5.9 Hz, 2H), 1.88 (hept, J = 6.9 Hz, 1H), 1.54 (d, J = 6.6 Hz, 6H), 0.81 (d, J = 6.6 Hz, 6H) |
| 80 | 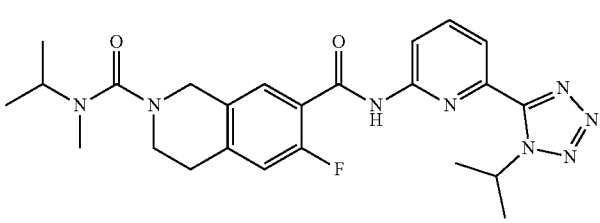 | 481.24 | ¹H NMR (500 MHz, DMSO-d₆) δ 10.95 (s, 1H), 8.30 (dd, J = 8.4, 0.9 Hz, 1H), 8.17-8.08 (m, 1H), 7.99 (dd, J = 7.6, 0.9 Hz, 1H), 7.56 (d, J = 7.1 Hz, 1H), 7.20 (d, J = 10.9 Hz, 1H), 6.01 (hept, J = 6.7 Hz, 1H), 4.33 (s, 2H), 3.95 (hept, J = 6.7 Hz, 1H), 3.37 (t, J = 5.8 Hz, 2H), 2.91 (t, J = 5.9 Hz, 2H), 2.67 (s, 3H), 1.54 (d, J = 6.7 Hz, 6H), 1.09 (d, J = 6.7 Hz, 6H) |

-continued

| Example | Structure | LC-MS [M + H]+ unless otherwise noted | H-NMR |
|---|---|---|---|
| 81 | 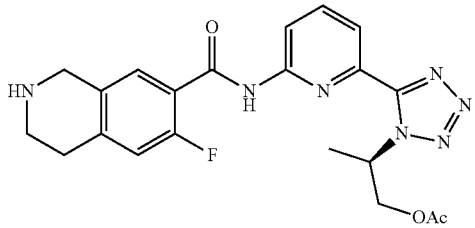 [SMILES: CC(=O)OC[C@@H](C)n1nnnc1-c1cccc(NC(=O)c2cc3c(cc2F)CCNC3)n1] | 440.17 | ¹H NMR (500 MHz, DMSO-d₆) δ 10.80 (s, 1H), 8.31 (dd, J = 8.4, 0.9 Hz, 1H), 8.13 (t, J = 8.0 Hz, 1H), 8.01 (dd, J = 7.6, 0.9 Hz, 1H), 7.41 (d, J = 7.3 Hz, 1H), 7.11 (d, J = 11.1 Hz, 1H), 6.31-6.24 (m, 1H), 4.50 (dd, J = 11.8, 3.8 Hz, 1H), 4.31 (dd, J = 11.8, 8.0 Hz, 1H), 3.87 (s, 2H), 2.93 (t, J = 5.9 Hz, 2H), 2.75 (t, J = 5.9 Hz, 2H), 1.73 (s, 3H), 1.63 (d, J = 6.9 Hz, 3H) |
| 82 | 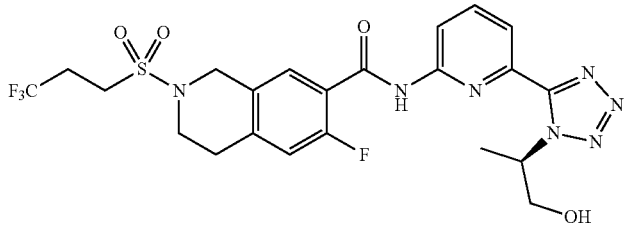 [SMILES: C[C@H](CO)n1nnnc1-c1cccc(NC(=O)c2cc3c(cc2F)CCN(S(=O)(=O)CCC(F)(F)F)C3)n1] | 558.16 | ¹H NMR (400 MHz, DMSO-d₆) δ 10.99 (s, 1H), 8.31 (dd, J = 8.4, 0.9 Hz, 1H), 8.11 (t, J = 7.9 Hz, 1H), 7.96 (dd, J = 7.6, 0.9 Hz, 1H), 7.58 (d, J = 7.1 Hz, 1H), 7.26 (d, J = 10.8 Hz, 1H), 5.96-5.82 (m, 1H), 4.90 (t, J = 5.7 Hz, 1H), 4.52 (s, 2H), 3.79-3.67 (m, 2H), 3.57 (t, J = 5.9 Hz, 2H), 3.49-3.41 (m, 2H), 2.98 (t, J = 5.9 Hz, 2H), 2.82-2.64 (m, 2H), 1.54 (d, J = 6.8 Hz, 3H) |
| 83 | 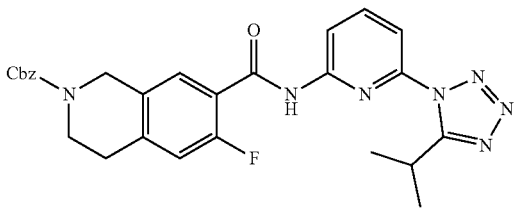 [SMILES: CC(C)c1nnnn1-c1cccc(NC(=O)c2cc3c(cc2F)CCN(C(=O)OCc2ccccc2)C3)n1] | 516.21 | ¹H NMR (400 MHz, DMSO-d₆) δ 11.06 (s, 1H), 8.33 (d, J = 8.3 Hz, 1H), 8.21 (t, J = 8.1 Hz, 1H), 7.71 (d, J = 7.7 Hz, 1H), 7.60 (d, J = 7.1 Hz, 1H), 7.45-7.29 (comp, 7H), 7.22 (d, J = 10.9 Hz, 1H), 5.13 (s, 2H), 4.63 (d, J = 16.5 Hz, 3H), 3.94 (hept, J = 6.9 Hz, 1H), 3.65 (s, 2H), 2.89 (t, J = 6.0 Hz, 2H), 1.30 (d, J = 6.8 Hz, 6H) |
| 84 | 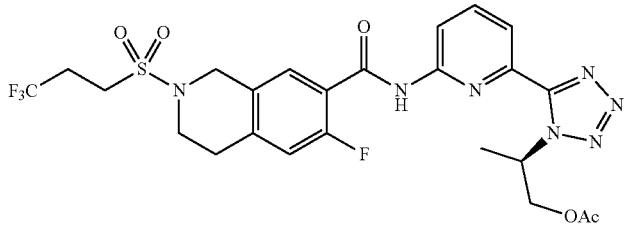 [SMILES: CC(=O)OC[C@@H](C)n1nnnc1-c1cccc(NC(=O)c2cc3c(cc2F)CCN(S(=O)(=O)CCC(F)(F)F)C3)n1] | 600.17 | ¹H NMR (400 MHz, DMSO-d₆) δ 10.91 (s, 1H), 8.32 (dd, J = 8.3, 0.9 Hz, 1H), 8.14 (t, J = 8.0 Hz, 1H), 8.02 (dd, J = 7.6, 0.9 Hz, 1H), 7.60 (d, J = 7.1 Hz, 1H), 7.27 (d, J = 10.8 Hz, 1H), 6.31-6.23 (m, 1 H), 4.53 (s, 2H), 4.50 (dd, J = 12.1, 4.2 Hz, 1H), 4.31 (dd, J = 11.8, 8.0 Hz, 1H), 3.57 (t, J = 5.9 Hz, 2H), 3.49-3.41 (m, 2H), 2.98 (t, J = 6.0 Hz, 2H), 2.85-2.63 (m, 2H), 1.73 (s, 3H), 1.64 (d, J = 6.8 Hz, 3H) |
| 85 | 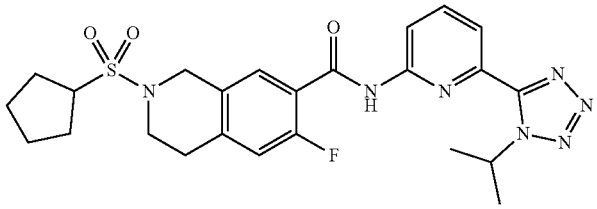 [SMILES: CC(C)n1nnnc1-c1cccc(NC(=O)c2cc3c(cc2F)CCN(S(=O)(=O)C2CCCC2)C3)n1] | 514.20 | ¹H NMR (400 MHz, DMSO-d₆) δ 10.99 (s, 1H), 8.31 (d, J = 8.3 Hz, 1H), 8.13 (t, J = 8.0 Hz, 1H), 8.00 (d, J = 7.6 Hz, 1H), 7.58 (d, J = 7.0 Hz, 1H), 7.24 (d, J = 10.9 Hz, 1H), 6.01 (hept, J = 6.6 Hz, 1H), 4.49 (s, 2H), 3.75 (p, J = 8.0 Hz, 1H), 3.55 (t, J = 5.9 Hz, 2H), 2.95 (t, J = 6.0 Hz, 2H), 2.01-1.76 (comp, 4H), 1.73-1.61 (comp, 2H), 1.62-1.49 (comp, 8H) |
| 86 | 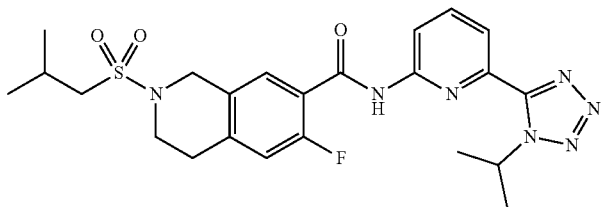 | 502.20 | ¹H NMR (400 MHz, DMSO-d₆) δ 10.99 (s, 1H), 8.31 (d, J = 8.4 Hz, 1H), 8.13 (t, J = 8.0 Hz, 1H), 8.00 (dd, J = 7.6, 1.0 Hz, 1H), 7.59 (d, J = 7.1 Hz, 1H), 7.25 (d, J = 10.8 Hz, 1H), 6.01 (hept, J = 6.6 Hz, 1H), 4.44 (s, 2H), 3.49 (t, J = 5.9 Hz, 2H), 3.01 (d, J = 6.5 Hz, 2H), 2.97 (t, J = 6.0 Hz, 2H), 2.14 (hept, J = 6.6 Hz, 1H), 1.54 (d, J = 6.7 Hz, 6H), 1.05 (d, J = 6.6 Hz, 6H) |

-continued

| Example | Structure | LC-MS [M + H]+ unless otherwise noted | H-NMR |
|---|---|---|---|
| 87 | 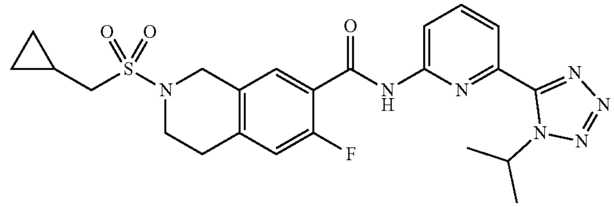 [SMILES: CC(C)n1nnnc1-c1cccc(NC(=O)c2cc3c(cc2F)CCN(S(=O)(=O)CC2CC2)C3)n1] | 500.18 | ¹H NMR (400 MHz, DMSO-d₆) δ 10.99 (s, 1H), 8.31 (d, J = 8.3 Hz, 1H), 8.13 (t, J = 8.0 Hz, 1H), 8.00 (dd, J = 1.6, 0.8 Hz, 1H), 7.58 (d, J = 7.0 Hz, 1H), 7.25 (d, J = 10.9 Hz, 1H), 6.01 (hept, J = 6.7 Hz, 1H), 4.48 (s, 2H), 3.53 (t, J = 5.9 Hz, 2H), 3.12 (d, J = 7.1 Hz, 2H), 2.96 (t, J = 6.0 Hz, 2H), 1.54 (d, J = 6.6 Hz, 6H), 1.06-0.97 (m, 1H), 0.65-0.54 (m, 2H), 0.41-0.30 (m, 2H) |
| 88 | 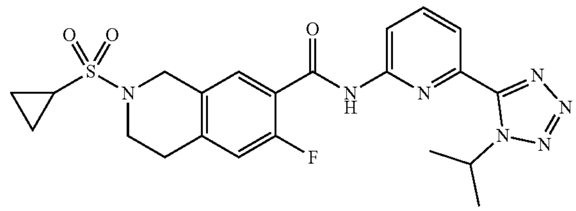 [SMILES: CC(C)n1nnnc1-c1cccc(NC(=O)c2cc3c(cc2F)CCN(S(=O)(=O)C2CC2)C3)n1] | 486.17 | ¹H NMR (400 MHz, DMSO-d₆) δ 10.98 (s, 1H), 8.31 (d, J = 8.4 Hz, 1H), 8.13 (t, J = 8.0 Hz, 1H), 8.00 (d, J = 7.6 Hz, 1H), 7.62 (d, J = 7.1 Hz, 1H), 7.25 (d, J = 11.0 Hz, 1H), 6.01 (hept, J = 6.6, 5.5 Hz, 1H), 4.48 (s, 2H), 3.53 (t, J = 5.9 Hz, 2H), 2.99 (t, J = 6.4 Hz, 2H), 2.69-2.60 (m, 1H), 1.54 (d, J = 6.5 Hz, 6H), 1.09-0.95 (comp, 4H) |
| 89 | 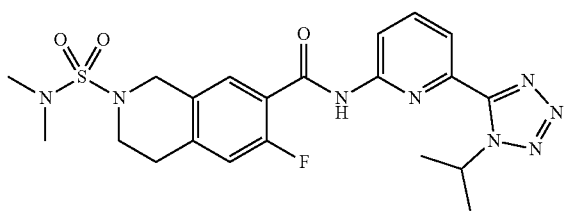 | 489.18 | ¹H NMR (400 MHz, DMSO-d₆) δ 10.99 (s, 1H), 8.30 (d, J = 8.3 Hz, 1H), 8.13 (t, J = 8.0 Hz, 1H), 8.00 (d, J = 7.5 Hz, 1H), 7.60 (d, J = 7.1 Hz, 1H), 7.24 (d, J = 10.9 Hz, 1H), 6.01 (hept, J = 6.5 Hz, 1H), 4.43 (s, 2H), 3.50 (t, J = 5.9 Hz, 2H), 2.95 (t, J = 6.0 Hz, 2H), 2.78 (s, 6H), 1.54 (d, J = 6.6 Hz, 6H) |
| 90 | 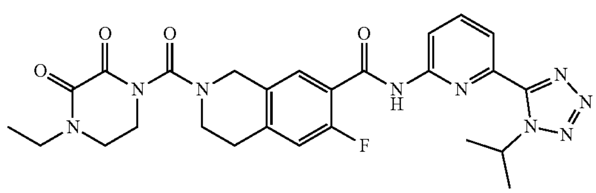 [SMILES: CCN1CCN(C(=O)N2CCc3cc(F)c(C(=O)Nc4cccc(-c5nnnn5C(C)C)n4)cc3C2)C(=O)C1=O] | 550.22 | ¹H NMR (400 MHz, DMSO-d₆) δ 10.98 (s, 1H), 8.30 (d, J = 8.3 Hz, 1H), 8.13 (t, J = 8.0 Hz, 1H), 8.00 (d, J = 7.6 Hz, 1H), 7.61 (d, J = 30.6 Hz, 1H), 7.27 (d, J = 10.8 Hz, 1H), 6.02 (hept, J = 6.6 Hz, 1H), 4.69 (s, 2H), 4.06-3.50 (comp, 6H), 3.49-3.32 (m, 2H), 2.95 (s, 2H), 1.54 (d, J = 6.6 Hz, 6H), 1.12 (t, J = 7.2 Hz, 3 Hz) |
| 91 | 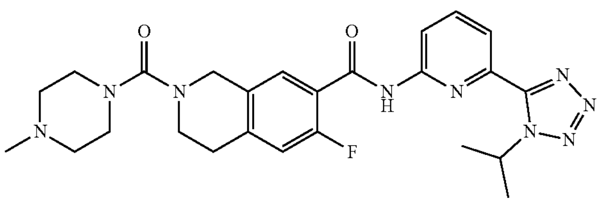 [SMILES: CC(C)n1nnnc1-c1cccc(NC(=O)c2cc3c(cc2F)CCN(C(=O)N2CCN(C)CC2)C3)n1] | 508.25 | ¹H NMR (400 MHz, Chloroform-d) δ 9.14 (d, J = 16.7 Hz, 1H), 8.52 (d, J = 8.3 Hz, 1H), 8.08 (dd, J = 7.7, 0.9 Hz, 1H), 7.99 (d, J = 8.1 Hz, 1H), 7.95 (d, J = 8.1 Hz, 1H), 7.01 (d, J = 12.8 Hz, 1H), 5.72 (hept, J = 6.7 Hz, 1H), 4.50 (s, 2H), 3.54 (t, J = 5.9 Hz, 2H), 3.49-3.40 (m, 4H), 2.98 (t, J = 5.9 Hz, 2H), 2.67-2.53 (m, 4H), 2.42 (s, 3H), 1.71 (d, J = 6.7 Hz, 6H) |
| 92 | 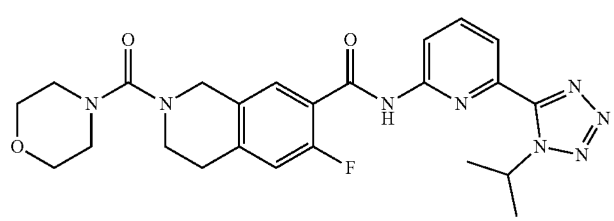 [SMILES: CC(C)n1nnnc1-c1cccc(NC(=O)c2cc3c(cc2F)CCN(C(=O)N2CCOCC2)C3)n1] | 495.22 | ¹H NMR (400 MHz, DMSO-d₆) δ 10.95 (s, 1H), 8.30 (d, J = 7.9 Hz, 1H), 8.13 (t, J = 8.0 Hz, 1H), 8.00 (dd, J = 7.7, 0.9 Hz, 1H), 7.58 (d, J = 7.1 Hz, 1H), 7.20 (d, J = 10.9 Hz, 1H), 6.01 (hept, J = 6.3 Hz, 1H), 4.43 (s, 2H), 3.60 (t, J = 4.6 Hz, 4H), 3.44 (t, J = 5.8 Hz, 2H), 3.18 (t, J = 4.6 Hz, 4H), 2.91 (t, J = 5.9 Hz, 2H), 1.54 (d, J = 6.6 Hz, 6H) |
| 93 | 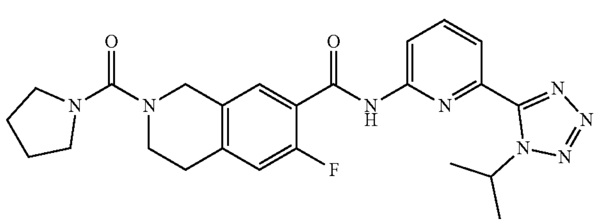 | 479.22 | ¹H NMR (400 MHz, DMSO-d₆) δ 10.95 (s, 1H), 8.30 (dd, J = 8.4, 0.9 Hz, 1H), 8.13 (t, J = 8.0 Hz, 1H), 8.00 (dd, J = 7.6, 0.9 Hz, 1H), 7.56 (d, J = 7.1 Hz, 1H), 7.20 (d, J = 10.9 Hz, 1H), 6.01 (hept, J = 6.5 Hz, 1H), 4.40 (s, 2H), 3.44 (t, J = 5.8 Hz, 2H), 3.33-3.30 (m, 4H), 2.90 (t, J = 5.8 Hz, 2H), 1.85-1.75 (m, 4H), 1.54 (d, J = 6.6 Hz, 6H) |

-continued

| Example | Structure | LC-MS [M + H]+ unless otherwise noted | H-NMR |
|---|---|---|---|
| 94 | 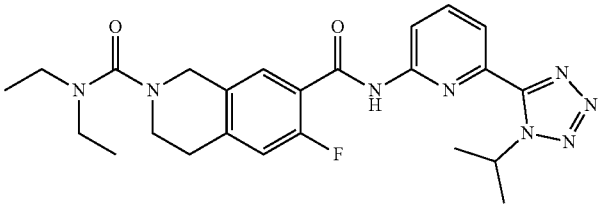 [SMILES: CCN(CC)C(=O)N1CCc2cc(F)c(C(=O)Nc3cccc(-c4nnnn4C(C)C)n3)cc2C1] | 481.24 | $^1$H NMR (400 MHz, DMSO-d$_6$) δ 10.96 (s, 1H), 8.30 (d, J = 8.4 Hz, 1H), 8.13 (t, J = 8.0 Hz, 1H), 8.00 (d, J = 7.9 Hz, 1H), 7.56 (d, J = 7.1 Hz, 1H), 7.20 (d, J = 10.9 Hz, 1H), 6.01 (hept, J = 6.6 Hz, 1H), 4.33 (s, 2H), 3.38 (t, J = 5.8 Hz, 2H), 3.16 (q, J = 7.0 Hz, 4H), 2.90 (t, J = 5.8 Hz, 2H), 1.54 (d, J = 6.6 Hz, 6H), 1.07 (t, J = 7.0 Hz, 6H) |
| 95 | 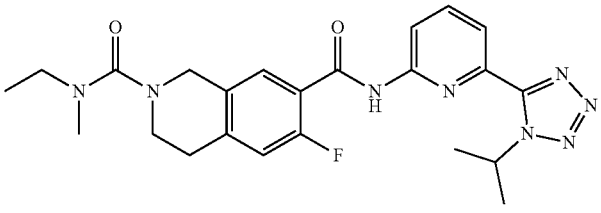 [SMILES: CCN(C)C(=O)N1CCc2cc(F)c(C(=O)Nc3cccc(-c4nnnn4C(C)C)n3)cc2C1] | 467.22 | $^1$H NMR (400 MHz, DMSO-d$_6$) δ 10.95 (s, 1H), 8.30 (d, J = 8.4 Hz, 1H), 8.13 (t, J = 8.0 Hz, 1H), 8.00 (d, J = 7.6 Hz, 1H), 7.56 (d, J = 7.1 Hz, 1H), 7.20 (d, J = 10.9 Hz, 1H), 6.01 (hept, J = 6.6 Hz, 1H), 4.34 (s, 2H), 3.39 (t, J = 5.8 Hz, 2H), 3.16 (q, J = 7.1 Hz, 2H), 2.91 (t, J = 5.8 Hz, 2H), 2.78 (s, 3H), 1.54 (d, J = 6.6 Hz, 6H), 1.08 (t, J = 7.0 Hz, 3H) |
| 96 | 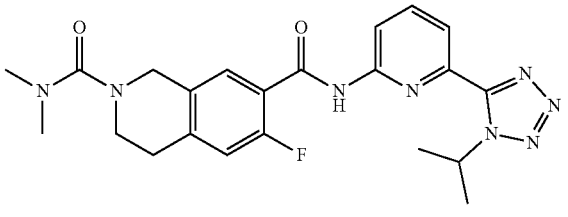 [SMILES: CC(C)n1nnnc1-c1cccc(NC(=O)c2cc3c(cc2F)CCN(C(=O)N(C)C)C3)n1] | 453.21 | $^1$H NMR (400 MHz, DMSO-d$_6$) δ 10.95 (s, 1H), 8.30 (d, J = 8.3 Hz, 1H), 8.13 (t, J = 8.0 Hz, 1H), 7.99 (d, J = 7.6 Hz, 1H), 7.55 (d, J = 7.1 Hz, 1H), 7.20 (d, J = 10.9 Hz, 1H), 6.01 (hept, J = 6.7, 6.1 Hz, 1H), 4.36 (s, 2H), 3.40 (t, J = 5.8 Hz, 2H), 2.91 (t, J = 5.8 Hz, 2H), 2.79 (s, 6H), 1.54 (d, J = 6.6 Hz, 6H) |
| 97 | 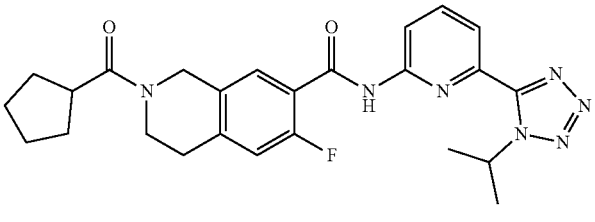 [SMILES: CC(C)n1nnnc1-c1cccc(NC(=O)c2cc3c(cc2F)CCN(C(=O)C2CCCC2)C3)n1] | 478.23 | $^1$H NMR (400 MHz, DMSO-d$_6$) δ 10.98 (s, 1H), 8.31 (d, J = 8.3 Hz, 1H), 8.13 (t, J = 8.0 Hz, 1H), 8.00 (d, J = 7.6 Hz, 1H), 7.63 (d, J = 7.1 Hz, 0.5H), 7.59 (d, J = 7.1 Hz, 0.5H), 7.24 (d, J = 11.4 Hz, 1H), 6.02 (hept, J = 6.6 Hz, 1H), 4.76 (s, 1H), 4.65 (s, 1H), 3.76 (t, J = 5.9 Hz, 1H), 3.69 (t, J = 6.1 Hz, 1H), 3.10-3.05 (m, 1H), 2.93 (t, J = 5.9 Hz, 1H), 2.84 (t, J = 6.0 Hz, 1H), 1.83-1.78 (comp, 4H), 1.73-1.45 (comp, 10H) |
| 98 | 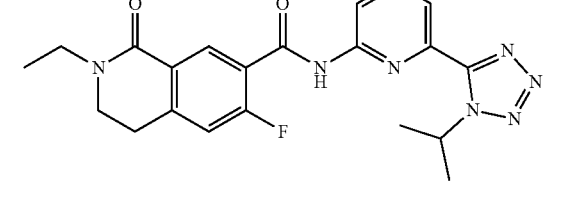 | 424.17 | $^1$H NMR (400 MHz, DMSO-d$_6$) δ 8.94 (d, J = 13.3 Hz, 1H), 8.87 (d, J = 8.1 Hz, 1H), 8.55 (dd, J = 8.3, 0.9 Hz, 1H), 8.08 (dd, J = 7.6, 1.0 Hz, 1H), 7.98 (t, J = 8.0 Hz, 1H), 7.06 (d, J = 11.8 Hz, 1H), 5.73 (hept, J = 6.7 Hz, 1H), 3.69-3.59 (comp, 4H), 3.08 (t, J = 6.5 Hz, 2H), 1.70 (d, J = 6.7 Hz, 6H), 1.24 (t, J = 7.2 Hz, 3H) |
| 99 | 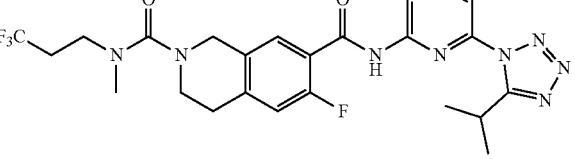 | 535.22 | $^1$H NMR (500 MHz, DMSO-d$_6$) δ 11.03 (s, 1H), 8.33 (dd, J = 8.4, 0.7 Hz, 1H), 8.21 (t, J = 8.0 Hz, 1H), 7.71 (dd, J = 7.8, 0.7 Hz, 1H), 7.55 (d, J = 7.1 Hz, 1H), 7.18 (d, J = 11.0 Hz, 1H), 4.34 (s, 2H), 3.94 (hept, J = 6.7 Hz, 1H), 3.38 (q, J = 7.5, 6.5 Hz, 4H), 2.90 (t, J = 5.7 Hz, 3H), 2.88 (s, 3H), 2.59-2.51 (m, 2H), 1.30 (d, J = 6.8 Hz, 6H) |

| Example | Structure | LC-MS [M + H]+ unless otherwise noted | H-NMR |
|---|---|---|---|
| 100 | 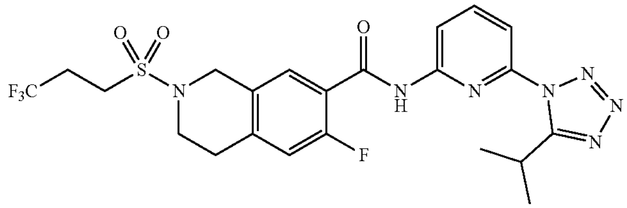 [SMILES: CC(C)c1nnnn1-c1cccc(NC(=O)c2cc3c(cc2F)CCN(S(=O)(=O)CCC(F)(F)F)C3)n1] | 542.16 | ¹H NMR (500 MHz, DMSO-d$_6$) δ 11.07 (s, 1H), 8.34 (d, J = 8.2 Hz, 1H), 8.22 (t, J = 8.0 Hz, 1H), 7.71 (dd, J = 7.8, 0.7 Hz, 1H), 7.57 (d, J = 7.0 Hz, 1H), 7.24 (d, J = 10.9 Hz, 1H), 4.51 (s, 2H), 3.94 (hept, J = 6.9 Hz, 1H), 3.56 (t, J = 6.0 Hz, 2H), 3.50-3.40 (m, 2H), 2.97 (t, J = 6.0 Hz, 2H), 2.81-2.67 (m, 2H), 1.30 (d, J = 6.9 Hz, 6H) |
| 101 | 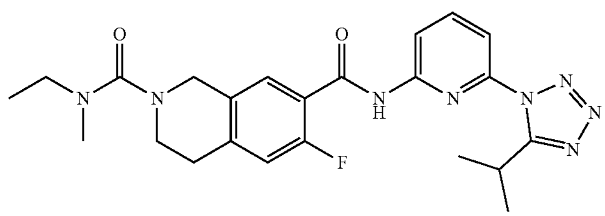 [SMILES: CCN(C)C(=O)N1CCc2cc(F)c(C(=O)Nc3cccc(-n4nnnc4C(C)C)n3)cc2C1] | 467.22 | ¹H NMR (500 MHz, DMSO-d$_6$) δ 11.03 (s, 1H), 8.33 (d, J = 8.6 Hz, 1H), 8.21 (t, J = 8.1 Hz, 1H), 7.71 (dd, J = 7.8, 0.7 Hz, 1H), 7.54 (d, J = 7.1 Hz, 1H), 7.18 (d, J = 11.0 Hz, 1H), 4.33 (s, 2H), 3.94 (hept, J = 6.7 Hz, 1H), 3.38 (t, J = 5.9 Hz, 2H), 3.15 (q, J = 7.1 Hz, 2H), 2.90 (t, J = 5.7 Hz, 2H), 2.78 (s, 4H), 1.30 (d, J = 6.9 Hz, 6H), 1.08 (t, J = 7.1 Hz, 3H) |
| 102 | 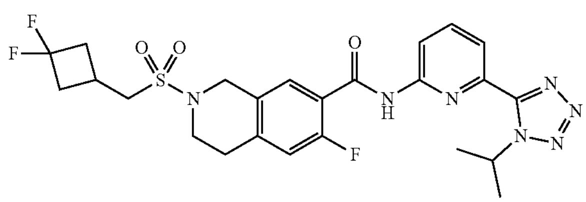 [SMILES: CC(C)n1nnnc1-c1cccc(NC(=O)c2cc3c(cc2F)CCN(S(=O)(=O)CC2CC(F)(F)C2)C3)n1] | 550.18 | ¹H NMR (400 MHz, Chloroform-d) δ 9.12 (d, J = 16.3 Hz, 1H), 8.52 (d, J = 8.3 Hz, 1H), 8.09 (d, J = 7.8 Hz, 1H), 8.02-7.94 (comp, 2H), 7.05 (d, J = 12.6 Hz, 1H), 5.71 (hept, J = 6.8 Hz, 1H), 4.54 (s, 2H), 3.63 (t, J = 5.9 Hz, 2H), 3.17 (d, J = 7.4 Hz, 2H), 3.05 (t, J = 5.9 Hz, 2H), 2.92-2.85 (m, 2H), 2.77-2.69 (m, 1H), 2.60-2.36 (m, 2H), 1.72 (d, J = 6.6 Hz, 6H) |
| 103 | 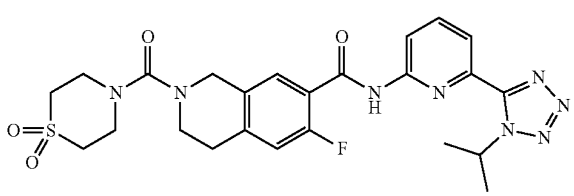 [SMILES: CC(C)n1nnnc1-c1cccc(NC(=O)c2cc3c(cc2F)CCN(C(=O)N2CCS(=O)(=O)CC2)C3)n1] | 510.15 | ¹H NMR (500 MHz, DMSO-d$_6$) δ 11.00 (s, 1H), 8.31 (d, J = 8.4 Hz, 1H), 8.13 (t, J = 8.0 Hz, 1H), 8.00 (dd, J = 7.7, 0.9 Hz, 1H), 7.59 (d, J = 7.1 Hz, 1H), 7.26 (d, J = 10.8 Hz, 1H), 6.41 (tt, J = 54.5, 4.4 Hz, 1H), 6.10-5.95 (m, 1H), 4.51 (s, 2H), 4.03 (td, J = 15.2, 4.5 Hz, 2H), 3.54 (t, J = 6.0 Hz, 2H), 2.99 (q, J = 7.1, 6.1 Hz, 2H), 1.54 (d, J = 6.6 Hz, 6H) |
| 104 | 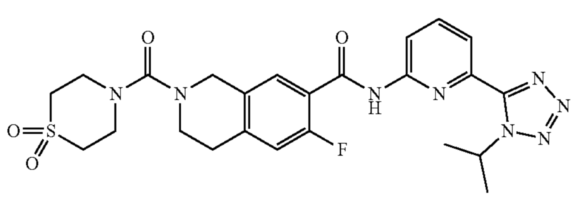 [SMILES: CC(C)n1nnnc1-c1cccc(NC(=O)c2cc3c(cc2F)CCN(C(=O)N2CCS(=O)(=O)CC2)C3)n1] | 543.19 | ¹H NMR (500 MHz, DMSO-d$_6$) δ 10.95 (s, 1H), 8.30 (dd, J = 8.4, 0.9 Hz, 1H), 8.13 (t, J = 8.0 Hz, 1H), 8.00 (dd, J = 7.6, 0.9 Hz, 1H), 7.60 (d, J = 7.1 Hz, 1H), 7.22 (d, J = 10.9 Hz, 1H), 6.01 (hept, J = 6.6 Hz, 1H), 4.48 (s, 2H), 3.59 (t, J = 5.3 Hz, 4H), 3.47 (t, J = 5.8 Hz, 2H), 3.21 (t, J = 5.3 Hz, 4H), 2.91 (t, J = 5.9 Hz, 2H), 1.54 (d, J = 6.6 Hz, 6H) |
| 105 | 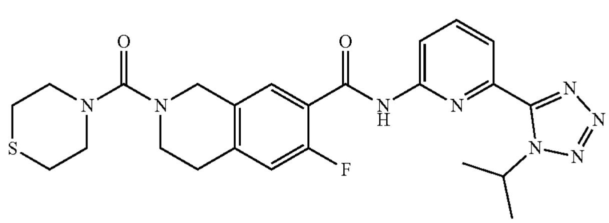 [SMILES: CC(C)n1nnnc1-c1cccc(NC(=O)c2cc3c(cc2F)CCN(C(=O)N2CCSCC2)C3)n1] | 511.20 | ¹H NMR (500 MHz, DMSO-d$_6$) δ 10.95 (s, 1H), 8.30 (dd, J = 8.4, 0.9 Hz, 1H), 8.13 (t, J = 8.0 Hz, 1H), 7.58 (d, J = 7.1 Hz, 1H), 7.20 (d, J = 10.8 Hz, 1H), 6.01 (hept, J = 6.7 Hz, 1H), 4.40 (s, 2H), 3.49-3.39 (comp, 6H), 2.90 (t, J = 5.9 Hz, 2H), 2.67-2.60 (m, 4H), 1.54 (d, J = 6.6 Hz, 6H) |
| 106 | 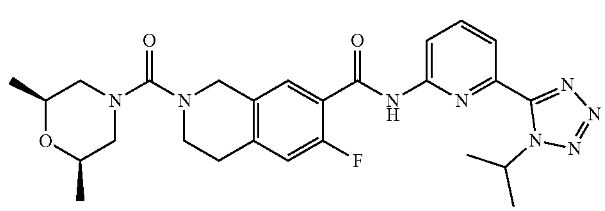 [SMILES: CC(C)n1nnnc1-c1cccc(NC(=O)c2cc3c(cc2F)CCN(C(=O)N2C[C@@H](C)O[C@@H](C)C2)C3)n1] | 523.25 | ¹H NMR (500 MHz, DMSO-d$_6$) δ 10.95 (s, 1H), 8.30 (dd, J = 8.4, 0.9 Hz, 1H), 8.13 (t, J = 8.0 Hz, 1H), 8.00 (dd, J = 7.6, 0.9 Hz, 1H), 7.57 (d, J = 7.1 Hz, 1H), 7.20 (d, J = 10.9 Hz, 1H), 6.01 (hept, J = 6.5 Hz, 1H), 4.41 (s, 2H), 3.61-3.51 (m, 2H), 3.47 (d, J = 12.8 Hz, 2H), 3.43 (t, J = 5.8 Hz, 2H), 2.91 (t, J = 5.9 Hz, 2H), 1.54 (d, J = 6.7 Hz, 6H), 1.08 (s, 3H), 1.07 (s, 3H) |

-continued

| Example | Structure | LC-MS [M + H]+ unless otherwise noted | H-NMR |
|---|---|---|---|
| 107 | 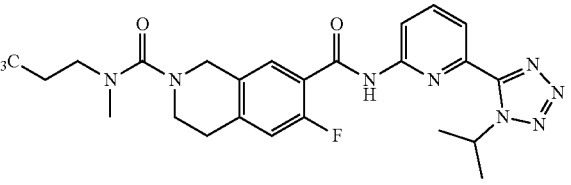 | 535.22 | ¹H NMR (500 MHz, DMSO-d₆) δ 10.95 (s, 1H), 8.30 (dd, J = 8.4, 0.9 Hz, 1H), 8.13 (t, J = 8.0 Hz, 1H), 8.00 (dd, J = 7.6, 0.9 Hz, 1H), 7.56 (d, J = 7.1 Hz, 1H), 7.21 (d, J = 10.8 Hz, 1H), 6.01 (hept, J = 6.6 Hz, 1H), 4.35 (s, 2H), 3.44-3.35 (comp, 4H), 2.91 (t, J = 6.0 Hz, 2H), 2.88 (s, 3H), 2.62-2.51 (m, 2H), 1.54 (d, J = 6.6 Hz, 6H) |
| 108 | 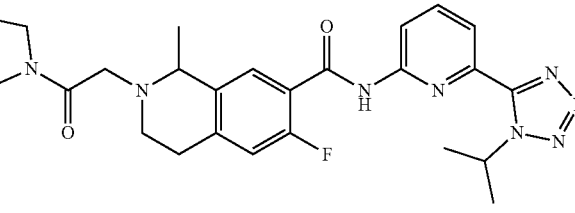 | 507.26 | ¹H NMR (400 MHz, DMSO-d₆) δ 10.95 (s, 1H), 8.31 (dd, J = 8.4, 0.9 Hz, 1H), 8.12 (t, J = 8.0 Hz, 1H), 7.99 (dd, J = 7.6, 0.9 Hz, 1H), 7.48 (d, J = 7.1 Hz, 1H), 7.12 (d, J = 11.0 Hz, 1H), 6.02 (p, J = 6.6 Hz, 1H), 4.01 (q, J = 6.6 Hz, 1H), 3.53-3.44 (m, 1H), 3.36-3.28 (comp, 3H), 3.04-2.94 (m, 1H), 2.94-2.65 (m, 3H), 1.84 (p, J = 6.7 Hz, 2H), 1.75 (p, J = 6.6 Hz, 2H), 1.54 (dd, J = 6.6, 4.3 Hz, 6H), 1.29 (d, J = 6.6 Hz, 3H), 0.94 (t, J = 7.2 Hz, 2H) |
| 109 | 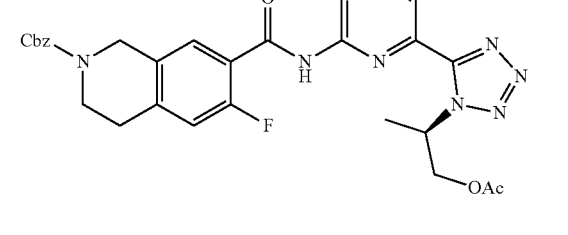 | 574.23 | ¹H NMR (400 MHz, DMSO-d₆) δ 10.90 (s, 1H), 8.31 (d, J = 8.3 Hz, 1H), 8.14 (t, J = 8.0 Hz, 1H), 8.02 (dd, J = 7.6, 0.9 Hz, 1H), 7.62 (d, J = 7.1 Hz, 1H), 7.42-7.29 (comp, 5H), 7.25 (d, J = 10.8 Hz, 1H), 6.30-6.20 (m, 1H), 5.14 (s, 2H), 4.64 (d, J = 17.2 Hz, 2H), 4.49 (dd, J = 11.8, 3.8 Hz, 1H), 4.31 (dd, J = 11.8, 8.0 Hz, 1H), 3.70-3.62 (m, 2H), 2.90 (t, J = 5.9 Hz, 2H), 1.73 (s, 3H), 1.63 (d, J = 6.9 Hz, 3H) |
| 110 | 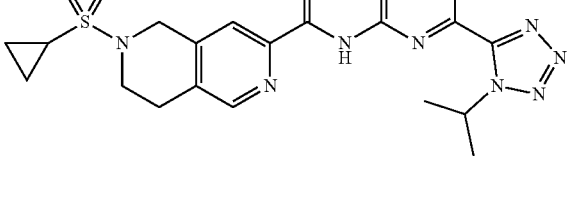 | 469.17 | ¹H NMR (500 MHz, DMSO-d₆) δ 10.78 (s, 1H), 8.62 (s, 1H), 8.41 (d, J = 8.6 Hz, 1H), 8.17 (t, J = 8.0 Hz, 1H), 8.13 (s, 1H), 7.99 (dd, J = 7.7, 0.9 Hz, 1H), 5.90 (hept, J = 6.7 Hz, 1H), 4.64 (s, 2H), 3.61 (t, J = 5.9 Hz, 2H), 3.06 (t, J = 6.0 Hz, 2H), 2.66 (dtd, J = 10.7, 6.7, 5.7, 4.3 Hz, 1H), 1.60 (d, J = 6.6 Hz, 6H), 1.04-0.92 (comp, 4H) |
| 111 | 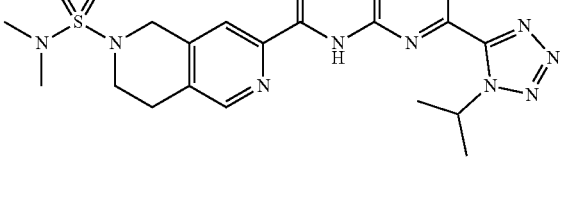 | 472.18 | ¹H NMR (500 MHz, DMSO-d₆) δ 10.77 (s, 1H), 8.61 (s, 1H), 8.41 (dd, J = 8.4, 0.8 Hz, 1H), 8.17 (t, J = 8.0 Hz, 1H), 8.12 (s, 1H), 7.99 (dd, J = 7.6, 0.9 Hz, 1H), 5.90 (hept, J = 6.7 Hz, 1H), 4.57 (s, 2H), 3.57 (t, J = 5.8 Hz, 2H), 3.01 (t, J = 5.9 Hz, 2H), 2.80 (s, 6H), 1.60 (d, J = 6.6 Hz, 6H) |
| 112 | 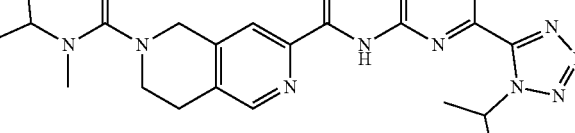 | 490.26 | ¹H NMR (500 MHz, DMSO-d₆) δ 10.76 (s, 1H), 8.57 (s, 1H), 8.41 (dd, J = 8.4, 0.8 Hz, 1H), 8.17 (t, J = 8.0 Hz, 1H), 8.08 (s, 1H), 7.98 (dd, J = 7.6, 0.9 Hz, 1H), 5.89 (hept, J = 6.7 Hz, 1H), 4.48 (s, 2H), 4.11 (p, J = 8.2 Hz, 1H), 3.44 (t, J = 5.7 Hz, 2H), 2.96 (t, J = 5.8 Hz, 2H), 2.72 (s, 3H), 1.84-1.70 (m, 2H), 1.72-1.40 (comp, 12H) |

-continued

| Example | Structure | LC-MS [M + H]+ unless otherwise noted | H-NMR |
|---|---|---|---|
| 113 | 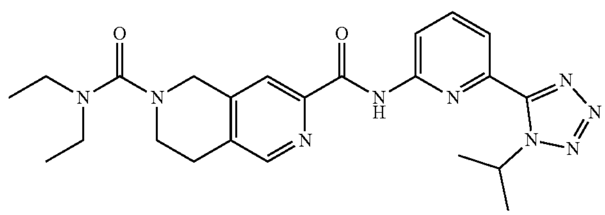 [SMILES: CCN(CC)C(=O)N1CCc2cnc(C(=O)Nc3cccc(-c4nnnn4C(C)C)n3)cc2C1] | 464.24 | ¹H NMR (500 MHz, DMSO-d₆) δ 10.76 (s, 1H), 8.57 (s, 1H), 8.41 (d, J = 8.3 Hz, 1H), 8.17 (t, J = 8.0 Hz, 1H), 8.08 (s, 1H), 7.98 (dd, J = 7.6, 0.9 Hz, 1H), 5.89 (hept, J = 6.6 Hz, 1H), 4.45 (s, 2H), 3.43 (t, J = 5.7 Hz, 2H), 3.19 (q, J = 7.0 Hz, 4H), 2.96 (t, J = 5.8 Hz, 2H), 1.60 (d, J = 6.6 Hz, 6H), 1.08 (t, J = 7.0 Hz, 6H) |
| 114 | 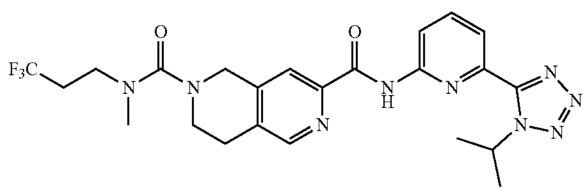 [SMILES: CC(C)n1nnnc1-c1cccc(NC(=O)c2cc3c(cn2)CCN(C(=O)N(C)CCC(F)(F)F)C3)n1] | 518.22 | ¹H NMR (500 MHz, DMSO-d₆) δ 10.77 (s, 1H), 8.57 (s, 1H), 8.41 (d, J = 8.3 Hz, 1H), 8.17 (t, J = 8.0 Hz, 1H), 8.07 (s, 1H), 7.99 (d, J = 7.6 Hz, 1H), 5.89 (hept, J = 6.6 Hz, 1H), 4.49 (s, 2H), 3.45 (t, J = 5.7 Hz, 2H), 3.39 (t, J = 7.2 Hz, 2H), 2.96 (t, J = 5.8 Hz, 2H), 2.91 (s, 3H), 2.63-2.52 (m, 2H), 1.60 (d, J = 6.6 Hz, 6H) |
| 115 | 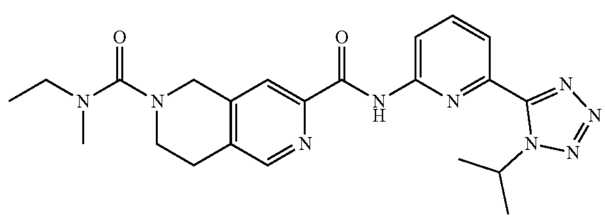 [SMILES: CCN(C)C(=O)N1CCc2cnc(C(=O)Nc3cccc(-c4nnnn4C(C)C)n3)cc2C1] | 450.23 | ¹H NMR (500 MHz, DMSO-d₆) δ 10.76 (s, 1H), 8.57 (s, 1H), 8.41 (d, J = 8.8 Hz, 1H), 8.17 (t, J = 8.0 Hz, 1H), 8.07 (s, 1H), 7.98 (d, J = 1.6 Hz, 1H), 5.89 (hept, J = 6.6 Hz, 1H), 4.47 (s, 2H), 3.44 (t, J = 5.7 Hz, 2H), 3.18 (q, J = 7.1 Hz, 2H), 2.96 (t, J = 5.8 Hz, 2H), 2.81 (s, 3H), 1.60 (d, J = 6.6 Hz, 6H), 1.09 (t, J = 7.1 Hz, 3H) |
| 116 | 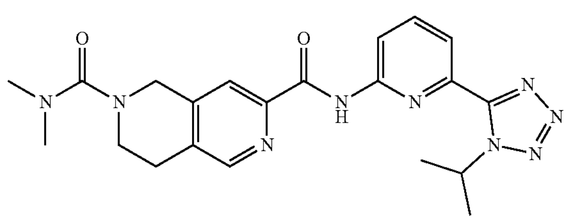 [SMILES: CC(C)n1nnnc1-c1cccc(NC(=O)c2cc3c(cn2)CCN(C(=O)N(C)C)C3)n1] | 436.21 | ¹H NMR (500 MHz, DMSO-d₆) δ 10.76 (s, 1H), 8.57 (s, 1H), 8.41 (d, J = 8.3 Hz, 1H), 8.17 (t, J = 8.0 Hz, 1H), 8.07 (s, 1H), 7.98 (d, J = 7.6 Hz, 1H), 5.89 (hept, J = 6.7 Hz, 1H), 4.49 (s, 2H), 3.45 (t, J = 5.7 Hz, 2H), 2.96 (t, J = 5.8 Hz, 2H), 2.81 (s, 6H), 1.60 (d, J = 6.6 Hz, 6H) |
| 117 | 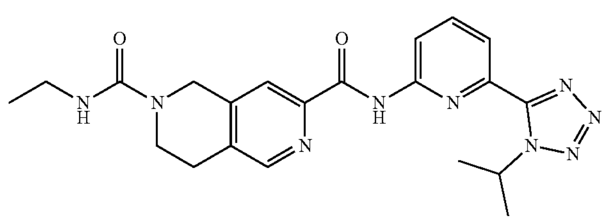 [SMILES: CCNC(=O)N1CCc2cnc(C(=O)Nc3cccc(-c4nnnn4C(C)C)n3)cc2C1] | 436.21 | ¹H NMR (400 MHz, DMSO-d₆) δ 10.77 (s, 1H), 8.58 (d, J = 0.7 Hz, 1H), 8.41 (dd, J = 8.4, 0.9 Hz, 1H), 8.20-8.14 (m, 1H), 8.01 (s, 1H), 7.99 (dd, J = 7.6, 0.9 Hz, 1H), 6.67 (t, J = 5.3 Hz, 1H), 5.89 (hept, J = 6.7 Hz, 1H), 5.76 (s, 1H), 4.66 (s, 2H), 3.63 (t, J = 5.8 Hz, 2H), 3.18-3.03 (m, 2H), 2.89 (t, J = 5.7 Hz, 2H), 1.60 (d, J = 6.6 Hz, 6H), 1.03 (t, J = 7.1 Hz, 3H) |
| 118 | 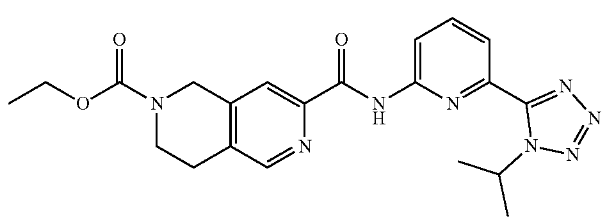 | 437.19 | ¹H NMR (500 MHz, DMSO-d₆) δ 10.77 (s, 1H), 8.59 (s, 1H), 8.41 (d, J = 8.3 Hz, 1H), 8.17 (t, J = 8.0 Hz, 1H), 8.10 (s, 1H), 7.99 (dd, J = 7.6, 0.8 Hz, 1H), 5.89 (hept, J = 6.6 Hz, 1H), 4.73 (s, 2H), 4.11 (q, J = 7.1 Hz, 2H), 3.68 (t, J = 5.9 Hz, 2H), 2.93 (t, J = 5.8 Hz, 2H), 1.60 (d, J = 6.7 Hz, 6H), 1.23 (t, J = 7.0 Hz, 3H) |

| Example | Structure | LC-MS [M + H]+ unless otherwise noted | H-NMR |
| --- | --- | --- | --- |
| 119 | 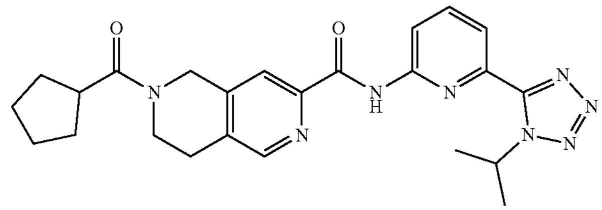 | 461.23 | ¹H NMR (500 MHz, DMSO-d₆) δ 10.77 (d, J = 9.1 Hz, 1H), 8.59 (d, J = 5.5 Hz, 1H), 8.41 (dd, J = 8.4, 4.4 Hz, 1H), 8.17 (t, J = 8.0 Hz, 1H), 8.12 (d, J = 18.1 Hz, 1H), 8.03-7.96 (m, 1H), 5.96-5.84 (m, 1H), 4.93 (s, 1H), 4.79 (s, 1H), 3.80 (dt, J = 25.0, 5.8 Hz, 2H), 3.18-3.04 (m, 1H), 2.99 (t, J = 5.8 Hz, 1H), 2.94-2.84 (m, 1H), 1.88-1.78 (m, 2H), 1.75-1.48 (comp, 12H) |
| 120 | 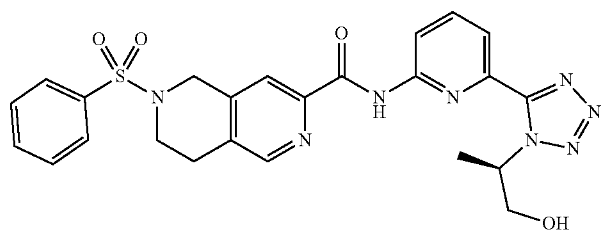 [SMILES: C[C@H](CO)n1nnnc1-c1cccc(NC(=O)c2cc3c(cn2)CCN(S(=O)(=O)c2ccccc2)C3)n1] | 521.20 | ¹H NMR (400 MHz, Chloroform-d) δ 10.48 (s, 1H), 8.44 (s, 1H), 8.35 (d, J = 8.2 Hz, 1H), 8.12-8.02 (comp, 2H), 7.97 (t, J = 7.8 Hz, 1H), 7.87 (d, J = 7.2 Hz, 2H), 7.69-7.54 (comp, 3H), 5.90-5.80 (m, 1H), 4.39 (s, 2H), 4.13 (s, 2H), 3.47 (t, J = 6.4 Hz, 2H), 3.07 (d, J = 6.2 Hz, 2H), 2.80 (br s, 1H), 1.67 (d, J = 6.6 Hz, 3H) |
| 121 | 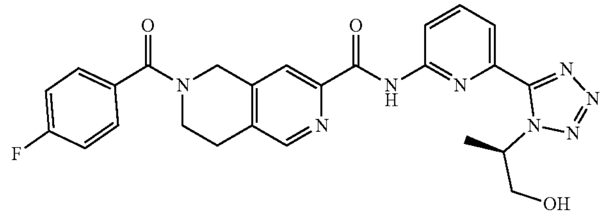 [SMILES: C[C@H](CO)n1nnnc1-c1cccc(NC(=O)c2cc3c(cn2)CCN(C(=O)c2ccc(F)cc2)C3)n1] | 503.30 | ¹H NMR (400 MHz, Chloroform-d) δ 10.47 (s, 1H), 8.49 (s, 1H), 8.39 (d, J = 8.1 Hz, 0H), 8.12-8.08 (comp, 2H), 7.99 (t, J = 8.0 Hz, 1H), 7.50 (t, J = 6.9 Hz, 2H), 7.16 (t, J = 8.4 Hz, 2H), 5.90-5.80 (m, 1H), 5.02-4.76 (m, 2H), 4.20-4.12 (m, 2jH), 4.03-3.75 (m, 2H), 3.19-2.98 (comp, 3H), 1.70 (d, J = 6.8 Hz, 3H) |
| 122 | 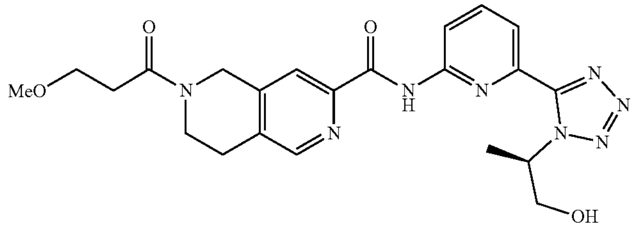 [SMILES: COCCC(=O)N1CCc2cnc(C(=O)Nc3cccc(-c4nnnn4[C@H](C)CO)n3)cc2C1] | 467.25 | ¹H NMR (400 MHz, Chloroform-d) δ 10.49 (s, 1H), 8.47 (d, J = 9.9 Hz, 1H), 8.40 (t, J = 9.7 Hz, 1H), 8.12-8.08 (comp, 2H), 7.99 (t, J = 7.9 Hz, 1H), 5.90-5.82 (m, 1H), 4.89 (s, 1H), 4.80 (s, 1H), 4.16 (d, J = 6.0 Hz, 2H), 3.98-3.90 (m, 1H), 3.86-3.78 (m, 1H), 3.75 (q, J = 5.8, 5.4 Hz, 2H), 3.38 (s, 2H), 3.32 (s, 1H), 3.06-2.98 (m, 2H), 3.00-2.93 (m, 1H), 2.72 (q, J = 5.6, 4.9 Hz, 2H), 1.70 (d, J = 6.8 Hz, 3H) |
| 123 | 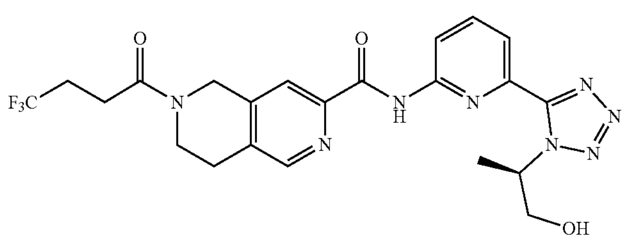 | 505.30 | ¹H NMR (400 MHz, Chloroform-d) δ 10.46 (s, 1H), 8.49 (d, J = 9.7 Hz, 1H), 8.40 (t, J = 8.4 Hz, 1H), 8.14-8.06 (comp, 2H), 7.99 (t, J = 8.0 Hz, 1H), 5.85 (dq, J = 12.9, 6.4 Hz, 1H), 4.89 (s, 1H), 4.76 (s, 1H), 4.22-4.10 (m, 2H), 3.95 (t, J = 5.8 Hz, 1H), 3.80 (t, J = 5.8 Hz, 1H), 3.05 (t, J = 5.8 Hz, 1H), 2.98 (t, J = 5.8 Hz, 1H), 2.75-2.64 (m, 2H), 2.65-2.48 (m, 2H), 1.70 (d, J = 6.8 Hz, 3H) |
| 124 | 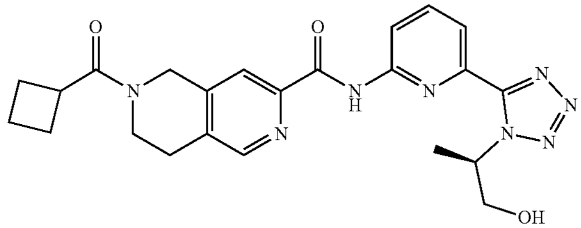 [SMILES: C[C@H](CO)n1nnnc1-c1cccc(NC(=O)c2cc3c(cn2)CCN(C(=O)C2CCC2)C3)n1] | 463.25 | ¹H NMR (400 MHz, Chloroform-d) δ 10.47 (s, 1H), 8.45 (d, J = 13.7 Hz, 1H), 8.38 (dd, J = 17.3, 8.3 Hz, 1H), 8.11-8.06 (comp, 2H), 7.99 (t, J = 8.0 Hz, 1H), 5.90-5.82 (m, 1H), 4.86 (s, 1H), 4.62 (s, 1H), 4.21-4.12 (m, 2H), 3.92 (t, J = 5.9 Hz, 1H), 3.67 (t, J =5.7 Hz, 1H), 3.37 (p, J = 8.3 Hz, 1H), 3.20 (br s, 1H), 2.96 (s, 2H), 2.46-2.34 (m 2H), 2.25-2.18 (m, 2H), 2.08-1.99 (m, 1H), 1.94-1.88 (m, 1H), 1.70 (d, J = 6.8 Hz, 3H) |

-continued

| Example | Structure | LC-MS [M + H]+ unless otherwise noted | H-NMR |
|---|---|---|---|
| 125 | 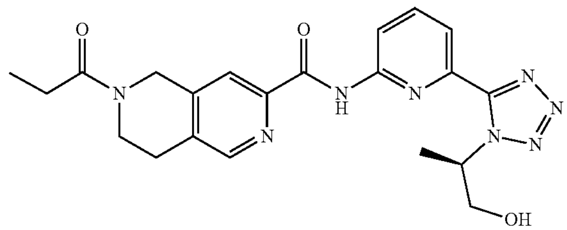 [SMILES: CCC(=O)N1CCc2cnc(C(=O)Nc3cccc(-c4nnnn4[C@H](C)CO)n3)cc2C1] | 437.20 | ¹H NMR (400 MHz, Chloroform-d) δ 10.48 (s, 1H), 8.47 (d, J = 11.4 Hz, 1H), 8.43-8.34 (m, 1H), 8.14-8.07 (comp, 2H), 7.99 (t, J = 8.0 Hz, 1H), 5.93-5.77 (m, 2H), 4.88 (s, 1H), 4.75 (s, 1H), 4.16 (d, J = 5.4 Hz, 2H), 3.93 (t, J = 5.6 Hz, 2H), 3.78 (t, J = 5.9 Hz, 1H), 3.13 (br s, 1H), 3.05-2.93 (m, 2H), 2.48 (q, J = 6.9 Hz, 2H), 1.70 (d, J = 6.8 Hz, 3H), 1.24-1.18 (m, 3H) |
| 126 | 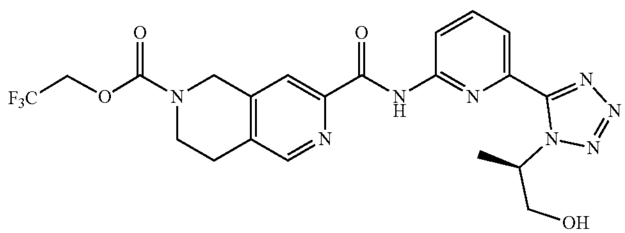 [SMILES: C[C@H](CO)n1nnnc1-c1cccc(NC(=O)c2cc3c(cn2)CCN(C(=O)OCC(F)(F)F)C3)n1] | 507.30 | ¹H NMR (400 MHz, Chloroform-d) δ 10.50 (s, 1H), 8.48 (s, 1H), 8.42-8.37 (m, 1H), 8.10 (comp, 2H), 7.99 (t, J = 8.0 Hz, 1H), 5.92-5.83 (m, 1H), 4.80 (s, 2H), 4.57 (q, J = 8.4 Hz, 2H), 4.16 (d, J = 5.8 Hz, 2H), 3.84 (t, J = 5.8 Hz, 2H), 3.01 (br s, 2H), 1.70 (d, J = 6.8 Hz, 3H) |
| 127 | 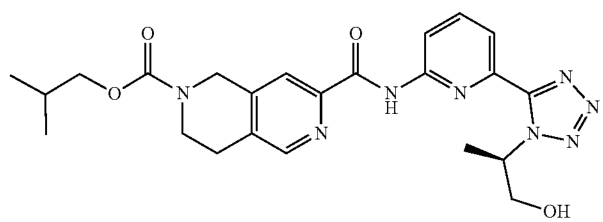 [SMILES: CC(C)COC(=O)N1CCc2cnc(C(=O)Nc3cccc(-c4nnnn4[C@H](C)CO)n3)cc2C1] | 481.35 | ¹H NMR (400 MHz, Chloroform-d) δ 10.48 (s, 1H), 8.46 (s, 1H), 8.38 (d, J = 8.2 Hz, 1H), 8.11-8.07 (comp, 2H), 7.98 (t, J = 8.0 Hz, 1H), 5.87 (h, J = 6.9 Hz, 1H), 4.76 (s, 2H), 4.16 (d, J = 5.3 Hz, 2H), 3.94 (d, J = 6.6 Hz, 2H), 3.80 (t, J = 5.8 Hz, 2H), 3.18 (s, 1H), 2.97 (t, J = 5.9 Hz, 2H), 1.99 (dp, J = 13.3, 6.6 Hz, 1H), 1.70 (d, J = 6.8 Hz, 3H), 0.97 (d, J = 6.7 Hz, 6H) |
| 128 | 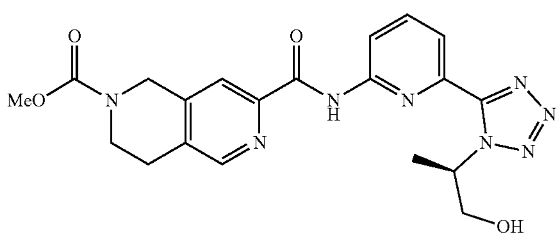 [SMILES: COC(=O)N1CCc2cnc(C(=O)Nc3cccc(-c4nnnn4[C@H](C)CO)n3)cc2C1] | 439.20 | ¹H NMR (400 MHz, Chloroform-d) δ 10.50 (s, 1H), 8.48 (s, 1H), 8.41 (d, J = 8.2 Hz, 1H), 8.13-8.10 (m, 2H), 8.03 (t, J = 8.0 Hz, 1H), 5.89 (m, 1H), 4.22-4.18 (m, 2H), 3.89-3.81 (m, 5H), 3.17 (s, 1H), 2.99 (t, J = 5.8 Hz, 2H), 2.24 (s, 1H), 1.72 (d, J = 6.8 Hz, 3H) |
| 129 | 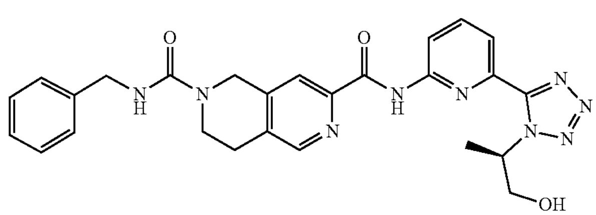 [SMILES: C[C@H](CO)n1nnnc1-c1cccc(NC(=O)c2cc3c(cn2)CCN(C(=O)NCc2ccccc2)C3)n1] | 514.20 | ¹H NMR (400 MHz, Chloroform-d) δ 10.52 (s, 1H), 8.48 (s, 1H), 8.39 (d, J = 8.3 Hz, 1H), 8.11-8.01 (m, 2H), 7.99 (t, J = 8.0 Hz, 1H), 7.42-7.28 (m, 5H), 5.89 (m, 1H), 4.94 (s, 1H), 4.72 (s, 2H), 4.51 (d, J = 3.8 Hz, 2H), 4.42 (s, 1H), 4.21-4.11 (m, 2H), 3.75 (t, J = 5.7 Hz, 2H), 3.01 (t, J = 5.7 Hz, 2H), 1.72 (d, J = 6.8 Hz, 3H) |
| 130 | 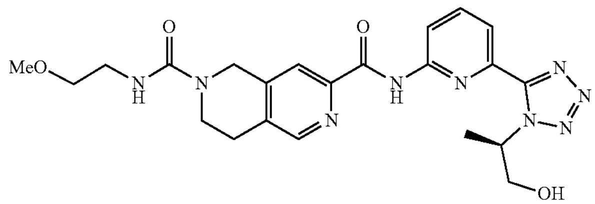 [SMILES: COCCNC(=O)N1CCc2cnc(C(=O)Nc3cccc(-c4nnnn4[C@H](C)CO)n3)cc2C1] | 482.15 | ¹H NMR (400 MHz, Chloroform-d) δ 10.52 (s, 1H), 8.49 (s, 1H), 8.41 (dd, J = 8.3, 1.0 Hz, 1H), 8.16-8.09 (m, 2H), 8.01 (t, J = 8.0 Hz, 1H), 5.89 (m, 1H), 4.99 (s, 1H), 4.71 (s, 2H), 4.17 (t, J = 5.8 Hz, 2H), 3.74 (t, J = 5.8 Hz, 2H), 3.55-3.51 (m, 4H), 3.41 (s, 3H), 3.01 (t, J = 5.8 Hz, 2H), 1.73 (d, J = 6.8 Hz, 3H) |

-continued

| Example | Structure | LC-MS [M + H]+ unless otherwise noted | H-NMR |
|---|---|---|---|
| 131 | 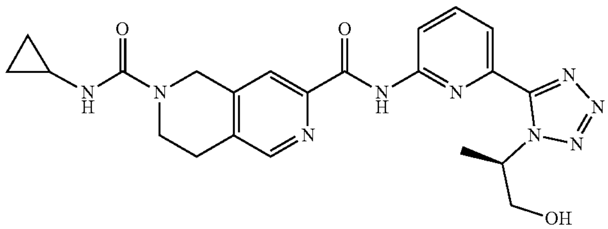 [SMILES: C[C@H](CO)n1nnnc1-c1cccc(NC(=O)c2cc3c(cn2)CCN(C(=O)NC2CC2)C3)n1] | 464.20 | ¹H NMR (400 MHz, Chloroform-d) δ 10.54 (s, 1H), 8.47 (s, 1H), 8.39 (dd, J = 8.3, 1.0 Hz, 1H), 8.12-8.02 (m, 2H), 8.00 (t, J = 8.0 Hz, 1H), 5.91 (m, 1H), 4.91 (s, 1H), 4.68 (s, 2H), 4.24-4.13 (m, 2H), 3.71 (t, J = 5.8 Hz, 2H), 3.00 (t, J = 5.8 Hz, 2H), 2.73 (m, 1H), 1.72 (d, J = 6.8 Hz, 3H), 0.80 (m, 2H, 0.55 (m, 2H) |
| 132 | 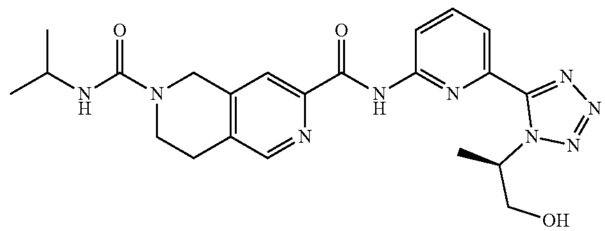 [SMILES: CC(C)NC(=O)N1CCc2cnc(C(=O)Nc3cccc(-c4nnnn4[C@H](C)CO)n3)cc2C1] | 466.25 | ¹H NMR (400 MHz, Chloroform-d) δ 10.51 (s, 1H), 8.49 (s, 1H), 8.41 (d, J = 8.3 Hz, 1H), 8.16-8.09 (m, 2H), 8.01 (t, J = 8.0 Hz, 1H), 5.89 (m, 1H), 4.68 (s, 2H), 4.34 (d, J = 7.4 Hz, 1H), 4.21-4.15 (m, 2H), 4.07 (m, 1H), 3.72 (t, J = 5.7 Hz, 2H), 3.15 (s, 1H), 3.01 (t, J = 5.6 Hz, 2H), 1.73 (d, J = 6.8 Hz, 3H), 1.23 (d, J = 6.5 Hz, 6H) |
| 133 | 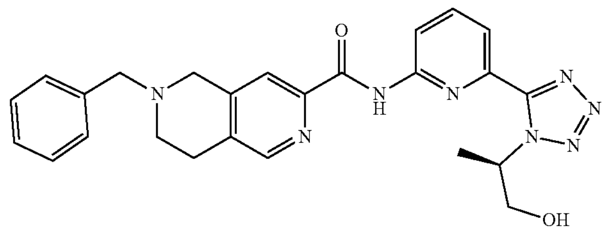 [SMILES: C[C@H](CO)n1nnnc1-c1cccc(NC(=O)c2cc3c(cn2)CCN(Cc2ccccc2)C3)n1] | 471.20 | ¹H NMR (400 MHz, Chloroform-d) δ 10.50 (s, 1H), 8.41 (s, 1H), 8.36 (d, J = 8.3 Hz, 1H), 8.13-8.06 (m, 1H), 8.05-7.94 (comp, 2H), 7.48-7.28 (comp, 5H), 5.87 (h, J = 6.5 Hz, 1H), 4.15 (d, J = 5.9 Hz, 2H), 3.80-3.70 (comp, 4H), 3.19 (br s, 1H), 3.01 (br s, 2H), 2.85 (br s, 2H), 1.70 (d, J = 6.8 Hz, 3H) |
| 134 | 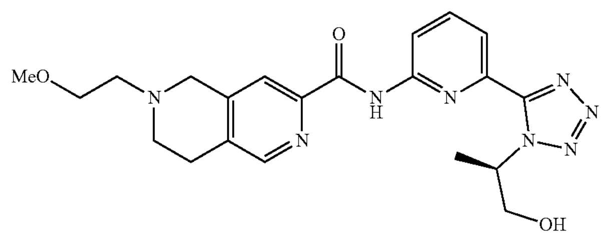 [SMILES: COCCN1CCc2cnc(C(=O)Nc3cccc(-c4nnnn4[C@H](C)CO)n3)cc2C1] | 439.25 | ¹H NMR (400 MHz, Chloroform-d) δ 10.51 (s, 1H), 8.40 (s, 1H), 8.37 (dd, J = 8.3, 0.9 Hz, 1H), 8.09 (dd, J = 7.6, 0.9 Hz, 1H), 8.01-7.95 (comp, 2H), 5.87 (h, J = 6.6 Hz, 1H), 4.15 (d, J = 5.9 Hz, 2H), 3.83 (br s, 2H), 3.64 (br s, 2H), 3.40 (s, 3H), 3.18 (br s, 1H), 3.03 (br s, 2H), 2.90 (br s, 2H), 2.83 (br s, 2H), 1.70 (d, J = 6.8 Hz, 3H) |
| 135 | 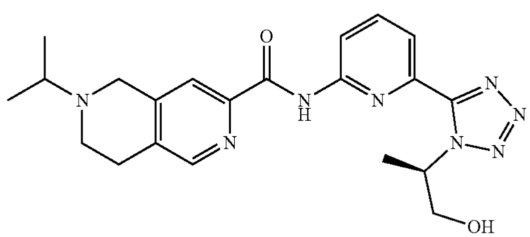 [SMILES: CC(C)N1CCc2cnc(C(=O)Nc3cccc(-c4nnnn4[C@H](C)CO)n3)cc2C1] | 423.25 | ¹H NMR (400 MHz, Chloroform-d) δ 10.51 (s, 1H), 8.40 (s, 1H), 8.37 (dd, J = 8.3, 0.9 Hz, 1H), 8.08 (dd, J = 7.6, 0.9 Hz, 1H), 8.01 (s, 1H), 7.97 (t, J = 8.0 Hz, 1H), 5.87 (h, J = 6.6 Hz, 1H), 4.15 (d, J = 6.0 Hz, 3H), 3.87 (br s, 2H), 3.10-2.98 (comp, 4H), 2.90 (br s, 2H), 1.70 (d, J = 6.8 Hz, 3H), 1.20 (d, J = 6.5 Hz, 6H) |
| 136 | 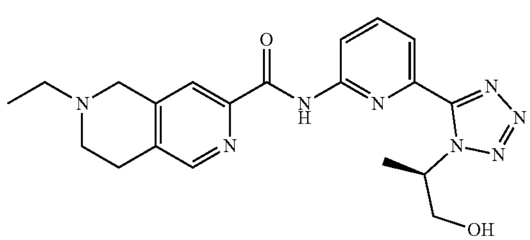 [SMILES: CCN1CCc2cnc(C(=O)Nc3cccc(-c4nnnn4[C@H](C)CO)n3)cc2C1] | 409.20 | ¹H NMR (400 MHz, Chloroform-d) δ 10.52 (s, 1H), 8.42 (s, 1H), 8.37 (d, J = 8.3 Hz, 1H), 8.09 (d, J = 7.5 Hz, 1H), 8.01 (s, 1H), 7.98 (t, J = 8.0 Hz, 1H), 5.87 (h, J = 6.6 Hz, 1H), 4.15 (d, J = 6.0 Hz, 2H), 3.77 (s, 2H), 3.16 (br s, 1H), 3.04 (br s, 2H), 2.86 (br s, 2H), 2.69 (br s, 2H), 1.70 (d, J = 6.8 Hz, 3H), 1.24 (t, J = 6.9 Hz, 3H) |

| Example | Structure | LC-MS [M + H]+ unless otherwise noted | H-NMR |
|---|---|---|---|
| 137 | 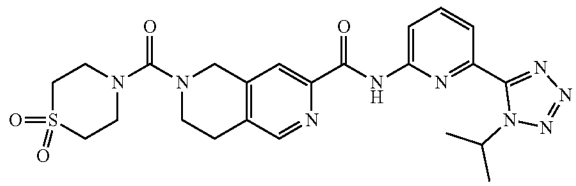 [SMILES: CC(C)n1nnnc1-c1cccc(NC(=O)c2cc3c(cn2)CCN(C(=O)N2CCS(=O)(=O)CC2)C3)n1] | 526.20 | ¹H NMR (500 MHz, DMSO-d₆) δ 10.77 (s, 1H), 8.58 (s, 1H), 8.41 (dd, J = 8.4, 0.8 Hz, 1H), 8.17 (t, J = 8.0 Hz, 1H), 8.12 (s, 1H), 7.99 (dd, J = 7.6, 0.9 Hz, 1H), 5.90 (hept, J = 6.6 Hz, 1H), 4.63 (s, 2H), 3.52 (t, J = 5.7 Hz, 2H), 3.24 (t, J = 5.3 Hz, 4H), 3.20-3.14 (m, 4H), 2.97 (t, J = 5.7 Hz, 2H), 1.60 (d, J = 6.6 Hz, 6H) |
| 138 | 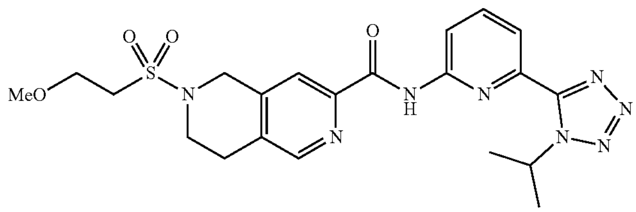 [SMILES: COCCS(=O)(=O)N1CCc2cnc(C(=O)Nc3cccc(-c4nnnn4C(C)C)n3)cc2C1] | 487.18 | ¹H NMR (500 MHz, DMSO-d₆) δ 10.78 (s, 1H), 8.61 (s, 1H), 8.41 (dd, 8.4, 0.9 Hz, 1H), 8.17 (t, J = 8.0 Hz, 1H), 8.09 (s, 1H), 7.99 (dd, J = 7.6, 0.9 Hz, 1H), 5.90 (hept, J = 6.6 Hz, 1H), 4.59 (s, 2H), 3.68 (t, J = 5.9 Hz, 2H), 3.56 (t, J = 5.8 Hz, 2H), 3.46 (t, J = 5.9 Hz, 2H), 3.21 (s, 3H), 3.02 (t, J = 5.9 Hz, 2H), 1.60 (d, J = 6.6 Hz, 6H) |
| 139 | 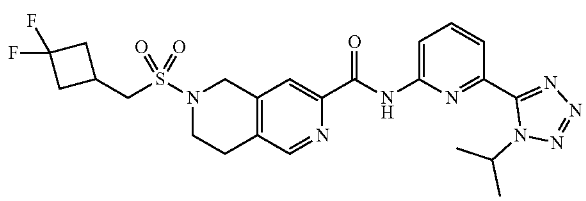 [SMILES: CC(C)n1nnnc1-c1cccc(NC(=O)c2cc3c(cn2)CCN(S(=O)(=O)CC2CC(F)(F)C2)C3)n1] | 533.19 | ¹H NMR (500 MHz, DMSO-d₆) δ 10.78 (s, 1H), 8.62 (s, 1H), 8.41 (d, J = 8.3 Hz, 1H), 8.17 (t, J = 8.0 Hz, 1H), 8.10 (s, 1H), 7.99 (d, J = 7.7 Hz, 1H), 5.90 (hept, J = 6.6 Hz, 1H), 4.62 (s, 2H), 3.58 (t, J = 5.8 Hz, 2H), 3.45 (d, J = 6.2 Hz, 2H), 3.03 (t, J = 5.9 Hz, 2H), 2.78-2.72 (m, 2H), 2.57-2.42 (comp, 3 H) 1.60 (d, J = 6.6 Hz, 6H) |
| 140 | 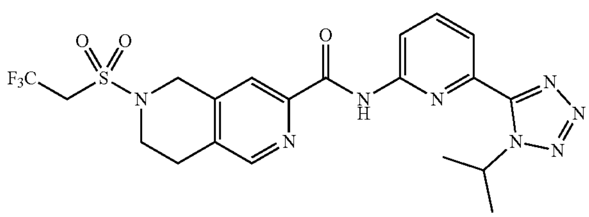 [SMILES: CC(C)n1nnnc1-c1cccc(NC(=O)c2cc3c(cn2)CCN(S(=O)(=O)CC(F)(F)F)C3)n1] | 511.14 | ¹H NMR (500 MHz, DMSO-d₆) δ 10.78 (s, 1H), 8.63 (s, 1H), 8.41 (dd, J = 8.4, 0.9 Hz, 1H), 8.17 (t, J = 8.0 Hz, 1H), 8.11 (s, 1H), 7.99 (dd, J = 7.6, 0.9 Hz, 1H), 5.90 (hept, J = 6.6 Hz, 1H), 4.70-4.60 (comp, 4H), 3.64 (t, J = 5.9 Hz, 2H), 3.06 (t, J = 5.9 Hz, 2H), 1.60 (d, J = 6.6 Hz, 6H) |
| 141 | 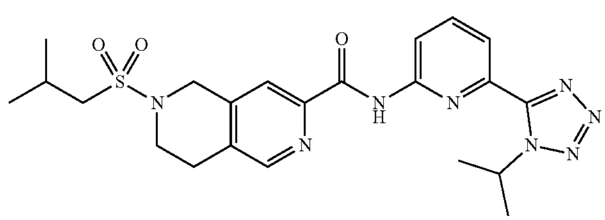 [SMILES: CC(C)CS(=O)(=O)N1CCc2cnc(C(=O)Nc3cccc(-c4nnnn4C(C)C)n3)cc2C1] | 485.20 | ¹H NMR (500 MHz, DMSO-d₆) δ 10.77 (s, 1H), 8.62 (s, 1H), 8.41 (dd, J = 8.4, 0.9 Hz, 1H), 8.17 (t, J = 8.0 Hz, 1H), 8.09 (s, 1H), 7.99 (dd, J = 7.5, 0.9 Hz, 1H), 5.89 (hept, J = 6.6 Hz, 1H), 3.56 (t, J = 5.9 Hz, 2H), 3.03 (dd, J = 8.6, 6.0 Hz, 4H), 2.14 (hept, J = 6.7 Hz, 1H), 1.60 (d, J = 6.6 Hz, 6H), 1.05 (d, J = 6.7 Hz, 6H) |
| 142 | 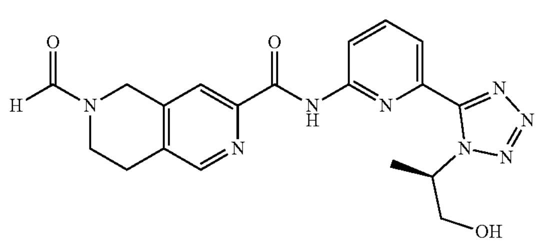 [SMILES: C[C@H](CO)n1nnnc1-c1cccc(NC(=O)c2cc3c(cn2)CCN(C=O)C3)n1] | 409.18 | ¹H NMR (400 MHz, DMSO-d₆) δ 10.78 (s, 0.3H), 10.77 (s, 0.7H), 8.60 (s, 1H), 8.44-8.39 (m, 1H), 8.26-8.05 (comp, 3H), 7.99-7.95 (m, 1H), 5.87-5.79 (m, 1H), 4.98 (t, J = 5.7 Hz, 1H), 4.79 (s, 0.7H), 4.74 (s, 1.3H), 3.84-3.69 (comp, 4H), 2.99 (t, J = 5.8 Hz, 1.3H), 2.91 (t, J = 6.1 Hz, 0.7H), 1.59 (d, J = 6.8 Hz, 3H) |

| Example | Structure | LC-MS [M + H]+ unless otherwise noted | H-NMR |
|---|---|---|---|
| 143 | 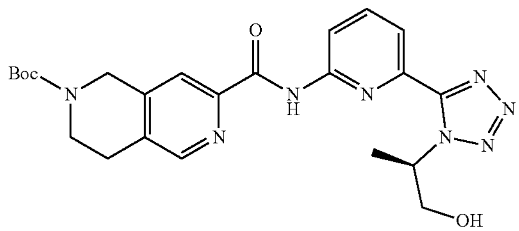 [SMILES: C[C@H](CO)n1nnnc1-c1cccc(NC(=O)c2cc3c(cn2)CCN(C(=O)OC(C)(C)C)C3)n1] | 481.23 | ¹H NMR (400 MHz, DMSO-d$_6$) δ 10.76 (s, 1H), 8.59 (s, 1H), 8.41 (dd, J = 8.4, 0.9 Hz, 1H), 8.16 (t, J = 8.0 Hz, 1H), 8.09 (s, 1H), 7.97 (dd, J = 7.6, 0.9 Hz, 1H), 5.90-5.77 (m, 1H), 4.99 (dd, J = 6.2, 5.3 Hz, 1H), 4.69 (s, 2H), 3.85-3.71 (m, 2H), 3.64 (t, J = 5.8 Hz, 2H), 2.91 (t, J = 5.8 Hz, 2H), 1.59 (d, J = 6.8 Hz, 3H), 1.44 (s, 9H) |
| 144 | 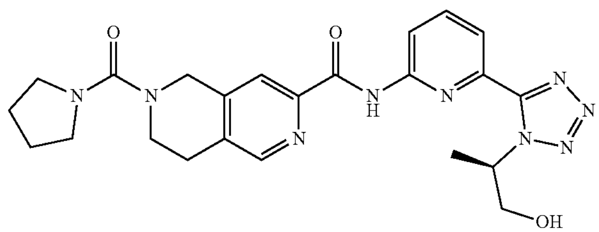 | 478.23 | ¹H NMR (400 MHz, DMSO-d$_6$) δ 10.76 (s, 1H), 8.58 (s, 1H), 8.42 (dd, J = 8.4, 0.9 Hz, 1H), 8.16 (t, J = 8.0 Hz, 1H), 8.08 (s, 1H), 7.97 (dd, J = 7.6, 0.9 Hz, 1H), 5.90-5.78 (m, 1H), 4.99 (t, J = 5.7 Hz, 1H), 4.54 (s, 2H), 3.83-3.73 (m, 2H), 3.50 (t, J = 5.7 Hz, 2H), 3.37-3.30 (m, 4H), 2.95 (t, J = 5.7 Hz, 2H), 1.83-1.74 (m, 4H), 1.59 (d, J = 6.8 Hz, 3H) |
| 145 | 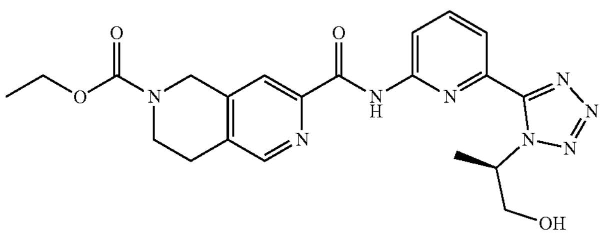 [SMILES: CCOC(=O)N1CCc2cnc(C(=O)Nc3cccc(-c4nnnn4[C@H](C)CO)n3)cc2C1] | 453.20 | ¹H NMR (400 MHz, DMSO-d$_6$) δ 10.77 (s, 1H), 8.60 (s, 1H), 8.42 (dd, J = 8.4, 0.9 Hz, 1H), 8.16 (t, J = 8.0 Hz, 1H), 8.11 (s, 1H), 7.97 (dd, J = 7.6, 0.9 Hz, 1H), 5.89-5.77 (m, 1H), 4.98 (dd, J = 6.2, 5.3 Hz, 1H), 4.74 (s, 2H), 4.11 (q, J = 7.1 Hz, 2H), 3.85-3.73 (m, 2H), 3.68 (t, J = 5.8 Hz, 2H), 2.94 (t, J = 5.8 Hz, 2H), 1.59 (d, J = 6.8 Hz, 3H), 1.23 (t, J = 7.1 Hz, 3H) |
| 146 | 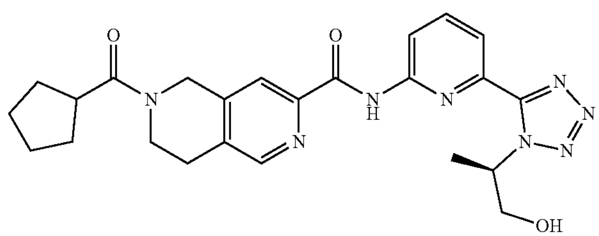 [SMILES: C[C@H](CO)n1nnnc1-c1cccc(NC(=O)c2cc3c(cn2)CCN(C(=O)C2CCCC2)C3)n1] | 477.24 | ¹H NMR (400 MHz, DMSO-d$_6$) δ 10.77 (d, J = 7.0 Hz, 1H), 8.60 (d, J = 4.4 Hz, 1H), 8.42 (d, J = 8.4 Hz, 1H), 8.24-8.07 (m, 2H), 7.97 (d, J = 7.6 Hz, 1H), 5.83 (p, J = 6.4 Hz, 1H), 4.99 (dd, J = 6.2, 5.2 Hz, 1H), 4.93 (s, 1H), 4.79 (s, 1H), 3.88-3.71 (comp, 4H), 3.19-3.05 (m, 1H), 3.00-2.98 (m, 1H), 2.90-2.87 (m, 1H), 1.86-1.77 (comp 2H), 1.76-1.46 (comp, 9H) |
| 147 | 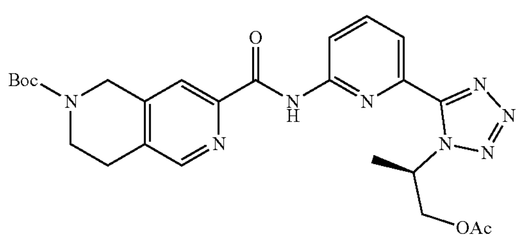 | 523.24 | ¹H NMR (400 MHz, DMSO-d$_6$) δ 10.77 (s, 1H), 8.59 (s, 1H), 8.44 (dd, J = 8.4, 0.9 Hz, 1H), 8.18 (t, J = 8.0 Hz, 1H), 8.09 (s, 1H), 8.01 (dd, J = 7.6, 0.9 Hz, 1H), 6.25-6.12 (m, 1H), 4.69 (s, 2H), 4.59 (dd, J = 11.7, 3.9 Hz, 1H), 4.31 (dd, J = 11.7, 8.4 Hz, 1H), 3.64 (t, J = 5.8 Hz, 2H), 2.92 (t, J = 5.8 Hz, 2H), 1.76 (s, 3H), 1.67 (d, J = 6.9 Hz, 3H), 1.44 (s, 9H) |
| 148 | 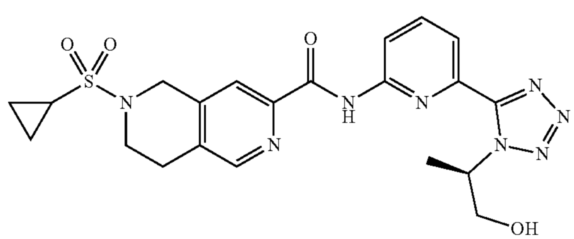 [SMILES: C[C@H](CO)n1nnnc1-c1cccc(NC(=O)c2cc3c(cn2)CCN(S(=O)(=O)C2CC2)C3)n1] | 485.20 | ¹H NMR (400 MHz, Chloroform-d) δ 10.46 (s, 1H), 8.49 (s, 1H), 8.39 (d, J = 8.3 Hz, 1H), 8.10 (d, J = 7.6 Hz, 1H), 8.07 (s, 1H), 7.99 (t, J = 8.0 Hz, 1H), 5.86 (h, J = 6.9 Hz, 1H), 4.63 (s, 2H), 4.21-4.11 (m, 2H), 3.71 (t, J = 5.8 Hz, 2H), 3.11 (t, J = 5.8 Hz, 2H), 2.35 (td, J = 8.0, 4.1 Hz, 1H), 1.70 (d, J = 6.8 Hz, 3H), 1.27 (dt, J = 7.0, 3.5 Hz, 2H), 1.11-0.99 (m, 2H) |

| Example | Structure | LC-MS [M + H]+ unless otherwise noted | H-NMR |
|---|---|---|---|
| 149 | 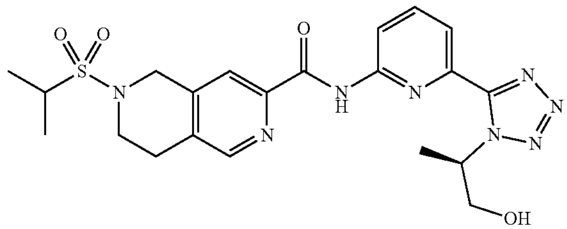 [SMILES: CC(C)S(=O)(=O)N1CCc2cnc(C(=O)Nc3cccc(-c4nnnn4[C@H](C)CO)n3)cc2C1] | 487.20 | ¹H NMR (400 MHz, Chloroform-d) δ 10.46 (s, 1H), 8.47 (s, 1H), 8.38 (dd, J = 8.3, 0.9 Hz, 1H), 8.10 (dd, J = 7.6, 0.9 Hz, 1H), 8.04 (s, 1H), 7.99 (t, J = 8.0 Hz, 1H), 5.86 (td, J = 7.0, 5.3 Hz, 1H), 4.66 (s, 2H), 4.16 (d, J = 5.3 Hz, 2H), 3.73 (t, J = 5.8 Hz, 2H), 3.30 (hept, J = 6.9 Hz, 1H), 3.13 (br s, 1H), 3.07 (t, J = 5.8 Hz, 2H), 1.70 (d, J = 6.8 Hz, 3H), 1.40 (d, J = 6.8 Hz, 6H) |
| 150 | 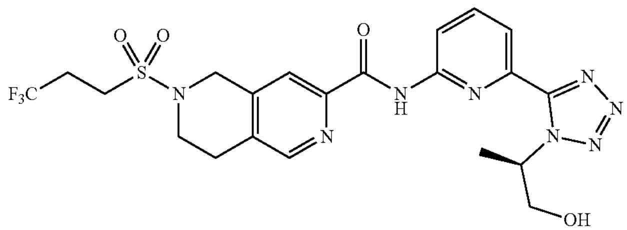 [SMILES: C[C@H](CO)n1nnnc1-c1cccc(NC(=O)c2cc3c(cn2)CCN(S(=O)(=O)CCC(F)(F)F)C3)n1] | 541.30 | ¹H NMR (400 MHz, Chloroform-d) δ 10.45 (s, 1H), 8.51 (s, 1H), 8.40 (d, J = 8.3 Hz, 1H), 8.11 (d, J = 7.6 Hz, 1H), 8.08 (s, 1H), 8.00 (t, J = 8.0 Hz, 1H), 5.89-5.81 (m, 1H), 4.64 (s, 2H), 4.16 (d, J = 5.1 Hz, 2H), 3.72 (t, J = 5.8 Hz, 2H), 3.28-3.20 (m, 2H), 3.11 (t, J = 5.9 Hz, 2H), 2.74-2.63 (m, 2H), 1.70 (d, J = 6.8 Hz, 3H) |
| 151 | 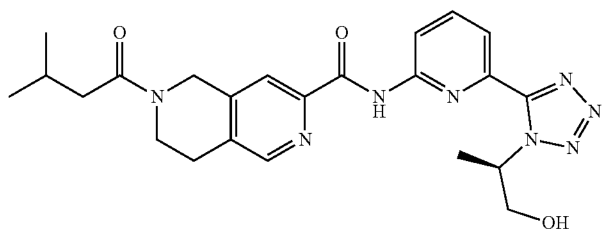 [SMILES: CC(C)CC(=O)N1CCc2cnc(C(=O)Nc3cccc(-c4nnnn4[C@H](C)CO)n3)cc2C1] | 465.30 | ¹H NMR (400 MHz, Chloroform-d) δ 10.48 (d, J = 11.4 Hz, 1H), 8.47 (d, J = 8.3 Hz, = 0.57H), 8.37 (d, J = 8.3 Hz, 0.43H), 8.14-8.06 (comp, 2H), 7.99 (t, J = 8.0 Hz, 1H), 5.92-5.80 (m, 1H), 4.88 (s, 1.19H), 4.76 (s, 0.81H), 4.21-4.10 (m, 2H), 3.97-3.88 (m, 1H), 3.80 (t, J = 5.2 Hz, 1H), 3.13 (br s, 1H), 3.02-2.95 (m, 2H), 2.35-2.32 (m, 2H), 2.27-2.11 (m, 1H), 1.70 (d, J = 6.8 Hz, 3H), 1.00 (t, J = 7.5 Hz, 6H) |
| 152 | 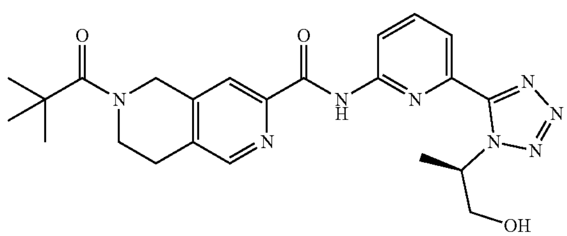 [SMILES: C[C@H](CO)n1nnnc1-c1cccc(NC(=O)c2cc3c(cn2)CCN(C(=O)C(C)(C)C)C3)n1] | 465.25 | ¹H NMR (400 MHz, Chloroform-d) δ 10.49 (s, 1H), 8.46 (s, 1H), 8.39 (d, J = 8.3 Hz, 1H), 8.12-8.08 (comp, 2H), 7.99 (t, J = 7.9 Hz, 1H), 5.86 (h, J = 6.9, 6.3 Hz, 1H), 4.89 (s, 2H), 4.16 (d, J = 5.9 Hz, 2H), 3.95 (t, J = 5.7 Hz, 2H), 3.00 (t, J = 5.8 Hz, 2H), 1.70 (d, J = 6.8 Hz, 3H), 1.35 (s, 9H) |
| 153 | 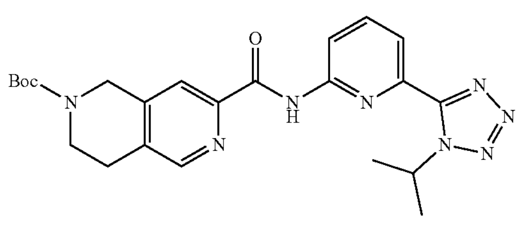 [SMILES: CC(C)n1nnnc1-c1cccc(NC(=O)c2cc3c(cn2)CCN(C(=O)OC(C)(C)C)C3)n1] | 465.23 | ¹H NMR (400 MHz, DMSO-d₆) δ 10.77 (s, 1H), 8.59 (s, 1H), 8.41 (dd, J = 8.4, 0.9 Hz, 1H), 8.17 (t, J = 8.0 Hz, 1H), 8.09 (s, 1H), 7.99 (dd, J = 7.6, 0.9 Hz, 1H), 5.90 (hept, J = 6.6 Hz, 1H), 4.69 (s, 2H), 3.63 (t, J = 5.7 Hz, 2H), 2.91 (t, J = 5.8 Hz, 2H), 1.60 (d, J = 6.6 Hz, 5H), 1.44 (s, 9H) |
| 154 | 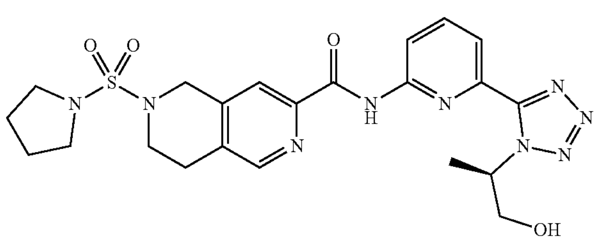 [SMILES: C[C@H](CO)n1nnnc1-c1cccc(NC(=O)c2cc3c(cn2)CCN(S(=O)(=O)N2CCCC2)C3)n1] | 514.25 | ¹H NMR (400 MHz, Chloroform-d) δ 10.48 (s, 1H), 8.47 (s, 1H), 8.39 (d, J = 8.2 Hz, 1H), 8.11 (d, J = 7.6 Hz, 1H), 8.06 (s, 1H), 8.00 (t, J = 7.9 Hz, 1H), 5.86 (h, J = 6.7 Hz, 1H), 4.53 (s, 2H), 4.16 (d, J = 5.8 Hz, 2H), 3.63 (t, J = 5.8 Hz, 2H), 3.42-3.32 (m, 4H), 3.07 (t, J = 5.9 Hz, 2H), 2.01-1.92 (m, 4H), 1.71 (d, J = 6.8 Hz, 3H) |

| Example | Structure | LC-MS [M + H]+ unless otherwise noted | H-NMR |
|---|---|---|---|
| 155 | 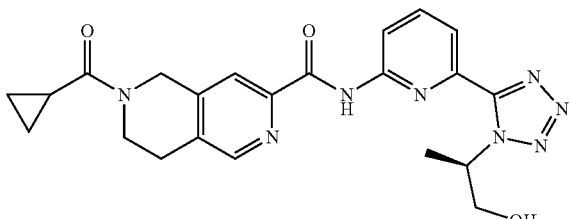 | 449.25 | ¹H NMR (400 MHz, Chloroform-d) δ 10.48 (s, 1H), 8.47 (s, 1H), 8.40 (d, J = 4.8 Hz, 1H), 8.11-8.08 (comp, 2H), 7.98 (t, J = 8.0 Hz, 1H), 5.92-5.82 (m, 1H), 5.03-4.82 (m, 2H), 4.16 (s, 2H), 4.02-3.92 (m, 2H), 3.23-2.88 (comp, 3H), 1.83 (br s, 1H), 1.70 (d, J = 6.8 Hz, 3H), 1.09-1.04 (m, 2H), 0.90-0.82 (m, 2H) |
| 156 | 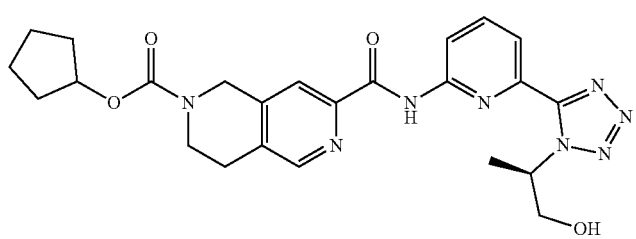 [SMILES: C[C@H](CO)n1nnnc1-c1cccc(NC(=O)c2cc3c(cn2)CCN(C(=O)OC2CCCC2)C3)n1] | 493.30 | ¹H NMR (400 MHz, Chloroform-d) δ 10.48 (s, 1H), 8.45 (s, 1H), 8.38 (d, J = 8.4 Hz, 1H), 8.11-8.08 (comp, 2H), 7.98 (t, J = 8.0 Hz, 1H), 5.89-5.85 (m, 1H), 5.22-5.15 (m, 1H), 4.77-4.68 (m, 2H), 4.20-4.12 (m, 2H), 3.81-3.72 (m, 2H), 3.22-3.11 (m, 1H), 2.98-2.92 (m, 2H), 1.95-1.84 (m, 2H), 1.80-1.72 (m, 2H), 1.70 (d, J = 6.9 Hz, 3H), 1.65-1.58 (m, 4H) |
| 157 | 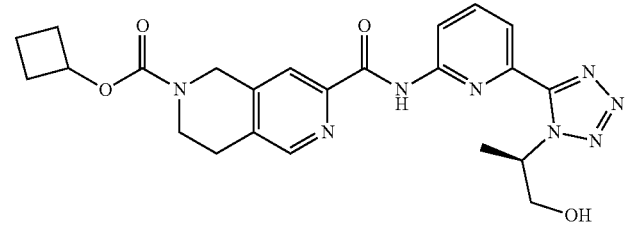 [SMILES: C[C@H](CO)n1nnnc1-c1cccc(NC(=O)c2cc3c(cn2)CCN(C(=O)OC2CCC2)C3)n1] | 479.25 | ¹H NMR (400 MHz, Chloroform-d) δ 10.48 (s, 1H), 8.45 (s, 1H), 8.38 (d, J = 8.3 Hz, 1H), 8.09 (d, J = 7.9 Hz, 2H), 7.98 (t, J = 8.0 Hz, 1H), 5.89-5.84 (m, 1H), 5.01 (p, J = 7.5 Hz, 1H), 4.74 (s, 2H), 4.18-4.11 (m, 2H), 3.78 (t, J = 5.8 Hz, 2H), 2.96 (t, J = 5.9 Hz, 2H), 2.37 (q, J = 9.1 Hz, 2H), 2.11 (p, J = 10.0 Hz, 2H), 1.80 (q, J = 10.5 Hz, 1H), 1.70 (d, J = 6.8 Hz, 3H), 1.66-1.54 (m, 1H) |
| 158 | 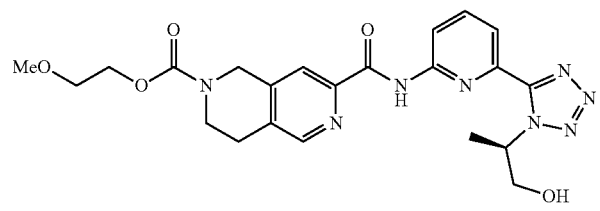 [SMILES: COCCOC(=O)N1CCc2cnc(C(=O)Nc3cccc(-c4nnnn4[C@H](C)CO)n3)cc2C1] | 483.25 | ¹H NMR (400 MHz, Chloroform-d) δ 10.48 (s, 1H), 8.46 (s, 1H), 8.39 (d, J = 8.3 Hz, 1H), 8.10 (comp 2H), 7.99 (t, J = 8.0 Hz, 1H), 5.86 (dq, J = 12.5, 6.5, 6.0 Hz, 1H), 4.77 (s, 2H), 4.32 (t, J = 4.6 Hz, 2H), 4.16 (s, 2H), 3.81 (t, J = 5.8 Hz, 2H), 3.64 (t, J = 4.6 Hz, 2H), 3.41 (s, 3H), 3.13 (s, 1H), 2.98 (d, J = 6.2 Hz, 2H), 1.70 (d, J = 6.8 Hz, 3H) |
| 159 | 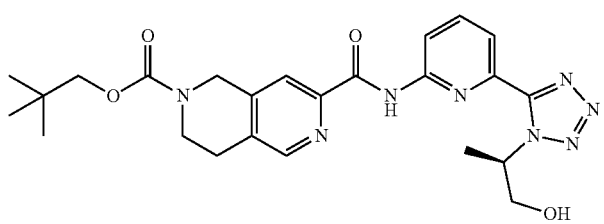 [SMILES: C[C@H](CO)n1nnnc1-c1cccc(NC(=O)c2cc3c(cn2)CCN(C(=O)OCC(C)(C)C)C3)n1] | 495.20 | ¹H NMR (400 MHz, Chloroform-d) δ 10.49 (s, 1H), 8.47 (s, 1H), 8.39 (d, J = 8.5 Hz, 1H), 8.10 (comp, 2H), 7.99 (t, J = 8.0 Hz, 1H), 5.86 (dq, J = 13.1, 6.5 Hz, 1H), 4.77 (s, 2H), 4.16 (d, J = 6.0 Hz, 2H), 3.86 (s, 2H), 3.81 (t, J = 5.8 Hz, 2H), 2.98 (t, J = 6.0 Hz, 2H), 1.71 (d, J = 6.8 Hz, 3H), 0.99 (s, 9H) |
| 160 | 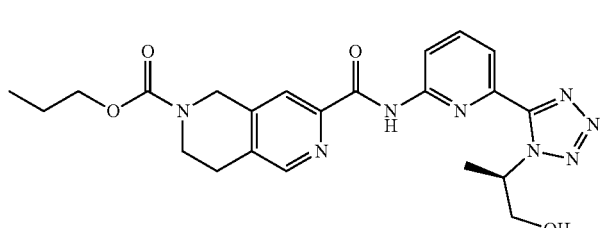 | 467.25 | ¹H NMR (400 MHz, Chloroform-d) δ 10.57 (s, 1H), 8.49 (s, 1H), 8.41 (d, J = 8.3 Hz, 1H), 8.17-8.10 (m, 2H), 8.02 (t, J = 8.0 Hz, 1H), 5.91 (m, 1H), 4.82-4.77 (m, 2H), 4.21-4.11 (m, 4H), 3.83 (t, J = 5.8 Hz, 2H), 3.00 (t, J = 5.8 Hz, 2H), 1.88-1.69 (m, 5H), 1.01 (t, J = 7.4 Hz, 3H) |

| Example | Structure | LC-MS [M + H]+ unless otherwise noted | H-NMR |
|---|---|---|---|
| 161 | 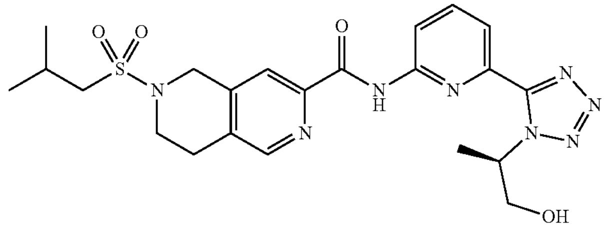 [SMILES: CC(C)CS(=O)(=O)N1CCc2cnc(C(=O)Nc3cccc(-c4nnnn4[C@H](C)CO)n3)cc2C1] | 501.25 | ¹H NMR (400 MHz, Chloroform-d) δ 10.46 (s, 1H), 8.48 (s, 1H), 8.39 (d, J = 8.3 Hz, 1H), 8.10 (d, J = 7.7 Hz, 1H), 8.06 (s, 1H), 7.99 (t, J = 8.0 Hz, 1H), 5.85 (dq, J = 13.8, 7.0 Hz, 1H), 4.59 (s, 2H), 4.16 (d, J = 5.4 Hz, 2H), 3.66 (t, J = 5.8 Hz, 2H), 3.09 (t, J = 5.9 Hz, 2H), 2.89 (d, J = 6.5 Hz, 2H), 2.33 (dp, J = 12.9, 6.5 Hz, 1H), 1.70 (d, J = 6.8 Hz, 3H), 1.14 (d, J = 6.7 Hz, 6H) |
| 162 | 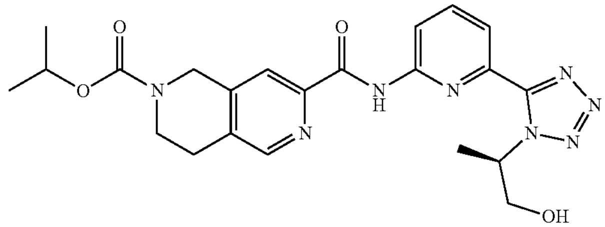 [SMILES: CC(C)OC(=O)N1CCc2cnc(C(=O)Nc3cccc(-c4nnnn4[C@H](C)CO)n3)cc2C1] | 467.22 | ¹H NMR (400 MHz, DMSO-d₆) δ 10.76 (s, 1H), 8.60 (s, 1H), 8.42 (dd, J = 8.4, 0.9 Hz, 1H), 8.16 (t, J = 8.0 Hz, 1H), 8.10 (s, 1H), 7.97 (dd, J = 7.6, 0.9 Hz, 1H), 5.90-5.77 (m, 1H), 4.98 (t, J = 5.7 Hz, 1H), 4.84 (hept, J = 6.3 Hz, 1H), 4.73 (s, 2H), 3.86-3.71 (comp, 2H), 3.67 (t, J = 5.8 Hz, 2H), 2.93 (t, J = 5.8 Hz, 2H), 1.59 (d, J = 6.8 Hz, 3H), 1.23 (d, J = 6.2 Hz, 6H) |
| 163 | 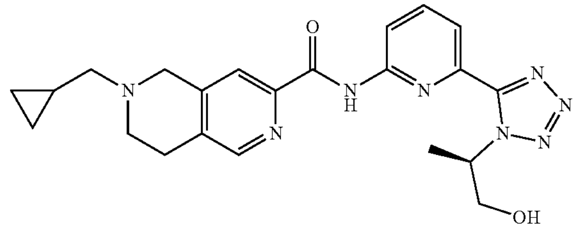 [SMILES: C[C@H](CO)n1nnnc1-c1cccc(NC(=O)c2cc3c(cn2)CCN(CC2CC2)C3)n1] | 435.20 | ¹H NMR (400 MHz, Chloroform-d) δ 10.52 (s, 1H), 8.41 (s, 1H), 8.37 (d, J = 8.3 Hz, 1H), 8.12-8.06 (m, 1H), 8.01 (s, 1H), 7.98 (t, J = 8.0 Hz, 1H), 5.88 (h, J = 6.5 Hz, 1H), 4.15 (d, J = 6.0 Hz, 2H), 3.83 (s, 2H), 3.22 br (s, 1H), 3.03 (t, J = 5.6 Hz, 3H), 2.90 (t, J = 5.5 Hz, 3H), 2.50 (d, J = 6.6 Hz, 2H), 1.70 (d, J = 6.8 Hz, 3H), 1.05-0.88 (m, 1H), 0.71-0.56 (m, 2H), 0.27-0.18 (m, 2H) |
| 164 | 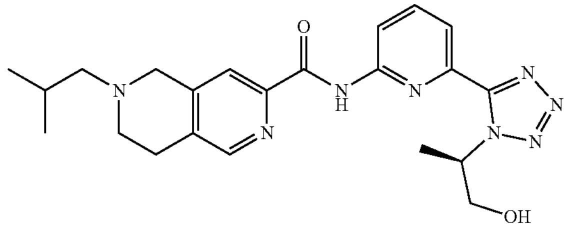 [SMILES: CC(C)CN1CCc2cnc(C(=O)Nc3cccc(-c4nnnn4[C@H](C)CO)n3)cc2C1] | 437.25 | ¹H NMR (400 MHz, Chloroform-d) δ 10.51 (s, 1H), 8.40 (s, 1H), 8.37 (d, J = 8.3 Hz, 1H), 8.09 (dd, J = 7.6, 1.0 Hz, 1H), 8.03-7.93 (comp, 2H), 5.87 (h, J = 6.6 Hz, 1H), 4.15 (d, J = 6.0 Hz, 2H), 3.71 (br s, 2H), 3.00 (br s, 2H), 2.79 (br s, 2H), 2.34 (br s, 2H), 1.93 (br s, 1H), 1.70 (d, J = 6.8 Hz, 3H), 0.97 (d, J = 6.5 Hz, 6H) |
| 165 | 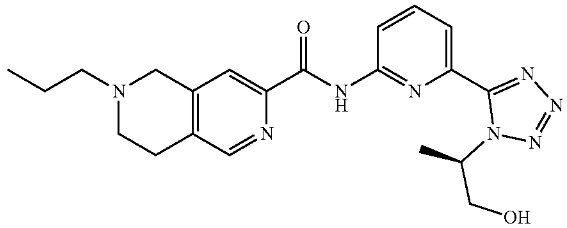 [SMILES: CCCN1CCc2cnc(C(=O)Nc3cccc(-c4nnnn4[C@H](C)CO)n3)cc2C1] | 423.30 | ¹H NMR (400 MHz, Chloroform-d) δ 10.51 (s, 1H), 8.43 (s, 1H), 8.37 (d, J = 8.3 Hz, 1H), 8.10 (d, J = 7.6 Hz, 1H), 8.01 (s, 1H), 8.03-7.94 (m, 1H), 5.87 (h, J = 6.5 Hz, 1H), 4.15 (d, J = 6.0 Hz, 2H), 3.82 (br s, 2H), 3.06 (br s, 2H), 2.91 (br s, 2H), 2.69-2.55 (m, 2H), 1.72-1.65 (comp, 5H), 0.99 (t, J = 7.4 Hz, 3H) |
| 166 | 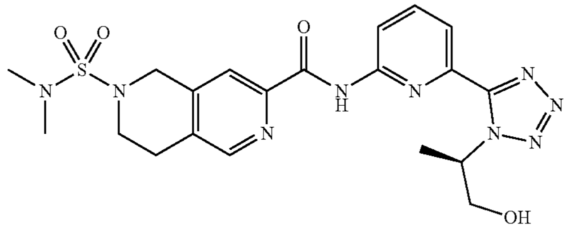 | 488.25 | ¹H NMR (400 MHz, Chloroform-d) δ 10.47 (s, 1H), 8.47 (s, 1H), 8.38 (d, J = 8.3 Hz, 1H), 8.10 (d, J = 7.5 Hz, 1H), 8.06 (s, 1H), 7.99 (t, J = 8.0 Hz, 1H), 5.87 (dt, J = 12.8, 6.7 Hz, 1H), 4.53 (s, 2H), 4.19-4.13 (m, 2H), 3.63 (t, J = 5.8 Hz, 2H), 3.12-3.04 (comp, 3H), 2.88 (s, 6H), 1.70 (d, J = 6.8 Hz. 3H) |

| Example | Structure | LC-MS [M + H]+ unless otherwise noted | H-NMR |
|---|---|---|---|
| 167 | 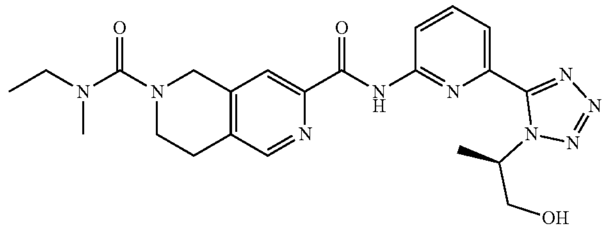 [SMILES: CCN(C)C(=O)N1CCc2cnc(C(=O)Nc3cccc(-c4nnnn4[C@H](C)CO)n3)cc2C1] | 466.30 | ¹H NMR (400 MHz, Chloroform-d) δ 10.50 (s, 1H), 8.44 (s, 1H), 8.38 (d, J = 8.3 Hz, 1H), 8.09 (d, J = 7.6 Hz, 1H), 8.06 (s, 1H), 7.98 (t, J = 8.0 Hz, 1H), 5.94-5.81 (m, 1H), 4.50 (s, 2H), 4.16 (d, J = 6.0 Hz, 2H), 3.54 (t, J = 5.9 Hz, 2H), 3.28 (q, J = 7.1 Hz, 2H), 3.02 (t, J = 5.8 Hz, 2H), 2.89 (s, 3H), 1.70 (d, J = 6.8 Hz, 3H), 1.19 (t, J = 7.2 Hz, 3H) |
| 168 | 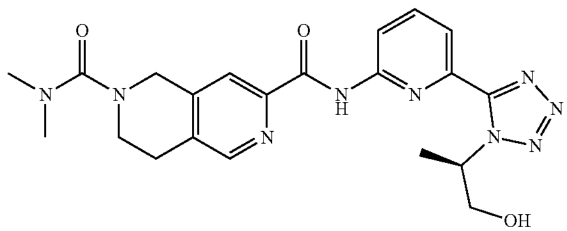 [SMILES: C[C@H](CO)n1nnnc1-c1cccc(NC(=O)c2cc3c(cn2)CCN(C(=O)N(C)C)C3)n1] | 452.25 | ¹H NMR (400 MHz, Chloroform-d) δ 10.49 (s, 1H), 8.44 (s, 1H), 8.38 (d, J = 8.3 Hz, 1H), 8.09 (d, J = 7.6 Hz, 1H), 8.06 (s, 1H), 7.98 (t, J = 8.0 Hz, 1H), 5.87 (h, J = 6.9 Hz, 1H), 4.52 (s, 2H), 4.16 (d, J = 5.9 Hz, 2H), 3.56 (t, J = 5.8 Hz, 2H), 3.19 (s, 1H), 3.02 (t, J = 5.8 Hz, 2H), 2.91 (s, 4H), 1.70 (d, J = 6.8 Hz, 3H) |
| 169 | 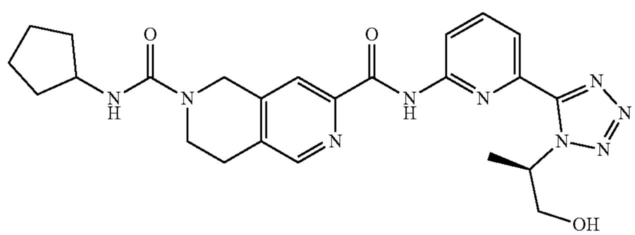 [SMILES: C[C@H](CO)n1nnnc1-c1cccc(NC(=O)c2cc3c(cn2)CCN(C(=O)NC2CCCC2)C3)n1] | 492.30 | ¹H NMR (400 MHz, Chloroform-d) δ 10.49 (s, 1H), 8.46 (s, 1H), 8.38 (d, J = 8.4 Hz, 1H), 8.12-8.08 (comp, 2H), 7.99 (t, J = 7.9 Hz, 1H), 5.94-5.79 (m, 1H), 4.66 (s, 2H), 4.45 (s, 1H), 4.18-4.14 (comp, 3H), 3.70 (s, 2H), 2.98 (s, 2H), 2.10-2.01 (m, 2H), 1.70 (d, J = 6.8 Hz, 3H), 1.65-1.55 (comp, 4H), 1.46-1.33 (comp, 2H) |
| 170 | 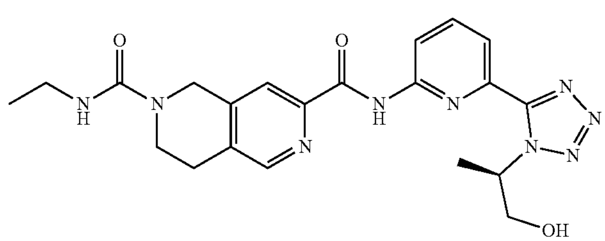 [SMILES: CCNC(=O)N1CCc2cnc(C(=O)Nc3cccc(-c4nnnn4[C@H](C)CO)n3)cc2C1] | 452.25 | ¹H NMR (400 MHz, Chloroform-d) δ 10.48 (s, 1H), 8.46 (s, 1H), 8.38 (d, J = 8.2 Hz, 1H), 8.11-8.07 (comp, 2H), 7.98 (t, J = 8.0 Hz, 1H), 5.94-5.80 (m, 1H), 4.67 (s, 2H), 4.54 (br s, 1H), 4.19-4.12 (m, 2H), 3.71 (t, J = 5.8 Hz, 2H), 3.40-3.29 (m, 2H), 3.17 (br s, 1H), 2.99 (d, J = 5.9 Hz, 2H), 1.70 (d, J = 6.8 Hz, 3H), 1.20 (t, J = 7.2 Hz, 3H) |
| 171 | 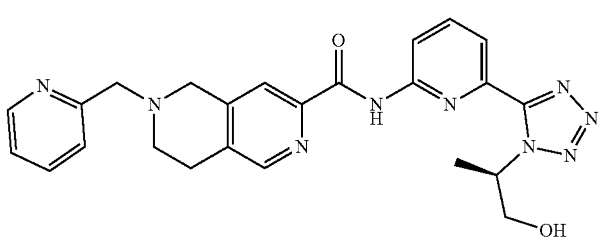 [SMILES: C[C@H](CO)n1nnnc1-c1cccc(NC(=O)c2cc3c(cn2)CCN(Cc2ccccn2)C3)n1] | 472.25 | ¹H NMR (400 MHz, Chloroform-d) δ 10.50 (s, 1H), 8.62 (d, J = 4.6 Hz, 1H), 8.43 (s, 1H), 8.36 (d, J = 8.3 Hz, 1H), 8.09 (d, J = 7.6 Hz, 1H), 8.02-7.94 (comp, 2H), 7.74 (t, J = 7.7 Hz, 1H), 7.53 (d, J = 7.1 Hz, 1H), 7.28-7.24 (m, 1H), 5.87 (h, J = 6.7 Hz, 1H), 4.15 (d, J = 6.0 Hz, 2H), 3.99 (br s, 2H), 3.91 (br s, 2H), 3.26-3.07 (comp, 3H), 3.00 (br s, 2H), 1.70 (d, J = 6.9 Hz, 3H) |
| 172 | 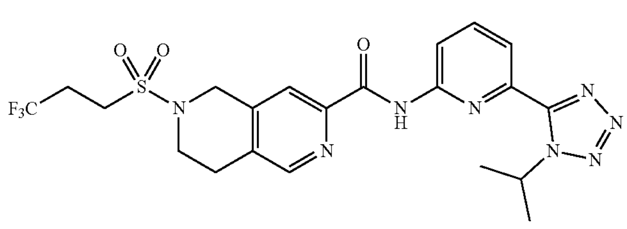 [SMILES: CC(C)n1nnnc1-c1cccc(NC(=O)c2cc3c(cn2)CCN(S(=O)(=O)CCC(F)(F)F)C3)n1] | 525.16 | ¹H NMR (400 MHz, DMSO-d₆) δ 10.78 (s, 1H), 8.63 (s, 1H), 8.41 (dd, J = 8.4, 0.9 Hz, 1H), 8.17 (t, J = 8.0 Hz, 1H), 8.09 (s, 1H), 7.99 (dd, J = 7.6, 0.9 Hz, 1H), 5.90 (hept, J = 6.6 Hz, 1H), 4.68 (s, 2H), 3.63 (t, J = 5.8 Hz, 2H), 3.54-3.43 (m, 2H), 3.04 (t, J = 5.8 Hz, 2H), 2.83-2.64 (m, 2H), 1.60 (d, J = 6.6 Hz, 6H) |

-continued

| Example | Structure | LC-MS [M + H]+ unless otherwise noted | H-NMR |
|---|---|---|---|
| 173 | 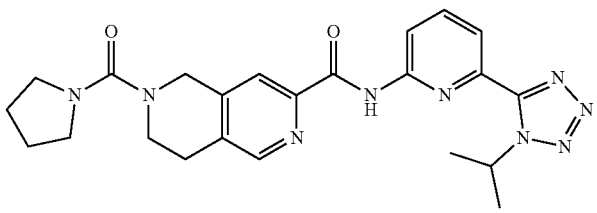 [SMILES: CC(C)n1nnnc1-c1cccc(NC(=O)c2cc3c(cn2)CCN(C(=O)N2CCCC2)C3)n1] | 462.22 | ¹H NMR (400 MHz, DMSO-d₆) δ 10.77 (s, 1H), 8.57 (s, 1H), 8.41 (dd, J = 8.4, 0.9 Hz, 1H), 8.17 (t, J = 8.0 Hz, 1H), 8.08 (s, 1H), 7.99 (dd, J = 7.6, 0.8 Hz, 1H), 5.89 (hept, J = 6.5 Hz, 1H), 4.53 (s, 2H), 3.50 (t, J = 5.7 Hz, 2H), 3.36-3.32 (m, 4 H), 2.95 (t, J = 5.8 Hz, 2H), 1.80-1.74 (m, 4 H), 1.60 (d, J = 6.6 Hz, 6H) |
| 174 | 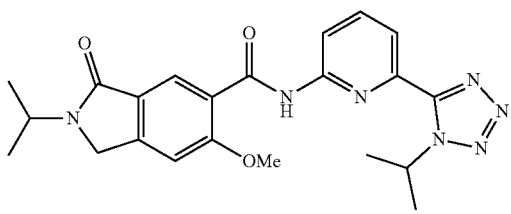 [SMILES: COc1cc2c(cc1C(=O)Nc1cccc(-c3nnnn3C(C)C)n1)C(=O)N(C(C)C)C2] | 436.39 | ¹H NMR (400 MHz, Chloroform-d) δ 10.20 (s, 1H), 8.78 (s, 1H), 8.59 (dd, J = 8.2, 1.1 Hz, 1H), 8.02 (dd, J = 7.6, 1.1 Hz, 1H), 7.96 (t, J = 7.9 Hz, 1H), 7.03 (s, 1H), 5.76 (hept, J = 6.9 Hz, 1H), 5.34 (s, 2H), 4.14-4.08 (m, 1H), 4.12 (s, 3H), 1.74 (d, J = 6.7 Hz, 6H), 1.24 (d, J = 6.4 Hz, 6H) |
| 175 | 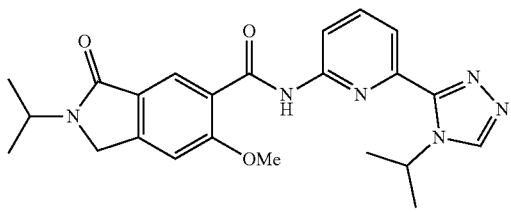 [SMILES: COc1cc2c(cc1C(=O)Nc1cccc(-c3nncn3C(C)C)n1)C(=O)N(C(C)C)C2] | 435.22 | ¹H NMR (400 MHz, Chloroform-d) δ 10.09 (s, 1H), 8.77 (s, 1H), 8.49 (dd, J = 8.3, 1.0 Hz, 1H), 8.37 (s, 1H), 8.00 (dd, J = 7.7, 1.0 Hz, 1H), 7.90 (t, J = 7.9 Hz, 1H), 7.01 (s, 1H), 5.53 (hept, J = 6.9 Hz, 1H), 5.33 (s, 2H), 4.15-4.07 (m, 1H), 4.10 (s, 3H), 1.62 (d, J = 6.7 Hz, 6H), 1.23 (d, J = 6.4 Hz, 6H) |
| 176 | 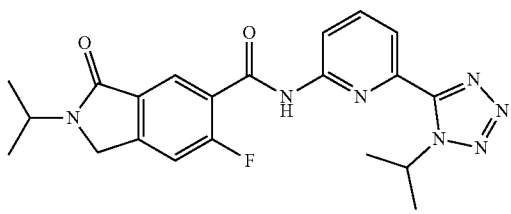 [SMILES: CC(C)N1Cc2cc(F)c(C(=O)Nc3cccc(-c4nnnn4C(C)C)n3)cc2C1=O] | 424.20 | ¹H NMR (400 MHz, Chloroform-d) δ 8.94 (d, J = 13.3 Hz, 1H), 8.65 (d, J = 6.9 Hz, 1H), 8.54 (dd, J = 8.3, 0.9 Hz, 1H), 8.10 (dd, J = 7.7, 1.0 Hz, 1H), 7.99 (t, J = 8.0 Hz, 1H), 7.24 (d, J = 11.0 Hz, 1H), 5.74 (hept, J = 6.6 Hz, 1H), 5.37 (s, 2H), 4.12 (hept, J = 6.4 Hz, 1H), 1.71 (d, J = 6.1 Hz, 6H), 1.24 (d, J = 6.4 Hz, 6H) |
| 177 | 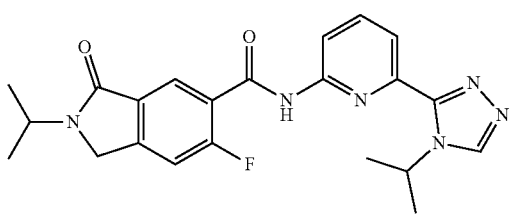 [SMILES: CC(C)N1Cc2cc(F)c(C(=O)Nc3cccc(-c4nncn4C(C)C)n3)cc2C1=O] | 423.20 | ¹H NMR (400 MHz, Chloroform-d) δ 8.88 (d, J = 13.1 Hz, 1H), 8.64 (d, J = 7.0 Hz, 1H), 8.44 (d, J = 7.7 Hz, 1H), 8.37 (s, 1H), 8.07 (dd, J = 7.7, 0.9 Hz, 1H), 7.93 (t, J = 8.0 Hz, 1H), 7.22 (d, J = 10.9 Hz, 1H), 5.52 (hept, J = 6.7 Hz, 1H), 5.36 (s, 2H), 4.11 (hept, J = 6.1 Hz, 1H), 1.59 (d, J = 6.8 Hz, 6H), 1.23 (d, J = 6.3 Hz, 6H) |
| 178 | 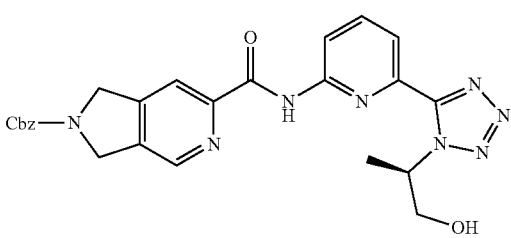 [SMILES: C[C@H](CO)n1nnnc1-c1cccc(NC(=O)c2cc3c(cn2)CN(C(=O)OCc2ccccc2)C3)n1] | 501.20 | ¹H NMR (400 MHz, Chloroform-d) δ 10.51 (d, J = 6.6 Hz, 1H), 8.60 (d, J = 23.4 Hz, 1H), 8.44-8.37 (m, 1H), 8.26 (d, J = 22.5 Hz, 1H), 8.11 (d, J = 7.6 Hz, 1H), 8.00 (t, J = 8.0 Hz, 1H), 7.48-7.32 (comp, 5H), 5.92-5.78 (m, 1H), 5.24 (s, 2H), 4.96-4.85 (comp, 4H), 4.23-4.10 (m, 2H), 3.07-3.03 (m, 1H), 1.71 (d, J = 6.8 Hz, 3H) |

| Example | Structure | LC-MS [M + H]+ unless otherwise noted | H-NMR |
|---|---|---|---|
| 179 | 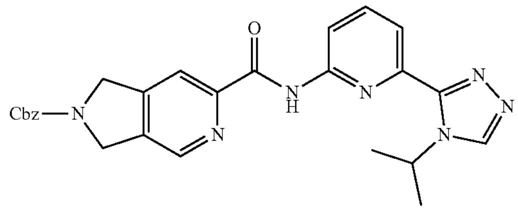 [SMILES: CC(C)n1cnnc1-c1cccc(NC(=O)c2cc3c(cn2)CN(C(=O)OCc2ccccc2)C3)n1] | 484.22 | ¹H NMR (400 MHz, Chloroform-d) δ 10.41 (d, J = 8.0 Hz, 1H), 8.59 (d, J = 24.1 Hz, 1H), 8.48 (dd, J = 8.3, 3.9 Hz, 1H), 8.37 (s, 1H), 8.26 (d, J = 22.2 Hz, 1H), 8.05 (dd, J = 7.7, 2.1 Hz, 1H), 7.93 (t, J = 8.0 Hz, 1H), 7.45-7.33 (comp, 5H), 5.65-5.56 (m, 1H), 5.24 (s, 2H), 4.93-4.85 (comp, 4H), 1.60 (d, J = 6.1 Hz, 6H) |
| 180 | 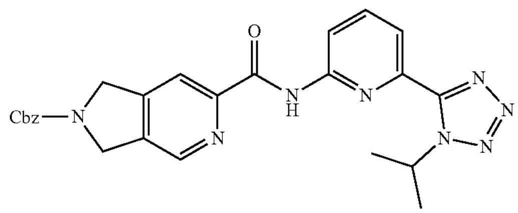 [SMILES: CC(C)n1nnnc1-c1cccc(NC(=O)c2cc3c(cn2)CN(C(=O)OCc2ccccc2)C3)n1] | 485.21 | ¹H NMR (400 MHz, Chloroform-d) δ 10.47 (d, J = 7.8 Hz, 1H), 8.68-8.53 (comp, 2H), 8.26 (d, J = 22.3 Hz, 1H), 8.08 (dt, J = 7.6, 1.2 Hz, 1H), 7.99 (t, J = 7.9 Hz, 1H), 7.49-7.30 (comp, 5H), 5.91-5.76 (m, 1H), 5.24 (s, 2H), 4.95-4.85 (comp, 4H), 1.73 (d, J = 6.7 Hz, 6H) |
| 181 | 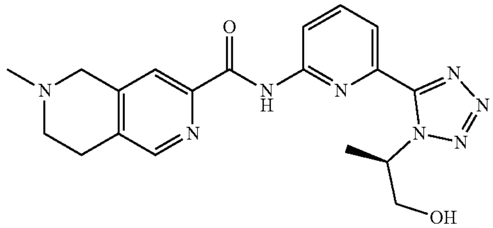 [SMILES: C[C@H](CO)n1nnnc1-c1cccc(NC(=O)c2cc3c(cn2)CCN(C)C3)n1] | 395.20 | ¹H NMR (400 MHz, Chloroform-d) δ 10.53 (s, 1H), 8.44 (s, 1H), 8.40 (d, J = 8.4 Hz, 1H), 8.11 (d, J = 7.6 Hz, 1H), 8.04-7.95 (m, 2H), 5.89 (m, 1H), 4.17 (d, J = 5.8 Hz, 2H), 3.70 (s, 2H), 3.26 (s, 1H), 3.04 (t, J = 6.0 Hz, 2H), 2.80 (t, J = 6.0 Hz, 2H), 2.54 (s, 3H), 1.72 (d, J = 6.7 Hz, 3H) |
| 182 | 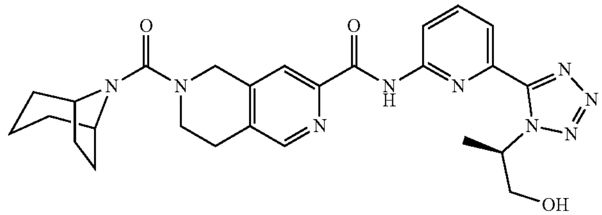 [SMILES: C[C@H](CO)n1nnnc1-c1cccc(NC(=O)c2cc3c(cn2)CCN(C(=O)N2C4CCCC2CC4)C3)n1] | 518.25 | ¹H NMR (400 MHz, Chloroform-d) δ 10.56 (s, 1H), 8.47 (s, 1H), 8.40 (d, J = 8.3 Hz, 1H), 8.16-8.08 (m, 2H), 8.01 (t, J = 8.0 Hz, 1H), 5.91 (m, 1H), 4.67 (s, 2H), 4.18 (d, J = 6.0 Hz, 2H), 4.13 (d, J = 5.2 Hz, 2H), 3.67 (t, J = 5.7 Hz, 2H), 3.05 (t, J = 5.7 Hz, 2H), 1.96 (dd, J = 7.7, 3.7 Hz, 2H), 1.84 (d, J = 12.7 Hz, 2H), 1.73 (d, J = 6.5 Hz, 6H), 1.63 (s, 1H), 1.55 (d, J = 12.4 Hz, 2H) |
| 183 | 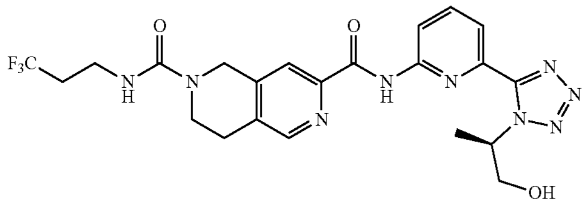 [SMILES: C[C@H](CO)n1nnnc1-c1cccc(NC(=O)c2cc3c(cn2)CCN(C(=O)NCCC(F)(F)F)C3)n1] | 520.15 | ¹H NMR (400 MHz, DMSO-d₆) δ 10.77 (s, 1H), 8.60 (s, 1H), 8.43 (d, J = 8.4 Hz, 1H), 8.18 (t, J = 8.0 Hz, 1H), 8.03 (s, 1H), 7.98 (d, J = 8.0 Hz), 6.96 (s, 1H), 5.83 (m, 1H), 5.00 (t, J = 5.7 Hz, 1H), 4.69 (s, 2H), 3.80 (t, J = 5.2 Hz, 2H), 3.64 (t, J = 5.2 Hz, 2H), 2.91 (t, J = 6.4 Hz, 2H), 2.43 (t, J = 6.4 Hz, 2H), 1.60 (d, J = 6.7 Hz, 3H) |
| 184 | 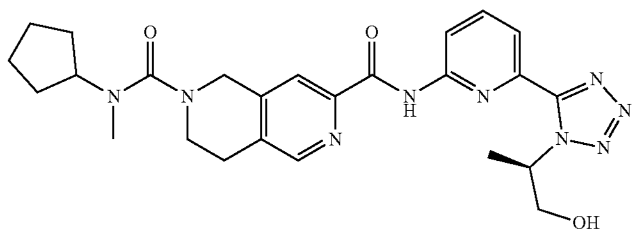 [SMILES: C[C@H](CO)n1nnnc1-c1cccc(NC(=O)c2cc3c(cn2)CCN(C(=O)N(C)C2CCCC2)C3)n1] | 506.25 | ¹H NMR (400 MHz, Methanol-d₄) δ 8.55 (s, 1H), 8.53 (d, J = 8.0 Hz, 2H), 8.12 (t, J = 8.1 Hz, 1H), 8.09 (s, 1H), 8.02 (d, J = 8.0 Hz), 5.99 (m, 1H), 4.57 (s, 2H), 4.22 (m, 1H), 4.06-3.93 (m, 2H), 3.60 (t, J = 5.7 Hz, 2H), 3.06 (t, J = 5.8 Hz, 2H), 2.86 (s, 3H), 1.91 (s, 2H), 1.90-1.54 (m, 9H) |

| Example | Structure | LC-MS [M + H]+ unless otherwise noted | H-NMR |
|---|---|---|---|
| 185 | 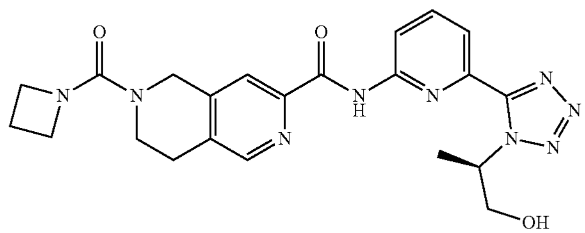 [SMILES: C[C@H](CO)n1nnnc1-c1cccc(NC(=O)c2cc3c(cn2)CCN(C(=O)N2CCC2)C3)n1] | 464.20 | $^1$H NMR (400 MHz, DMSO-d$_6$) δ 10.77 (s, 1H), 8.58 (s, 1H), 8.42 (d, J = 8.4 Hz, 1H), 8.17 (t, J = 8.1 Hz, 1H), 8.11 (s, 1H), 7.98 (d, J = 7.6 Hz, 1H), 5.83 (m, 1H), 4.99 (t, J = 5.6 Hz, 1H), 4.59 (s, 2H), 3.98 (t, J = 7.7 Hz, 4H), 3.80-3.73 (m, 2H), 3.54 (t, J = 5.9 Hz, 2H), 2.91 (t, J = 5.7 Hz, 2H), 2.19 (m, 2H), 1.60 (d, J = 6.8 Hz, 3H) |
| 186 | 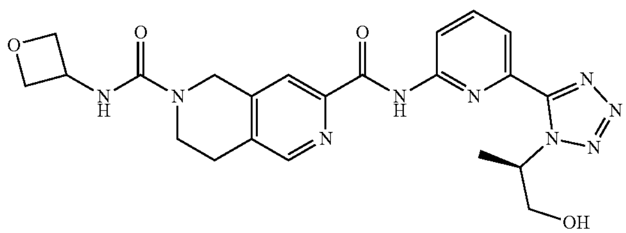 [SMILES: C[C@H](CO)n1nnnc1-c1cccc(NC(=O)c2cc3c(cn2)CCN(C(=O)NC2COC2)C3)n1] | 480.30 | $^1$H NMR (400 MHz, DMSO-d$_6$) δ 10.76 (s, 1H), 8.60 (s, 1H), 8.42 (d, J = 8.4 Hz, 1H), 8.17 (t, J = 8.0 Hz, 1H), 8.08 (s, 1H), 7.97 (d, J = 7.6 Hz, 1H), 5.82 (m, 1H), 5.00 (m, 1H), 4.66 (s, 3H), 4.36 (t, J = 8.4 Hz, 1H), 4.17 (t, J = 7.2 Hz, 1H), 3.99 (s, 1H), 3.79 (d, J = 6.6 Hz, 2H), 3.64 (t, J = 5.7 Hz, 2H), 3.48 (d, J = 10.6 Hz, 1H), 2.95 (t, J = 6.0 Hz, 2H), 1.60 (d, J = 6.7 Hz, 3H) |
| 187 | 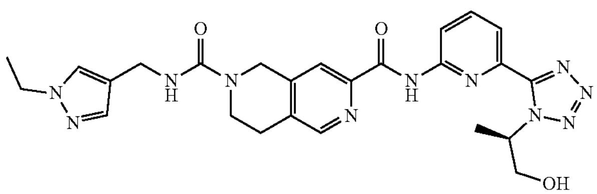 [SMILES: CCn1cc(CNC(=O)N2CCc3cnc(C(=O)Nc4cccc(-c5nnnn5[C@H](C)CO)n4)cc3C2)cn1] | 532.20 | $^1$H NMR (400 MHz, DMSO-d$_6$) δ 10.77 (s, 1H), 8.59 (s, 1H), 8.43 (d, J = 8.4 Hz, 1H), 8.17 (t, J = 8.0 Hz, 1H), 8.04-7.95 (m, 2H), 7.58 (s, 1H), 7.32 (s, 1H), 7.01 (t, J = 5.5 Hz, 1H), 5.83 (m, 1H), 5.00 (t, J = 5.8 Hz, 1H), 4.69 (s, 2H), 4.14-4.05 (m, 4H), 3.80 (t, J = 4.0 Hz, 2H), 3.66 (t, J = 5.8 Hz, 2H), 2.90 (t, J = 5.8 Hz, 2H), 1.60 (d, J = 6.8 Hz, 3H), 1.33 (t, J = 7.3 Hz, 3H) |
| 188 | 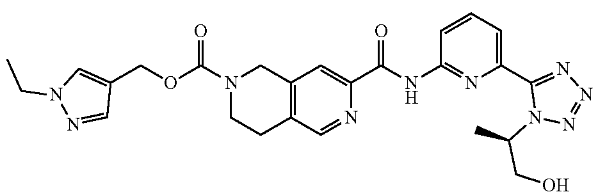 [SMILES: CCn1cc(COC(=O)N2CCc3cnc(C(=O)Nc4cccc(-c5nnnn5[C@H](C)CO)n4)cc3C2)cn1] | 533.23 | $^1$H NMR (400 MHz, Chloroform-d) δ 10.48 (s, 1H), 8.45 (s, 1H), 8.40 (d, J = 8.2 Hz, 1H), 8.10 (d, J = 7.5 Hz, 1H), 8.07 (s, 1H), 7.99 (t, J = 8.0 Hz, 1H), 7.57 (s, 1H), 7.52 (s, 1H), 5.88 (m, 1H), 5.10 (s, 2H), 4.75 (s, 2H), 4.24-4.11 (m, 4H), 3.80 (s, 2H), 2.97 (s, 2H), 1.72 (d, J = 6.8 Hz, 3H), 1.51 (t, J = 7.3 Hz, 3H) |
| 189 | 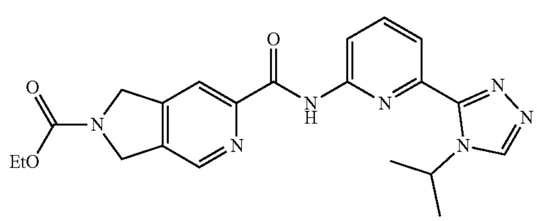 [SMILES: CCOC(=O)N1Cc2cnc(C(=O)Nc3cccc(-c4nncn4C(C)C)n3)cc2C1] | 422.21 | $^1$H NMR (400 MHz, DMSO-d$_6$) δ 10.63 (d, J = 3.6 Hz, 1H), 8.90 (s, 1H), 8.75 (d, J = 9.2 Hz, 1H), 8.32 (d, J = 8.3 Hz, 1H), 8.25 (d, J = 7.1 Hz, 1H), 8.09 (t, J = 8.0 Hz, 1H), 7.89 (d, J = 7.6 Hz, 1H), 5.50 (hept, J = 6.2 Hz, 1H), 4.81-4.77 (comp, 4H), 4.14 (q, J = 7.1 Hz, 2H), 1.50 (d, J = 6.7 Hz, 6H), 1.25 (t, J = 7.1 Hz, 3H) |
| 190 | 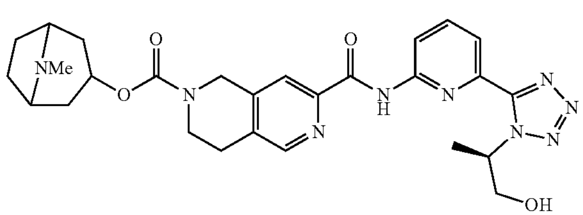 [SMILES: C[C@H](CO)n1nnnc1-c1cccc(NC(=O)c2cc3c(cn2)CCN(C(=O)OC2CC4CCC(C2)N4C)C3)n1] | 548.25 | $^1$H NMR (400 MHz, Chloroform-d) δ 10.50 (s, 1H), 8.49 (s, 1H), 8.42 (s, 1H), 8.11 (m, 2H), 8.01 (t, J = 8.0 Hz, 1H), 5.89 (m, 1H), 5.02 (d, J = 5.6 Hz, 1H), 4.78 (s, 2H), 4.18 (d, J = 5.7 Hz, 2H), 3.82 (t, J = 5.9 Hz, 2H), 3.27-3.07 (m, 2H), 3.01 (t, J = 5.8 Hz, 2H), 2.32 (s, 3H), 2.24-2.07 (m, 5H), 1.95 (d, J = 7.8 Hz, 2H), 1.80 (d, J = 15.0 Hz, 2H), 1.72 (d, J = 6.7 Hz, 3H) |

-continued

| Example | Structure | LC-MS [M + H]+ unless otherwise noted | H-NMR |
|---|---|---|---|
| 191 | 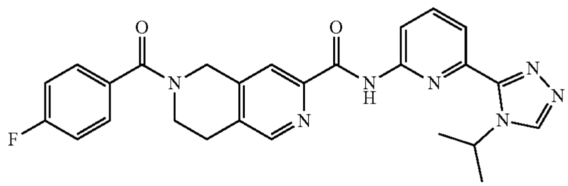 [SMILES: CC(C)n1cnnc1-c1cccc(NC(=O)c2cc3c(cn2)CCN(C(=O)c2ccc(F)cc2)C3)n1] | 486.2 | |
| 192 | 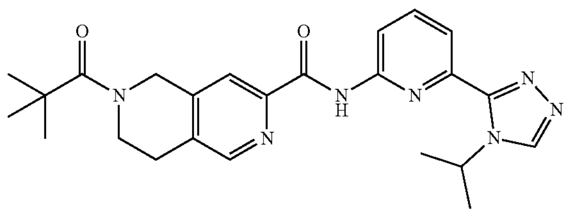 [SMILES: CC(C)n1cnnc1-c1cccc(NC(=O)c2cc3c(cn2)CCN(C(=O)C(C)(C)C)C3)n1] | 448.3 | |
| 193 | 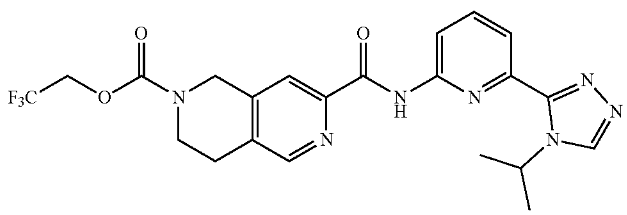 [SMILES: CC(C)n1cnnc1-c1cccc(NC(=O)c2cc3c(cn2)CCN(C(=O)OCC(F)(F)F)C3)n1] | 490.3 | |
| 194 | 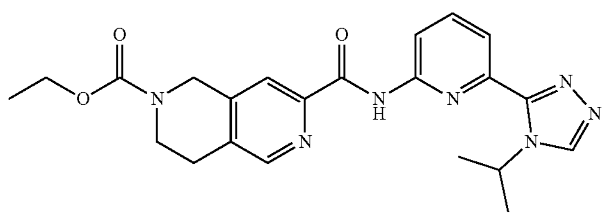 [SMILES: CCOC(=O)N1CCc2cnc(C(=O)Nc3cccc(-c4nncn4C(C)C)n3)cc2C1] | 436.3 | |
| 195 | 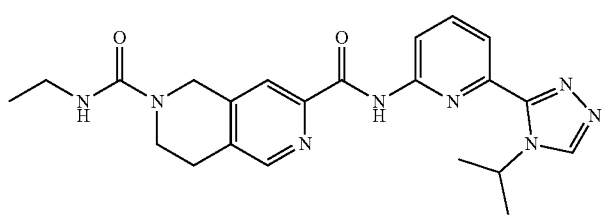 [SMILES: CCNC(=O)N1CCc2cnc(C(=O)Nc3cccc(-c4nncn4C(C)C)n3)cc2C1] | 435.4 | |
| 196 | 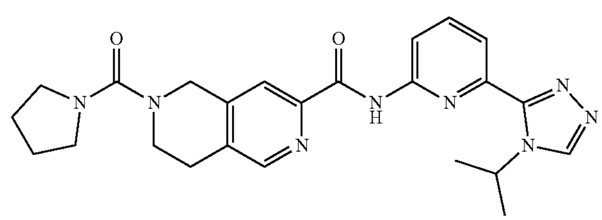 [SMILES: CC(C)n1cnnc1-c1cccc(NC(=O)c2cc3c(cn2)CCN(C(=O)N2CCCC2)C3)n1] | 461.3 | |
| 197 | 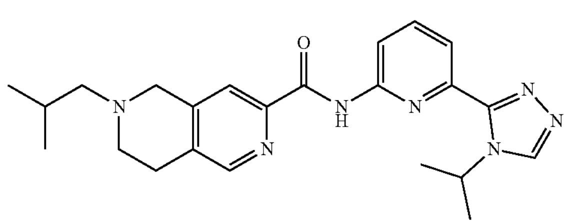 [SMILES: CC(C)CN1CCc2cnc(C(=O)Nc3cccc(-c4nncn4C(C)C)n3)cc2C1] | 420.3 | |

-continued

| Example | Structure | LC-MS [M + H]+ unless otherwise noted | H-NMR |
|---|---|---|---|
| 198 | 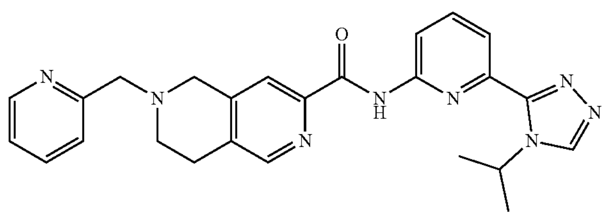 [SMILES: CC(C)n1cnnc1-c1cccc(NC(=O)c2cc3c(cn2)CCN(Cc2ccccn2)C3)n1] | 455.4 | |
| 199 | 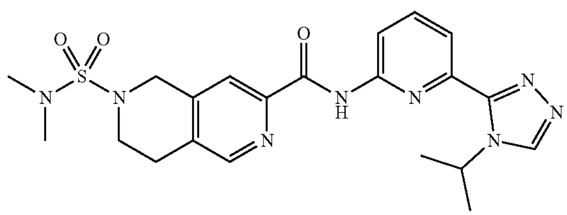 [SMILES: CC(C)n1cnnc1-c1cccc(NC(=O)c2cc3c(cn2)CCN(S(=O)(=O)N(C)C)C3)n1] | 471.3 | |
| 200 | 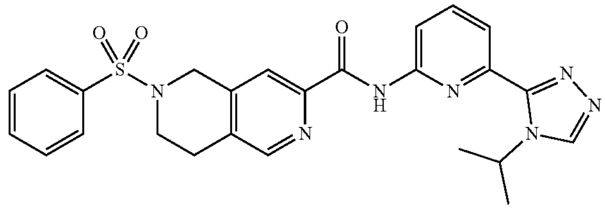 [SMILES: CC(C)n1cnnc1-c1cccc(NC(=O)c2cc3c(cn2)CCN(S(=O)(=O)c2ccccc2)C3)n1] | 504.3 | |
| 201 | 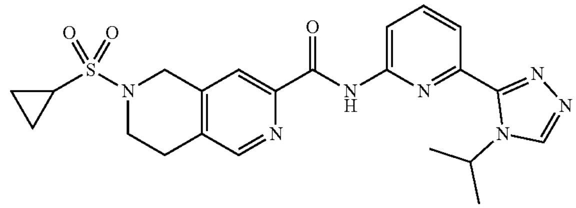 [SMILES: CC(C)n1cnnc1-c1cccc(NC(=O)c2cc3c(cn2)CCN(S(=O)(=O)C2CC2)C3)n1] | 468.3 | |
| 202 | 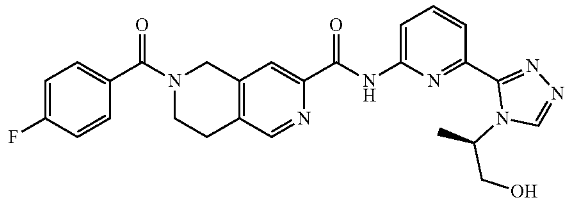 [SMILES: C[C@H](CO)n1cnnc1-c1cccc(NC(=O)c2cc3c(cn2)CCN(C(=O)c2ccc(F)cc2)C3)n1] | 502.3 | |
| 203 | 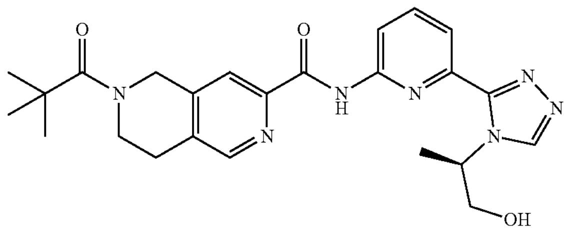 [SMILES: C[C@H](CO)n1cnnc1-c1cccc(NC(=O)c2cc3c(cn2)CCN(C(=O)C(C)(C)C)C3)n1] | 464.3 | |

| Example | Structure | LC-MS [M + H]+ unless otherwise noted | H-NMR |
|---|---|---|---|
| 204 | 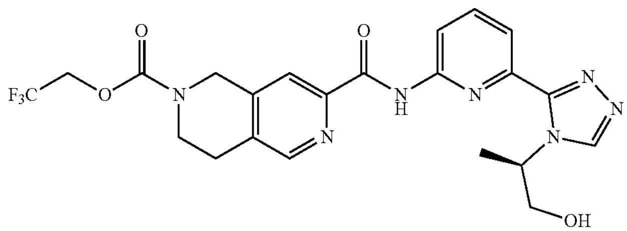 [SMILES: C[C@H](CO)n1cnnc1-c1cccc(NC(=O)c2cc3c(cn2)CCN(C(=O)OCC(F)(F)F)C3)n1] | 506.2 | |
| 205 | 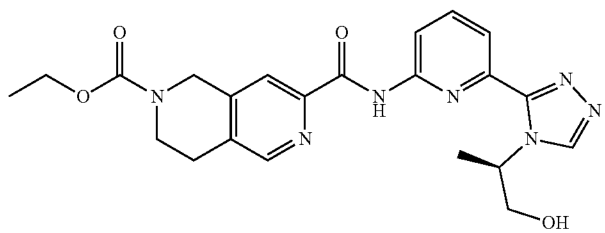 [SMILES: CCOC(=O)N1CCc2cnc(C(=O)Nc3cccc(-c4nncn4[C@H](C)CO)n3)cc2C1] | 452.3 | |
| 206 | 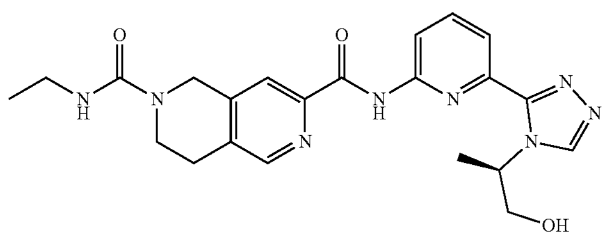 [SMILES: CCNC(=O)N1CCc2cnc(C(=O)Nc3cccc(-c4nncn4[C@H](C)CO)n3)cc2C1] | 451.3 | |
| 207 | 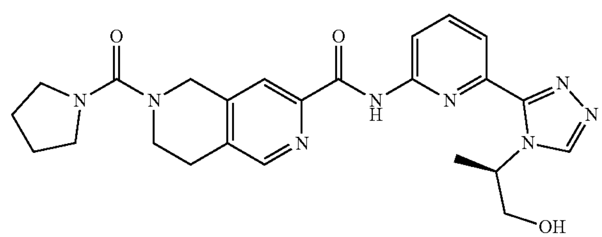 [SMILES: C[C@H](CO)n1cnnc1-c1cccc(NC(=O)c2cc3c(cn2)CCN(C(=O)N2CCCC2)C3)n1] | 477.3 | |
| 208 | 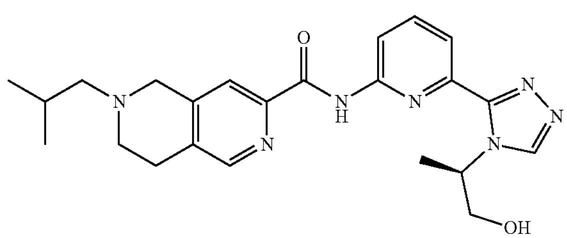 [SMILES: CC(C)CN1CCc2cnc(C(=O)Nc3cccc(-c4nncn4[C@H](C)CO)n3)cc2C1] | 436.3 | |
| 209 | 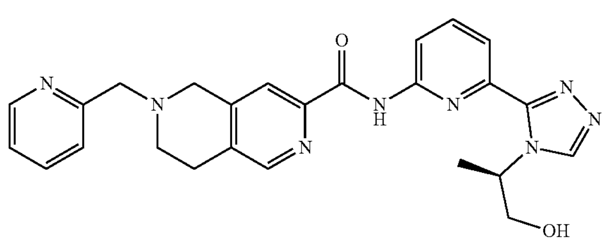 [SMILES: C[C@H](CO)n1cnnc1-c1cccc(NC(=O)c2cc3c(cn2)CCN(Cc2ccccn2)C3)n1] | 471.3 | |

| Example | Structure | LC-MS [M + H]+ unless otherwise noted | H-NMR |
|---|---|---|---|
| 210 | 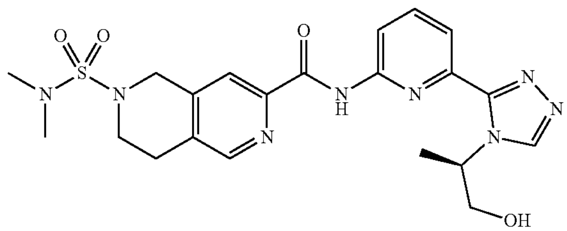 [SMILES: C[C@H](CO)n1cnnc1-c1cccc(NC(=O)c2cc3c(cn2)CCN(S(=O)(=O)N(C)C)C3)n1] | 487.3 | |
| 211 | 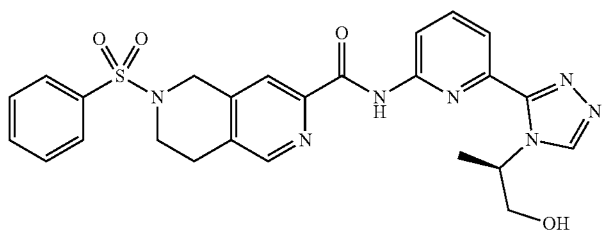 [SMILES: C[C@H](CO)n1cnnc1-c1cccc(NC(=O)c2cc3c(cn2)CCN(S(=O)(=O)c2ccccc2)C3)n1] | 520.3 | |
| 212 | 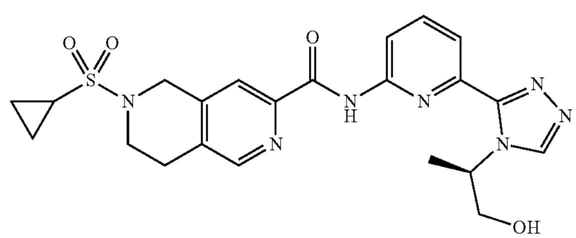 [SMILES: C[C@H](CO)n1cnnc1-c1cccc(NC(=O)c2cc3c(cn2)CCN(S(=O)(=O)C2CC2)C3)n1] | 484.3 | |
| 183a | 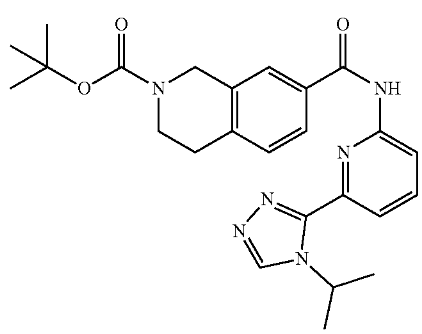 [SMILES: CC(C)n1cnnc1-c1cccc(NC(=O)c2ccc3c(c2)CN(C(=O)OC(C)(C)C)CC3)n1] | — | |

Examples 213-248 are prepared from 7-chloro-6-methoxy-1,2,3,4-tetrahydroisoquinoline utilizing the procedures herein described.

Examples 249-283 are prepared in analogous fashion to example 189.

Examples 284-319 are prepared from tert-butyl 5-chloro-6-methoxyisoindoline-2-carboxylate, which is prepared as in WO 2006082001, utilizing the procedures herein described.

Examples 320-355 are prepared from tert-butyl 5-bromo-6-fluoroisoindoline-2-carboxylate, which is prepared as in US 20150315198, utilizing the procedures herein described.

Examples 356-363 are prepared using procedures similar to those described above.

| Example | Structure |
|---|---|
| 213 | 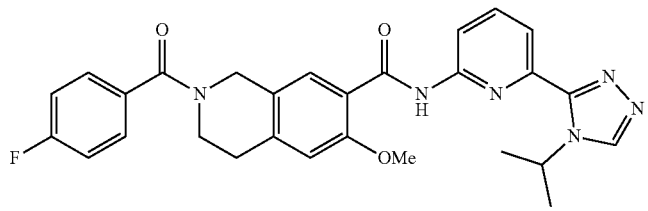 [SMILES: COc1cc2c(cc1C(=O)Nc1cccc(-c3nncn3C(C)C)n1)CN(C(=O)c1ccc(F)cc1)CC2] |
| 214 | 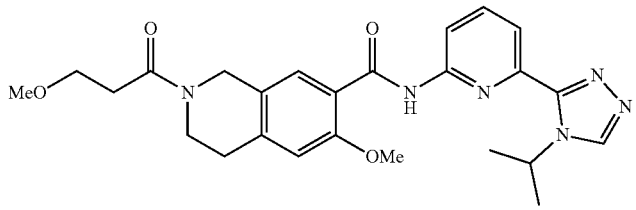 [SMILES: COCCC(=O)N1CCc2cc(OC)c(C(=O)Nc3cccc(-c4nncn4C(C)C)n3)cc2C1] |
| 215 | 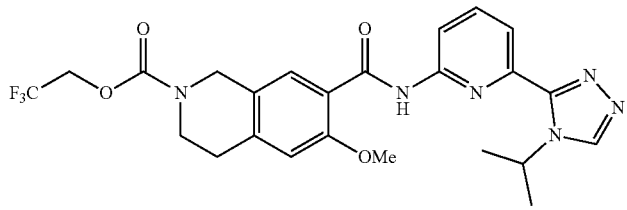 [SMILES: COc1cc2c(cc1C(=O)Nc1cccc(-c3nncn3C(C)C)n1)CN(C(=O)OCC(F)(F)F)CC2] |
| 216 | 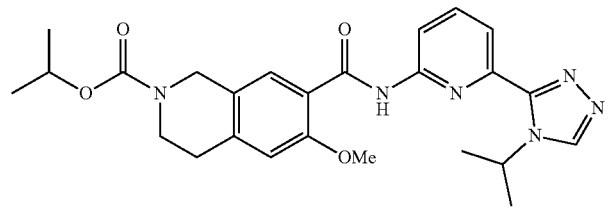 [SMILES: COc1cc2c(cc1C(=O)Nc1cccc(-c3nncn3C(C)C)n1)CN(C(=O)OC(C)C)CC2] |
| 217 | 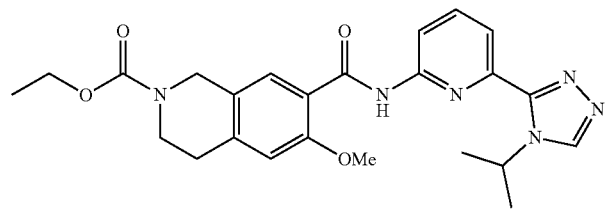 [SMILES: CCOC(=O)N1CCc2cc(OC)c(C(=O)Nc3cccc(-c4nncn4C(C)C)n3)cc2C1] |
| 218 | 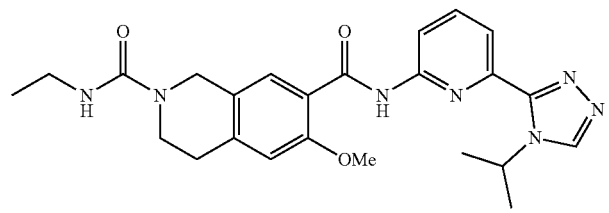 [SMILES: CCNC(=O)N1CCc2cc(OC)c(C(=O)Nc3cccc(-c4nncn4C(C)C)n3)cc2C1] |
| 219 | 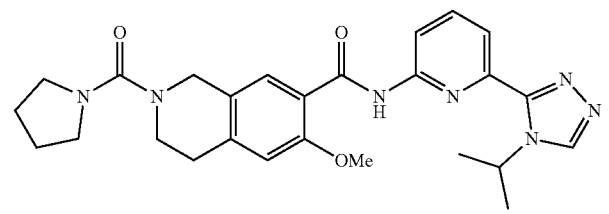 |

-continued
| Example | Structure |
|---|---|
| 220 | 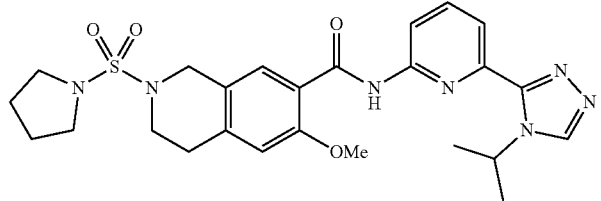 [SMILES: COc1cc2c(cc1C(=O)Nc1cccc(-c3nncn3C(C)C)n1)CN(S(=O)(=O)N1CCCC1)CC2] |
| 221 | 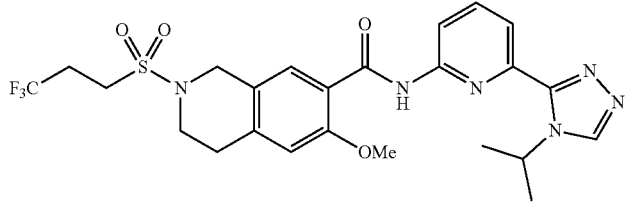 [SMILES: COc1cc2c(cc1C(=O)Nc1cccc(-c3nncn3C(C)C)n1)CN(S(=O)(=O)CCC(F)(F)F)CC2] |
| 222 | 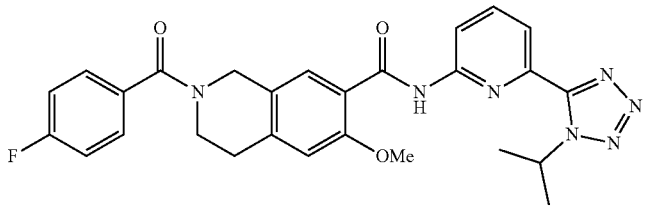 [SMILES: COc1cc2c(cc1C(=O)Nc1cccc(-c3nnnn3C(C)C)n1)CN(C(=O)c1ccc(F)cc1)CC2] |
| 223 | 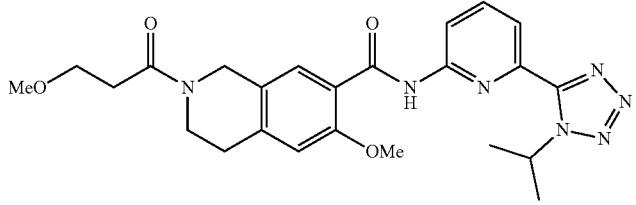 |
| 224 | 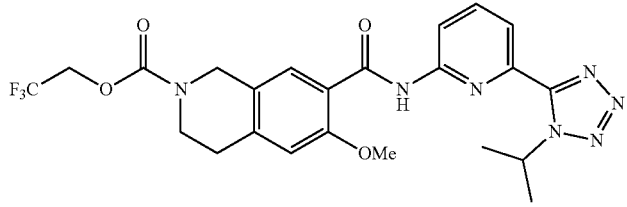 [SMILES: COc1cc2c(cc1C(=O)Nc1cccc(-c3nnnn3C(C)C)n1)CN(C(=O)OCC(F)(F)F)CC2] |
| 225 | 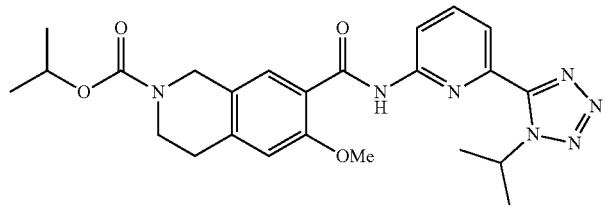 [SMILES: COc1cc2c(cc1C(=O)Nc1cccc(-c3nnnn3C(C)C)n1)CN(C(=O)OC(C)C)CC2] |
| 226 | 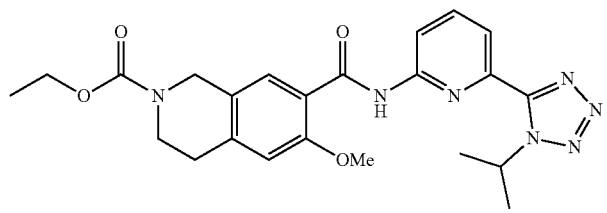 [SMILES: CCOC(=O)N1CCc2cc(OC)c(C(=O)Nc3cccc(-c4nnnn4C(C)C)n3)cc2C1] |

| Example | Structure |
|---|---|
| 227 | 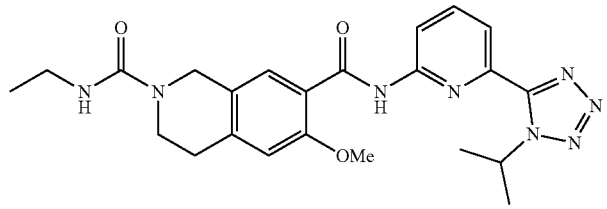 |
| 228 | 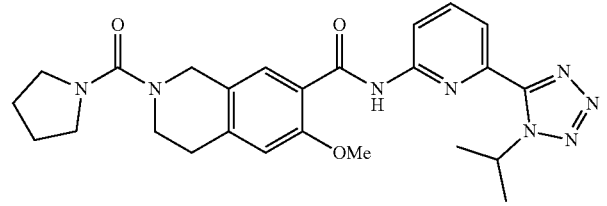 [SMILES: COc1cc2c(cc1C(=O)Nc1cccc(-c3nnnn3C(C)C)n1)CN(C(=O)N1CCCC1)CC2] |
| 229 | 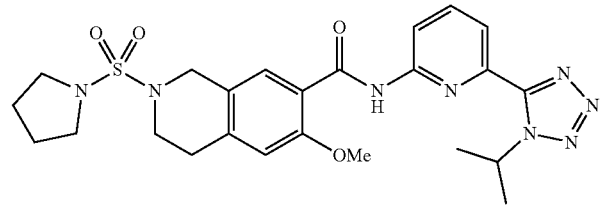 [SMILES: COc1cc2c(cc1C(=O)Nc1cccc(-c3nnnn3C(C)C)n1)CN(S(=O)(=O)N1CCCC1)CC2] |
| 230 | 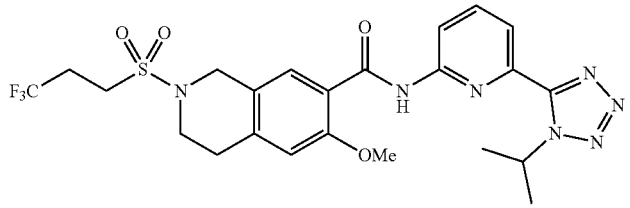 [SMILES: COc1cc2c(cc1C(=O)Nc1cccc(-c3nnnn3C(C)C)n1)CN(S(=O)(=O)CCC(F)(F)F)CC2] |
| 231 | 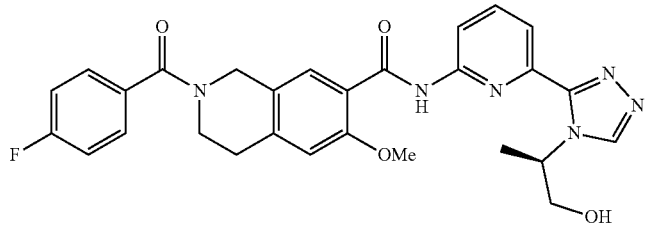 [SMILES: COc1cc2c(cc1C(=O)Nc1cccc(-c3nncn3[C@H](C)CO)n1)CN(C(=O)c1ccc(F)cc1)CC2] |
| 232 | 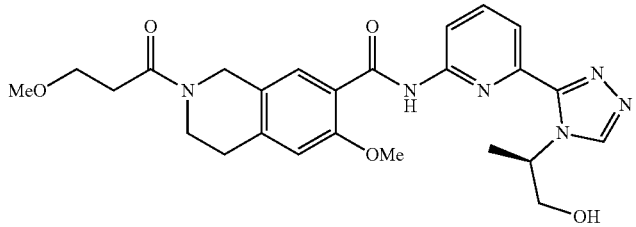 [SMILES: COCCC(=O)N1CCc2cc(OC)c(C(=O)Nc3cccc(-c4nncn4[C@H](C)CO)n3)cc2C1] |
| 233 | 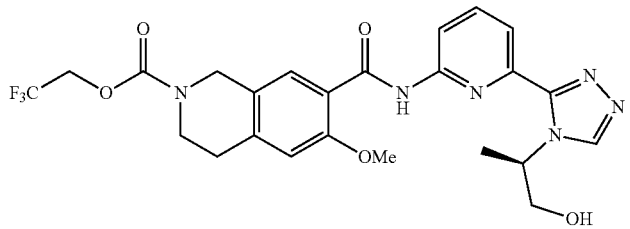 [SMILES: COc1cc2c(cc1C(=O)Nc1cccc(-c3nncn3[C@H](C)CO)n1)CN(C(=O)OCC(F)(F)F)CC2] |

-continued
| Example | Structure |
|---|---|
| 234 | 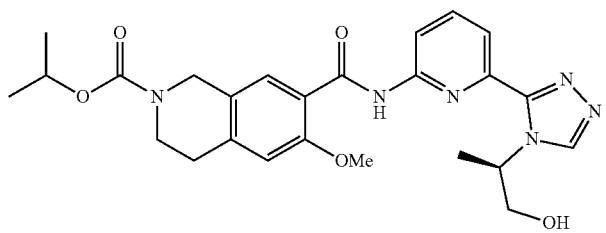 [SMILES: COc1cc2c(cc1C(=O)Nc1cccc(-c3nncn3[C@H](C)CO)n1)CN(C(=O)OC(C)C)CC2] |
| 235 | 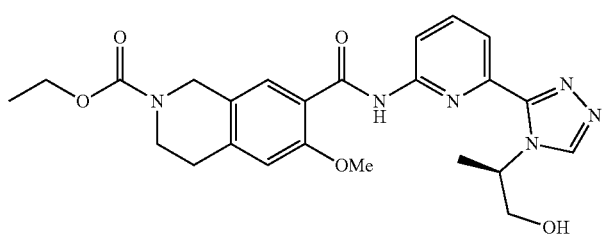 [SMILES: CCOC(=O)N1CCc2cc(OC)c(C(=O)Nc3cccc(-c4nncn4[C@H](C)CO)n3)cc2C1] |
| 236 | 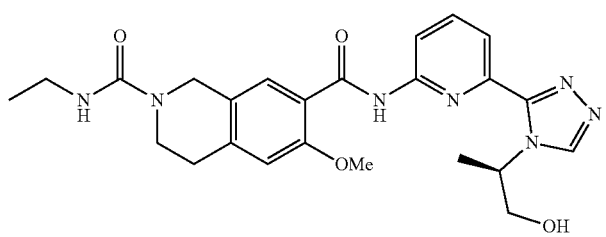 [SMILES: CCNC(=O)N1CCc2cc(OC)c(C(=O)Nc3cccc(-c4nncn4[C@H](C)CO)n3)cc2C1] |
| 237 | 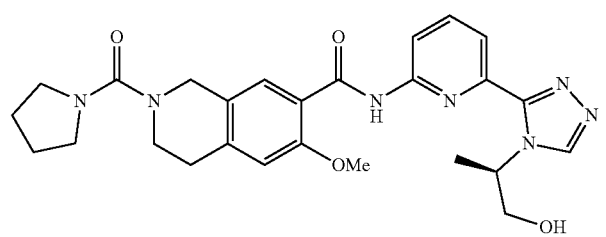 [SMILES: COc1cc2c(cc1C(=O)Nc1cccc(-c3nncn3[C@H](C)CO)n1)CN(C(=O)N1CCCC1)CC2] |
| 238 | 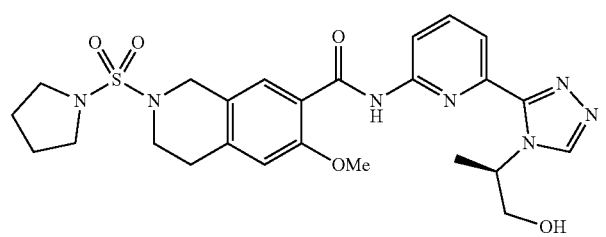 [SMILES: COc1cc2c(cc1C(=O)Nc1cccc(-c3nncn3[C@H](C)CO)n1)CN(S(=O)(=O)N1CCCC1)CC2] |
| 239 | 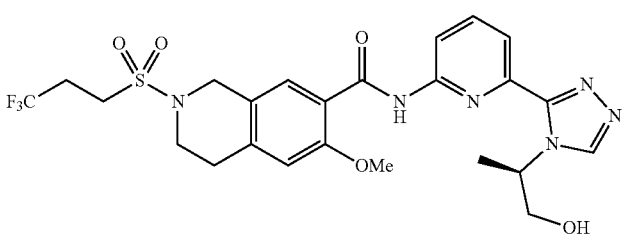 [SMILES: COc1cc2c(cc1C(=O)Nc1cccc(-c3nncn3[C@H](C)CO)n1)CN(S(=O)(=O)CCC(F)(F)F)CC2] |

| Example | Structure |
|---|---|
| 240 | 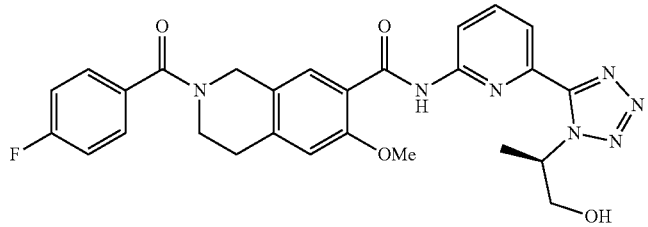 [SMILES: COc1cc2c(cc1C(=O)Nc1cccc(-c3nnnn3[C@H](C)CO)n1)CN(C(=O)c1ccc(F)cc1)CC2] |
| 241 | 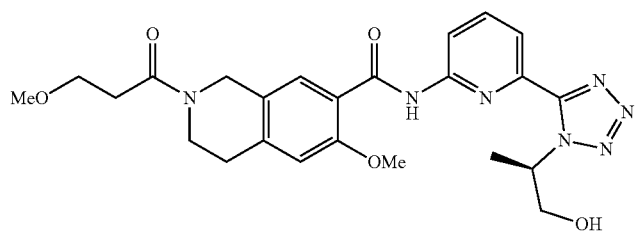 [SMILES: COCCC(=O)N1CCc2cc(OC)c(C(=O)Nc3cccc(-c4nnnn4[C@H](C)CO)n3)cc2C1] |
| 242 | 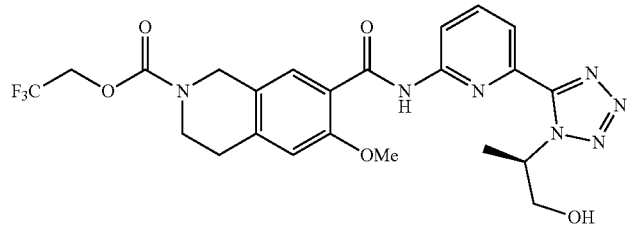 [SMILES: COc1cc2c(cc1C(=O)Nc1cccc(-c3nnnn3[C@H](C)CO)n1)CN(C(=O)OCC(F)(F)F)CC2] |
| 243 | 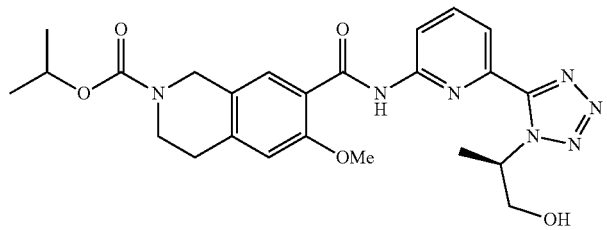 [SMILES: COc1cc2c(cc1C(=O)Nc1cccc(-c3nnnn3[C@H](C)CO)n1)CN(C(=O)OC(C)C)CC2] |
| 244 | 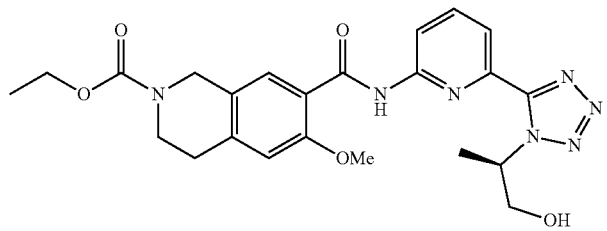 [SMILES: CCOC(=O)N1CCc2cc(OC)c(C(=O)Nc3cccc(-c4nnnn4[C@H](C)CO)n3)cc2C1] |
| 245 | 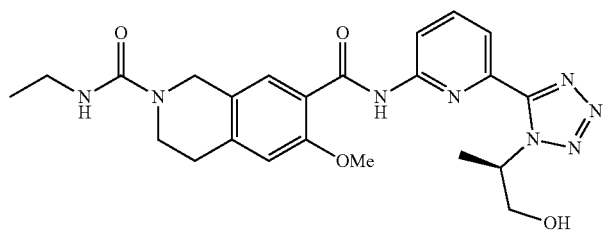 [SMILES: CCNC(=O)N1CCc2cc(OC)c(C(=O)Nc3cccc(-c4nnnn4[C@H](C)CO)n3)cc2C1] |

| Example | Structure |
|---|---|
| 246 | 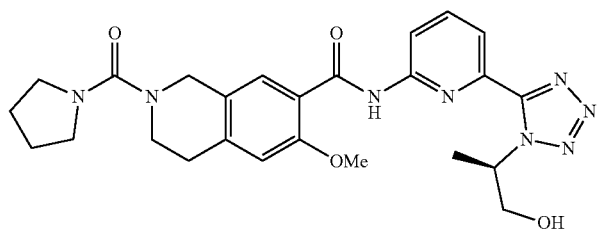 [SMILES: COc1cc2c(cc1C(=O)Nc1cccc(-c3nnnn3[C@H](C)CO)n1)CN(C(=O)N1CCCC1)CC2] |
| 247 | 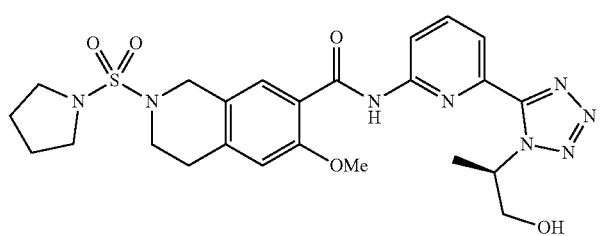 |
| 248 | 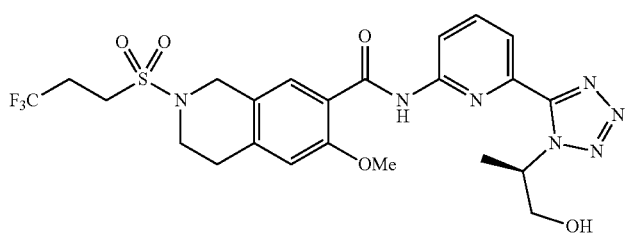 [SMILES: COc1cc2c(cc1C(=O)Nc1cccc(-c3nnnn3[C@H](C)CO)n1)CN(S(=O)(=O)CCC(F)(F)F)CC2] |
| 249 | 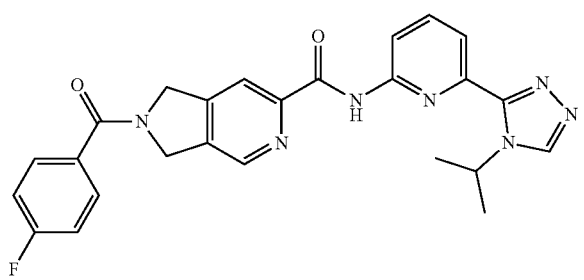 [SMILES: CC(C)n1cnnc1-c1cccc(NC(=O)c2cc3c(cn2)CN(C(=O)c2ccc(F)cc2)C3)n1] |
| 250 | 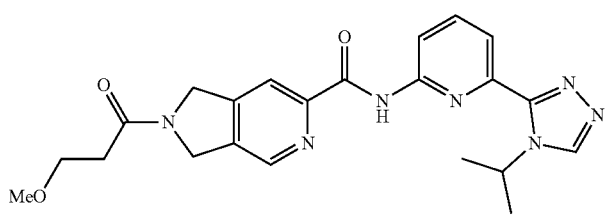 [SMILES: COCCC(=O)N1Cc2cnc(C(=O)Nc3cccc(-c4nncn4C(C)C)n3)cc2C1] |
| 251 | 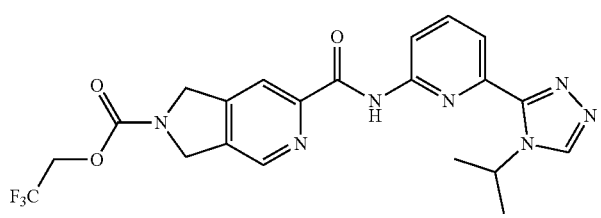 [SMILES: CC(C)n1cnnc1-c1cccc(NC(=O)c2cc3c(cn2)CN(C(=O)OCC(F)(F)F)C3)n1] |

-continued
| Example | Structure |
|---------|-----------|
| 252 | 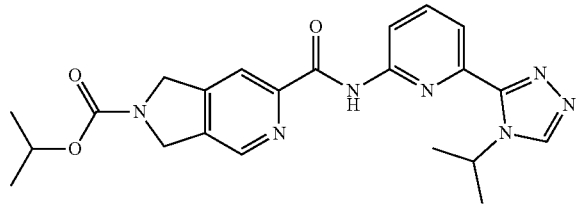 [SMILES: CC(C)OC(=O)N1Cc2cnc(C(=O)Nc3cccc(-c4nncn4C(C)C)n3)cc2C1] |
| 253 | 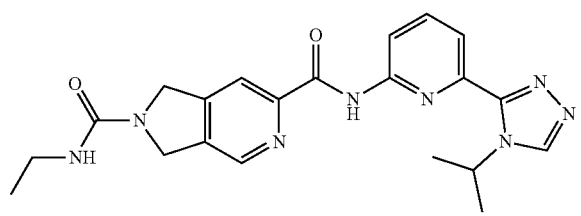 [SMILES: CCNC(=O)N1Cc2cnc(C(=O)Nc3cccc(-c4nncn4C(C)C)n3)cc2C1] |
| 254 | 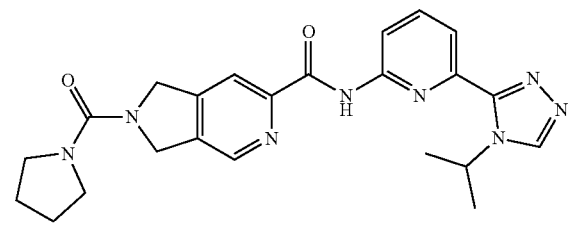 |
| 255 | 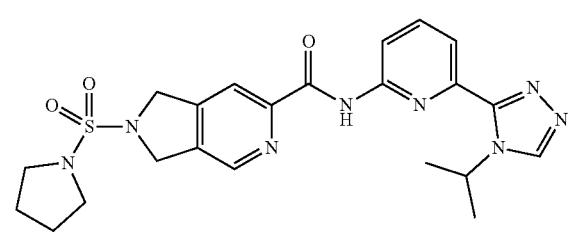 [SMILES: CC(C)n1cnnc1-c1cccc(NC(=O)c2cc3c(cn2)CN(S(=O)(=O)N2CCCC2)C3)n1] |
| 256 | 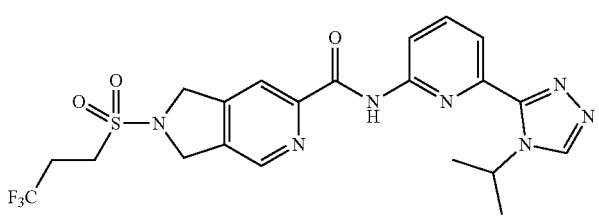 [SMILES: CC(C)n1cnnc1-c1cccc(NC(=O)c2cc3c(cn2)CN(S(=O)(=O)CCC(F)(F)F)C3)n1] |
| 257 | 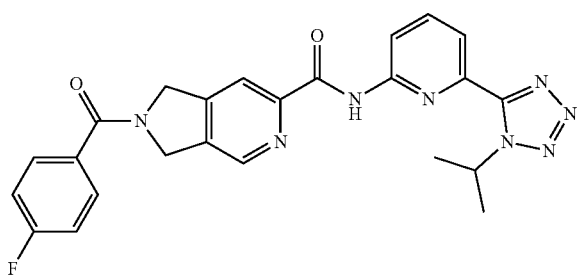 |

| Example | Structure |
|---------|-----------|
| 258 | 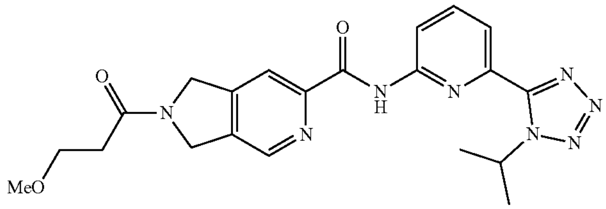 |
| 259 | 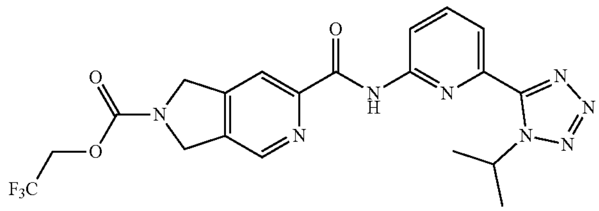 [SMILES: CC(C)n1nnnc1-c1cccc(NC(=O)c2cc3c(cn2)CN(C(=O)OCC(F)(F)F)C3)n1] |
| 260 | 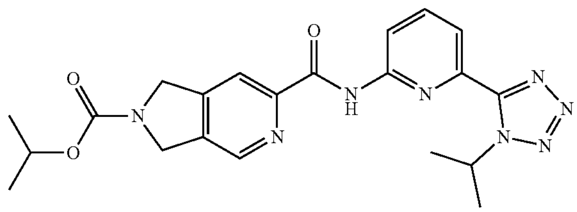 [SMILES: CC(C)OC(=O)N1Cc2cnc(C(=O)Nc3cccc(-c4nnnn4C(C)C)n3)cc2C1] |
| 261 | 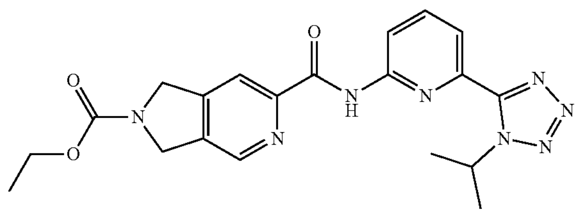 [SMILES: CCOC(=O)N1Cc2cnc(C(=O)Nc3cccc(-c4nnnn4C(C)C)n3)cc2C1] |
| 262 | 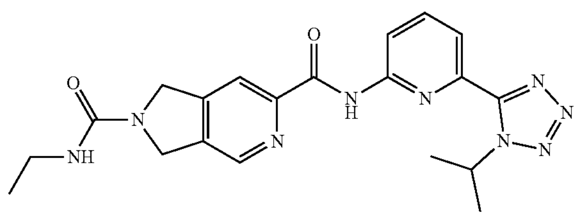 |
| 263 | 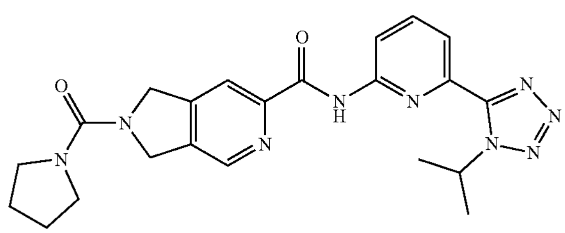 [SMILES: CC(C)n1nnnc1-c1cccc(NC(=O)c2cc3c(cn2)CN(C(=O)N2CCCC2)C3)n1] |
| 264 | 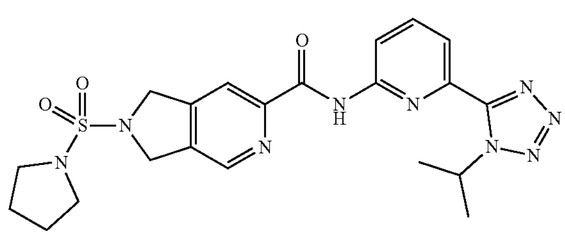 [SMILES: CC(C)n1nnnc1-c1cccc(NC(=O)c2cc3c(cn2)CN(S(=O)(=O)N2CCCC2)C3)n1] |

| Example | Structure |
|---|---|
| 265 | 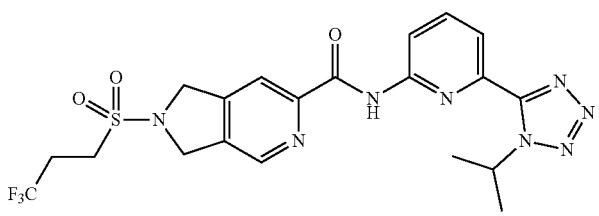 [SMILES: CC(C)n1nnnc1-c1cccc(NC(=O)c2cc3c(cn2)CN(S(=O)(=O)CCC(F)(F)F)C3)n1] |
| 266 | 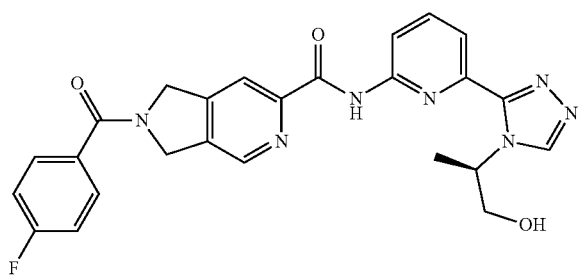 [SMILES: C[C@H](CO)n1cnnc1-c1cccc(NC(=O)c2cc3c(cn2)CN(C(=O)c2ccc(F)cc2)C3)n1] |
| 267 | 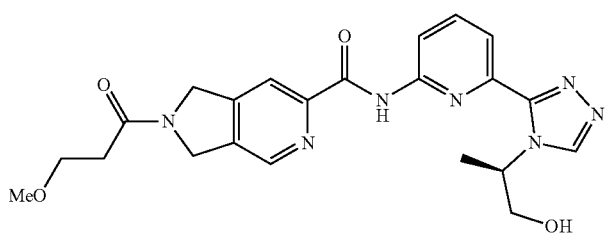 [SMILES: COCCC(=O)N1Cc2cnc(C(=O)Nc3cccc(-c4nncn4[C@H](C)CO)n3)cc2C1] |
| 268 | 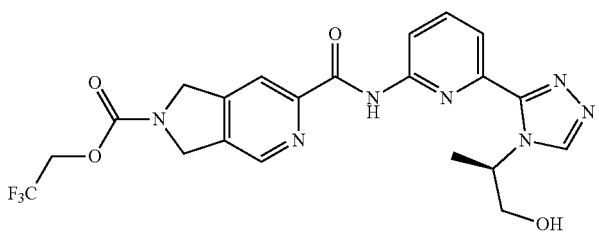 [SMILES: C[C@H](CO)n1cnnc1-c1cccc(NC(=O)c2cc3c(cn2)CN(C(=O)OCC(F)(F)F)C3)n1] |
| 269 | 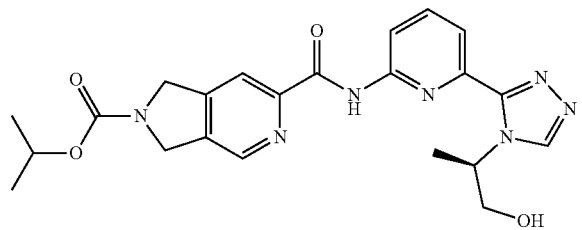 [SMILES: CC(C)OC(=O)N1Cc2cnc(C(=O)Nc3cccc(-c4nncn4[C@H](C)CO)n3)cc2C1] |
| 270 | 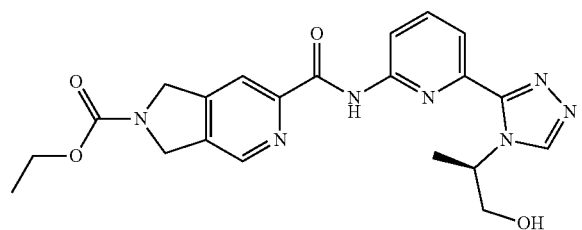 [SMILES: CCOC(=O)N1Cc2cnc(C(=O)Nc3cccc(-c4nncn4[C@H](C)CO)n3)cc2C1] |

-continued
| Example | Structure |
|---|---|
| 271 | 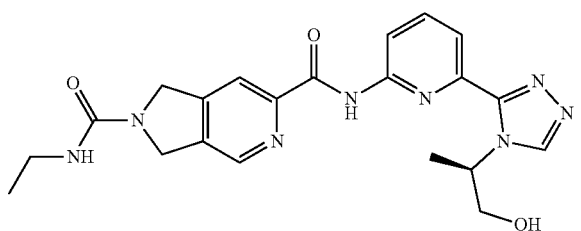 [SMILES: CCNC(=O)N1Cc2cnc(C(=O)Nc3cccc(-c4nncn4[C@H](C)CO)n3)cc2C1] |
| 272 | 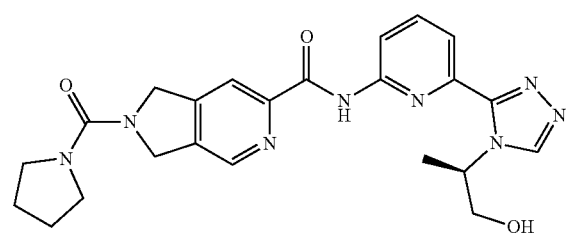 [SMILES: C[C@H](CO)n1cnnc1-c1cccc(NC(=O)c2cc3c(cn2)CN(C(=O)N2CCCC2)C3)n1] |
| 273 | 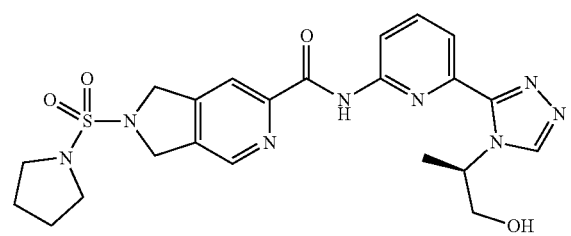 [SMILES: C[C@H](CO)n1cnnc1-c1cccc(NC(=O)c2cc3c(cn2)CN(S(=O)(=O)N2CCCC2)C3)n1] |
| 274 | 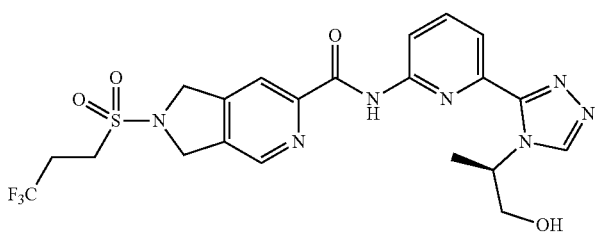 [SMILES: C[C@H](CO)n1cnnc1-c1cccc(NC(=O)c2cc3c(cn2)CN(S(=O)(=O)CCC(F)(F)F)C3)n1] |
| 275 | 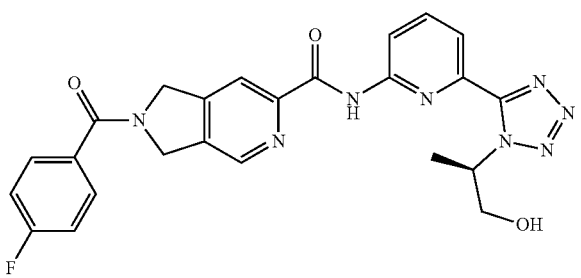 [SMILES: C[C@H](CO)n1nnnc1-c1cccc(NC(=O)c2cc3c(cn2)CN(C(=O)c2ccc(F)cc2)C3)n1] |
| 276 | 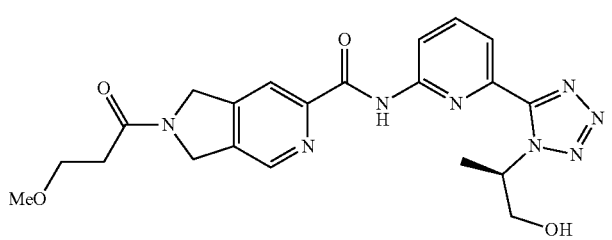 [SMILES: COCCC(=O)N1Cc2cnc(C(=O)Nc3cccc(-c4nnnn4[C@H](C)CO)n3)cc2C1] |

| Example | Structure |
|---|---|
| 277 | 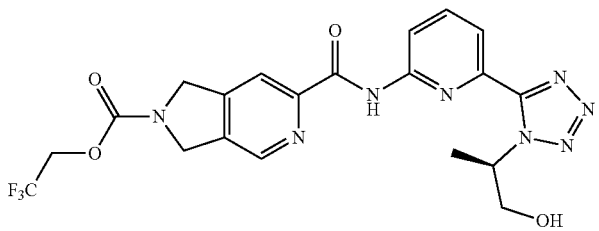 [SMILES: C[C@H](CO)n1nnnc1-c1cccc(NC(=O)c2cc3c(cn2)CN(C(=O)OCC(F)(F)F)C3)n1] |
| 278 | 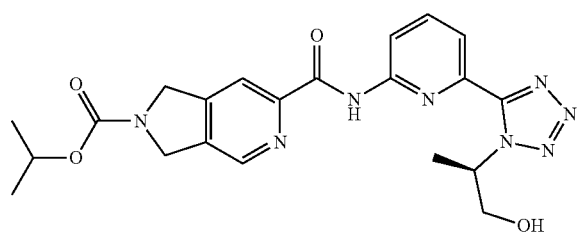 |
| 279 | 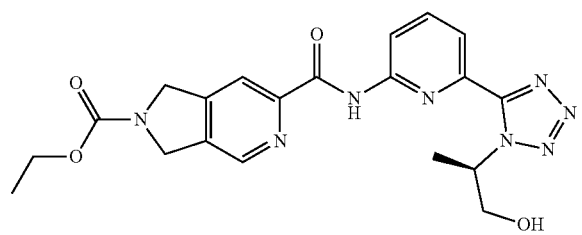 [SMILES: CCOC(=O)N1Cc2cnc(C(=O)Nc3cccc(-c4nnnn4[C@H](C)CO)n3)cc2C1] |
| 280 | 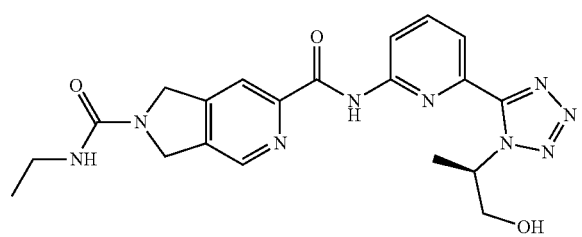 [SMILES: CCNC(=O)N1Cc2cnc(C(=O)Nc3cccc(-c4nnnn4[C@H](C)CO)n3)cc2C1] |
| 281 | 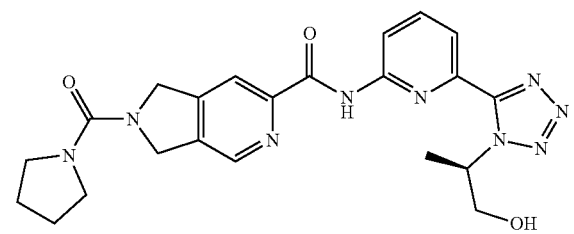 [SMILES: C[C@H](CO)n1nnnc1-c1cccc(NC(=O)c2cc3c(cn2)CN(C(=O)N2CCCC2)C3)n1] |
| 282 | 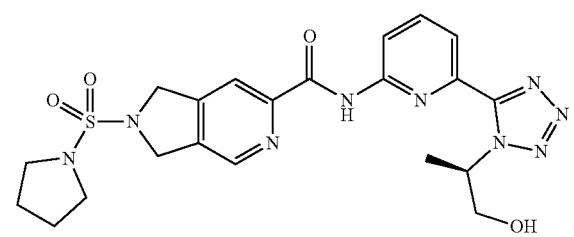 [SMILES: C[C@H](CO)n1nnnc1-c1cccc(NC(=O)c2cc3c(cn2)CN(S(=O)(=O)N2CCCC2)C3)n1] |

-continued
| Example | Structure |
|---|---|
| 283 | 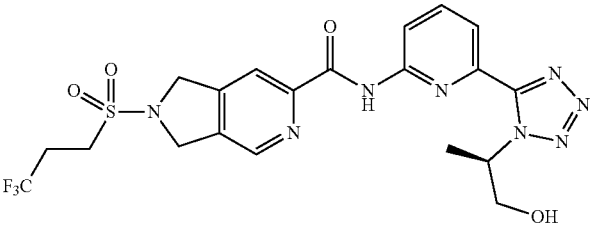 [SMILES: C[C@H](CO)n1nnnc1-c1cccc(NC(=O)c2cc3c(cn2)CN(S(=O)(=O)CCC(F)(F)F)C3)n1] |
| 284 | 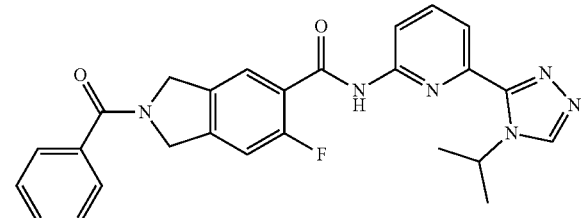 |
| 285 | 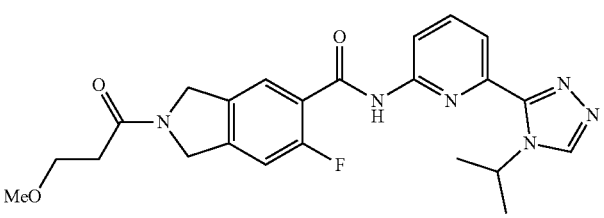 [SMILES: COCCC(=O)N1Cc2cc(F)c(C(=O)Nc3cccc(-c4nncn4C(C)C)n3)cc2C1] |
| 286 | 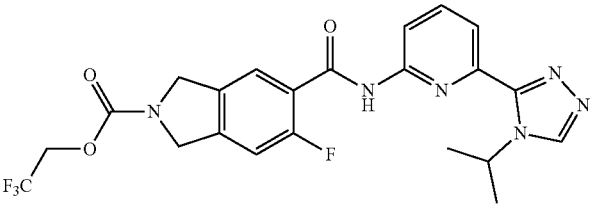 [SMILES: CC(C)n1cnnc1-c1cccc(NC(=O)c2cc3c(cc2F)CN(C(=O)OCC(F)(F)F)C3)n1] |
| 287 | 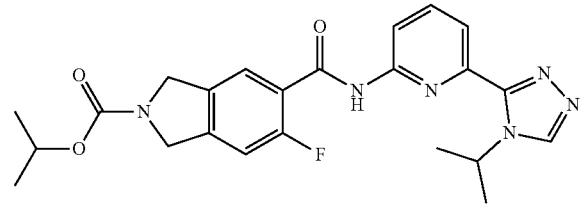 [SMILES: CC(C)OC(=O)N1Cc2cc(F)c(C(=O)Nc3cccc(-c4nncn4C(C)C)n3)cc2C1] |
| 288 | 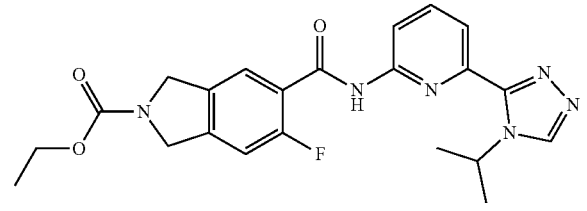 [SMILES: CCOC(=O)N1Cc2cc(F)c(C(=O)Nc3cccc(-c4nncn4C(C)C)n3)cc2C1] |
| 289 | 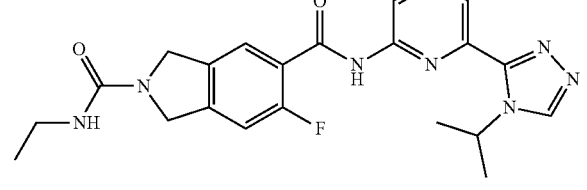 |

| Example | Structure |
|---|---|
| 290 | 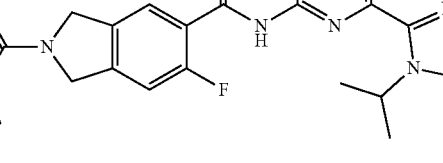 |
| 291 | 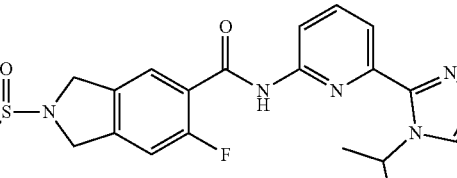 |
| 292 | 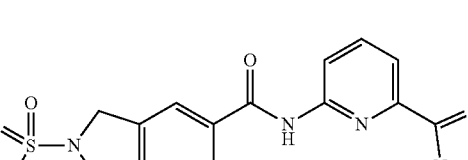 |
| 293 | 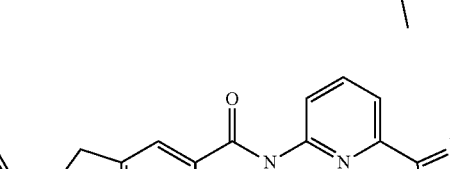 |
| 294 | 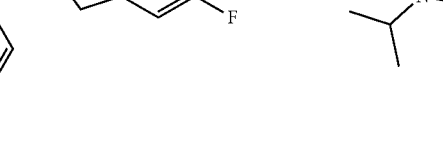 |
| 295 | 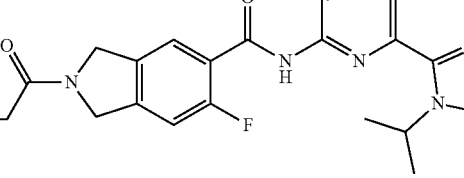 |

-continued
| Example | Structure |
|---|---|
| 296 | 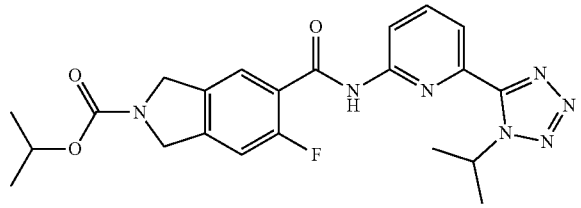 [SMILES: CC(C)OC(=O)N1Cc2cc(F)c(C(=O)Nc3cccc(-c4nnnn4C(C)C)n3)cc2C1] |
| 297 | 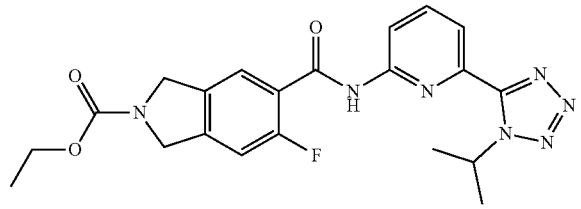 |
| 298 | 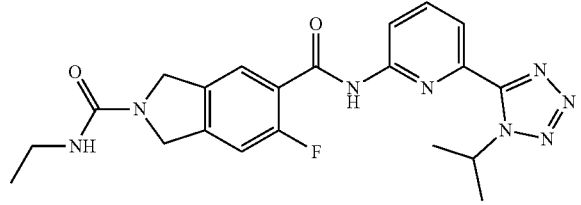 [SMILES: CCOC(=O)N1Cc2cc(F)c(C(=O)Nc3cccc(-c4nnnn4C(C)C)n3)cc2C1] |
| 299 | 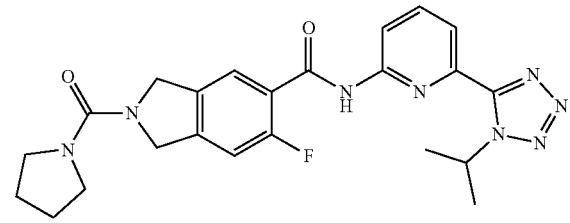 |
| 300 | 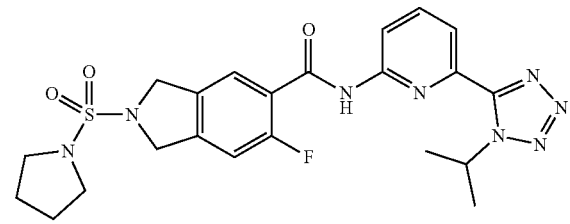 [SMILES: CC(C)n1nnnc1-c1cccc(NC(=O)c2cc3c(cc2F)CN(S(=O)(=O)N2CCCC2)C3)n1] |
| 301 | 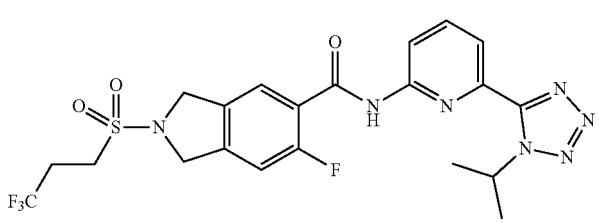 [SMILES: CC(C)n1nnnc1-c1cccc(NC(=O)c2cc3c(cc2F)CN(S(=O)(=O)CCC(F)(F)F)C3)n1] |

-continued
| Example | Structure |
|---|---|
| 302 | 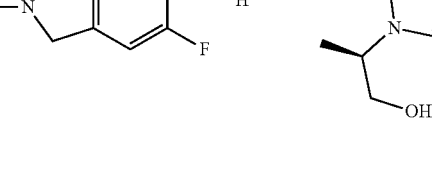 |
| 303 | 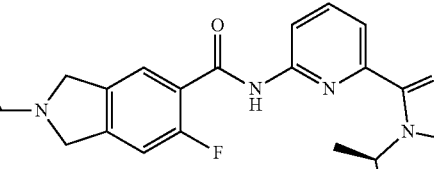 |
| 304 | 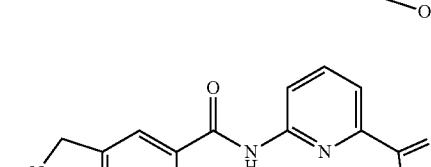 |
| 305 | 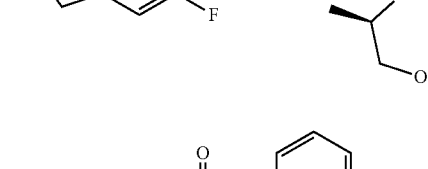 |
| 306 | 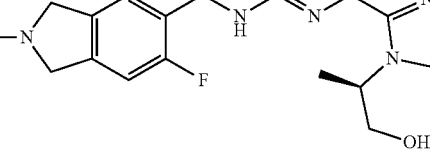 |
| 307 | 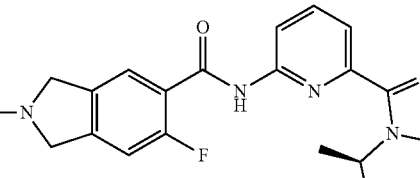 |

-continued
| Example | Structure |
|---|---|
| 308 | 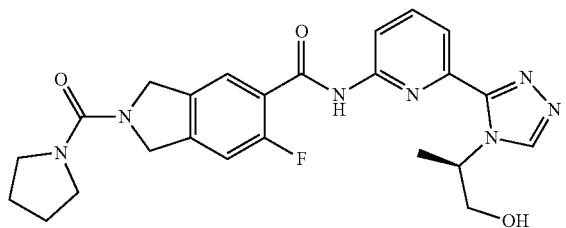 [SMILES: C[C@H](CO)n1cnnc1-c1cccc(NC(=O)c2cc3c(cc2F)CN(C(=O)N2CCCC2)C3)n1] |
| 309 | 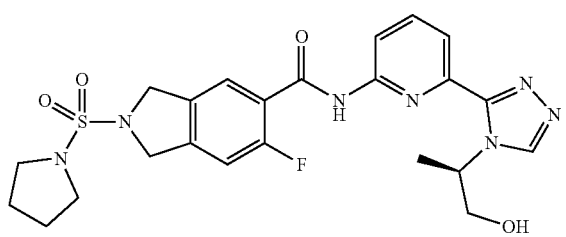 [SMILES: C[C@H](CO)n1cnnc1-c1cccc(NC(=O)c2cc3c(cc2F)CN(S(=O)(=O)N2CCCC2)C3)n1] |
| 310 | 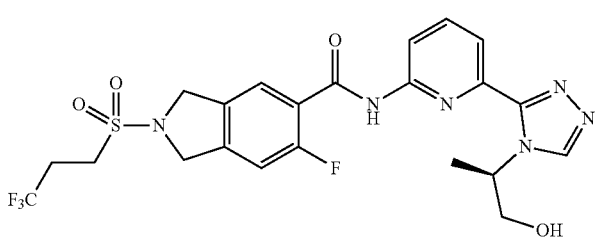 [SMILES: C[C@H](CO)n1cnnc1-c1cccc(NC(=O)c2cc3c(cc2F)CN(S(=O)(=O)CCC(F)(F)F)C3)n1] |
| 311 | 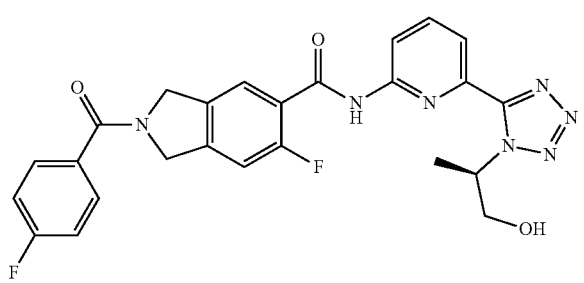 |
| 312 | 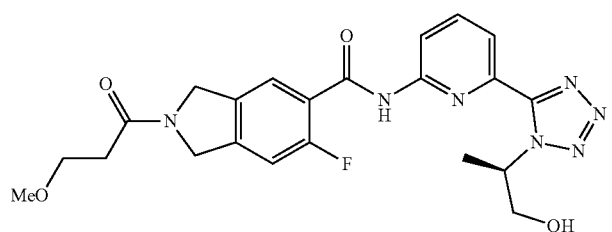 [SMILES: COCCC(=O)N1Cc2cc(F)c(C(=O)Nc3cccc(-c4nnnn4[C@H](C)CO)n3)cc2C1] |
| 313 | 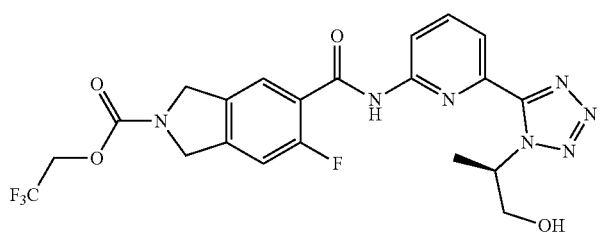 [SMILES: C[C@H](CO)n1nnnc1-c1cccc(NC(=O)c2cc3c(cc2F)CN(C(=O)OCC(F)(F)F)C3)n1] |

| Example | Structure |
|---|---|
| 314 | 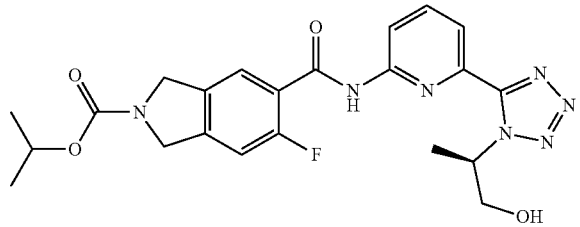 [SMILES: CC(C)OC(=O)N1Cc2cc(F)c(C(=O)Nc3cccc(-c4nnnn4[C@H](C)CO)n3)cc2C1] |
| 315 | 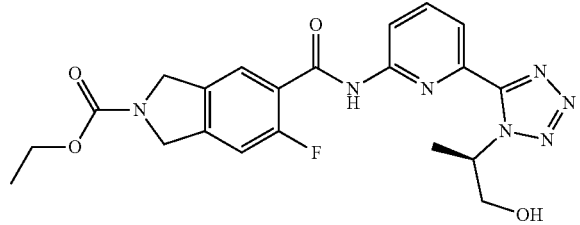 [SMILES: CCOC(=O)N1Cc2cc(F)c(C(=O)Nc3cccc(-c4nnnn4[C@H](C)CO)n3)cc2C1] |
| 316 | 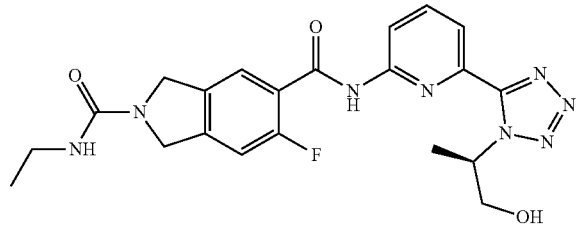 |
| 317 | 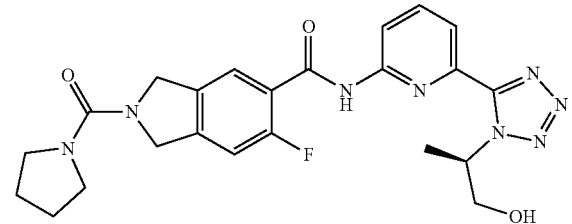 [SMILES: C[C@H](CO)n1nnnc1-c1cccc(NC(=O)c2cc3c(cc2F)CN(C(=O)N2CCCC2)C3)n1] |
| 318 | 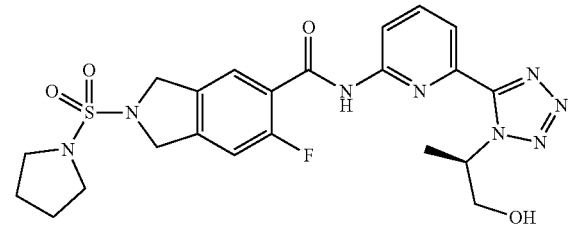 [SMILES: C[C@H](CO)n1nnnc1-c1cccc(NC(=O)c2cc3c(cc2F)CN(S(=O)(=O)N2CCCC2)C3)n1] |
| 319 | 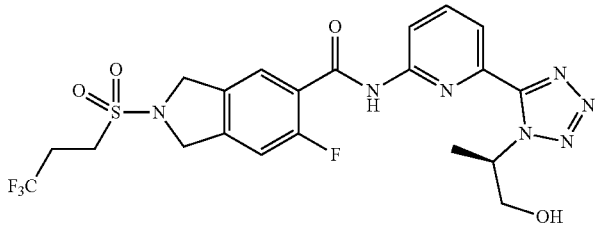 |

-continued
| Example | Structure |
|---|---|
| 320 | 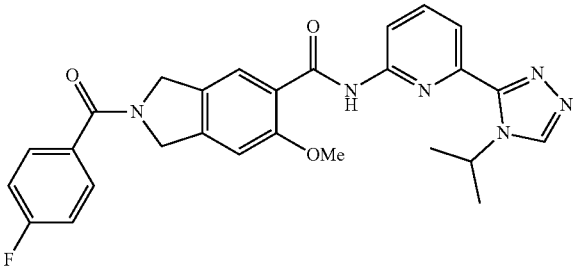 [SMILES: COc1cc2c(cc1C(=O)Nc1cccc(-c3nncn3C(C)C)n1)CN(C(=O)c1ccc(F)cc1)C2] |
| 321 | 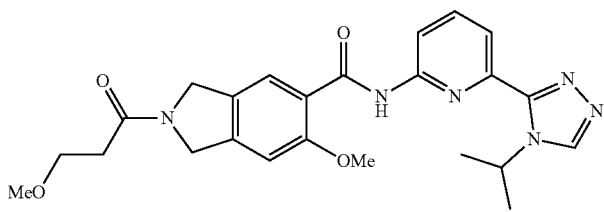 [SMILES: COCCC(=O)N1Cc2cc(OC)c(C(=O)Nc3cccc(-c4nncn4C(C)C)n3)cc2C1] |
| 322 | 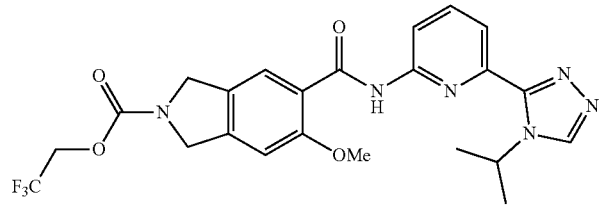 [SMILES: COc1cc2c(cc1C(=O)Nc1cccc(-c3nncn3C(C)C)n1)CN(C(=O)OCC(F)(F)F)C2] |
| 323 | 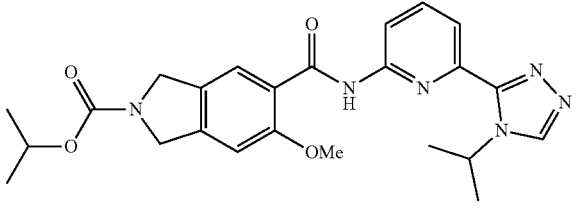 [SMILES: COc1cc2c(cc1C(=O)Nc1cccc(-c3nncn3C(C)C)n1)CN(C(=O)OC(C)C)C2] |
| 324 | 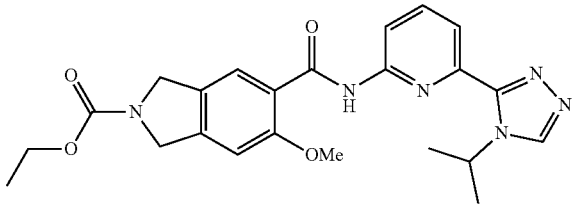 [SMILES: CCOC(=O)N1Cc2cc(OC)c(C(=O)Nc3cccc(-c4nncn4C(C)C)n3)cc2C1] |
| 325 | 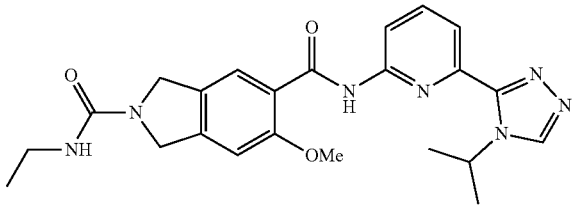 [SMILES: CCNC(=O)N1Cc2cc(OC)c(C(=O)Nc3cccc(-c4nncn4C(C)C)n3)cc2C1] |
| 326 | 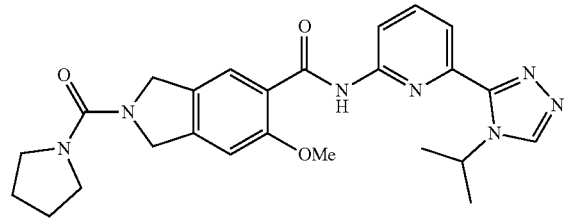 [SMILES: COc1cc2c(cc1C(=O)Nc1cccc(-c3nncn3C(C)C)n1)CN(C(=O)N1CCCC1)C2] |

-continued
| Example | Structure |
|---|---|
| 327 | 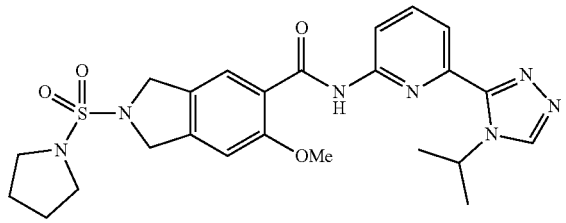 [SMILES: COc1cc2c(cc1C(=O)Nc1cccc(-c3nncn3C(C)C)n1)CN(S(=O)(=O)N1CCCC1)C2] |
| 328 | 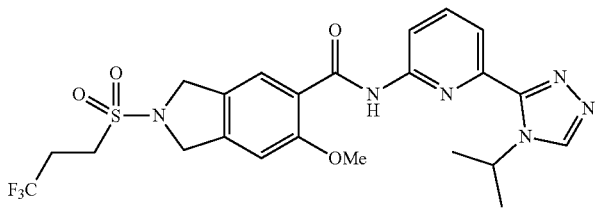 [SMILES: COc1cc2c(cc1C(=O)Nc1cccc(-c3nncn3C(C)C)n1)CN(S(=O)(=O)CCC(F)(F)F)C2] |
| 329 | 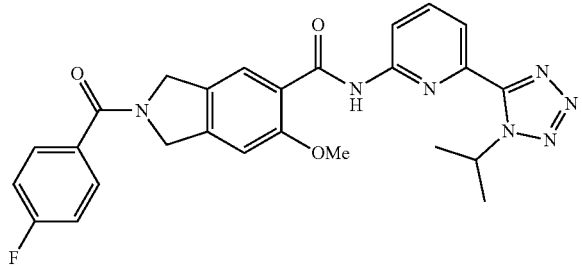 |
| 330 | 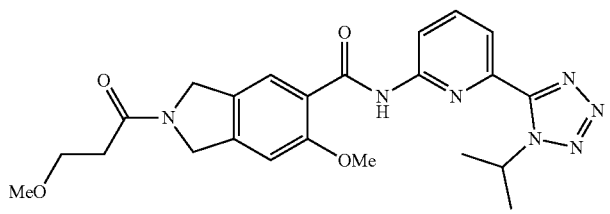 [SMILES: COCCC(=O)N1Cc2cc(OC)c(C(=O)Nc3cccc(-c4nnnn4C(C)C)n3)cc2C1] |
| 331 | 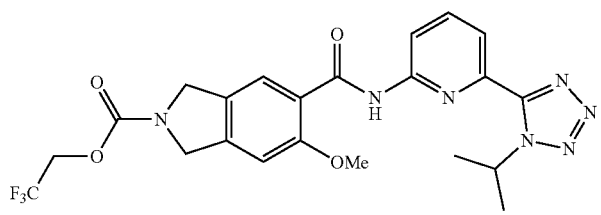 [SMILES: COc1cc2c(cc1C(=O)Nc1cccc(-c3nnnn3C(C)C)n1)CN(C(=O)OCC(F)(F)F)C2] |
| 332 | 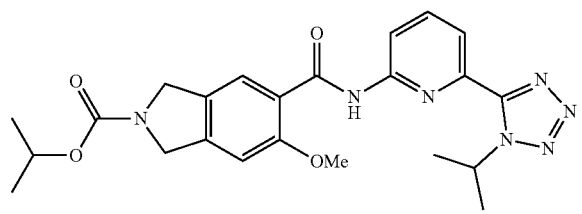 [SMILES: COc1cc2c(cc1C(=O)Nc1cccc(-c3nnnn3C(C)C)n1)CN(C(=O)OC(C)C)C2] |

-continued
| Example | Structure |
|---|---|
| 333 | 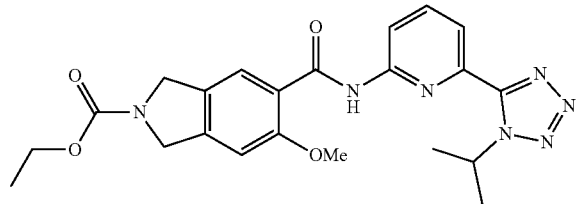 [SMILES: CCOC(=O)N1Cc2cc(OC)c(C(=O)Nc3cccc(-c4nnnn4C(C)C)n3)cc2C1] |
| 334 | 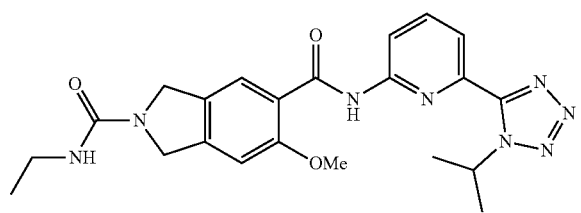 [SMILES: CCNC(=O)N1Cc2cc(OC)c(C(=O)Nc3cccc(-c4nnnn4C(C)C)n3)cc2C1] |
| 335 | 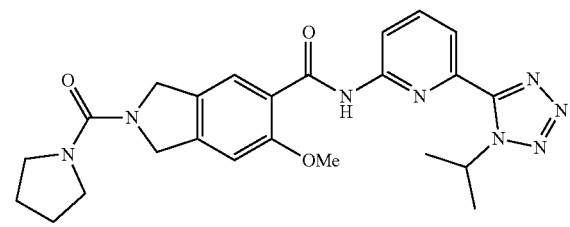 [SMILES: COc1cc2c(cc1C(=O)Nc1cccc(-c3nnnn3C(C)C)n1)CN(C(=O)N1CCCC1)C2] |
| 336 | 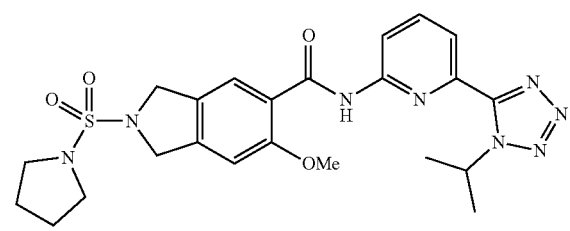 [SMILES: COc1cc2c(cc1C(=O)Nc1cccc(-c3nnnn3C(C)C)n1)CN(S(=O)(=O)N1CCCC1)C2] |
| 337 | 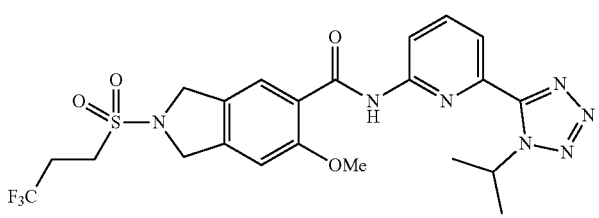 |
| 338 | 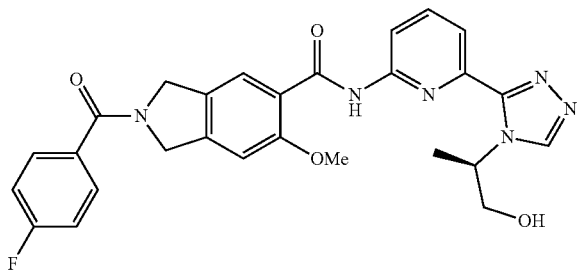 [SMILES: COc1cc2c(cc1C(=O)Nc1cccc(-c3nncn3[C@H](C)CO)n1)CN(C(=O)c1ccc(F)cc1)C2] |

-continued
| Example | Structure |
|---|---|
| 339 | 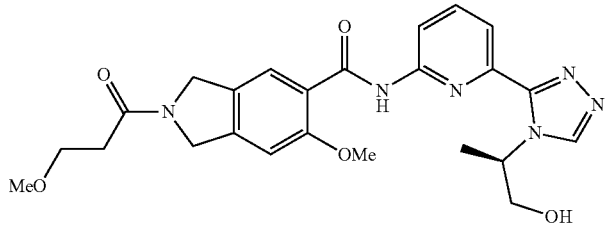 [SMILES: COCCC(=O)N1Cc2cc(OC)c(C(=O)Nc3cccc(-c4nncn4[C@H](C)CO)n3)cc2C1] |
| 340 | 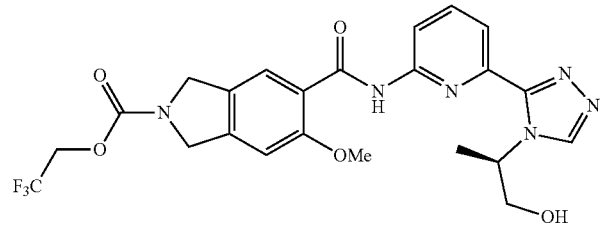 [SMILES: COc1cc2c(cc1C(=O)Nc1cccc(-c3nncn3[C@H](C)CO)n1)CN(C(=O)OCC(F)(F)F)C2] |
| 341 | 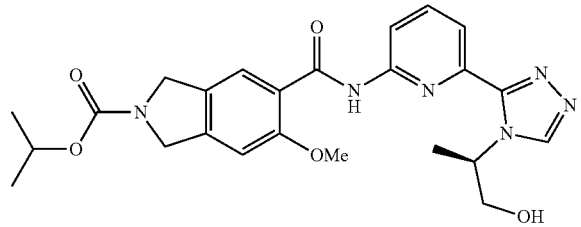 [SMILES: COc1cc2c(cc1C(=O)Nc1cccc(-c3nncn3[C@H](C)CO)n1)CN(C(=O)OC(C)C)C2] |
| 342 | 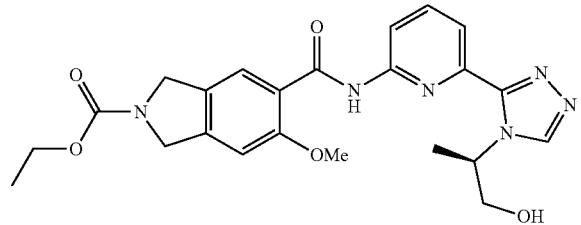 [SMILES: CCOC(=O)N1Cc2cc(OC)c(C(=O)Nc3cccc(-c4nncn4[C@H](C)CO)n3)cc2C1] |
| 343 | 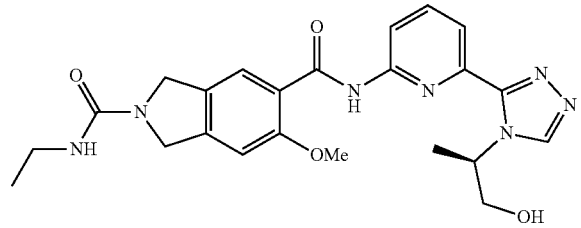 [SMILES: CCNC(=O)N1Cc2cc(OC)c(C(=O)Nc3cccc(-c4nncn4[C@H](C)CO)n3)cc2C1] |
| 344 | 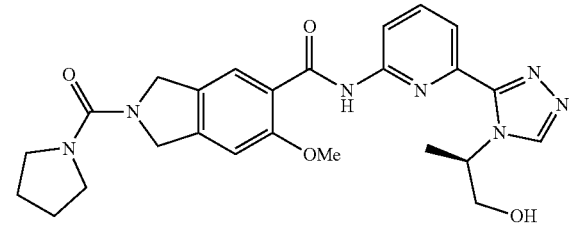 [SMILES: COc1cc2c(cc1C(=O)Nc1cccc(-c3nncn3[C@H](C)CO)n1)CN(C(=O)N1CCCC1)C2] |

-continued
| Example | Structure |
|---|---|
| 345 | 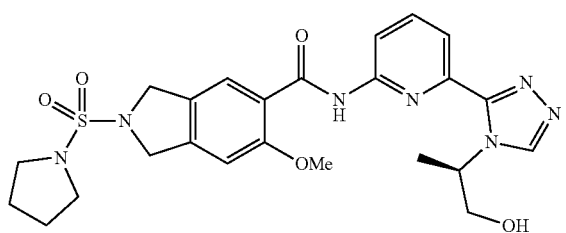 [SMILES: COc1cc2c(cc1C(=O)Nc1cccc(-c3nncn3[C@H](C)CO)n1)CN(S(=O)(=O)N1CCCC1)C2] |
| 346 | 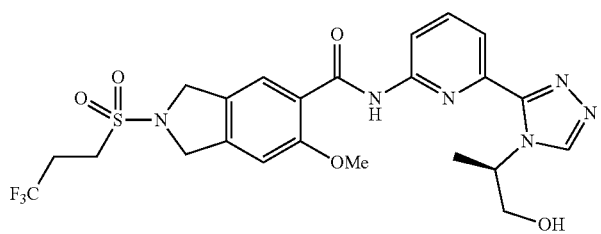 [SMILES: COc1cc2c(cc1C(=O)Nc1cccc(-c3nncn3[C@H](C)CO)n1)CN(S(=O)(=O)CCC(F)(F)F)C2] |
| 347 | 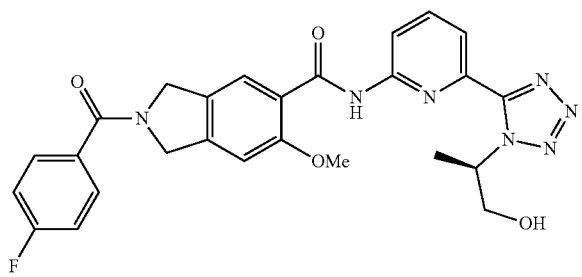 [SMILES: COc1cc2c(cc1C(=O)Nc1cccc(-c3nnnn3[C@H](C)CO)n1)CN(C(=O)c1ccc(F)cc1)C2] |
| 348 | 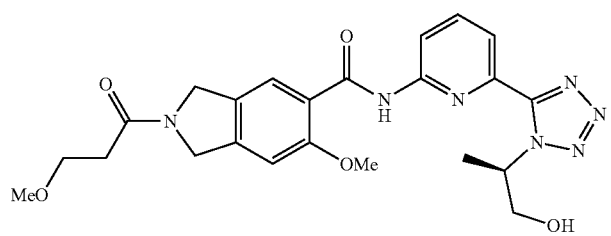 [SMILES: COCCC(=O)N1Cc2cc(OC)c(C(=O)Nc3cccc(-c4nnnn4[C@H](C)CO)n3)cc2C1] |
| 349 | 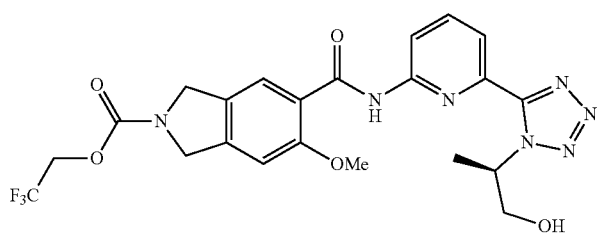 [SMILES: COc1cc2c(cc1C(=O)Nc1cccc(-c3nnnn3[C@H](C)CO)n1)CN(C(=O)OCC(F)(F)F)C2] |
| 350 | 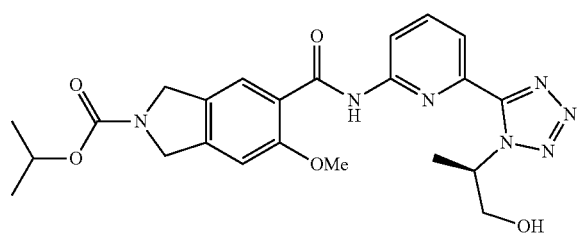 [SMILES: COc1cc2c(cc1C(=O)Nc1cccc(-c3nnnn3[C@H](C)CO)n1)CN(C(=O)OC(C)C)C2] |

| Example | Structure |
|---|---|
| 351 | 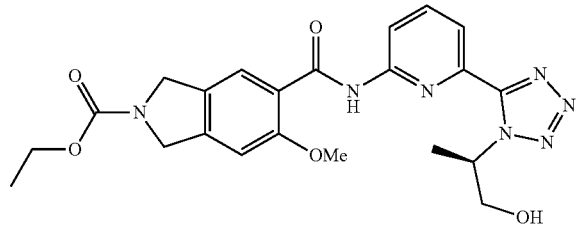 |
| 352 | 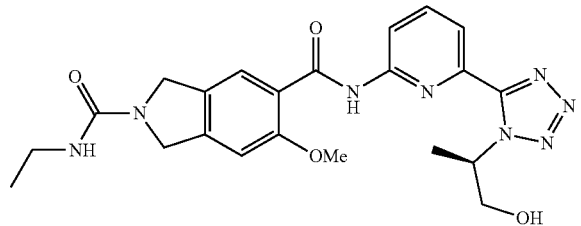 [SMILES: CCNC(=O)N1Cc2cc(OC)c(C(=O)Nc3cccc(-c4nnnn4[C@H](C)CO)n3)cc2C1] |
| 353 | 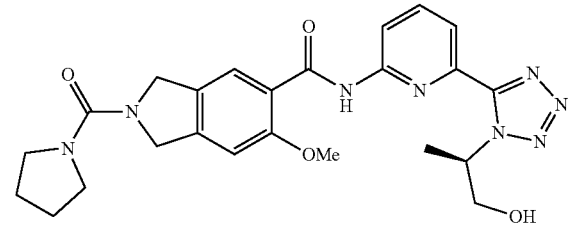 [SMILES: COc1cc2c(cc1C(=O)Nc1cccc(-c3nnnn3[C@H](C)CO)n1)CN(C(=O)N1CCCC1)C2] |
| 354 | 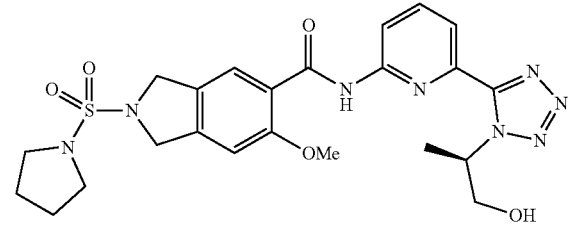 [SMILES: COc1cc2c(cc1C(=O)Nc1cccc(-c3nnnn3[C@H](C)CO)n1)CN(S(=O)(=O)N1CCCC1)C2] |
| 355 | 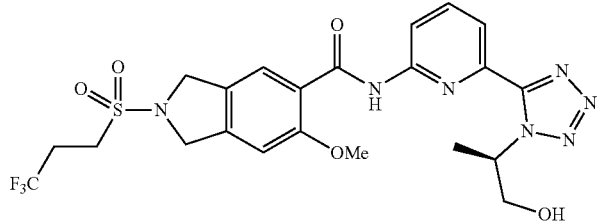 [SMILES: COc1cc2c(cc1C(=O)Nc1cccc(-c3nnnn3[C@H](C)CO)n1)CN(S(=O)(=O)CCC(F)(F)F)C2] |
| 356 | 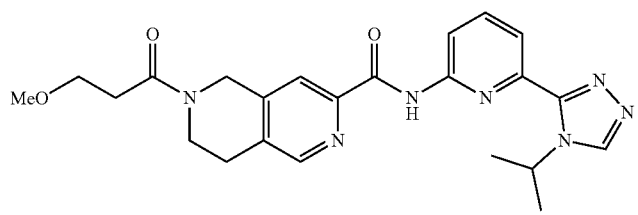 |

| Example | Structure |
|---|---|
| 357 | 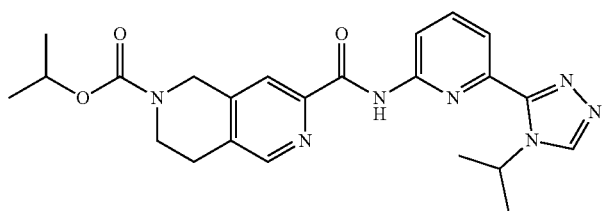 [SMILES: CC(C)OC(=O)N1CCc2cnc(C(=O)Nc3cccc(-c4nncn4C(C)C)n3)cc2C1] |
| 358 | 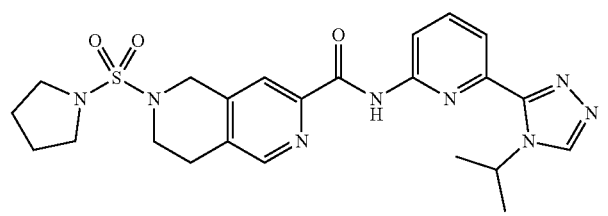 [SMILES: CC(C)n1cnnc1-c1cccc(NC(=O)c2cc3c(cn2)CCN(S(=O)(=O)N2CCCC2)C3)n1] |
| 359 | 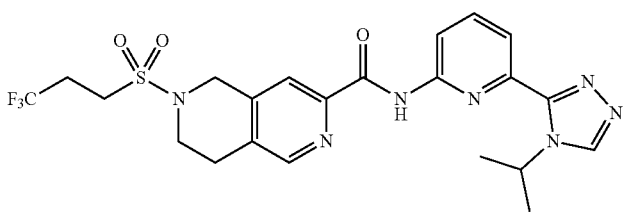 [SMILES: CC(C)n1cnnc1-c1cccc(NC(=O)c2cc3c(cn2)CCN(S(=O)(=O)CCC(F)(F)F)C3)n1] |
| 360 | 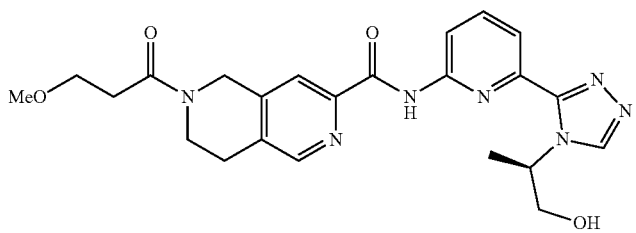 [SMILES: COCCC(=O)N1CCc2cnc(C(=O)Nc3cccc(-c4nncn4[C@H](C)CO)n3)cc2C1] |
| 361 | 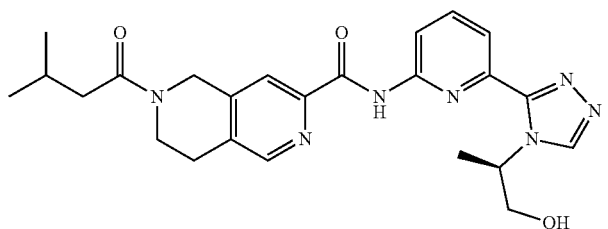 |
| 362 | 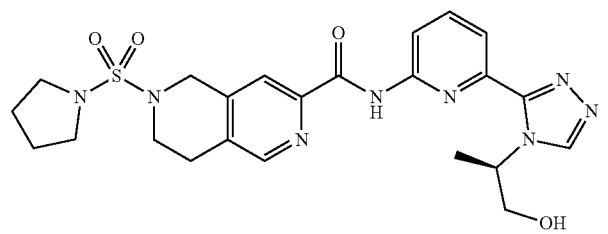 [SMILES: C[C@H](CO)n1cnnc1-c1cccc(NC(=O)c2cc3c(cn2)CCN(S(=O)(=O)N2CCCC2)C3)n1] |
| 363 | 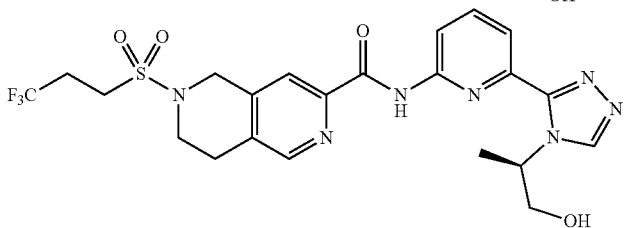 |

Assay
HTRF® KinEASE™ Assay

ASK1 was purchased from Thermofisher (Catalogue # PV4011), ATP was purchased from Sigma (Catalogue # A7699), HI-TRF® KinEASE™ Assay System was obtained from Cisbio (Bedford, Mass.). 1/2 Area plate was purchased from Perkin Elmer (Catalogue # #6005560). HTRF® KinEASE™-STK is a generic method for measuring serine/threonine kinase activities using a time-resolved fluorescence resonance energy transfer (TR-FRET) immunoassay. The $IC_{50}$ value for each compound was determined in the presence of compound (various concentration from 0 to 10 µM) and a fixed amount of ATP and peptide substrates. The test compound, 1 Um STK3 peptide substrate, and 5 Nm of ASK1 kinase are incubated with kinase reaction buffer containing 50 Mm HEPES Ph 7.5, 0.01% BRIJ-35, 10 Mm MgCl2, and 1 Mm EGTA for 30 minutes. 100 Um ATP is added to start kinase reaction and incubated for 3 hours. The STK3-antibody labeled with $Eu^{3+}$-Cryptate and 125 Nm streptavidin-XL665 are mixed in a single addition with stop reagents provided by the Cisbio kit used to stop the kinase reaction. Fluorescence is detected using an Envision Multilabeled 2014 reader from PerkinElmer. The Fluorescence is measured at 615 nm (Cryptate) and 665 nm (XL665) and a ratio of 665 nm/615 nm is calculated for each well. The resulting TR-FRET is proportional to the phosphorylation level. Staurosporine was used as the positive control. $IC_{50}$ was determined by Xlfit 5.3.

By using above method, the inhibition of ASK1 was evaluated for the compounds of Formula (I). $IC_{50}$ ranges are as follows: A=$IC_{50}$<1 Nm; B=1 Nm<$IC_{50}$<10 Nm; C=10 Nm<$IC_{50}$<100 Nm; D=100 Nm<$IC_{50}$<1 µM; E=$IC_{50}$>1 µM

TABLE 4

| Example | $IC_{50}$ | Example | $IC_{50}$ |
|---|---|---|---|
| 1 | D | 2 | E |
| 3 | C | 4 | D |
| 5 | D | 6 | D |
| 7 | D | 8 | E |
| 9 | E | 10 | E |
| 11 | D | 12 | D |
| 13 | E | 14 | E |
| 15 | E | 16 | E |
| 17 | C | 18 | C |
| 19 | C | 20 | B |
| 21 | B | 22 | B |
| 23 | B | 24 | B |
| 25 | B | 26 | B |
| 27 | C | 28 | C |
| 29 | B | 30 | C |
| 31 | C | 32 | C |
| 33 | C | 34 | C |
| 35 | C | 36 | C |
| 37 | D | 38 | D |
| 39 | D | 40 | C |
| 41 | B | 42 | B |
| 43 | C | 44 | B |
| 45 | B | 46 | B |
| 47 | B | 48 | B |
| 49 | B | 50 | C |
| 51 | B | 52 | B |
| 53 | C | 54 | C |
| 55 | C | 56 | C |
| 57 | C | 58 | D |
| 59 | C | 60 | C |
| 61 | C | 62 | B |
| 63 | B | 64 | C |
| 65 | C | 66 | C |
| 67 | C | 68 | D |
| 69 | C | 70 | C |
| 71 | E | 72 | E |
| 73 | E | 74 | D |
| 75 | C | 76 | B |
| 77 | C | 78 | C |
| 79 | C | 80 | C |
| 81 | E | 82 | B |
| 83 | E | 84 | E |
| 85 | C | 86 | C |
| 87 | C | 88 | E |
| 89 | C | 90 | C |
| 91 | C | 92 | C |
| 93 | C | 94 | B |
| 95 | C | 96 | C |
| 97 | C | 98 | E |
| 99 | D | 100 | E |
| 101 | E | 102 | C |
| 103 | C | 104 | C |
| 105 | C | 106 | C |
| 107 | C | 108 | D |
| 109 | E | 110 | B |
| 111 | C | 112 | C |
| 113 | B | 114 | C |
| 115 | B | 116 | B |
| 117 | B | 118 | B |
| 119 | B | 120 | B |
| 121 | B | 122 | B |
| 123 | B | 124 | B |
| 125 | B | 126 | A |
| 127 | B | 128 | B |
| 129 | B | 130 | B |
| 131 | B | 132 | B |
| 133 | B | 134 | B |
| 135 | C | 136 | C |
| 137 | B | 138 | B |
| 139 | B | 140 | C |
| 141 | B | 142 | B |
| 143 | B | 144 | B |
| 145 | B | 146 | B |
| 147 | D | 148 | B |
| 149 | B | 150 | B |
| 151 | B | 152 | B |
| 153 | C | 154 | B |
| 155 | B | 156 | B |
| 157 | B | 158 | B |
| 159 | B | 160 | B |
| 161 | B | 162 | B |
| 163 | B | 164 | B |
| 165 | B | 166 | B |
| 167 | B | 168 | B |
| 169 | B | 170 | B |
| 171 | B | 172 | B |
| 173 | B | 174 | D |
| 175 | C | 176 | E |
| 177 | E | 178 | B |
| 179 | C | 180 | E |
| 181 | B | 182 | B |
| 183 | B | 184 | E |
| 185 | B | 186 | C |
| 187 | A | 188 | B |
| 189 | C | 190 | B |
| 183a | E | | |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula I, or a pharmaceutically acceptable salt thereof:

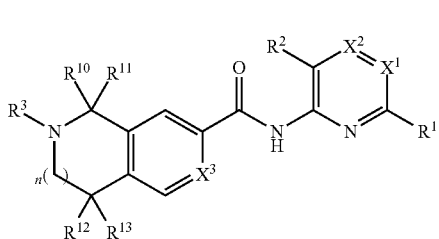

(I)

wherein $X^1$ and $X^2$ are each independently $C(R^8)$ or N;

$X^3$ is $C(R^9)$ or N, wherein $R^9$ is selected from the group consisting of hydrogen, optionally substituted —$C_1$-$C_8$ alkyl, optionally substituted —$C_1$-$C_8$ alkoxy and halo;

$R^1$ is selected from

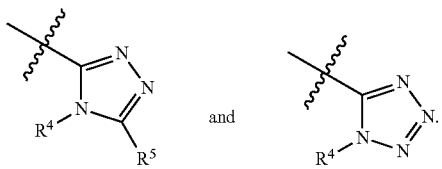

and $R^4$ is selected from the group consisting of:
1) Hydrogen;
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted 3- to 8-membered heterocycloalkyl;
9) Substituted or unsubstituted heteroaryl; and
10) Substituted or unsubstituted heteroarylalkyl;

$R^2$, $R^5$ and $R^8$ are each independently selected from the group consisting of:
1) Hydrogen;
2) Halogen;
3) —$NO_2$;
4) Cyano;
5) Substituted or unsubstituted —$C_1$-$C_8$ alkyl;
6) Substituted or unsubstituted —$C_2$-$C_8$ alkenyl;
7) Substituted or unsubstituted —$C_2$-$C_8$ alkynyl;
8) Substituted or unsubstituted —$C_3$-$C_8$ cycloalkyl;
9) Substituted or unsubstituted aryl;
10) Substituted or unsubstituted arylalkyl;
11) Substituted or unsubstituted heterocycloalkyl;
12) Substituted or unsubstituted heteroaryl;
13) Substituted or unsubstituted heteroarylalkyl;
14) —$N(R^6)(R^7)$;
15) —$S(O)_2N(R^6)(R^7)$;
16) —$N(R^6)C(O)R^7$; and
17) —$N(R^6)S(O)_2R^6$;

$R^6$ and $R^7$ are independently selected from the group consisting of hydrogen, —$C_1$-$C_8$ alkyl, —$C_1$-$C_8$ alkenyl, —$C_1$-$C_8$ alkynyl, —$C_3$-$C_8$ cycloalkyl, —$C_3$-$C_8$ cycloalkyl-alkyl, aryl, arylalkyl, heterocycloalkyl, heteroaryl, and heteroarylalkyl, wherein the —$C_1$-$C_8$ alkyl, —$C_1$-$C_8$ alkenyl, —$C_1$-$C_8$ alkynyl, —$C_3$-$C_8$ cycloalkyl, aryl, arylalkyl, heterocycloalkyl, heteroaryl, and heteroarylalkyl is optionally substituted with 1-3 substituents independently selected from halo, alkyl, —$C_3$-$C_8$ cycloalkyl, alkylamino, dialkylamino, alkylC(O)NH—, arylC(O)NH—, heteroarylC(O)NH—, —CN, alkoxy, —$CF_3$, aryl, and heteroaryl; or $R^6$ and $R^7$ are taken together with the nitrogen atom to which they are attached to form an optionally substituted heterocycloalkyl;

$R^3$ is selected from the group consisting of:
1) Hydrogen
2) Substituted or unsubstituted —$C_1$-$C_8$ alkyl;
3) Substituted or unsubstituted —$C_2$-$C_8$ alkenyl;
4) Substituted or unsubstituted —$C_2$-$C_8$ alkynyl;
5) Substituted or unsubstituted —$C_3$-$C_8$ cycloalkyl;
6) Substituted or unsubstituted aryl;
7) Substituted or unsubstituted arylalkyl;
8) Substituted or unsubstituted heterocycloalkyl;
9) Substituted or unsubstituted heteroaryl;
10) Substituted or unsubstituted heteroarylalkyl;
11) —$C(O)R^6$;
12) —$C(O)OR^6$;
13) —$C(O)N(R^6)(R^7)$; and
14) —$SO_2R^6$;

$R^{10}$ and $R^{11}$ are each independently selected from the group consisting of hydrogen, hydroxyl, and optionally substituted —$C_1$-$C_8$ alkyl; or alternatively, $R^{10}$ and $R^{11}$ are taken together with the carbon atom to which they are attached to form $C(O)$, spiro-$C_3$-$C_8$ cycloalkyl, or spiro-3- to 8-membered heterocycloalkyl;

$R^{12}$ and $R^{13}$ are each independently selected from the group consisting of hydrogen, halo, and optionally substituted —$C_1$-$C_8$ alkyl; and n is 0, 1 or 2.

2. The compound of claim 1, represented by Formula II, or a pharmaceutically acceptable salt thereof:

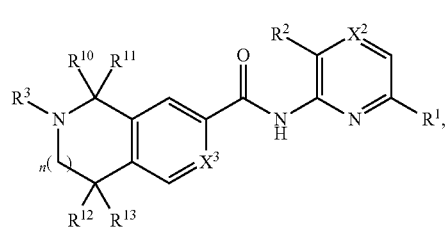

(II)

wherein $R^1$, $R^2$, $R^3$, $R^{10}$, $R^{11}$, $R^{12}$, $R^{13}$, $X^2$, $X^3$ and n are as defined in claim.

3. The compound of claim 1, represented by Formula III, or a pharmaceutically acceptable salt thereof:

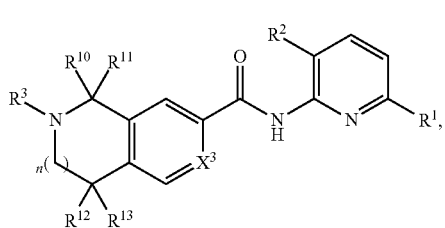

(III)

wherein $R^1$, $R^2$, $R^3$, $R^{10}$, $R^{11}$, $R^{12}$, $R^{13}$, $X^3$ and n are as defined in claim 1.

4. The compound of claim 1, represented by Formula IV, or a pharmaceutically acceptable salt thereof:

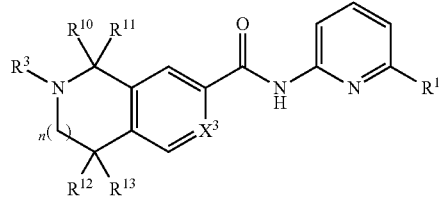

(IV)

wherein $R^1$, $R^3$, $R^{10}$, $R^{11}$, $R^{12}$, $R^{13}$, $X^3$ and n are as defined in claim 1.

5. The compound of claim 1, represented by Formula V, or a pharmaceutically acceptable salt thereof:

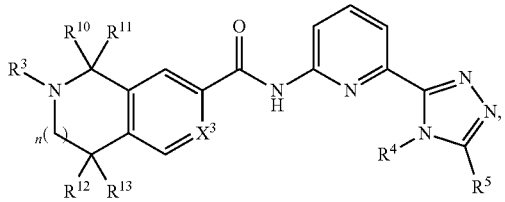

(V)

wherein $R^3$, $R^4$, $R^5$, $R^{10}$, $R^{11}$, $R^{12}$, $R^{13}$, $X^3$ and n are as defined in claim 1.

6. The compound of claim 1, represented by Formula VI, or a pharmaceutically acceptable salt thereof:

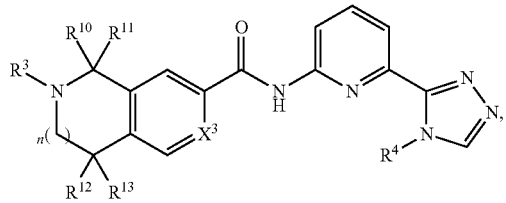

(VI)

wherein $R^3$, $R^4$, $R^{10}$, $R^{11}$, $R^{12}$, $R^{13}$, $X^3$ and n are as defined in claim 1.

7. The compound of claim 1, represented by Formula VII, or a pharmaceutically acceptable salt thereof:

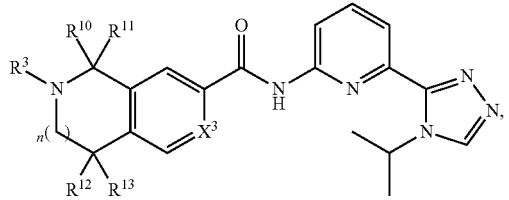

(VII)

wherein $R^3$, $R^{10}$, $R^{11}$, $R^{12}$, $R^{13}$, $X^3$ and n are as defined in claim 1.

8. The compound of claim 1, which is selected from compounds of Formula VIII, or a pharmaceutically acceptable salt thereof:

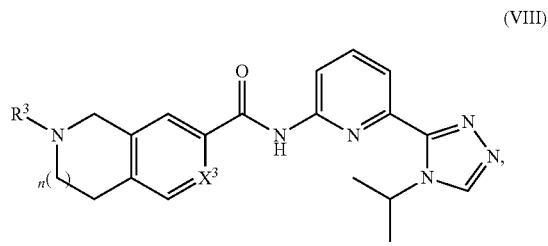

(VIII)

wherein $X^3$, $R^3$, and n are delineated for each compound in Table 1:

TABLE 1

| Compound | $R^3$ | $X^3$ | n |
|---|---|---|---|
| 1 | H | C—H | 0 |
| 2 | Methyl | C—H | 0 |
| 3 | Ethyl | C—H | 0 |
| 4 | Propyl | C—H | 0 |
| 5 | Allyl | C—H | 0 |
| 6 | i-Propyl | C—H | 0 |
| 7 | ⸺⸺OMe | C—H | 0 |
| 8 | i-Butyl | C—H | 0 |
| 9 | t-Butyl | C—H | 0 |
| 10 | cyclopentyl | C—H | 0 |
| 11 | cyclohexyl | C—H | 0 |
| 12 | phenyl | C—H | 0 |
| 13 | 4-t-butylphenyl | C—H | 0 |
| 14 | acetyl | C—H | 0 |
| 15 | propanoyl | C—H | 0 |
| 16 | methoxy-propanoyl | C—H | 0 |

TABLE 1-continued

| Compound | R³ | X³ | n |
|---|---|---|---|
| 17 | propyl ketone | C—H | 0 |
| 18 | isopropyl ketone | C—H | 0 |
| 19 | tert-butyl ketone | C—H | 0 |
| 20 | phenyl ketone | C—H | 0 |
| 21 | 4-tert-butylphenyl ketone | C—H | 0 |
| 22 | thiazol-2-yl ketone | C—H | 0 |
| 23 | methyl ester | C—H | 0 |
| 24 | ethyl ester | C—H | 0 |
| 25 | 2-fluoroethyl ester | C—H | 0 |
| 26 | 2-methoxyethyl ester | C—H | 0 |
| 27 | propyl ester | C—H | 0 |
| 28 | allyl ester | C—H | 0 |
| 29 | isopropyl ester | C—H | 0 |
| 30 | butyl ester | C—H | 0 |
| 31 | but-3-enyl ester | C—H | 0 |
| 32 | isobutyl ester | C—H | 0 |
| 33 | tert-butyl ester | C—H | 0 |
| 34 | cyclopentyl ester | C—H | 0 |
| 35 | cyclohexyl ester | C—H | 0 |
| 36 | benzyl ester | C—H | 0 |
| 37 | N-ethyl amide | C—H | 0 |
| 38 | N-(2-methoxyethyl) amide | C—H | 0 |

TABLE 1-continued

| Compound | R³ | X³ | n |
|---|---|---|---|
| 39 | -C(O)NH-propyl | C—H | 0 |
| 40 | -C(O)NH-allyl | C—H | 0 |
| 41 | -C(O)NH-butyl | C—H | 0 |
| 42 | -C(O)NH-isopropyl | C—H | 0 |
| 43 | -C(O)NH-isobutyl | C—H | 0 |
| 44 | -C(O)NH-t-butyl | C—H | 0 |
| 45 | -C(O)NH-cyclopentyl | C—H | 0 |
| 46 | -C(O)NH-benzyl | C—H | 0 |
| 47 | -C(O)NH-phenyl | C—H | 0 |
| 48 | -C(O)N(Me)₂ | C—H | 0 |
| 49 | -C(O)-pyrrolidinyl | C—H | 0 |
| 50 | -C(O)-piperidinyl | C—H | 0 |
| 51 | H | C—F | 0 |
| 52 | Methyl | C—F | 0 |
| 53 | Ethyl | C—F | 0 |
| 54 | Propyl | C—F | 0 |
| 55 | Allyl | C—F | 0 |
| 56 | i-Propyl | C—F | 0 |
| 57 | -(CH₂)₃-OMe | C—F | 0 |
| 58 | i-Butyl | C—F | 0 |
| 59 | t-Butyl | C—F | 0 |
| 60 | cyclopentyl | C—F | 0 |
| 61 | cyclohexyl | C—F | 0 |
| 62 | phenyl | C—F | 0 |
| 63 | 4-t-butylphenyl | C—F | 0 |
| 64 | -C(O)Me | C—F | 0 |
| 65 | -C(O)Et | C—F | 0 |
| 66 | -C(O)CH₂CH₂OMe | C—F | 0 |
| 67 | -C(O)propyl | C—F | 0 |
| 68 | -C(O)-i-propyl | C—F | 0 |

TABLE 1-continued

| Compound | R³ | X³ | n |
|---|---|---|---|
| 69 | pivaloyl (C(=O)C(CH₃)₃) | C—F | 0 |
| 70 | benzoyl | C—F | 0 |
| 71 | 4-tert-butylbenzoyl | C—F | 0 |
| 72 | thiazol-2-yl carbonyl | C—F | 0 |
| 73 | —C(=O)OMe | C—F | 0 |
| 74 | —C(=O)OEt | C—F | 0 |
| 75 | —C(=O)OCH₂CH₂F | C—F | 0 |
| 76 | —C(=O)OCH₂CH₂OMe | C—F | 0 |
| 77 | —C(=O)O-n-propyl | C—F | 0 |
| 78 | —C(=O)O-allyl | C—F | 0 |
| 79 | —C(=O)O-iPr | C—F | 0 |

TABLE 1-continued

| Compound | R³ | X³ | n |
|---|---|---|---|
| 80 | —C(=O)O-n-butyl | C—F | 0 |
| 81 | —C(=O)OCH₂CH₂CH=CH₂ | C—F | 0 |
| 82 | —C(=O)O-isobutyl | C—F | 0 |
| 83 | —C(=O)O-tBu | C—F | 0 |
| 84 | —C(=O)O-cyclopentyl | C—F | 0 |
| 85 | —C(=O)O-cyclohexyl | C—F | 0 |
| 86 | —C(=O)OBn | C—F | 0 |
| 87 | —C(=O)NHEt | C—F | 0 |
| 88 | —C(=O)NHCH₂CH₂OMe | C—F | 0 |
| 89 | —C(=O)NH-n-propyl | C—F | 0 |
| 90 | —C(=O)NH-allyl | C—F | 0 |

TABLE 1-continued
| Compound | R³ | X³ | n |
|---|---|---|---|
| 91 | 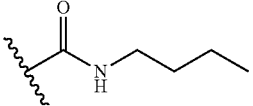 [SMILES: *C(=O)NCCCC] | C—F | 0 |
| 92 | 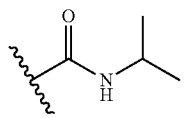 [SMILES: *C(=O)NC(C)C] | C—F | 0 |
| 93 | 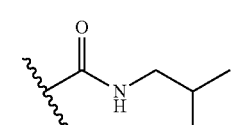 | C—F | 0 |
| 94 | 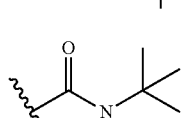 | C—F | 0 |
| 95 | 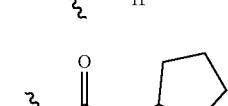 | C—F | 0 |
| 96 | 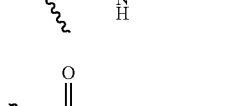 | C—F | 0 |
| 97 | 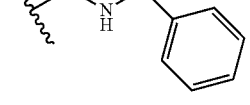 | C—F | 0 |
| 98 | 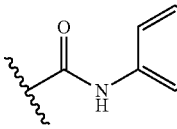 | C—F | 0 |
| 99 | 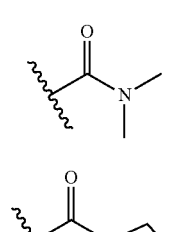 | C—F | 0 |
| 100 | 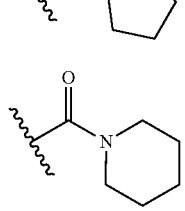 | C—F | 0 |
| 101 | H | N | 0 |
| 102 | Methyl | N | 0 |
| 103 | Ethyl | N | 0 |
| 104 | Propyl | N | 0 |
| 105 | Allyl | N | 0 |
| 106 | i-Propyl | N | 0 |
| 107 | 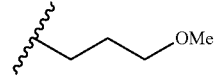 | N | 0 |
| 108 | i-Butyl | N | 0 |
| 109 | t-Butyl | N | 0 |
| 110 | 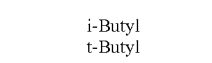 | N | 0 |
| 111 | 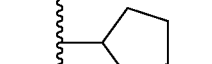 | N | 0 |
| 112 | 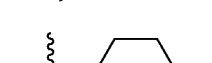 | N | 0 |
| 113 | 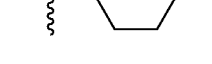 | N | 0 |
| 114 | 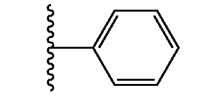 | N | 0 |
| 115 | 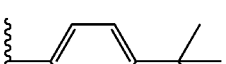 | N | 0 |
| 116 | 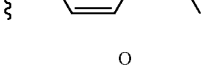 | N | 0 |
| 117 | 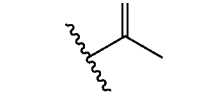 | N | 0 |
| 118 | 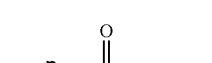 | N | 0 |
| 119 |  | N | 0 |
| 120 | 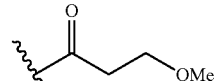 | N | 0 |

TABLE 1-continued

| Compound | R³ | X³ | n |
|---|---|---|---|
| 121 | 4-tert-butylbenzoyl | N | 0 |
| 122 | thiazole-2-carbonyl | N | 0 |
| 123 | -C(O)OMe | N | 0 |
| 124 | -C(O)OEt | N | 0 |
| 125 | -C(O)OCH₂CH₂F | N | 0 |
| 126 | -C(O)OCH₂CH₂OMe | N | 0 |
| 127 | -C(O)O-n-propyl | N | 0 |
| 128 | -C(O)OCH₂CH=CH₂ | N | 0 |
| 129 | -C(O)O-iPr | N | 0 |
| 130 | -C(O)O-n-butyl | N | 0 |
| 131 | -C(O)OCH₂CH₂CH=CH₂ | N | 0 |
| 132 | -C(O)O-isobutyl | N | 0 |
| 133 | -C(O)O-tBu | N | 0 |
| 134 | -C(O)O-cyclopentyl | N | 0 |
| 135 | -C(O)O-cyclohexyl | N | 0 |
| 136 | -C(O)OBn | N | 0 |
| 137 | -C(O)NHEt | N | 0 |
| 138 | -C(O)NHCH₂CH₂OMe | N | 0 |
| 139 | -C(O)NH-n-propyl | N | 0 |
| 140 | -C(O)NHCH₂CH=CH₂ | N | 0 |
| 141 | -C(O)NH-n-butyl | N | 0 |
| 142 | -C(O)NH-iPr | N | 0 |

TABLE 1-continued
| Compound | R³ | X³ | n |
|---|---|---|---|
| 143 | 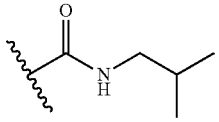 | N | 0 |
| 144 | 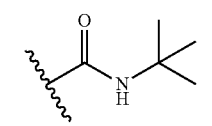 [SMILES: *C(=O)NC(C)(C)C] | N | 0 |
| 145 | 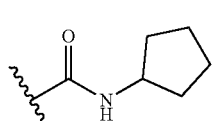 | N | 0 |
| 146 | 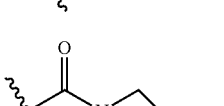 | N | 0 |
| 147 | 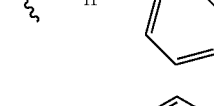 | N | 0 |
| 148 | 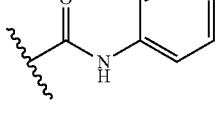 | N | 0 |
| 149 | 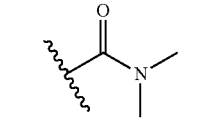 [SMILES: *C(=O)N(C)C] | N | 0 |
| 150 | 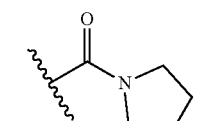 | N | 0 |
| 151 | H | C—H | 1 |
| 152 | Methyl | C—H | 1 |
| 153 | Ethyl | C—H | 1 |
| 154 | Propyl | C—H | 1 |
| 155 | Allyl | C—H | 1 |
| 156 | i-Propyl | C—H | 1 |
| 157 | 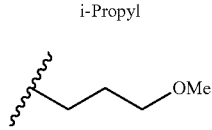 | C—H | 1 |
| 158 | i-Butyl | C—H | 1 |
| 159 | t-Butyl | C—H | 1 |
| 160 | 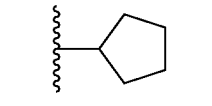 | C—H | 1 |
| 161 | 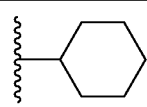 | C—H | 1 |
| 162 | 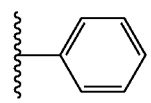 | C—H | 1 |
| 163 | 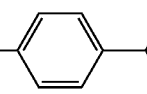 | C—H | 1 |
| 164 | 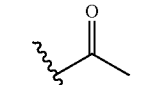 | C—H | 1 |
| 165 | 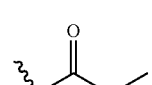 | C—H | 1 |
| 166 | 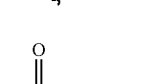 | C—H | 1 |
| 167 | 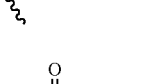 | C—H | 1 |
| 168 | 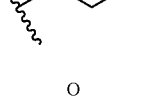 | C—H | 1 |
| 169 | 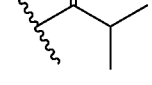 | C—H | 1 |
| 170 | 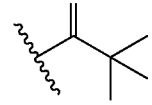 | C—H | 1 |
| 171 | 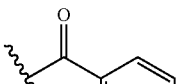 | C—H | 1 |

TABLE 1-continued
| Compound | R³ | X³ | n |
|---|---|---|---|
| 172 | 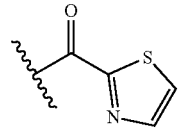 [SMILES: *C(=O)c1nccs1] | C—H | 1 |
| 173 | 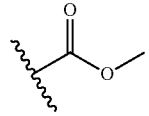 [SMILES: *C(=O)OC] | C—H | 1 |
| 174 | 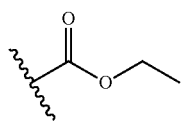 [SMILES: *C(=O)OCC] | C—H | 1 |
| 175 | 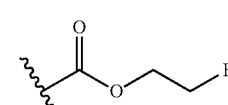 | C—H | 1 |
| 176 | 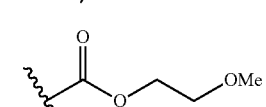 | C—H | 1 |
| 177 | 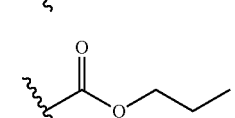 | C—H | 1 |
| 178 | 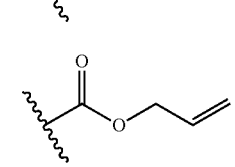 | C—H | 1 |
| 179 | 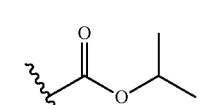 | C—H | 1 |
| 180 | 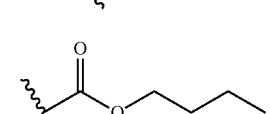 | C—H | 1 |
| 181 | 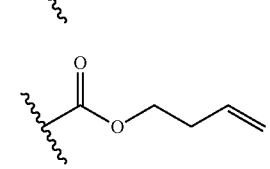 | C—H | 1 |
| 182 | 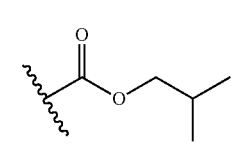 [SMILES: *C(=O)OCC(C)C] | C—H | 1 |
| 183 | 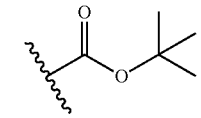 [SMILES: *C(=O)OC(C)(C)C] | C—H | 1 |
| 184 | 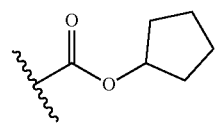 [SMILES: *C(=O)OC1CCCC1] | C—H | 1 |
| 185 | 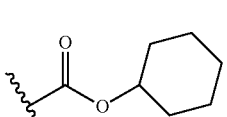 | C—H | 1 |
| 186 | 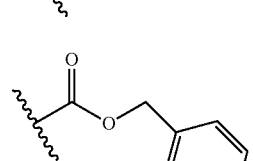 | C—H | 1 |
| 187 | 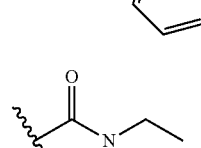 | C—H | 1 |
| 188 | 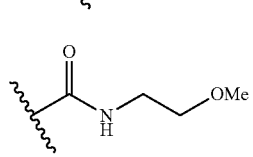 | C—H | 1 |
| 189 | 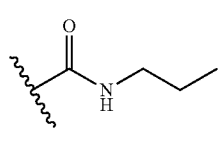 [SMILES: *C(=O)NCCC] | C—H | 1 |
| 190 | 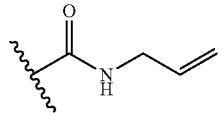 [SMILES: *C(=O)NCC=C] | C—H | 1 |
| 191 | 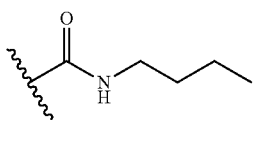 [SMILES: *C(=O)NCCCC] | C—H | 1 |
| 192 | 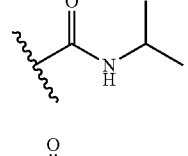 | C—H | 1 |
| 193 | 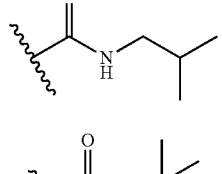 | C—H | 1 |
| 194 | 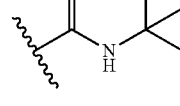 | C—H | 1 |

TABLE 1-continued

| Compound | R³ | X³ | n |
|---|---|---|---|
| 195 | *cyclopentyl amide* (-C(O)NH-cyclopentyl) | C—H | 1 |
| 196 | *benzyl amide* (-C(O)NHCH₂Ph) | C—H | 1 |
| 197 | *phenyl amide* (-C(O)NHPh) | C—H | 1 |
| 198 | *N,N-dimethyl amide* (-C(O)N(CH₃)₂) | C—H | 1 |
| 199 | *pyrrolidinyl amide* | C—H | 1 |
| 200 | *piperidinyl amide* | C—H | 1 |
| 201 | H | C—F | 1 |
| 202 | Methyl | C—F | 1 |
| 203 | Ethyl | C—F | 1 |
| 204 | Propyl | C—F | 1 |
| 205 | Allyl | C—F | 1 |
| 206 | i-Propyl | C—F | 1 |
| 207 | -(CH₂)₃-OMe | C—F | 1 |
| 208 | i-Butyl | C—F | 1 |
| 209 | t-Butyl | C—F | 1 |
| 210 | cyclopentyl | C—F | 1 |
| 211 | cyclohexyl | C—F | 1 |
| 212 | phenyl | C—F | 1 |
| 213 | 4-t-butylphenyl | C—F | 1 |
| 214 | -C(O)CH₃ | C—F | 1 |
| 215 | -C(O)CH₂CH₃ | C—F | 1 |
| 216 | -C(O)CH₂OMe | C—F | 1 |
| 217 | -C(O)CH₂CH₂CH₃ | C—F | 1 |
| 218 | -C(O)CH(CH₃)₂ | C—F | 1 |
| 219 | -C(O)C(CH₃)₃ | C—F | 1 |
| 220 | -C(O)Ph | C—F | 1 |
| 221 | -C(O)(4-t-butylphenyl) | C—F | 1 |
| 222 | -C(O)(thiazol-2-yl) | C—F | 1 |
| 223 | -C(O)OMe | C—F | 1 |

TABLE 1-continued

| Compound | R³ | X³ | n |
|---|---|---|---|
| 224 | ethyl ester | C—F | 1 |
| 225 | 2-fluoroethyl ester | C—F | 1 |
| 226 | 2-methoxyethyl ester | C—F | 1 |
| 227 | propyl ester | C—F | 1 |
| 228 | allyl ester | C—F | 1 |
| 229 | isopropyl ester | C—F | 1 |
| 230 | butyl ester | C—F | 1 |
| 231 | but-3-enyl ester | C—F | 1 |
| 232 | isobutyl ester | C—F | 1 |
| 233 | tert-butyl ester | C—F | 1 |
| 234 | cyclopentyl ester | C—F | 1 |
| 235 | cyclohexyl ester | C—F | 1 |
| 236 | benzyl ester | C—F | 1 |
| 237 | N-ethyl amide | C—F | 1 |
| 238 | N-(2-methoxyethyl) amide | C—F | 1 |
| 239 | N-propyl amide | C—F | 1 |
| 240 | N-allyl amide | C—F | 1 |
| 241 | N-butyl amide | C—F | 1 |
| 242 | N-isopropyl amide | C—F | 1 |
| 243 | N-isobutyl amide | C—F | 1 |
| 244 | N-tert-butyl amide | C—F | 1 |
| 245 | N-cyclopentyl amide | C—F | 1 |
| 246 | N-benzyl amide | C—F | 1 |

TABLE 1-continued

| Compound | R³ | X³ | n |
|---|---|---|---|
| 247 | -C(O)NH-phenyl | C—F | 1 |
| 248 | -C(O)N(CH₃)₂ | C—F | 1 |
| 249 | -C(O)-pyrrolidinyl | C—F | 1 |
| 250 | -C(O)-piperidinyl | C—F | 1 |
| 251 | H | N | 1 |
| 252 | Methyl | N | 1 |
| 253 | Ethyl | N | 1 |
| 254 | Propyl | N | 1 |
| 255 | Allyl | N | 1 |
| 256 | i-Propyl | N | 1 |
| 257 | -CH(CH₂CH₂OMe)- | N | 1 |
| 258 | i-Butyl | N | 1 |
| 259 | t-Butyl | N | 1 |
| 260 | cyclopentyl | N | 1 |
| 261 | cyclohexyl | N | 1 |
| 262 | phenyl | N | 1 |
| 263 | 4-t-butylphenyl | N | 1 |
| 264 | -C(O)CH₃ | N | 1 |
| 265 | -C(O)CH₂CH₃ | N | 1 |
| 266 | -C(O)CH₂CH₂OMe | N | 1 |
| 267 | -C(O)CH₂CH₂CH₃ | N | 1 |
| 268 | -C(O)CH(CH₃)₂ | N | 1 |
| 269 | -C(O)C(CH₃)₃ | N | 1 |
| 270 | -C(O)-phenyl | N | 1 |
| 271 | -C(O)-(4-t-butylphenyl) | N | 1 |
| 272 | -C(O)-thiazol-2-yl | N | 1 |
| 273 | -C(O)OMe | N | 1 |
| 274 | -C(O)OEt | N | 1 |
| 275 | -C(O)OCH₂CH₂F | N | 1 |
| 276 | -C(O)OCH₂CH₂OMe | N | 1 |

TABLE 1-continued

| Compound | R³ | X³ | n |
|---|---|---|---|
| 277 | –C(O)O-propyl | N | 1 |
| 278 | –C(O)O-allyl | N | 1 |
| 279 | –C(O)O-isopropyl | N | 1 |
| 280 | –C(O)O-butyl | N | 1 |
| 281 | –C(O)O-(3-butenyl) | N | 1 |
| 282 | –C(O)O-isobutyl | N | 1 |
| 283 | –C(O)O-tert-butyl | N | 1 |
| 284 | –C(O)O-cyclopentyl | N | 1 |
| 285 | –C(O)O-cyclohexyl | N | 1 |
| 286 | –C(O)O-benzyl | N | 1 |
| 287 | –C(O)NH-ethyl | N | 1 |
| 288 | –C(O)NH-CH₂CH₂OMe | N | 1 |
| 289 | –C(O)NH-propyl | N | 1 |
| 290 | –C(O)NH-allyl | N | 1 |
| 291 | –C(O)NH-butyl | N | 1 |
| 292 | –C(O)NH-isopropyl | N | 1 |
| 293 | –C(O)NH-isobutyl | N | 1 |
| 294 | –C(O)NH-tert-butyl | N | 1 |
| 295 | –C(O)NH-cyclopentyl | N | 1 |
| 296 | –C(O)NH-benzyl | N | 1 |
| 297 | –C(O)NH-phenyl | N | 1 |
| 298 | –C(O)N(Me)₂ | N | 1 |

TABLE 1-continued

| Compound | R³ | X³ | n |
|---|---|---|---|
| 299 | 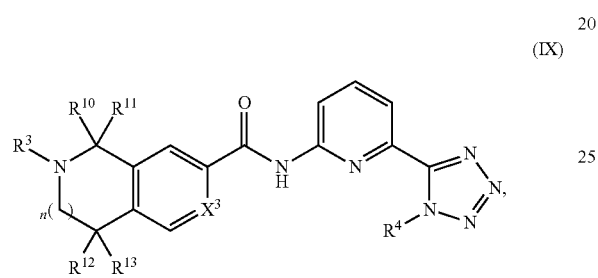 | N | 1 |
| 300 | 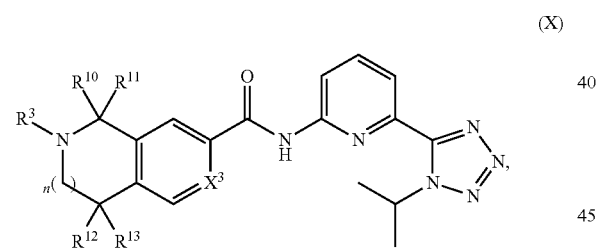 | N | 1. |

9. The compound of claim 1, represented by Formula IX, or a pharmaceutically acceptable salt thereof:

(IX)

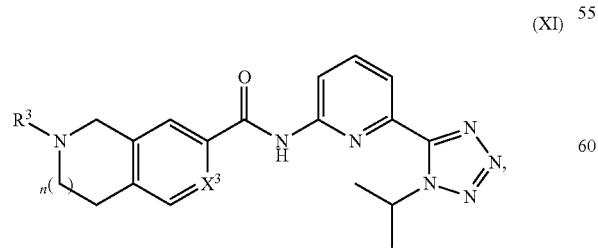

wherein R³, R⁴, R¹⁰, R¹¹, R¹², R¹³, X³ and n are as defined in claim 1.

10. The compound of claim 1, represented by Formula X, or a pharmaceutically acceptable salt thereof:

(X)

wherein R³, R¹⁰, R¹¹, R¹², R¹³, X³ and n are as defined in claim 1.

11. The compound of claim 1, which is selected from compounds of Formula XI, or a pharmaceutically acceptable salt thereof:

(XI)

wherein X³, R³, and n are delineated for each compound in Table 2:

TABLE 2

| Compound | R³ | X³ | n |
|---|---|---|---|
| 301 | H | C—H | 0 |
| 302 | Methyl | C—H | 0 |
| 303 | Ethyl | C—H | 0 |
| 304 | Propyl | C—H | 0 |
| 305 | Allyl | C—H | 0 |
| 306 | i-Propyl | C—H | 0 |
| 307 | ~~~OMe | C—H | 0 |
| 308 | i-Butyl | C—H | 0 |
| 309 | t-Butyl | C—H | 0 |
| 310 | cyclopentyl | C—H | 0 |
| 311 | cyclohexyl | C—H | 0 |
| 312 | phenyl | C—H | 0 |
| 313 | 4-t-butylphenyl | C—H | 0 |
| 314 | acetyl | C—H | 0 |
| 315 | propanoyl | C—H | 0 |
| 316 | —C(O)CH₂CH₂OMe | C—H | 0 |
| 317 | butanoyl | C—H | 0 |
| 318 | isobutanoyl | C—H | 0 |
| 319 | pivaloyl | C—H | 0 |

TABLE 2-continued

| Compound | R³ | X³ | n |
|---|---|---|---|
| 320 | benzoyl | C—H | 0 |
| 321 | 4-tert-butylbenzoyl | C—H | 0 |
| 322 | thiazole-2-carbonyl | C—H | 0 |
| 323 | methyl ester | C—H | 0 |
| 324 | ethyl ester | C—H | 0 |
| 325 | 2-fluoroethyl ester | C—H | 0 |
| 326 | 2-methoxyethyl ester | C—H | 0 |
| 327 | propyl ester | C—H | 0 |
| 328 | allyl ester | C—H | 0 |
| 329 | isopropyl ester | C—H | 0 |
| 330 | butyl ester | C—H | 0 |

TABLE 2-continued

| Compound | R³ | X³ | n |
|---|---|---|---|
| 331 | but-3-enyl ester | C—H | 0 |
| 332 | isobutyl ester | C—H | 0 |
| 333 | tert-butyl ester | C—H | 0 |
| 334 | cyclopentyl ester | C—H | 0 |
| 335 | cyclohexyl ester | C—H | 0 |
| 336 | benzyl ester | C—H | 0 |
| 337 | ethyl amide | C—H | 0 |
| 338 | 2-methoxyethyl amide | C—H | 0 |
| 339 | propyl amide | C—H | 0 |
| 340 | allyl amide | C—H | 0 |
| 341 | butyl amide | C—H | 0 |

TABLE 2-continued

| Compound | R³ | X³ | n |
|---|---|---|---|
| 342 | -C(O)NH-iPr | C—H | 0 |
| 343 | -C(O)NH-iBu | C—H | 0 |
| 344 | -C(O)NH-tBu | C—H | 0 |
| 345 | -C(O)NH-cyclopentyl | C—H | 0 |
| 346 | -C(O)NH-CH₂Ph | C—H | 0 |
| 347 | -C(O)NH-Ph | C—H | 0 |
| 348 | -C(O)N(Me)₂ | C—H | 0 |
| 349 | -C(O)-pyrrolidinyl | C—H | 0 |
| 350 | -C(O)-piperidinyl | C—H | 0 |
| 351 | H | C—F | 0 |
| 352 | Methyl | C—F | 0 |
| 353 | Ethyl | C—F | 0 |
| 354 | Propyl | C—F | 0 |
| 355 | Allyl | C—F | 0 |
| 356 | i-Propyl | C—F | 0 |
| 357 | -(CH₂)₃-OMe | C—F | 0 |
| 358 | i-Butyl | C—F | 0 |
| 359 | t-Butyl | C—F | 0 |

TABLE 2-continued

| Compound | R³ | X³ | n |
|---|---|---|---|
| 360 | cyclopentyl | C—F | 0 |
| 361 | cyclohexyl | C—F | 0 |
| 362 | phenyl | C—F | 0 |
| 363 | 4-tBu-phenyl | C—F | 0 |
| 364 | -C(O)CH₃ | C—F | 0 |
| 365 | -C(O)CH₂CH₃ | C—F | 0 |
| 366 | -C(O)CH₂CH₂OMe | C—F | 0 |
| 367 | -C(O)CH₂CH₂CH₃ | C—F | 0 |
| 368 | -C(O)CH(CH₃)₂ | C—F | 0 |
| 369 | -C(O)C(CH₃)₃ | C—F | 0 |
| 370 | -C(O)Ph | C—F | 0 |
| 371 | -C(O)-(4-tBu-phenyl) | C—F | 0 |

TABLE 2-continued
| Compound | R³ | X³ | n |
|---|---|---|---|
| 372 | 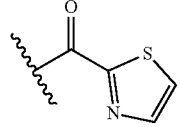 [SMILES: *C(=O)c1nccs1] | C—F | 0 |
| 373 | 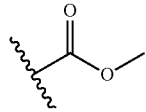 | C—F | 0 |
| 374 | 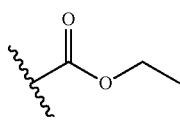 [SMILES: *C(=O)OCC] | C—F | 0 |
| 375 | 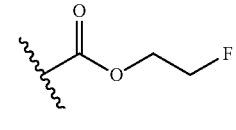 [SMILES: *C(=O)OCCF] | C—F | 0 |
| 376 | 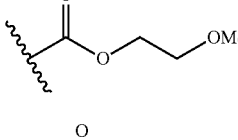 | C—F | 0 |
| 377 | 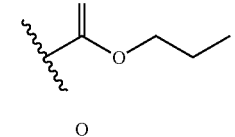 | C—F | 0 |
| 378 | 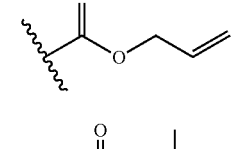 | C—F | 0 |
| 379 | 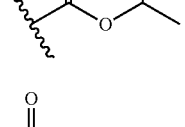 | C—F | 0 |
| 380 | 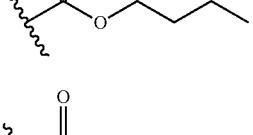 | C—F | 0 |
| 381 | 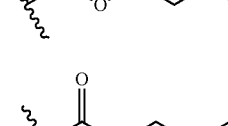 | C—F | 0 |
| 382 | 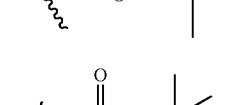 | C—F | 0 |
| 383 | 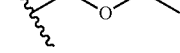 | C—F | 0 |
| 384 | 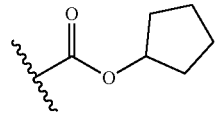 [SMILES: *C(=O)OC1CCCC1] | C—F | 0 |
| 385 | 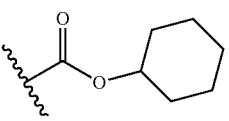 [SMILES: *C(=O)OC1CCCCC1] | C—F | 0 |
| 386 | 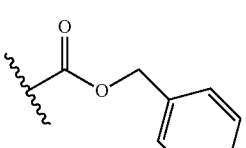 | C—F | 0 |
| 387 | 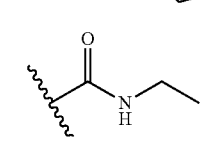 | C—F | 0 |
| 388 | 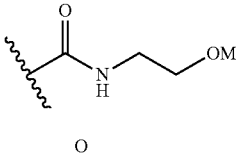 | C—F | 0 |
| 389 | 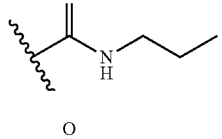 | C—F | 0 |
| 390 | 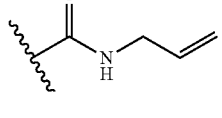 | C—F | 0 |
| 391 | 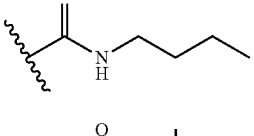 | C—F | 0 |
| 392 | 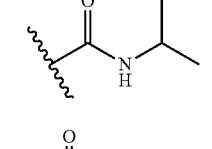 | C—F | 0 |
| 393 | 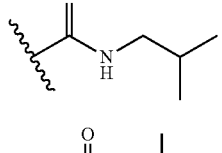 | C—F | 0 |
| 394 | 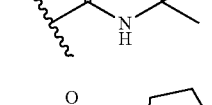 | C—F | 0 |
| 395 | 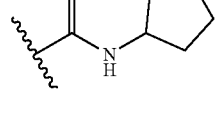 | C—F | 0 |

TABLE 2-continued

| Compound | R³ | X³ | n |
|---|---|---|---|
| 396 | -C(O)NH-benzyl | C—F | 0 |
| 397 | -C(O)NH-phenyl | C—F | 0 |
| 398 | -C(O)N(Me)₂ | C—F | 0 |
| 399 | -C(O)-pyrrolidinyl | C—F | 0 |
| 400 | -C(O)-piperidinyl | C—F | 0 |
| 401 | H | N | 0 |
| 402 | Methyl | N | 0 |
| 403 | Ethyl | N | 0 |
| 404 | Propyl | N | 0 |
| 405 | Allyl | N | 0 |
| 406 | i-Propyl | N | 0 |
| 407 | -(CH₂)₃-OMe | N | 0 |
| 408 | i-Butyl | N | 0 |
| 409 | t-Butyl | N | 0 |
| 410 | cyclopentyl | N | 0 |
| 411 | cyclohexyl | N | 0 |
| 412 | phenyl | N | 0 |
| 413 | 4-t-butylphenyl | N | 0 |
| 414 | -C(O)CH₃ | N | 0 |
| 415 | -C(O)CH₂CH₃ | N | 0 |
| 416 | -C(O)CH₂CH₂OMe | N | 0 |
| 417 | -C(O)CH₂CH₂CH₃ | N | 0 |
| 418 | -C(O)CH(CH₃)₂ | N | 0 |
| 419 | -C(O)C(CH₃)₃ | N | 0 |
| 420 | -C(O)-phenyl | N | 0 |
| 421 | -C(O)-(4-t-butylphenyl) | N | 0 |
| 422 | -C(O)-thiazol-2-yl | N | 0 |
| 423 | -C(O)OMe | N | 0 |
| 424 | -C(O)OEt | N | 0 |

TABLE 2-continued

| Compound | R³ | X³ | n |
|---|---|---|---|
| 425 | -C(O)O-CH₂CH₂F | N | 0 |
| 426 | -C(O)O-CH₂CH₂OMe | N | 0 |
| 427 | -C(O)O-propyl | N | 0 |
| 428 | -C(O)O-allyl | N | 0 |
| 429 | -C(O)O-isopropyl | N | 0 |
| 430 | -C(O)O-butyl | N | 0 |
| 431 | -C(O)O-CH₂CH₂CH=CH₂ | N | 0 |
| 432 | -C(O)O-isobutyl | N | 0 |
| 433 | -C(O)O-tert-butyl | N | 0 |
| 434 | -C(O)O-cyclopentyl | N | 0 |
| 435 | -C(O)O-cyclohexyl | N | 0 |
| 436 | -C(O)O-benzyl | N | 0 |
| 437 | -C(O)NH-ethyl | N | 0 |
| 438 | -C(O)NH-CH₂CH₂OMe | N | 0 |
| 439 | -C(O)NH-propyl | N | 0 |
| 440 | -C(O)NH-allyl | N | 0 |
| 441 | -C(O)NH-butyl | N | 0 |
| 442 | -C(O)NH-isopropyl | N | 0 |
| 443 | -C(O)NH-isobutyl | N | 0 |
| 444 | -C(O)NH-tert-butyl | N | 0 |
| 445 | -C(O)NH-cyclopentyl | N | 0 |
| 446 | -C(O)NH-benzyl | N | 0 |
| 447 | -C(O)NH-phenyl | N | 0 |

TABLE 2-continued

| Compound | R³ | X³ | n |
|---|---|---|---|
| 448 | —C(O)N(CH₃)₂ | N | 0 |
| 449 | —C(O)-pyrrolidinyl | N | 0 |
| 450 | —C(O)-piperidinyl | N | 0 |
| 451 | H | C—H | 1 |
| 452 | Methyl | C—H | 1 |
| 453 | Ethyl | C—H | 1 |
| 454 | Propyl | C—H | 1 |
| 455 | Allyl | C—H | 1 |
| 456 | i-Propyl | C—H | 1 |
| 457 | —(CH₂)₃OMe | C—H | 1 |
| 458 | i-Butyl | C—H | 1 |
| 459 | t-Butyl | C—H | 1 |
| 460 | cyclopentyl | C—H | 1 |
| 461 | cyclohexyl | C—H | 1 |
| 462 | phenyl | C—H | 1 |
| 463 | 4-t-butylphenyl | C—H | 1 |
| 464 | —C(O)CH₃ | C—H | 1 |
| 465 | —C(O)CH₂CH₃ | C—H | 1 |
| 466 | —C(O)CH₂CH₂OMe | C—H | 1 |
| 467 | —C(O)CH₂CH₂CH₃ | C—H | 1 |
| 468 | —C(O)CH(CH₃)₂ | C—H | 1 |
| 469 | —C(O)C(CH₃)₃ | C—H | 1 |
| 470 | —C(O)phenyl | C—H | 1 |
| 471 | —C(O)(4-t-butylphenyl) | C—H | 1 |
| 472 | —C(O)(thiazol-2-yl) | C—H | 1 |
| 473 | —C(O)OMe | C—H | 1 |
| 474 | —C(O)OEt | C—H | 1 |
| 475 | —C(O)OCH₂CH₂F | C—H | 1 |
| 476 | —C(O)OCH₂CH₂OMe | C—H | 1 |
| 477 | —C(O)OCH₂CH₂CH₃ | C—H | 1 |

TABLE 2-continued

| Compound | R³ | X³ | n |
|---|---|---|---|
| 478 | allyl ester | C—H | 1 |
| 479 | isopropyl ester | C—H | 1 |
| 480 | n-butyl ester | C—H | 1 |
| 481 | but-3-enyl ester | C—H | 1 |
| 482 | isobutyl ester | C—H | 1 |
| 483 | tert-butyl ester | C—H | 1 |
| 484 | cyclopentyl ester | C—H | 1 |
| 485 | cyclohexyl ester | C—H | 1 |
| 486 | benzyl ester | C—H | 1 |
| 487 | N-ethyl amide | C—H | 1 |
| 488 | N-(2-methoxyethyl) amide | C—H | 1 |

TABLE 2-continued

| Compound | R³ | X³ | n |
|---|---|---|---|
| 489 | N-propyl amide | C—H | 1 |
| 490 | N-allyl amide | C—H | 1 |
| 491 | N-butyl amide | C—H | 1 |
| 492 | N-isopropyl amide | C—H | 1 |
| 493 | N-isobutyl amide | C—H | 1 |
| 494 | N-tert-butyl amide | C—H | 1 |
| 495 | N-cyclopentyl amide | C—H | 1 |
| 496 | N-benzyl amide | C—H | 1 |
| 497 | N-phenyl amide | C—H | 1 |
| 498 | N,N-dimethyl amide | C—H | 1 |
| 499 | pyrrolidinyl amide | C—H | 1 |

TABLE 2-continued

| Compound | R³ | X³ | n |
|---|---|---|---|
| 500 | *piperidin-1-yl carbonyl* | C—H | 1 |
| 501 | H | C—F | 1 |
| 502 | Methyl | C—F | 1 |
| 503 | Ethyl | C—F | 1 |
| 504 | Propyl | C—F | 1 |
| 505 | Allyl | C—F | 1 |
| 506 | i-Propyl | C—F | 1 |
| 507 | *-(CH₂)₃-OMe* | C—F | 1 |
| 508 | i-Butyl | C—F | 1 |
| 509 | t-Butyl | C—F | 1 |
| 510 | cyclopentyl | C—F | 1 |
| 511 | cyclohexyl | C—F | 1 |
| 512 | phenyl | C—F | 1 |
| 513 | 4-t-butylphenyl | C—F | 1 |
| 514 | acetyl | C—F | 1 |
| 515 | propanoyl | C—F | 1 |
| 516 | 4-methoxy-3-oxobutyl | C—F | 1 |
| 517 | pentan-3-oyl | C—F | 1 |
| 518 | isobutyryl | C—F | 1 |

TABLE 2-continued

| Compound | R³ | X³ | n |
|---|---|---|---|
| 519 | pivaloyl | C—F | 1 |
| 520 | benzoyl | C—F | 1 |
| 521 | 4-t-butylbenzoyl | C—F | 1 |
| 522 | thiazol-2-ylcarbonyl | C—F | 1 |
| 523 | methoxycarbonyl | C—F | 1 |
| 524 | ethoxycarbonyl | C—F | 1 |
| 525 | 2-fluoroethoxycarbonyl | C—F | 1 |
| 526 | 2-methoxyethoxycarbonyl | C—F | 1 |
| 527 | propoxycarbonyl | C—F | 1 |
| 528 | allyloxycarbonyl | C—F | 1 |
| 529 | isopropoxycarbonyl | C—F | 1 |

TABLE 2-continued

| Compound | R³ | X³ | n |
|---|---|---|---|
| 530 | -C(O)O-butyl | C—F | 1 |
| 531 | -C(O)O-CH₂CH=CH₂ (allyl ester, but shown as -OCH₂CH₂CH=CH₂) | C—F | 1 |
| 532 | -C(O)O-CH₂CH(CH₃)₂ (isobutyl ester) | C—F | 1 |
| 533 | -C(O)O-t-Bu | C—F | 1 |
| 534 | -C(O)O-cyclopentyl | C—F | 1 |
| 535 | -C(O)O-cyclohexyl | C—F | 1 |
| 536 | -C(O)O-CH₂-phenyl (benzyl ester) | C—F | 1 |
| 537 | -C(O)NH-ethyl | C—F | 1 |
| 538 | -C(O)NH-CH₂CH₂-OMe | C—F | 1 |
| 539 | -C(O)NH-propyl | C—F | 1 |
| 540 | -C(O)NH-allyl | C—F | 1 |
| 541 | -C(O)NH-butyl | C—F | 1 |
| 542 | -C(O)NH-isopropyl | C—F | 1 |
| 543 | -C(O)NH-isobutyl | C—F | 1 |
| 544 | -C(O)NH-t-Bu | C—F | 1 |
| 545 | -C(O)NH-cyclopentyl | C—F | 1 |
| 546 | -C(O)NH-benzyl | C—F | 1 |
| 547 | -C(O)NH-phenyl | C—F | 1 |
| 548 | -C(O)N(Me)₂ | C—F | 1 |
| 549 | -C(O)-pyrrolidinyl | C—F | 1 |
| 550 | -C(O)-piperidinyl | C—F | 1 |
| 551 | H | N | 1 |
| 552 | Methyl | N | 1 |
| 553 | Ethyl | N | 1 |
| 554 | Propyl | N | 1 |
| 555 | Allyl | N | 1 |
| 556 | i-Propyl | N | 1 |
| 557 | -CH₂CH₂CH₂-OMe | N | 1 |
| 558 | i-Butyl | N | 1 |
| 559 | t-Butyl | N | 1 |

TABLE 2-continued
| Compound | R³ | X³ | n |
|---|---|---|---|
| 560 | 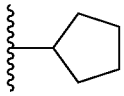 cyclopentyl | N | 1 |
| 561 | 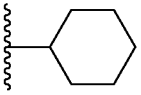 [SMILES: *C1CCCCC1] cyclohexyl | N | 1 |
| 562 | 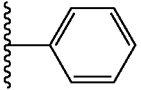 phenyl | N | 1 |
| 563 | 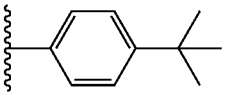 [SMILES: *c1ccc(C(C)(C)C)cc1] 4-tert-butylphenyl | N | 1 |
| 564 | 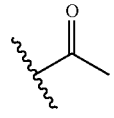 | N | 1 |
| 565 | 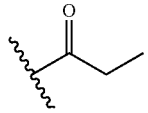 [SMILES: *C(=O)CC] | N | 1 |
| 566 | 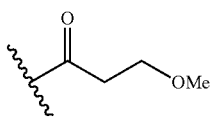 [SMILES: *C(=O)CCOC] | N | 1 |
| 567 | 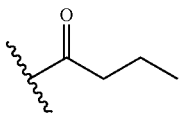 [SMILES: *C(=O)CCC] | N | 1 |
| 568 | 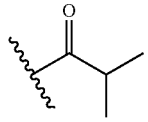 [SMILES: *C(=O)C(C)C] | N | 1 |
| 569 | 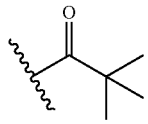 [SMILES: *C(=O)C(C)(C)C] | N | 1 |
| 570 | 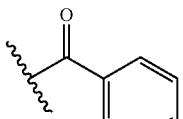 | N | 1 |
| 571 | 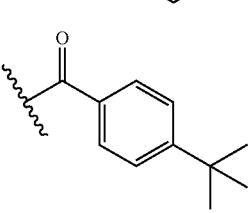 | N | 1 |
| 572 | 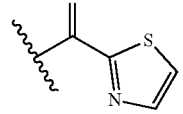 | N | 1 |
| 573 | 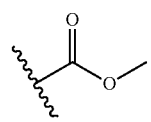 [SMILES: *C(=O)OC] | N | 1 |
| 574 | 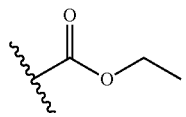 [SMILES: *C(=O)OCC] | N | 1 |
| 575 | 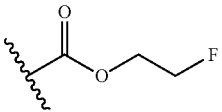 [SMILES: *C(=O)OCCF] | N | 1 |
| 576 | 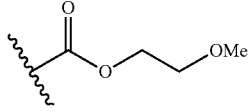 [SMILES: *C(=O)OCCOC] | N | 1 |
| 577 | 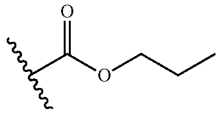 [SMILES: *C(=O)OCCC] | N | 1 |
| 578 | 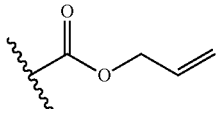 [SMILES: *C(=O)OCC=C] | N | 1 |
| 579 | 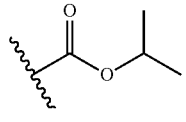 [SMILES: *C(=O)OC(C)C] | N | 1 |
| 580 | 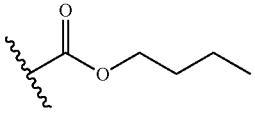 [SMILES: *C(=O)OCCCC] | N | 1 |
| 581 | 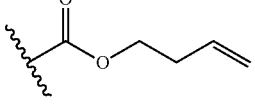 | N | 1 |
| 582 | 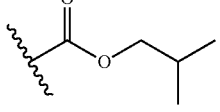 | N | 1 |
| 583 | 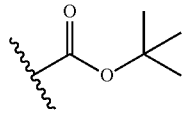 [SMILES: *C(=O)OC(C)(C)C] | N | 1 |

TABLE 2-continued

| Compound | R³ | X³ | n |
|---|---|---|---|
| 584 | cyclopentyl ester | N | 1 |
| 585 | cyclohexyl ester | N | 1 |
| 586 | benzyl ester | N | 1 |
| 587 | N-ethyl amide | N | 1 |
| 588 | N-(2-methoxyethyl) amide | N | 1 |
| 589 | N-propyl amide | N | 1 |
| 590 | N-allyl amide | N | 1 |
| 591 | N-butyl amide | N | 1 |
| 592 | N-isopropyl amide | N | 1 |
| 593 | N-isobutyl amide | N | 1 |
| 594 | N-tert-butyl amide | N | 1 |
| 595 | N-cyclopentyl amide | N | 1 |
| 596 | N-benzyl amide | N | 1 |
| 597 | N-phenyl amide | N | 1 |
| 598 | N,N-dimethyl amide | N | 1 |
| 599 | pyrrolidinyl amide | N | 1 |
| 600 | piperidinyl amide | N | 1. |

12. The compound of claim 1, represented by Formula XII-a or Formula XII-b, or a pharmaceutically acceptable salt thereof:

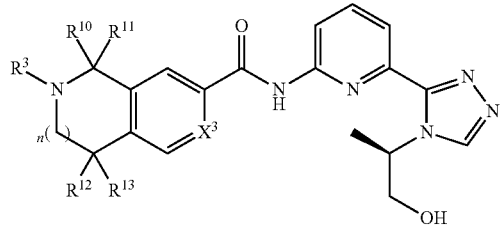

(XII-a)

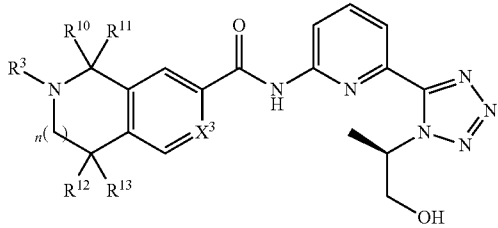

(XII-b)

wherein $R^3$, $R^{10}$, $R^{11}$, $R^{12}$, $R^{13}$, $X^3$ and n are as defined in claim 1.

13. The compound of claim 1, represented by Formula XIII-a, Formula XIII-b, Formula XIV-a, Formula XIV-b, Formula XV-a, or Formula XV-b, or a pharmaceutically acceptable salt thereof:
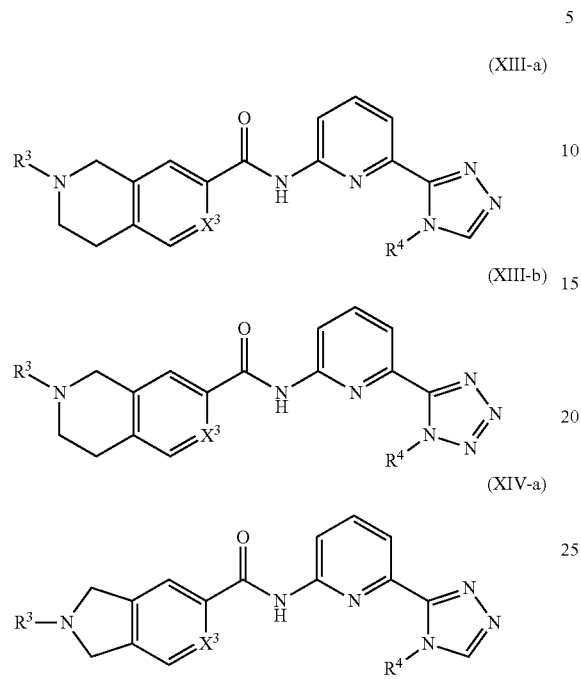
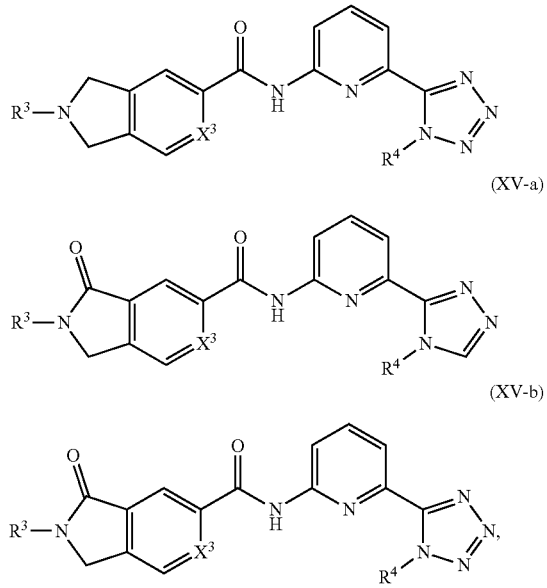
wherein $R^3$, $R^4$, and $X^3$ are as defined in claim 1.
14. The compound of claim 1, selected from the compounds set forth below, or a pharmaceutically acceptable salt thereof:
| Compound | Structure |
|---|---|
| 1 | 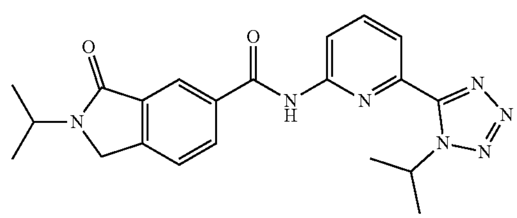 [SMILES: CC(C)N1Cc2ccc(C(=O)Nc3cccc(-c4nnnn4C(C)C)n3)cc2C1=O] |
| 2 | 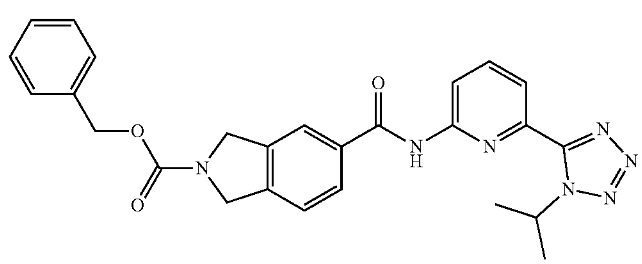 [SMILES: CC(C)n1nnnc1-c1cccc(NC(=O)c2ccc3c(c2)CN(C(=O)OCc2ccccc2)C3)n1] |
| 3 | 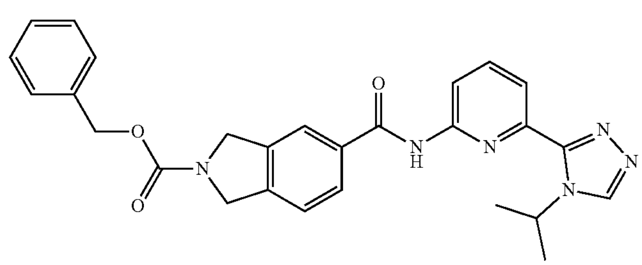 [SMILES: CC(C)n1cnnc1-c1cccc(NC(=O)c2ccc3c(c2)CN(C(=O)OCc2ccccc2)C3)n1] |

-continued

| Compound | Structure |
|---|---|
| 4 | (structure: 2-(3,3,3-trifluoropropylsulfonyl)isoindoline-5-carboxamide linked to N-(6-(4-isopropyl-4H-1,2,4-triazol-3-yl)pyridin-2-yl)) |
| 5 | (structure: 2-(ethyl(methyl)carbamoyl)isoindoline-5-carboxamide linked to N-(6-(4-isopropyl-4H-1,2,4-triazol-3-yl)pyridin-2-yl)) |
| 6 | (structure: 2-(2-methoxyethylsulfonyl)isoindoline-5-carboxamide linked to N-(6-(4-isopropyl-4H-1,2,4-triazol-3-yl)pyridin-2-yl)) |
| 7 | (structure: ethyl 5-((6-(4-isopropyl-4H-1,2,4-triazol-3-yl)pyridin-2-yl)carbamoyl)isoindoline-2-carboxylate) |
| 8 | (structure: isoindoline-5-carboxamide linked to N-(6-(1-isopropyl-1H-tetrazol-5-yl)pyridin-2-yl)) |
| 9 | (structure: isoindoline-5-carboxamide linked to N-(6-(4-isopropyl-4H-1,2,4-triazol-3-yl)pyridin-2-yl)) |
| 10 | (structure: 2-(N,N-dimethylsulfamoyl)isoindoline-5-carboxamide linked to N-(6-(1-isopropyl-1H-tetrazol-5-yl)pyridin-2-yl)) |

-continued

| Compound | Structure |
|---|---|
| 11 | 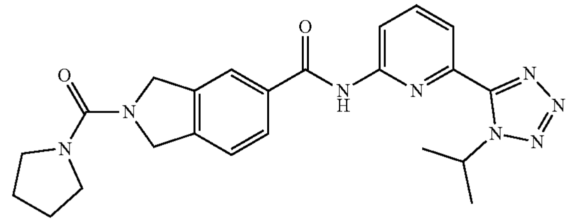 [SMILES: CC(C)n1nnnc1-c1cccc(NC(=O)c2ccc3c(c2)CN(C(=O)N2CCCC2)C3)n1] |
| 12 | 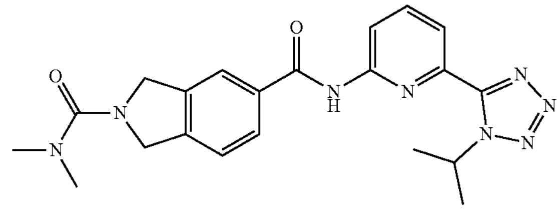 [SMILES: CC(C)n1nnnc1-c1cccc(NC(=O)c2ccc3c(c2)CN(C(=O)N(C)C)C3)n1] |
| 13 | 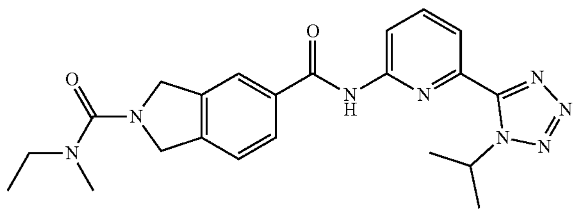 [SMILES: CCN(C)C(=O)N1Cc2ccc(C(=O)Nc3cccc(-c4nnnn4C(C)C)n3)cc2C1] |
| 14 | 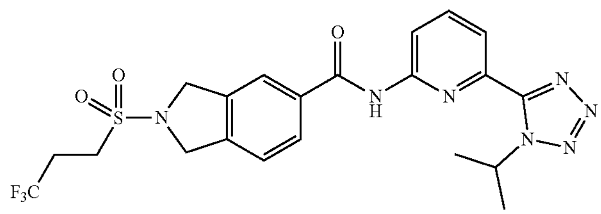 [SMILES: CC(C)n1nnnc1-c1cccc(NC(=O)c2ccc3c(c2)CN(S(=O)(=O)CCC(F)(F)F)C3)n1] |
| 15 | 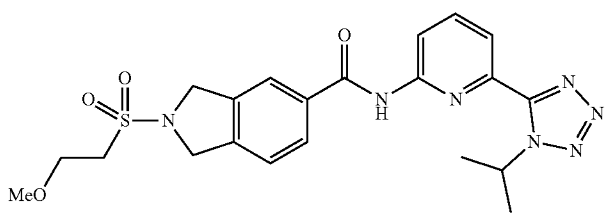 [SMILES: COCCS(=O)(=O)N1Cc2ccc(C(=O)Nc3cccc(-c4nnnn4C(C)C)n3)cc2C1] |
| 16 | 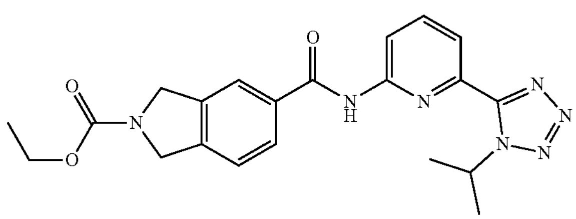 [SMILES: CCOC(=O)N1Cc2ccc(C(=O)Nc3cccc(-c4nnnn4C(C)C)n3)cc2C1] |
| 17 | 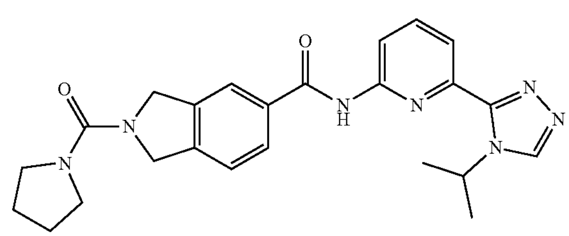 [SMILES: CC(C)n1cnnc1-c1cccc(NC(=O)c2ccc3c(c2)CN(C(=O)N2CCCC2)C3)n1] |

-continued

| Compound | Structure |
|---|---|
| 18 | 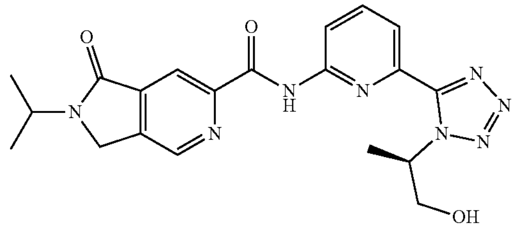 [SMILES: CC(C)N1Cc2cnc(C(=O)Nc3cccc(-c4nnnn4[C@H](C)CO)n3)cc2C1=O] |
| 19 | 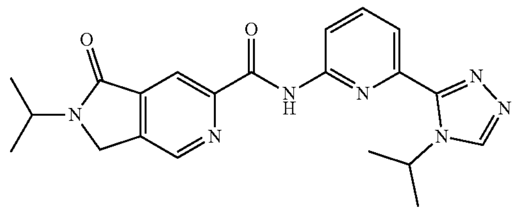 [SMILES: CC(C)N1Cc2cnc(C(=O)Nc3cccc(-c4nncn4C(C)C)n3)cc2C1=O] |
| 20 | 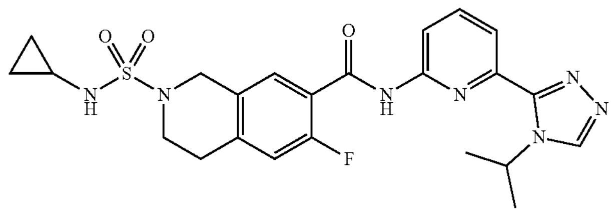 [SMILES: CC(C)n1cnnc1-c1cccc(NC(=O)c2cc3c(cc2F)CCN(S(=O)(=O)NC2CC2)C3)n1] |
| 21 | 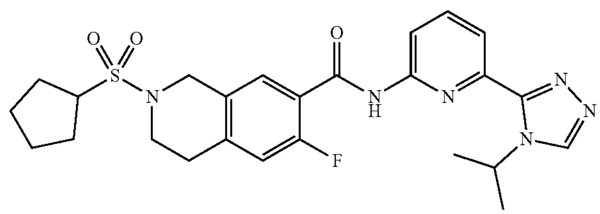 [SMILES: CC(C)n1cnnc1-c1cccc(NC(=O)c2cc3c(cc2F)CCN(S(=O)(=O)C2CCCC2)C3)n1] |
| 22 | 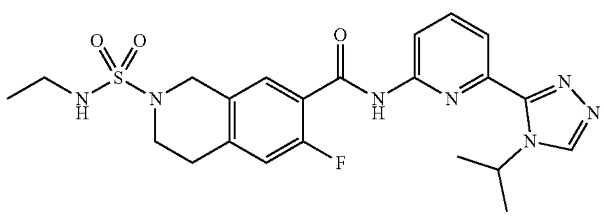 [SMILES: CCNS(=O)(=O)N1CCc2cc(F)c(C(=O)Nc3cccc(-c4nncn4C(C)C)n3)cc2C1] |
| 23 | 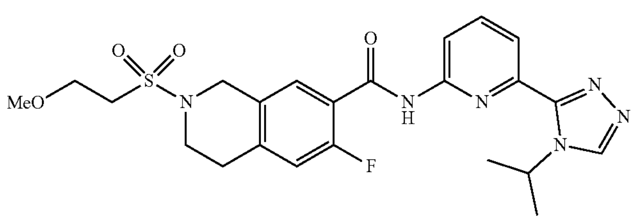 [SMILES: COCCS(=O)(=O)N1CCc2cc(F)c(C(=O)Nc3cccc(-c4nncn4C(C)C)n3)cc2C1] |
| 24 | 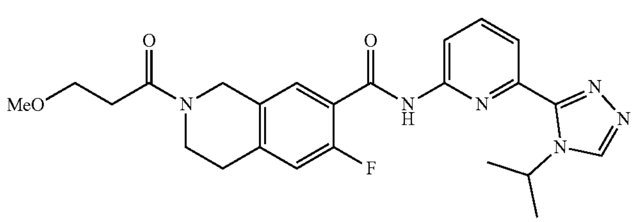 [SMILES: COCCC(=O)N1CCc2cc(F)c(C(=O)Nc3cccc(-c4nncn4C(C)C)n3)cc2C1] |

| Compound | Structure |
|---|---|
| 25 | (cyclopentyl carbamate-tetrahydroisoquinoline with F, carboxamide linked to pyridine-tetrazole with isopropyl) |
| 26 | (ethyl carbamate-tetrahydroisoquinoline with F, carboxamide linked to pyridine-tetrazole with isopropyl) |
| 27 | (tetrahydroisoquinoline NH with F, carboxamide linked to pyridine-triazole with isopropyl) |
| 28 | (MeO-propanoyl-tetrahydroisoquinoline with F, carboxamide linked to pyridine-tetrazole with isopropyl) |
| 29 | (ethylaminocarbonyl-tetrahydroisoquinoline with F, carboxamide linked to pyridine-tetrazole with isopropyl) |
| 30 | (ethyl carbamate-tetrahydroisoquinoline with F, carboxamide linked to pyridine-tetrazole with isopropyl) |
| 31 | (benzyl carbamate-tetrahydroisoquinoline with F, carboxamide linked to pyridine-tetrazole with isopropyl) |

| Compound | Structure |
|---|---|
| 32 | 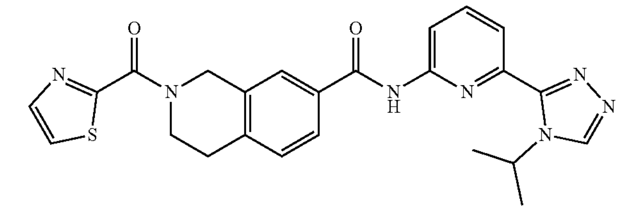 [SMILES: CC(C)n1cnnc1-c1cccc(NC(=O)c2ccc3c(c2)CN(C(=O)c2nccs2)CC3)n1] |
| 33 | 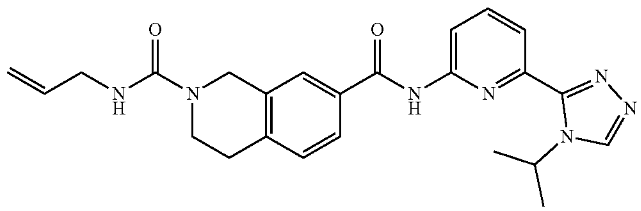 [SMILES: C=CCNC(=O)N1CCc2ccc(C(=O)Nc3cccc(-c4nncn4C(C)C)n3)cc2C1] |
| 34 | 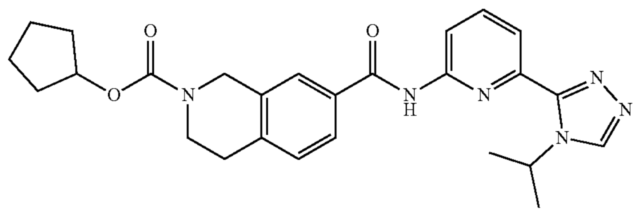 [SMILES: CC(C)n1cnnc1-c1cccc(NC(=O)c2ccc3c(c2)CN(C(=O)OC2CCCC2)CC3)n1] |
| 35 | 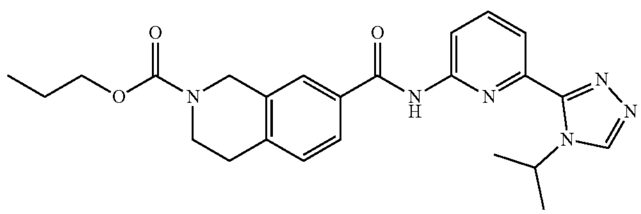 [SMILES: CCCOC(=O)N1CCc2ccc(C(=O)Nc3cccc(-c4nncn4C(C)C)n3)cc2C1] |
| 36 | 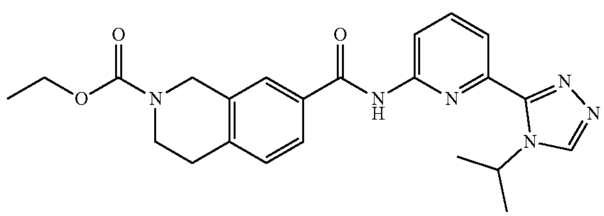 [SMILES: CCOC(=O)N1CCc2ccc(C(=O)Nc3cccc(-c4nncn4C(C)C)n3)cc2C1] |
| 37 | 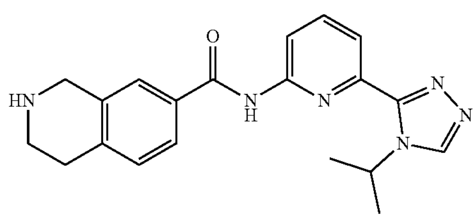 [SMILES: CC(C)n1cnnc1-c1cccc(NC(=O)c2ccc3c(c2)CNCC3)n1] |
| 38 | 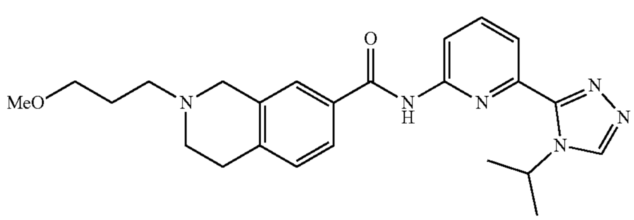 [SMILES: COCCCN1CCc2ccc(C(=O)Nc3cccc(-c4nncn4C(C)C)n3)cc2C1] |

-continued

| Compound | Structure |
|---|---|
| 39 | 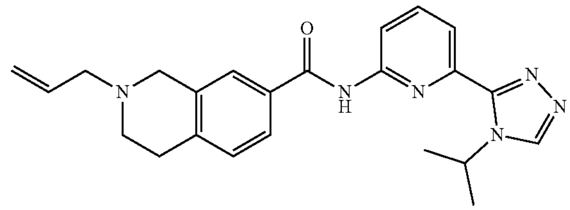 [SMILES: C=CCN1CCc2ccc(C(=O)Nc3cccc(-c4nncn4C(C)C)n3)cc2C1] |
| 40 | 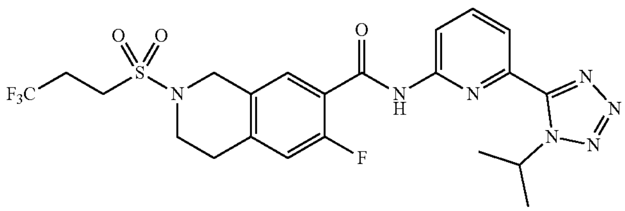 [SMILES: CC(C)n1nnnc1-c1cccc(NC(=O)c2cc3c(cc2F)CCN(S(=O)(=O)CCC(F)(F)F)C3)n1] |
| 41 | 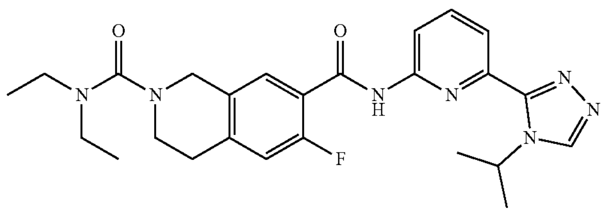 [SMILES: CCN(CC)C(=O)N1CCc2cc(F)c(C(=O)Nc3cccc(-c4nncn4C(C)C)n3)cc2C1] |
| 42 | 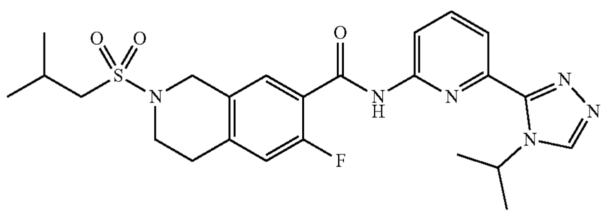 [SMILES: CC(C)CS(=O)(=O)N1CCc2cc(F)c(C(=O)Nc3cccc(-c4nncn4C(C)C)n3)cc2C1] |
| 43 | 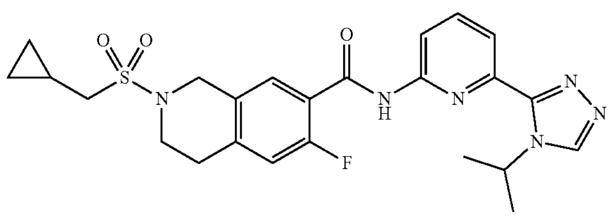 [SMILES: CC(C)n1cnnc1-c1cccc(NC(=O)c2cc3c(cc2F)CCN(S(=O)(=O)CC2CC2)C3)n1] |
| 44 | 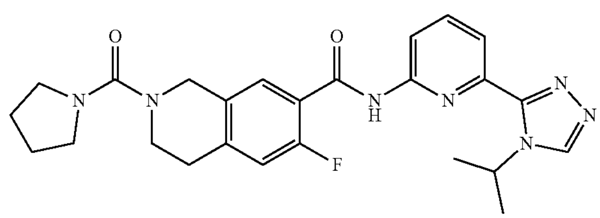 [SMILES: CC(C)n1cnnc1-c1cccc(NC(=O)c2cc3c(cc2F)CCN(C(=O)N2CCCC2)C3)n1] |
| 45 | 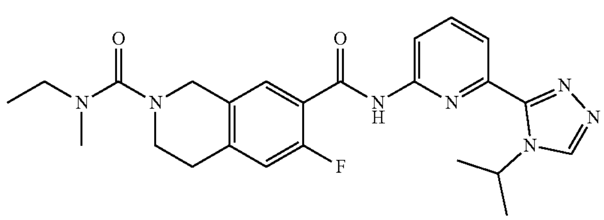 [SMILES: CCN(C)C(=O)N1CCc2cc(F)c(C(=O)Nc3cccc(-c4nncn4C(C)C)n3)cc2C1] |

-continued

| Compound | Structure |
|---|---|
| 46 | 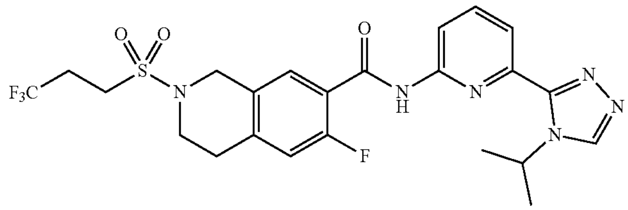 [SMILES: CC(C)n1cnnc1-c1cccc(NC(=O)c2cc3c(cc2F)CCN(S(=O)(=O)CCC(F)(F)F)C3)n1] |
| 47 | 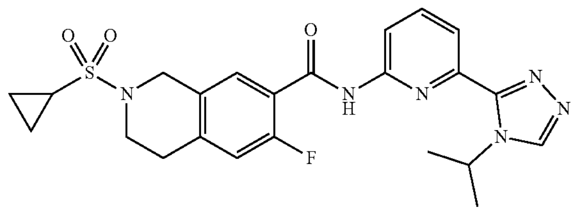 [SMILES: CC(C)n1cnnc1-c1cccc(NC(=O)c2cc3c(cc2F)CCN(S(=O)(=O)C2CC2)C3)n1] |
| 48 | 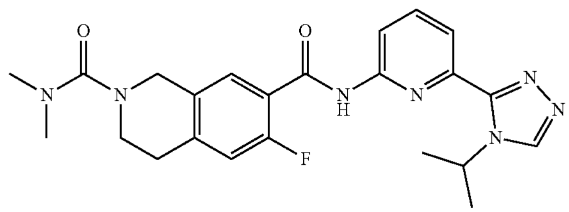 [SMILES: CC(C)n1cnnc1-c1cccc(NC(=O)c2cc3c(cc2F)CCN(C(=O)N(C)C)C3)n1] |
| 49 | 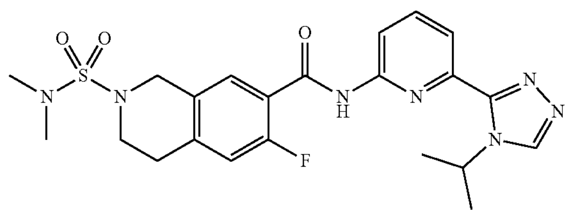 [SMILES: CC(C)n1cnnc1-c1cccc(NC(=O)c2cc3c(cc2F)CCN(S(=O)(=O)N(C)C)C3)n1] |
| 50 | 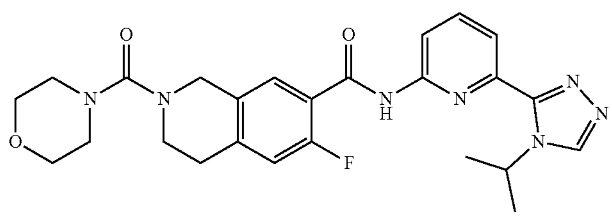 [SMILES: CC(C)n1cnnc1-c1cccc(NC(=O)c2cc3c(cc2F)CCN(C(=O)N2CCOCC2)C3)n1] |
| 51 | 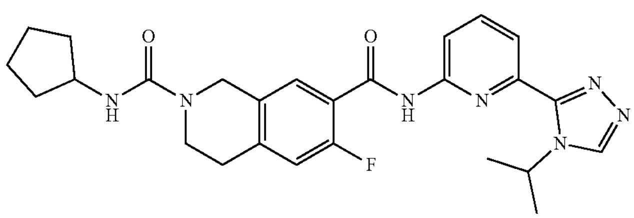 [SMILES: CC(C)n1cnnc1-c1cccc(NC(=O)c2cc3c(cc2F)CCN(C(=O)NC2CCCC2)C3)n1] |
| 52 | 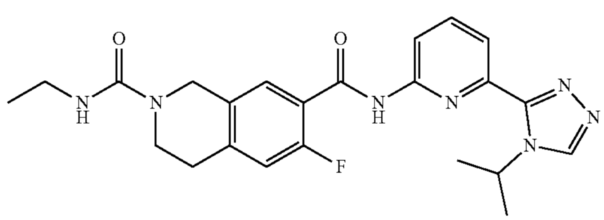 [SMILES: CCNC(=O)N1CCc2cc(F)c(C(=O)Nc3cccc(-c4nncn4C(C)C)n3)cc2C1] |

-continued

| Compound | Structure |
|---|---|
| 53 | 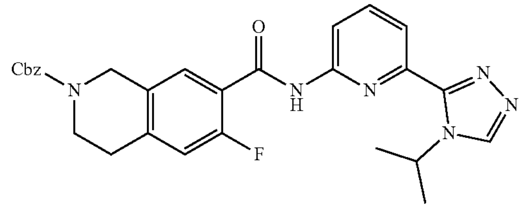 [SMILES: CC(C)n1cnnc1-c1cccc(NC(=O)c2cc3c(cc2F)CCN(C(=O)OCc2ccccc2)C3)n1] |
| 54 | 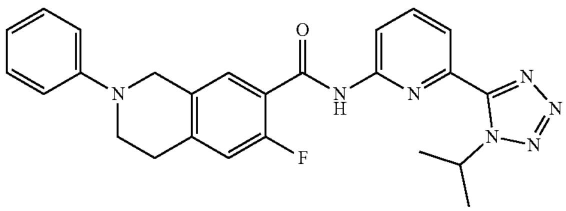 [SMILES: CC(C)n1nnnc1-c1cccc(NC(=O)c2cc3c(cc2F)CCN(c2ccccc2)C3)n1] |
| 55 | 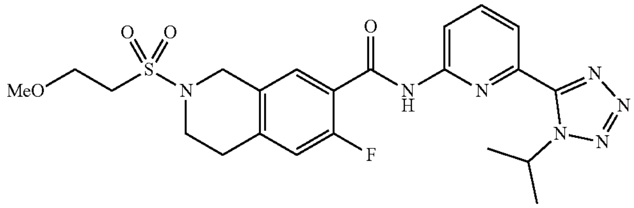 [SMILES: COCCS(=O)(=O)N1CCc2cc(F)c(C(=O)Nc3cccc(-c4nnnn4C(C)C)n3)cc2C1] |
| 56 | 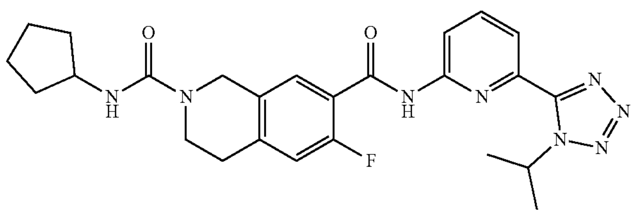 [SMILES: CC(C)n1nnnc1-c1cccc(NC(=O)c2cc3c(cc2F)CCN(C(=O)NC2CCCC2)C3)n1] |
| 57 | 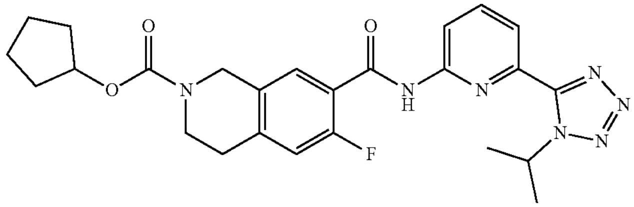 [SMILES: CC(C)n1nnnc1-c1cccc(NC(=O)c2cc3c(cc2F)CCN(C(=O)OC2CCCC2)C3)n1] |
| 58 | 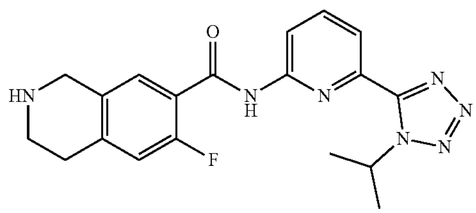 [SMILES: CC(C)n1nnnc1-c1cccc(NC(=O)c2cc3c(cc2F)CCNC3)n1] |
| 59 | 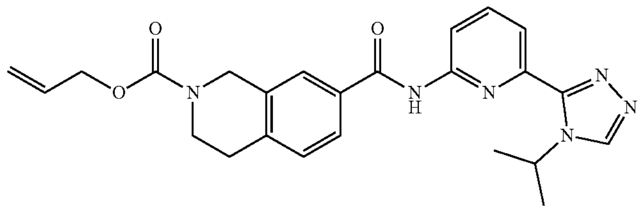 [SMILES: C=CCOC(=O)N1CCc2ccc(C(=O)Nc3cccc(-c4nncn4C(C)C)n3)cc2C1] |

-continued

| Compound | Structure |
|---|---|
| 60 | 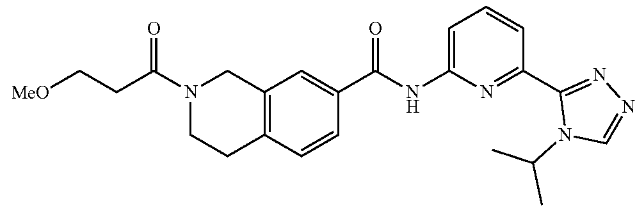 [SMILES: COCCC(=O)N1CCc2ccc(C(=O)Nc3cccc(-c4nncn4C(C)C)n3)cc2C1] |
| 61 | 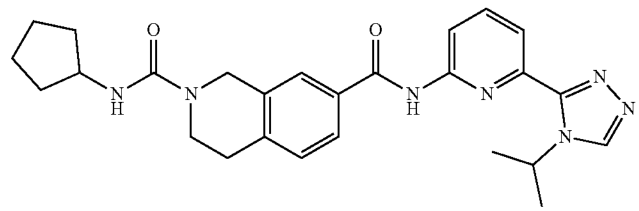 [SMILES: CC(C)n1cnnc1-c1cccc(NC(=O)c2ccc3c(c2)CN(C(=O)NC2CCCC2)CC3)n1] |
| 62 | 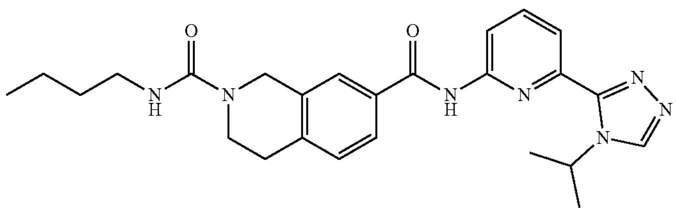 [SMILES: CCCCNC(=O)N1CCc2ccc(C(=O)Nc3cccc(-c4nncn4C(C)C)n3)cc2C1] |
| 63 | 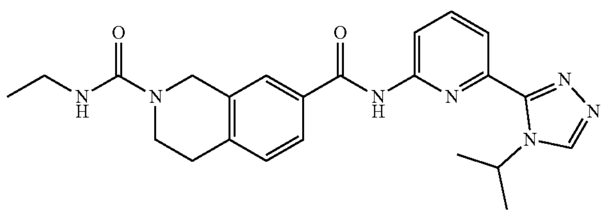 [SMILES: CCNC(=O)N1CCc2ccc(C(=O)Nc3cccc(-c4nncn4C(C)C)n3)cc2C1] |
| 64 | 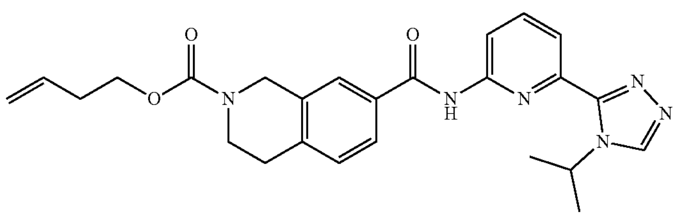 [SMILES: C=CCCOC(=O)N1CCc2ccc(C(=O)Nc3cccc(-c4nncn4C(C)C)n3)cc2C1] |
| 65 | 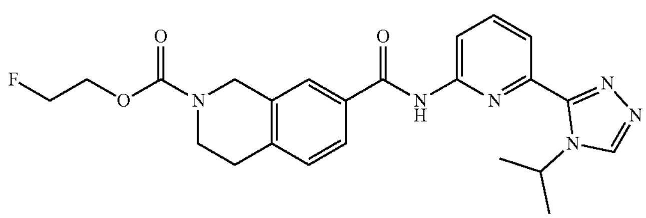 [SMILES: CC(C)n1cnnc1-c1cccc(NC(=O)c2ccc3c(c2)CN(C(=O)OCCF)CC3)n1] |
| 66 | 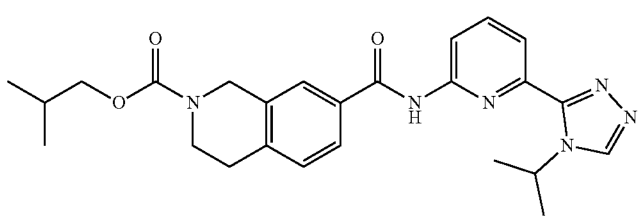 [SMILES: CC(C)COC(=O)N1CCc2ccc(C(=O)Nc3cccc(-c4nncn4C(C)C)n3)cc2C1] |

| Compound | Structure |
|---|---|
| 67 | 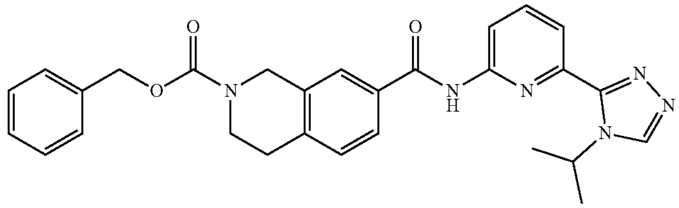 [SMILES: CC(C)n1cnnc1-c1cccc(NC(=O)c2ccc3c(c2)CN(C(=O)OCc2ccccc2)CC3)n1] |
| 68 | 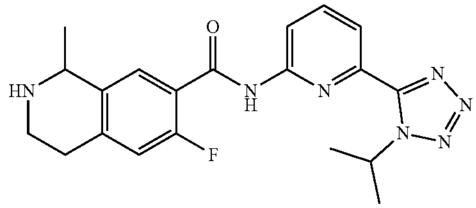 [SMILES: CC1NCCc2cc(F)c(C(=O)Nc3cccc(-c4nnnn4C(C)C)n3)cc21] |
| 69 | 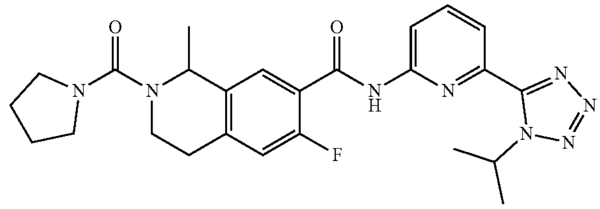 [SMILES: CC1c2cc(C(=O)Nc3cccc(-c4nnnn4C(C)C)n3)c(F)cc2CCN1C(=O)N1CCCC1] |
| 70 | 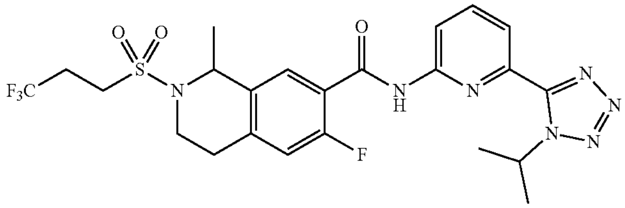 [SMILES: CC1c2cc(C(=O)Nc3cccc(-c4nnnn4C(C)C)n3)c(F)cc2CCN1S(=O)(=O)CCC(F)(F)F] |
| 71 | 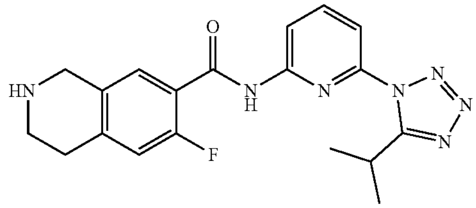 [SMILES: CC(C)c1nnnn1-c1cccc(NC(=O)c2cc3c(cc2F)CCNC3)n1] |
| 72 | 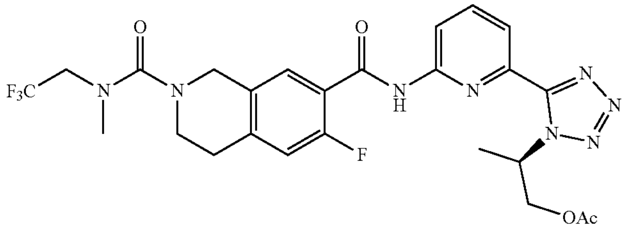 [SMILES: CC(=O)OC[C@@H](C)n1nnnc1-c1cccc(NC(=O)c2cc3c(cc2F)CCN(C(=O)N(C)CC(F)(F)F)C3)n1] |
| 73 | 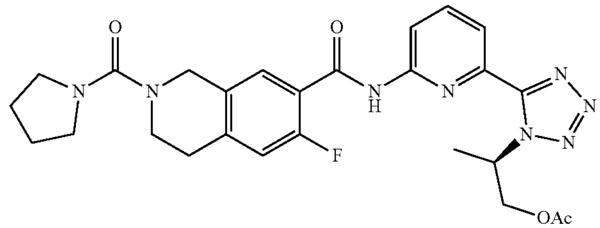 [SMILES: CC(=O)OC[C@@H](C)n1nnnc1-c1cccc(NC(=O)c2cc3c(cc2F)CCN(C(=O)N2CCCC2)C3)n1] |

-continued

| Compound | Structure |
|---|---|
| 74 | *(structure)* |
| 75 | *(structure)* |
| 76 | *(structure)* |
| 77 | *(structure)* |
| 78 | *(structure)* |
| 79 | *(structure)* |
| 80 | *(structure)* |

-continued

| Compound | Structure |
|---|---|
| 81 | *(structure image)* |
| 82 | *(structure image)* |
| 83 | *(structure image)* |
| 84 | *(structure image)* |
| 85 | *(structure image)* |
| 86 | *(structure image)* |
| 87 | *(structure image)* |

-continued

| Compound | Structure |
|---|---|
| 88 | 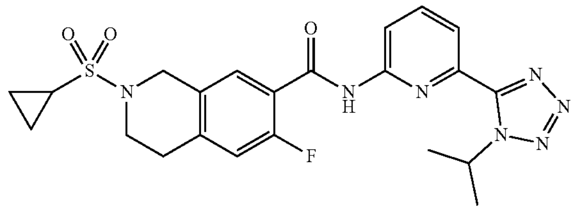 [SMILES: CC(C)n1nnnc1-c1cccc(NC(=O)c2cc3c(cc2F)CCN(S(=O)(=O)C2CC2)C3)n1] |
| 89 | 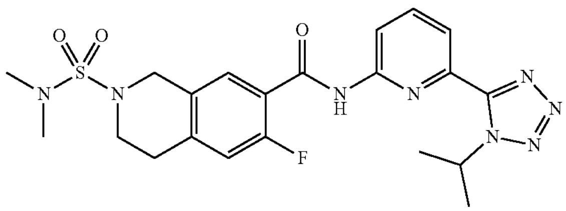 [SMILES: CC(C)n1nnnc1-c1cccc(NC(=O)c2cc3c(cc2F)CCN(S(=O)(=O)N(C)C)C3)n1] |
| 90 | 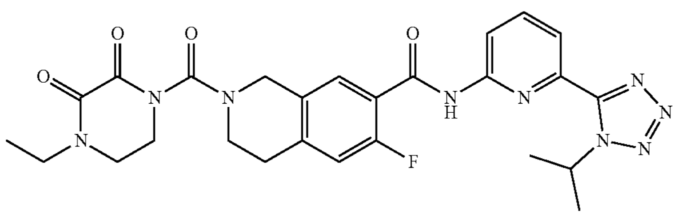 [SMILES: CCN1CCN(C(=O)N2CCc3cc(F)c(C(=O)Nc4cccc(-c5nnnn5C(C)C)n4)cc3C2)C(=O)C1=O] |
| 91 | 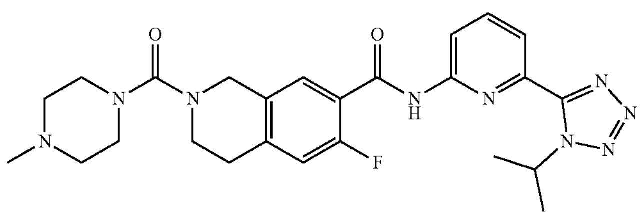 [SMILES: CC(C)n1nnnc1-c1cccc(NC(=O)c2cc3c(cc2F)CCN(C(=O)N2CCN(C)CC2)C3)n1] |
| 92 | 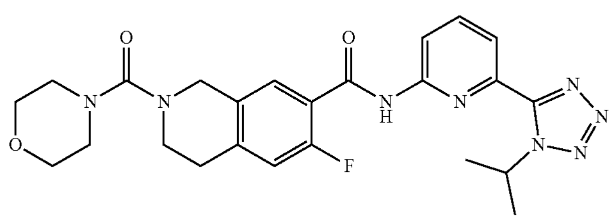 [SMILES: CC(C)n1nnnc1-c1cccc(NC(=O)c2cc3c(cc2F)CCN(C(=O)N2CCOCC2)C3)n1] |
| 93 | 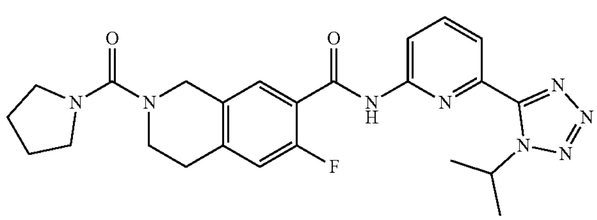 [SMILES: CC(C)n1nnnc1-c1cccc(NC(=O)c2cc3c(cc2F)CCN(C(=O)N2CCCC2)C3)n1] |
| 94 | 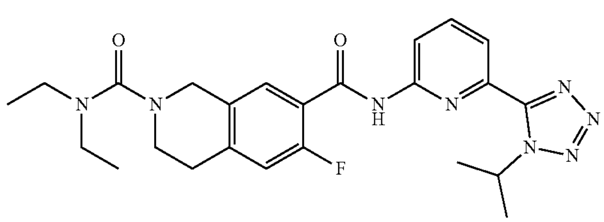 [SMILES: CCN(CC)C(=O)N1CCc2cc(F)c(C(=O)Nc3cccc(-c4nnnn4C(C)C)n3)cc2C1] |

-continued

| Compound | Structure |
|---|---|
| 95 | 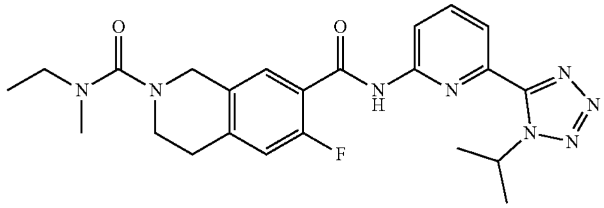 [SMILES: CCN(C)C(=O)N1CCc2cc(F)c(C(=O)Nc3cccc(-c4nnnn4C(C)C)n3)cc2C1] |
| 96 | 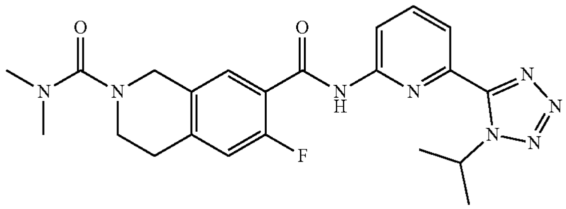 [SMILES: CC(C)n1nnnc1-c1cccc(NC(=O)c2cc3c(cc2F)CCN(C(=O)N(C)C)C3)n1] |
| 97 | 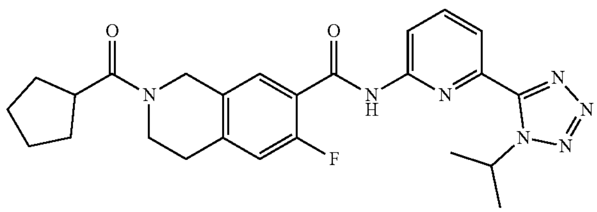 [SMILES: CC(C)n1nnnc1-c1cccc(NC(=O)c2cc3c(cc2F)CCN(C(=O)C2CCCC2)C3)n1] |
| 98 | 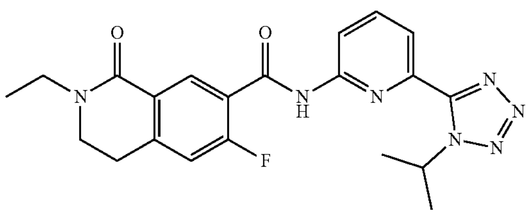 [SMILES: CCN1CCc2cc(F)c(C(=O)Nc3cccc(-c4nnnn4C(C)C)n3)cc2C1=O] |
| 99 | 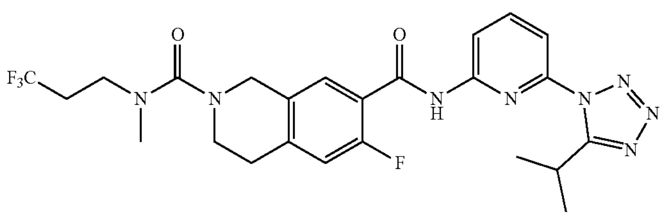 [SMILES: CC(C)c1nnnn1-c1cccc(NC(=O)c2cc3c(cc2F)CCN(C(=O)N(C)CCC(F)(F)F)C3)n1] |
| 100 | 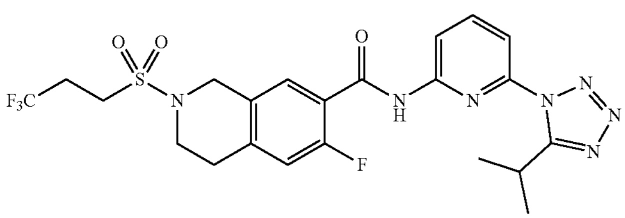 [SMILES: CC(C)c1nnnn1-c1cccc(NC(=O)c2cc3c(cc2F)CCN(S(=O)(=O)CCC(F)(F)F)C3)n1] |
| 101 | 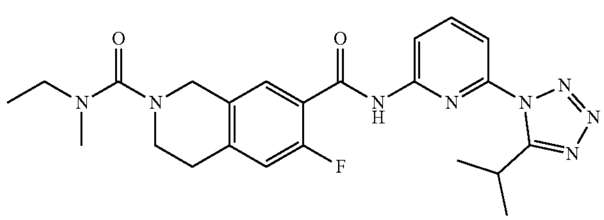 [SMILES: CCN(C)C(=O)N1CCc2cc(F)c(C(=O)Nc3cccc(-n4nnnc4C(C)C)n3)cc2C1] |

-continued

| Compound | Structure |
|---|---|
| 102 | 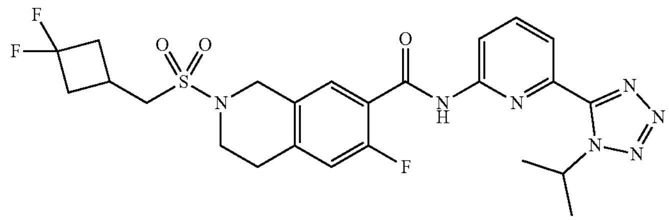 [SMILES: CC(C)n1nnnc1-c1cccc(NC(=O)c2cc3c(cc2F)CCN(S(=O)(=O)CC2CC(F)(F)C2)C3)n1] |
| 103 | 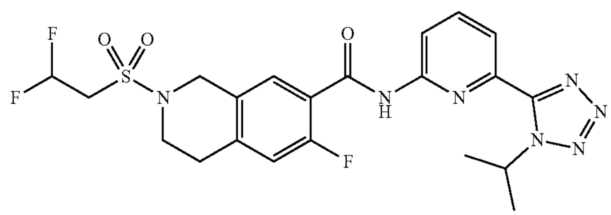 [SMILES: CC(C)n1nnnc1-c1cccc(NC(=O)c2cc3c(cc2F)CCN(S(=O)(=O)CC(F)F)C3)n1] |
| 104 | 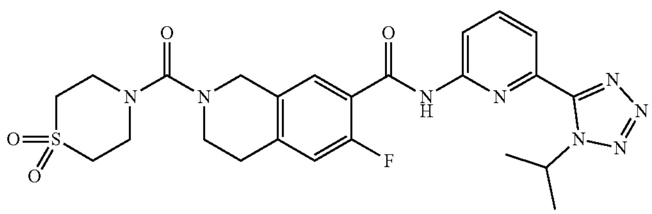 [SMILES: CC(C)n1nnnc1-c1cccc(NC(=O)c2cc3c(cc2F)CCN(C(=O)N2CCS(=O)(=O)CC2)C3)n1] |
| 105 | 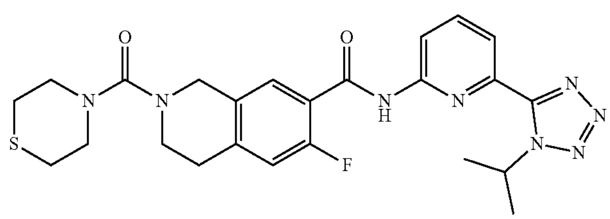 [SMILES: CC(C)n1nnnc1-c1cccc(NC(=O)c2cc3c(cc2F)CCN(C(=O)N2CCSCC2)C3)n1] |
| 106 | 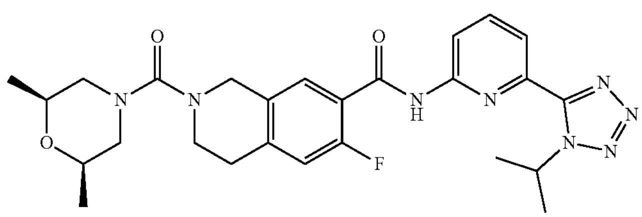 [SMILES: CC(C)n1nnnc1-c1cccc(NC(=O)c2cc3c(cc2F)CCN(C(=O)N2C[C@@H](C)O[C@@H](C)C2)C3)n1] |
| 107 | 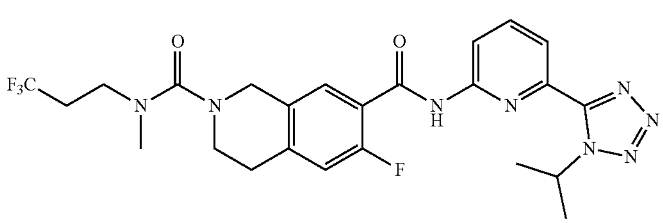 [SMILES: CC(C)n1nnnc1-c1cccc(NC(=O)c2cc3c(cc2F)CCN(C(=O)N(C)CCC(F)(F)F)C3)n1] |
| 108 | 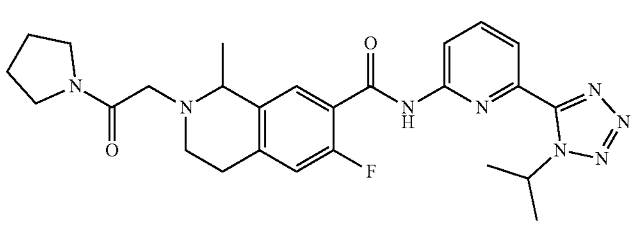 [SMILES: CC1c2cc(C(=O)Nc3cccc(-c4nnnn4C(C)C)n3)c(F)cc2CCN1CC(=O)N1CCCC1] |

-continued

| Compound | Structure |
|---|---|
| 109 | *(structure)* |
| 110 | *(structure)* |
| 111 | *(structure)* |
| 112 | *(structure)* |
| 113 | *(structure)* |
| 114 | *(structure)* |
| 115 | *(structure)* |

-continued

| Compound | Structure |
|---|---|
| 116 | 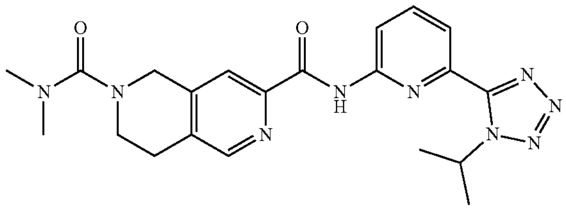 [SMILES: CC(C)n1nnnc1-c1cccc(NC(=O)c2cc3c(cn2)CCN(C(=O)N(C)C)C3)n1] |
| 117 | 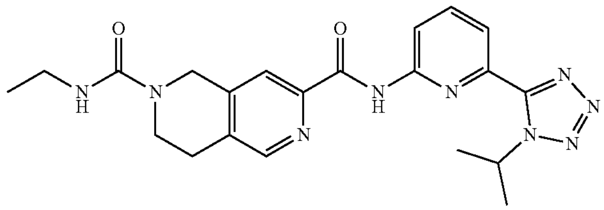 |
| 118 | 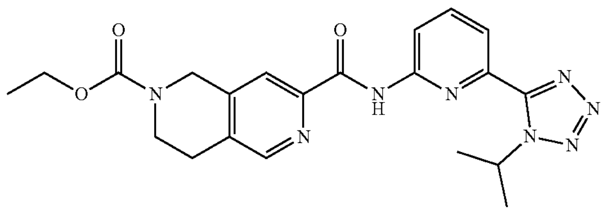 |
| 119 | 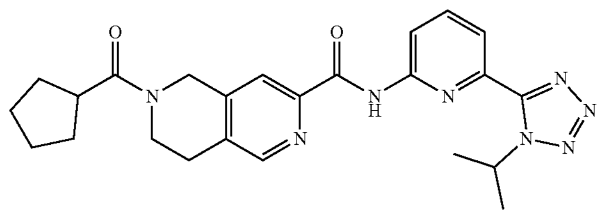 [SMILES: CC(C)n1nnnc1-c1cccc(NC(=O)c2cc3c(cn2)CCN(C(=O)C2CCCC2)C3)n1] |
| 120 | 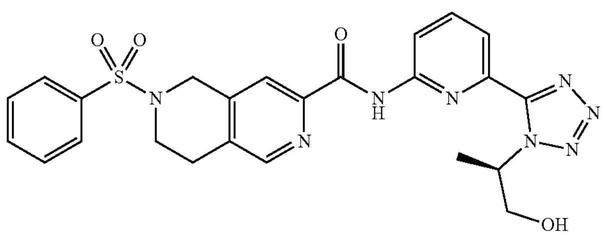 [SMILES: C[C@H](CO)n1nnnc1-c1cccc(NC(=O)c2cc3c(cn2)CCN(S(=O)(=O)c2ccccc2)C3)n1] |
| 121 | 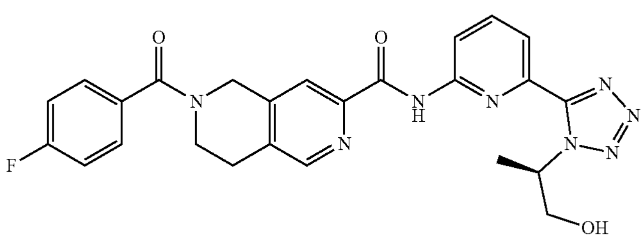 [SMILES: C[C@H](CO)n1nnnc1-c1cccc(NC(=O)c2cc3c(cn2)CCN(C(=O)c2ccc(F)cc2)C3)n1] |
| 122 | 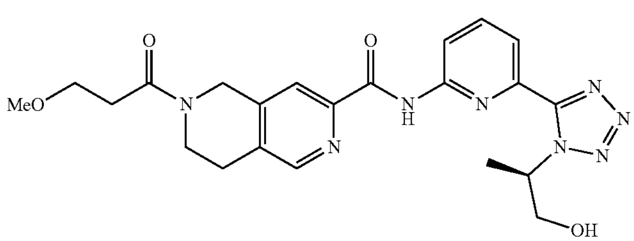 [SMILES: COCCC(=O)N1CCc2cnc(C(=O)Nc3cccc(-c4nnnn4[C@H](C)CO)n3)cc2C1] |

-continued
| Compound | Structure |
|---|---|
| 123 | 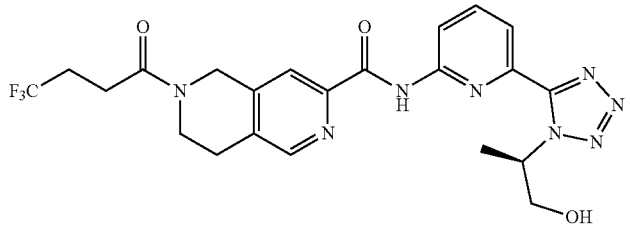 |
| 124 | 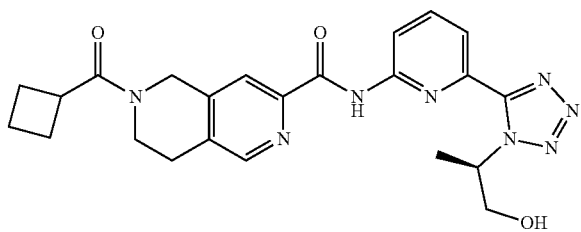 [SMILES: C[C@H](CO)n1nnnc1-c1cccc(NC(=O)c2cc3c(cn2)CCN(C(=O)C2CCC2)C3)n1] |
| 125 | 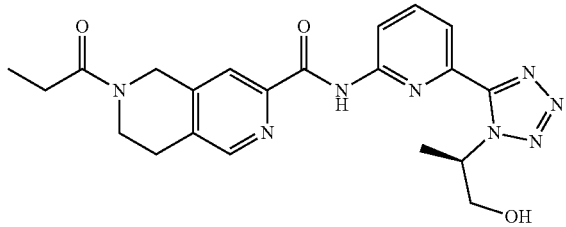 [SMILES: CCC(=O)N1CCc2cnc(C(=O)Nc3cccc(-c4nnnn4[C@H](C)CO)n3)cc2C1] |
| 126 | 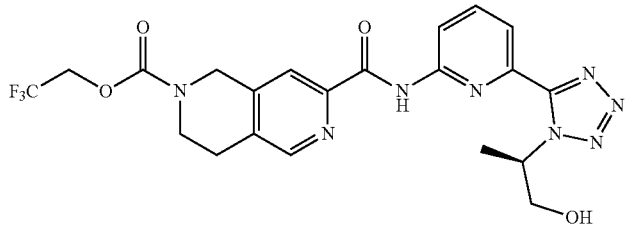 [SMILES: C[C@H](CO)n1nnnc1-c1cccc(NC(=O)c2cc3c(cn2)CCN(C(=O)OCC(F)(F)F)C3)n1] |
| 127 | 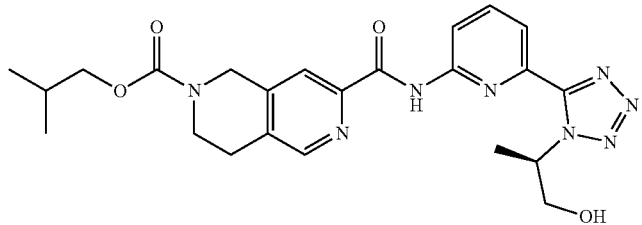 [SMILES: CC(C)COC(=O)N1CCc2cnc(C(=O)Nc3cccc(-c4nnnn4[C@H](C)CO)n3)cc2C1] |
| 128 | 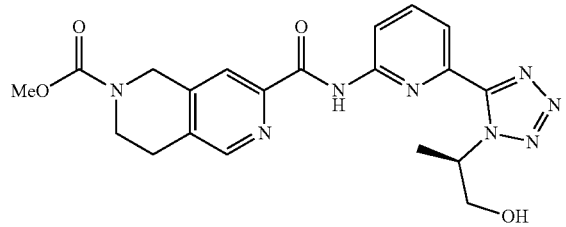 [SMILES: COC(=O)N1CCc2cnc(C(=O)Nc3cccc(-c4nnnn4[C@H](C)CO)n3)cc2C1] |

| Compound | Structure |
|---|---|
| 129 | 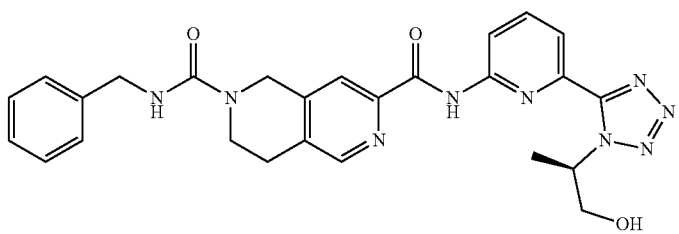 [SMILES: C[C@H](CO)n1nnnc1-c1cccc(NC(=O)c2cc3c(cn2)CCN(C(=O)NCc2ccccc2)C3)n1] |
| 130 | 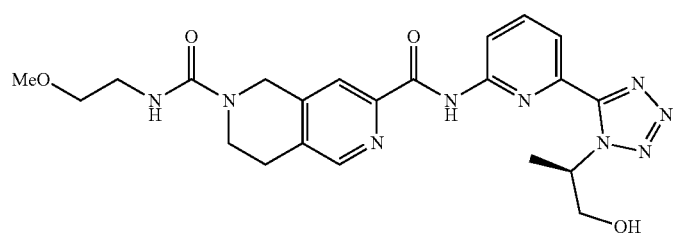 [SMILES: COCCNC(=O)N1CCc2cnc(C(=O)Nc3cccc(-c4nnnn4[C@H](C)CO)n3)cc2C1] |
| 131 | 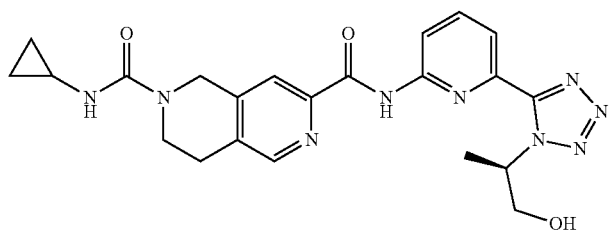 [SMILES: C[C@H](CO)n1nnnc1-c1cccc(NC(=O)c2cc3c(cn2)CCN(C(=O)NC2CC2)C3)n1] |
| 132 | 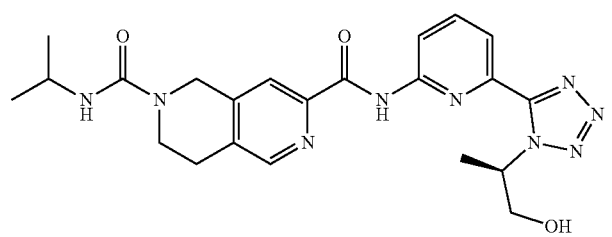 [SMILES: CC(C)NC(=O)N1CCc2cnc(C(=O)Nc3cccc(-c4nnnn4[C@H](C)CO)n3)cc2C1] |
| 133 | 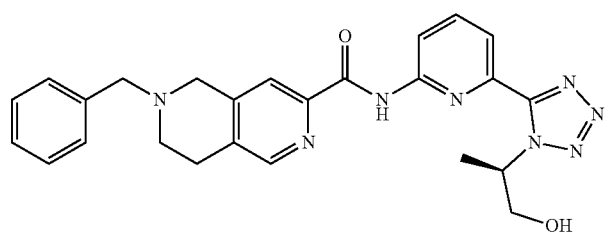 [SMILES: C[C@H](CO)n1nnnc1-c1cccc(NC(=O)c2cc3c(cn2)CCN(Cc2ccccc2)C3)n1] |
| 134 | 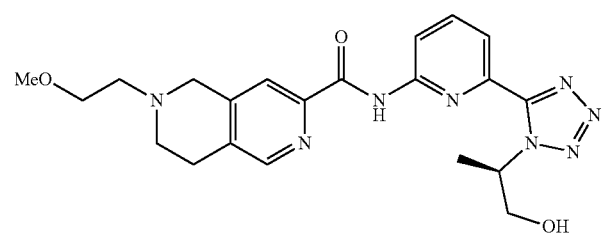 [SMILES: COCCN1CCc2cnc(C(=O)Nc3cccc(-c4nnnn4[C@H](C)CO)n3)cc2C1] |

-continued

| Compound | Structure |
|---|---|
| 135 | 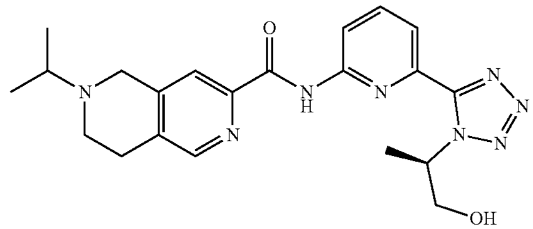 [SMILES: CC(C)N1CCc2cnc(C(=O)Nc3cccc(-c4nnnn4[C@H](C)CO)n3)cc2C1] |
| 136 | 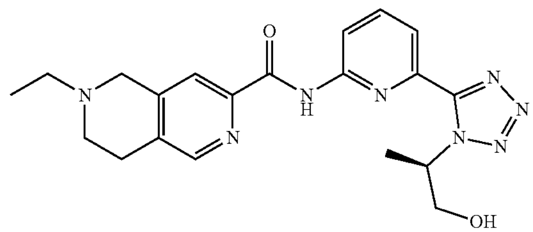 [SMILES: CCN1CCc2cnc(C(=O)Nc3cccc(-c4nnnn4[C@H](C)CO)n3)cc2C1] |
| 137 | 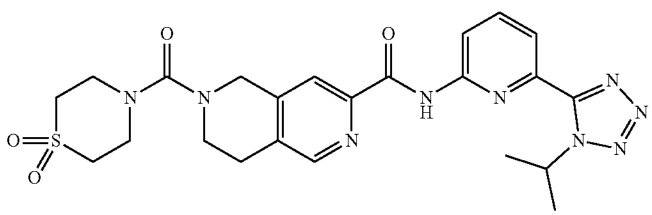 [SMILES: CC(C)n1nnnc1-c1cccc(NC(=O)c2cc3c(cn2)CCN(C(=O)N2CCS(=O)(=O)CC2)C3)n1] |
| 138 | 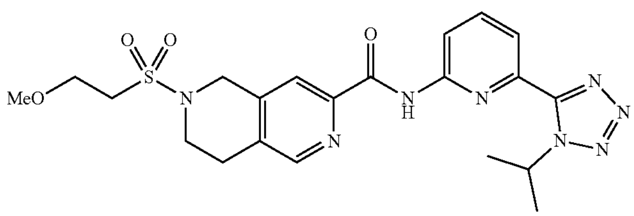 [SMILES: COCCS(=O)(=O)N1CCc2cnc(C(=O)Nc3cccc(-c4nnnn4C(C)C)n3)cc2C1] |
| 139 | 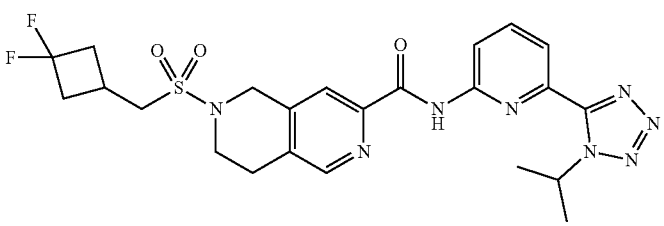 [SMILES: CC(C)n1nnnc1-c1cccc(NC(=O)c2cc3c(cn2)CCN(S(=O)(=O)CC2CC(F)(F)C2)C3)n1] |
| 140 | 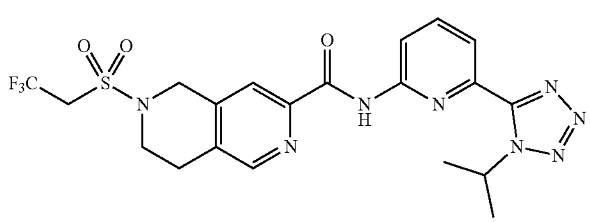 [SMILES: CC(C)n1nnnc1-c1cccc(NC(=O)c2cc3c(cn2)CCN(S(=O)(=O)CC(F)(F)F)C3)n1] |
| 141 | 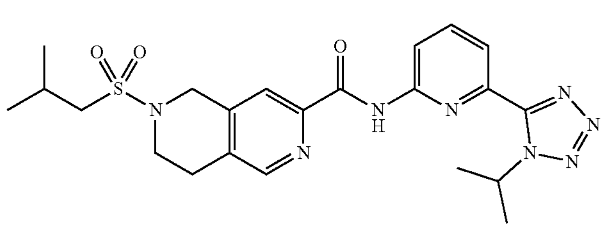 [SMILES: CC(C)CS(=O)(=O)N1CCc2cnc(C(=O)Nc3cccc(-c4nnnn4C(C)C)n3)cc2C1] |

-continued
| Compound | Structure |
|---|---|
| 142 | 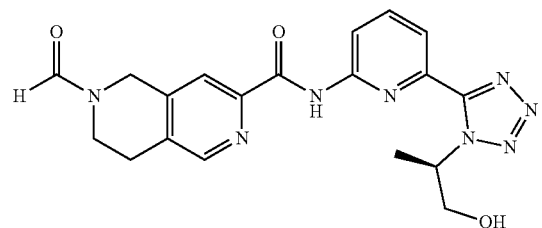 [SMILES: C[C@H](CO)n1nnnc1-c1cccc(NC(=O)c2cc3c(cn2)CCN(C=O)C3)n1] |
| 143 | 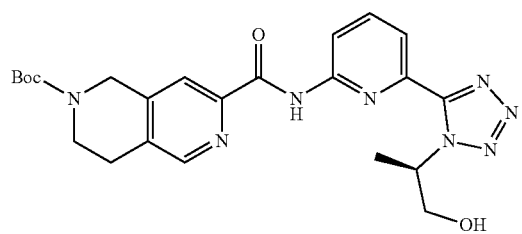 [SMILES: C[C@H](CO)n1nnnc1-c1cccc(NC(=O)c2cc3c(cn2)CCN(C(=O)OC(C)(C)C)C3)n1] |
| 144 | 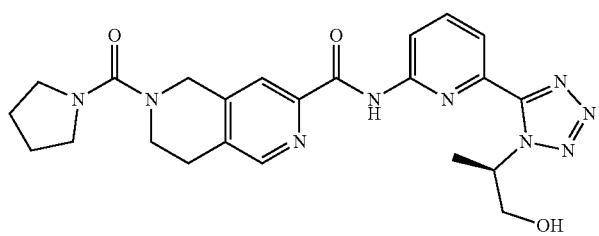 [SMILES: C[C@H](CO)n1nnnc1-c1cccc(NC(=O)c2cc3c(cn2)CCN(C(=O)N2CCCC2)C3)n1] |
| 145 | 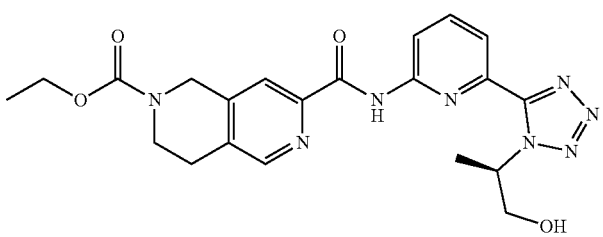 [SMILES: CCOC(=O)N1CCc2cnc(C(=O)Nc3cccc(-c4nnnn4[C@H](C)CO)n3)cc2C1] |
| 146 | 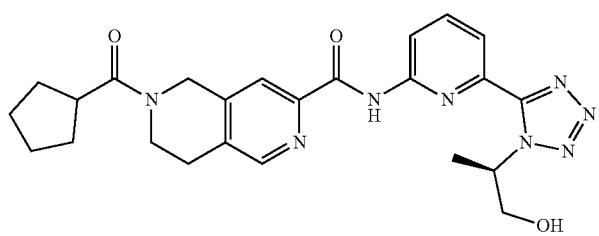 [SMILES: C[C@H](CO)n1nnnc1-c1cccc(NC(=O)c2cc3c(cn2)CCN(C(=O)C2CCCC2)C3)n1] |
| 147 | 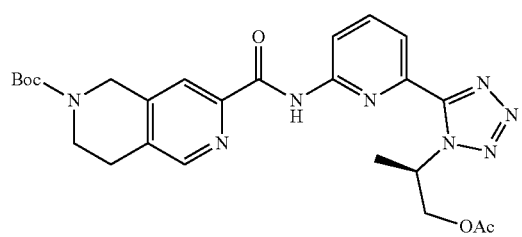 [SMILES: CC(=O)OC[C@@H](C)n1nnnc1-c1cccc(NC(=O)c2cc3c(cn2)CCN(C(=O)OC(C)(C)C)C3)n1] |

| Compound | Structure |
|---|---|
| 148 | 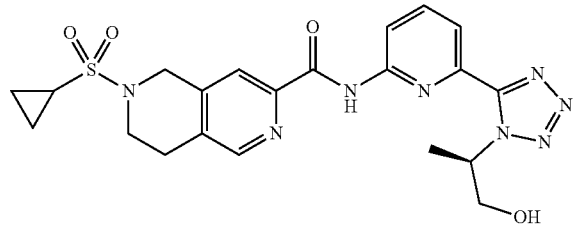 [SMILES: C[C@H](CO)n1nnnc1-c1cccc(NC(=O)c2cc3c(cn2)CCN(S(=O)(=O)C2CC2)C3)n1] |
| 149 | 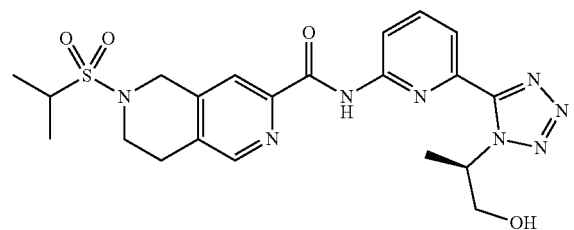 |
| 150 | 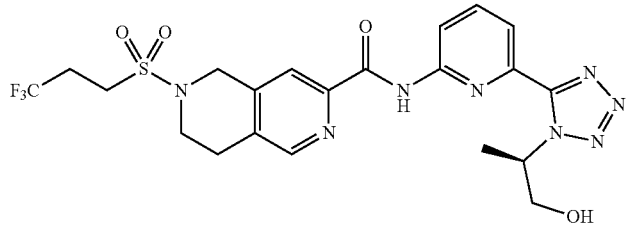 [SMILES: C[C@H](CO)n1nnnc1-c1cccc(NC(=O)c2cc3c(cn2)CCN(S(=O)(=O)CCC(F)(F)F)C3)n1] |
| 151 | 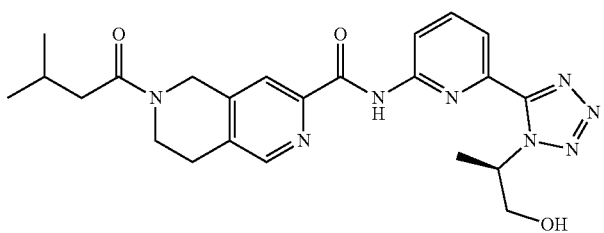 [SMILES: CC(C)CC(=O)N1CCc2cnc(C(=O)Nc3cccc(-c4nnnn4[C@H](C)CO)n3)cc2C1] |
| 152 | 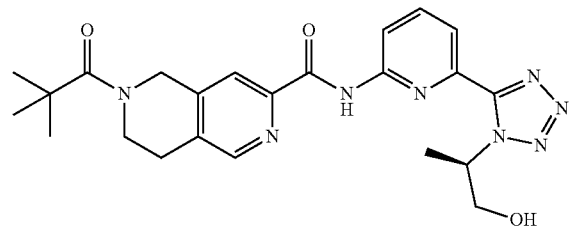 [SMILES: C[C@H](CO)n1nnnc1-c1cccc(NC(=O)c2cc3c(cn2)CCN(C(=O)C(C)(C)C)C3)n1] |
| 153 | 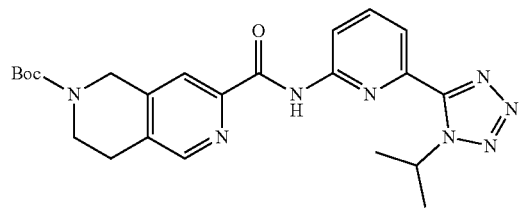 [SMILES: CC(C)n1nnnc1-c1cccc(NC(=O)c2cc3c(cn2)CCN(C(=O)OC(C)(C)C)C3)n1] |

-continued
| Compound | Structure |
|---|---|
| 154 | 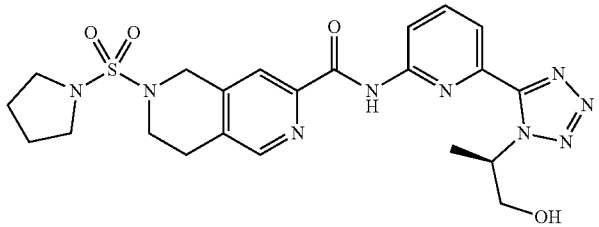 [SMILES: C[C@H](CO)n1nnnc1-c1cccc(NC(=O)c2cc3c(cn2)CCN(S(=O)(=O)N2CCCC2)C3)n1] |
| 155 | 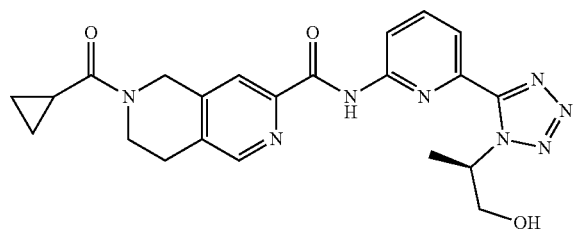 [SMILES: C[C@H](CO)n1nnnc1-c1cccc(NC(=O)c2cc3c(cn2)CCN(C(=O)C2CC2)C3)n1] |
| 156 | 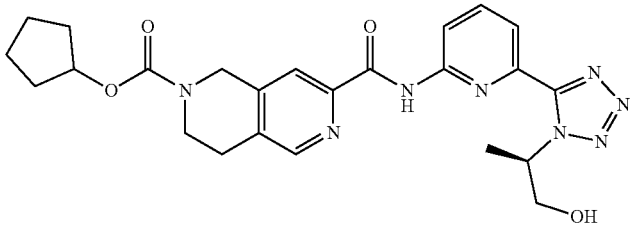 [SMILES: C[C@H](CO)n1nnnc1-c1cccc(NC(=O)c2cc3c(cn2)CCN(C(=O)OC2CCCC2)C3)n1] |
| 157 | 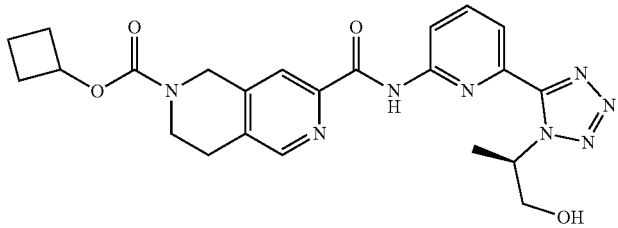 [SMILES: C[C@H](CO)n1nnnc1-c1cccc(NC(=O)c2cc3c(cn2)CCN(C(=O)OC2CCC2)C3)n1] |
| 158 | 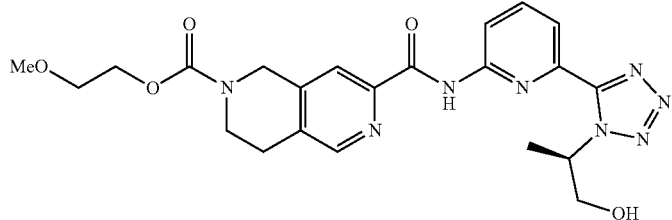 [SMILES: COCCOC(=O)N1CCc2cnc(C(=O)Nc3cccc(-c4nnnn4[C@H](C)CO)n3)cc2C1] |
| 159 | 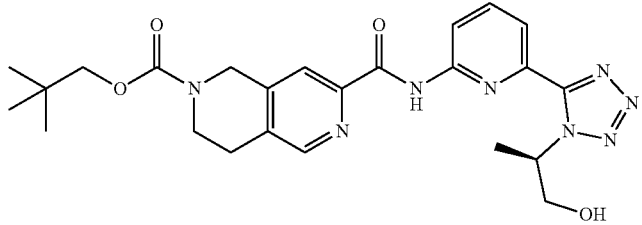 [SMILES: C[C@H](CO)n1nnnc1-c1cccc(NC(=O)c2cc3c(cn2)CCN(C(=O)OCC(C)(C)C)C3)n1] |

| Compound | Structure |
|---|---|
| 160 | 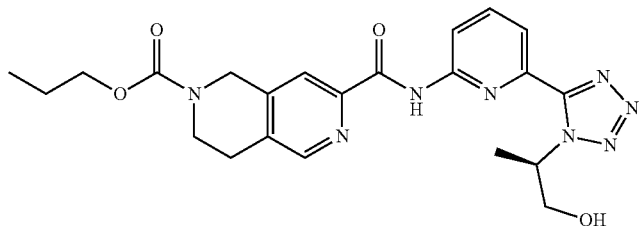 [SMILES: CCCOC(=O)N1CCc2cnc(C(=O)Nc3cccc(-c4nnnn4[C@H](C)CO)n3)cc2C1] |
| 161 | 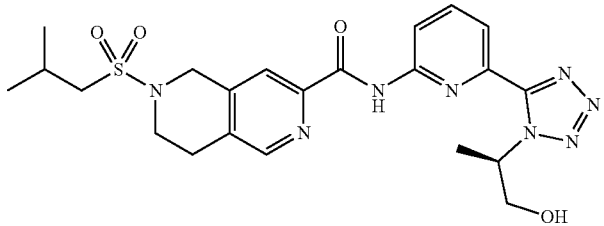 [SMILES: CC(C)CS(=O)(=O)N1CCc2cnc(C(=O)Nc3cccc(-c4nnnn4[C@H](C)CO)n3)cc2C1] |
| 162 | 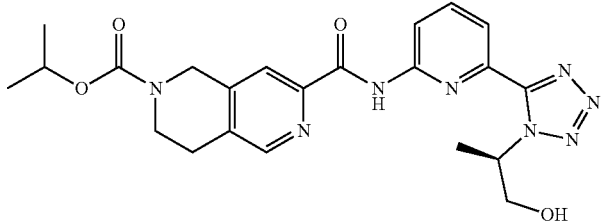 [SMILES: CC(C)OC(=O)N1CCc2cnc(C(=O)Nc3cccc(-c4nnnn4[C@H](C)CO)n3)cc2C1] |
| 163 | 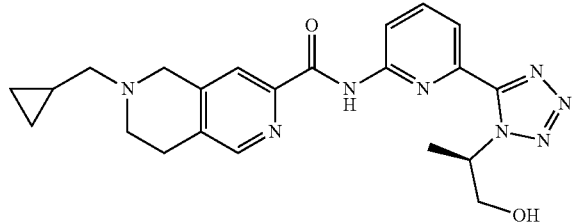 [SMILES: C[C@H](CO)n1nnnc1-c1cccc(NC(=O)c2cc3c(cn2)CCN(CC2CC2)C3)n1] |
| 164 | 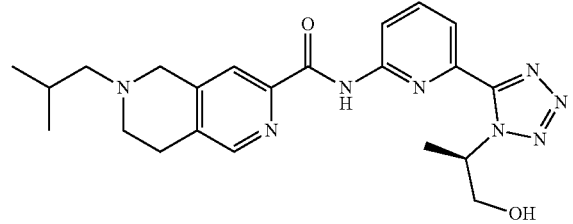 [SMILES: CC(C)CN1CCc2cnc(C(=O)Nc3cccc(-c4nnnn4[C@H](C)CO)n3)cc2C1] |
| 165 | 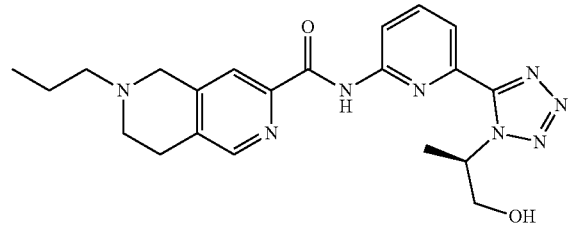 [SMILES: CCCN1CCc2cnc(C(=O)Nc3cccc(-c4nnnn4[C@H](C)CO)n3)cc2C1] |

| Compound | Structure |
|---|---|
| 166 | 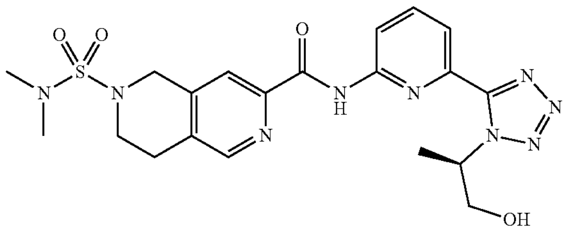 [SMILES: C[C@H](CO)n1nnnc1-c1cccc(NC(=O)c2cc3c(cn2)CCN(S(=O)(=O)N(C)C)C3)n1] |
| 167 | 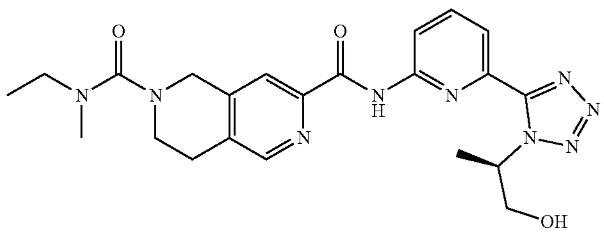 [SMILES: CCN(C)C(=O)N1CCc2cnc(C(=O)Nc3cccc(-c4nnnn4[C@H](C)CO)n3)cc2C1] |
| 168 | 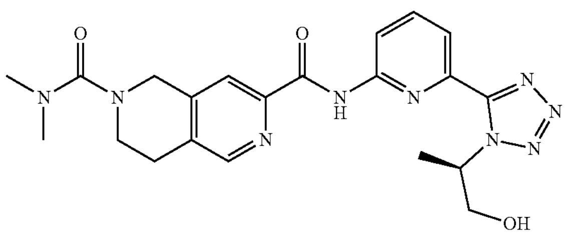 [SMILES: C[C@H](CO)n1nnnc1-c1cccc(NC(=O)c2cc3c(cn2)CCN(C(=O)N(C)C)C3)n1] |
| 169 | 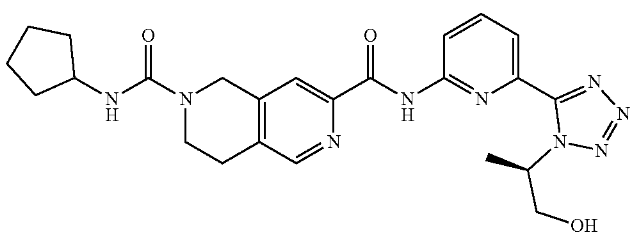 [SMILES: C[C@H](CO)n1nnnc1-c1cccc(NC(=O)c2cc3c(cn2)CCN(C(=O)NC2CCCC2)C3)n1] |
| 170 | 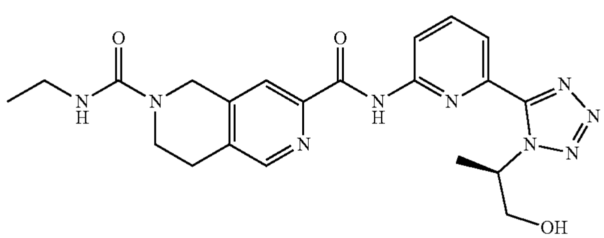 [SMILES: CCNC(=O)N1CCc2cnc(C(=O)Nc3cccc(-c4nnnn4[C@H](C)CO)n3)cc2C1] |
| 171 | 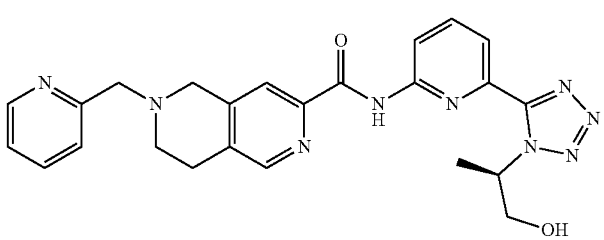 [SMILES: C[C@H](CO)n1nnnc1-c1cccc(NC(=O)c2cc3c(cn2)CCN(Cc2ccccn2)C3)n1] |

| Compound | Structure |
|---|---|
| 172 | 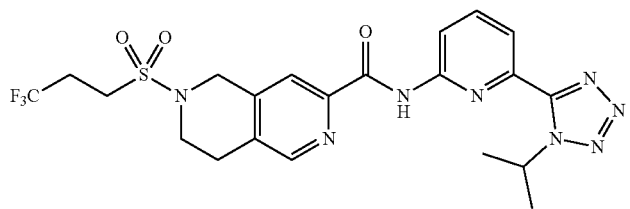 [SMILES: CC(C)n1nnnc1-c1cccc(NC(=O)c2cc3c(cn2)CCN(S(=O)(=O)CCC(F)(F)F)C3)n1] |
| 173 | 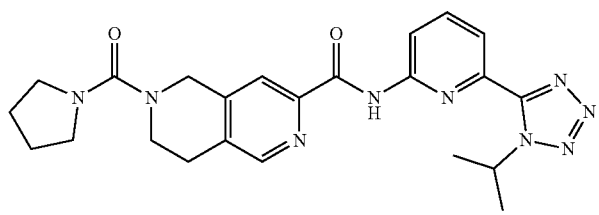 |
| 174 | 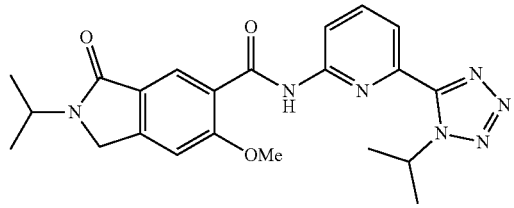 |
| 175 | 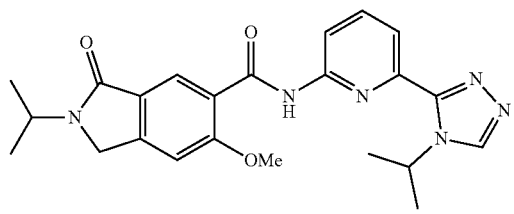 |
| 176 | 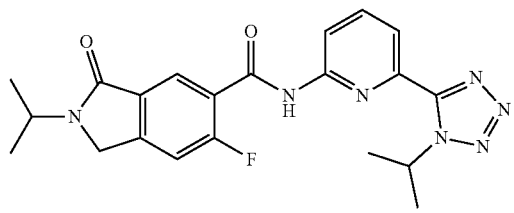 [SMILES: CC(C)N1Cc2cc(F)c(C(=O)Nc3cccc(-c4nnnn4C(C)C)n3)cc2C1=O] |
| 177 | 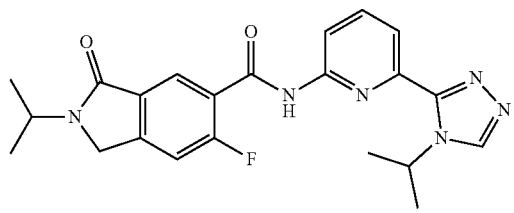 |
| 178 | 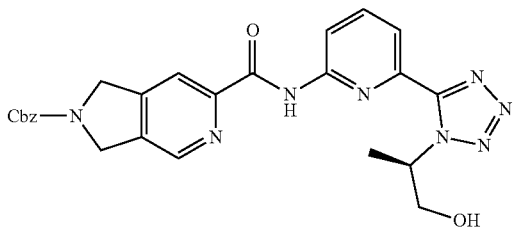 [SMILES: C[C@H](CO)n1nnnc1-c1cccc(NC(=O)c2cc3c(cn2)CN(C(=O)OCc2ccccc2)C3)n1] |

-continued
| Compound | Structure |
|---|---|
| 179 | 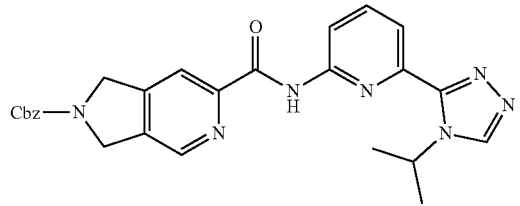 [SMILES: CC(C)n1cnnc1-c1cccc(NC(=O)c2cc3c(cn2)CN(C(=O)OCc2ccccc2)C3)n1] |
| 180 | 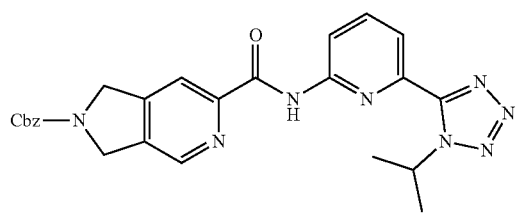 [SMILES: CC(C)n1nnnc1-c1cccc(NC(=O)c2cc3c(cn2)CN(C(=O)OCc2ccccc2)C3)n1] |
| 181 | 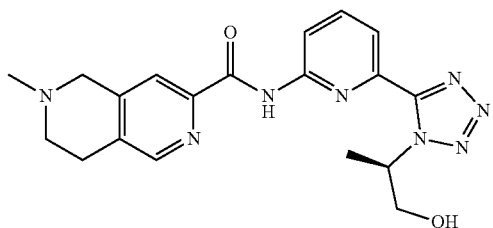 [SMILES: C[C@H](CO)n1nnnc1-c1cccc(NC(=O)c2cc3c(cn2)CCN(C)C3)n1] |
| 182 | 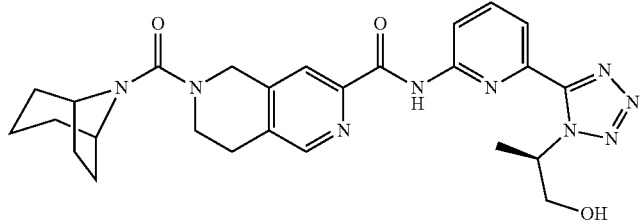 [SMILES: C[C@H](CO)n1nnnc1-c1cccc(NC(=O)c2cc3c(cn2)CCN(C(=O)N2C4CCCC2CC4)C3)n1] |
| 183 | 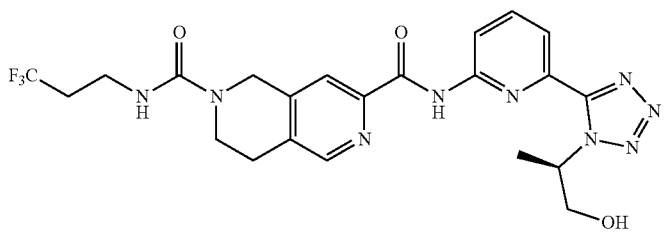 [SMILES: C[C@H](CO)n1nnnc1-c1cccc(NC(=O)c2cc3c(cn2)CCN(C(=O)NCCC(F)(F)F)C3)n1] |
| 184 | 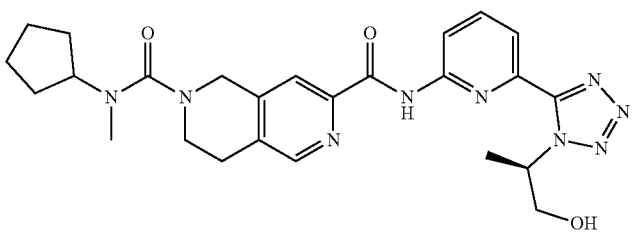 [SMILES: C[C@H](CO)n1nnnc1-c1cccc(NC(=O)c2cc3c(cn2)CCN(C(=O)N(C)C2CCCC2)C3)n1] |

-continued

| Compound | Structure |
|---|---|
| 185 | 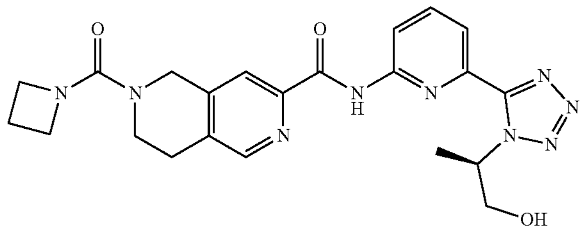 [SMILES: C[C@H](CO)n1nnnc1-c1cccc(NC(=O)c2cc3c(cn2)CCN(C(=O)N2CCC2)C3)n1] |
| 186 | 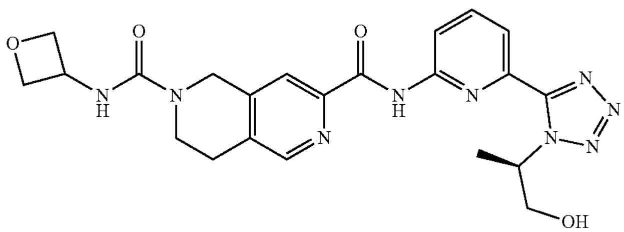 [SMILES: C[C@H](CO)n1nnnc1-c1cccc(NC(=O)c2cc3c(cn2)CCN(C(=O)NC2COC2)C3)n1] |
| 187 | 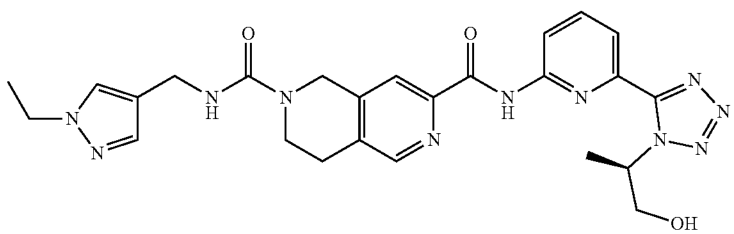 [SMILES: CCn1cc(CNC(=O)N2CCc3cnc(C(=O)Nc4cccc(-c5nnnn5[C@H](C)CO)n4)cc3C2)cn1] |
| 188 | 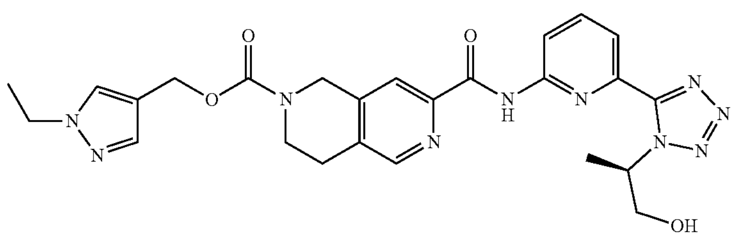 [SMILES: CCn1cc(COC(=O)N2CCc3cnc(C(=O)Nc4cccc(-c5nnnn5[C@H](C)CO)n4)cc3C2)cn1] |
| 189 | 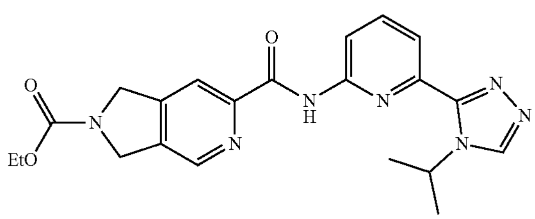 [SMILES: CCOC(=O)N1Cc2cnc(C(=O)Nc3cccc(-c4nncn4C(C)C)n3)cc2C1] |
| 190 | 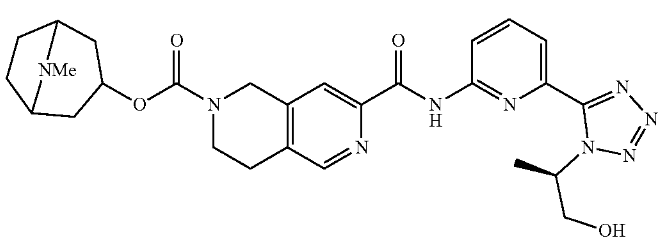 [SMILES: C[C@H](CO)n1nnnc1-c1cccc(NC(=O)c2cc3c(cn2)CCN(C(=O)OC2CC4CCC(C2)N4C)C3)n1] |

| Compound | Structure |
|---|---|
| 191 | 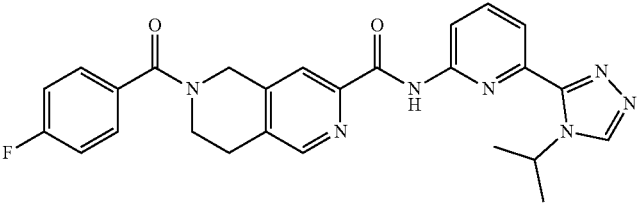 [SMILES: CC(C)n1cnnc1-c1cccc(NC(=O)c2cc3c(cn2)CCN(C(=O)c2ccc(F)cc2)C3)n1] |
| 192 | 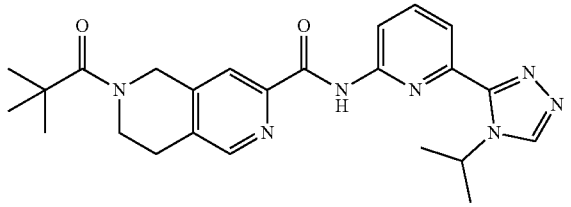 [SMILES: CC(C)n1cnnc1-c1cccc(NC(=O)c2cc3c(cn2)CCN(C(=O)C(C)(C)C)C3)n1] |
| 193 | 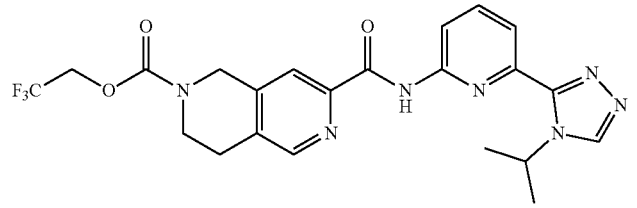 [SMILES: CC(C)n1cnnc1-c1cccc(NC(=O)c2cc3c(cn2)CCN(C(=O)OCC(F)(F)F)C3)n1] |
| 194 | 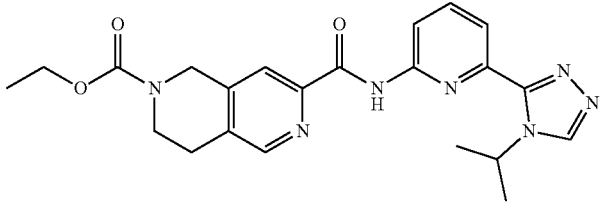 [SMILES: CCOC(=O)N1CCc2cnc(C(=O)Nc3cccc(-c4nncn4C(C)C)n3)cc2C1] |
| 195 | 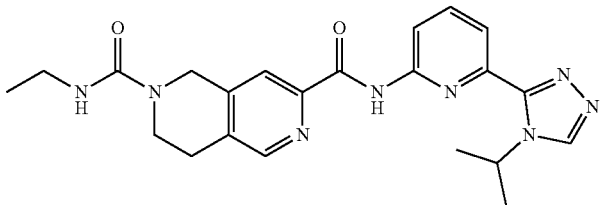 [SMILES: CCNC(=O)N1CCc2cnc(C(=O)Nc3cccc(-c4nncn4C(C)C)n3)cc2C1] |
| 196 | 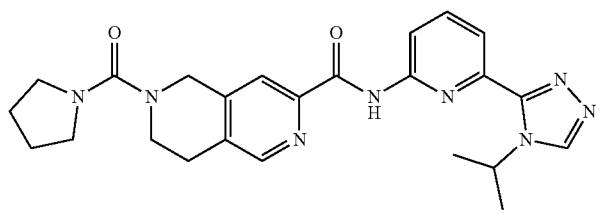 [SMILES: CC(C)n1cnnc1-c1cccc(NC(=O)c2cc3c(cn2)CCN(C(=O)N2CCCC2)C3)n1] |
| 197 | 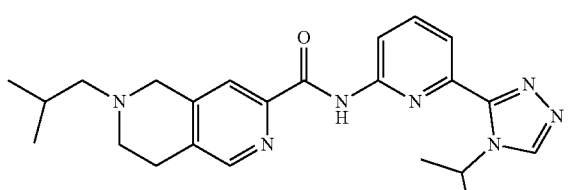 |

| Compound | Structure |
|---|---|
| 198 | 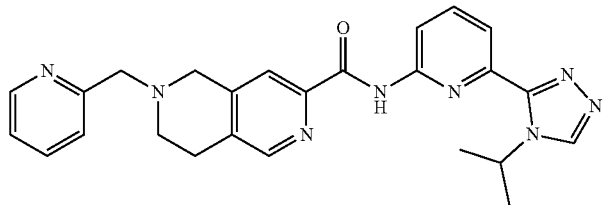 [SMILES: CC(C)n1cnnc1-c1cccc(NC(=O)c2cc3c(cn2)CCN(Cc2ccccn2)C3)n1] |
| 199 | 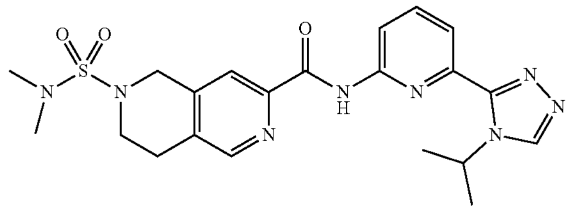 [SMILES: CC(C)n1cnnc1-c1cccc(NC(=O)c2cc3c(cn2)CCN(S(=O)(=O)N(C)C)C3)n1] |
| 200 | 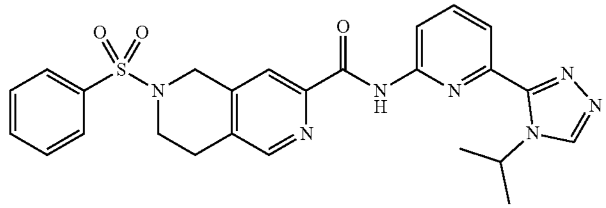 [SMILES: CC(C)n1cnnc1-c1cccc(NC(=O)c2cc3c(cn2)CCN(S(=O)(=O)c2ccccc2)C3)n1] |
| 201 | 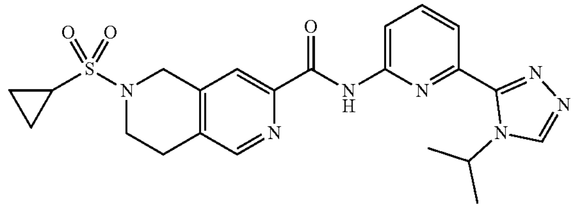 [SMILES: CC(C)n1cnnc1-c1cccc(NC(=O)c2cc3c(cn2)CCN(S(=O)(=O)C2CC2)C3)n1] |
| 202 | 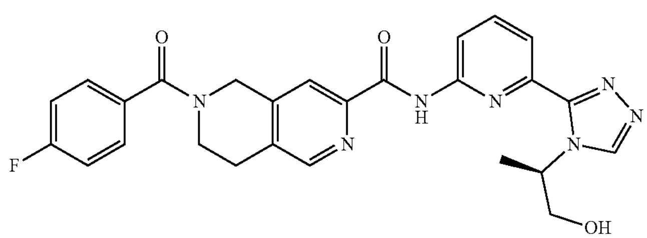 [SMILES: C[C@H](CO)n1cnnc1-c1cccc(NC(=O)c2cc3c(cn2)CCN(C(=O)c2ccc(F)cc2)C3)n1] |
| 203 | 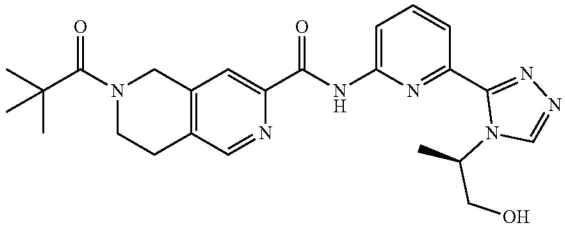 [SMILES: C[C@H](CO)n1cnnc1-c1cccc(NC(=O)c2cc3c(cn2)CCN(C(=O)C(C)(C)C)C3)n1] |
| 204 | 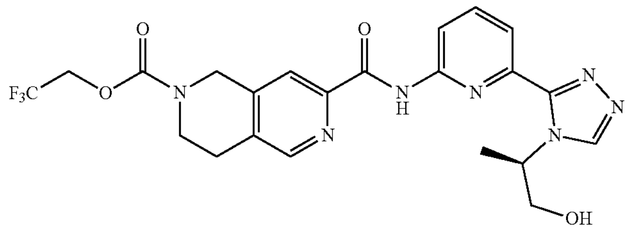 [SMILES: C[C@H](CO)n1cnnc1-c1cccc(NC(=O)c2cc3c(cn2)CCN(C(=O)OCC(F)(F)F)C3)n1] |

-continued

| Compound | Structure |
|---|---|
| 205 | 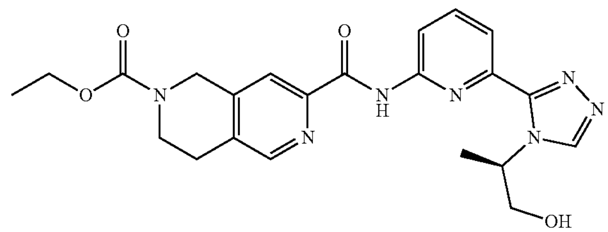 [SMILES: CCOC(=O)N1CCc2cnc(C(=O)Nc3cccc(-c4nncn4[C@H](C)CO)n3)cc2C1] |
| 206 | 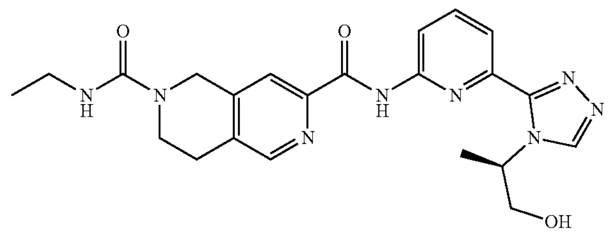 [SMILES: CCNC(=O)N1CCc2cnc(C(=O)Nc3cccc(-c4nncn4[C@H](C)CO)n3)cc2C1] |
| 207 | 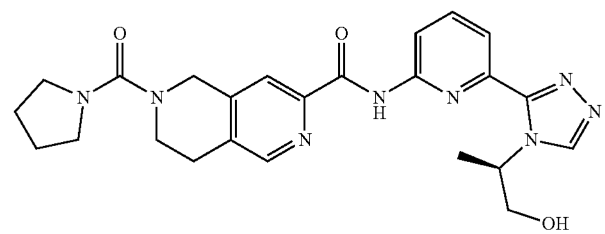 [SMILES: C[C@H](CO)n1cnnc1-c1cccc(NC(=O)c2cc3c(cn2)CCN(C(=O)N2CCCC2)C3)n1] |
| 208 | 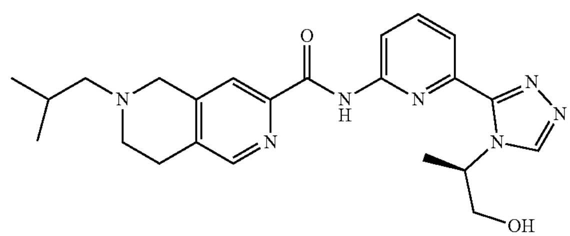 [SMILES: CC(C)CN1CCc2cnc(C(=O)Nc3cccc(-c4nncn4[C@H](C)CO)n3)cc2C1] |
| 209 | 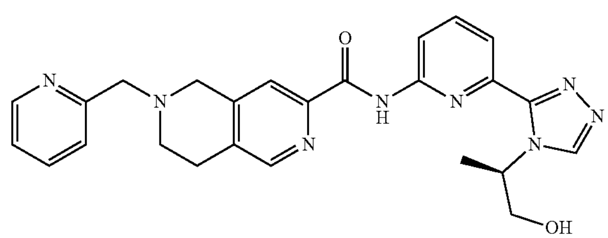 [SMILES: C[C@H](CO)n1cnnc1-c1cccc(NC(=O)c2cc3c(cn2)CCN(Cc2ccccn2)C3)n1] |
| 210 | 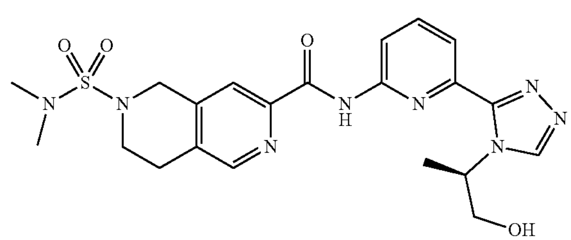 [SMILES: C[C@H](CO)n1cnnc1-c1cccc(NC(=O)c2cc3c(cn2)CCN(S(=O)(=O)N(C)C)C3)n1] |

| Compound | Structure |
|---|---|
| 211 | 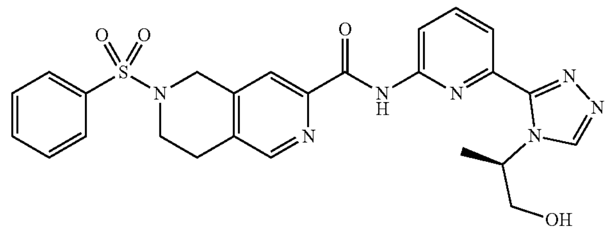 [SMILES: C[C@H](CO)n1cnnc1-c1cccc(NC(=O)c2cc3c(cn2)CCN(S(=O)(=O)c2ccccc2)C3)n1] |
| 212 | 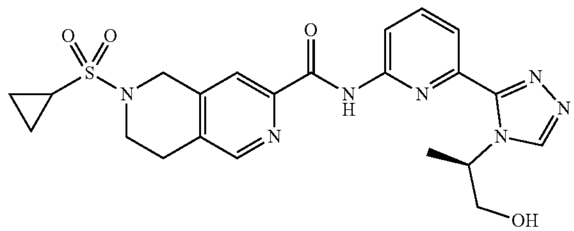 [SMILES: C[C@H](CO)n1cnnc1-c1cccc(NC(=O)c2cc3c(cn2)CCN(S(=O)(=O)C2CC2)C3)n1] |
| 213 | 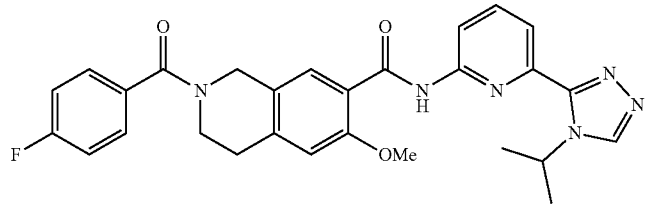 [SMILES: COc1cc2c(cc1C(=O)Nc1cccc(-c3nncn3C(C)C)n1)CN(C(=O)c1ccc(F)cc1)CC2] |
| 214 | 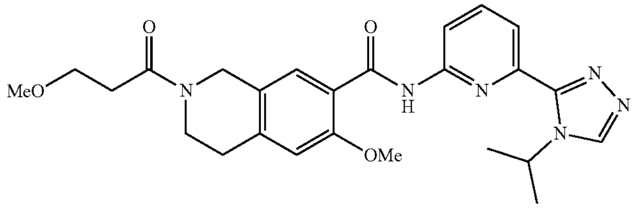 [SMILES: COCCC(=O)N1CCc2cc(OC)c(C(=O)Nc3cccc(-c4nncn4C(C)C)n3)cc2C1] |
| 215 | 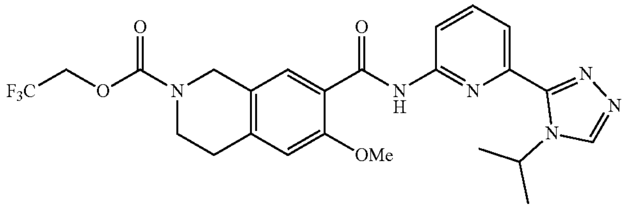 [SMILES: COc1cc2c(cc1C(=O)Nc1cccc(-c3nncn3C(C)C)n1)CN(C(=O)OCC(F)(F)F)CC2] |
| 216 | 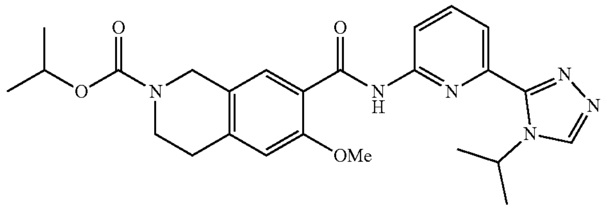 [SMILES: COc1cc2c(cc1C(=O)Nc1cccc(-c3nncn3C(C)C)n1)CN(C(=O)OC(C)C)CC2] |
| 217 | 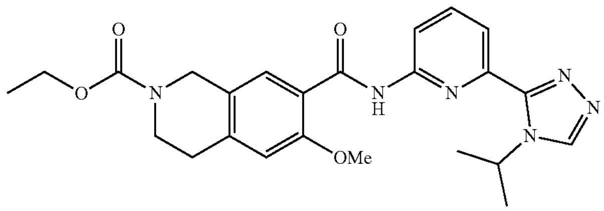 [SMILES: CCOC(=O)N1CCc2cc(OC)c(C(=O)Nc3cccc(-c4nncn4C(C)C)n3)cc2C1] |

-continued

| Compound | Structure |
|---|---|
| 218 | 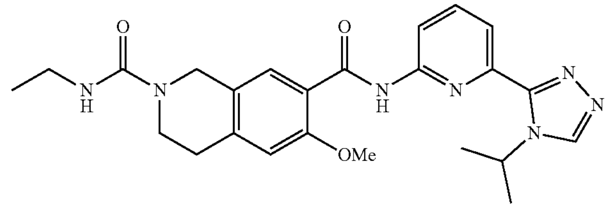 |
| 219 | 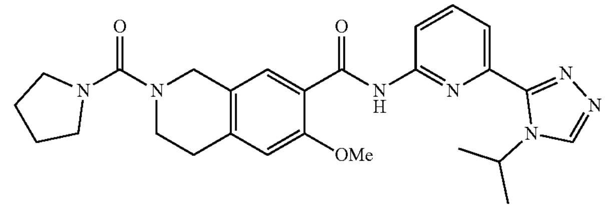 [SMILES: COc1cc2c(cc1C(=O)Nc1cccc(-c3nncn3C(C)C)n1)CN(C(=O)N1CCCC1)CC2] |
| 220 | 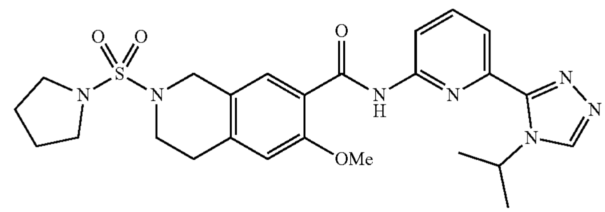 [SMILES: COc1cc2c(cc1C(=O)Nc1cccc(-c3nncn3C(C)C)n1)CN(S(=O)(=O)N1CCCC1)CC2] |
| 221 | 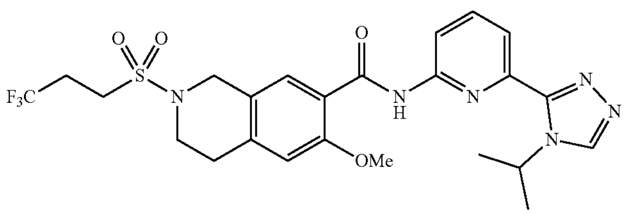 [SMILES: COc1cc2c(cc1C(=O)Nc1cccc(-c3nncn3C(C)C)n1)CN(S(=O)(=O)CCC(F)(F)F)CC2] |
| 222 | 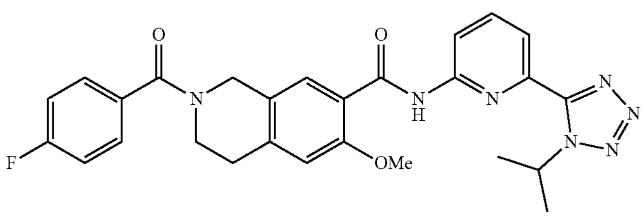 [SMILES: COc1cc2c(cc1C(=O)Nc1cccc(-c3nnnn3C(C)C)n1)CN(C(=O)c1ccc(F)cc1)CC2] |
| 223 | 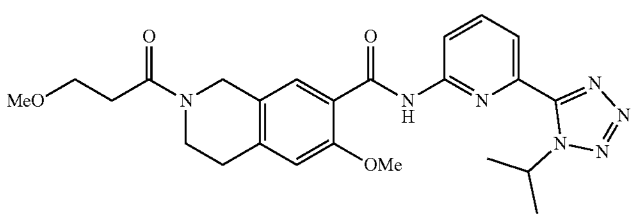 [SMILES: COCCC(=O)N1CCc2cc(OC)c(C(=O)Nc3cccc(-c4nnnn4C(C)C)n3)cc2C1] |
| 224 | 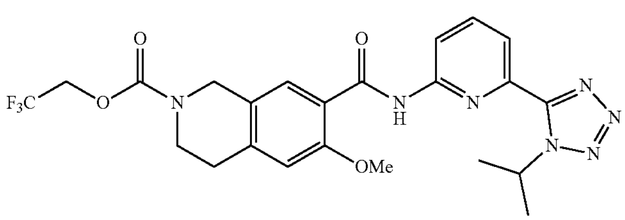 [SMILES: COc1cc2c(cc1C(=O)Nc1cccc(-c3nnnn3C(C)C)n1)CN(C(=O)OCC(F)(F)F)CC2] |

| Compound | Structure |
|---|---|
| 225 | 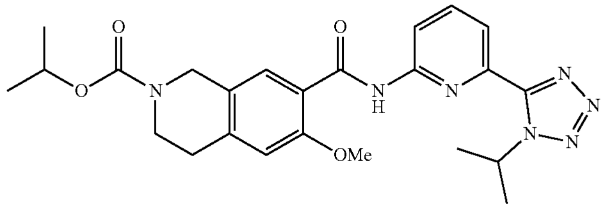 [SMILES: COc1cc2c(cc1C(=O)Nc1cccc(-c3nnnn3C(C)C)n1)CN(C(=O)OC(C)C)CC2] |
| 226 | 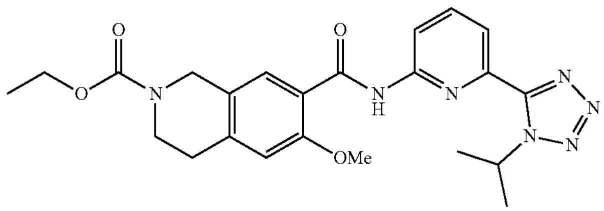 [SMILES: CCOC(=O)N1CCc2cc(OC)c(C(=O)Nc3cccc(-c4nnnn4C(C)C)n3)cc2C1] |
| 227 | 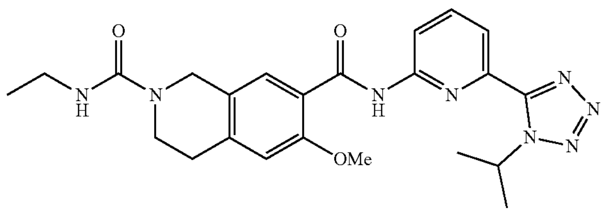 [SMILES: CCNC(=O)N1CCc2cc(OC)c(C(=O)Nc3cccc(-c4nnnn4C(C)C)n3)cc2C1] |
| 228 | 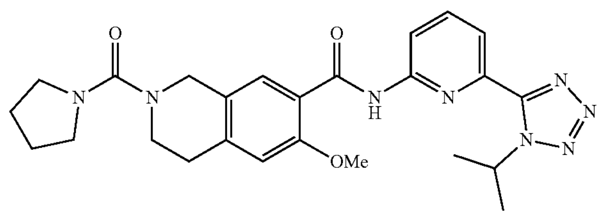 [SMILES: COc1cc2c(cc1C(=O)Nc1cccc(-c3nnnn3C(C)C)n1)CN(C(=O)N1CCCC1)CC2] |
| 229 | 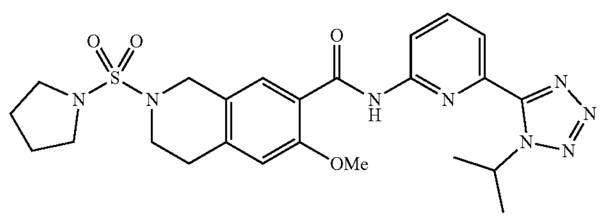 [SMILES: COc1cc2c(cc1C(=O)Nc1cccc(-c3nnnn3C(C)C)n1)CN(S(=O)(=O)N1CCCC1)CC2] |
| 230 | 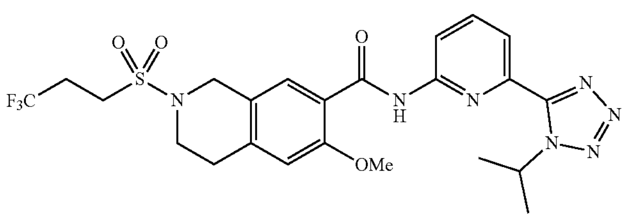 [SMILES: COc1cc2c(cc1C(=O)Nc1cccc(-c3nnnn3C(C)C)n1)CN(S(=O)(=O)CCC(F)(F)F)CC2] |
| 231 | 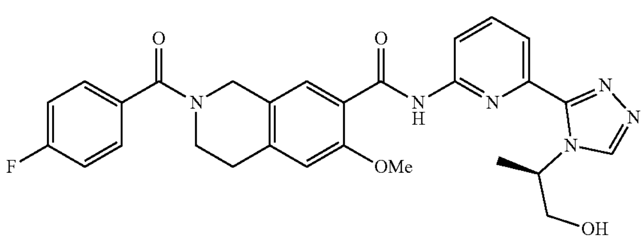 [SMILES: COc1cc2c(cc1C(=O)Nc1cccc(-c3nncn3[C@H](C)CO)n1)CN(C(=O)c1ccc(F)cc1)CC2] |

| Compound | Structure |
|---|---|
| 232 | 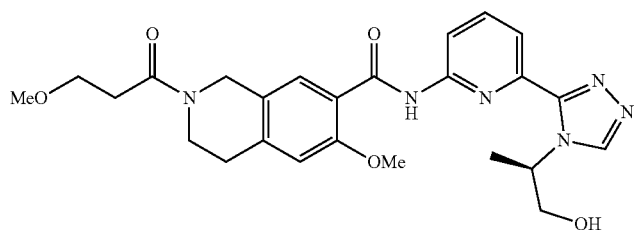 [SMILES: COCCC(=O)N1CCc2cc(OC)c(C(=O)Nc3cccc(-c4nncn4[C@H](C)CO)n3)cc2C1] |
| 233 | 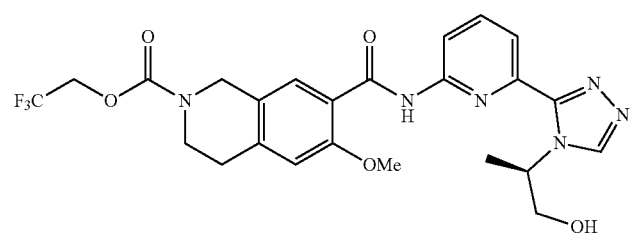 |
| 234 | 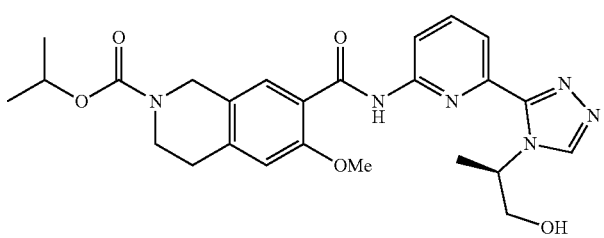 [SMILES: COc1cc2c(cc1C(=O)Nc1cccc(-c3nncn3[C@H](C)CO)n1)CN(C(=O)OC(C)C)CC2] |
| 235 | 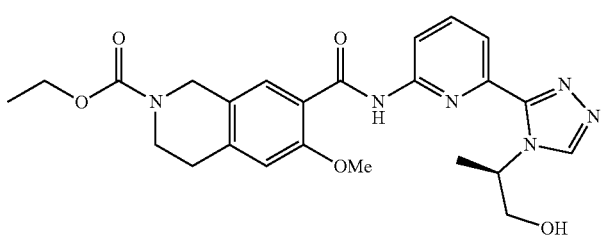 [SMILES: CCOC(=O)N1CCc2cc(OC)c(C(=O)Nc3cccc(-c4nncn4[C@H](C)CO)n3)cc2C1] |
| 236 | 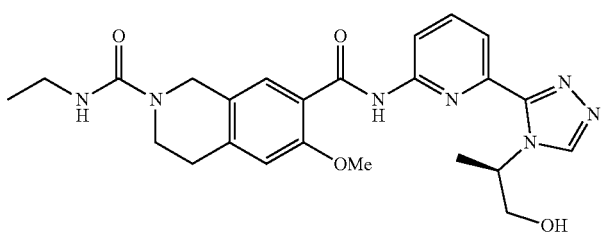 [SMILES: CCNC(=O)N1CCc2cc(OC)c(C(=O)Nc3cccc(-c4nncn4[C@H](C)CO)n3)cc2C1] |
| 237 | 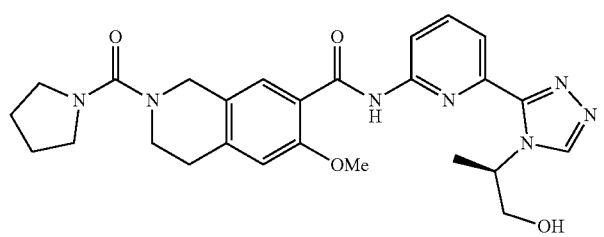 [SMILES: COc1cc2c(cc1C(=O)Nc1cccc(-c3nncn3[C@H](C)CO)n1)CN(C(=O)N1CCCC1)CC2] |

-continued
| Compound | Structure |
|---|---|
| 238 | 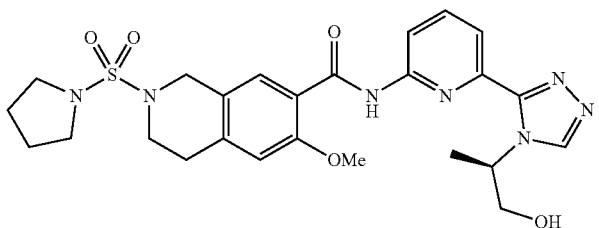 [SMILES: COc1cc2c(cc1C(=O)Nc1cccc(-c3nncn3[C@H](C)CO)n1)CN(S(=O)(=O)N1CCCC1)CC2] |
| 239 | 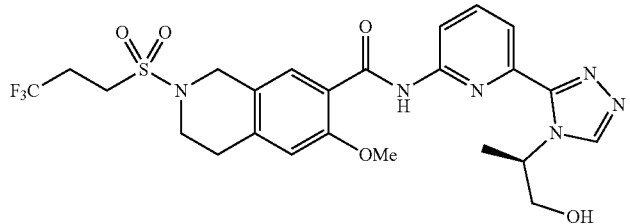 [SMILES: COc1cc2c(cc1C(=O)Nc1cccc(-c3nncn3[C@H](C)CO)n1)CN(S(=O)(=O)CCC(F)(F)F)CC2] |
| 240 | 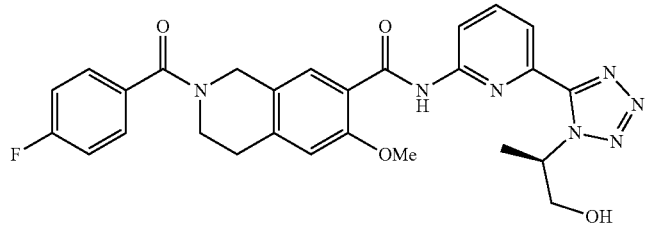 [SMILES: COc1cc2c(cc1C(=O)Nc1cccc(-c3nnnn3[C@H](C)CO)n1)CN(C(=O)c1ccc(F)cc1)CC2] |
| 241 | 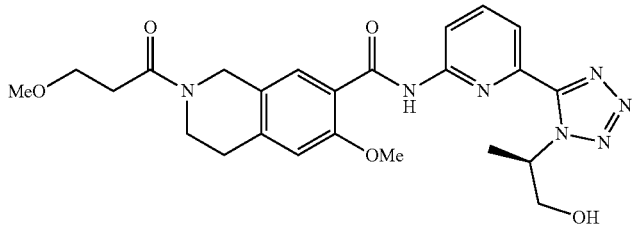 [SMILES: COCCC(=O)N1CCc2cc(OC)c(C(=O)Nc3cccc(-c4nnnn4[C@H](C)CO)n3)cc2C1] |
| 242 | 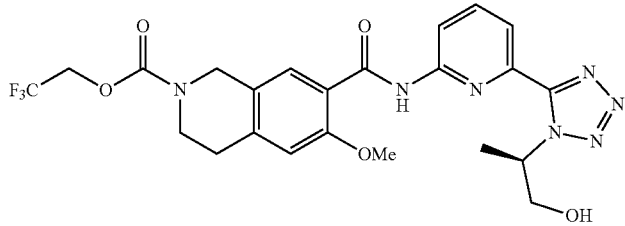 [SMILES: COc1cc2c(cc1C(=O)Nc1cccc(-c3nnnn3[C@H](C)CO)n1)CN(C(=O)OCC(F)(F)F)CC2] |
| 243 | 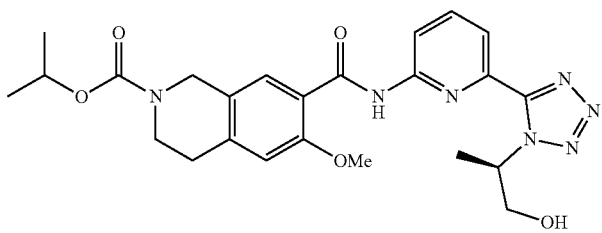 [SMILES: COc1cc2c(cc1C(=O)Nc1cccc(-c3nnnn3[C@H](C)CO)n1)CN(C(=O)OC(C)C)CC2] |

| Compound | Structure |
|---|---|
| 244 | 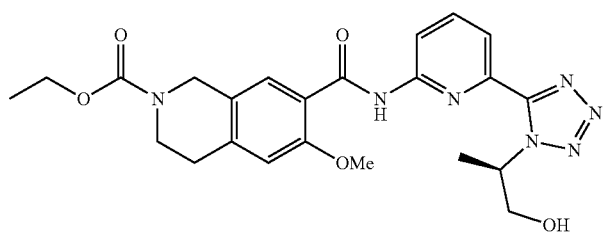 [SMILES: CCOC(=O)N1CCc2cc(OC)c(C(=O)Nc3cccc(-c4nnnn4[C@H](C)CO)n3)cc2C1] |
| 245 | 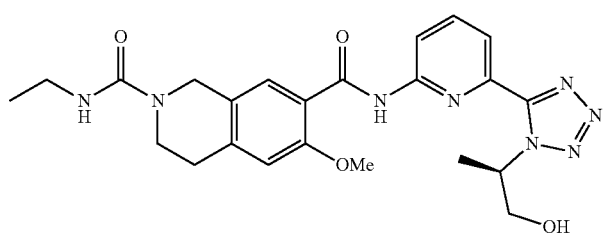 [SMILES: CCNC(=O)N1CCc2cc(OC)c(C(=O)Nc3cccc(-c4nnnn4[C@H](C)CO)n3)cc2C1] |
| 246 | 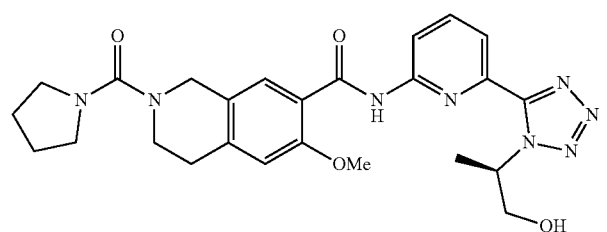 [SMILES: COc1cc2c(cc1C(=O)Nc1cccc(-c3nnnn3[C@H](C)CO)n1)CN(C(=O)N1CCCC1)CC2] |
| 247 | 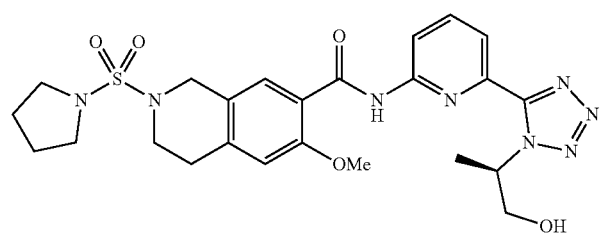 [SMILES: COc1cc2c(cc1C(=O)Nc1cccc(-c3nnnn3[C@H](C)CO)n1)CN(S(=O)(=O)N1CCCC1)CC2] |
| 248 | 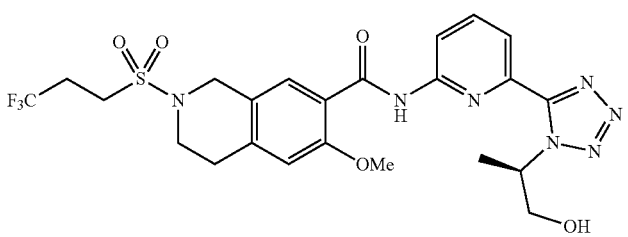 [SMILES: COc1cc2c(cc1C(=O)Nc1cccc(-c3nnnn3[C@H](C)CO)n1)CN(S(=O)(=O)CCC(F)(F)F)CC2] |
| 249 | 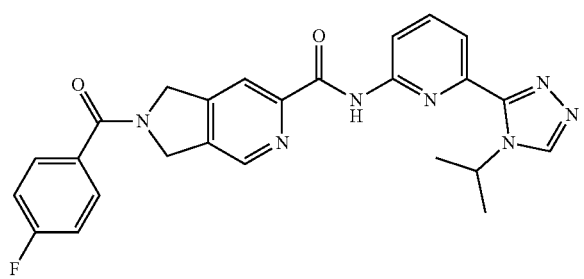 [SMILES: CC(C)n1cnnc1-c1cccc(NC(=O)c2cc3c(cn2)CN(C(=O)c2ccc(F)cc2)C3)n1] |

-continued
| Compound | Structure |
|---|---|
| 250 | 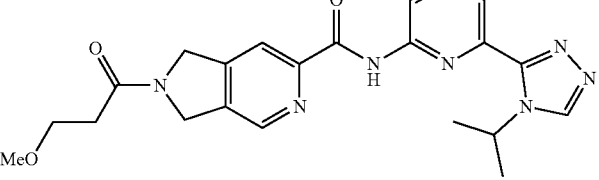 |
| 251 | 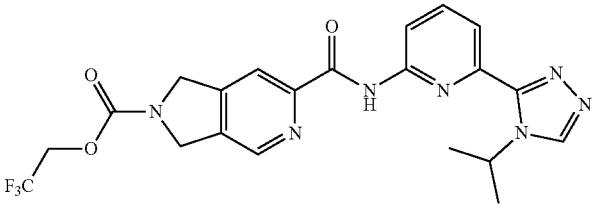 |
| 252 | 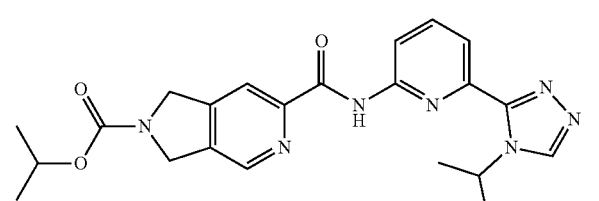 |
| 253 | 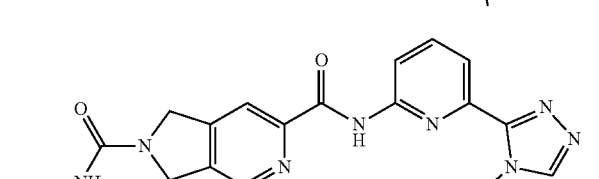 |
| 254 | 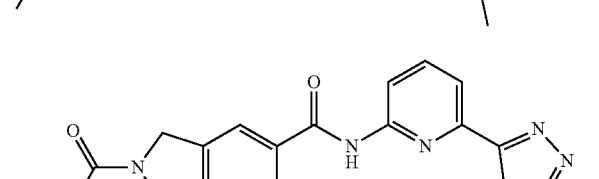 |
| 255 | 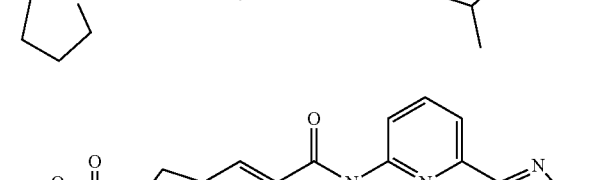 |
| 256 | 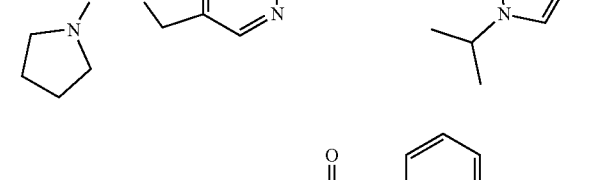 |

-continued

| Compound | Structure |
|---|---|
| 257 | 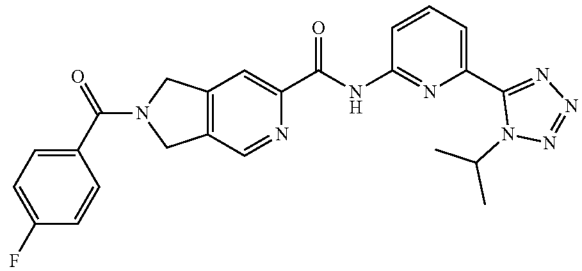 |
| 258 | 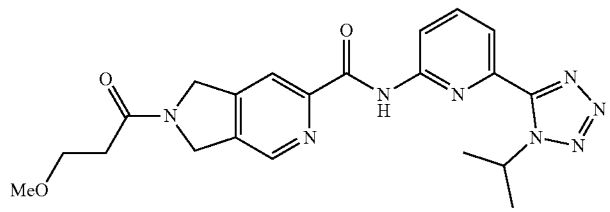 |
| 259 | 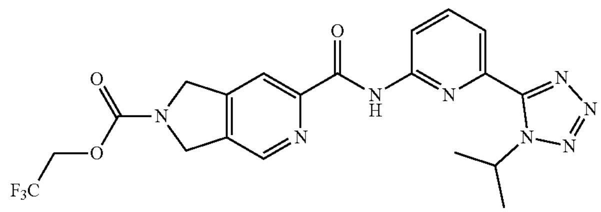 [SMILES: CC(C)n1nnnc1-c1cccc(NC(=O)c2cc3c(cn2)CN(C(=O)OCC(F)(F)F)C3)n1] |
| 260 | 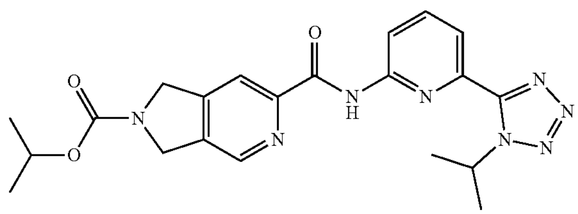 [SMILES: CC(C)OC(=O)N1Cc2cnc(C(=O)Nc3cccc(-c4nnnn4C(C)C)n3)cc2C1] |
| 261 | 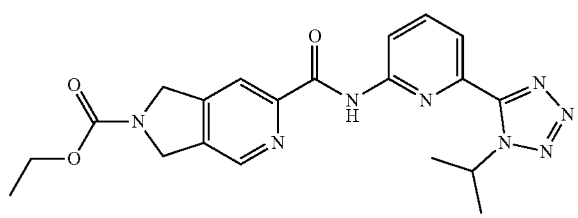 [SMILES: CCOC(=O)N1Cc2cnc(C(=O)Nc3cccc(-c4nnnn4C(C)C)n3)cc2C1] |
| 262 | 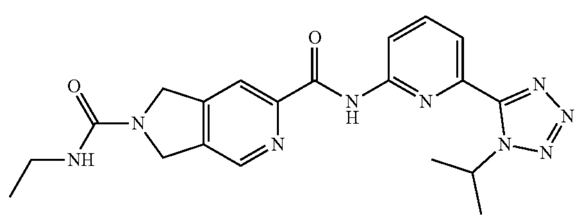 |
| 263 | 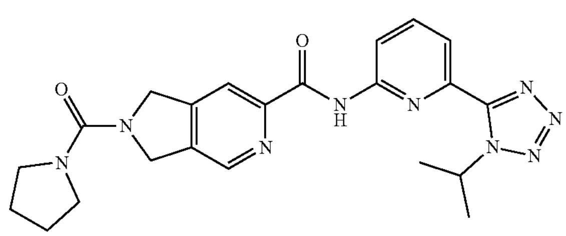 [SMILES: CC(C)n1nnnc1-c1cccc(NC(=O)c2cc3c(cn2)CN(C(=O)N2CCCC2)C3)n1] |

-continued

| Compound | Structure |
|---|---|
| 264 | 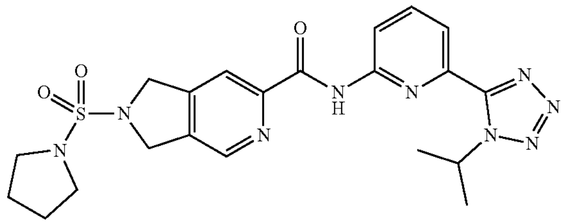 [SMILES: CC(C)n1nnnc1-c1cccc(NC(=O)c2cc3c(cn2)CN(S(=O)(=O)N2CCCC2)C3)n1] |
| 265 | 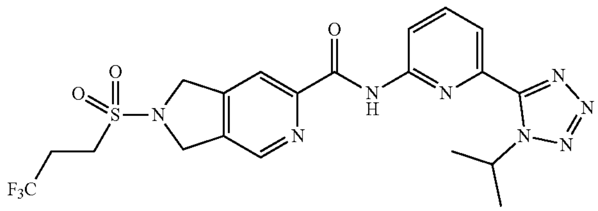 [SMILES: CC(C)n1nnnc1-c1cccc(NC(=O)c2cc3c(cn2)CN(S(=O)(=O)CCC(F)(F)F)C3)n1] |
| 266 | 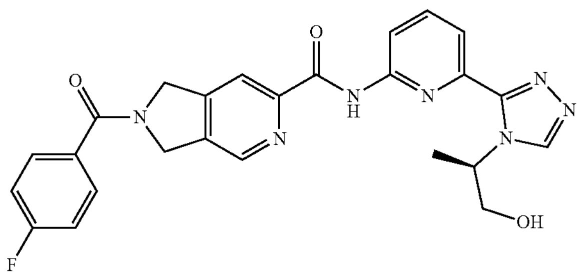 |
| 267 | 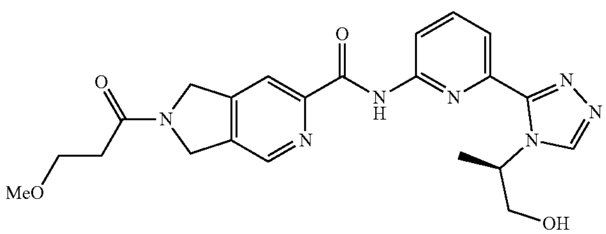 [SMILES: COCCC(=O)N1Cc2cnc(C(=O)Nc3cccc(-c4nncn4[C@H](C)CO)n3)cc2C1] |
| 268 | 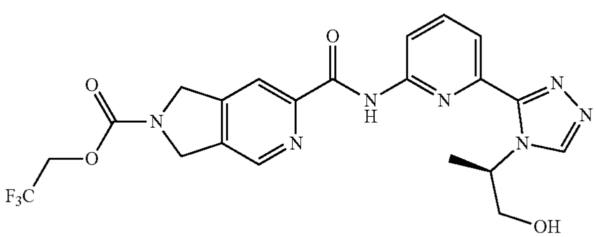 [SMILES: C[C@H](CO)n1cnnc1-c1cccc(NC(=O)c2cc3c(cn2)CN(C(=O)OCC(F)(F)F)C3)n1] |
| 269 | 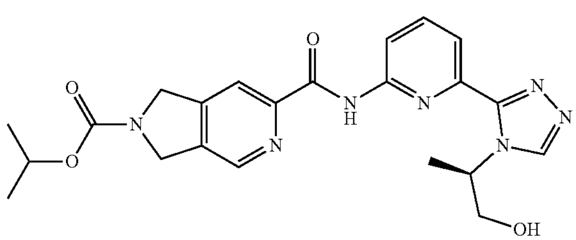 [SMILES: CC(C)OC(=O)N1Cc2cnc(C(=O)Nc3cccc(-c4nncn4[C@H](C)CO)n3)cc2C1] |

US 10,450,301 B2
-continued
| Compound | Structure |
|---|---|
| 270 | 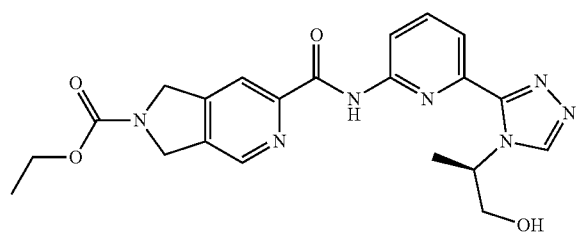 [SMILES: CCOC(=O)N1Cc2cnc(C(=O)Nc3cccc(-c4nncn4[C@H](C)CO)n3)cc2C1] |
| 271 | 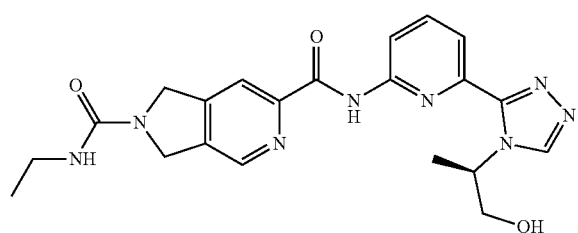 [SMILES: CCNC(=O)N1Cc2cnc(C(=O)Nc3cccc(-c4nncn4[C@H](C)CO)n3)cc2C1] |
| 272 | 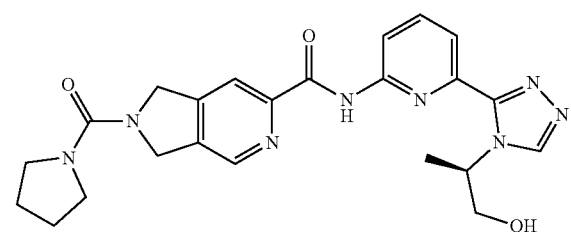 [SMILES: C[C@H](CO)n1cnnc1-c1cccc(NC(=O)c2cc3c(cn2)CN(C(=O)N2CCCC2)C3)n1] |
| 273 | 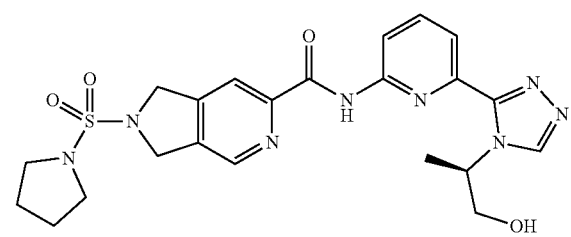 [SMILES: C[C@H](CO)n1cnnc1-c1cccc(NC(=O)c2cc3c(cn2)CN(S(=O)(=O)N2CCCC2)C3)n1] |
| 274 | 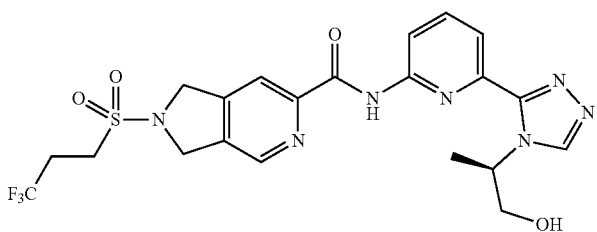 [SMILES: C[C@H](CO)n1cnnc1-c1cccc(NC(=O)c2cc3c(cn2)CN(S(=O)(=O)CCC(F)(F)F)C3)n1] |
| 275 | 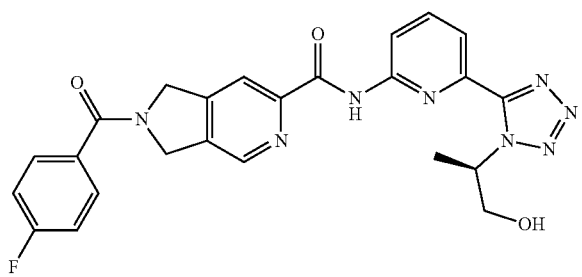 [SMILES: C[C@H](CO)n1nnnc1-c1cccc(NC(=O)c2cc3c(cn2)CN(C(=O)c2ccc(F)cc2)C3)n1] |

-continued
| Compound | Structure |
|---|---|
| 276 | 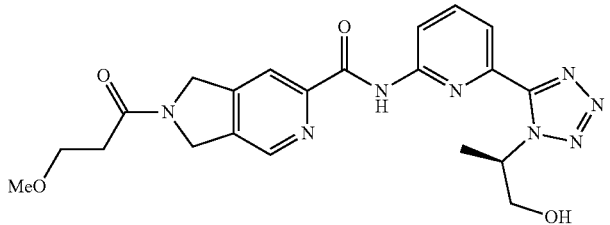 |
| 277 | 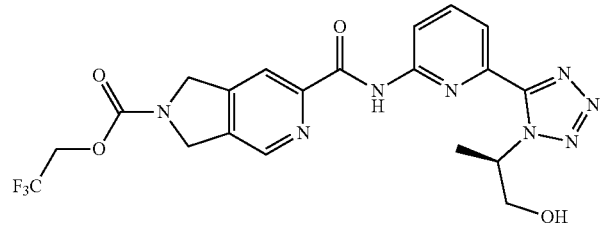 |
| 278 | 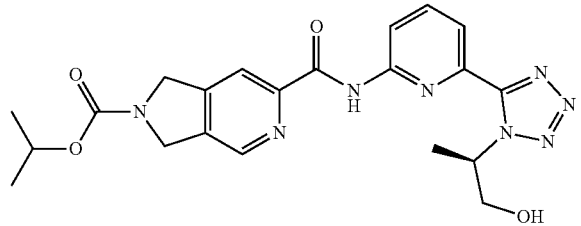 [SMILES: CC(C)OC(=O)N1Cc2cnc(C(=O)Nc3cccc(-c4nnnn4[C@H](C)CO)n3)cc2C1] |
| 279 | 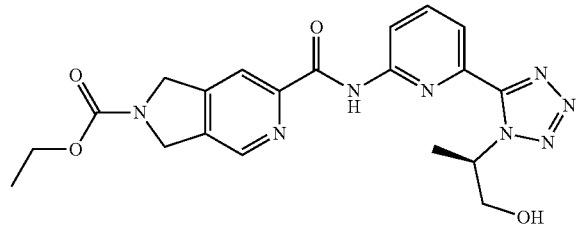 [SMILES: CCOC(=O)N1Cc2cnc(C(=O)Nc3cccc(-c4nnnn4[C@H](C)CO)n3)cc2C1] |
| 280 | 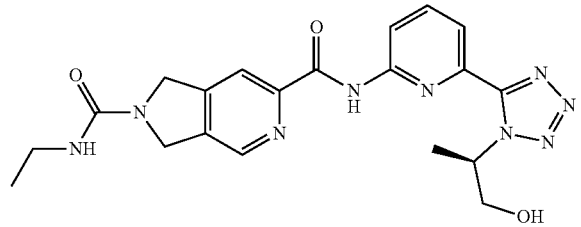 [SMILES: CCNC(=O)N1Cc2cnc(C(=O)Nc3cccc(-c4nnnn4[C@H](C)CO)n3)cc2C1] |
| 281 | 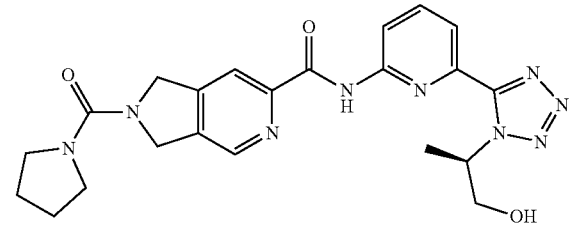 |

| Compound | Structure |
|---|---|
| 282 | 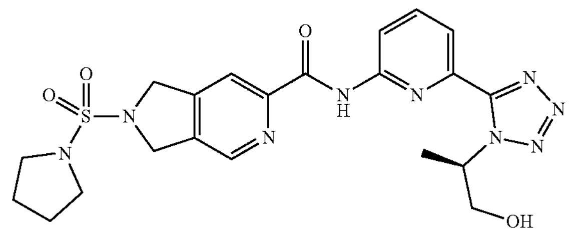 |
| 283 | 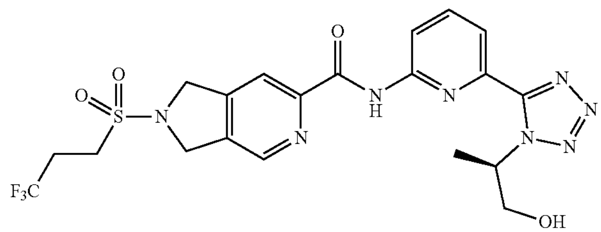 [SMILES: C[C@H](CO)n1nnnc1-c1cccc(NC(=O)c2cc3c(cn2)CN(S(=O)(=O)CCC(F)(F)F)C3)n1] |
| 284 | 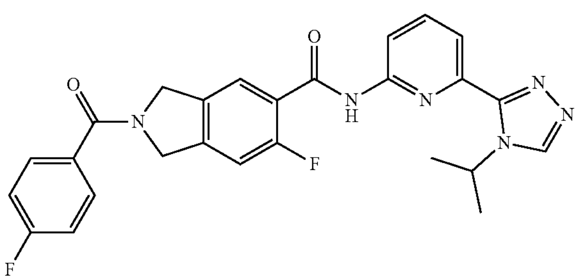 [SMILES: CC(C)n1cnnc1-c1cccc(NC(=O)c2cc3c(cc2F)CN(C(=O)c2ccc(F)cc2)C3)n1] |
| 285 | 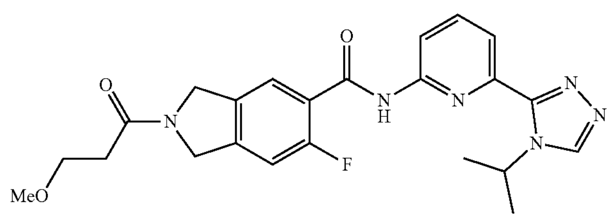 [SMILES: COCCC(=O)N1Cc2cc(F)c(C(=O)Nc3cccc(-c4nncn4C(C)C)n3)cc2C1] |
| 286 | 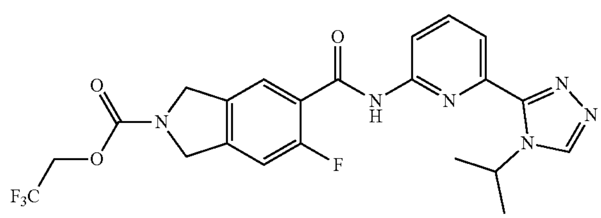 [SMILES: CC(C)n1cnnc1-c1cccc(NC(=O)c2cc3c(cc2F)CN(C(=O)OCC(F)(F)F)C3)n1] |
| 287 | 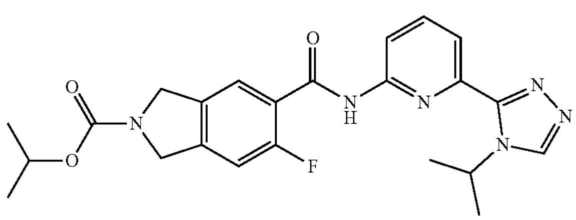 [SMILES: CC(C)OC(=O)N1Cc2cc(F)c(C(=O)Nc3cccc(-c4nncn4C(C)C)n3)cc2C1] |

-continued

| Compound | Structure |
|---|---|
| 288 | 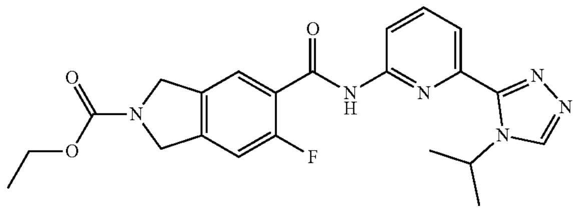 [SMILES: CCOC(=O)N1Cc2cc(F)c(C(=O)Nc3cccc(-c4nncn4C(C)C)n3)cc2C1] |
| 289 | 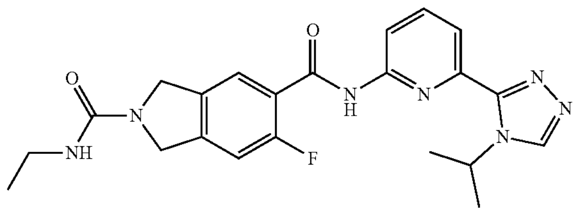 |
| 290 | 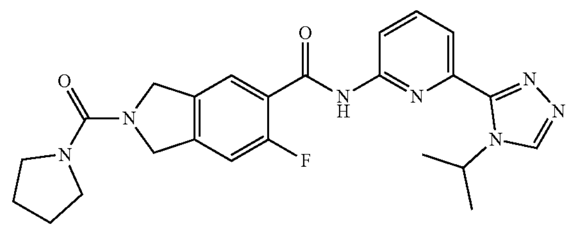 [SMILES: CC(C)n1cnnc1-c1cccc(NC(=O)c2cc3c(cc2F)CN(C(=O)N2CCCC2)C3)n1] |
| 291 | 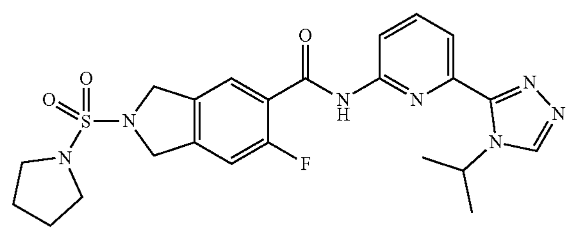 [SMILES: CC(C)n1cnnc1-c1cccc(NC(=O)c2cc3c(cc2F)CN(S(=O)(=O)N2CCCC2)C3)n1] |
| 292 | 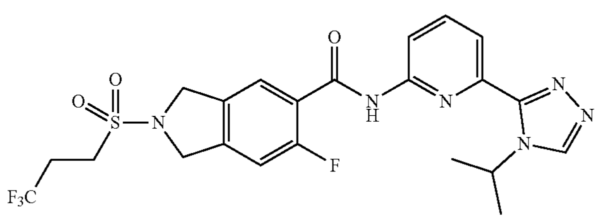 |
| 293 | 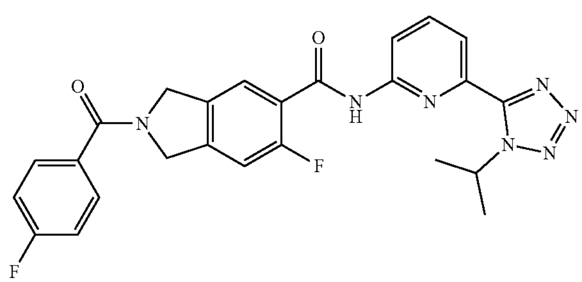 [SMILES: CC(C)n1nnnc1-c1cccc(NC(=O)c2cc3c(cc2F)CN(C(=O)c2ccc(F)cc2)C3)n1] |

-continued

| Compound | Structure |
|---|---|
| 294 | 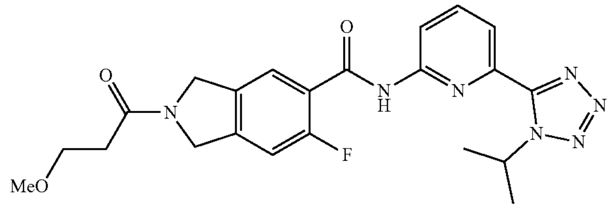 [SMILES: COCCC(=O)N1Cc2cc(F)c(C(=O)Nc3cccc(-c4nnnn4C(C)C)n3)cc2C1] |
| 295 | 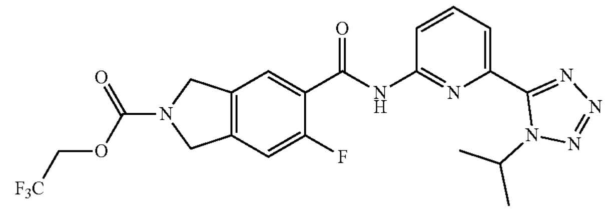 [SMILES: CC(C)n1nnnc1-c1cccc(NC(=O)c2cc3c(cc2F)CN(C(=O)OCC(F)(F)F)C3)n1] |
| 296 | 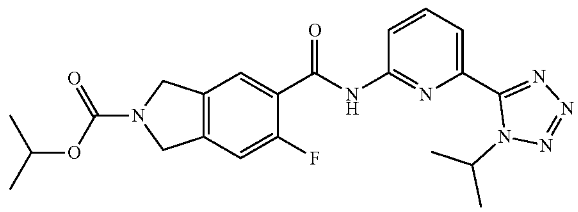 [SMILES: CC(C)OC(=O)N1Cc2cc(F)c(C(=O)Nc3cccc(-c4nnnn4C(C)C)n3)cc2C1] |
| 297 | 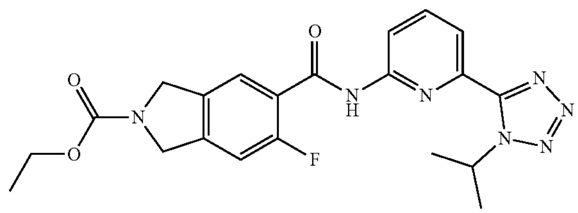 [SMILES: CCOC(=O)N1Cc2cc(F)c(C(=O)Nc3cccc(-c4nnnn4C(C)C)n3)cc2C1] |
| 298 | 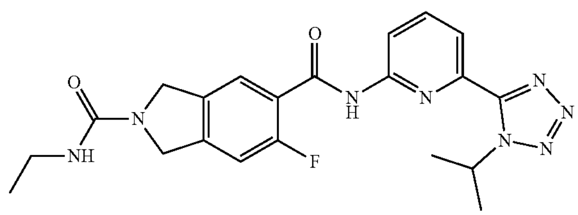 [SMILES: CCNC(=O)N1Cc2cc(F)c(C(=O)Nc3cccc(-c4nnnn4C(C)C)n3)cc2C1] |
| 299 | 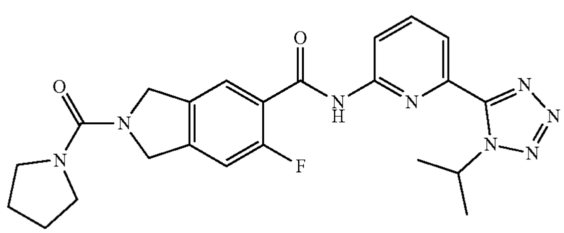 [SMILES: CC(C)n1nnnc1-c1cccc(NC(=O)c2cc3c(cc2F)CN(C(=O)N2CCCC2)C3)n1] |
| 300 | 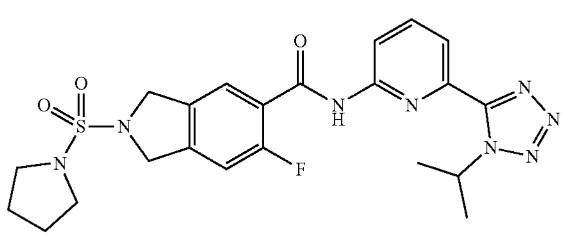 [SMILES: CC(C)n1nnnc1-c1cccc(NC(=O)c2cc3c(cc2F)CN(S(=O)(=O)N2CCCC2)C3)n1] |

-continued
| Compound | Structure |
|---|---|
| 301 | 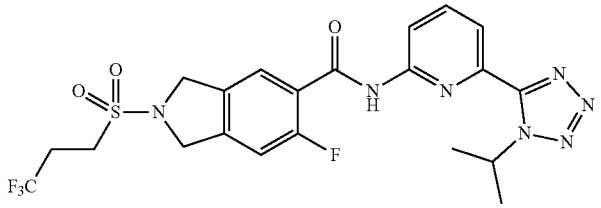 [SMILES: CC(C)n1nnnc1-c1cccc(NC(=O)c2cc3c(cc2F)CN(S(=O)(=O)CCC(F)(F)F)C3)n1] |
| 302 | 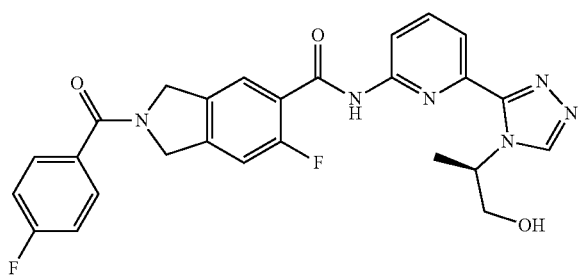 |
| 303 | 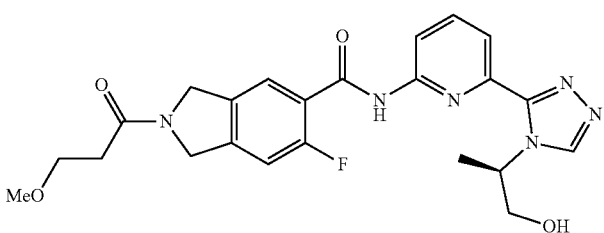 [SMILES: COCCC(=O)N1Cc2cc(F)c(C(=O)Nc3cccc(-c4nncn4[C@H](C)CO)n3)cc2C1] |
| 304 | 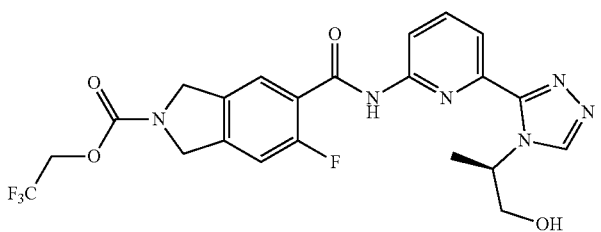 |
| 305 | 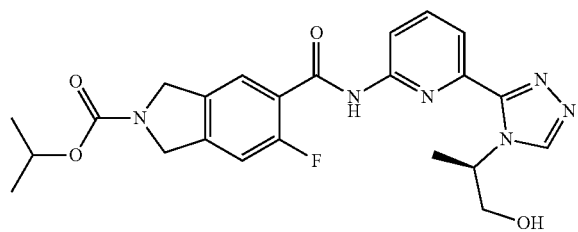 |
| 306 | 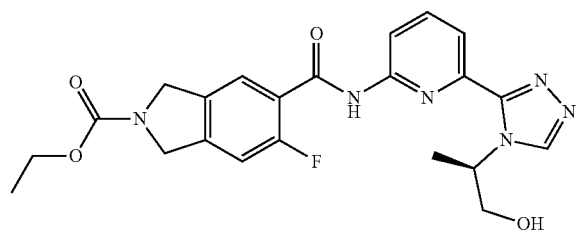 [SMILES: CCOC(=O)N1Cc2cc(F)c(C(=O)Nc3cccc(-c4nncn4[C@H](C)CO)n3)cc2C1] |

-continued
| Compound | Structure |
|---|---|
| 307 | 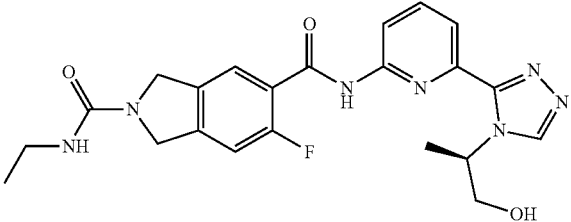 [SMILES: CCNC(=O)N1Cc2cc(F)c(C(=O)Nc3cccc(-c4nncn4[C@H](C)CO)n3)cc2C1] |
| 308 | 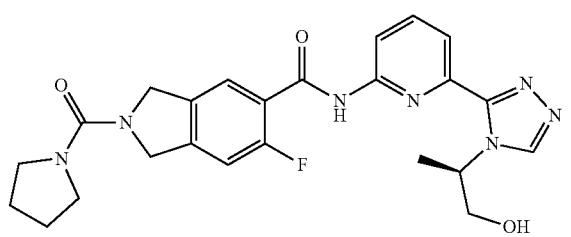 [SMILES: C[C@H](CO)n1cnnc1-c1cccc(NC(=O)c2cc3c(cc2F)CN(C(=O)N2CCCC2)C3)n1] |
| 309 | 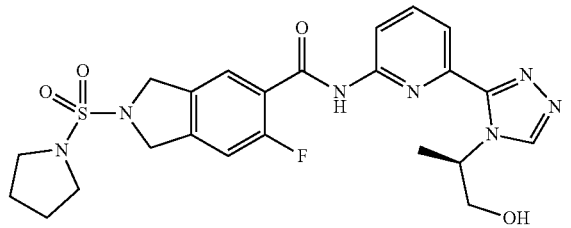 [SMILES: C[C@H](CO)n1cnnc1-c1cccc(NC(=O)c2cc3c(cc2F)CN(S(=O)(=O)N2CCCC2)C3)n1] |
| 310 | 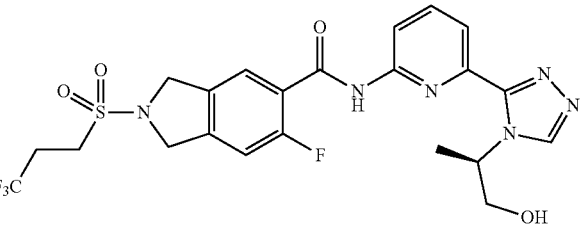 |
| 311 | 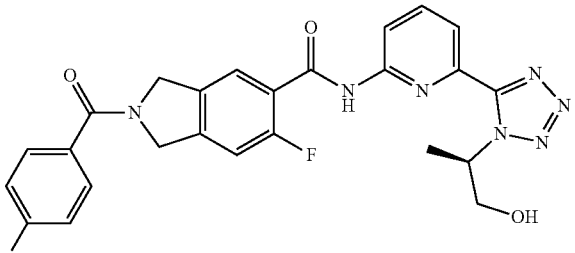 |
| 312 | 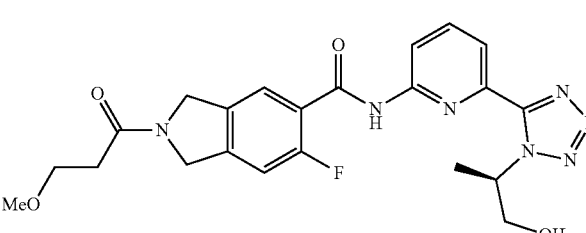 |

-continued
| Compound | Structure |
|---|---|
| 313 | 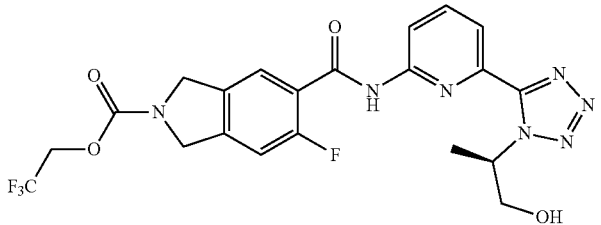 |
| 314 | 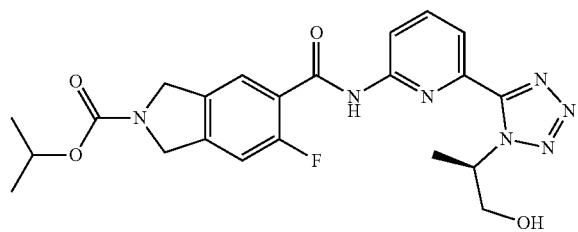 [SMILES: CC(C)OC(=O)N1Cc2cc(F)c(C(=O)Nc3cccc(-c4nnnn4[C@H](C)CO)n3)cc2C1] |
| 315 | 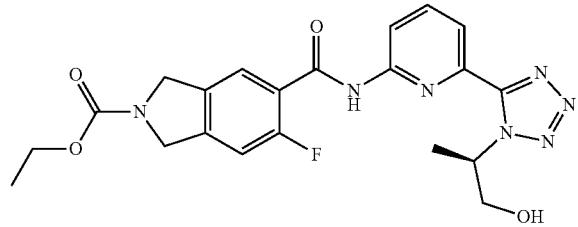 [SMILES: CCOC(=O)N1Cc2cc(F)c(C(=O)Nc3cccc(-c4nnnn4[C@H](C)CO)n3)cc2C1] |
| 316 | 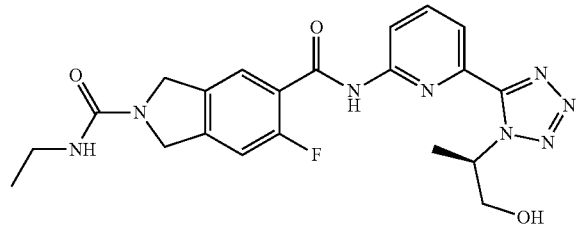 [SMILES: CCNC(=O)N1Cc2cc(F)c(C(=O)Nc3cccc(-c4nnnn4[C@H](C)CO)n3)cc2C1] |
| 317 | 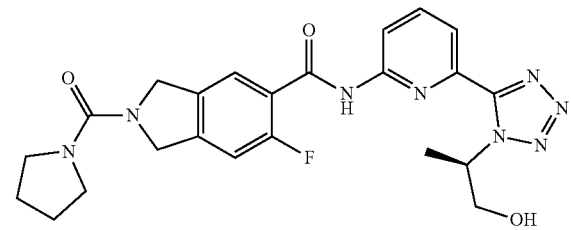 [SMILES: C[C@H](CO)n1nnnc1-c1cccc(NC(=O)c2cc3c(cc2F)CN(C(=O)N2CCCC2)C3)n1] |
| 318 | 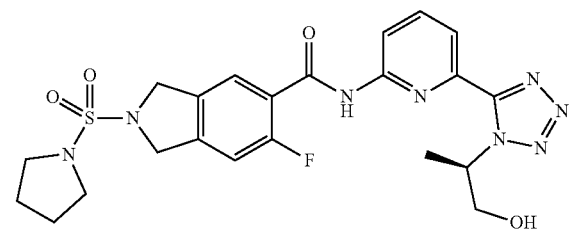 [SMILES: C[C@H](CO)n1nnnc1-c1cccc(NC(=O)c2cc3c(cc2F)CN(S(=O)(=O)N2CCCC2)C3)n1] |

-continued
| Compound | Structure |
|---|---|
| 319 | 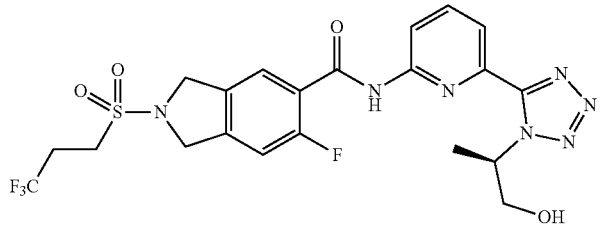 |
| 320 | 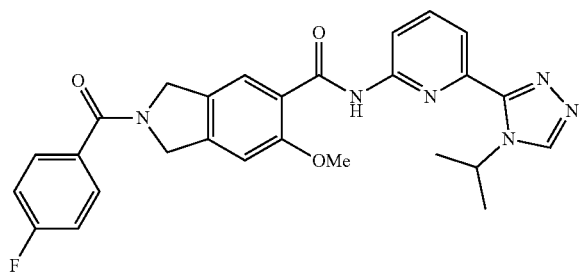 |
| 321 | 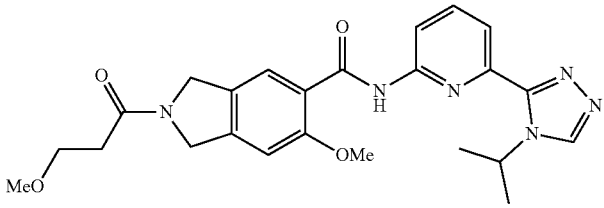 [SMILES: COCCC(=O)N1Cc2cc(OC)c(C(=O)Nc3cccc(-c4nncn4C(C)C)n3)cc2C1] |
| 322 | 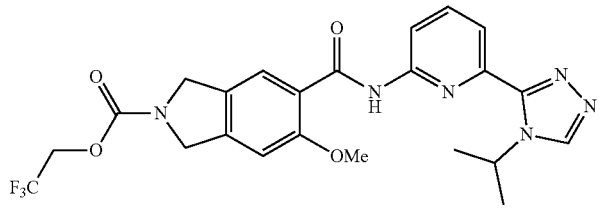 |
| 323 | 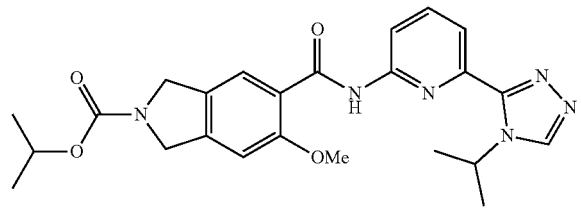 [SMILES: COc1cc2c(cc1C(=O)Nc1cccc(-c3nncn3C(C)C)n1)CN(C(=O)OC(C)C)C2] |
| 324 | 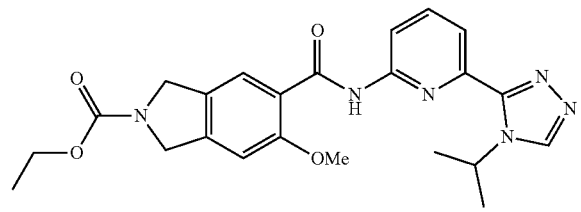 [SMILES: CCOC(=O)N1Cc2cc(OC)c(C(=O)Nc3cccc(-c4nncn4C(C)C)n3)cc2C1] |

| Compound | Structure |
|---|---|
| 325 | 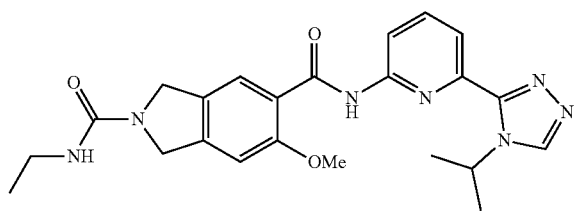 [SMILES: CCNC(=O)N1Cc2cc(OC)c(C(=O)Nc3cccc(-c4nncn4C(C)C)n3)cc2C1] |
| 326 | 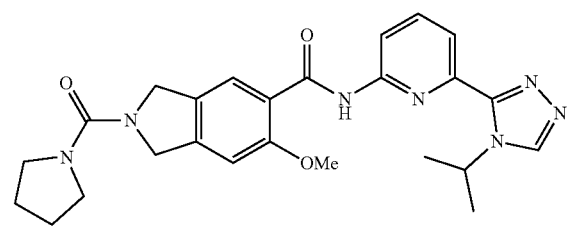 [SMILES: COc1cc2c(cc1C(=O)Nc1cccc(-c3nncn3C(C)C)n1)CN(C(=O)N1CCCC1)C2] |
| 327 | 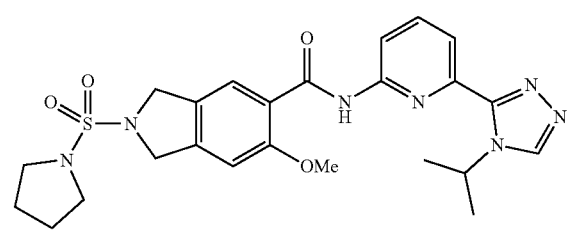 [SMILES: COc1cc2c(cc1C(=O)Nc1cccc(-c3nncn3C(C)C)n1)CN(S(=O)(=O)N1CCCC1)C2] |
| 328 | 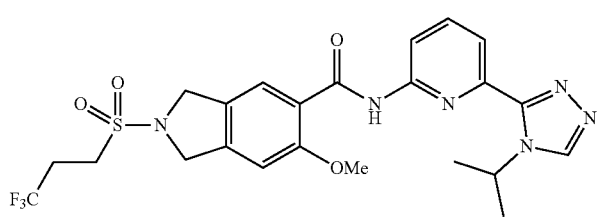 |
| 329 | 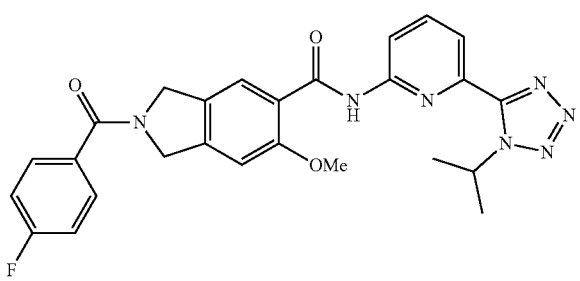 |
| 330 | 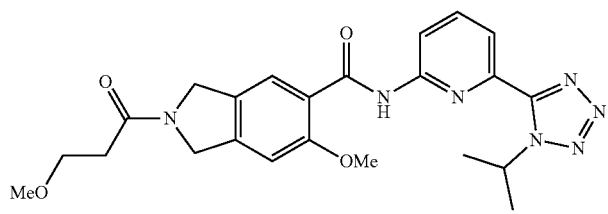 [SMILES: COCCC(=O)N1Cc2cc(OC)c(C(=O)Nc3cccc(-c4nnnn4C(C)C)n3)cc2C1] |

-continued

| Compound | Structure |
|---|---|
| 331 | 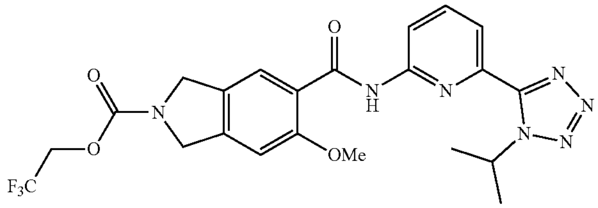 [SMILES: COc1cc2c(cc1C(=O)Nc1cccc(-c3nnnn3C(C)C)n1)CN(C(=O)OCC(F)(F)F)C2] |
| 332 | 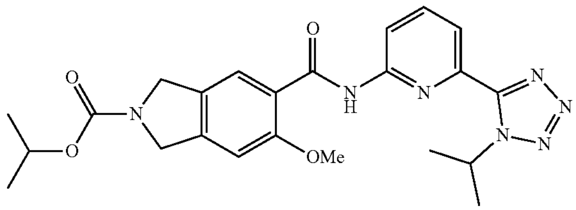 [SMILES: COc1cc2c(cc1C(=O)Nc1cccc(-c3nnnn3C(C)C)n1)CN(C(=O)OC(C)C)C2] |
| 333 | 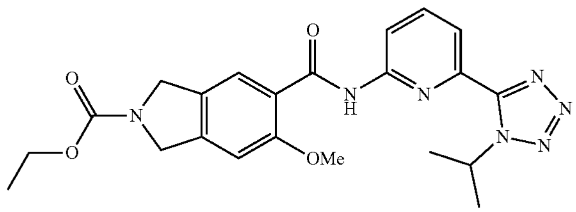 |
| 334 | 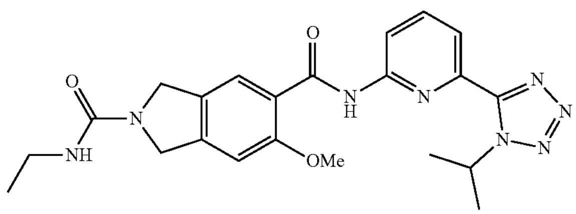 [SMILES: CCNC(=O)N1Cc2cc(OC)c(C(=O)Nc3cccc(-c4nnnn4C(C)C)n3)cc2C1] |
| 335 | 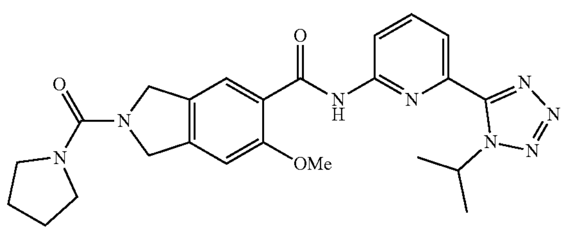 [SMILES: COc1cc2c(cc1C(=O)Nc1cccc(-c3nnnn3C(C)C)n1)CN(C(=O)N1CCCC1)C2] |
| 336 | 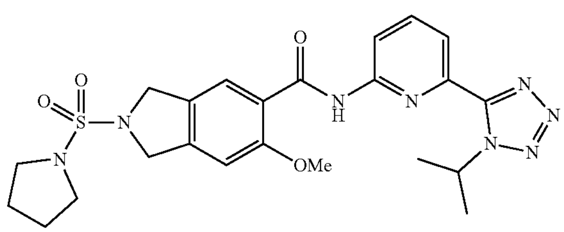 |
| 337 | 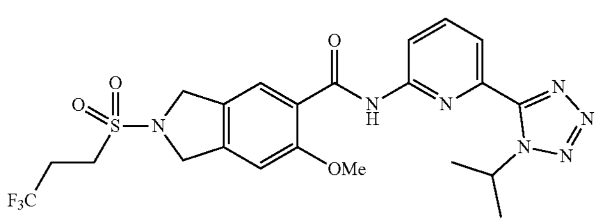 [SMILES: COc1cc2c(cc1C(=O)Nc1cccc(-c3nnnn3C(C)C)n1)CN(S(=O)(=O)CCC(F)(F)F)C2] |

-continued

| Compound | Structure |
|---|---|
| 338 | 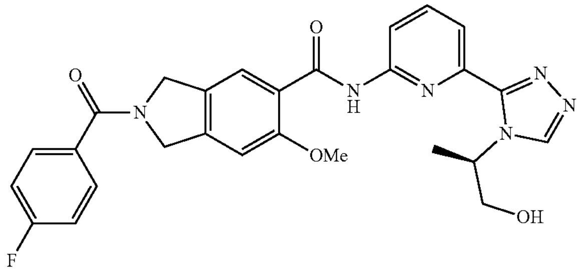 [SMILES: COc1cc2c(cc1C(=O)Nc1cccc(-c3nncn3[C@H](C)CO)n1)CN(C(=O)c1ccc(F)cc1)C2] |
| 339 | 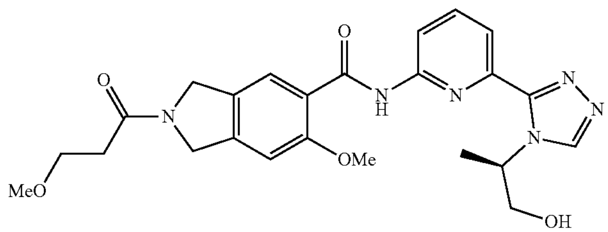 [SMILES: COCCC(=O)N1Cc2cc(OC)c(C(=O)Nc3cccc(-c4nncn4[C@H](C)CO)n3)cc2C1] |
| 340 | 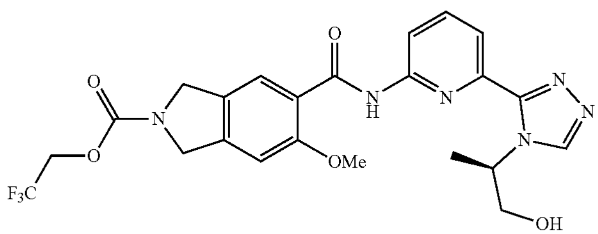 [SMILES: COc1cc2c(cc1C(=O)Nc1cccc(-c3nncn3[C@H](C)CO)n1)CN(C(=O)OCC(F)(F)F)C2] |
| 341 | 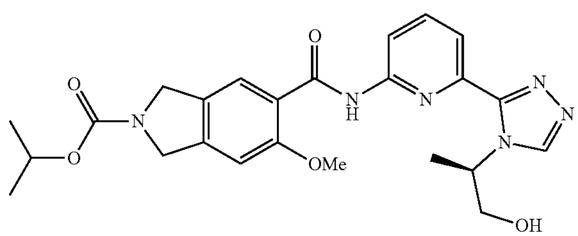 [SMILES: COc1cc2c(cc1C(=O)Nc1cccc(-c3nncn3[C@H](C)CO)n1)CN(C(=O)OC(C)C)C2] |
| 342 | 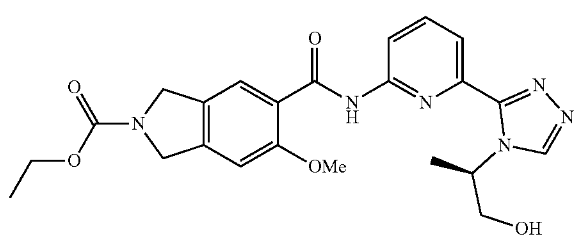 [SMILES: CCOC(=O)N1Cc2cc(OC)c(C(=O)Nc3cccc(-c4nncn4[C@H](C)CO)n3)cc2C1] |
| 343 | 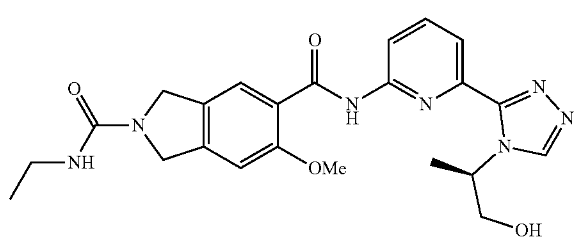 [SMILES: CCNC(=O)N1Cc2cc(OC)c(C(=O)Nc3cccc(-c4nncn4[C@H](C)CO)n3)cc2C1] |

-continued

| Compound | Structure |
|---|---|
| 344 | 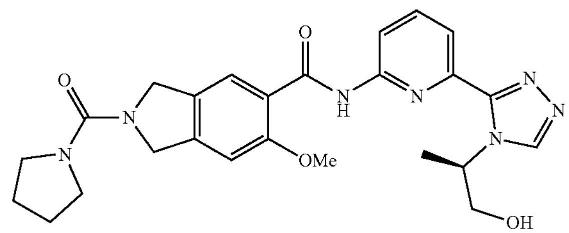 [SMILES: COc1cc2c(cc1C(=O)Nc1cccc(-c3nncn3[C@H](C)CO)n1)CN(C(=O)N1CCCC1)C2] |
| 345 | 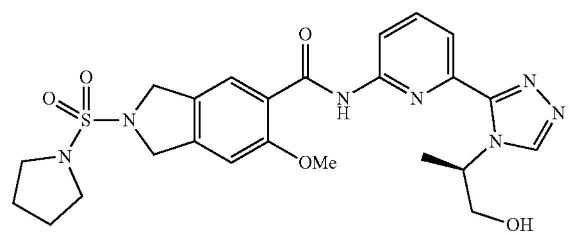 [SMILES: COc1cc2c(cc1C(=O)Nc1cccc(-c3nncn3[C@H](C)CO)n1)CN(S(=O)(=O)N1CCCC1)C2] |
| 346 | 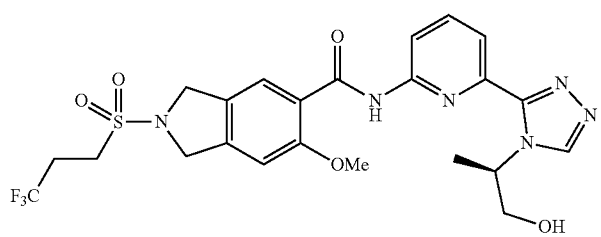 [SMILES: COc1cc2c(cc1C(=O)Nc1cccc(-c3nncn3[C@H](C)CO)n1)CN(S(=O)(=O)CCC(F)(F)F)C2] |
| 347 | 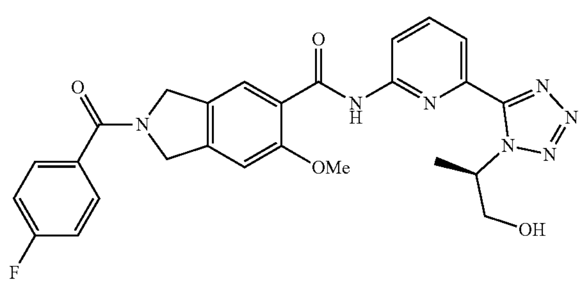 |
| 348 | 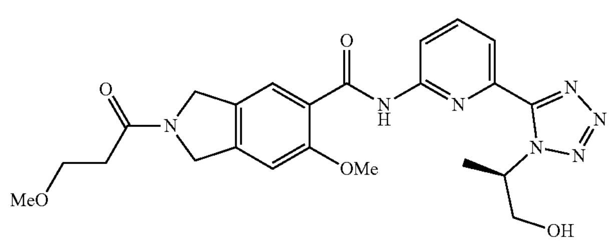 [SMILES: COCCC(=O)N1Cc2cc(OC)c(C(=O)Nc3cccc(-c4nnnn4[C@H](C)CO)n3)cc2C1] |
| 349 | 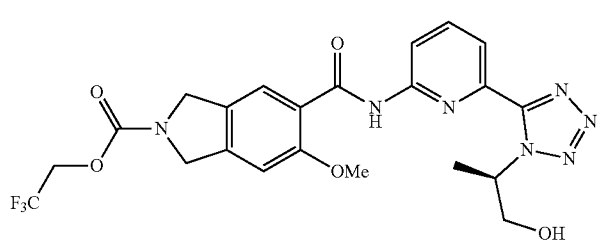 [SMILES: COc1cc2c(cc1C(=O)Nc1cccc(-c3nnnn3[C@H](C)CO)n1)CN(C(=O)OCC(F)(F)F)C2] |

-continued
| Compound | Structure |
|---|---|
| 350 | 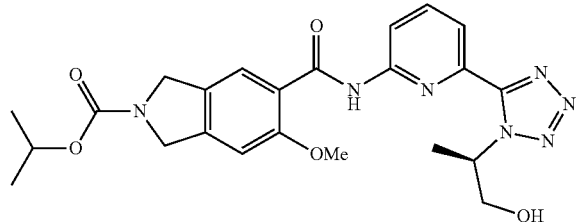 [SMILES: COc1cc2c(cc1C(=O)Nc1cccc(-c3nnnn3[C@H](C)CO)n1)CN(C(=O)OC(C)C)C2] |
| 351 | 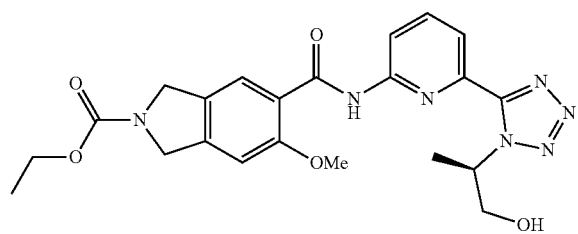 [SMILES: CCOC(=O)N1Cc2cc(OC)c(C(=O)Nc3cccc(-c4nnnn4[C@H](C)CO)n3)cc2C1] |
| 352 | 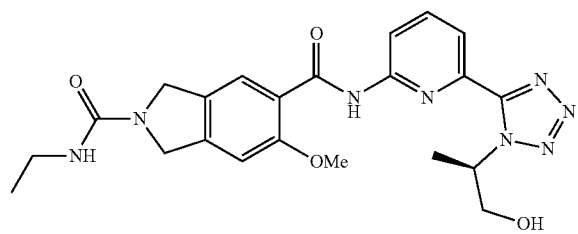 [SMILES: CCNC(=O)N1Cc2cc(OC)c(C(=O)Nc3cccc(-c4nnnn4[C@H](C)CO)n3)cc2C1] |
| 353 | 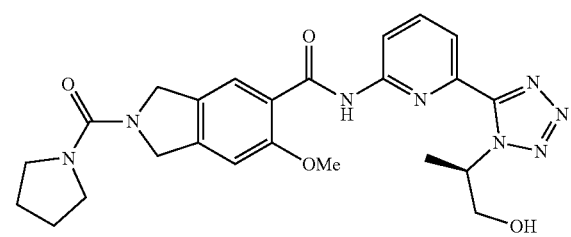 [SMILES: COc1cc2c(cc1C(=O)Nc1cccc(-c3nnnn3[C@H](C)CO)n1)CN(C(=O)N1CCCC1)C2] |
| 354 | 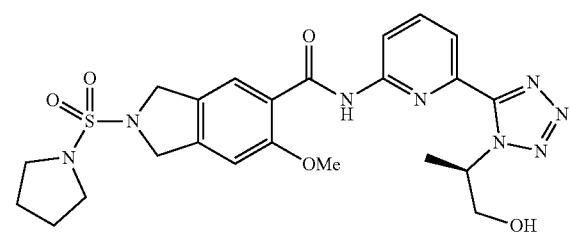 [SMILES: COc1cc2c(cc1C(=O)Nc1cccc(-c3nnnn3[C@H](C)CO)n1)CN(S(=O)(=O)N1CCCC1)C2] |
| 355 | 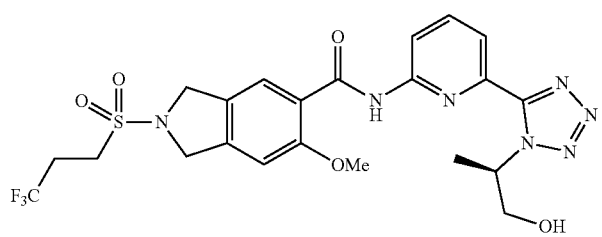 [SMILES: COc1cc2c(cc1C(=O)Nc1cccc(-c3nnnn3[C@H](C)CO)n1)CN(S(=O)(=O)CCC(F)(F)F)C2] |

-continued

| Compound | Structure |
|---|---|
| 356 | 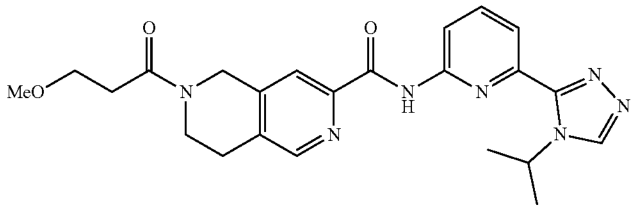 [SMILES: COCCC(=O)N1CCc2cnc(C(=O)Nc3cccc(-c4nncn4C(C)C)n3)cc2C1] |
| 357 | 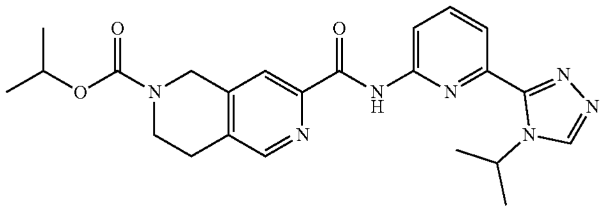 [SMILES: CC(C)OC(=O)N1CCc2cnc(C(=O)Nc3cccc(-c4nncn4C(C)C)n3)cc2C1] |
| 358 | 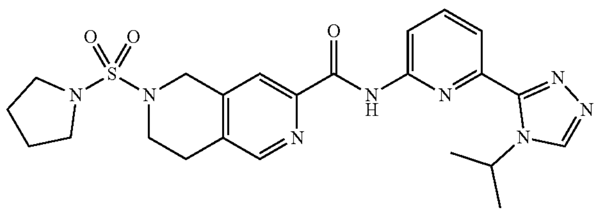 [SMILES: CC(C)n1cnnc1-c1cccc(NC(=O)c2cc3c(cn2)CCN(S(=O)(=O)N2CCCC2)C3)n1] |
| 359 | 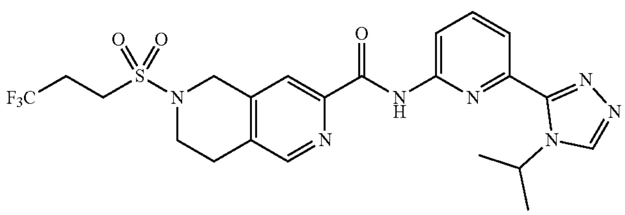 [SMILES: CC(C)n1cnnc1-c1cccc(NC(=O)c2cc3c(cn2)CCN(S(=O)(=O)CCC(F)(F)F)C3)n1] |
| 360 | 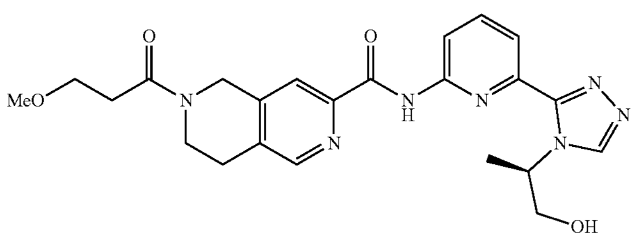 [SMILES: COCCC(=O)N1CCc2cnc(C(=O)Nc3cccc(-c4nncn4[C@H](C)CO)n3)cc2C1] |
| 361 | 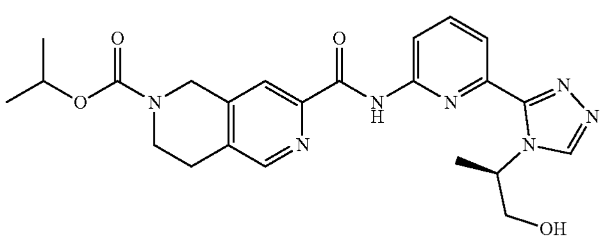 [SMILES: CC(C)OC(=O)N1CCc2cnc(C(=O)Nc3cccc(-c4nncn4[C@H](C)CO)n3)cc2C1] |
| 362 | 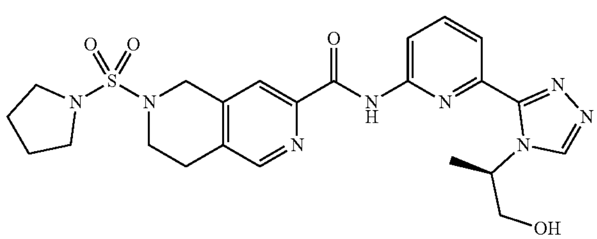 [SMILES: C[C@H](CO)n1cnnc1-c1cccc(NC(=O)c2cc3c(cn2)CCN(S(=O)(=O)N2CCCC2)C3)n1] |

-continued

| Compound | Structure |
|---|---|
| 363 | 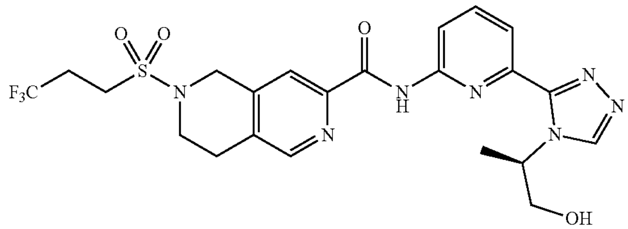 [SMILES: C[C@H](CO)n1cnnc1-c1cccc(NC(=O)c2cc3c(cn2)CCN(S(=O)(=O)CCC(F)(F)F)C3)n1] |
| 183a | 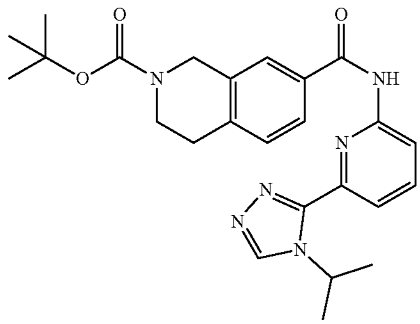 |

15. A pharmaceutical composition comprising a compound according to claim 1, and a pharmaceutically acceptable excipient or carrier.

16. A method for the treatment of an ASK-1 mediated disease or condition in a subject in need thereof, comprising administering to the subject a therapeutically effective amount of a compound according to claim 1.

17. A method for treating a disease selected from the group consisting of glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, inflammatory bowel disease, ulcerative colitis, Crohn's disease, psoriasis, graft vs. host disease, multiple sclerosis, Sjoegren's syndrome, stroke, heart attacks, myocardial ischemia, organ hypoxia, vascular hyperplasia, cardiac hypertrophy, hepatic ischemia, congestive heart failure, pathologic immune responses, thrombin-induced platelet aggregation, osteoporosis, osteoarthritis, multiple myeloma-related bone disorder, Alzheimer's disease, Parkinson's disease, amyotrophic lateral sclerosis (ALS), epilepsy, seizures, Huntington's disease, polyglutamine diseases, traumatic brain injury, ischemic and hemorrhaging stroke, cerebral ischemias or neurodegenerative disease, in a subject in need thereof, comprising administering to the subject a therapeutically effective amount of a compound according to claim 1.

18. The method according to claim 16, wherein the ASK-1 mediated disease is selected from the group consisting of primary biliary cirrhosis, cerebrotendinous xanthomatosis, primary sclerosing cholangitis, drug induced cholestasis, intrahepatic cholestasis of pregnancy, parenteral nutrition associated cholestasis, bacterial overgrowth or sepsis associated cholestasis, autoimmune hepatitis, chronic viral hepatitis, alcoholic liver disease, nonalcoholic fatty liver disease, nonalcoholic steatohepatitis, liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha 1-antitrypsin deficiency.

19. The method according to claim 18, wherein the ASK-1 mediated disease is selected from the group consisting of primary biliary cirrhosis, nonalcoholic fatty liver disease, and nonalcoholic steatohepatitis.

20. The method according to claim 16, wherein the ASK-1 mediated disease is selected from the group consisting of diabetic nephropathy, focal segmental glomerulosclerosis, hypertensive nephrosclerosis, chronic glomerulonephritis, chronic transplant glomerulopathy, chronic interstitial nephritis, polycystic kidney disease, atherosclerosis, arteriosclerosis, reperfusion/ischemia in stroke, cardiac hypertrophy, respiratory diseases, heart attacks, myocardial ischemia, insulin resistance, Type I and Type II diabetes, obesity, polycystic kidney disease, pyelonephritis, kidney fibrosis and glomerulonephritis.

* * * * *